US012703725B2

(12) United States Patent
Santos et al.

(10) Patent No.: US 12,703,725 B2
(45) Date of Patent: Aug. 11, 2026

(54) SILK-BASED PRODUCTS, FORMULATIONS, AND METHODS OF USE

(71) Applicant: Cocoon Biotech Inc., Mansfield, MA (US)

(72) Inventors: Michael Santos, Mansfield, MA (US); Scott Delisle, Mansfield, MA (US); Lindsey Easthon, Mansfield, MA (US); Riale T. Gilligan, Boston, MA (US)

(73) Assignee: Cocoon Biotech Inc., Mansfield, MA (US)

( * ) Notice: Subject to any disclaimer, the term of this patent is extended or adjusted under 35 U.S.C. 154(b) by 700 days.

(21) Appl. No.: 17/615,737

(22) PCT Filed: Jun. 4, 2020

(86) PCT No.: PCT/US2020/036073
§ 371 (c)(1),
(2) Date: Apr. 21, 2022

(87) PCT Pub. No.: WO2020/247594
PCT Pub. Date: Dec. 10, 2020

(65) Prior Publication Data

US 2024/0352079 A1 Oct. 24, 2024

Related U.S. Application Data

(60) Provisional application No. 62/944,534, filed on Dec. 6, 2019, provisional application No. 62/926,855, filed on Oct. 28, 2019, provisional application No. 62/893,836, filed on Aug. 30, 2019, provisional application No. 62/893,834, filed on Aug. 30, 2019, provisional application No. 62/856,936, filed on Jun. 4, 2019.

(51) Int. Cl.
*C07K 1/34* (2006.01)
*C07K 1/14* (2006.01)
*C07K 14/435* (2006.01)

(52) U.S. Cl.
CPC ........ *C07K 14/43586* (2013.01); *C07K 1/145* (2013.01); *C07K 1/34* (2013.01)

(58) Field of Classification Search
CPC ..... C07K 14/43586; C07K 1/145; C07K 1/34
USPC ........................................................ 8/115.51
See application file for complete search history.

(56) References Cited

U.S. PATENT DOCUMENTS 4,233,211 A 11/1980 Ohtomo
9,187,538 B2 11/2015 Altman
9,511,012 B2 12/2016 Altman
9,517,191 B2 12/2016 Altman
9,522,107 B2 12/2016 Altman
9,522,108 B2 12/2016 Altman
9,545,369 B2 1/2017 Altman
10,588,843 B2 3/2020 Altman
10,610,478 B2 4/2020 Altman
10,987,294 B2 4/2021 Altman
11,298,310 B2 4/2022 Altman
11,298,311 B2 4/2022 Altman
11,376,329 B2 7/2022 Kluge
11,857,663 B2 1/2024 Altman
11,857,664 B2 1/2024 Altman
12,024,538 B2 7/2024 Delisle et al.
2004/0005363 A1 1/2004 Tsukada
2004/0219630 A1 11/2004 Tsubouchi
2007/0297981 A1 12/2007 Ousler, III
2009/0286959 A1 11/2009 Lee et al.
2014/0235554 A1 8/2014 Lawrence
2015/0094267 A1 4/2015 Vandegriff
2016/0046679 A1 2/2016 Kluge et al.
2016/0095695 A1 4/2016 Altman
2016/0215103 A1 7/2016 Omenetto
2016/0331815 A1 11/2016 Lawrence
2021/0228684 A1 7/2021 Delisle

FOREIGN PATENT DOCUMENTS

CN 107041972 A * 8/2017 ............. A61L 31/02
KR 20170062028 A 6/2017
WO WO 03022909 A1 3/2003
WO 1431023 A * 7/2003 ............. A61L 15/32
WO WO 2010126640 A2 11/2010
WO WO-2011022771 A1 * 3/2011 ............... C07K 1/14
WO WO 2014012099 A1 1/2014
WO WO 2017123383 A2 7/2017
WO WO 2017139684 * 8/2017 ........... A61K 31/415
WO WO 2017139684 A1 8/2017
WO WO 2019094700 A1 5/2019
WO WO 2019094702 A1 5/2019

(Continued)

OTHER PUBLICATIONS https://www.waters.com/content/dam/waters/en/app-notes/2015/720005214/720005214-en.pdf Successful Transfer of Size-Exclusion Separations Between HPLC and UPLC, Koza, Feb. 2015.*

(Continued)

*Primary Examiner* — Amina S Khan

(74) *Attorney, Agent, or Firm* — Karen LeCuyer; DeWitt LLP

(57) ABSTRACT

Embodiments of the present disclosure include formulations of silk-based product (SBP) formulations and related methods of preparation and use in a variety of applications in the fields of human therapeutics, veterinary medicine, agriculture, and material science.

4 Claims, No Drawings

Specification includes a Sequence Listing.

(56) References Cited

FOREIGN PATENT DOCUMENTS

WO WO 2020247594 A1 12/2020

OTHER PUBLICATIONS

National Center for Biotechnology Information (2024). PubChem Compound Summary for CID 10340, Sodium Carbonate. Retrieved Aug. 30, 2024 from https://oubchem.ncbi.nim.nih.gov/compound/Sodium-Carbonate.
Cho et al., "Molecular weight distribution and solution properties of silk fibroins with different dissolution conditions", International Journal of Biological Macromolecules, 51 (2012) 336-341.
International Search Report and Written Opinion, dated Sep. 30, 2020, from PCT Application No. PCT/US2020/036073.
Pritchard and Kaplan, "Silk fibroin biomaterials for controlled release drug delivery", Expert Opin. Drug Deliv. 8(6): 797-811, 2011.
Pritchard et al., "Effect of Silk Protein Processing on Drug Delivery from Silk Films", Macromol Biosci., 3(3), 311-320 (2013).
Pritchard et al., "Incorporation of Proteinase Inhibitors into Silk-Based Delivery Devices for Enhanced Control of Degradation and Drug Release", Biomaterials 32(3): 909-918 (2011).
Rockwood et al., "Materials fabrication from Bombyx mori silk fibroin", Nature Protocols, 6(10), 2011, 1612-1631.
Sah et al., Regenerated Silk Fibroin from B. mori Silk Cocoon for Tissue Engineering Applications, Int. J. Sci. Dev. (2010) 1(5), pp. 404-408.
Fan et al. "Silk materials for medical, electronic and optical applications", Sci China Tech Sci, 62 (2019) 903-918.
Volkov et al., "On the routines of wild-type silk fibroin processing toward silk-inspired materials: A review", Macromol. Mater. Eng, 12 (2015) 1199-1216.
Wenk et al., "Silk fibroin as a vehicle for drug delivery applications", Journal of Controlled Release 150 (2011) 128-141.
Wray et al., "Effect of Processing on silk-based biomaterials: Reproducibility and Biocompatibility", J Biomed Mater Res Part B, 2011:99B:89-101.
Overcoming Viscosity Challenges in High Concentration Tangential Flow Filtration (TFF). Millipore Sigma. from https://www.sigmaaldrich.com/US/en/technical-documents/technical-article/pahrmaceutical-and-biopharmaceutical-manufacturing/downstream-processing/viscosity-reduction-tangential-flow-filtration.
Cole, Jane et al. Artificial Tears: What Matters and Why, Review of Optometry. Nov. 15, 2020. pp. 1-9.
Tran, Simon H. et al. A Review of the Emerging Role of Silk for the Treatment of the Eye, Pharm Res (2018) 35: 28, 1-16.

* cited by examiner

SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Sequence repeat -continued

```
<400> SEQUENCE: 1

Gly Ala Gly Ala Gly Ser
1               5
```

SILK-BASED PRODUCTS, FORMULATIONS, AND METHODS OF USE

CROSS REFERENCE TO RELATED APPLICATIONS

This application is a National Stage application of PCT/US2020/036073, filed Jun. 4, 2020, which claims the benefit of priority to U.S. Provisional Applications 62/856,936 filed Jun. 4, 2019, 62/893,834 filed Aug. 30, 2019, 62/893,836 filed Aug. 30, 2019, 62/926,855 filed Oct. 28, 2019, and 62/944,534 filed Dec. 6, 2019, all of which are incorporated by reference in their entirety herein.

SEQUENCE LISTING

The Instant Application contains a Sequence Listing which has been submitted electronically in ASCII format and is hereby incorporated by reference in its entirety. Said ASCII copy, created on Dec. 1, 2021 is named "Sequence List TXT file CBH0001US3_ST25" and is 823 bytes in size.

FIELD OF THE DISCLOSURE

The present disclosure relates to formulations and methods. Specifically provided are silk-based product formulations.

BACKGROUND OF THE DISCLOSURE

Silk is a naturally occurring polymer. Most silk fibers are derived from silkworm moth (*Bombyx mori*) cocoons and include silk fibroin and sericin proteins. Silk fibroin is a fibrous material that forms a polymeric matrix bonded together with sericin. In nature, silk is formed from a concentrated solution of these proteins that are extruded through silkworm spinnerets to produce a highly insoluble fiber. These fibers have been used for centuries to form threads used in garments and other textiles.

Many properties of silk make it an attractive candidate for products serving a variety of industries. Polymer strength and flexibility has supported classical uses of silk in textiles and materials, while silk biocompatibility has gained attention more recently for applications in the fields of medicine and agriculture. Additional uses for silk in applications related to material science are being explored as technologies for producing and processing silk advance.

Although a variety of products and uses related to silk are being developed, there remains a need for methods of producing and processing silk and silk-based products that can meet the demands of modern medicine. Additionally, there remains a need for silk-based products that can leverage silk polymer strength, flexibility, and biocompatibility to meet needs in the fields of medicine, agriculture, and material sciences. The present disclosure addresses these needs by providing methods for producing and processing silk as well as formulations of silk-based products useful in a variety of industries.

SUMMARY OF THE DISCLOSURE

In some embodiments, the present disclosure provides silk-based product (SBP) formulations that comprise processed silk and at least one excipient, wherein the processed silk comprises or is derived from one or more articles, said one or more articles is selected from the group consisting of raw silk, silk fiber, silk fibroin, and a silk fibroin fragment.

The SBP formulation may comprises or may be combined with one or more members selected from the group consisting of: (a) a therapeutic agent; (b) a cargo; (c) a microorganism; and (d) a biological system.

The processed silk and/or other SBP component (excipient, therapeutic agent, microbe, cargo, and/or biological system) may be present in SBP formulations at a concentration (by weight, volume, or concentration) of from about 0.0001% to about 0.001%, from about 0.001% to about 0.01%, from about 0.01% to about 1%, from about 0.05% to about 2%, from about 1% to about 5%, from about 2% to about 10%, from about 4% to about 16%, from about 5% to about 20%, from about 8% to about 24%, from about 10% to about 30%, from about 12% to about 32%, from about 14% to about 34%, from about 16% to about 36%, from about 18% to about 38%, from about 20% to about 40%, from about 22% to about 42%, from about 24% to about 44%, from about 26% to about 46%, from about 28% to about 48%, from about 30% to about 50%, from about 35% to about 55%, from about 40% to about 60%, from about 45% to about 65%, from about 50% to about 70%, from about 55% to about 75%, from about 60% to about 80%, from about 65% to about 85%, from about 70% to about 90%, from about 75% to about 95%, from about 80% to about 96%, from about 85% to about 97%, from about 90% to about 98%, from about 95% to about 99%, from about 96% to about 99.2%, from about 97% to about 99.5%, from about 98% to about 99.8%, from about 99% to about 99.9%, or greater than 99.9%.

The SBP formulation may have processed silk and/or other SBP components (excipient, therapeutic agent, microbe, cargo, and/or biological system) present at a concentration of from about 0.01 pg/mL to about 1 pg/mL, from about 0.05 pg/mL to about 2 pg/mL, from about 1 pg/mL to about 5 pg/mL, from about 2 pg/mL to about 10 pg/mL, from about 4 pg/mL to about 16 pg/mL, from about 5 pg/mL to about 20 pg/mL, from about 8 pg/mL to about 24 pg/mL, from about 10 pg/mL to about 30 pg/mL, from about 12 pg/mL to about 32 pg/mL, from about 14 pg/mL to about 34 pg/mL, from about 16 pg/mL to about 36 pg/mL, from about 18 pg/mL to about 38 pg/mL, from about 20 pg/mL to about 40 pg/mL, from about 22 pg/mL to about 42 pg/mL, from about 24 pg/mL to about 44 pg/mL, from about 26 pg/mL to about 46 pg/mL, from about 28 pg/mL to about 48 pg/mL, from about 30 pg/mL to about 50 pg/mL, from about 35 pg/mL to about 55 pg/mL, from about 40 pg/mL to about 60 pg/mL, from about 45 pg/mL to about 65 pg/mL, from about 50 pg/mL to about 75 pg/mL, from about 60 pg/mL to about 240 pg/mL, from about 70 pg/mL to about 350 pg/mL, from about 80 pg/mL to about 400 pg/mL, from about 90 pg/mL to about 450 pg/mL, from about 100 pg/mL to about 500 pg/mL, from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 μg/mL to about 1 μg/mL, from about 0.05 μg/mL to about 2 μg/mL, from about 1 pg/mL to about 5 μg/mL, from about 2 μg/mL to about 10 μg/mL, from about 4 μg/mL to about 16 pg/mL, from about 5 μg/mL to about 20 μg/mL, from about 8 μg/mL to about 24 μg/mL, from about 10 μg/mL to about 30 μg/mL, from about 12 μg/mL to about 32 μg/mL, from about 14 μg/mL to about 34 μg/mL, from about 16 μg/mL to about 36 μg/mL, from about 18 μg/mL to about 38 μg/mL, from about 20 μg/mL to about 40 μg/mL, from about 22 μg/mL to about 42 μg/mL, from about 24 μg/mL to about 44 μg/mL, from about 26 μg/mL to about 46 μg/mL, from about 28 μg/mL to about 48 μg/mL, from about 30 μg/mL to about 50 μg/mL, from about 35 μg/mL to about 55 μg/mL, from about 40 μg/mL to about 60 μg/mL, from about 45 μg/mL to about 65 μg/mL, from about 50 μg/mL to about 75 μg/mL, from about 60 μg/mL to about 240 g/mL, from about 70 μg/mL to about 350 μg/mL, from about 80 μg/mL to about 400 μg/mL, from about 90 μg/mL to about 450 μg/mL, from about 100 μg/mL to about 500 g/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 1 g/mL to about 5 g/mL, from about 2 g/mL to about 10 g/mL, from about 4 g/mL to about 16 g/mL, or from about 5 g/mL to about 20 g/mL.

The SBP formulation may have processed silk and/or other SBP components (excipient, therapeutic agent, microbe, cargo, and/or biological system) present in SBPs at a concentration of from about 0.01 pg/kg to about 1 pg/kg, from about 0.05 pg/kg to about 2 pg/kg, from about 1 pg/kg to about 5 pg/kg, from about 2 pg/kg to about 10 pg/kg, from about 4 pg/kg to about 16 pg/kg, from about 5 pg/kg to about 20 pg/kg, from about 8 pg/kg to about 24 pg/kg, from about 10 pg/kg to about 30 pg/kg, from about 12 pg/kg to about 32 pg/kg, from about 14 pg/kg to about 34 pg/kg, from about 16 pg/kg to about 36 pg/kg, from about 18 pg/kg to about 38 pg/kg, from about 20 pg/kg to about 40 pg/kg, from about 22 pg/kg to about 42 pg/kg, from about 24 pg/kg to about 44 pg/kg, from about 26 pg/kg to about 46 pg/kg, from about 28 pg/kg to about 48 pg/kg, from about 30 pg/kg to about 50 pg/kg, from about 35 pg/kg to about 55 pg/kg, from about 40 pg/kg to about 60 pg/kg, from about 45 pg/kg to about 65 pg/kg, from about 50 pg/kg to about 75 pg/kg, from about 60 pg/kg to about 240 pg/kg, from about 70 pg/kg to about 350 pg/kg, from about 80 pg/kg to about 400 pg/kg, from about 90 pg/kg to about 450 pg/kg, from about 100 pg/kg to about 500 pg/kg, from about 0.01 ng/kg to about 1 ng/kg, from about 0.05 ng/kg to about 2 ng/kg, from about 1 ng/kg to about 5 ng/kg, from about 2 ng/kg to about 10 ng/kg, from about 4 ng/kg to about 16 ng/kg, from about 5 ng/kg to about 20 ng/kg, from about 8 ng/kg to about 24 ng/kg, from about 10 ng/kg to about 30 ng/kg, from about 12 ng/kg to about 32 ng/kg, from about 14 ng/kg to about 34 ng/kg, from about 16 ng/kg to about 36 ng/kg, from about 18 ng/kg to about 38 ng/kg, from about 20 ng/kg to about 40 ng/kg, from about 22 ng/kg to about 42 ng/kg, from about 24 ng/kg to about 44 ng/kg, from about 26 ng/kg to about 46 ng/kg, from about 28 ng/kg to about 48 ng/kg, from about 30 ng/kg to about 50 ng/kg, from about 35 ng/kg to about 55 ng/kg, from about 40 ng/kg to about 60 ng/kg, from about 45 ng/kg to about 65 ng/kg, from about 50 ng/kg to about 75 ng/kg, from about 60 ng/kg to about 240 ng/kg, from about 70 ng/kg to about 350 ng/kg, from about 80 ng/kg to about 400 ng/kg, from about 90 ng/kg to about 450 ng/kg, from about 100 ng/kg to about 500 ng/kg, from about 0.01 μg/kg to about 1 μg/kg, from about 0.05 μg/kg to about 2 μg/kg, from about 1 μg/kg to about 5 jug/kg, from about 2 μg/kg to about 10 μg/kg, from about 4 μg/kg to about 16 μg/kg, from about 5 μg/kg to about 20 μg/kg, from about 8 μg/kg to about 24 jug/kg, from about 10 μg/kg to about 30 μg/kg, from about 12 μg/kg to about 32 μg/kg, from about 14 μg/kg to about 34 μg/kg, from about 16 μg/kg to about 36 μg/kg, from about 18 μg/kg to about 38 μg/kg, from about 20 μg/kg to about 40 μg/kg, from about 22 μg/kg to about 42 μg/kg, from about 24 μg/kg to about 44 μg/kg, from about 26 μg/kg to about 46 μg/kg, from about 28 μg/kg to about 48 μg/kg, from about 30 μg/kg to about 50 μg/kg, from about 35 μg/kg to about 55 μg/kg, from about 40 μg/kg to about 60 μg/kg, from about 45 μg/kg to about 65 μg/kg, from about 50 μg/kg to about 75 μg/kg, from about 60 μg/kg to about 240 μg/kg, from about 70 μg/kg to about 350 μg/kg, from about 80 μg/kg to about 400 μg/kg, from about 90 μg/kg to about 450 μg/kg, from about 100 μg/kg to about 500 μg/kg, from about 0.01 mg/kg to about 1 mg/kg, from about 0.05 mg/kg to about 2 mg/kg, from about 1 mg/kg to about 5 mg/kg, from about 2 mg/kg to about 10 mg/kg, from about 4 mg/kg to about 16 mg/kg, from about 5 mg/kg to about 20 mg/kg, from about 8 mg/kg to about 24 mg/kg, from about 10 mg/kg to about 30 mg/kg, from about 12 mg/kg to about 32 mg/kg, from about 14 mg/kg to about 34 mg/kg, from about 16 mg/kg to about 36 mg/kg, from about 18 mg/kg to about 38 mg/kg, from about 20 mg/kg to about 40 mg/kg, from about 22 mg/kg to about 42 mg/kg, from about 24 mg/kg to about 44 mg/kg, from about 26 mg/kg to about 46 mg/kg, from about 28 mg/kg to about 48 mg/kg, from about 30 mg/kg to about 50 mg/kg, from about 35 mg/kg to about 55 mg/kg, from about 40 mg/kg to about 60 mg/kg, from about 45 mg/kg to about 65 mg/kg, from about 50 mg/kg to about 75 mg/kg, from about 60 mg/kg to about 240 mg/kg, from about 70 mg/kg to about 350 mg/kg, from about 80 mg/kg to about 400 mg/kg, from about 90 mg/kg to about 450 mg/kg, from about 100 mg/kg to about 500 mg/kg, from about 0.01 g/kg to about 1 g/kg, from about 0.05 g/kg to about 2 g/kg, from about 1 g/kg to about 5 g/kg, from about 2 g/kg to about 10 g/kg, from about 4 g/kg to about 16 g/kg, or from about 5 g/kg to about 20 g/kg, from about 10 g/kg to about 50 g/kg, from about 15 g/kg to about 100 g/kg, from about 20 g/kg to about 150 g/kg, from about 25 g/kg to about 200 g/kg, from about 30 g/kg to about 250 g/kg, from about 35 g/kg to about 300 g/kg, from about 40 g/kg to about 350 g/kg, from about 45 g/kg to about 400 g/kg, from about 50 g/kg to about 450 g/kg, from about 55 g/kg to about 500 g/kg, from about 60 g/kg to about 550 g/kg, from about 65 g/kg to about 600 g/kg, from about 70 g/kg to about 650 g/kg, from about 75 g/kg to about 700 g/kg, from about 80 g/kg to about 750 g/kg, from about 85 g/kg to about 800 g/kg, from about 90 g/kg to about 850 g/kg, from about 95 g/kg to about 900 g/kg, from about 100 g/kg to about 950 g/kg, or from about 200 g/kg to about 1000 g/kg.

The SBP formulation may comprise processed silk and/or other SBP components (excipient, therapeutic agent, microbe, cargo, and/or biological system) present in SBPs at a concentration of from about 0.1 pM to about 1 pM, from about 1 pM to about 10 pM, from about 2 pM to about 20 pM, from about 3 pM to about 30 pM, from about 4 pM to about 40 pM, from about 5 pM to about 50 pM, from about 6 pM to about 60 pM, from about 7 pM to about 70 pM, from about 8 pM to about 80 pM, from about 9 pM to about 90 pM, from about 10 pM to about 100 pM, from about 11 pM to about 110 pM, from about 12 pM to about 120 pM, from about 13 pM to about 130 pM, from about 14 pM to about 140 pM, from about 15 pM to about 150 pM, from about 16 pM to about 160 pM, from about 17 pM to about 170 pM, from about 18 pM to about 180 pM, from about 19 pM to about 190 pM, from about 20 pM to about 200 pM, from about 21 pM to about 210 pM, from about 22 pM to about 220 pM, from about 23 pM to about 230 pM, from about 24 pM to about 240 pM, from about 25 pM to about 250 pM, from about 26 pM to about 260 pM, from about 27 pM to about 270 pM, from about 28 pM to about 280 pM, from about 29 pM to about 290 pM, from about 30 pM to about 300 pM, from about 31 pM to about 310 pM, from about 32 pM to about 320 pM, from about 33 pM to about 330 pM, from about 34 pM to about 340 pM, from about 35 pM to about 350 pM, from about 36 pM to about 360 pM, from about 37 pM to about 370 pM, from about 38 pM to about 380 pM, from about 39 pM to about 390 pM, from about 40 pM to about 400 pM, from about 41 pM to about 410 pM, from about 42 pM to about 420 pM, from about 43 pM to about 430 pM, from about 44 pM to about 440 pM, from about 45 pM to about 450 pM, from about 46 pM to about 460 pM, from about 47 pM to about 470 pM, from about 48 pM to about 480 pM, from about 49 pM to about 490 pM, from about 50 pM to about 500 pM, from about 51 pM to about 510 pM, from about 52 pM to about 520 pM, from about 53 pM to about 530 pM, from about 54 pM to about 540 pM, from about 55 pM to about 550 pM, from about 56 pM to about 560 pM, from about 57 pM to about 570 pM, from about 58 pM to about 580 pM, from about 59 pM to about 590 pM, from about 60 pM to about 600 pM, from about 61 pM to about 610 pM, from about 62 pM to about 620 pM, from about 63 pM to about 630 pM, from about 64 pM to about 640 pM, from about 65 pM to about 650 pM, from about 66 pM to about 660 pM, from about 67 pM to about 670 pM, from about 68 pM to about 680 pM, from about 69 pM to about 690 pM, from about 70 pM to about 700 pM, from about 71 pM to about 710 pM, from about 72 pM to about 720 pM, from about 73 pM to about 730 pM, from about 74 pM to about 740 pM, from about 75 pM to about 750 pM, from about 76 pM to about 760 pM, from about 77 pM to about 770 pM, from about 78 pM to about 780 pM, from about 79 pM to about 790 pM, from about 80 pM to about 800 pM, from about 81 pM to about 810 pM, from about 82 pM to about 820 pM, from about 83 pM to about 830 pM, from about 84 pM to about 840 pM, from about 85 pM to about 850 pM, from about 86 pM to about 860 pM, from about 87 pM to about 870 pM, from about 88 pM to about 880 pM, from about 89 pM to about 890 pM, from about 90 pM to about 900 pM, from about 91 pM to about 910 pM, from about 92 pM to about 920 pM, from about 93 pM to about 930 pM, from about 94 pM to about 940 pM, from about 95 pM to about 950 pM, from about 96 pM to about 960 pM, from about 97 pM to about 970 pM, from about 98 pM to about 980 pM, from about 99 pM to about 990 pM, from about 100 pM to about 1 nM, from about 0.1 nM to about 1 nM, from about 1 nM to about 10 nM, from about 2 nM to about 20 nM, from about 3 nM to about 30 nM, from about 4 nM to about 40 nM, from about 5 nM to about 50 nM, from about 6 nM to about 60 nM, from about 7 nM to about 70 nM, from about 8 nM to about 80 nM, from about 9 nM to about 90 nM, from about 10 nM to about 100 nM, from about 11 nM to about 110 nM, from about 12 nM to about 120 nM, from about 13 nM to about 130 nM, from about 14 nM to about 140 nM, from about 15 nM to about 150 nM, from about 16 nM to about 160 nM, from about 17 nM to about 170 nM, from about 18 nM to about 180 nM, from about 19 nM to about 190 nM, from about 20 nM to about 200 nM, from about 21 nM to about 210 nM, from about 22 nM to about 220 nM, from about 23 nM to about 230 nM, from about 24 nM to about 240 nM, from about 25 nM to about 250 nM, from about 26 nM to about 260 nM, from about 27 nM to about 270 nM, from about 28 nM to about 280 nM, from about 29 nM to about 290 nM, from about 30 nM to about 300 nM, from about 31 nM to about 310 nM, from about 32 nM to about 320 nM, from about 33 nM to about 330 nM, from about 34 nM to about 340 nM, from about 35 nM to about 350 nM, from about 36 nM to about 360 nM, from about 37 nM to about 370 nM, from about 38 nM to about 380 nM, from about 39 nM to about 390 nM, from about 40 nM to about 400 nM, from about 41 nM to about 410 nM, from about 42 nM to about 420 nM, from about 43 nM to about 430 nM, from about 44 nM to about 440 nM, from about 45 nM to about 450 nM, from about 46 nM to about 460 nM, from about 47 nM to about 470 nM, from about 48 nM to about 480 nM, from about 49 nM to about 490 nM, from about 50 nM to about 500 nM, from about 51 nM to about 510 nM, from about 52 nM to about 520 nM, from about 53 nM to about 530 nM, from about 54 nM to about 540 nM, from about 55 nM to about 550 nM, from about 56 nM to about 560 nM, from about 57 nM to about 570 nM, from about 58 nM to about 580 nM, from about 59 nM to about 590 nM, from about 60 nM to about 600 nM, from about 61 nM to about 610 nM, from about 62 nM to about 620 nM, from about 63 nM to about 630 nM, from about 64 nM to about 640 nM, from about 65 nM to about 650 nM, from about 66 nM to about 660 nM, from about 67 nM to about 670 nM, from about 68 nM to about 680 nM, from about 69 nM to about 690 nM, from about 70 nM to about 700 nM, from about 71 nM to about 710 nM, from about 72 nM to about 720 nM, from about 73 nM to about 730 nM, from about 74 nM to about 740 nM, from about 75 nM to about 750 nM, from about 76 nM to about 760 nM, from about 77 nM to about 770 nM, from about 78 nM to about 780 nM, from about 79 nM to about 790 nM, from about 80 nM to about 800 nM, from about 81 nM to about 810 nM, from about 82 nM to about 820 nM, from about 83 nM to about 830 nM, from about 84 nM to about 840 nM, from about 85 nM to about 850 nM, from about 86 nM to about 860 nM, from about 87 nM to about 870 nM, from about 88 nM to about 880 nM, from about 89 nM to about 890 nM, from about 90 nM to about 900 nM, from about 91 nM to about 910 nM, from about 92 nM to about 920 nM, from about 93 nM to about 930 nM, from about 94 nM to about 940 nM, from about 95 nM to about 950 nM, from about 96 nM to about 960 nM, from about 97 nM to about 970 nM, from about 98 nM to about 980 nM, from about 99 nM to about 990 nM, from about 100 nM to about 1 pM, from about 0.1 μM to about 1 μM, from about 1 μM to about 10 μM, from about 2 μM to about 20 μM, from about 3 μM to about 30 μM, from about 4 μM to about 40 μM, from about 5 μM to about 50 μM, from about 6 μM to about 60 μM, from about 7 μM to about 70 μM, from about 8 μM to about 80 μM, from about 9 μM to about 90 μM, from about 10 μM to about 100 μM, from about 11 μM to about 110 μM, from about 12 μM to about 120 μM, from about 13 μM to about 130 μM, from about 14 μM to about 140 μM, from about 15 μM to about 150 μM, from about 16 μM to about 160 μM, from about 17 μM to about 170 μM, from about 18 μM to about 180 μM, from about 19 μM to about 190 μM, from about 20 μM to about 200 μM, from about 21 μM to about 210 μM, from about 22 μM to about 220 μM, from about 23 μM to about 230 μM, from about 24 μM to about 240 μM, from about 25 μM to about 250 μM, from about 26 μM to about 260 μM, from about 27 μM to about 270 μM, from about 28 μM to about 280 μM, from about 29 μM to about 290 μM, from about 30 μM to about 300 μM, from about 31 μM to about 310 μM, from about 32 μM to about 320 μM, from about 33 μM to about 330 μM, from about 34 μM to about 340 μM, from about 35 μM to about 350 μM, from about 36 μM to about 360 μM, from about 37 μM to about 370 μM, from about 38 μM to about 380 μM, from about 39 μM to about 390 μM, from about 40 μM to about 400 μM, from about 41 μM to about 410 μM, from about 42 μM to about 420 μM, from about 43 μM to about 430 μM, from about 44 μM to about 440 μM, from about 45 μM to about 450 μM, from about 46 μM to about 460 μM, from about 47 μM to about 470 μM, from about 48 μM to about 480 μM, from about 49 μM to about 490 μM, from about 50 μM to about 500 μM, from about 51 μM to about 510 μM, from about 52 μM to about 520 μM, from about 53 μM to about 530 μM, from about 54 μM to about 540 μM, from about 55 μM to about 550 μM, from about 56 μM to about 560 μM, from about 57 μM to about 570 μM, from about 58 μM to about 580 μM, from about 59 μM to about 590 μM, from about 60 μM to about 600 μM, from about 61 μM to about 610 μM, from about 62 μM to about 620 μM, from about 63 μM to about 630 μM, from about 64 μM to about 640 μM, from about 65 μM to about 650 μM, from about 66 μM to about 660 μM, from about 67 μM to about 670 μM, from about 68 μM to about 680 μM, from about 69 μM to about 690 μM, from about 70 μM to about 700 μM, from about 71 μM to about 710 μM, from about 72 μM to about 720 μM, from about 73 μM to about 730 μM, from about 74 μM to about 740 μM, from about 75 μM to about 750 μM, from about 76 μM to about 760 μM, from about 77 μM to about 770 μM, from about 78 μM to about 780 μM, from about 79 μM to about 790 μM, from about 80 μM to about 800 μM, from about 81 μM to about 810 μM, from about 82 μM to about 820 μM, from about 83 μM to about 830 μM, from about 84 μM to about 840 μM, from about 85 μM to about 850 μM, from about 86 μM to about 860 μM, from about 87 μM to about 870 μM, from about 88 μM to about 880 μM, from about 89 μM to about 890 μM, from about 90 μM to about 900 μM, from about 91 μM to about 910 μM, from about 92 μM to about 920 μM, from about 93 μM to about 930 μM, from about 94 μM to about 940 μM, from about 95 μM to about 950 μM, from about 96 μM to about 960 μM, from about 97 μM to about 970 μM, from about 98 μM to about 980 μM, from about 99 μM to about 990 μM, from about 100 μM to about 1 mM, from about 0.1 mM to about 1 mM, from about 1 mM to about 10 mM, from about 2 mM to about 20 mM, from about 3 mM to about 30 mM, from about 4 mM to about 40 mM, from about 5 mM to about 50 mM, from about 6 mM to about 60 mM, from about 7 mM to about 70 mM, from about 8 mM to about 80 mM, from about 9 mM to about 90 mM, from about 10 mM to about 100 mM, from about 11 mM to about 110 mM, from about 12 mM to about 120 mM, from about 13 mM to about 130 mM, from about 14 mM to about 140 mM, from about 15 mM to about 150 mM, from about 16 mM to about 160 mM, from about 17 mM to about 170 mM, from about 18 mM to about 180 mM, from about 19 mM to about 190 mM, from about 20 mM to about 200 mM, from about 21 mM to about 210 mM, from about 22 mM to about 220 mM, from about 23 mM to about 230 mM, from about 24 mM to about 240 mM, from about 25 mM to about 250 mM, from about 26 mM to about 260 mM, from about 27 mM to about 270 mM, from about 28 mM to about 280 mM, from about 29 mM to about 290 mM, from about 30 mM to about 300 mM, from about 31 mM to about 310 mM, from about 32 mM to about 320 mM, from about 33 mM to about 330 mM, from about 34 mM to about 340 mM, from about 35 mM to about 350 mM, from about 36 mM to about 360 mM, from about 37 mM to about 370 mM, from about 38 mM to about 380 mM, from about 39 mM to about 390 mM, from about 40 mM to about 400 mM, from about 41 mM to about 410 mM, from about 42 mM to about 420 mM, from about 43 mM to about 430 mM, from about 44 mM to about 440 mM, from about 45 mM to about 450 mM, from about 46 mM to about 460 mM, from about 47 mM to about 470 mM, from about 48 mM to about 480 mM, from about 49 mM to about 490 mM, from about 50 mM to about 500 mM, from about 51 mM to about 510 mM, from about 52 mM to about 520 mM, from about 53 mM to about 530 mM, from about 54 mM to about 540 mM, from about 55 mM to about 550 mM, from about 56 mM to about 560 mM, from about 57 mM to about 570 mM, from about 58 mM to about 580 mM, from about 59 mM to about 590 mM, from about 60 mM to about 600 mM, from about 61 mM to about 610 mM, from about 62 mM to about 620 mM, from about 63 mM to about 630 mM, from about 64 mM to about 640 mM, from about 65 mM to about 650 mM, from about 66 mM to about 660 mM, from about 67 mM to about 670 mM, from about 68 mM to about 680 mM, from about 69 mM to about 690 mM, from about 70 mM to about 700 mM, from about 71 mM to about 710 mM, from about 72 mM to about 720 mM, from about 73 mM to about 730 mM, from about 74 mM to about 740 mM, from about 75 mM to about 750 mM, from about 76 mM to about 760 mM, from about 77 mM to about 770 mM, from about 78 mM to about 780 mM, from about 79 mM to about 790 mM, from about 80 mM to about 800 mM, from about 81 mM to about 810 mM, from about 82 mM to about 820 mM, from about 83 mM to about 830 mM, from about 84 mM to about 840 mM, from about 85 mM to about 850 mM, from about 86 mM to about 860 mM, from about 87 mM to about 870 mM, from about 88 mM to about 880 mM, from about 89 mM to about 890 mM, from about 90 mM to about 900 mM, from about 91 mM to about 910 mM, from about 92 mM to about 920 mM, from about 93 mM to about 930 mM, from about 94 mM to about 940 mM, from about 95 mM to about 950 mM, from about 96 mM to about 960 mM, from about 97 mM to about 970 mM, from about 98 mM to about 980 mM, from about 99 mM to about 990 mM, from about 100 mM to about 1 μM, from about 1 M to about 10 μM, from about 2 μM to about 20 μM, from about 3 μM to about 30 μM, from about 4 μM to about 40 M, from about 5 μM to about 50 μM, from about 6 μM to about 60 μM, from about 7 μM to about 70 μM, from about 8 μM to about 80 μM, from about 9 μM to about 90 μM, from about 10 μM to about 100 μM, from about 11 M to about 110 μM, from about 12 μM to about 120 μM, from about 13 μM to about 130 μM, from about 14 M to about 140 μM, from about 15 μM to about 150 μM, from about 16 μM to about 160 μM, from about 17 μM to about 170 μM, from about 18 μM to about 180 μM, from about 19 μM to about 190 μM, from about 20 μM to about 200 μM, from about 21 μM to about 210 μM, from about 22 μM to about 220 μM, from about 23 μM to about 230 μM, from about 24 μM to about 240 μM, from about 25 μM to about 250 μM, from about 26 μM to about 260 μM, from about 27 M to about 270 μM, from about 28 μM to about 280 μM, from about 29 μM to about 290 μM, from about 30 M to about 300 μM, from about 31 μM to about 310 μM, from about 32 μM to about 320 μM, from about 33 M to about 330 μM, from about 34 μM to about 340 μM, from about 35 μM to about 350 μM, from about 36 μM to about 360 μM, from about 37 μM to about 370 μM, from about 38 μM to about 380 μM, from about 39 μM to about 390 μM, from about 40 μM to about 400 μM, from about 41 μM to about 410 μM, from about 42 μM to about 420 μM, from about 43 μM to about 430 μM, from about 44 μM to about 440 μM, from about 45 μM to about 450 μM, from about 46 M to about 460 μM, from about 47 μM to about 470 μM, from about 48 μM to about 480 μM, from about 49 M to about 490 μM, or from about 50 μM to about 500 M.

The processed silk of the SBP formulation may comprise silk fibroin, wherein the silk fibroin comprises a beta-sheet, an alpha-helix, a coiled coil, and/or a random coil. Silk fibroin may comprise a silk fibroin polymer, a silk fibroin monomer, and/or a silk fibroin fragment. The processed silk may comprise a silk fibroin fragment, wherein the silk fibroin fragment comprises a silk fibroin heavy chain fragment and/or a silk fibroin light chain fragment. The processed silk may comprise silk fibroin, wherein the silk fibroin comprises a plurality of silk fibroin fragments. The plurality of silk fibroin fragments may comprise a molecular weight of from about 1 kDa to about 350 kDa.

The SBP may comprise one or more formats selected from the group consisting of adhesives, capsules, cakes, coatings, cocoons, combs, cones, cylinders, discs, emulsions, fibers, films, foams, gels, grafts, hydrogels, implants, mats, membranes, microspheres, nanofibers, nanoparticles, nanospheres, nets, organogels, particles, patches, powders, rods, scaffolds, sheets, solids, solutions, sponges, sprays, spuns, suspensions, tablets, threads, tubes, vapors, and yarns. The format may be a solution. The format may be a hydrogel. The format may be a cake. The format may be a powder. The format may be a film.

The processed silk of the SBP formulation may comprise silk fibroin at a concentration between 0.5% and 5%. In one aspect, the silk fibroin is present at a concentration of 0.5%. In one aspect, the silk fibroin is present at a concentration of 1%. In one aspect, the silk fibroin is present at a concentration of 2.5%. In one aspect, the silk fibroin is present at a concentration of 3%. In one aspect, the silk fibroin is present at a concentration of 5%.

The SBP formulation is in a solution which may be, but is not limited to, phosphate buffer, borate buffer, and phosphate buffered saline. The solution may further comprise propylene glycol, sucrose and/or trehalose. Propylene glycol may be present in a concentration of 1%. Sucrose may be present in a concentration such as, but not limited to, 10 mM, 50 mM, 100 mM and 150 mM. Trehalose may be present in a concentration such as, but not limited to, 10 mM, 50 mM, 100 mM and 150 mM.

In some embodiments, the present disclosure provides a silk-based product (SBP) for ocular lubrication that includes processed silk and an ocular therapeutic agent. The processed silk may be silk fibroin. The SBP may include from about 0.0001% to about 35% (w/v) of silk fibroin. The silk fibroin may be prepared by degumming for a time of a 30-minute boil, a 60-minute boil, a 90-minute boil, a 120-minute boil, and a 480-minute boil. The SBP may be stressed. The SBP may be stressed by one or more methods which includes heating the SBP to 60° C. and autoclaving the SBP. The SBP may include one or more excipients. The one or more excipients may include one or more of sucrose, lactose, phosphate salts, sodium chloride, potassium phosphate monobasic, potassium phosphate dibasic, sodium phosphate dibasic, sodium phosphate monobasic, polysorbate 80, phosphate buffer, phosphate buffered saline, sodium hydroxide, sorbitol, mannitol, lactose USP, Starch 1500, microcrystalline cellulose, potassium chloride, sodium borate, boric acid, sodium borate decahydrate, magnesium chloride hexahydrate, calcium chloride dihydrate, sodium hydroxide, Avicel, dibasic calcium phosphate dehydrate, tartaric acid, citric acid, fumaric acid, succinic acid, malic acid, hydrochloric acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, trehalose, and sodium carboxymethylcellulose. One or more of the excipients may include phosphate buffer. One or more of the excipients may include phosphate buffered saline. One or more of the excipients may include sucrose. The excipients may include boric acid, sodium borate decahydrate, sodium chloride, potassium chloride, magnesium chloride hexahydrate, calcium chloride dihydrate, sodium hydroxide, and hydrochloric acid. The SBP may include at least one excipient selected from one or more members of the group consisting of sorbitol, triethylamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol, glycerol EL (cremophor EL), cremophor RH 40, cremophor RH 60, dalpha-tocopherol, PEG 1000 succinate, polysorbate 20, polysorbate 80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, medium chain triglycerides of coconut oil, medium chain triglycerides of palm seed oil, beeswax, d-alpha-tocopherol, oleic acid, medium-chain mono-glycerides, medium-chain di-glycerides, alpha-cyclodextrin, betacyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alpha-dimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), polyoxyl 8 stearate (PEG 400 monosterate), polysorbate 20, polysorbate 80, polyvinyl pyrrolidone, propylene carbonate, propylene glycol, solutol HS15, sorbitan monooleate (Span 20), sulfobutylether-beta-cyclodextrin, transcutol, triacetin, I-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, glycerin, and PEG 4 kDa. The SBP may be formulated, and the formulation may be as hydrogels and solutions. The formulation may be a hydrogel. The formulation may be a solution. The silk fibroin concentration in the solution may be below 1% (w/v). The SBP may be a solution, and the SBP may be stressed. The SBP may be a hydrogel, and the SBP may be stressed. The SBP may be a solution, and the solution may shear thin. The solutions may have the viscosity of a gel at a lower shear rate. The solutions may have the viscosity of a fluid at higher shear rates. The ocular therapeutic agent may be a nonsteroidal anti-inflammatory drug (NSAID) or protein. The SBP may be formulated for topical administration. The SBP may be formulated for ocular administration. The SBP may be biocompatible. The SBP may include any of the samples listed in any of the Tables 1-4.

In some embodiments, the present disclosure provides a method of preparing the SBP formulations comprising: (a) preparing the processed silk, wherein the processed silk comprises or is derived from one or more articles selected from the group consisting of raw silk, silk fiber, silk fibroin, and a silk fibroin fragment; and (b) preparing the SBP formulation using the processed silk. In some embodiments, the present disclosure provides a method of treating an ocular indication of a subject that includes administering to the subject any of the SBPs described herein. The ocular indication may be dry eye disease. The SBP may be administered to the eye. The SBP may be administered via topical administration. The topical administration of SBP may be as drops or sprays. The SBP may shear thin. The shear thinning of the SBPs may tune the residence time in the eye. The residence time of the SBP may be increased.

DETAILED DESCRIPTION OF THE DISCLOSURE

Embodiments of the present disclosure relate to silk-based products (SBPs), formulations and their methods of use. The term "silk" generally refers to a fibrous material formed by insects and some other species that includes tightly bonded protein filaments. Herein, the term "silk" is used in the broadest sense and may embrace any forms, variants, or derivatives of silk discussed.

Silk fibers from silkworm moth (*Bombyx mori*) cocoons include two main components, sericin (usually present in a range of 20-30%) and silk fibroin (usually present in a range of 70-80%). Structurally, silk fibroin forms the center of the silk fibers and sericin acts as the gum coating the fibers. Sericin is a gelatinous protein that holds silk fibers together with many of the characteristic properties of silk (see Qi et al. (2017) Int J Mol Sci 18:237 and Deptuch et al. (2017) Materials 10:1417, the contents of each of which are herein incorporated by reference in their entireties). Silk fibroin is an insoluble fibrous protein consisting of layers of antiparallel beta sheets. Its primary structure mainly consists of recurrent serine, alanine, and glycine repeating units. The isoelectric point of silk fibroin has been determined to be around 4.2. Silk fibroin monomers include a complex of heavy chain (around 350 kDa) and light chain (around 25 kDa) protein components. Typically, the chains are joined by a disulfide bond. With some forms, heavy chain and light chain segments are non-covalently bound to a glycoprotein, p25. Polymers of silk fibroin monomers may form through hydrogen bonding between monomers, typically increasing mechanical strength (see Qi et al. (2017) Int J Mol Sci 18:237). During silk processing, fragments of silk fibroin monomers may be produced, including, but not limited to, fragments of heavy and/or light chains. These fragments may retain the ability to form hydrogen bonds with silk fibroin monomers and fragments thereof. Herein, the term "silk fibroin" is used in its broadest sense and embraces silk fibroin polymers, silk fibroin monomers, silk fibroin heavy and light chains, silk fibroin fragments, and variants, derivatives, or mixtures thereof from any of the wild type, genetically modified, or synthetic sources of silk described herein.

The present disclosure includes methods of preparing processed silk and SBPs, different forms of SBP formulations, and a variety of applications for utilizing processed silk, SBPs, and SBP formulations alone or in combination with various compounds, compositions, and devices.

I. Silk-Based Products and Formulations

As used herein, the term "silk-based product" or "SBP" refers to any compound, mixture, or other entity that is made up of or that is combined with processed silk. "Processed silk," as used herein, refers to any forms of silk harvested, obtained, synthesized, formatted, manipulated, or altered through at least one human intervention. SBPs may include a variety of different formats suited for a variety of different applications. Examples of SBP formats include, but are not limited to, fibers, nanofibers, mats, films, foams, membranes, rods, tubes, gels, hydrogels, microspheres, nanospheres, solutions, patches, grafts, adhesives, capsules, cones, cylinders, cakes, discs, emulsions, nanoparticles, nets, organogels, particles, scaffolds, sheets, solids, sponges, sprays, spuns, suspensions, tablets, threads, vapors, yarns, and powders. Additional formats are described herein.

SBPs may find utility in variety of fields and for a variety of applications. Such utility may be due to the unique physical and chemical properties of silk. These physical and chemical properties include, but are not limited to, biocompatibility, biodegradability, bioresorbability, solubility, crystallinity, porosity, mechanical strength, thermal stability, hydrophobicity, and transparency. In some embodiments, SBPs may be used for one or more therapeutic applications, agricultural applications, and/or material science applications. Such SBPs may include processed silk, wherein the processed silk is or is derived from one or more of raw silk, silk fibers, silk fibroin, and silk fibroin fragments. Processed silk present in some SBPs may include one or more silk fibroin polymers, silk fibroin monomers, and/or silk fibroin fragments. In some embodiments, silk fibroin fragments include silk fibroin heavy chain fragments and/or silk fibroin light chain fragments. Some silk fibroin present in SBPs include a plurality of silk fibroin fragments. Each of the plurality of silk fibroin fragments may have a molecular weight of from about 1 kDa to about 400 kDa. As a non-limiting example, the silk fibroin fragment may have a molecular weight of 1 kDa, 2 kDa, 3 kDa, 4 kDa, 5 kDa, 6 kDa, 7 kDa, 8 kDa, 9 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, 100 kDa, 105 kDa, 110 kDa, 115 kDa, 120 kDa, 125 kDa, 130 kDa, 135 kDa, 140 kDa, 145 kDa, 150 kDa, 155 kDa, 160 kDa, 165 kDa, 170 kDa, 175 kDa, 180 kDa, 185 kDa, 190 kDa, 195 kDa, 200 kDa, 205 kDa, 210 kDa, 215 kDa, 220 kDa, 225 kDa, 230 kDa, 235 kDa, 240 kDa, 245 kDa, 250 kDa, 255 kDa, 260 kDa, 265 kDa, 270 kDa, 275 kDa, 280 kDa, 285 kDa, 290 kDa, 295 kDa, 300 kDa, 305 kDa, 310 kDa, 315 kDa, 320 kDa, 325 kDa, 330 KDa, 335 kDa, 340 kDa, 345 kDa, or 350 kDa. As a non-limiting example, the silk fibroin fragment may have a molecular weight of 1-5 kDa, 1-10 kDa, 1-15 kDa, 1-25 kDa, 1-50 kDa, 1-75 kDa, 1-100 kDa, 1-150 kDa, 1-200 kDa, 1-250 kDa, 1-300 kDa, 1-350 kDa, 5-10 kDa, 5-15 kDa, 5-25 kDa, 5-50 kDa, 5-75 kDa, 5-100 kDa, 5-150 kDa, 5-200 kDa, 5-250 kDa, 5-300 kDa, 5-350 kDa, 10-15 kDa, 10-25 kDa, 10-50 kDa, 10-75 kDa, 10-100 kDa, 10-150 kDa, 10-200 kDa, 10-250 kDa, 10-300 kDa, 10-350 kDa, 15-25 kDa, 15-50 kDa, 15-75 kDa, 15-100 kDa, 15-150 kDa, 15-200 kDa, 15-250 kDa, 15-300 kDa, 15-350 kDa, 25-50 kDa, 25-75 kDa, 25-100 kDa, 25-150 kDa, 25-200 kDa, 25-250 kDa, 25-300 kDa, 25-350 kDa, 50-75 kDa, 50-100 kDa, 50-150 kDa, 50-200 kDa, 50-250 kDa, 50-300 kDa, 50-350 kDa, 75-100 kDa, 75-150 kDa, 75-200 kDa, 75-250 kDa, 75-300 kDa, 75-350 kDa, 100-150 kDa, 100-200 kDa, 100-250 kDa, 100-300 kDa, 100-350 kDa, 150-200 kDa, 150-250 kDa, 150-300 kDa, 150-350 kDa, 200-250 kDa, 200-300 kDa, 200-350 kDa, 250-300 kDa, 250-350 kDa, and 300-350 kDa In some embodiments, SBPs may be formulations (e.g., SBP formulations). As used herein, the term "formulation" refers to a mixture of two or more components or the process of preparing such mixtures. In some embodiments, the formulations are low cost and eco-friendly. In some embodiments, the preparation or manufacturing of formulations is low cost and eco-friendly. In some embodiments, the preparation or manufacturing of formulations is scalable. In some embodiments, SBPs are prepared by extracting silk fibroin via degumming silk yarn. In some embodiments, the yarn is medical grade. In some embodiments the yarn may be silk sutures. The extracted silk fibroin may then be dissolved in a solvent (e.g. water, aqueous solution, organic solvent). The dissolved silk fibroin may then be dried (e.g., oven dried, air dried, or freeze-dried). In some embodiments, dried silk fibroin is formed into formats described herein. In some embodiments, that format is a solution. In some embodiments, that format is a powder. In some embodiments, that format is a hydrogel. In some embodiments, formulations include one or more excipients, carriers, additional components, and/or therapeutic agents to generate SBPs. In some embodiments, formulations of processed silks are prepared during the manufacture of SBPs.

Formulation components and/or component ratios may be modulated to affect one or more SBP properties, effects, and/or applications. Variations in the concentration of silk fibroin, choice of excipient, the concentration of excipient, the osmolarity of the formulation, and the method of formulation represent non-limiting examples of differences in formulation that may alter properties, effects, and applications of SBPs. In some embodiments, the formulation of SBPs may modulate their physical properties. Examples of physical properties include solubility, density, and thickness. In some embodiments, the formulation of SBPs may modulate their mechanical properties. Examples of mechanical properties that may be modulated include, but are not limited to, mechanical strength, tensile strength, elongation capabilities, elasticity, compressive strength, stiffness, shear strength, toughness, torsional stability, temperature stability, moisture stability, viscosity, and reeling rate.

In some embodiments, the formulations are prepared to be sterile. As used herein, the term "sterile" refers to something that is aseptic. In some embodiments, SBPs are prepared from sterile materials. In some embodiments, SBPs are prepared and then sterilized. In some embodiments, processed silk is degummed and then sterilized. In some embodiments, processed silk is sterilized and then degummed. Processed silk and/or SBPs may be sterilized via gamma radiation, autoclave (e.g., autoclave sterilization), filtration, electron beam, and any other method known to those skilled in the art.

A pharmaceutical composition (e.g., SBP formulation) in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of therapeutic agent or other compounds. The amount of therapeutic agent may generally be equal to the dosage of therapeutic agent administered to a subject and/or a convenient fraction of such dosage including, but not limited to, one-half or one-third of such a dosage.

Sources of Silk

SBP formulations may include processed silk obtained from one or more of a variety of sources. Processed silk may include raw silk. "Raw silk," as used herein, refers to silk that has been harvested, purified, isolated, or otherwise collected from silk producers. The term "silk producer," as used herein, refers to any organism capable of producing silk. Raw silk has been processed in large quantities for thousands of years, primarily from silkworms (*Bombyx mori*), which use silk to form their cocoon. Raw silk from silkworm cocoons includes silk fibroin and sericin that is secreted onto silk fibroin during cocoon formation. Raw silk may be harvested as a silk fiber. As used herein, the term "silk fiber" refers to any silk that is in the form of a filament or thread. Silk fibers may vary in length and width and may include, but are not limited to, yarns, strings, threads, and nanofibers. In some embodiments, raw silk may be obtained in the form of a yarn.

SBPs may include processed silk obtained from any one of a variety of sources. Processed silk may include raw silk. "Raw silk," as used herein, refers to silk that has been harvested, purified, isolated, or otherwise collected from silk producers. The term "silk producer," as used herein, refers to any organism capable of producing silk. Raw silk has been processed in large quantities for thousands of years, primarily from silkworms (*Bombyx mori*), which use silk to form their cocoon. Raw silk from silkworm cocoons includes silk fibroin and sericin that is secreted onto silk fibroin during cocoon formation. Raw silk may be harvested as a silk fiber. As used herein, the term "silk fiber" refers to any silk that is in the form of a filament or thread. Silk fibers may vary in length and width and may include, but are not limited to, yarns, strings, threads, and nanofibers. In some embodiments, raw silk may be obtained in the form of a yarn.

In some embodiments, processed silk includes silk obtained from a silk producer. Silk producers may be organisms found in nature (referred to herein as "wild type organisms") or they may be genetically modified organisms. There are many species of silk producers in nature capable of producing silk. Silk producers may be insect species, such as silkworms. Some silk producers include arachnid species. In some embodiments, silk producers include species of mollusk. Silk produced by different silk producing species may vary in physical and/or chemical properties. Such properties may include amino acid content, secondary structure (e.g. beta-sheet content), mechanical properties (e.g. elasticity), and others. In some embodiments, the present disclosure provides blends of processed silk from multiple silk producers or other sources (e.g., recombinant or synthetic silk). Such blends may have synergistic properties that are absent from processed silk obtained from single sources or from alternative blends. For example, Janani G et al. describe a silk scaffold fabricated by blending *Bombyx mori* silk fibroin with cell adhesion motif (RGD) rich *Antheraea assamensis* silk fibroin which displays enhanced liver-specific functions of cultured hepatocytes (Acta Biomater. 2018 February; 67:167-182, the contents of which are herein incorporated by reference in their entirety).

In some embodiments, processed silk may be obtained from the silkworm species *Bombyx mori*. Other examples of silk producer species include, but are not limited to, *Bombyx mandarina, Bombyx sinesis, Anaphe moloneyi, Anaphe panda, Anaphe reticulate, Anaphe ambrizia, Anaphe carteri, Anaphe venata, Anapha infracta, Antheraea assamensis, Antheraea assama, Antheraea mylitta, Antheraea pernyi, Antheraea yamamai, Antheraea polyphemus, Antheraea oculea, Anisota senatoria, Apis mellifera, Araneus diadematus, Araneus cavaticus, Automeris io, Atticus atlas, Copaxa multifenestrata, Coscinocera hercules, Callosamia promethea, Eupackardia calieta, Eurprosthenops australis, Gonometa postica, Gonometa rufobrunnea, Hyalophora cecropia, Hyalophora euryalus, Hyalophora gioveri, Miranda auretia, Nephila madagascarensis, Nephila clavipes, Pachypasa otus, Pachypasa atus, Philosamia ricini, Pinna squamosa, Rothschildia hesperis, Rothschildia lebeau, Samia Cynthia*, and *Samia ricini*.

Genetically Modified Organisms

In some embodiments, silk producers are genetically modified organisms. As used herein, the term "genetically modified organism" or "GMO" refers to any living entity that includes or is derived from some form of genetic manipulation. The genetic manipulation may include any human intervention that alters the genetic material of an organism. In some embodiments, the genetic manipulation is limited to selecting organisms for reproduction based on genotype or phenotype. In some embodiments, genetic manipulation includes adding, deleting, and/or substituting one or more nucleotides of a wild type DNA sequence. The genetic manipulation may include the use of recombinant DNA technology. Recombinant DNA technology involves the exchange of DNA sections between DNA molecules. Some genetic manipulation involves the transfer of genetic material from another organism to the GMO. GMOs including such transferred genetic material are referred to as "transgenic organisms." Some genetic materials may be synthetically produced (see e.g., Price et al. (2014) J Control Release 190:304-313; and Deptuch et al. (2017) Materials 10:1417, the contents of each of which are herein incorporated by reference in their entirety). The genetic material may be transferred by way of a vector. The vector may be a plasmid. In some embodiments the vector is a virus. Some genetic manipulations involve the use of inhibitory RNA. In some embodiments, genetic manipulations are carried out using clustered regularly interspaced short palindromic repeats (CRISPR) technology.

GMO silk producers may be species generally known to produce silk (e.g., any of those described above). Some GMO silk producers are species not generally known to produce silk, but that are genetically manipulated to produce silk. Such organisms may be genetically modified to include at least one nucleic acid encoding at least one silk protein (e.g., silk fibroin, silk fibroin heavy chains, silk fibroin light chains, sericin, or fragments or derivates thereof). Some GMO silk producers are genetically manipulated to produce silk with one or more altered silk properties (e.g., strength, stability, texture, etc.). Some genetic manipulations affect characteristics of the GMO that are not directly related to silk production or silk properties (e.g., disease resistance, reproduction, etc.).

In some embodiments, GMO silk producers include genetically modified silkworms (e.g., *Bombyx mori*). Genetically modified silkworms may include genetic manipulations that result in silkworm production of silk fibroin strands that include degradable linkers. In some embodiments, GMOs are arachnids (e.g., spiders).

In some embodiments, GMO silk producers are cells. Such cells may be grown in culture and may include any type of cell capable of expressing protein. The cells may be prokaryotic or eukaryotic cells. In some embodiments, silk producer cells include bacterial cells, insect cells, yeast cells, mammalian cells, or plant cells. Cells may be transformed or transduced with nucleic acids encoding one or more silk proteins (e.g., silk fibroin, sericin, or fragments or derivates thereof).

In some embodiments, GMO silk producers may include, but are not limited to, *Bombyx mori*, soybeans, *Arabidopsis, Escherichia coli, Pichia pastoris*, potato, tobacco, baby hamster kidney cells, mice, and goats (e.g., see Tokareva et al. (2013) Microb Biotechnol 6 (6): 651-63 and Deptuch et al. (2017) Materials 10:1417). In some embodiments, silk may be produced in green plants (e.g., see International Publication Number WO2001090389, the contents of which are herein incorporated by reference in their entirety).

Recombinant Silk

As used herein, the term "recombinant silk" refers to any form of silk produced using recombinant DNA technology. Recombinant silk proteins may include amino acid sequences corresponding to silk proteins produced by wild type organisms; amino acid sequences not found in nature; and/or amino acid sequences found in nature, but not associated with silk. Some recombinant silk includes amino acid sequences with repetitive sequences that contribute to polymer formation and/or silk properties (e.g., see Deptuch et al. (2017) Materials 10:1417). Nucleic acid segments encoding repetitive sequences may be incorporated into plasmids after self-ligation into multimers (e.g., see Price et al. (2014) J Control Release 190:304-313).

In some embodiments, recombinant silk may be encoded by expression plasmids.

In some embodiments, recombinant silk may be expressed as a monomer. The monomers may be combined with other monomers or other silk proteins to obtain multimers (e.g., see Deptuch et al. (2017) Materials 10:1417). Some monomers may be combined according to methods known in the art. Such methods may include, but are not limited to, ligation, step-by-step ligation, recursive directional ligation, native chemical ligation, and concatemerization.

In some embodiments, recombinant silk may be expressed using the "PiggyBac" vector. The PiggyBac vector includes a spider transposon that is compatible with expression in silkworms.

In some embodiments, recombinant silk may be produced in a silk producing species. Examples of silk producing species include, but are not limited to, *Bombyx mori, Bombyx mandarina, Bombyx sinesis, Anaphe moloneyi, Anaphe panda, Anaphe reticulate, Anaphe ambrizia, Anaphe carteri, Anaphe venata, Anapha infracta, Antheraea assamensis, Antheraea paphis, Antheraea assama, Antheraea mylitta, Antheraea pernyi, Antheraea yamamai, Antheraea polyphemus, Antheraea oculea, Anisota senatoria, Apis mellifera, Araneus diadematus, Araneus cavaticus, Automeris io, Atticus atlas, Coscinocera hercules, Callosamia promethea, Copaxa multifenestrata, Eupackardia calleta, Eurprosthenops australis, Gonometa postica, Gonometa rufobrunnea, Hyalophora cecropia, Hyalophora euryalus, Hyalophora gloveri, Miranda auretia, Nephila madagascarensis, Nephila clavipes, Pachypasa otus, Pachypasa*

*atus, Philosamia ricini, Pinna squamosa, Rothschildia hesperis, Rothschildia lebeau, Samia Cynthia*, and *Samia ricini*.

Synthetic Silk

In some embodiments, SBP formulations include synthetic silk. As used herein, the term "synthetic silk" refers to silk prepared without the aid of a silk producer. Synthetic silk may be prepared using standard methods of peptide synthesis. Such methods typically include the formation of amino acid polymers through successive rounds of polymerization. Amino acids used may be obtained through commercial sources and may include natural or non-natural amino acids. In some embodiments, synthetic silk polypeptides are prepared using solid-phase synthesis methods. The polypeptides may be linked to resin during synthesis. In some embodiments, polypeptide synthesis may be conducted using automated methods.

In some embodiments synthetic silk may be prepared using cell-free peptide synthesis (CFPS). As used herein, the term "cell-free peptide synthesis" may be defined as production of peptides or proteins using cellular extracts but, in a system, devoid of living organisms. The cellular extracts may be prepared by lysing cells. In one embodiment, the cellular extracts may be prepared from the cells of a silk producer. In some embodiments, cellular extracts may be prepared by lysing cells derived from but not limited to *E. coli*, rabbit, wheat germ, insects, and/or humans. Cellular extracts may include additional components required for CFPS such as but not limited to RNA polymerases for mRNA transcription, ribosomes for polypeptide translation, tRNA and amino acids, enzymatic cofactors, an energy source, and/or cellular components essential for proper protein folding. In some embodiments, cellular extracts may be supplemented with additional components that may be required for CFPS include but are not limited to an energy source, amino acids, minerals, and/or metals. In some embodiments, CFPS may include nucleic acids encoding silk proteins produced by wild type organisms; amino acid sequences not found in nature; and/or amino acid sequences found in nature, but not associated with silk. In some embodiments, synthetic silk may be encoded by expression plasmids.

Synthetic silk may include polypeptides that are identical to wild type silk proteins (e.g., silk fibroin heavy chain, silk fibroin light chain, or sericin) or fragments thereof. In some embodiments, synthetic silk includes polypeptides that are variants of silk proteins or silk protein fragments. Some synthetic silk includes polypeptides with repeating units that correspond with or are variations of those found in silk fibroin heavy chain proteins.

Processed Silk

In some embodiments, SBP formulations include processed silk. Various processing methods may be used to obtain specific forms or formats of processed silk. Such processing methods may include, but are not limited to, acidifying, air drying, alkalinizing, annealing, autoclaving, chemical crosslinking, chemical modification, concentration, cross-linking, degumming, diluting, dissolving, dry spinning, drying, electrifying, electrospinning, electrospraying, emulsifying, encapsulating, extraction, extrusion, gelation, harvesting, heating, lyophilization, molding, oven drying, pH alteration, precipitation, purification, shearing, sonication, spinning, spray drying, spray freezing, spraying, vapor annealing, vortexing, and water annealing. The processing steps may be used to prepare final SBPs or they may be used to generate processed silk preparations. As used herein, the term "processed silk preparation" is generally used to refer to processed silk or compositions that include processed silk that are prepared for or obtained during or after one or more processing steps. Processed silk preparations may be SBPs, may be components of SBPs, SBP formulations or may be used as a starting or intermediate composition in the preparation of SBPs. Processed silk preparations may include other components related to processing (e.g., solvents, solutes, impurities, catalysts, enzymes, intermediates, etc.). Processed silk preparations that include silk fibroin may be referred to as silk fibroin preparations. In some embodiments, processed silk manufacturing is simple, scalable, and/or cost effective.

In some embodiments, processed silk may be prepared as, provided as, or included in a yarn, thread, string, a nanofiber, a textile, a cloth, a fabric, a particle, a nanoparticle, a microsphere, a nanosphere, a powder, a solution, a gel, a hydrogel, an organogel, a mat, a film, a foam, a membrane, a rod, a tube, a patch, a sponge, a scaffold, a capsule, an excipient, an implant, a solid, a coating, and/or a graft.

In some embodiments, processed silk may be stored frozen or dried to a stable soluble form. Processed silk may be frozen with cryoprotectants. Cryoprotectants may include, but are not limited to, phosphate buffer, sucrose, trehalose, histidine, and any other cryoprotectant known to one of skill in the art. In some embodiments, SBPs may be stored frozen or dried to a stable soluble form. In some embodiments, the SBPs may be solutions.

In some embodiments, preparation of processed silk and/or SBP formulations may be scaled up for manufacturing at a large scale. In some embodiments, production of processed silk and/or SBP formulations may be accomplished with automated machinery.

Any of the methods known in the art and/or described herein may be used to extract silk fibroin. The yield of silk fibroin from extraction may be, but is not limited to, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99%.

Silk Properties

In some embodiments, processed silk may be selected based on or prepared to include features affecting one or more properties of the processed silk. Such properties may include, but are not limited to, stability, complex stability, composition stability, payload retention or release, payload release rate, wettability, mechanical strength, tensile strength, elongation capabilities, elasticity, compressive strength, stiffness, shear strength, toughness, hydrophobicity, torsional stability, temperature stability, moisture stability, strength, flexibility, solubility, crystallinity, viscosity, and porosity. Features affecting one or more processed silk properties may include silk secondary structure. Secondary structure refers to three-dimensional arrangements of polypeptide chains based on local interactions between neighboring residues. Common secondary structures include β-pleated sheets and α-helices. Silk secondary structure may enhance or attenuate solubility. In some embodiments, β-sheet secondary structure content may enhance processed silk crystallinity. "Crystallinity" refers to the degree of structure and arrangement between atoms or molecules in a compound, with increased structure yielding greater crystallinity. β-sheet structures may be antiparallel β-sheets. In some embodiments, processed silk includes polypeptides with random coil secondary structure. Some processed silk includes polypeptides with coiled coil secondary structure. In some embodiments, processed silk includes a combination of two or more forms of secondary structure. In some embodiments, processed silk may include polypeptides with multiple repeats. As used herein when referring to polypeptides, the term "multiple repeat" refers to an amino acid sequence that is duplicated two or more times in succession within a polypeptide. Silk fibroin heavy chains include multiple repeats that enable static interactions between parallel silk fibroin heavy chains. Multiple repeats may include repeats of the sequences GAGAGS (SEQ ID NO: 1) and/or GA. In some embodiments, the A of GA dipeptides may be replaced with S or Y. In some embodiments, multiple repeats may include any of those presented in Qi et al. (2017) Int J Mol Sci 18:237, the contents of which are herein incorporated by reference in their entirety. Multiple repeats may enable formation of stable, crystalline regions of antiparallel β-sheets.

Processed silk may include silk fibroin forms described by Qi et al. (2017) Int J Mol Sci 18:237 and Cao et al. (2009) Int J Mol Sci 10:1514-1524, the contents of each of which are herein incorporated by reference in their entirety. These silk fibroin forms are referred to as silk I, silk II, and silk III. Silk I and silk II forms are commonly found in nature. Silk I predominantly includes random coil secondary structures. Silk II predominantly includes β-sheet secondary structure. Silk III predominantly includes an unstable structure.

Processed silk may be treated to modulate β-sheet content and/or crystallinity. In some embodiments these treatments are used to reduce the solubility and/or hydrophobicity of the silk fibroin or silk fibroin composition. Treatments may include, but are not limited to, alteration of the pH, sonication of the silk fibroin, incorporation of an excipient, increasing or decreasing the temperature, treatment with acid, treatment with formic acid, treatment with glycerol, treatment with an alcohol, treatment with methanol, treatment with ethanol, treatment with isopropanol, and/or treatment with a mixture of alcohol and water. In some embodiments, treatments result in transition between forms of silk I, II, or III. Such methods may include any of those described in Cao et al. (2009) Int J Mol Sci 10:1514-1524).

Strength and Stability

Processed silk strength and stability are important factors for many applications. In some embodiments, processed silk may be selected based on or prepared to maximize mechanical strength, tensile strength, elongation capabilities, elasticity, flexibility, compressive strength, stiffness, shear strength, toughness, torsional stability, biological stability, resistance to degradation, and/or moisture stability. In some embodiments, processed silk had a non-acidic microenvironment. In some embodiments, the non-acidic microenvironment enhances the stability of processed silk and or SBPs. In some embodiments, the non-acidic microenvironment enhances the stability of therapeutic agents formulated with the processed silk and/or SBP.

Biocompatibility

In some embodiments, processed silk may be selected based on or prepared to maximize biocompatibility. As used herein, the term "biocompatibility" refers to the degree with which a substance avoids provoking a negative biological response in an organism exposed to the substance. The negative biological response may include an inflammatory response and/or local sensitization, hemorrhage, and/or other complications known to those skilled in the art. In some embodiments, administration of processed silk or an SBP does not induce an inflammatory response, local sensitization, hemorrhage, and/or other complications known to those skilled in the art. In some embodiments, contact with processed silk or an SBP does not induce an inflammatory response, local sensitization, hemorrhage, and/or other complications known to those skilled in the art. In some embodiments, no inflammatory response, local sensitization, hemorrhage, and/or other complications occur after up to 7 months of contact with processed silk or an SBP. In some embodiments, processed silk biocompatibility is enhanced through preparations that produce only non-toxic byproducts during degradation. In some embodiments, exposure to an SBP generates a tolerable biological response, within an acceptable threshold known to those skilled in the art. In some embodiments, processed silk is biocompatible in humans and human whole blood. In some embodiments, processed silk is biocompatible in animals. In some embodiments, processed silk produces no adverse reactions, no acute inflammation, and no immunogenicity in vivo. In some embodiments, the processed silk or SBP is safe to use in vivo. In some embodiments, processed silk or SBPs are biocompatible and/or tolerable in vitro. In some embodiments, processed silk or SBPs are biocompatible and/or tolerable in vivo. In some embodiments, no inflammatory response, local sensitization, hemorrhage, and/or other complications occur after up to 1 day, up to 3 days, up to 1 week, up to 1 month, up to 2 months, up to 3 months, up to 4 months, up to 5 months, up to 6 months, up to 7 months, up to 8 months, up to 9 months, up to 10 months, up to 11 months, or up to 1 year of contact with processed silk or an SBP.

Biodegradability

In some embodiments, processed silk may be selected based on or prepared to maximize biodegradability. As used herein, the term "biodegradability" refers to the degree with which a substance avoids provoking a negative response to an environment exposed to the substance as it deteriorates. The negative environmental response may include a response to toxic byproducts generated as a substance deteriorates. In some embodiments, processed silk biodegradability is enhanced through preparations that produce only non-toxic byproducts during degradation. In some embodiments, processed silk biodegradability is enhanced through preparations that produce only inert amino acid byproducts. In some embodiments, the SBP and/or SBP by products are considered naturally derived and environmentally and/or eco-friendly.

Anti-Evaporative Properties

In some embodiments, processed silk may be selected based on or prepared to reduce the evaporation of a solution. In some embodiments, processed silk may reduce the evaporation of a solution. In some embodiments, an SBP may demonstrate anti-evaporative properties by creating a water and/or water vapor barrier, as taught in Marelli et al. (2008) Sci Rep 6:25263, the contents of which are herein incorporated by reference in their entirety. In some embodiments, processed silk may extend the lifetime or residence time of an SBP product due to its ability to prevent evaporation. In some embodiments, processed silk may increase the amount of time required for a solution to evaporate. In some embodiments, processed silk may be selected based on or prepared to reduce the evaporation of a solution. In some embodiments, processed silk may reduce the evaporation of a solution. In some embodiments, processed silk may extend the lifetime or residence time of an SBP product due to its ability to prevent evaporation. In some embodiments, processed silk may increase the amount of time required for a solution to evaporate.

Demulcent

In some embodiments, processed silk and/or SBPs may act as demulcents. As used herein, the term "demulcent" refers to a substance that relieves irritation or inflammation of the mucous membranes by forming a protective film. This film may mimic a mucous membrane. Demulcents may also provide lubrication. Demulcents may include non-polymeric demulcents and polymer demulcents. Added demulcents may modulate the viscosity of an SBP or product containing an SBP.

Surfactant

In some embodiments, processed silk and/or SBPs may act as a surfactant. As used herein, the term "surfactant" refers to a substance that reduces the surface tension between two materials. In some embodiments, the SBP is a solution. In some embodiments, the SBP is a hydrogel. In some embodiments, the SBP has a surface tension similar to that of water. In some embodiments, the SBP has a surface tension similar to that of human tears. Human tears have been reported to have a surface tension of 43.6 mN/m, as described in Sweeney et al. (2013) Experimental Eye Research 117:28-38, the contents of which are herein incorporated by reference in their entirety. In some embodiments, the surface tension of the SBP may be controlled by the concentration of processed silk. In some embodiments, the surface tension is about 30-60 mN/m. In some embodiments, the surface tension of an SBP is about 35-55 mN/m. In some embodiments, the surface tension of an SBP is about 40-50 mN/m.

Antimicrobial and Bacteriostatic Properties

In some embodiments, processed silk may be based on or prepared to maximize antimicrobial properties. As used herein, the term "antimicrobial" properties refer to the ability of processed silk or SBPs to inhibit, deter the growth of microorganisms and/or kill the microorganisms. Microorganisms may include bacteria, fungi, protozoans, and viruses. In some embodiments, the antimicrobial properties may include but are not limited to antibacterial, antifungal, antiseptic, and/or disinfectant properties. In some embodiments, antimicrobial properties of silk may be modulated during one or more processing steps or during fabrication of a SBP. In some embodiments, antimicrobial properties may be modulated by the varying the source of silk utilized for the preparation of SBPs (Mirghani, M et al. 2012, Investigation of the spider web of antibacterial activity, (MICOTriBE) 2012; the contents of which are incorporated by reference in their entirety). In some embodiments, processed silk and SBPs described herein may possess antimicrobial properties against gram positive bacteria. In some embodiments, processed silk and SBPs described herein may possess antimicrobial properties against gram negative bacteria.

In some embodiments, processed silk may be based on or prepared to maximize bacteriostatic properties. As used herein, the term "bacteriostatic" refers to a substance that prevents bacterial reproduction and may or may not kill said bacteria. Bacteriostatic agents prevent the growth of bacteria. In some embodiments, bacteriostatic properties of silk may be modulated during one or more processing steps or during fabrication of a SBP. In some embodiments, bacteriostatic properties may be modulated by the varying the source of silk utilized for the preparation of SBPs. In some embodiments, processed silk and SBPs described herein may possess bacteriostatic properties against gram positive bacteria. In some embodiments, processed silk and SBPs described herein may possess bacteriostatic properties against gram negative bacteria.

Anti-Inflammatory Properties

In some embodiments, processed silk or SBPs may have or be prepared to maximize anti-inflammatory properties. It has been reported that silk fibroin peptide derived from silkworm *Bombyx mori* exhibited anti-inflammatory activity in a mice model of inflammation (Kim et al., (2011) BMB Rep 44 (12): 787-92; the contents of which are incorporated by reference in their entirety). In some embodiments, processed silk or SBPs may be administered to a subject alone or in combination with other therapeutic agents to elicit anti-inflammatory effects. It is contemplated that processed silk or SBPs alone or combination with other therapeutic agents may be used to treat various inflammatory diseases. For example, processed silk or SBPs may reduce signs and symptoms of inflammation, such as but not limited to, swelling, redness, tenderness, rashes, fever, and pain.

Harvesting Silk

In some embodiments, processed silk is harvested from silk producer cocoons. Cocoons may be prepared by cultivating silkworm moths and allowing them to pupate. Once fully formed, cocoons may be treated to soften sericin and allow for unwinding of the cocoon to form raw silk fiber. The treatment may include treatment with hot air, steam, and/or boiling water. Raw silk fibers may be produced by unwinding multiple cocoons simultaneously. The resulting raw silk fibers include both silk fibroin and sericin. Subsequent processing may be carried out to remove sericin from the raw silk fibers or from later forms of processed silk or SBPs. In some embodiments, raw silk may be harvested directly from the silk glands of silk producers. Raw silk may be harvested from wild type or GMO silk producers.

Extraction of Sericin/Degumming

In some embodiments, sericin may be removed from processed silk, a process referred to herein as "degumming." The processed silk may include raw silk, which includes sericin secreted during cocoon formation. Methods of degumming may include heating (e.g., boiling) in a degumming solution. As used herein, the term "degumming solution" refers to a composition used for sericin removal that includes at least one degumming agent. As used herein, a "degumming agent" refers to any substance that may be used for sericin removal. Heating in degumming solution may reduce or eliminate sericin from processed silk. In some embodiments, heating in degumming solution includes boiling. Heating in degumming solution may be followed by rinsing to enhance removal of sericin that remains after heating. In some embodiments, raw silk is degummed before further processing or utilization in SBPs. In other embodiments, raw silk is further processed or otherwise incorporated into a SBP prior to degumming. Such methods may include any of those presented in European Patent No. EP2904134 or United States Patent Publication No. US2017031287, the contents of each of which are herein incorporated by reference in their entirety.

Degumming agents and/or degumming solutions may include, but are not limited to water, alcohols, soaps, acids, alkaline solutions, and enzyme solutions. In some embodiments, degumming solutions may include salt-containing alkaline solutions. Such solutions may include sodium carbonate. Sodium carbonate concentration may be from about 0.01 μM to about 0.3 M. In some embodiments, sodium carbonate concentration may be from about 0.01 μM to about 0.05 M, about 0.05 μM to about 0.1 M, from about 0.1 μM to about 0.2 M, or from about 0.2 μM to about 0.3 M. In some embodiments, sodium carbonate concentration may be 0.02 M. In some embodiments, degumming solutions may include from about 0.01% to about 1% (w/v) sodium carbonate. In some embodiments, degumming solutions may include from about 0.01% to about 10% (w/v) sodium carbonate. In some embodiments, degumming solutions may include from about 0.01% (w/v) to about 1% (w/v), from about 1% (w/v) to about 2% (w/v), from about 2% (w/v) to about 3% (w/v), from about 3% (w/v) to about 4% (w/v), from about 4% (w/v) to about 5% (w/v), or from about 5% (w/v) to about 10% (w/v) sodium carbonate. In some embodiments, degumming solutions may include sodium dodecyl sulfate (SDS). Such degumming solutions may include any those described in Zhang et al. (2012) J Translational Med 10:117, the contents of which are herein incorporated by reference in their entirety. In some embodiments, degumming solutions include boric acid. Such solutions may include any of those taught in European Patent No. EP2904134, the contents of which are herein incorporated by reference in their entirety. In some embodiments, the degumming solution may have a pH of from about 0 to about 5, from about 2 to about 7, from about 4 to about 9, from about 5 to about 11, from about 6 to about 12, from about 6.5 to about 8.5, from about 7 to about 10, from about 8 to about 12, and from about 10 to about 14. In some embodiments, processed silk is present in degumming solutions at concentrations of from about 0.1% to about 2%, from about 0.5% to about 3%, from about 1% to about 4%, or from about 2% to about 5% (w/v). In some embodiments, processed silk is present in degumming solutions at concentrations of greater than 5% (w/v).

Degumming may be carried out by “boiling” in degumming solutions at or near atmospheric boiling temperatures. As used herein, “boiling” does not necessarily mean at or above 100° C. Boiling may be properly used to describe heating the solution at a temperature that is less than or greater than 100° C. Some boiling temperatures may be from about 60° C. to about 115° C. In some embodiments, boiling is carried out at 100° C. In some embodiments, boiling is carried out at about 60° C., about 65° C., about 70° C., about 75° C., about 80° C., about 85° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C., about 110° C., about 111° C., about 112° C., about 113° C., about 114° C., about 115° C., or greater than 115° C.

In some embodiments, degumming includes heating in degumming solution for a period of from about 10 seconds to about 45 seconds, from about 30 seconds to about 90 seconds, from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 400 min, from about 270 min to about 450 min, from about 300 min to about 500 min, from about 330 min to about 550 min, from about 360 min to about 600 min, from about 390 min to about 700 min, from about 420 min to about 800 min, from about 450 min to about 900 min, from about 480 min to about 1000 min, from about 510 min to about 1100 min, from about 540 min to about 1200 min, from about 570 min to about 1300 min, from about 600 min to about 1400 min, from about 630 min to about 1500 min, from about 660 min to about 1600 min, from about 690 min to about 1700 min, from about 720 min to about 1800 min, from about 1440 min to about 1900 min, from about 1480 min to about 2000 min, or longer than 2000 min.

In some embodiments, processed silk preparations are characterized by the number of minutes boiling was carried out for preparation, a value referred to herein as “minute boil” or “mb.” The minute boil value of a preparation may be associated with known or presumed characteristics of similar preparations with the same minute boil value. Such characteristics may include concentration and/or molecular weight of preparation compounds, proteins, or protein fragments altered during boiling. In some embodiments, processed silk preparations (e.g., silk fibroin preparations) have an mb value of from about 1 mb to about 5 mb, from about 2 mb to about 10 mb, from about 5 mb to about 15 mb, from about 10 mb to about 25 mb, from about 20 mb to about 35 mb, from about 30 mb to about 50 mb, from about 45 mb to about 75 mb, from about 60 mb to about 95 mb, from about 90 mb to about 125 mb, from about 120 mb to about 175 mb, from about 150 mb to about 200 mb, from about 180 mb to about 250 mb, from about 210 mb to about 350 mb, from about 240 mb to about 400 mb, from about 270 mb to about 450 mb, from about 300 mb to about 480 mb, or greater than 480 mb.

In some embodiments, degumming may be carried out by treatment with high temperatures and/or pressures. Such methods may include any of those presented International Patent Application Publication No. WO2017200659, the contents of which are herein incorporated by reference in their entirety.

Silk Fibroin Boiling Time

SBP formulations may comprise processed silk with varying molecular weights. SBP formulations may include low molecular weight silk fibroin. As used herein, the term “low molecular weight silk fibroin” refers to silk fibroin with a molecular weight below 200 kDa. Some SBP formulations may include high molecular weight silk fibroin. As used herein, the term “high molecular weight silk fibroin” refers to silk fibroin with a molecular weight equal to or greater than 200 kDa. In some embodiments, the silk fibroin molecular weight is defined by the degumming boiling time. In some embodiments, silk fibroin with a 480-minute boil, or “mb” may produce be a low molecular weight silk fibroin when compared to a silk fibroin produced with a 120-minute boil, or “mb”. In some aspects, the 120 mb silk fibroin is considered to be high molecular weight silk fibroin in comparison to the 480 mb silk fibroin. In some embodiments, a longer boiling time is considered to be lower molecular weight silk fibroin. In some embodiments, a shorter boiling time is considered to be a higher molecular weight silk fibroin. In some embodiments, the boiling time is about 15 minutes, about 30 minutes, about 60 minutes, about 90 minutes, about 120 minutes, or about 480 minutes. In some embodiments, an SBP is prepared with processed silk with a single boiling time. In some embodiments, an SBP contains a blend of processed silk with different boiling times.

In one embodiment, the SBP formulation includes 30 mb silk fibroin.

In one embodiment, the SBP formulation includes 60 mb silk fibroin.

In one embodiment, the SBP formulation includes 90 mb silk fibroin.

In one embodiment, the SBP formulation includes 120 mb silk fibroin.

In one embodiment, the SBP formulation includes 480 mb silk fibroin.

Processed Silk Preparation Characterization

Preparations of processed silk sometimes include mixtures of silk fibroin polymers, silk fibroin monomers, silk fibroin heavy chains, silk fibroin light chains, sericin, and/or fragments of any of the foregoing. Where the exact contents and ratios of components in such processed silk preparations are unknown, the preparations may be characterized by one or more properties of the preparation or by conditions or methods used to obtain the preparations.

Solubility and Concentration

Processed silk preparations may include solutions that include processed silk (also referred to herein as "processed silk solutions"). Processed silk solutions may be characterized by processed silk concentration. For example, processed silk may be dissolved in a solvent after degumming to generate a processed silk solution of silk fibroin for subsequent use. Solvent used to dissolve processed silk may be a buffer. In some embodiments, solvent used is an organic solvent. Organic solvents may include, but are not limited to hexafluoroisopropanol (HFIP), methanol, isopropanol, ethanol, or combinations thereof. In some embodiments, solvents include a mixture of an organic solvent and water or an aqueous solution. Solvents may include water or aqueous solutions. Aqueous solutions may include aqueous salt solutions that include one or more salts. Such salts may include but are not limited to lithium bromide (LiBr), lithium thiocyanate, Ajisawa's reagent, a chaotropic agent, calcium nitrate, or other salts capable of solubilizing silk, including any of those disclosed in U.S. Pat. No. 9,623,147 (the content of which is herein incorporated by reference in its entirety). In some embodiments, solvents used in processed silk solutions include high salt solutions. In some embodiments, the solution comprises 5 to 13 M LiBr. The concentration of LiBr may be 9.3 M. In some embodiments, solvents used in processed silk solutions may include Ajisawa's reagent, as described in Zheng et al. (2016) Journal of Biomaterials Applications 31:450-463, the content of which is herein incorporated by reference in its entirety. Ajisawa's reagent comprises a mixture of calcium chloride, ethanol, and water in a molar ratio of 1:2:8 respectively.

In some embodiments, processed silk may be present in processed silk solutions at a concentration of from about 0.01% (w/v) to about 1% (w/v), from about 0.05% (w/v) to about 2% (w/v), from about 1% (w/v) to about 5% (w/v), from about 2% (w/v) to about 10% (w/v), from about 4% (w/v) to about 16% (w/v), from about 5% (w/v) to about 20% (w/v), from about 8% (w/v) to about 24% (w/v), from about 10% (w/v) to about 30% (w/v), from about 12% (w/v) to about 32% (w/v), from about 14% (w/v) to about 34% (w/v), from about 16% (w/v) to about 36% (w/v), from about 18% (w/v) to about 38% (w/v), from about 20% (w/v) to about 40% (w/v), from about 22% (w/v) to about 42% (w/v), from about 24% (w/v) to about 44% (w/v), from about 26% (w/v) to about 46% (w/v), from about 28% (w/v) to about 48% (w/v), from about 30% (w/v) to about 50% (w/v), from about 35% (w/v) to about 55% (w/v), from about 40% (w/v) to about 60% (w/v), from about 45% (w/v) to about 65% (w/v), from about 50% (w/v) to about 70% (w/v), from about 55% (w/v) to about 75% (w/v), from about 60% (w/v) to about 80% (w/v), from about 65% (w/v) to about 85% (w/v), from about 70% (w/v) to about 90% (w/v), from about 75% (w/v) to about 95% (w/v), from about 80% (w/v) to about 96% (w/v), from about 85% (w/v) to about 97% (w/v), from about 90% (w/v) to about 98% (w/v), from about 95% (w/v) to about 99% (w/v), from about 96% (w/v) to about 99.2% (w/v), from about 97% (w/v) to about 99.5% (w/v), from about 98% (w/v) to about 99.8% (w/v), from about 99% (w/v) to about 99.9% (w/v), or greater than 99.9% (w/v). In some embodiments, the processed silk is silk fibroin.

Processed silk solutions may be characterized by the length of time and/or temperature needed for processed silk to dissolve. The length of time used to dissolve processed silk in solvent is referred to herein as "dissolution time." Dissolution times for dissolution of processed silk in various solvents may be from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 360 min, from about 270 min to about 420 min, from about 300 min to about 480 min, or longer than 480 minutes.

The temperature used to dissolve processed silk in solvent is referred to herein as "dissolution temperature." Dissolution temperatures used for dissolution of processed silk in solvent may include room temperature. In some embodiments, dissolution temperature may be from about 0° C. to about 10° C., from about 4° C. to about 25° C., from about 20° C. to about 35° C., from about 30° C. to about 45° C., from about 40° C. to about 55° C., from about 50° C. to about 65° C., from about 60° C. to about 75° C., from about 70° C. to about 85° C., from about 80° C. to about 95° C., from about 90° C. to about 105° C., from about 100° C. to about 115° C., from about 110° C. to about 125° C., from about 120° C. to about 135° C., from about 130° C. to about 145° C., from about 140° C. to about 155° C., from about 150° C. to about 165° C., from about 160° C. to about 175° C., from about 170° C. to about 185° C., from about 180° C. to about 200° C., or greater than 200° C. In some embodiments, the processed silk is silk fibroin. Dissolution of some processed silk solutions may use a dissolution temperature of 60° C. Dissolution of some processed silk solutions may use a dissolution temperature of 80° C., as described in Zheng et al. (2016) Journal of Biomaterials Applications 31:450-463. In some embodiments, dissolution includes boiling. In some embodiments, dissolution may be carried out by autoclaving.

In some embodiments, dissolution may be carried out by autoclaving. In some embodiments, silk fibroin solutions may be prepared according to any of the methods described in International Publication Numbers WO2016029034, WO2017200659, and WO2018031973, U.S. Pat. Nos. 9,394,355, and 9,907,836, US Publication Number US20180193429 or Abdel-Naby (2017) PLOS One 12 (11): e0188154), the contents of each of which are herein incorporated by reference in their entirety. For example, silk fibroin may be autoclaved while it is combined with lithium bromide (LiBr) in an aqueous solution. The aqueous solution may contain LiBr at a concentration of about 8 μM to about 10M. Silk fibroin solution may be heated to a temperature in the range of about 105 to about 125° C. under a pressure of about 10 PSI to about 20 PSI. Silk fibroin solution may be heated for any desired duration of time, e.g., for about 10 minutes, about 20 minutes, about 30 minutes, about 45 minutes, about 1 hour, or longer than 1 hour.

In some embodiments, one or more of sucrose, phosphate buffer, tris buffer, trehalose, mannitol, citrate buffer, ascorbate, histidine, and/or a cryoprotective agent is added to processed silk solutions.

Chaotropic Agents

In some embodiments, processed silk may be dissolved with the aid of a chaotropic agent. As used herein, a "chaotropic agent" refers to a substance that disrupts hydrogen bonding networks in aqueous solutions to facilitate dissolution of a solute. Chaotropic agents typically modify the impact of hydrophobicity on dissolution. Chaotropic agents may be organic compounds. Such compounds may include, but are not limited to, sodium dodecyl sulfate, ethanol, methanol, phenol, 2-propanol, thiourea, urea, n-butanol, and any other chemicals capable of solubilizing silk. In some embodiments, the chaotropic agent is a salt, including, but not limited to, zinc chloride, calcium nitrate, lithium perchlorate, lithium acetate, sodium thiocyanate, calcium thiocyanate, magnesium thiocyanate, calcium chloride, magnesium chloride, guanidinium chloride, lithium bromide, lithium thiocyanate, copper salts, and other salts capable of solubilizing silk. Such salts typically create high ionic strength in the aqueous solutions which destabilizes the beta-sheet interactions in silk fibroin. In some embodiments, a combination of chaotropic agents is used to facilitate the dissolution of silk fibroin. In some embodiments, a chaotropic agent is used to dissolve raw silk during processing.

Molecular Weight

In some embodiments, processed silk preparations may be characterized by the molecular weight of proteins present in the preparations. Different molecular weights may be present as a result of different levels of silk fibroin dissociation and/or fragmentation during degumming or other processing. When referring to silk fibroin molecular weight herein, it should be understood that the molecular weight may be associated with silk fibroin polymers, silk fibroin monomers, silk fibroin heavy and/or light chains, silk fibroin fragments, or variants, derivates, or mixtures thereof. Accordingly, silk fibroin molecular weight values may vary depending on the nature of the silk fibroin or silk fibroin preparation. In some embodiments, processed silk preparations are characterized by average molecular weight of silk fibroin fragments present in the preparation; by a range of silk fibroin fragment molecular weights; by a threshold of silk fibroin fragment molecular weights; or by combinations of averages, ranges, and thresholds.

In some embodiments, processed silk preparation may include silk fibroin, fibroin fragments, or a plurality of fibroin fragments with a molecular weight of, average molecular weight of, upper molecular weight threshold of, lower molecular weight threshold of, or range of molecular weights with an upper or lower range value of from about 1 kDa to about 4 kDa, from about 2 kDa to about 5 kDa, from about 3.5 kDa to about 10 kDa, from about 5 kDa to about 20 kDa, from about 10 kDa to about 35 kDa, from about 15 kDa to about 40 kDa, from about 20 kDa to about 45 kDa, from about 25 kDa to about 50 kDa, from about 30 kDa to about 55 kDa, from about 35 kDa to about 60 kDa, from about 40 kDa to about 65 kDa, from about 45 kDa to about 70 kDa, from about 50 kDa to about 75 kDa, from about 55 kDa to about 80 kDa, from about 60 kDa to about 85 kDa, from about 65 kDa to about 90 kDa, from about 70 kDa to about 95 kDa, from about 75 kDa to about 100 kDa, from about 80 kDa to about 105 kDa, from about 85 kDa to about 110 kDa, from about 90 kDa to about 115 kDa, from about 95 kDa to about 120 kDa, from about 100 kDa to about 125 kDa, from about 105 kDa to about 130 kDa, from about 110 kDa to about 135 kDa, from about 115 kDa to about 140 kDa, from about 120 kDa to about 145 kDa, from about 125 kDa to about 150 kDa, from about 130 kDa to about 155 kDa, from about 135 kDa to about 160 kDa, from about 140 kDa to about 165 kDa, from about 145 kDa to about 170 kDa, from about 150 kDa to about 175 kDa, from about 160 kDa to about 200 kDa, from about 170 kDa to about 210 kDa, from about 180 kDa to about 220 kDa, from about 190 kDa to about 230 kDa, from about 200 kDa to about 240 kDa, from about 210 kDa to about 250 kDa, from about 220 kDa to about 260 kDa, from about 230 kDa to about 270 kDa, from about 240 kDa to about 280 kDa, from about 250 kDa to about 290 kDa, from about 260 kDa to about 300 kDa, from about 270 kDa to about 310 kDa, from about 280 kDa to about 320 kDa, from about 290 kDa to about 330 kDa, from about 300 kDa to about 340 kDa, from about 310 kDa to about 350 kDa, from about 320 kDa to about 360 kDa, from about 330 kDa to about 370 kDa, from about 340 kDa to about 380 kDa, from about 350 kDa to about 390 kDa, from about 360 kDa to about 400 kDa, from about 370 kDa to about 410 kDa, from about 380 kDa to about 420 kDa, from about 390 kDa to about 430 kDa, from about 400 kDa to about 440 kDa, from about 410 kDa to about 450 kDa, from about 420 kDa to about 460 kDa, from about 430 kDa to about 470 kDa, from about 440 kDa to about 480 kDa, from about 450 kDa to about 490 kDa, from about 460 kDa to about 500 kDa, or greater than 500 kDa.

In one embodiment, the silk preparation may include silk fibroin with a molecular weight of or an average molecular weight of 5-60 kDa.

In one embodiment, the silk preparation may include silk fibroin with a molecular weight of or an average molecular weight of 30-60 kDa. In one aspect, silk fibroin in this range maybe referred to as low molecular weight.

In one embodiment, the silk preparation may include silk fibroin with a molecular weight of or an average molecular weight of 100-300 kDa. In one aspect, silk fibroin in this range maybe referred to as high molecular weight.

In one embodiment, the silk preparation may include silk fibroin with a molecular weight of or an average molecular weight of 361 kDa.

Processed silk preparations may be analyzed, for example, by polyacrylamide gel electrophoresis (PAGE) alongside molecular weight standards to determine predominate molecular weights of proteins and/or polymers present. Additional methods for determining the molecular weight range or average molecular weight for a processed silk preparation may include, but are not limited to, sodium dodecyl sulfate (SDS)-PAGE, size-exclusion chromatography (SEC), high pressure liquid chromatography (HPLC), non-denaturing PAGE, and mass spectrometry (MS).

In some embodiments, silk fibroin molecular weight is modulated by the method of degumming used during processing. In some embodiments, longer heating times during degumming are used (e.g., see International Patent Application Publication No. WO2014145002, the contents of which are herein incorporated by reference in their entirety). Longer heating (e.g., boiling) time may be used during the degumming process to prepare silk fibroin with lower average molecular weights. In some embodiments, heating times may be from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 400 min, from about 270 min to about 450 min, from about 300 min to about 480 min, or more than 480 min. Additionally, the sodium carbonate concentration used in the degumming process, as well as the heating temperature, may also be altered to modulate the molecular weight of silk fibroin.

In some embodiments, silk fibroin molecular weight is presumed, without actual analysis, based on methods used to prepare the silk fibroin. For example, silk fibroin may be presumed to be low molecular weight silk fibroin or high molecular weight silk fibroin based on the length of time that heating is carried out (e.g., by minute boil value). In some embodiments, the molecular weight range for silk fibroin with a 480 mb is between 5-20 kDa. In some embodiments, the molecular weight as defined by the minute boil is as described in International Patent Application Publication No. WO2017139684.

In some embodiments, SBPs include a plurality of silk fibroin fragments generated using a dissociation procedure. The dissociation procedure may include one or more of heating, acid treatment, chaotropic agent treatment, sonication, and electrolysis. Some SBPs include a plurality of silk fibroin fragments dissociated from raw silk, silk fiber, and/or silk fibroin by heating. The heating may be carried out at a temperature of from about 30° C. to about 1,000° C. In some embodiments, heating is carried out by boiling. The raw silk, silk fiber, and/or silk fibroin may be boiled for from about 1 second to about 24 hours.

Bond and Amino Acid Content

In some embodiments, processed silk preparations may be characterized by the content of various amino acids present in the preparations. Different ratios and/or percentages of one or more amino acids may be present as a result of degumming or other processing. Such amino acids may include serine, glycine, and alanine. Amino acid content of processed silk preparations may be measured by any method known to one of skill in the art, including, but not limited to amino acid analysis and mass spectrometry. In some embodiments, the amino acid content of a processed silk preparation is measured for one amino acid (e.g. serine). In some embodiments, the amino acid content of a processed silk preparation may be measured for a combination of two or more amino acids (e.g. serine, glycine, and alanine). In some embodiments, processed silk preparations of the present disclosure may contain from about 0% to about 1%, from about 1% to about 5%, from about 5% to about 10%, from about 10% to about 15%, from about 15% to about 20%, from about 20% to about 25%, from about 25% to about 30%, from about 30% to about 35%, from about 35% to about 40%, or from about 40% to about 45% of any of the one or more amino acids described herein.

In some embodiments, the amino acid content of silk fibroin may be altered after processing (e.g. degumming). In some embodiments, the serine content of silk fibroin may decrease after processing (e.g. degumming). The serine content of silk fibroin in processed silk preparations may decrease by about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or about 25%.

In some embodiments, processed silk preparations may be characterized by the content of disulfide bonds present in the preparations. Different ratios and/or percentages of disulfide bonds may be present as a result of degumming or other processing. Disulfide bond content of processed silk preparations may be measured by any method known to one of skill in the art. In some embodiments, the disulfide bond content of silk fibroin may be altered after processing (e.g. degumming and/or boiling). In some embodiments, the disulfide bond content of silk fibroin may decrease after processing (e.g. degumming and/or boiling). The disulfide bond content of silk fibroin in processed silk preparations may decrease by about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37% 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100%.

Purification and Concentration

In some embodiments, processed silk preparations may be purified. Purification, as used herein, refers to any process used to segregate or extract one entity from another. In some embodiments, purification is manual or automated. Purification may include the removal of salts, impurities, or contaminants from processed silk preparations.

In some embodiments, processed silk may be purified by concentration from a processed silk solution. Methods of concentrating silk fibroin from processed silk solutions may include any of those described in the International Patent Application Publication No. WO2017139684, the contents of which are incorporated herein by reference in their entirety. In some embodiments, purification and/or concentration may be carried out by one or more of dialysis, centrifugation, air drying, vacuum drying, filtration, and/or Tangential Flow Filtration (TFF).

In some embodiments, processed silk solutions are purified by dialysis. Dialysis may be carried out to remove undesired salts and/or contaminants. In some embodiments, processed silk solutions are concentrated via dialysis. Purification and/or concentration of processed silk by dialysis may be carried out as described in International Patent Application Publication No. WO2005012606, the contents of which are herein incorporated by reference in their entirety. In some embodiments, the dialysis is performed against a hygroscopic polymer to concentrate the silk fibroin solution. In some embodiments the dialysis is manual, with the use of a membrane and manual solvent changes. In some embodiments, the solvent is changed between 1 and 10 times over the course of the procedure. In some embodiments, the membrane is a dialysis cassette. The dialysis cassette may be a slide-a-lyzer dialysis cassette. In some embodiments, the membrane is dialysis tubing. The dialysis tubing may be regenerated cellulose dialysis tubing and/or snake skin. The dialysis tubing or cassette may be rinsed in distilled water for 30 minutes to prepare the membrane for use. In some embodiments, the dialysis tubing has a molecular weight cutoff of 3.5 kDa. In some embodiments, the dialysis is performed at a temperature of from about 1° C. to about 30° C. In some embodiments, dialysis is performed at room temperature. In other embodiments, the dialysis is performed at 4° C. Dialysis may be performed until desired concentrations of silk fibroin and salt are obtained from processed silk solutions. Dialysis may be performed for periods of time from about 30 minutes to about 24 hours or beyond. For example, dialysis may be carried out for from about 30 minutes to about 2 hours, from about 1 hour to about 6 hours, from about 3 hours to about 10 hours, from about 5 hours, to about 12 hours, from about 7 hours to about 15 hours, from about 11 hours to about 20 hours, or from about 16 hours to about 24 hours.

In some embodiments, dialysis may be automated. The dialysis may use an automated water change system. Such systems may include tanks of up to 10 L and may be able to hold multiple dialysis cassettes (e.g., see International Patent Application Publication No. WO2017106631, the contents of which are herein incorporated by reference in their entirety). Automated equipment may enable purification of larger volumes of solution with greater efficiency. Automated controllers, programmed with the proper times and volumes, may be used to facilitate changes of solvent or buffer over the course of dialysis. The solvent may be replaced from about 1 to about 20 times or more during dialysis. In some embodiments, automated dialysis may be completed in about 48 hours.

Dialysis may be performed with various solvents depending on the nature of the preparation being processed. In some embodiments the solvent is water. In some embodiments, the solvent is an aqueous solution. In some embodiments the solvent includes a hygroscopic polymer. Hygroscopic polymers may include, but are not limited to, polyethylene glycol (PEG), polyethylene oxide (PEO), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, and polyanhydrides. Additional examples of polymers, hygroscopic polymers, and related dialysis methods that may be employed include any of those found in International Patent Application Publication Nos. WO2005012606, WO2005012606, and WO2017106631, and U.S. Pat. Nos. 6,302,848; 6,395,734; 6,127,143; 5,263,992; 6,379,690; 5,015,476; 4,806,355; 6,372,244; 6,310,188; 5,093,489; 6,325,810; 6,337,198; 6,267,776; 5,576,881; 6,245,537; 5,902,800; and 5,270,419; the contents of each of which are herein incorporated by reference in their entirety. Hygroscopic polymer concentrations may be from about 20% (w/v) to about 50% (w/v). In some embodiments, dialysis may be performed in a stepwise manner in a urea solution, and the urea solution may be subsequently be replaced with urea solutions of a lower concentration during buffer changes, until it is ultimately replaced with water, as described in Zheng et al. (2016) Journal of Biomaterials Applications 31:450-463.

In some embodiments, processed silk preparations may be purified by filtration. Such filtration may include trans flow filtration (TFF), also known as tangential flow filtration. During TFF, solutions may be passed across a filter membrane. Anything larger than the membrane pores is retained, and anything smaller passes through the membrane (e.g., see International Patent Application Publication No. WO2017106631, the contents of which are herein incorporated by reference in their entirety). With the positive pressure and flow along the membrane, instead of through it, particles trapped in the membrane may be washed away. TFF may be carried out using an instrument. The instrument may be automated. The membranes may be housed in TFF tubes with vertical inlets and outlets. The flow of solvent may be controlled by peristaltic pumps. Some TFF tubes may include a dual chamber element. The dual chamber element may enable TFF filtration of processed silk solutions at higher concentrations, while reducing aggregation via the reduction of shear forces.

In some embodiments, processed silk solutions are purified and/or concentrated by centrifugation. Centrifugation may be performed before or after other forms of purification, which include, but are not limited to dialysis and tangential flow filtration. Centrifugation times and speeds may be varied to optimize purification and/or concentration according to optimal time frames. Purification and/or concentration by centrifugation may include pelleting of the processed silk and removal of supernatant. In some cases, centrifugation is used to push solvent through a filter, while retaining processed silk. Centrifugation may be repeated as many times as needed. In some embodiments, silk fibroin solutions are centrifuged two or more times during concentration and/or purification.

In some embodiments, processed silk may be purified by any method known to one of skill in the art. In some embodiments, processed silk is purified to remove salts (e.g. lithium bromide). In some embodiments, processed silk is purified to isolate processed silk of a desired molecular weight. In some embodiments, processed silk is purified by chromatography. Chromatography may include preparatory-scale, gravity, size exclusion chromatography (SEC). In some embodiments, processed silk is purified by gel permeation chromatography. Processed silk may be purified at any scale. In some embodiments, processed silk is purified on a milligram scale. In some embodiments, processed silk is purified on a gram scale. In some embodiments, processed silk is purified on a kilogram scale.

In some embodiments, SBP formulations may be directly prepared from dialyzed silk fibroin. In some embodiments, SBP formulations may be directly prepared from dialyzed and filtered silk fibroin.

Drying Methods

In some embodiments, processed silk preparations are dried to remove solvent. In some embodiments, SBP formulations may be rinsed prior to drying. Methods of drying may include, but are not limited to, air drying, oven drying, lyophilization, spray drying, spray freezing, and vacuum drying. Drying may be carried out to alter the consistency and/or other properties of processed silk preparations. One or more compounds or excipients may be combined with processed silk preparations to improve processed silk recovery and/or reconstitution after the drying process. For example, sucrose may be added to improve silk fibroin recovery and reconstitution from dried solutions. In some embodiments, drying may be carried out in the fabrication of a processed silk format or a SBP. Examples include, but are not limited to fabrication of fibers, nanofibers, mats, films, foams, membranes, rods, tubes, gels, hydrogels, microspheres, nanospheres, solutions, patches, grafts and powders. In some embodiments, drying processed silk is carried out by oven drying, lyophilizing, and/or air drying.

Oven drying refers to any drying method that uses an oven. According to some methods, ovens are maintained at temperatures of from about 30° C. to about 90° C. or more. In some embodiment, oven drying is carried out at a temperature of 60° C. Processed silk preparations may be placed in ovens for a period of from about 1 hour to about 24 hours or more. In one embodiment, SBP formulations are oven dried at 60° C. for 2 hours. Oven drying may be used to dry silk fibroin preparations. In some embodiments, silk fibroin preparations are oven dried for 16 hours at 60° C. to obtain a desired format. In some cases, silk fibroin solutions are oven dried overnight. Examples of formats obtained by oven drying may include, but are not limited to, fibers, nanofibers, mats, films, foams, membranes, rods, tubes, gels, hydrogels, microspheres, nanospheres, solutions, patches, grafts, and powders.

In some embodiments, processed silk preparations are freeze dried. Freeze drying may be carried out by lyophilization. Freeze drying may require processed silk preparations to be frozen prior to freeze drying. Freezing may be carried out at temperatures of from about 5° C. and about −85° C. In some embodiments, freeze drying is carried out by lyophilization for up to 75 hours. In some embodiments, lyophilization is used to prepare processed silk formats or SBPs. Such formats may include, but are not limited to, fibers, nanofibers, mats, films, foams, membranes, rods, tubes, gels, hydrogels, microspheres, nanospheres, solutions, patches, grafts and powders. The use of lyophilization to fabricate SBPs may be carried out according to any of the methods described in Zhou et al. (2017) Acta Biomater S1742-7061 (17) 30569; Yang et al. (2017) Int J Nanomedicine 12:6721-6733; Seo et al. (2017) J Biomater Appl 32 (4):

484-491; Ruan et al. (2017) Biomed Pharmacother 97:600-606; Wu et al. (2017) J Mech Behav Biomed Mater 77:671-682; Zhao et al. (2017) Materials Letters 211:110-113; Chen et al. (2017) PLOS One 12 (11): e0187880; Min et al. (2017) Int J Biol Macromol 17:32855-8; Sun et al. Journal of Materials Chemistry B 5:8770; and Thai et al. J Biomed Mater (2017) 13 (1): 015009, the contents of each of which are herein incorporated by reference in their entirety.

In some embodiments, processed silk preparations may be dried by air drying. "Air drying," as used herein refers to the removal of moisture by exposure to ambient or circulated gasses. Air drying may include exposing a preparation to air at room temperature (from about 18° C. to about 29° C.). Air drying may be carried out for from about 30 minutes to about 24 hours or more. In some embodiments, silk fibroin preparations are air dried to prepare SBPs. SBP formats that may be prepared may include, but are not limited to, fibers, nanofibers, mats, films, foams, membranes, rods, tubes, gels, hydrogels, microspheres, nanospheres, solutions, patches, grafts and powders. Some examples of the use of air drying for fabrication of SBPs are presented in Susanin et al. (2017) Fibre Chemistry 49 (2): 88-96; Lo et al. J Tissue Eng Regen Med (2017) doi. 10.1002/term.2616; and Mane et al. Scientific Reports 7:15531, the contents of each of which are herein incorporated by reference in their entirety.

Spinning

In some embodiments, processed silk may be prepared by spinning. As used herein, the term "spinning" refers to a process of twisting materials together. Spinning may include the process of preparing a silk fiber by twisting silk proteins as they are secreted from silk producers. Other forms of spinning include spinning one or more forms of processed silk together to form a thread, filament, fiber, or yarn. The processed silk may already consist of a filamentous format prior to spinning. In some embodiments, processed silk is processed by spinning from a non-filamentous format (e.g., from a film, mat, or solution).

In some embodiments, spinning includes the technique of electrospinning. Electrospinning may be used to prepare silk fibers from silk fibroin. The silk fibroin may be dissolved in water or an aqueous solution before electrospinning. In other embodiments, silk fibroin is dissolved in an organic solvent before electrospinning. The organic solvent may be hexafluoroisopropanol (HFIP). In some embodiments, electrospinning may be carried out as described in Yu et al. (2017) Biomed Mater Res A doi. 10.1002/jbm.a.36297 or Chantawong et al. (2017) Mater Sci Mater Med 28 (12): 191, the contents of each of which are herein incorporated by reference in their entirety.

Electrospinning typically includes the use of an electrospinning apparatus. Processed silk may be added to the apparatus to produce silk fiber. The processed silk may be silk fibroin in solution. Electrospinning apparatus components may include one or more of a spinneret (also referred to spinnerette), needle, mandrel, power source, pump, and grounded collector. The apparatus may apply voltage to the dissolved silk fibroin, causing electrostatic repulsion that generates a charged liquid that is extruded from the end. Electrostatic repulsion also enables fiber elongation as it forms, and charged liquid cohesion prevents it from breaking apart. Resulting fiber may be deposited on the collector. In some embodiments, electrospinning methods may be carried out according to those described in European Patent No. EP3206725; Manchineella et al. (2017) European Journal of Organic Chemistry 30:4363-4369; Park et al. (2017) Int J Biomacromol S0141-8130 (17): 32645-4; Wang et al. (2017) J Biomed Mater Res A doi. 10.1002/jbm.a.36225; Chendang et al. (2017) J Biomaterials and Tissue Engineering 7:858-862; Kambe et al. (2017) Materials (Basel) 10 (10): E1153; Chouhan et al. (2017) J Tissue Eng Reneg Med doi. 10.1002/term.2581; Genovese et al. (2017) ACS Appl Mater Interfaces doi. 10.1021acsami.7b13372; Yu et al. (2017) Biomed Mater Res A doi. 10.1002/jbm.a.36297; Chantawong et al. (2017) Mater Sci Mater Med 28 (12): 191, the contents of each of which are herein incorporated by reference in their entirety.

In some embodiments, spinning may be carried out as dry spinning. Dry spinning may be carried out using a dry spinning apparatus. Dry spinning may be used to prepare silk fibers from SBP formulations. The preparations may include silk fibroin solutions. The preparations may be aqueous solutions. Dry spinning apparatuses typically use hot air to dry processed silk as it is extruded. In some embodiments, dry spinning may be carried out according to any of the methods presented in Zhang et al. (2017) Int J Biol Macromol pii: S0141-8130 (17): 32857, the contents of which are herein incorporated by reference in their entirety.

Processing Methods: Spraying

In some embodiments, processing methods include spraying. As used herein, the term "spraying" refers to the sprinkling or showering of a compound or composition in the form of small drops or particles. Spraying may be used to prepare SBPs by spraying processed silk. Spraying may be carried out using electrospraying. Processed silk used for spraying may include processed silk in solution. The solution may be a silk fibroin solution. Solutions may be aqueous solutions. Some solutions may include organic solvents. Electrospraying may be carried out in a manner similar to that of electrospinning, except that the charged liquid lacks cohesive force necessary to prevent extruding material from breaking apart. In some embodiments, spraying methods may include any of those presented in United States Publication No. US2017/333351 or Cao et al. (2017) Scientific Reports 7:11913, the contents of each of which are herein incorporated by reference in their entirety. In some embodiments, electrospray methods include a coaxial system for coaxial spraying.

In some embodiments, spraying is carried out as spray drying. Spray drying is a method of producing a dry powder from a liquid or slurry by rapidly drying with a hot gas. For example, the silk fibroin solution may be introduced as a fine spray or mist into a tower or chamber with heated air. The large surface area of the spray droplets causes evaporation of the water to occur rapidly, converting the droplets into dry powder particles. The heat and drying process may induce beta-sheet formation in the silk fibroin. Additional advantages of spray drying may include low heat, speed, reproducibility, and scalability.

In one embodiment, the spraying is carried out as spray drying using the electrostatic spray drying methods known in the art.

In some embodiments, spraying is carried out as spray coating. For example, SBP formulations may be sprayed onto the surface of a substance to form a coating. The spray coating processing may be a thermal spray coating process where SBP formulations are heated or melted by a heat source, for example, by electrical means (plasma or arc) or chemical means (combustion flame). Thermal spraying techniques that may be used herein include, but are not limited to, plasma spraying, detonation spraying, wire arc spraying, flame spraying, high velocity oxy-fuel coating spraying (HVOF), high velocity air fuel (HVAF), warm spraying, and cold spraying.

In one embodiment, the spray coating may be used for enteric capsules.

Processing Methods: Precipitation

In some embodiments, processing methods include precipitation. As used herein, the term "precipitation" refers to the deposition of a substance in solid form from a solution. Precipitation may be used to obtain solid processed silk from processed silk solutions. The processed silk may be silk fibroin. Processed silk may be precipitate from a solution. The solvent may be aqueous. In some embodiments, the solvent is organic. Examples of organic solvents include, but are not limited to, HFIP, methanol, ethanol, and other alcohols. In some embodiments, the solvent is water. In some embodiments the solvent is a mixture of an organic solvent and water. Aqueous solvents may contain one or more salts. Processed silk may be precipitated from processed silk solutions by modulating one or more components of the solution to alter the solubility of the processed silk and promote precipitation. Additional processing steps may be employed to initiate or speed precipitation. Such methods may include, but are not limited to sonication, centrifugation, increasing the concentration of processed silk, altering the concentration of salt, adding additional salt or salts, altering the pH, applying shear stress, adding excipients, or applying chemical modifications.

Processing Methods: Milling

In some embodiments, processing methods include milling. As used herein, "milling" generally refers to the process of breaking down a solid substance into smaller pieces using physical forces such as grinding, crushing, pressing and/or cutting. As a non-limiting example, SBP formulations may be milled to create powders. The density of powder formulations may be controlled during the milling process. As another non-limiting example, solid encapsulation of a therapeutic agent or cargo with another substance (e.g., SBPs) may be prepared by milling. The therapeutic agent or cargo may include any one of those described herein. In some embodiments, the therapeutic agent or cargo to be encapsulated by another substance may include SBPs.

Altering Mechanical Properties

In some embodiments, the mechanical properties of processed silk may be altered by modulating physical and/or chemical properties of the processed silk. The mechanical properties include, but are not limited to, mechanical strength, tensile strength, elongation capabilities, elasticity, compressive strength, stiffness, shear strength, toughness, torsional stability, temperature stability, moisture stability, viscosity and reeling rate. In some embodiments, the tensile strength of processed silk is stronger than steel. In some embodiments, the tensile strength of SBPs is stronger than steel. Examples of the physical and chemical properties used to tune the mechanical properties of processed silk include, but are not limited to, the temperature, formulations, silk concentration, β-sheet content, crosslinking, the molecular weight of the silk, the storage of the silk, storage, methods of preparation, dryness, methods of drying, purity, and degumming. Methods of tuning the mechanical strength of processed silk are taught in International Patent Application Publication No. WO2017123383, European Patent No. EP2904134, European Patent No. EP3212246, Fang et al., Wu et al., Susanin et al., Zhang et al., Jiang et al., Yu et al., Chantawong et al., and Zhang et al. (Fang et al. (2017) Journal of Materials Chemistry B 5 (30): 6042-6048; Wu et al. (2017) J Mech Behav Biomed Mater 77:671-682; Susanin et al. (2017) Fibre Chemistry 49 (2): 88-96; Zhang et al. (2017) Fibers and Polymers 203:9-16; Jiang et al. (2017) J Biomater Sci Polym Ed 15:1-36; Yu et al. (2017) Biomed Mater Res A doi. 10.1002/jbm.a.36297; Chantawong et al. (2017) Mater Sci Mater Med 28 (12): 191; Zhang et al. (2017) Int J Biomacromol S0141-8310 (17): 32857), the contents of each of which are herein incorporated by reference in their entirety.

In some embodiments, the excipients which may be incorporated in a formulation may be used to control the modulus of SBP formulations. In some embodiments, these SBP formulations are hydrogels.

In some embodiments, processed silk hydrogels are prepared with different excipients and tested for their mechanical properties, including the modulus. SBP formulations may be assessed for modulus, shear storage modulus, shear loss modulus, phase angle, and viscosity using a rheometer, and/or any other method known to one skilled in the art. Rheometer geometry may be selected based on sample viscosity, shear rates, and shear stresses desired, as well as sample volumes. Geometries that are suitable for measuring the rheological properties of SBP formulations include, not are not limited to, cone and plate, parallel plates, concentric cylinders (or Bob and Cup), and double gap cylinders. In one embodiment, a cone and plate geometry is used. In another embodiment, a concentric cylinder geometry is used. SBP formulations may be tested both before and after gelation. In some embodiments, SBP formulations are prepared, optionally with different excipients, and tested for their mechanical properties, including the shear storage modulus, the shear loss modulus, phase angle, and viscosity. As used herein, the term "shear storage modulus" refers to the measure of a material's elasticity or reversible deformation as determined by the material's stored energy. As used herein, the term "shear loss modulus" refer to the measure of a material's ability to dissipate energy, usually in the form of heat. As used herein, the term "phase angle" refers to the difference in the stress and strain applied to a material during the application of oscillating shear stress. As used herein, the term "viscosity" refers to a material's ability to resist deformation due to shear forces, and the ability of a fluid to resist flow. In some embodiments, processed silk hydrogels may possess similar viscosities, but vary in the modulus.

In some embodiments, the concentration of processed silk may enable silk preparations to shear thin. In some embodiments the silk preparation is an SBP. In some embodiments, the SBP is a hydrogel. In some embodiments, the molecular weight of processed silk hydrogels may enable hydrogels to shear thin. In some embodiments, hydrogels prepared with low molecular weight silk fibroin may be injected with much less force than hydrogels of similar viscosity that are prepared with higher molecular weight silk fibroin. In some embodiments, hydrogels with low molecular weight silk fibroin display higher viscosity than hydrogels with high molecular weight silk fibroin.

In some embodiments, the concentration of silk fibroin may be used to control the shear storage modulus and/or the shear loss modulus of processed silk preparations. In some embodiments, a preparation with stressed silk may be used to control the shear storage modulus and the shear loss modulus. In some embodiments, the excipients incorporated in a formulation may be used to control the shear storage modulus and/or the shear loss modulus of processed silk preparations. In some embodiments, these processed silk preparations are hydrogels. In some embodiments, these processed silk preparations are solutions. In some embodiments, processed silk preparations are prepared, optionally with different excipients, and tested for their mechanical and physical properties, including the shear storage modulus, the shear loss modulus, phase angle, and viscosity. As used herein, the term "shear storage modulus" refers to the measure of a material's elasticity or reversible deformation as determined by the material's stored energy. As used herein, the term "shear loss modulus" refers to the measure of a material's ability to dissipate energy, usually in the form of heat. As used herein, the term "phase angle" refers to the difference in the stress and strain applied to a material during the application of oscillating shear stress. As used herein, the term "viscosity" refers to a material's ability to resist deformation due to shear forces, and the ability of a material to resist flow. Processed silk preparations may be assessed for shear storage modulus, shear loss modulus, phase angle, and viscosity using a rheometer, and/or any other method known to one skilled in the art. Rheometer geometry may be selected based on sample viscosity, shear rates, and shear stresses desired, as well as sample volumes. Geometries that are suitable for measuring the rheological properties of SBP formulations include, not are not limited to, cone and plate, parallel plates, concentric cylinders (or Bob and Cup), and double gap cylinders. In one embodiment, a cone and plate geometry is used. In another embodiment, a concentric cylinder geometry is used. Processed silk preparations may be tested both before and after gelation. In some embodiments, processed silk preparations may possess similar viscosities, but vary in the modulus. In some embodiments, the processed silk preparations may have the viscosity of a liquid. In some embodiments, the processed silk preparations may have the viscosity of a gel.

In some embodiments, the processed silk preparations may shear thin or display shear thinning properties. As used herein, the term "shear thinning" refers to a decrease in viscosity at increasing shear rates. As used herein, the term "shear rate" refers to the rate of change in the ratio of displacement of material upon the application of a shear force to the height of the material. This ratio is also known as strain. In some embodiments, the boiling time during degumming of processed silk may enable processed silk preparations to shear thin. In some embodiments, the concentration of processed silk may enable silk preparations to shear thin. In some embodiments, the processed silk preparations may have the viscosity of a liquid at higher shear rates. In some embodiments, the processed silk preparations may have the viscosity of a gel at lower shear rates.

In some embodiments, the mechanical properties of processed silk preparations may be tuned by a preparation with stressed silk. As used herein, the term "stress" or "stressed" refers to a treatment that may alter the shelf life and/or stability of processed silk and/or an SBP. In some embodiments, processed silk is stressed by treatment with heat. In some embodiments, processed silk is stressed by heating to 60° C. In some embodiments, processed silk is stressed by heating overnight. In some embodiments, processed silk is stressed by autoclave. In some embodiments, processed silk is stressed by overnight heating to 60° C. followed by autoclave. In some embodiments, silk is stressed during the preparation of processed silk. In some embodiments, processed silk is stressed during the preparation of SBPs. In some embodiments, SBPs are stressed. Stressed silk or SBPs may be used in any of the embodiments described in the present disclosure.

In some embodiments, boiling silk fibroin in 0.02M sodium carbonate for 480 minutes may result in a polydisperse mixture of peptides ranging in molecular weight from about 200,000 Da to about 7000 Da, with an average molecular weight of about 35,000 Da. In some embodiments, the molecular weight of polymers (e.g. processed silk) may have a dramatic effect on properties such as stability, viscosity, surface tension, gelation and bioactivity. In some embodiments, polydisperse processed silk (e.g. silk fibroin degummed with a 480 minute boil) may be separated into narrow molecular weight fractions. In some embodiments, the separation of polydisperse processed silk may optimize one or more properties of an SBP (e.g. stability, viscosity, surface tension, gelation and bioactivity). Polydisperse mixtures of processed silk may be separated into fractions by any method known to one of skill in the art. In some embodiments, fractionation of processed silk may be used to isolate processed silk with narrower polydispersity. In some embodiments, processed silk is fractionated by preparatory-scale, gravity, size exclusion chromatography (SEC). In some embodiments, processed silk is fractionated by gel permeation chromatography. Processed silk may be fractionated at any scale. In some embodiments, processed silk is fractionated on a milligram scale. In some embodiments, processed silk is fractionated on a gram scale. In some embodiments, processed silk is fractionated on a kilogram scale.

Modulating Degradation and Resorption

In some embodiments, processed silks are, or are processed to be, biocompatible. As used herein, a "biocompatible" substance is any substance that is not harmful to most living organisms or tissues. With some processed silk, degradation may result in products that are biocompatible, making such processed silk attractive for a variety of applications. Some processed silk may degrade into smaller proteins or amino acids. Some processed silk may be resorbable under physiological conditions. In some embodiments, products of silk degradation may be resorbable in vivo. In some embodiments, the rate of degradation of processed silk may be tuned by altering processed silk properties. Examples of these properties include, but are not limited to, type and concentration of certain proteins, β-sheet content, crosslinking, silk fibroin molecular weight, and purity. In some embodiments, rate of processed silk degradation may be modulated by method of storage, methods of preparation, dryness, methods of drying, reeling rate, and degumming process.

In some embodiments, the bioresorbability and degradation of processed silk is modulated by the addition of sucrose, as taught in Li et al. (Li et al. (2017) Biomacromolecules 18 (9): 2900-2905), the contents of which are herein incorporated by reference in their entirety. Processed silk may be formulated with sucrose to enhance thermal stability. Furthermore, processed silk with sucrose may also be formulated with antiplasticizing agents to further enhance thermal stability of processed silk, SBPs, and/or therapeutic agents included in SBPs. Methods of increasing thermal stability using antiplasticizing agents may include any of those described in Li et al. (Li et al. (2017) Biomacromolecules 18 (9): 2900-2905), the contents of which are herein incorporated by reference in their entirety. In some embodiments, the addition of sucrose to processed silk preparations prior to lyophilization leads to an increased reconstitution efficiency. In some embodiments, the addition of sucrose may be used to create higher molecular weight processed silk preparations as well as to maintain long term storage stability. In some embodiments, the incorporation of sucrose into processed silk preparations described herein enables slower freezing during lyophilization cycle.

In some embodiments, an SBP maintains and or improves stability by at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 14 weeks, at least 4 months, at least 18 weeks, at least 5 months, at least 22 weeks, at least 6 months, at least 7 months, at least 8 months, at least 9 months, at least 10 months, at least 11 months, at least a year, at least 2 years, at least 3 years, at least 4 years, at least 5 years, or more than 5 years. In some embodiments, an SBP preparation reduces stability by In some embodiments, an SBP maintains and or improves stability by at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 14 weeks, at least 4 months, at least 18 weeks, at least 5 months, at least 22 weeks, at least 6 months, at least 7 months, at least 8 months, at least 9 months, at least 10 months, at least 11 months, at least a year, at least 2 years, at least 3 years, at least 4 years, at least 5 years, or more than 5 years. In some embodiments, an SBP may have a shelf life of least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 14 weeks, at least 4 months, at least 18 weeks, at least 5 months, at least 22 weeks, at least 6 months, at least 7 months, at least 8 months, at least 9 months, at least 10 months, at least 11 months, at least a year, at least 2 years, at least 3 years, at least 4 years, at least 5 years, or more than 5 years.

In some embodiments, the bioresorbability and degradation of processed silk may be tuned through formulation with additional bioresorbable polymer matrices, as taught in International Patent Application Publication Numbers WO2017177281 and WO2017179069, the contents of each of which are herein incorporated by reference in their entirety. In some embodiments, the polymer matrix is polyurethane. In some embodiments, these polymer matrices may be polycaprolactone and a ceramic filler. The ceramic filler may include MgO.

In some embodiments, the bioresorbability and degradation of processed silk is tuned through the fabrication of a composite scaffold. Composite scaffolds, combinations of scaffolds or scaffolds formed from more than one material, may be formed from two or more SBP formulations. In some embodiments, processed silk scaffolds comprising a combination of silk fibroin microspheres within a larger processed silk preparation may demonstrate slower degradation in comparison with other scaffolds, as taught in European Patent No. EP3242967, the contents of which are herein incorporated by reference in their entirety.

Analytics

In some embodiments, processed silk products may be analyzed for properties such as molecular weight, aggregation, amino acid content, lithium content, heavy metal content, bromide content and endotoxin level. Such properties may be evaluated via any analytical methods known in the art. As a non-limiting example, the Ultra-Performance Liquid Chromatography (UPLC)-Size Exclusion Chromatography (SEC) method may be used to assess the molecular weight and/or aggregation of the silk fibroin proteins in the processed silk products.

In some embodiments, processed silk products may be analyzed for silk fibroin concentration. Such properties may be evaluated via any analytical methods known in the art. As a non-limiting example, gravimetry and/or ultraviolet-visible spectroscopy (UV-Vis) may be used.

In some embodiments, silk fibroin molecular weight is modulated by the method of degumming used during processing. In some embodiments, longer heating times during degumming are used (e.g., see International Publication No. WO2014145002, the contents of which are herein incorporated by reference in their entirety). Longer heating (e.g., boiling) time may be used during the degumming process to prepare silk fibroin with lower average molecular weights. In some embodiments, heating times may be from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 400 min, from about 270 min to about 450 min, from about 300 min to about 480 min, or more than 480 min. Additionally, the sodium carbonate concentration used in the degumming process, as well as the heating temperature, may also be altered to modulate the molecular weight of silk fibroin. In one embodiment, the alteration may cause an increase in the molecular weight of silk fibroin. As compared to silk fibroin where the sodium carbonate concentration and/or the heating temperature was not altered, the increase of the molecular weight may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% higher. In one embodiment, the alteration may cause a decrease in the molecular weight of silk fibroin. As compared to silk fibroin where the sodium carbonate concentration and/or the heating temperature was not altered, the decrease of the molecular weight may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% lower.

In some embodiments, silk fibroin molecular weight may be presumed, without actual analysis, based on methods used to prepare the silk fibroin. For example, silk fibroin may be presumed to be low molecular weight silk fibroin or high molecular weight silk fibroin based on the length of time that heating is carried out (e.g., by minute boil value).

In some embodiments, SBP formulations include a plurality of silk fibroin fragments generated using a dissociation procedure. The dissociation procedure may include one or more of heating, acid treatment, base treatment, chaotropic agent treatment, sonication, and electrolysis. Some SBPs include a plurality of silk fibroin fragments dissociated from raw silk, silk fiber, and/or silk fibroin by heating. The heating may be carried out at a temperature of from about 30° C. to about 1,000° C. In some embodiments, heating is carried out by boiling. The raw silk, silk fiber, and/or silk fibroin may be boiled for from about 1 second to about 24 hours.

Porosity

In some embodiments, processed silk may include variations in porosity. As used herein, the term "porosity" refers to the frequency with which holes, pockets, channels, or other spaces occur in a material, in some cases influencing the movement of elements to and/or from the material. Processed silk porosity may influence one or more other silk properties or properties of an SBP that includes the processed silk. These properties may include, but are not limited to, stability, payload retention or release, payload release rate, wettability, mechanical strength, tensile strength, elongation capabilities, density, thickness, elasticity, compressive strength, stiffness, shear strength, toughness, torsional stability, temperature stability, and moisture stability. In some embodiments, processed silk porosity may control the diffusion or transport of agents from, within, or into the processed silk or SBP. Such agents may include, but are not limited to, therapeutics, biologics, chemicals, small molecules, oxidants, antioxidants, macromolecules, microspheres, nanospheres, cells, or any payloads described herein.

Processed silk porosity may be modulated during one or more processing steps or during fabrication of a SBP (e.g., see International Publication No. WO2014125505 and U.S. Pat. No. 8,361,617, the contents of each of which are herein incorporated by reference in their entirety). In some embodiments, processed silk porosity may be modulated by one or more of sonication, centrifugation, modulating silk fibroin concentration, modulating salt concentration, modulating pH, modulating secondary structural formats, applying shear stress, modulating excipient concentration, chemical modification, crosslinking, or combining with cells, bacteria, and/or viral particles.

Strength and Stability

Processed silk strength and stability are important factors for many applications. In some embodiments, processed silk may be selected based on or prepared to maximize mechanical strength, tensile strength, elongation capabilities, elasticity, flexibility, compressive strength, stiffness, shear strength, toughness, torsional stability, biological stability, resistance to degradation, and/or moisture stability. In some embodiments, processed silk has a non-acidic microenvironment. In some embodiments, the non-acidic microenvironment enhances the stability of processed silk and or SBPs. In some embodiments, the non-acidic microenvironment enhances the stability of therapeutic agents formulated with processed silk and/or SBP. In some embodiments, the tensile strength of processed silk is stronger than steel. In some embodiments, the tensile strength of an SBP is stronger than steel.

In some embodiments, processed silk may demonstrate stability and/or is determined to be stable under various conditions. As used herein, "stability" and "stable" refers to the capacity of a substance (e.g. an SBP) to remain unchanged over time under the described conditions. Those conditions may be in vitro, in vivo, or ex vivo. In some embodiments, an SBP may be stable for up to 1 hour, up to 3 days, up to 1 week, up to 1 month, up to 3 months, up to 4 months, up to 6 months, up to 7 months, up to 1 year, up to 2 years, or up to 5 years.

Injectability

In some embodiments, processed silk may be selected based on or prepared to modulate the injectability of an SBP formulation. As used herein, the term "injectability" refers to the force required to push a composition through a syringe or syringe and needle. Injections may be used to administer SBP formulations. The SBP formulations may be administered via syringe to a subject. Injectability may be measured by the force required to push the composition through the desired syringe. The force may be, but is not limited to 10, 20, 30, 40, 50, 60, 70, 80, 90, 100, 110, 120, 130, 140, 150, 160, 170, 180, 190, or 200 N, or a range of 10-50, 10-60, 10-90, 10-100, 10-110, 10-150, 10-200, 20-50, 20-70, 20-100, 20-120, 20-150, 20-200, 30-50, 30-80, 30-100, 30-110, 30-130, 30-150, 30-200, 40-50, 40-90, 40-100, 40-120, 40-140, 40-150, 40-200, 50-100, 50-130, 50-150, 50-200, 60-100, 60-110, 60-140, 60-150, 60-160, 60-200, 70-100, 70-120, 70-150, 70-170, 70-200, 80-100, 80-130, 80-150, 80-160, 80-180, 80-200, 90-100, 90-140, 90-150, 90-170, 90-190, 90-200, 100-150, 100-180, 100-200, 110-150, 110-160, 110-190, 110-200, 120-150, 120-170, 120-200, 130-150, 130-180, 130-200, 140-150, 140-190, 140-200, 150-200, 160-200, 170-200, 180-200, or 190-200 N.

In some embodiments, the SBP formulations described herein may be injected with a force of 200 N or less.

In some embodiments, the SBP formulations described herein may be injected with a force of 150 N or less.

In some embodiments, the SBP formulations described herein may be injected with a force of 100 N or less.

In some embodiments, the SBP formulations described herein may be injected with a force of 50 N or less.

In some embodiments, the SBP formulations described herein may be injected with a force of 20 N or less.

In some embodiments, the SBP formulations described herein may be injected with a force of 10 N or less.

In some embodiments, the SBP formulations described herein may be injected with a force of 5 N or less.

In some embodiments, injectability may also be analyzed by maximum force. As used herein, the term "maximum force" refers to the highest force achieved during injection. The maximum force may occur at the beginning of an injection. The maximum force may be, but is not limited to, 5, 10, 20, 25, 30, 40, 50, 60, 70, 75, 80, 90, 100, 110, 120, 125, 130, 140, 150, 160, 170, 175, 180, 190, or 200 N, or 5-10, 5-25, 10-50, 10-60, 10-90, 10-100, 10-110, 10-150, 10-200, 20-50, 20-70, 20-100, 20-120, 20-150, 20-200, 25-50, 30-50, 30-80, 30-100, 30-110, 30-130, 30-150, 30-200, 40-50, 40-90, 40-100, 40-120, 40-140, 40-150, 40-200, 50-100, 50-130, 50-150, 50-200, 60-100, 60-110, 60-140, 60-150, 60-160, 60-200, 70-100, 70-120, 70-150, 70-170, 70-200, 75-100, 80-100, 80-130, 80-150, 80-160, 80-180, 80-200, 90-100, 90-140, 90-150, 90-170, 90-190, 90-200, 100-150, 100-180, 100-200, 110-150, 110-160, 110-190, 110-200, 120-150, 120-170, 120-200, 125-150, 130-150, 130-180, 130-200, 140-150, 140-190, 140-200, 150-175, 150-200, 160-200, 170-200, 175-200, 180-200, or 190-200 N.

In some embodiments, the maximum force is from about 5 N to about 200 N. In some embodiments, the maximum force may be from about 0.001 N to about 5 N, from about 5 N to about 25 N, from about 25 N to about 50 N, from about 50 N to about 75 N, from about 75 N to about 100 N, from about 100 N to about 125 N, from about 125 N to about 150 N, from about 150 N to about 175 N, or from about 175 N to about 200 N.

In some embodiments, the SBP formulation may be delivered using a syringe with a 1, 2, 3, 4, 5, 6, 7, 8, 9, 10, 15, 20, 25, 30, 35, 40, 45, 50, 60, 70, 80, 90, 100 ml syringe which has an applicator which is 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, or more than 10 mm.

In one embodiment, the SBP formulation may be delivered using a 3 ml syringe with a 1.5 mm applicator.

pH

In some embodiments, the SBP formulation may be optimized for a specific pH. The pH of the SBP formulation may be, but is not limited, to 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, and 14.

In one embodiment, the SBP formulation may be optimized for a specific pH range. The pH range may be, but is not limited to, 0-4, 1-5, 2-6, 3-7, 4-8, 5-9, 6-10, 7-11, 8-12, 9-13, 10-14, 0-4, 1-5, 2-6, 3-7, 4-8, 5-9, 6-10, 7-11, 8-12, 9-13, 10-14, 0-4.5, 1-5.5, 2-6.5, 3-7.5, 4-8.5, 5-9.5, 6-10.5, 7-11.5, 8-12.5, 9-13.5, 0-1.5, 1-2.5, 2-3.5, 3-4.5, 4-5.5, 5-6.5, 6-7.5, 7-8.5, 8-9.5, 9-10.5, 10-11.5, 11-12.5, 12-13.5, 0-1, 1-2, 2-3, 3-4, 4-5, 5-6, 6-7, 6.5-7.5, 7-8, 8-9, 9-10, 10-11, 11-12, 12-13, 13-14, 0-0.5, 0.5-1, 1-1.5, 1.5-2, 2-2.5, 2.5-3, 3-3.5, 3.5-4, 4-4.5, 4.5-5, 5-5.5, 5.5-6, 6-6.5, 6.5-7, 7-7.5, 7.5-8, 8-8.5, 8.5-9, 9-9.5, 9.5-10, 10-10.5, 10.5-11, 11-11.5, 11.5-12, 12-12.5, 12.5-13, 13-13.5, or 13.5-14.

In one embodiment, the pH of the SBP formulation is between 4-8.5.

In one embodiment, the pH of the SBP formulation is between 6.5-7.5

In one embodiment, the pH of the SBP formulation is between 7-7.5.

Specific Gravity

In some embodiments, the SBP formulation may be optimized for a specific gravity. The specific gravity of the SBP formulation may be, but is not limited, to 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5.

In some embodiments, the specific gravity of the SBP formulation may be, but is not limited to, 0.1-5 g/mL, 0.2-5 g/mL, 0.3-5 g/mL, 0.4-5 g/mL, 0.5-5 g/mL, 0.6-5 g/mL, 0.7-5 g/mL, 0.8-5 g/mL, 0.9-5 g/mL, 1-5 g/mL, 1.1-5 g/mL, 1.2-5 g/mL, 1.3-5 g/mL, 1.4-5 g/mL, 1.5-5 g/mL, 1.6-5 g/mL, 1.7-5 g/mL, 1.8-5 g/mL, 1.9-5 g/mL, 2-5 g/mL, 2.1-5 g/mL, 2.2-5 g/mL, 2.3-5 g/mL, 2.4-5 g/mL, 2.5-5 g/mL, 2.6-5 g/mL, 2.7-5 g/mL, 2.8-5 g/mL, 2.9-5 g/mL, 3-5 g/mL, 3.1-5 g/mL, 3.2-5 g/mL, 3.3-5 g/mL, 3.4-5 g/mL, 3.5-5 g/mL, 3.6-5 g/mL, 3.7-5 g/mL, 3.8-5 g/mL, 3.9-5 g/mL, 4-5 g/mL, 4.1-5 g/mL, 4.2-5 g/mL, 4.3-5 g/mL, 4.4-5 g/mL, 4.5-5 g/mL, 4.6-5 g/mL, 4.7-5 g/mL, 4.8-5 g/mL, 4.9-5 g/mL, 0.1-0.3 g/mL, 0.2-0.4 g/mL, 0.3-0.5 g/mL, 0.4-0.6 g/mL, 0.5-0.7 g/mL, 0.6-0.8 g/mL, 0.7-0.9 g/mL, 0.8-1 g/mL, 0.9-1.1 g/mL, 1-1.2 g/mL, 1.1-1.3 g/mL, 1.2-1.4 g/mL, 1.3-1.5 g/mL, 1.4-1.6 g/mL, 1.5-1.7 g/mL, 1.6-1.8 g/mL, 1.7-1.9 g/mL, 1.8-2 g/mL, 1.9-2.1 g/mL, 2-2.2 g/mL, 2.1-2.3 g/mL, 2.2-2.4 g/mL, 2.3-2.5 g/mL, 2.4-2.6 g/mL, 2.5-2.7 g/mL, 2.6-2.8 g/mL, 2.7-2.9 g/mL, 2.8-3 g/mL, 2.9-3.1 g/mL, 3-3.2 g/mL, 3.1-3.3 g/mL, 3.2-3.4 g/mL, 3.3-3.5 g/mL, 3.4-3.6 g/mL, 3.5-3.7 g/mL, 3.6-3.8 g/mL, 3.7-3.9 g/mL, 3.8-4 g/mL, 3.9-4.1 g/mL, 4-4.2 g/mL, 4.1-4.3 g/mL, 4.2-4.4 g/mL, 4.3-4.5 g/mL, 4.4-4.6 g/mL, 4.5-4.7 g/mL, 4.6-4.8 g/mL, 4.7-4.9 g/mL, 4.8-5 g/mL, 0.1-0.4 g/mL, 0.2-0.5 g/mL, 0.3-0.6 g/mL, 0.4-0.7 g/mL, 0.5-0.8 g/mL, 0.6-0.9 g/mL, 0.7-1 g/mL, 0.8-1.1 g/mL, 0.9-1.2 g/mL, 1-1.3 g/mL, 1.1-1.4 g/mL, 1.2-1.5 g/mL, 1.3-1.6 g/mL, 1.4-1.7 g/mL, 1.5-1.8 g/mL, 1.6-1.9 g/mL, 1.7-2 g/mL, 1.8-2.1 g/mL, 1.9-2.2 g/mL, 2-2.3 g/mL, 2.1-2.4 g/mL, 2.2-2.5 g/mL, 2.3-2.6 g/mL, 2.4-2.7 g/mL, 2.5-2.8 g/mL, 2.6-2.9 g/mL, 2.7-3 g/mL, 2.8-3.1 g/mL, 2.9-3.2 g/mL, 3-3.3 g/mL, 3.1-3.4 g/mL, 3.2-3.5 g/mL, 3.3-3.6 g/mL, 3.4-3.7 g/mL, 3.5-3.8 g/mL, 3.6-3.9 g/mL, 3.7-4 g/mL, 3.8-4.1 g/mL, 3.9-4.2 g/mL, 4-4.3 g/mL, 4.1-4.4 g/mL, 4.2-4.5 g/mL, 4.3-4.6 g/mL, 4.4-4.7 g/mL, 4.5-4.8 g/mL, 4.6-4.9 g/mL, 4.7-5 g/mL, 0.1-0.5 g/mL, 0.2-0.6 g/mL, 0.3-0.7 g/mL, 0.4-0.8 g/mL, 0.5-0.9 g/mL, 0.6-1 g/mL, 0.7-1.1 g/mL, 0.8-1.2 g/mL, 0.9-1.3 g/mL, 1-1.4 g/mL, 1.1-1.5 g/mL, 1.2-1.6 g/mL, 1.3-1.7 g/mL, 1.4-1.8 g/mL, 1.5-1.9 g/mL, 1.6-2 g/mL, 1.7-2.1 g/mL, 1.8-2.2 g/mL, 1.9-2.3 g/mL, 2-2.4 g/mL, 2.1-2.5 g/mL, 2.2-2.6 g/mL, 2.3-2.7 g/mL, 2.4-2.8 g/mL, 2.5-2.9 g/mL, 2.6-3 g/mL, 2.7-3.1 g/mL, 2.8-3.2 g/mL, 2.9-3.3 g/mL, 3-3.4 g/mL, 3.1-3.5 g/mL, 3.2-3.6 g/mL, 3.3-3.7 g/mL, 3.4-3.8 g/mL, 3.5-3.9 g/mL, 3.6-4 g/mL, 3.7-4.1 g/mL, 3.8-4.2 g/mL, 3.9-4.3 g/mL, 4-4.4 g/mL, 4.1-4.5 g/mL, 4.2-4.6 g/mL, 4.3-4.7 g/mL, 4.4-4.8 g/mL, 4.5-4.9 g/mL, 4.6-5 g/mL, 0.1-0.6 g/mL, 0.2-0.7 g/mL, 0.3-0.8 g/mL, 0.4-0.9 g/mL, 0.5-1 g/mL, 0.6-1.1 g/mL, 0.7-1.2 g/mL, 0.8-1.3 g/mL, 0.9-1.4 g/mL, 1-1.5 g/mL, 1.1-1.6 g/mL, 1.2-1.7 g/mL, 1.3-1.8 g/mL, 1.4-1.9 g/mL, 1.5-2 g/mL, 1.6-2.1 g/mL, 1.7-2.2 g/mL, 1.8-2.3 g/mL, 1.9-2.4 g/mL, 2-2.5 g/mL, 2.1-2.6 g/mL, 2.2-2.7 g/mL, 2.3-2.8 g/mL, 2.4-2.9 g/mL, 2.5-3 g/mL, 2.6-3.1 g/mL, 2.7-3.2 g/mL, 2.8-3.3 g/mL, 2.9-3.4 g/mL, 3-3.5 g/mL, 3.1-3.6 g/mL, 3.2-3.7 g/mL, 3.3-3.8 g/mL, 3.4-3.9 g/mL, 3.5-4 g/mL, 3.6-4.1 g/mL, 3.7-4.2 g/mL, 3.8-4.3 g/mL, 3.9-4.4 g/mL, 4-4.5 g/mL, 4.1-4.6 g/mL, 4.2-4.7 g/mL, 4.3-4.8 g/mL, 4.4-4.9 g/mL, 4.5-5 g/mL, 0.1-0.7 g/mL, 0.2-0.8 g/mL, 0.3-0.9 g/mL, 0.4-1 g/mL, 0.5-1.1 g/mL, 0.6-1.2 g/mL, 0.7-1.3 g/mL, 0.8-1.4 g/mL, 0.9-1.5 g/mL, 1-1.6 g/mL, 1.1-1.7 g/mL, 1.2-1.8 g/mL, 1.3-1.9 g/mL, 1.4-2 g/mL, 1.5-2.1 g/mL, 1.6-2.2 g/mL, 1.7-2.3 g/mL, 1.8-2.4 g/mL, 1.9-2.5 g/mL, 2-2.6 g/mL, 2.1-2.7 g/mL, 2.2-2.8 g/mL, 2.3-2.9 g/mL, 2.4-3 g/mL, 2.5-3.1 g/mL, 2.6-3.2 g/mL, 2.7-3.3 g/mL, 2.8-3.4 g/mL, 2.9-3.5 g/mL, 3-3.6 g/mL, 3.1-3.7 g/mL, 3.2-3.8 g/mL, 3.3-3.9 g/mL, 3.4-4 g/mL, 3.5-4.1 g/mL, 3.6-4.2 g/mL, 3.7-4.3 g/mL, 3.8-4.4 g/mL, 3.9-4.5 g/mL, 4-4.6 g/mL, 4.1-4.7 g/mL, 4.2-4.8 g/mL, 4.3-4.9 g/mL, 4.4-5 g/mL, 0.1-0.8 g/mL, 0.2-0.9 g/mL, 0.3-1 g/mL, 0.4-1.1 g/mL, 0.5-1.2 g/mL, 0.6-1.3 g/mL, 0.7-1.4 g/mL, 0.8-1.5 g/mL, 0.9-1.6 g/mL, 1-1.7 g/mL, 1.1-1.8 g/mL, 1.2-1.9 g/mL, 1.3-2 g/mL, 1.4-2.1 g/mL, 1.5-2.2 g/mL, 1.6-2.3 g/mL, 1.7-2.4 g/mL, 1.8-2.5 g/mL, 1.9-2.6 g/mL, 2-2.7 g/mL, 2.1-2.8 g/mL, 2.2-2.9 g/mL, 2.3-3 g/mL, 2.4-3.1 g/mL, 2.5-3.2 g/mL, 2.6-3.3 g/mL, 2.7-3.4 g/mL, 2.8-3.5 g/mL, 2.9-3.6 g/mL, 3-3.7 g/mL, 3.1-3.8 g/mL, 3.2-3.9 g/mL, 3.3-4 g/mL, 3.4-4.1 g/mL, 3.5-4.2 g/mL, 3.6-4.3 g/mL, 3.7-4.4 g/mL, 3.8-4.5 g/mL, 3.9-4.6 g/mL, 4-4.7 g/mL, 4.1-4.8 g/mL, 4.2-4.9 g/mL, 4.3-5 g/mL, 0.1-0.9 g/mL, 0.2-1 g/mL, 0.3-1.1 g/mL, 0.4-1.2 g/mL, 0.5-1.3 g/mL, 0.6-1.4 g/mL, 0.7-1.5 g/mL, 0.8-1.6 g/mL, 0.9-1.7 g/mL, 1-1.8 g/mL, 1.1-1.9 g/mL, 1.2-2 g/mL, 1.3-2.1 g/mL, 1.4-2.2 g/mL, 1.5-2.3 g/mL, 1.6-2.4 g/mL, 1.7-2.5 g/mL, 1.8-2.6 g/mL, 1.9-2.7 g/mL, 2-2.8 g/mL, 2.1-2.9 g/mL, 2.2-3 g/mL, 2.3-3.1 g/mL, 2.4-3.2 g/mL, 2.5-3.3 g/mL, 2.6-3.4 g/mL, 2.7-3.5 g/mL, 2.8-3.6 g/mL, 2.9-3.7 g/mL, 3-3.8 g/mL, 3.1-3.9 g/mL, 3.2-4 g/mL, 3.3-4.1 g/mL, 3.4-4.2 g/mL, 3.5-4.3 g/mL, 3.6-4.4 g/mL, 3.7-4.5 g/mL, 3.8-4.6 g/mL, 3.9-4.7 g/mL, 4-4.8 g/mL, 4.1-4.9 g/mL, 4.2-5 g/mL, 0.1-1 g/mL, 0.2-1.1 g/mL, 0.3-1.2 g/mL, 0.4-1.3 g/mL, 0.5-1.4 g/mL, 0.6-1.5 g/mL, 0.7-1.6 g/mL, 0.8-1.7 g/mL, 0.9-1.8 g/mL, 1-1.9 g/mL, 1.1-2 g/mL, 1.2-2.1 g/mL, 1.3-2.2 g/mL, 1.4-2.3 g/mL, 1.5-2.4 g/mL, 1.6-2.5 g/mL, 1.7-2.6 g/mL, 1.8-2.7 g/mL, 1.9-2.8 g/mL, 2-2.9 g/mL, 2.1-3 g/mL, 2.2-3.1 g/mL, 2.3-3.2 g/mL, 2.4-3.3 g/mL, 2.5-3.4 g/mL, 2.6-3.5 g/mL, 2.7-3.6 g/mL, 2.8-3.7 g/mL, 2.9-3.8 g/mL, 3-3.9 g/mL, 3.1-4 g/mL, 3.2-4.1 g/mL, 3.3-4.2 g/mL, 3.4-4.3 g/mL, 3.5-4.4 g/mL, 3.6-4.5 g/mL, 3.7-4.6 g/mL, 3.8-4.7 g/mL, 3.9-4.8 g/mL, 4-4.9 g/mL, 4.1-5 g/mL, 0.1-1.1 g/mL, 0.2-1.2 g/mL, 0.3-1.3 g/mL, 0.4-1.4 g/mL, 0.5-1.5 g/mL, 0.6-1.6 g/mL, 0.7-1.7 g/mL, 0.8-1.8 g/mL, 0.9-1.9 g/mL, 1-2 g/mL, 1.1-2.1 g/mL, 1.2-2.2 g/mL, 1.3-2.3 g/mL, 1.4-2.4 g/mL, 1.5-2.5 g/mL, 1.6-2.6 g/mL, 1.7-2.7 g/mL, 1.8-2.8 g/mL, 1.9-2.9 g/mL, 2-3 g/mL, 2.1-3.1 g/mL, 2.2-3.2 g/mL, 2.3-3.3 g/mL, 2.4-3.4 g/mL, 2.5-3.5 g/mL, 2.6-3.6 g/mL, 2.7-3.7 g/mL, 2.8-3.8 g/mL, 2.9-3.9 g/mL, 3-4 g/mL, 3.1-4.1 g/mL, 3.2-4.2 g/mL, 3.3-4.3 g/mL, 3.4-4.4 g/mL, 3.5-4.5 g/mL, 3.6-4.6 g/mL, 3.7-4.7 g/mL, 3.8-4.8 g/mL, 3.9-4.9 g/mL, 4-5 g/mL, 0.1-1.6 g/mL, 0.2-1.7 g/mL, 0.3-1.8 g/mL, 0.4-1.9 g/mL, 0.5-2 g/mL, 0.6-2.1 g/mL, 0.7-2.2 g/mL, 0.8-2.3 g/mL, 0.9-2.4 g/mL, 1-2.5 g/mL, 1.1-2.6 g/mL, 1.2-2.7 g/mL, 1.3-2.8 g/mL, 1.4-2.9 g/mL, 1.5-3 g/mL, 1.6-3.1 g/mL, 1.7-3.2 g/mL, 1.8-3.3 g/mL, 1.9-3.4 g/mL, 2-3.5 g/mL, 2.1-3.6 g/mL, 2.2-3.7 g/mL, 2.3-3.8 g/mL, 2.4-3.9 g/mL, 2.5-4 g/mL, 2.6-4.1 g/mL, 2.7-4.2 g/mL, 2.8-4.3 g/mL, 2.9-4.4 g/mL, 3-4.5 g/mL, 3.1-4.6 g/mL, 3.2-4.7 g/mL, 3.3-4.8 g/mL, 3.4-4.9 g/mL, 3.5-5 g/mL, 0.1-2.1 g/mL, 0.2-2.2 g/mL, 0.3-2.3 g/mL, 0.4-2.4 g/mL, 0.5-2.5 g/mL, 0.6-2.6 g/mL, 0.7-2.7 g/mL, 0.8-2.8 g/mL, 0.9-2.9 g/mL, 1-3 g/mL, 1.1-3.1 g/mL, 1.2-3.2 g/mL, 1.3-3.3 g/mL, 1.4-3.4 g/mL, 1.5-3.5 g/mL, 1.6-3.6 g/mL, 1.7-3.7 g/mL, 1.8-3.8 g/mL, 1.9-3.9 g/mL, 2-4 g/mL, 2.1-4.1 g/mL, 2.2-4.2 g/mL, 2.3-4.3 g/mL, 2.4-4.4 g/mL, 2.5-4.5 g/mL, 2.6-4.6 g/mL, 2.7-4.7 g/mL, 2.8-4.8 g/mL, 2.9-4.9 g/mL, 3-5 g/mL, 0.1-2.6 g/mL, 0.2-2.7 g/mL, 0.3-2.8 g/mL, 0.4-2.9 g/mL, 0.5-3 g/mL, 0.6-3.1 g/mL, 0.7-3.2 g/mL, 0.8-3.3 g/mL, 0.9-3.4 g/mL, 1-3.5 g/mL, 1.1-3.6 g/mL, 1.2-3.7 g/mL, 1.3-3.8 g/mL, 1.4-3.9 g/mL, 1.5-4 g/mL, 1.6-4.1 g/mL, 1.7-4.2 g/mL, 1.8-4.3 g/mL, 1.9-4.4 g/mL, 2-4.5 g/mL, 2.1-4.6 g/mL, 2.2-4.7 g/mL, 2.3-4.8 g/mL, 2.4-4.9 g/mL, 2.5-5 g/mL, 0.1-3.1 g/mL, 0.2-3.2 g/mL, 0.3-3.3 g/mL, 0.4-3.4 g/mL, 0.5-3.5 g/mL, 0.6-3.6 g/mL, 0.7-3.7 g/mL, 0.8-3.8 g/mL, 0.9-3.9 g/mL, 1-4 g/mL, 1.1-4.1 g/mL, 1.2-4.2 g/mL, 1.3-4.3 g/mL, 1.4-4.4 g/mL, 1.5-4.5 g/mL, 1.6-4.6 g/mL, 1.7-4.7 g/mL, 1.8-4.8 g/mL, 1.9-4.9 g/mL, and 2-5 g/mL.

In one embodiment, the specific gravity of the SBP formulation may be between 1.2-2 g/mL.

In one embodiment, the specific gravity of the SBP formulation may be 1.8-2 g/mL.

Shear Recovery

In some embodiments, the SBP formulation may optimized for shear recovery. As described herein, "shear recovery" describes the ability of a physical property of an SBP formulation to recover to a specific percent of its original measure within a specified time post-shear application. Properties that can be measured by methods known in the art may include, but are not limited to, G', G", phase angle, and/or viscosity.

In one embodiment, the shear recovery of the SBP formulation is greater than 75% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 75% at 1 minute. As a non-limiting example, the shear recovery of the SBP formulation is greater than 75% at 10 seconds.

In one embodiment, the shear recovery of the SBP formulation is greater than 80% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 80% at 1 minute. As a non-limiting example, the shear recovery of the SBP formulation is greater than 80% at 10 seconds.

In one embodiment, the shear recovery of the SBP formulation is greater than 85% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 85% at 1 minute. As a non-limiting example, the shear recovery of the SBP formulation is greater than 85% at 10 seconds.

In one embodiment, the shear recovery of the SBP formulation is greater than 90% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 90% at 1 minute. As a non-limiting example, the shear recovery of the SBP formulation is greater than 90% at 10 seconds.

In one embodiment, the shear recovery of the SBP formulation is greater than 95% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 95% at 1 minute. As a non-limiting example, the shear recovery of the SBP formulation is greater than 95% at 10 seconds.

In one embodiment, the shear recovery of the SBP formulation is greater than 99% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 99% at 1 minute. As a non-limiting example, the shear recovery of the SBP formulation is greater than 99% at 10 seconds.

Stability and Degradation

In some embodiments, the SBP formulation may optimized for stability.

In one embodiment, the SBP formulation may have an in vivo degradation rate of greater than 10 days, 20 days, 30 days, 40 days, 50 days, 60 days, 70 days, 80 days, 90 days, 100 days, 120 days, 140 days, 160 days, 180 days, 200 days, 250 days, 300 days, 350 days, or 400 days. As a non-limiting example, the in vivo degradation rate is greater than 60 days. As another non-limiting example, the in vivo degradation rate is greater than 120 days.

In one embodiment, the SBP formulation may have an in vivo degradation rate of greater than 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7, 8, 9, 10, 11, 12, 13, 14 days, 1, 2, 3, 4 weeks, or 1, 2, 3, 4, 5, 6, 7, 8, 9, 10, 11, 12 months. In some instances, there is no change in weight of the sample over the period. As a non-limiting example, the SBP formulation may have an in vivo degradation rate of greater than 7 days and there is no change in weight in the sample. As a non-limiting example, the SBP formulation may have an in vivo degradation rate of greater than 14 days and there is no change in weight in the sample.

In one embodiment, the SBP formulation may be stable at room temperature for at least 1 month, 2 months, 3 months, 4 months, 5 months, 6 months, 7 months, 8 months, 9 months, 10 months, 11 months, 12 months, 18 months, 1 year, 2 years, 3 years, 4 years, 5 years, 6 years, 7 years, 8 years, 9 years or more than 9 years. As a non-limiting example, the SBP formulation is stable at room temperature for 2 years. As another non-limiting example, the SBP formulation is stable at room temperature for 3 years.

Endotoxin

In some embodiments, the SBP formulation may optimized for a lower endotoxin level.

In one embodiment, the endotoxin level in the SBP formulation is less than 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or 100 EU/g. As a non-limiting example, the endotoxin level is less than 100 EU/g.

In one embodiment, the endotoxin level in the SBP formulation is less than 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or 100 EU/mL. As a non-limiting example, the endotoxin level is less than 1 EU/mL by the Limulus amebocyte lysate (LAL) method.

In one embodiment, the endotoxin level in the SBP formulation is between 0.5-5, 1-10, 5-10, 5-15, 10-20, 10-25, 10-30, 10-40, 10-50, 10-60, 10-70, 10-80, 10-90, 10-100, 25-50, 25-75, 25-100, 50-75, 50-100, or 75-100 EU/g. As a non-limiting example, the endotoxin level of the SBP formulation is between 0.5-5 EU/g.

Rheological Properties

In some embodiments, SBP formulations may be optimized to modulate SBP rheological properties, including, but not limited to, viscosity, storage modulus (G'), loss modulus, and phase angle. As used herein, the term "viscosity" refers to a measure of a material's resistance to flow and may include shear viscosity or interfacial viscosity. As used herein, the term "shear storage modulus" refers to the measure of a material's elasticity or reversible deformation as determined by the material's stored energy. As used herein, the term "shear loss modulus" refers to the measure of a material's ability to dissipate energy, usually in the form of heat. As used herein, the term "phase angle" refers to the difference in the stress and strain applied to a material during the application of oscillating shear stress. The viscosity and other rheological properties of a composition (e.g., a gel, e.g., hydrogel or organogel) provided herein can be determined using a rotational viscometer or rheometer. Additional methods for determining the rheological properties of a composition (e.g., gel, e.g., hydrogel or organogel) and other properties of the composition are known in the art. In some embodiments, SBP rheological properties may be altered by the incorporation of an excipient that is a gelling agent. In some embodiments, the identity of the excipient (e.g. PEG or poloxamer) may be altered to tune the rheological properties of SBPs. In some embodiments, the rheological properties of SBPs may be tuned for the desired application (e.g. tissue engineering scaffold, drug delivery system, surgical implant, etc.).

In some embodiments, the viscosity of SBPs is tunable between 1-1000 centipoise (cP). In some embodiments, the viscosity of an SBP is tunable from about 0.0001 to about 1000 Pascal seconds (Pa*s). In some embodiments, the viscosity of an SBP is from about 1 cP to about 10 cP, from about 2 cP to about 20 cP, from about 3 cP to about 30 cP, from about 4 cP to about 40 cP, from about 5 cP to about 50 cP, from about 6 cP to about 60 cP, from about 7 cP to about 70 cP, from about 8 cP to about 80 cP, from about 9 cP to about 90 cP, from about 10 cP to about 100 cP, from about 100 cP to about 150 cP, from about 150 cP to about 200 cP, from about 200 cP to about 250 cP, from about 250 cP to about 300 cP, from about 300 cP to about 350 cP, from about 350 cP to about 400 cP, from about 400 cP to about 450 cP, from about 450 cP to about 500 cP, from about 500 cP to about 600 cP, from about 550 cP to about 700 cP, from about 600 cP to about 800 cP, from about 650 cP to about 900 cP, or from about 700 cP to about 1000 cP. In some embodiments, the viscosity of an SBP is from about 0.0001 Pa*s to about 0.001 Pa*s, from about 0.001 Pa*s to about 0.01 Pa*s, from about 0.01 Pas to about 0.1 Pa*s, from about 0.1 Pa*s to about 1 Pa*s, from about 1 Pa*s to about 10 Pas, from about 2 Pa*s to about 20 Pa*s, from about 3 Pa*s to about 30 Pa*s, from about 4 Pa*s to about 40 Pa*s, from about 5 Pa*s to about 50 Pa*s, from about 6 Pa*s to about 60 Pa*s, from about 7 Pa*s to about 70 Pa*s, from about 8 Pa*s to about 80 Pa*s, from about 9 Pa*s to about 90 Pa*s, from about 10 Pa*s to about 100 Pa*s, from about 100 Pa*s to about 150 Pa*s, from about 150 Pa*s to about 200 Pa*s, from about 200 Pa*s to about 250 Pa*s, from about 250 Pa*s to about 300 Pa*s, from about 300 Pa*s to about 350 Pa*s, from about 350 Pa*s to about 400 Pa*s, from about 400 Pa*s to about 450 Pa*s, from about 450 Pa*s to about 500 Pa*s, from about 500 Pa*s to about 600 Pa*s, from about 550 Pa*s to about 700 Pa*s, from about 600 Pa*s to about 800 Pa*s, from about 650 Pa*s to about 900 Pa*s, from about 700 Pa*s to about 1000 Pa*s or from about 10 Pa*s to about 2500 Pa*s.

In some embodiments, the SBP formulations may shear thin or display shear thinning properties. As used herein, the term "shear thinning" refers to a decrease in viscosity at increasing shear rates. As used herein, the term "shear rate" refers to the rate of change in the ratio of displacement of material upon the application of a shear force to the height of the material. This ratio is also known as strain.

In some embodiments, the storage modulus and/or the loss modulus (G' and G" respectively) of SBPs is tunable between 0.0001-20000 Pascals (Pa). In some embodiments, the storage modulus and/or the loss modulus of SBPs is from about 0.0001 Pa to about 0.001 Pa, from about 0.001 Pa to about 0.01 Pa, from about 0.01 Pa to about 0.1 Pa, from about 0.1 Pa to about 1 Pa, from about 1 Pa to about 10 Pa, from about 2 Pa to about 20 Pa, from about 3 Pa to about 30 Pa, from about 4 Pa to about 40 Pa, from about 5 Pa to about 50 Pa, from about 6 Pa to about 60 Pa, from about 7 Pa to about 70 Pa, from about 8 Pa to about 80 Pa, from about 9 Pa to about 90 Pa, from about 10 Pa to about 100 Pa, from about 100 Pa to about 150 Pa, from about 150 Pa to about 200 Pa, from about 200 Pa to about 250 Pa, from about 250 Pa to about 300 Pa, from about 300 Pa to about 350 Pa, from about 350 Pa to about 400 Pa, from about 400 Pa to about 450 Pa, from about 450 Pa to about 500 Pa, from about 500 Pa to about 600 Pa, from about 550 Pa to about 700 Pa, from about 600 Pa to about 800 Pa, from about 650 Pa to about 900 Pa, from about 700 Pa to about 1000 Pa, from about 1000 Pa to about 1500 Pa, from about 1500 Pa to about 2000 Pa, from about 2000 Pa to about 2500 Pa, from about 2500 Pa to about 3000 Pa, from about 3000 Pa to about 3500 Pa, from about 3500 Pa to about 4000 Pa, from about 4000 Pa to about 4500 Pa, from about 4500 Pa to about 5000 Pa, from about 5000 Pa to about 5500 Pa, from about 5500 Pa to about 6000 Pa, from about 6000 Pa to about 6500 Pa, from about 6500 Pa to about 7000 Pa, from about 7000 Pa to about 7500 Pa, from about 7500 Pa to about 8000 Pa, from about 8000 Pa to about 8500 Pa, from about 8500 Pa to about 9000 Pa, from about 9000 Pa to about 9500 Pa, from about 9500 Pa to about 10000 Pa, from about 10000 Pa to about 11000 Pa, from about 11000 Pa to about 12000 Pa, from about 12000 Pa to about 13000 Pa, from about 13000 Pa to about 14000 Pa, from about 14000 Pa to about 15000 Pa, from about 15000 Pa to about 16000 Pa, from about 16000 Pa to about 17000 Pa, from about 17000 Pa to about 18000 Pa, from about 18000 Pa to about 19000 Pa, or from about 19000 Pa to about 20000 Pa.

In some embodiments, the phase angle of SBPs is tunable between 1°-90°). In some embodiments, the phase angle of SBPs is from about 1° to about 2°, from about 2° to about 3°, from about 3° to about 4°, from about 4° to about 5°, from about 5° to about 6°, from about 6° to about 7°, from about 7° to about 8°, from about 8° to about 9°, from about 9° to about 10°, from about 10° to about 15°, from about 15° to about 20°, from about 20° to about 25°, from about 25° to about 30°, from about 30° to about 35°, from about 35° to about 40°, from about 40° to about 45°, from about 45° to about 50°, from about 50° to about 55°, from about 55° to about 60°, from about 60° to about 65°, from about 65° to about 70°, from about 70° to about 75°, from about 75° to about 80°, from about 80° to about 85°, or from about 85° to about 90°.

Stress Resistance

In some embodiments, SBPs may be formulated to modulate SBP resistance to stress. Resistance to stress may be measured using one or more rheological measurements. Such measurements may include, but are not limited to tensile elasticity, shear or rigidity, volumetric elasticity, and compression. Additional rheological measurements and properties may include any of those taught in Zhang et al. (2017) Fiber and Polymers 18 (10): 1831-1840; McGill et al. (2017) Acta Biomaterialia 63:76-84; and Choi et al. (2015) In-Situ Gelling Polymers, Series in BioEngineering doi. 10.1007/978-981-287-152-7_2, the contents of each of which are herein incorporated by reference in their entirety. In some embodiments, stress resistance may be modulated through incorporation of excipients (e.g., PEG or poloxamer). In some embodiments, SBP stress-resistance properties may be modulated to suit a specific application (e.g., tissue engineering scaffold, drug delivery system, surgical implant, etc.).

In some embodiments, stress resistance may be measured by shear recovery experiments. In some embodiments, the SBPs recover 100% of their viscosity from before the application of shear forces. In some embodiments, the SBPs recover from 0.1%-5%, from 5%-10%, from 10% to 25%, from 25% to 50%, from 50% to 75%, or from 75% to 100% of their viscosity from before the application of shear forces. Shear recovery may be measured via any method known to one skilled in the art. In some embodiments, shear recovery occurs over the course of 1 second, 10 seconds, 30 seconds, or one minute.

Osmolarity

In some embodiments, SBP formulations may include processed silk with or without other components (e.g., excipients and cargo). The SBP formulations may contain an from about 1 mOsm to about 10 mOsm, from about 2 mOsm to about 20 mOsm, from about 3 mOsm to about 30 mOsm, from about 4 mOsm to about 40 mOsm, from about 5 mOsm to about 50 mOsm, from about 6 mOsm to about 60 mOsm, from about 7 mOsm to about 70 mOsm, from about 8 mOsm to about 80 mOsm, from about 9 mOsm to about 90 mOsm, from about 10 mOsm to about 100 mOsm, from about 15 mOsm to about 150 mOsm, from about 25 mOsm to about 200 mOsm, from about 35 mOsm to about 250 mOsm, from about 45 mOsm to about 300 mOsm, from about 55 mOsm to about 350 mOsm, from about 65 mOsm to about 400 mOsm, from about 75 mOsm to about 450 mOsm, from about 85 mOsm to about 500 mOsm, from about 125 mOsm to about 600 mOsm, from about 175 mOsm to about 700 mOsm, from about 225 mOsm to about 800 mOsm, from about 275 mOsm to about 285 mOsm, from about 280 mOsm to about 900 mOsm, or from about 325 mOsm to about 1000 mOsm. The SBPs may have an osmolarity of from about 1 mOsm/L to about 10 mOsm/L, from about 2 mOsm/L to about 20 mOsm/L, from about 3 mOsm/L to about 30 mOsm/L, from about 4 mOsm/L to about 40 mOsm/L, from about 5 mOsm/L to about 50 mOsm/L, from about 6 mOsm/L to about 60 mOsm/L, from about 7 mOsm/L to about 70 mOsm/L, from about 8 mOsm/L to about 80 mOsm/L, from about 9 mOsm/L to about 90 mOsm/L, from about 10 mOsm/L to about 100 mOsm/L, from about 15 mOsm/L to about 150 mOsm/L, from about 25 mOsm/L to about 200 mOsm/L, from about 35 mOsm/L to about 250 mOsm/L, from about 45 mOsm/L to about 300 mOsm/L, from about 55 mOsm/L to about 350 mOsm/L, from about 65 mOsm/L to about 400 mOsm/L, from about 75 mOsm/L to about 450 mOsm/L, from about 85 mOsm/L to about 500 mOsm/L, from about 125 mOsm/L to about 600 mOsm/L, from about 175 mOsm/L to about 700 mOsm/L, from about 225 mOsm/L to about 800 mOsm/L, from about 275 mOsm/L to about 285 mOsm/L, from about 280 mOsm/L to about 900 mOsm/L, or from about 325 mOsm/L to about 1000 mOsm/L.

In some embodiments, the SBP formulation has an osmolarity from about 290-320 mOsm/L.

In some embodiment, the SBP formulation has an osmolarity of 280 mOsm/L.

In some embodiment, the SBP formulation has an osmolarity of 290 mOsm/L.

Concentrations and Ratios of SBP Components

SBP formulations may include formulations of processed silk with other components (e.g., excipient, therapeutic agent, microbe, cargo, and/or biological system), wherein each component is present at a specific concentration, ratio, or range of concentrations or ratios, depending on application. In some embodiments, the concentration of processed silk or other SBP component (e.g., excipient, therapeutic agent, microbe, cargo, and/or biological system) is present in SBP formulations at a concentration (by weight, volume, or concentration) of from about 0.0001% to about 0.001%, from about 0.001% to about 0.01%, from about 0.01% to about 1%, from about 0.05% to about 2%, from about 1% to about 5%, from about 2% to about 10%, from about 4% to about 16%, from about 5% to about 20%, from about 8% to about 24%, from about 10% to about 30%, from about 12% to about 32%, from about 14% to about 34%, from about 16% to about 36%, from about 18% to about 38%, from about 20% to about 40%, from about 22% to about 42%, from about 24% to about 44%, from about 26% to about 46%, from about 28% to about 48%, from about 30% to about 50%, from about 35% to about 55%, from about 40% to about 60%, from about 45% to about 65%, from about 50% to about 70%, from about 55% to about 75%, from about 60% to about 80%, from about 65% to about 85%, from about 70% to about 90%, from about 75% to about 95%, from about 80% to about 96%, from about 85% to about 97%, from about 90% to about 98%, from about 95% to about 99%, from about 96% to about 99.2%, from about 97% to about 99.5%, from about 98% to about 99.8%, from about 99% to about 99.9%, or greater than 99.9%.

In some embodiments, the concentration of processed silk or other SBP component (e.g., excipient, therapeutic agent, microbe, cargo, and/or biological system) is present in SBP formulations at a concentration of from about 0.0001% (w/v) to about 0.001% (w/v), from about 0.001% (w/v) to about 0.01% (w/v), from about 0.01% (w/v) to about 1% (w/v), from about 0.05% (w/v) to about 2% (w/v), from about 1% (w/v) to about 5% (w/v), from about 2% (w/v) to about 10% (w/v), from about 4% (w/v) to about 16% (w/v), from about 5% (w/v) to about 20% (w/v), from about 8% (w/v) to about 24% (w/v), from about 10% (w/v) to about 30% (w/v), from about 12% (w/v) to about 32% (w/v), from about 14% (w/v) to about 34% (w/v), from about 16% (w/v) to about 36% (w/v), from about 18% (w/v) to about 38% (w/v), from about 20% (w/v) to about 40% (w/v), from about 22% (w/v) to about 42% (w/v), from about 24% (w/v) to about 44% (w/v), from about 26% (w/v) to about 46% (w/v), from about 28% (w/v) to about 48% (w/v), from about 30% (w/v) to about 50% (w/v), from about 35% (w/v) to about 55% (w/v), from about 40% (w/v) to about 60% (w/v), from about 45% (w/v) to about 65% (w/v), from about 50% (w/v) to about 70% (w/v), from about 55% (w/v) to about 75% (w/v), from about 60% (w/v) to about 80% (w/v), from about 65% (w/v) to about 85% (w/v), from about 70% (w/v) to about 90% (w/v), from about 75% (w/v) to about 95% (w/v), from about 80% (w/v) to about 96% (w/v), from about 85% (w/v) to about 97% (w/v), from about 90% (w/v) to about 98% (w/v), from about 95% (w/v) to about 99% (w/v), from about 96% (w/v) to about 99.2% (w/v), from about 97% (w/v) to about 99.5% (w/v), from about 98% (w/v) to about 99.8% (w/v), from about 99% (w/v) to about 99.9% (w/v), or greater than 99.9% (w/v).

In some embodiments, the concentration of processed silk or other SBP component (e.g., excipient, therapeutic agent, microbe, cargo, and/or biological system) is present in SBP formulations at a concentration of from about 0.0001% (v/v) to about 0.001% (v/v), from about 0.001% (v/v) to about 0.01% (v/v), from about 0.01% (v/v) to about 1% (v/v), from about 0.05% (v/v) to about 2% (v/v), from about 1% (v/v) to about 5% (v/v), from about 2% (v/v) to about 10% (v/v), from about 4% (v/v) to about 16% (v/v), from about 5% (v/v) to about 20% (v/v), from about 8% (v/v) to about 24% (v/v), from about 10% (v/v) to about 30% (v/v), from about 12% (v/v) to about 32% (v/v), from about 14% (v/v) to about 34% (v/v), from about 16% (v/v) to about 36% (v/v), from about 18% (v/v) to about 38% (v/v), from about 20% (v/v) to about 40% (v/v), from about 22% (v/v) to about 42% (v/v), from about 24% (v/v) to about 44% (v/v), from about 26% (v/v) to about 46% (v/v), from about 28% (v/v) to about 48% (v/v), from about 30% (v/v) to about 50% (v/v), from about 35% (v/v) to about 55% (v/v), from about 40% (v/v) to about 60% (v/v), from about 45% (v/v) to about 65% (v/v), from about 50% (v/v) to about 70% (v/v), from about 55% (v/v) to about 75% (v/v), from about 60% (v/v) to about 80% (v/v), from about 65% (v/v) to about 85% (v/v), from about 70% (v/v) to about 90% (v/v), from about 75% (v/v) to about 95% (v/v), from about 80% (v/v) to about 96% (v/v), from about 85% (v/v) to about 97% (v/v), from about 90% (v/v) to about 98% (v/v), from about 95% (v/v) to about 99% (v/v), from about 96% (v/v) to about 99.2% (v/v), from about 97% (v/v) to about 99.5% (v/v), from about 98% (v/v) to about 99.8% (v/v), from about 99% (v/v) to about 99.9% (v/v), or greater than 99.9% (v/v).

In some embodiments, the concentration of processed silk or other SBP component (e.g., excipient, therapeutic agent, microbe, cargo, and/or biological system) is present in SBP formulations at a concentration of from about 0.0001% (w/w) to about 0.001% (w/w), from about 0.001% (w/w) to about 0.01% (w/w), from about 0.01% (w/w) to about 1% (w/w), from about 0.05% (w/w) to about 2% (w/w), from about 1% (w/w) to about 5% (w/w), from about 2% (w/w) to about 10% (w/w), from about 4% (w/w) to about 16% (w/w), from about 5% (w/w) to about 20% (w/w), from about 8% (w/w) to about 24% (w/w), from about 10% (w/w) to about 30% (w/w), from about 12% (w/w) to about 32% (w/w), from about 14% (w/w) to about 34% (w/w), from about 16% (w/w) to about 36% (w/w), from about 18% (w/w) to about 38% (w/w), from about 20% (w/w) to about 40% (w/w), from about 22% (w/w) to about 42% (w/w), from about 24% (w/w) to about 44% (w/w), from about 26% (w/w) to about 46% (w/w), from about 28% (w/w) to about 48% (w/w), from about 30% (w/w) to about 50% (w/w), from about 35% (w/w) to about 55% (w/w), from about 40% (w/w) to about 60% (w/w), from about 45% (w/w) to about 65% (w/w), from about 50% (w/w) to about 70% (w/w), from about 55% (w/w) to about 75% (w/w), from about 60% (w/w) to about 80% (w/w), from about 65% (w/w) to about 85% (w/w), from about 70% (w/w) to about 90% (w/w), from about 75% (w/w) to about 95% (w/w), from about 80% (w/w) to about 96% (w/w), from about 85% (w/w) to about 97% (w/w), from about 90% (w/w) to about 98% (w/w), from about 95% (w/w) to about 99% (w/w), from about 96% (w/w) to about 99.2% (w/w), from about 97% (w/w) to about 99.5% (w/w), from about 98% (w/w) to about 99.8% (w/w), from about 99% (w/w) to about 99.9% (w/w), or greater than 99.9% (w/w).

In one embodiment, the concentration of processed silk or other SBP component (e.g., excipient or cargo) is present in SBPs at a concentration of 1% (w/v).

In one embodiment, the concentration of processed silk or other SBP component (e.g., excipient or cargo) is present in SBPs at a concentration of 2% (w/v).

In one embodiment, the concentration of processed silk or other SBP component (e.g., excipient or cargo) is present in SBPs at a concentration of 3% (w/v).

In one embodiment, the concentration of processed silk or other SBP component (e.g., excipient or cargo) is present in SBPs at a concentration of 4% (w/v).

In one embodiment, the concentration of processed silk or other SBP component (e.g., excipient or cargo) is present in SBPs at a concentration of 5% (w/v).

In one embodiment, the concentration of processed silk or other SBP component (e.g., excipient or cargo) is present in SBPs at a concentration of 6% (w/v).

In one embodiment, the concentration of processed silk or other SBP component (e.g., excipient or cargo) is present in SBPs at a concentration of 10% (w/v).

In one embodiment, the concentration of processed silk or other SBP component (e.g., excipient or cargo) is present in SBPs at a concentration of 20% (w/v).

In one embodiment, the concentration of processed silk or other SBP component (e.g., excipient or cargo) is present in SBPs at a concentration of 30% (w/v).

In one embodiment, the concentration of processed silk or other SBP component (e.g., excipient or cargo) is present in SBPs at a concentration of 16.7% (w/w).

In one embodiment, the concentration of processed silk or other SBP component (e.g., excipient or cargo) is present in SBPs at a concentration of 20% (w/w).

In one embodiment, the concentration of processed silk or other SBP component (e.g., excipient or cargo) is present in SBPs at a concentration of 23% (w/w).

In one embodiment, the concentration of processed silk or other SBP component (e.g., excipient or cargo) is present in SBPs at a concentration of 25% (w/w).

In one embodiment, the concentration of processed silk or other SBP component (e.g., excipient or cargo) is present in SBPs at a concentration of 27.3% (w/w).

In one embodiment, the concentration of processed silk or other SBP component (e.g., excipient or cargo) is present in SBPs at a concentration of 28.6% (w/w).

In one embodiment, the concentration of processed silk or other SBP component (e.g., excipient or cargo) is present in SBPs at a concentration of 33.3% (w/w).

In one embodiment, the concentration of processed silk or other SBP component (e.g., excipient or cargo) is present in SBPs at a concentration of 40% (w/w).

In one embodiment, the concentration of processed silk or other SBP component (e.g., excipient or cargo) is present in SBPs at a concentration of 50% (w/w).

In some embodiments, the concentration of processed silk (e.g., silk fibroin) or other SBP component (e.g., excipient, therapeutic agent, microbe, cargo, and/or biological system) is present in SBP formulations at a concentration of from about 0.01 pg/mL to about 1 pg/mL, from about 0.05 pg/mL to about 2 pg/mL, from about 1 pg/mL to about 5 pg/mL, from about 2 pg/mL to about 10 pg/mL, from about 4 pg/mL to about 16 pg/mL, from about 5 pg/mL to about 20 pg/mL, from about 8 pg/mL to about 24 pg/mL, from about 10 pg/mL to about 30 pg/mL, from about 12 pg/mL to about 32 pg/mL, from about 14 pg/mL to about 34 pg/mL, from about 16 pg/mL to about 36 pg/mL, from about 18 pg/mL to about 38 pg/mL, from about 20 pg/mL to about 40 pg/mL, from about 22 pg/mL to about 42 pg/mL, from about 24 pg/mL to about 44 pg/mL, from about 26 pg/mL to about 46 pg/mL, from about 28 pg/mL to about 48 pg/mL, from about 30 pg/mL to about 50 pg/mL, from about 35 pg/mL to about 55 pg/mL, from about 40 pg/mL to about 60 pg/mL, from about 45 pg/mL to about 65 pg/mL, from about 50 pg/mL to about 75 pg/mL, from about 60 pg/mL to about 240 pg/mL, from about 70 pg/mL to about 350 pg/mL, from about 80 pg/mL to about 400 pg/mL, from about 90 pg/mL to about 450 pg/mL, from about 100 pg/mL to about 500 pg/mL, from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 μg/mL to about 1 μg/mL, from about 0.05 μg/mL to about 2 μg/mL, from about 1 μg/mL to about 5 μg/mL, from about 2 μg/mL to about 10 μg/mL, from about 4 μg/mL to about 16 μg/mL, from about 5 μg/mL to about 20 μg/mL, from about 8 μg/mL to about 24 μg/mL, from about 10 μg/mL to about 30 μg/mL, from about 12 μg/mL to about 32 μg/mL, from about 14 μg/mL to about 34 μg/mL, from about 16 μg/mL to about 36 μg/mL, from about 18 μg/mL to about 38 μg/mL, from about 20 μg/mL to about 40 μg/mL, from about 22 μg/mL to about 42 μg/mL, from about 24 μg/mL to about 44 μg/mL, from about 26 μg/mL to about 46 μg/mL, from about 28 μg/mL to about 48 μg/mL, from about 30 μg/mL to about 50 μg/mL, from about 35 μg/mL to about 55 μg/mL, from about 40 μg/mL to about 60 μg/mL, from about 45 μg/mL to about 65 μg/mL, from about 50 μg/mL to about 75 μg/mL, from about 60 μg/mL to about 240 μg/mL, from about 70 μg/mL to about 350 μg/mL, from about 80 μg/mL to about 400 μg/mL, from about 90 μg/mL to about 450 μg/mL, from about 100 μg/mL to about 500 μg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 1 g/mL to about 5 g/mL, from about 2 g/mL to about 10 g/mL, from about 4 g/mL to about 16 g/mL, or from about 5 g/mL to about 20 g/mL.

In some embodiments, the concentration of processed silk (e.g., silk fibroin) or other SBP component (e.g., excipient, therapeutic agent, microbe, cargo, and/or biological system) is present in SBP formulations at a concentration of from about 0.01 pg/kg to about 1 pg/kg, from about 0.05 pg/kg to about 2 pg/kg, from about 1 pg/kg to about 5 pg/kg, from about 2 pg/kg to about 10 pg/kg, from about 4 pg/kg to about 16 pg/kg, from about 5 pg/kg to about 20 pg/kg, from about 8 pg/kg to about 24 pg/kg, from about 10 pg/kg to about 30 pg/kg, from about 12 pg/kg to about 32 pg/kg, from about 14 pg/kg to about 34 pg/kg, from about 16 pg/kg to about 36 pg/kg, from about 18 pg/kg to about 38 pg/kg, from about 20 pg/kg to about 40 pg/kg, from about 22 pg/kg to about 42 pg/kg, from about 24 pg/kg to about 44 pg/kg, from about 26 pg/kg to about 46 pg/kg, from about 28 pg/kg to about 48 pg/kg, from about 30 pg/kg to about 50 pg/kg, from about 35 pg/kg to about 55 pg/kg, from about 40 pg/kg to about 60 pg/kg, from about 45 pg/kg to about 65 pg/kg, from about 50 pg/kg to about 75 pg/kg, from about 60 pg/kg to about 240 pg/kg, from about 70 pg/kg to about 350 pg/kg, from about 80 pg/kg to about 400 pg/kg, from about 90 pg/kg to about 450 pg/kg, from about 100 pg/kg to about 500 pg/kg, from about 0.01 ng/kg to about 1 ng/kg, from about 0.05 ng/kg to about 2 ng/kg, from about 1 ng/kg to about 5 ng/kg, from about 2 ng/kg to about 10 ng/kg, from about 4 ng/kg to about 16 ng/kg, from about 5 ng/kg to about 20 ng/kg, from about 8 ng/kg to about 24 ng/kg, from about 10 ng/kg to about 30 ng/kg, from about 12 ng/kg to about 32 ng/kg, from about 14 ng/kg to about 34 ng/kg, from about 16 ng/kg to about 36 ng/kg, from about 18 ng/kg to about 38 ng/kg, from about 20 ng/kg to about 40 ng/kg, from about 22 ng/kg to about 42 ng/kg, from about 24 ng/kg to about 44 ng/kg, from about 26 ng/kg to about 46 ng/kg, from about 28 ng/kg to about 48 ng/kg, from about 30 ng/kg to about 50 ng/kg, from about 35 ng/kg to about 55 ng/kg, from about 40 ng/kg to about 60 ng/kg, from about 45 ng/kg to about 65 ng/kg, from about 50 ng/kg to about 75 ng/kg, from about 60 ng/kg to about 240 ng/kg, from about 70 ng/kg to about 350 ng/kg, from about 80 ng/kg to about 400 ng/kg, from about 90 ng/kg to about 450 ng/kg, from about 100 ng/kg to about 500 ng/kg, from about 0.01 μg/kg to about 1 μg/kg, from about 0.05 μg/kg to about 2 μg/kg, from about 1 μg/kg to about 5 μg/kg, from about 2 μg/kg to about 10 μg/kg, from about 4 μg/kg to about 16 μg/kg, from about 5 μg/kg to about 20 μg/kg, from about 8 μg/kg to about 24 μg/kg, from about 10 μg/kg to about 30 μg/kg, from about 12 μg/kg to about 32 μg/kg, from about 14 μg/kg to about 34 μg/kg, from about 16 μg/kg to about 36 μg/kg, from about 18 μg/kg to about 38 μg/kg, from about 20 μg/kg to about 40 μg/kg, from about 22 μg/kg to about 42 μg/kg, from about 24 μg/kg to about 44 μg/kg, from about 26 μg/kg to about 46 μg/kg, from about 28 μg/kg to about 48 μg/kg, from about 30 μg/kg to about 50 μg/kg, from about 35 μg/kg to about 55 μg/kg, from about 40 μg/kg to about 60 μg/kg, from about 45 μg/kg to about 65 μg/kg, from about 50 μg/kg to about 75 μg/kg, from about 60 μg/kg to about 240 μg/kg, from about 70 μg/kg to about 350 μg/kg, from about 80 μg/kg to about 400 μg/kg, from about 90 μg/kg to about 450 μg/kg, from about 100 μg/kg to about 500 μg/kg, from about 0.01 mg/kg to about 1 mg/kg, from about 0.05 mg/kg to about 2 mg/kg, from about 1 mg/kg to about 5 mg/kg, from about 2 mg/kg to about 10 mg/kg, from about 4 mg/kg to about 16 mg/kg, from about 5 mg/kg to about 20 mg/kg, from about 8 mg/kg to about 24 mg/kg, from about 10 mg/kg to about 30 mg/kg, from about 12 mg/kg to about 32 mg/kg, from about 14 mg/kg to about 34 mg/kg, from about 16 mg/kg to about 36 mg/kg, from about 18 mg/kg to about 38 mg/kg, from about 20 mg/kg to about 40 mg/kg, from about 22 mg/kg to about 42 mg/kg, from about 24 mg/kg to about 44 mg/kg, from about 26 mg/kg to about 46 mg/kg, from about 28 mg/kg to about 48 mg/kg, from about 30 mg/kg to about 50 mg/kg, from about 35 mg/kg to about 55 mg/kg, from about 40 mg/kg to about 60 mg/kg, from about 45 mg/kg to about 65 mg/kg, from about 50 mg/kg to about 75 mg/kg, from about 60 mg/kg to about 240 mg/kg, from about 70 mg/kg to about 350 mg/kg, from about 80 mg/kg to about 400 mg/kg, from about 90 mg/kg to about 450 mg/kg, from about 100 mg/kg to about 500 mg/kg, from about 0.01 g/kg to about 1 g/kg, from about 0.05 g/kg to about 2 g/kg, from about 1 g/kg to about 5 g/kg, from about 2 g/kg to about 10 g/kg, from about 4 g/kg to about 16 g/kg, or from about 5 g/kg to about 20 g/kg, from about 10 g/kg to about 50 g/kg, from about 15 g/kg to about 100 g/kg, from about 20 g/kg to about 150 g/kg, from about 25 g/kg to about 200 g/kg, from about 30 g/kg to about 250 g/kg, from about 35 g/kg to about 300 g/kg, from about 40 g/kg to about 350 g/kg, from about 45 g/kg to about 400 g/kg, from about 50 g/kg to about 450 g/kg, from about 55 g/kg to about 500 g/kg, from about 60 g/kg to about 550 g/kg, from about 65 g/kg to about 600 g/kg, from about 70 g/kg to about 650 g/kg, from about 75 g/kg to about 700 g/kg, from about 80 g/kg to about 750 g/kg, from about 85 g/kg to about 800 g/kg, from about 90 g/kg to about 850 g/kg, from about 95 g/kg to about 900 g/kg, from about 100 g/kg to about 950 g/kg, or from about 200 g/kg to about 1000 g/kg.

In some embodiments, the concentration of processed silk or other SBP component (e.g., excipient, therapeutic agent, microbe, cargo, and/or biological system) is present in SBP formulations at a concentration of from about 0.1 pM to about 1 pM, from about 1 pM to about 10 pM, from about 2 pM to about 20 pM, from about 3 pM to about 30 pM, from about 4 pM to about 40 pM, from about 5 pM to about 50 pM, from about 6 pM to about 60 pM, from about 7 pM to about 70 pM, from about 8 pM to about 80 pM, from about 9 pM to about 90 pM, from about 10 pM to about 100 pM, from about 11 pM to about 110 pM, from about 12 pM to about 120 pM, from about 13 pM to about 130 pM, from about 14 pM to about 140 pM, from about 15 pM to about 150 pM, from about 16 pM to about 160 pM, from about 17 pM to about 170 pM, from about 18 pM to about 180 pM, from about 19 pM to about 190 pM, from about 20 pM to about 200 pM, from about 21 pM to about 210 pM, from about 22 pM to about 220 pM, from about 23 pM to about 230 pM, from about 24 pM to about 240 pM, from about 25 pM to about 250 pM, from about 26 pM to about 260 pM, from about 27 pM to about 270 pM, from about 28 pM to about 280 pM, from about 29 pM to about 290 pM, from about 30 pM to about 300 pM, from about 31 pM to about 310 pM, from about 32 pM to about 320 pM, from about 33 pM to about 330 pM, from about 34 pM to about 340 pM, from about 35 pM to about 350 pM, from about 36 pM to about 360 pM, from about 37 pM to about 370 pM, from about 38 pM to about 380 pM, from about 39 pM to about 390 pM, from about 40 pM to about 400 pM, from about 41 pM to about 410 pM, from about 42 pM to about 420 pM, from about 43 pM to about 430 pM, from about 44 pM to about 440 pM, from about 45 pM to about 450 pM, from about 46 pM to about 460 pM, from about 47 pM to about 470 pM, from about 48 pM to about 480 pM, from about 49 pM to about 490 pM, from about 50 pM to about 500 pM, from about 51 pM to about 510 pM, from about 52 pM to about 520 pM, from about 53 pM to about 530 pM, from about 54 pM to about 540 pM, from about 55 pM to about 550 pM, from about 56 pM to about 560 pM, from about 57 pM to about 570 pM, from about 58 pM to about 580 pM, from about 59 pM to about 590 pM, from about 60 pM to about 600 pM, from about 61 pM to about 610 pM, from about 62 pM to about 620 pM, from about 63 pM to about 630 pM, from about 64 pM to about 640 pM, from about 65 pM to about 650 pM, from about 66 pM to about 660 pM, from about 67 pM to about 670 pM, from about 68 pM to about 680 pM, from about 69 pM to about 690 pM, from about 70 pM to about 700 pM, from about 71 pM to about 710 pM, from about 72 pM to about 720 pM, from about 73 pM to about 730 pM, from about 74 pM to about 740 pM, from about 75 pM to about 750 pM, from about 76 pM to about 760 pM, from about 77 pM to about 770 pM, from about 78 pM to about 780 pM, from about 79 pM to about 790 pM, from about 80 pM to about 800 pM, from about 81 pM to about 810 pM, from about 82 pM to about 820 pM, from about 83 pM to about 830 pM, from about 84 pM to about 840 pM, from about 85 pM to about 850 pM, from about 86 pM to about 860 pM, from about 87 pM to about 870 pM, from about 88 pM to about 880 pM, from about 89 pM to about 890 pM, from about 90 pM to about 900 pM, from about 91 pM to about 910 pM, from about 92 pM to about 920 pM, from about 93 pM to about 930 pM, from about 94 pM to about 940 pM, from about 95 pM to about 950 pM, from about 96 pM to about 960 pM, from about 97 pM to about 970 pM, from about 98 pM to about 980 pM, from about 99 pM to about 990 pM, from about 100 pM to about 1 nM, from about 0.1 nM to about 1 nM, from about 1 nM to about 10 nM, from about 2 nM to about 20 nM, from about 3 nM to about 30 nM, from about 4 nM to about 40 nM, from about 5 nM to about 50 nM, from about 6 nM to about 60 nM, from about 7 nM to about 70 nM, from about 8 nM to about 80 nM, from about 9 nM to about 90 nM, from about 10 nM to about 100 nM, from about 11 nM to about 110 nM, from about 12 nM to about 120 nM, from about 13 nM to about 130 nM, from about 14 nM to about 140 nM, from about 15 nM to about 150 nM, from about 16 nM to about 160 nM, from about 17 nM to about 170 nM, from about 18 nM to about 180 nM, from about 19 nM to about 190 nM, from about 20 nM to about 200 nM, from about 21 nM to about 210 nM, from about 22 nM to about 220 nM, from about 23 nM to about 230 nM, from about 24 nM to about 240 nM, from about 25 nM to about 250 nM, from about 26 nM to about 260 nM, from about 27 nM to about 270 nM, from about 28 nM to about 280 nM, from about 29 nM to about 290 nM, from about 30 nM to about 300 nM, from about 31 nM to about 310 nM, from about 32 nM to about 320 nM, from about 33 nM to about 330 nM, from about 34 nM to about 340 nM, from about 35 nM to about 350 nM, from about 36 nM to about 360 nM, from about 37 nM to about 370 nM, from about 38 nM to about 380 nM, from about 39 nM to about 390 nM, from about 40 nM to about 400 nM, from about 41 nM to about 410 nM, from about 42 nM to about 420 nM, from about 43 nM to about 430 nM, from about 44 nM to about 440 nM, from about 45 nM to about 450 nM, from about 46 nM to about 460 nM, from about 47 nM to about 470 nM, from about 48 nM to about 480 nM, from about 49 nM to about 490 nM, from about 50 nM to about 500 nM, from about 51 nM to about 510 nM, from about 52 nM to about 520 nM, from about 53 nM to about 530 nM, from about 54 nM to about 540 nM, from about 55 nM to about 550 nM, from about 56 nM to about 560 nM, from about 57 nM to about 570 nM, from about 58 nM to about 580 nM, from about 59 nM to about 590 nM, from about 60 nM to about 600 nM, from about 61 nM to about 610 nM, from about 62 nM to about 620 nM, from about 63 nM to about 630 nM, from about 64 nM to about 640 nM, from about 65 nM to about 650 nM, from about 66 nM to about 660 nM, from about 67 nM to about 670 nM, from about 68 nM to about 680 nM, from about 69 nM to about 690 nM, from about 70 nM to about 700 nM, from about 71 nM to about 710 nM, from about 72 nM to about 720 nM, from about 73 nM to about 730 nM, from about 74 nM to about 740 nM, from about 75 nM to about 750 nM, from about 76 nM to about 760 nM, from about 77 nM to about 770 nM, from about 78 nM to about 780 nM, from about 79 nM to about 790 nM, from about 80 nM to about 800 nM, from about 81 nM to about 810 nM, from about 82 nM to about 820 nM, from about 83 nM to about 830 nM, from about 84 nM to about 840 nM, from about 85 nM to about 850 nM, from about 86 nM to about 860 nM, from about 87 nM to about 870 nM, from about 88 nM to about 880 nM, from about 89 nM to about 890 nM, from about 90 nM to about 900 nM, from about 91 nM to about 910 nM, from about 92 nM to about 920 nM, from about 93 nM to about 930 nM, from about 94 nM to about 940 nM, from about 95 nM to about 950 nM, from about 96 nM to about 960 nM, from about 97 nM to about 970 nM, from about 98 nM to about 980 nM, from about 99 nM to about 990 nM, from about 100 nM to about 1 μM, from about 0.1 μM to about 1 μM, from about 1 μM to about 10 μM, from about 2 μM to about 20 μM, from about 3 μM to about 30 μM, from about 4 μM to about 40 μM, from about 5 μM to about 50 μM, from about 6 μM to about 60 μM, from about 7 μM to about 70 μM, from about 8 μM to about 80 μM, from about 9 μM to about 90 μM, from about 10 μM to about 100 μM, from about 11 μM to about 110 μM, from about 12 μM to about 120 μM, from about 13 μM to about 130 μM, from about 14 μM to about 140 μM, from about 15 μM to about 150 μM, from about 16 μM to about 160 μM, from about 17 μM to about 170 μM, from about 18 μM to about 180 μM, from about 19 μM to about 190 μM, from about 20 μM to about 200 μM, from about 21 μM to about 210 μM, from about 22 μM to about 220 μM, from about 23 μM to about 230 μM, from about 24 μM to about 240 μM, from about 25 μM to about 250 μM, from about 26 μM to about 260 μM, from about 27 μM to about 270 μM, from about 28 μM to about 280 μM, from about 29 μM to about 290 μM, from about 30 μM to about 300 μM, from about 31 μM to about 310 μM, from about 32 μM to about 320 μM, from about 33 μM to about 330 μM, from about 34 μM to about 340 μM, from about 35 μM to about 350 μM, from about 36 μM to about 360 μM, from about 37 μM to about 370 μM, from about 38 μM to about 380 μM, from about 39 μM to about 390 μM, from about 40 μM to about 400 μM, from about 41 μM to about 410 μM, from about 42 μM to about 420 μM, from about 43 μM to about 430 μM, from about 44 μM to about 440 μM, from about 45 μM to about 450 μM, from about 46 μM to about 460 μM, from about 47 μM to about 470 μM, from about 48 μM to about 480 μM, from about 49 μM to about 490 μM, from about 50 μM to about 500 μM, from about 51 μM to about 510 μM, from about 52 μM to about 520 μM, from about 53 μM to about 530 μM, from about 54 μM to about 540 μM, from about 55 μM to about 550 μM, from about 56 μM to about 560 μM, from about 57 μM to about 570 μM, from about 58 μM to about 580 μM, from about 59 μM to about 590 μM, from about 60 μM to about 600 μM, from about 61 μM to about 610 μM, from about 62 μM to about 620 μM, from about 63 μM to about 630 μM, from about 64 μM to about 640 μM, from about 65 μM to about 650 μM, from about 66 μM to about 660 μM, from about 67 μM to about 670 μM, from about 68 μM to about 680 μM, from about 69 μM to about 690 μM, from about 70 μM to about 700 μM, from about 71 μM to about 710 μM, from about 72 μM to about 720 μM, from about 73 μM to about 730 μM, from about 74 μM to about 740 μM, from about 75 μM to about 750 μM, from about 76 μM to about 760 μM, from about 77 μM to about 770 μM, from about 78 μM to about 780 μM, from about 79 μM to about 790 μM, from about 80 μM to about 800 μM, from about 81 μM to about 810 μM, from about 82 μM to about 820 μM, from about 83 μM to about 830 μM, from about 84 μM to about 840 μM, from about 85 μM to about 850 μM, from about 86 μM to about 860 μM, from about 87 μM to about 870 μM, from about 88 μM to about 880 μM, from about 89 μM to about 890 μM, from about 90 μM to about 900 μM, from about 91 μM to about 910 μM, from about 92 μM to about 920 μM, from about 93 μM to about 930 μM, from about 94 μM to about 940 μM, from about 95 μM to about 950 μM, from about 96 μM to about 960 μM, from about 97 μM to about 970 μM, from about 98 μM to about 980 μM, from about 99 μM to about 990 μM, from about 100 μM to about 1 mM, from about 0.1 mM to about 1 mM, from about 1 mM to about 10 mM, from about 2 mM to about 20 mM, from about 3 mM to about 30 mM, from about 4 mM to about 40 mM, from about 5 mM to about 50 mM, from about 6 mM to about 60 mM, from about 7 mM to about 70 mM, from about 8 mM to about 80 mM, from about 9 mM to about 90 mM, from about 10 mM to about 100 mM, from about 11 mM to about 110 mM, from about 12 mM to about 120 mM, from about 13 mM to about 130 mM, from about 14 mM to about 140 mM, from about 15 mM to about 150 mM, from about 16 mM to about 160 mM, from about 17 mM to about 170 mM, from about 18 mM to about 180 mM, from about 19 mM to about 190 mM, from about 20 mM to about 200 mM, from about 21 mM to about 210 mM, from about 22 mM to about 220 mM, from about 23 mM to about 230 mM, from about 24 mM to about 240 mM, from about 25 mM to about 250 mM, from about 26 mM to about 260 mM, from about 27 mM to about 270 mM, from about 28 mM to about 280 mM, from about 29 mM to about 290 mM, from about 30 mM to about 300 mM, from about 31 mM to about 310 mM, from about 32 mM to about 320 mM, from about 33 mM to about 330 mM, from about 34 mM to about 340 mM, from about 35 mM to about 350 mM, from about 36 mM to about 360 mM, from about 37 mM to about 370 mM, from about 38 mM to about 380 mM, from about 39 mM to about 390 mM, from about 40 mM to about 400 mM, from about 41 mM to about 410 mM, from about 42 mM to about 420 mM, from about 43 mM to about 430 mM, from about 44 mM to about 440 mM, from about 45 mM to about 450 mM, from about 46 mM to about 460 mM, from about 47 mM to about 470 mM, from about 48 mM to about 480 mM, from about 49 mM to about 490 mM, from about 50 mM to about 500 mM, from about 51 mM to about 510 mM, from about 52 mM to about 520 mM, from about 53 mM to about 530 mM, from about 54 mM to about 540 mM, from about 55 mM to about 550 mM, from about 56 mM to about 560 mM, from about 57 mM to about 570 mM, from about 58 mM to about 580 mM, from about 59 mM to about 590 mM, from about 60 mM to about 600 mM, from about 61 mM to about 610 mM, from about 62 mM to about 620 mM, from about 63 mM to about 630 mM, from about 64 mM to about 640 mM, from about 65 mM to about 650 mM, from about 66 mM to about 660 mM, from about 67 mM to about 670 mM, from about 68 mM to about 680 mM, from about 69 mM to about 690 mM, from about 70 mM to about 700 mM, from about 71 mM to about 710 mM, from about 72 mM to about 720 mM, from about 73 mM to about 730 mM, from about 74 mM to about 740 mM, from about 75 mM to about 750 mM, from about 76 mM to about 760 mM, from about 77 mM to about 770 mM, from about 78 mM to about 780 mM, from about 79 mM to about 790 mM, from about 80 mM to about 800 mM, from about 81 mM to about 810 mM, from about 82 mM to about 820 mM, from about 83 mM to about 830 mM, from about 84 mM to about 840 mM, from about 85 mM to about 850 mM, from about 86 mM to about 860 mM, from about 87 mM to about 870 mM, from about 88 mM to about 880 mM, from about 89 mM to about 890 mM, from about 90 mM to about 900 mM, from about 91 mM to about 910 mM, from about 92 mM to about 920 mM, from about 93 mM to about 930 mM, from about 94 mM to about 940 mM, from about 95 mM to about 950 mM, from about 96 mM to about 960 mM, from about 97 mM to about 970 mM, from about 98 mM to about 980 mM, from about 99 mM to about 990 mM, from about 100 mM to about 1 M, from about 1 M to about 10 M, from about 2 M to about 20 M, from about 3 M to about 30 M, from about 4 M to about 40 M, from about 5 M to about 50 M, from about 6 M to about 60 M, from about 7 M to about 70 M, from about 8 M to about 80 M, from about 9 M to about 90 M, from about 10 M to about 100 M, from about 11 M to about 110 M, from about 12 M to about 120 M, from about 13 M to about 130 M, from about 14 M to about 140 M, from about 15 M to about 150 M, from about 16 M to about 160 M, from about 17 M to about 170 M, from about 18 M to about 180 M, from about 19 M to about 190 M, from about 20 M to about 200 M, from about 21 M to about 210 M, from about 22 M to about 220 M, from about 23 M to about 230 M, from about 24 M to about 240 M, from about 25 M to about 250 M, from about 26 M to about 260 M, from about 27 M to about 270 M, from about 28 M to about 280 M, from about 29 M to about 290 M, from about 30 M to about 300 M, from about 31 M to about 310 M, from about 32 M to about 320 M, from about 33 M to about 330 M, from about 34 M to about 340 M, from about 35 M to about 350 M, from about 36 M to about 360 M, from about 37 M to about 370 M, from about 38 M to about 380 M, from about 39 M to about 390 M, from about 40 M to about 400 M, from about 41 M to about 410 M, from about 42 M to about 420 M, from about 43 M to about 430 M, from about 44 M to about 440 M, from about 45 M to about 450 M, from about 46 M to about 460 M, from about 47 M to about 470 M, from about 48 M to about 480 M, from about 49 M to about 490 M, or from about 50 M to about 500 M.

SBPs may include a ratio of silk fibroin (by weight, volume, or concentration) to at least one excipient and/or therapeutic agent (by weight, volume, or concentration) of from about 0.001:1 to about 1:1, from about 0.005:1 to about 5:1, from about 0.01:1 to about 0.5:1, from about 0.01:1 to about 10:1, from about 0.02:1 to about 20:1, from about 0.03:1 to about 30:1, from about 0.04:1 to about 40:1, from about 0.05:1 to about 50:1, from about 0.06:1 to about 60:1, from about 0.07:1 to about 70:1, from about 0.08:1 to about 80:1, from about 0.09:1 to about 90:1, from about 0.1:1 to about 100:1, from about 0.2:1 to about 150:1, from about 0.3:1 to about 200:1, from about 0.4:1 to about 250:1, from about 0.5:1 to about 300:1, from about 0.6:1 to about 350:1, from about 0.7:1 to about 400:1, from about 0.8:1 to about 450:1, from about 0.9:1 to about 500:1, from about 1:1 to about 550:1, from about 2:1 to about 600:1, from about 3:1 to about 650:1, from about 4:1 to about 700:1, from about 5:1 to about 750:1, from about 6:1 to about 800:1, from about 7:1 to about 850:1, from about 8:1 to about 900:1, from about 9:1 to about 950:1, from about 10:1 to about 960:1, from about 50:1 to about 970:1, from about 100:1 to about 980:1, from about 200:1 to about 990:1, or from about 500:1 to about 1000:1. In some embodiments, SBP formulations contain trace amounts of excipient.

In some embodiments, the concentration processed silk and/or other components may be determined by absorbance. In some embodiments, the concentration of processed silk and/or other components may be determined by their absorbance at 280 nm.

Appearance: Transparent, Opaque, Translucent

In some embodiments, the appearance of SBP formulations described in the present disclosure may be tuned for the application for which they were designed. In some embodiments, SBP formulations may be transparent. In some embodiments, SBP formulations may be translucent. In some embodiments, SBP formulations may be opaque. In some embodiments, SBP preparation methods may be used to modulate clarity, as taught in International Patent Application Publication No. WO2012170655, the contents of which are herein incorporated by reference in their entirety. In some embodiments, the incorporation of excipients may be used to tune the clarity of processed silk preparations. In some embodiments, the excipient is sucrose. In some embodiments, the sucrose may also increase protein reconstitution during lyophilization. In some embodiments, sucrose may improve processed silk hydrogel clarity (optically transparent). The transparency of SBP formulations, as well as other properties, may render resulting labels edible, biodegradable, and/or holographic.

Solubility

In some embodiments, SBP formulations or components thereof are water soluble. The water solubility, along with the rate of degradation, of SBPs may modulate payload (e.g., therapeutic agent) release rate and/or release period. An increasing amount of payload may be released into surrounding medium as surrounding matrix dissolves (e.g., see International Publication Numbers WO2013126799 and WO2017165922; and U.S. Pat. No. 8,530,625, the contents of each of which are herein incorporated by reference in their entirety). Longer time periods required to dissolve SBPs or components thereof may result in longer release periods. In some embodiments, SBP solubility may be modulated in order to control the rate of payload release in the surrounding medium. The solubility of SBPs may be modulated via any method known to those skilled in the art. In some embodiments, SBP solubility may be modulated by altering included silk fibroin secondary structure (e.g., increasing beta-sheet content and/or crystallinity). In some embodiments, SBP solubility may be modulated by altering SBP format. In some embodiments, SBP solubility and/or rate of degradation may be modulated to facilitate extended release of therapeutic agent payloads in vitro and/or in vivo.

Residence Time

In some embodiments, SBP formulations may be prepared to have desired residence time according to the application for which they are designed. As used herein, the term "residence time" refers to the average length of time during which a substance (e.g., SBP formulations) is in a given location or condition. In some embodiments, residence time of SBP formulations described herein may vary from a few hours to several months. For example, residence time of SBP formulations may be about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, or longer than 1 year.

Excipients

In some embodiments, SBP formulations include one or more excipients. In some embodiments, SBP formulation may not include an excipient. As used herein, the term "excipient" refers to any substance included in a composition with an active agent or primary component, often serving as a carrier, diluent, or vehicle for the active agent or primary component. In some embodiments, excipients may be compounds or compositions approved for use by the US Food and Drug Administration (FDA). In some embodiments, SBPs may include excipients that increase SBP stability or stability of one or more other SBP components. Some SBPs may include an excipient that modulates payload release. Excipients may include, but are not limited to, solvents, diluents, liquid vehicles, dispersion or suspension media or aids, surfactants, thickening agents, emulsifying agents, lipids, liposomes, isotonic agents, buffers, and preservatives. In some embodiments, excipients include lipidoids, lipid nanoparticles, polymers, lipoplexes, particles, core-shell nanoparticles, peptides, proteins, cells, hyaluronidase, and/or nanoparticle mimics. In some embodiments, processed silk and/or SBPs may be used as an excipient. In some embodiments, excipients included in SBPs are selected from one or more of sucrose, lactose, phosphate salts, sodium chloride, potassium phosphate monobasic, potassium phosphate dibasic, sodium phosphate dibasic, sodium phosphate monobasic, polysorbate 80, phosphate buffer, phosphate buffered saline, sodium hydroxide, sorbitol, mannitol, lactose USP, Starch 1500, microcrystalline cellulose, potassium chloride, sodium borate, boric acid, sodium borate decahydrate, magnesium chloride hexahydrate, calcium chloride dihydrate, sodium hydroxide, Avicel, dibasic calcium phosphate dehydrate, tartaric acid, citric acid, fumaric acid, succinic acid, malic acid, hydrochloric acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, and sodium carboxymethylcellulose. Excipients may include phosphate buffered saline. Excipients may be present in SBPs at any concentration. In some embodiments, excipients are present at a concentration of from about 0.0001% weight per weight (w/w) of excipient to total SBP weight to about 20% (w/w). In some embodiments, excipients are present at a concentration of from about 0.0001% weight per weight (w/w) of excipient to total SBP weight to about 50% (w/w).

In some embodiments, excipients included in SBPs may be selected from one or more of sorbitol, triethylamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol, glycerol EL (cremophor EL), cremophor RH 40, cremophor RH 60, dalpha-tocopherol, PEG 1000 succinate, polysorbate 20, polysorbate 80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, medium chain triglycerides of coconut oil, medium chain triglycerides of palm seed oil, beeswax, d-alpha-tocopherol, oleic acid, medium-chain mono-glycerides, medium-chain di-glycerides, alpha-cyclodextrin, betacyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alpha-dimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), polyoxyl 8 stearate (PEG 400 monosterate), polysorbate 20, polysorbate 80, polyvinyl pyrrolidone, propylene carbonate, propylene glycol, solutol HS15, sorbitan monooleate (Span 20), sulfobutylether-beta-cyclodextrin, transcutol, triacetin, I-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, glycerin, and PEG 4 kDa. Such SBPs may include hydrogels. In some embodiments, SBP hydrogels include one or more of polysorbate 80, poloxamer-188, PEG 4 kDa, and glycerol.

In some embodiments, excipients included in SBPs are selected from one or more of those listed in Table 1. In the Table, example categories are indicated for each excipient. These categories are not limiting and each excipient may fall under multiple categories (e.g., any of the categories of excipients described herein).

TABLE 1

Excipients

| Excipient | Example Category |
| --- | --- |
| Agirilene | Anti-aging agent |
| Retinol | Anti-aging agent |
| Ajurana | Anti-aging agent |
| Beta glucan | Anti-aging agent |
| Carrot Cells | Anti-aging agent |
| Ceramide | Anti-aging agent |
| Coenzyme Q10 | Anti-aging agent |
| Collagen protein | Anti-aging agent |
| Edelweiss extract | Anti-aging agent |
| Penta peptide | Anti-aging agent |
| Ginger root extract | Anti-aging agent |
| Ginkgo biloba extract | Anti-aging agent |
| Goji berry extract | Anti-aging agent |
| Helichrysum extract | Anti-aging agent |
| Hyaluronic acid | Anti-aging agent |
| Jojoba protein | Anti-aging agent |
| Knotgrass flavoinoids | Anti-aging agent |
| Lacto-ceramide | Anti-aging agent |
| Lingonberry stem cells | Anti-aging agent |
| LiPeptide | Anti-aging agent |
| Mallow extract | Anti-aging agent |
| Orange stem cells | Anti-aging agent |
| Orchid stem cells | Anti-aging agent |
| Palmitoyl isoleucine | Anti-aging agent |
| Palmitoyl peptide | Anti-aging agent |
| Palmitoyl tripeptide-38 | Anti-aging agent |
| Pearl powder | Anti-aging agent |
| Provitamin B5 | Anti-aging agent |
| SN-KE peptide | Anti-aging agent |
| Teprenone | Anti-aging agent |
| Tomato lycopene | Anti-aging agent |
| Tripeptide-5 | Anti-aging agent |
| Retinyl pamitate | Anti-aging agent |
| Retinol | Anti-aging agent |
| Niacinamide | Anti-aging agent |
| Watermelon extract | Anti-aging agent |
| Salicylic acid | Anti-acne agent |
| Tretinoin | Anti-acne agent |
| Salicylic acid | Anti-dandruff agent |
| Ketoconzole | Anti-dandruff agent |
| Zinc pyrithione | Anti-dandruff agent |
| Selenium disulfide | Anti-dandruff agent |
| Sulfur | Anti-dandruff agent |
| Coal tar | Anti-dandruff agent |
| Ajurana extract | Anti-dark circles agent |
| Palmitoyl peptide | Anti-dark circles agent |
| Soy-rice peptide | Anti-dark circles agent |
| Aminopropyl kojyl phosphate | Antioxidant |
| Ascorbyl 3-aminopropyl dihydrogen phosphate | Antioxidant |
| BHT | Antioxidant |
| Beta carotene | Antioxidant |
| Chaparral extract | Antioxidant |
| Citric Acid | Antioxidant |

TABLE 1-continued

| Excipients | |
|---|---|
| Excipient | Example Category |
| Coenzyme Q10 | Antioxidant |
| Cucumber extract | Antioxidant |
| Folic acid | Antioxidant |
| Greentea extract | Antioxidant |
| Goldenseal extract | Antioxidant |
| Kakadu plum extract | Antioxidant |
| Mallow extract | Antioxidant |
| Mulberry root extract | Antioxidant |
| Bisabolol | Antioxidant |
| Resveratrol | Antioxidant |
| Saccharomyces- copper ferment | Antioxidant |
| Saphora japonica | Antioxidant |
| Sea buckthorn | Antioxidant |
| Soapwort extract | Antioxidant |
| Superoxide dismutase | Antioxidant |
| T-resveratrol | Antioxidant |
| 3-glyceryl ascorbate | Antioxidant |
| L-ascorbic acid | Antioxidant |
| L-ascorbyl palmitate | Antioxidant |
| Magnesium ascorbyl phosphate | Antioxidant |
| Sodium ascorbyl phosphate | Antioxidant |
| Tetrahexadecyl ascorbate | Antioxidant |
| dl-alpha tocopherol | Antioxidant |
| dl-alpha tocopherol acetate | Antioxidant |
| White tea extract | Antioxidant |
| Aluminum chlorohydrate | Antiperspirant |
| Hexamethylenetetramine | Antiperspirant |
| Acai fruit extract | Anti-wrinkle agent |
| Agirilene | Anti-wrinkle agent |
| Adenosine, beta-cyclodextrin | Anti-wrinkle agent |
| Aminopropyl dihydrogen phosphate | Anti-wrinkle agent |
| Asparagus officinalis stem extract | Anti-wrinkle agent |
| Baicalin | Anti-wrinkle agent |
| Benzylsulfonyl D-seryl homophenylalanine amidinobenzamide acetate | Anti-wrinkle agent |
| Beta glucan | Anti-wrinkle agent |
| Blue flax extract | Anti-wrinkle agent |
| Carob tree gum | Anti-wrinkle agent |
| Casein | Anti-wrinkle agent |
| Ceramide | Anti-wrinkle agent |
| Cephalin | Anti-wrinkle agent |
| Chili pepper fruit extract | Anti-wrinkle agent |
| Cinnamon extract | Anti-wrinkle agent |
| Cocoa extract | Anti-wrinkle agent |
| Coffee seed extract | Anti-wrinkle agent |
| Coenzyme Q10 | Anti-wrinkle agent |
| Collagen protein | Anti-wrinkle agent |
| Dihydromyricetin | Anti-wrinkle agent |
| Dunaliella salina micro-algae extract | Anti-wrinkle agent |
| Elderberry flower extract | Anti-wrinkle agent |
| Fisetin and raspberry ketone | Anti-wrinkle agent |
| Folic aid | Anti-wrinkle agent |
| Ginger root extract | Anti-wrinkle agent |
| Ginkgo biloba | Anti-wrinkle agent |
| Glycan peptide | Anti-wrinkle agent |
| Glycosaminoglycans | Anti-wrinkle agent |
| Grape leaf extract | Anti-wrinkle agent |
| Helichrysum extract | Anti-wrinkle agent |
| Hydroxystearic acid | Anti-wrinkle agent |
| Hydrolyzed pearl | Anti-wrinkle agent |
| Indian soapberry extract | Anti-wrinkle agent |
| Jojoba | Anti-wrinkle agent |
| Kali musli extract | Anti-wrinkle agent |
| Knotgrass flavonoid | Anti-wrinkle agent |
| Licorice root extract | Anti-wrinkle agent |
| Lingonberry stem cells | Anti-wrinkle agent |
| LiPeptide | Anti-wrinkle agent |
| Marrubium extract | Anti-wrinkle agent |
| Marine seaweed extract | Anti-wrinkle agent |
| Masterwort leaf extract | Anti-wrinkle agent |
| Orange stem cells | Anti-wrinkle agent |
| Orange blossom flower extract | Anti-wrinkle agent |
| Orchid stem cells | Anti-wrinkle agent |
| Paeonia lactiflora extract | Anti-wrinkle agent |
| Palmitoyl isoleucine | Anti-wrinkle agent |
| Palmitoyl tripeptide-38 | Anti-wrinkle agent |
| Paulina cupana seed extract | Anti-wrinkle agent |

TABLE 1-continued

| Excipients | |
|---|---|
| Excipient | Example Category |
| Peppermint leaf extract | Anti-wrinkle agent |
| Polymethylsilsesquioxane | Anti-wrinkle agent |
| Porica cocos polysaccharides | Anti-wrinkle agent |
| Pumpkin fruit extract | Anti-wrinkle agent |
| Rhapontic rhubarb extract | Anti-wrinkle agent |
| Red clover extract | Anti-wrinkle agent |
| Red date seed extract | Anti-wrinkle agent |
| Retinyl palmitate | Anti-wrinkle agent |
| Retinyl acetate | Anti-wrinkle agent |
| Retinol | Anti-wrinkle agent |
| Rosa hybrid flower extract | Anti-wrinkle agent |
| Roselle plant extract | Anti-wrinkle agent |
| Rosemary leaf extract | Anti-wrinkle agent |
| Royal jelly extract | Anti-wrinkle agent |
| Saccharomyces-Copper ferment | Anti-wrinkle agent |
| Scenedesmus rubescens micro-algae extract | Anti-wrinkle agent |
| Scutellaria root extract | Anti-wrinkle agent |
| Seaweed oil | Anti-wrinkle agent |
| Sericin protein | Anti-wrinkle agent |
| Sesame seed extract | Anti-wrinkle agent |
| Sodium hyaluronate | Anti-wrinkle agent |
| Soybean Germ | Anti-wrinkle agent |
| Strawberry fruit extract | Anti-wrinkle agent |
| Summer lilac extract | Anti-wrinkle agent |
| Superoxide dismutase | Anti-wrinkle agent |
| Tripeptide-5 | Anti-wrinkle agent |
| Niacin | Anti-wrinkle agent |
| Niacinamide | Anti-wrinkle agent |
| Vitamin E | Anti-wrinkle agent |
| Vitamin F glyceric ester | Anti-wrinkle agent |
| Wheat gluten | Anti-wrinkle agent |
| White genepi extract | Anti-wrinkle agent |
| Wheat germ extract | Anti-wrinkle agent |
| Wheat milk | Anti-wrinkle agent |
| Yeast extract | Anti-wrinkle agent |
| Allantoin | Hair repair agents |
| Amaranthus seed extract | Hair repair agents |
| Artichoke leaf extract | Hair repair agents |
| Baobab protein | Hair repair agents |
| Collagen protein | Hair repair agents |
| Elastin protein | Hair repair agents |
| Maltodextrin | Hair repair agents |
| Jojoba protein | Hair repair agents |
| Keratin protein | Hair repair agents |
| Lupine protein | Hair repair agents |
| Milk protein | Hair repair agents |
| Oat amino acids | Hair repair agents |
| d-panthenol | Hair repair agents |
| dl-panthenol | Hair repair agents |
| Quinoa protein | Hair repair agents |
| Rhodiola | Hair repair agents |
| Wheat protein | Hair repair agents |
| Bilberry fruit extract | Botanical extract |
| Acacia fruit extract | Botanical extract |
| Acerola extract | Botanical extract |
| Agrimony extract | Botanical extract |
| Alfalfa extract | Botanical extract |
| Almond extract | Botanical extract |
| Aloe vera extract | Botanical extract |
| Angelica extract | Botanical extract |
| Anise extract | Botanical extract |
| Apple extract | Botanical extract |
| Apricot fruit extract | Botanical extract |
| Apricot leaves extract | Botanical extract |
| Avocado extract | Botanical extract |
| Balm gilead extract | Botanical extract |
| Balm mint extract | Botanical extract |
| Balsam 72anada extract | Botanical extract |
| Banana extract | Botanical extract |
| Barley malt extract | Botanical extract |
| Basil extract | Botanical extract |
| Bay laurel extract | Botanical extract |
| Bayberry bark extract | Botanical extract |
| Bee balm leaves extract | Botanical extract |
| Bee pollen extract | Botanical extract |
| Benzoin extract | Botanical extract |

TABLE 1-continued

| Excipients | |
|---|---|
| Excipient | Example Category |
| Birch bark extract | Botanical extract |
| Birch leaf extract | Botanical extract |
| Black cohosh extract | Botanical extract |
| Black walnut shells extract | Botanical extract |
| Blackberry leaves extract | Botanical extract |
| Bladderwrack extract | Botanical extract |
| Blue agave extract | Botanical extract |
| Blue flag extract | Botanical extract |
| Blue vervain extract | Botanical extract |
| Blueberry fruit extract | Botanical extract |
| Borage extract | Botanical extract |
| Burdock root extract | Botanical extract |
| Butcher's broom extract | Botanical extract |
| Capsicum extract | Botanical extract |
| Carrot seed extract | Botanical extract |
| Cedar wood extract | Botanical extract |
| Chardonnay extract | Botanical extract |
| Cherimoya extract | Botanical extract |
| Chrysanthemum extract | Botanical extract |
| Cinnamon extract | Botanical extract |
| Clove flower extract | Botanical extract |
| Coltsfoot extract | Botanical extract |
| Comfrey extract | Botanical extract |
| Coneflower extract | Botanical extract |
| Coriander extract | Botanical extract |
| Corn extract | Botanical extract |
| Cornflower extract | Botanical extract |
| Cranberry extract | Botanical extract |
| Cypress extract | Botanical extract |
| Dandelion extract | Botanical extract |
| Dill extract | Botanical extract |
| Dong quai extract | Botanical extract |
| Elder flower extract | Botanical extract |
| Elderberry extract | Botanical extract |
| Eucalyptus extract | Botanical extract |
| Evening primrose extract | Botanical extract |
| Eyebright extract | Botanical extract |
| Fennel extract | Botanical extract |
| Fir needle extract | Botanical extract |
| Gardenia extract | Botanical extract |
| Gentian extract | Botanical extract |
| Geranium extract | Botanical extract |
| Ginseng extract | Botanical extract |
| Grape extract | Botanical extract |
| Grapefruit extract | Botanical extract |
| Guarana extract | Botanical extract |
| Guava extract | Botanical extract |
| Hawaiian white ginger extract | Botanical extract |
| Hibiscus extract | Botanical extract |
| Honey extract | Botanical extract |
| Honeydew extract | Botanical extract |
| Honeysuckle extract | Botanical extract |
| Hops extract | Botanical extract |
| Lupine seed extract | Botanical extract |
| Horseradish extract | Botanical extract |
| Horsetail extract | Botanical extract |
| Hyssop extract | Botanical extract |
| Iceland moss extract | Botanical extract |
| Olive leaf extract | Botanical extract |
| Ivy extract | Botanical extract |
| Jaborandi extract | Botanical extract |
| Jasmine extract | Botanical extract |
| Jojoba meal extract | Botanical extract |
| Juniper extract | Botanical extract |
| Kiwi fruit extract | Botanical extract |
| Kola nut extract | Botanical extract |
| Kumquat extract | Botanical extract |
| Lady's mantle extract | Botanical extract |
| Lady's slipper extract | Botanical extract |
| Lavender extract | Botanical extract |
| Lemon bioflavonoids extract | Botanical extract |
| Lemon fruit extract | Botanical extract |
| Lemon peel extract | Botanical extract |
| Lemongrass extract | Botanical extract |
| Lichen extract | Botanical extract |
| Lime flower extract | Botanical extract |

TABLE 1-continued

| Excipients | |
|---|---|
| Excipient | Example Category |
| Lime fruit extract | Botanical extract |
| Linden flower extract | Botanical extract |
| Loquat extract | Botanical extract |
| Magnolia bark extract | Botanical extract |
| Mandarin orange extract | Botanical extract |
| Mango extract | Botanical extract |
| Marjoram extract | Botanical extract |
| Marshmallow root extract | Botanical extract |
| Meadowsweet extract | Botanical extract |
| Milk vetch extract | Botanical extract |
| Mimosa bark extract | Botanical extract |
| Mistletow extract | Botanical extract |
| Mugwort extract | Botanical extract |
| Mulberry leaf extract | Botanical extract |
| Mullein leaf extract | Botanical extract |
| Mustard seed extract | Botanical extract |
| Myrrh extract | Botanical extract |
| Nettle extract | Botanical extract |
| Neutral henna extract | Botanical extract |
| Norway spruce extract | Botanical extract |
| Oak bark extract | Botanical extract |
| Orange blossom extract | Botanical extract |
| Orange fruit extract | Botanical extract |
| Orange peel extract | Botanical extract |
| Orchid extract | Botanical extract |
| Orris root extract | Botanical extract |
| Pansy extract | Botanical extract |
| Papaya fruit extract | Botanical extract |
| Papaya leaves extract | Botanical extract |
| Parsley leaves extract | Botanical extract |
| Passion fruit extract | Botanical extract |
| Peach kernel extract | Botanical extract |
| Peach leaves extract | Botanical extract |
| Pear extract | Botanical extract |
| Pellitory extract | Botanical extract |
| Pennyroyal extract | Botanical extract |
| Peony flower extract | Botanical extract |
| Peony root extract | Botanical extract |
| Peppermint extract | Botanical extract |
| Periwinkle extract | Botanical extract |
| Pine back extract | Botanical extract |
| Pine cone extract | Botanical extract |
| Pineapple extract | Botanical extract |
| Pomegranate extract | Botanical extract |
| Poppy extract | Botanical extract |
| Prickly ash bark extract | Botanical extract |
| Prickly pear cactus extract | Botanical extract |
| Psoralea extract | Botanical extract |
| Pumpkin extract | Botanical extract |
| Quince seed extract | Botanical extract |
| Raspberry extract | Botanical extract |
| Red clover blossom extract | Botanical extract |
| Rice bran extract | Botanical extract |
| Rosehips extract | Botanical extract |
| Royal jelly extract | Botanical extract |
| Slippery elm bark extract | Botanical extract |
| Soybean extract | Botanical extract |
| Spearmint extract | Botanical extract |
| Spirulina extract | Botanical extract |
| St John's Wort extract | Botanical extract |
| Strawberry extract | Botanical extract |
| Sunflower seed extract | Botanical extract |
| Thyme extract | Botanical extract |
| Tomato extract | Botanical extract |
| Valerian root extract | Botanical extract |
| Vanilla extract | Botanical extract |
| Violet extract | Botanical extract |
| Wheat germ extract | Botanical extract |
| White lily bulb extract | Botanical extract |
| Wild cherry bark extract | Botanical extract |
| Wild yam extract | Botanical extract |
| Wintergreen extract | Botanical extract |
| Yarrow extract | Botanical extract |
| Yellow dock extract | Botanical extract |
| Yucca extract | Botanical extract |
| Coffee extract | Botanical extract |

TABLE 1-continued

| Excipients | |
|---|---|
| Excipient | Example Category |
| Mangosteen extract | Botanical extract |
| Neem extract | Botanical extract |
| Flax seed extract | Botanical extract |
| Soap bark extract | Botanical extract |
| Rosa centifolia flower extract | Botanical extract |
| White genepi extract | Botanical extract |
| Summer lilac extract | Botanical extract |
| Masterwort leaf extract | Botanical extract |
| Blue flax extract | Botanical extract |
| Elderberry flower extract | Botanical extract |
| Thymus hydrolysate | Botanical extract |
| Alpine willowherb extract | Botanical extract |
| Acai fruit extract | Botanical extract |
| Rhapontic rhubarb extract | Botanical extract |
| Kali musli extract | Botanical extract |
| Cocoa extract | Botanical extract |
| Coffee seed extract | Botanical extract |
| Roselle plant extract | Botanical extract |
| Licorice root extract | Botanical extract |
| Peppermint leaf extract | Botanical extract |
| Red date extract | Botanical extract |
| Indian soapberry extract | Botanical extract |
| Yeast extract | Botanical extract |
| Amber powder | Botanical extract |
| Olive seed powder | Botanical extract |
| Round leaf buchu extract | Botanical extract |
| Lotus flower extract | Botanical extract |
| False daisy extract | Botanical extract |
| Oat straw extract | Botanical extract |
| Red algae extract | Botanical extract |
| Potamogeton crispus extract | Botanical extract |
| Avicel | bulking agent |
| bulking agent | bulking agent |
| copolymers of vinylpyrrolidone and vinylacetate | bulking agent |
| dibasic calcium phosphate dehydrate | bulking agent |
| fumaric acid | bulking agent |
| hydroxypropylmethylcellulose | bulking agent |
| lactose USP | bulking agent |
| malic acid | bulking agent |
| microcrystalline cellulose | bulking agent |
| polyvinylpyrrolidone | bulking agent |
| tartaric acid | bulking agent |
| (12Z,15Z)-N,N-dimethyl-2-nonylhenicosa-12,15-dien-1-amine | cationic lipid |
| (12Z,15Z)-N,N-dimethylhenicosa-12,15-dien-4-amine | cationic lipid |
| (13Z,16Z)-N,N-dimethyl-3-nonyldocosa-I3,16-dien-I-amine | cationic lipid |
| (13Z,16Z)-N,N-dimethyldocosa-13,16-dien-5-amine | cationic lipid |
| (14Z)-N,N-dimethylnonacos-14-en-I0-amine | cationic lipid |
| (14Z,17Z)-N,N-dimethyltricosa-14,17-dien-4-amine | cationic lipid |
| (14Z,17Z)-N,N-dimethyltricosa-14,17-dien-6-amine | cationic lipid |
| (15Z)-N,N-dimethyl eptacos-15-en-I 0-amine | cationic lipid |
| (15Z,18Z)-N,N-dimethyltetracosa-15,18-dien-7-amine | cationic lipid |
| (15Z,18Z)-N,N-dimethyltetracosa-15,18-dien-5-amine | cationic lipid |
| (16Z)-N,N-dimethylpentacos-16-en-8-amine | cationic lipid |
| (16Z,19Z)-N,N-dimethylpentacosa-16,19-dien-6-amine | cationic lipid |
| (17Z)-N,N-dimethylhexacos-17-en-9-amine | cationic lipid |
| (17Z)-N,N-dimethylnonacos-17-en-I0-amine | cationic lipid |
| (17Z,20Z)-N,N-dimemylhexacosa-17,20-dien-9-amine | cationic lipid |
| (17Z,20Z)-N,N-dimethylhexacosa-17,20-dien-7-amine | cationic lipid |
| (18Z)-N,N-dimetylheptacos-18-en-10-amine | cationic lipid |
| (18Z,21Z)-N,N-dimethylheptacosa-18,21-dien-8-amine | cationic lipid |
| (18Z,21Z)-N,N-dimethylheptacosa-18,21-dien-10-amine | cationic lipid |
| (19Z,22Z)-N,N-dimeihyloctacosa-19,22-dien-9-amine | cationic lipid |
| (19Z,22Z)-N,N-dimethyloctacosa-19,22-dien-7-amine | cationic lipid |
| (1IE,20Z,23Z)-N,N-dimethylnonacosa-I1,20,2-trien-10-amine | cationic lipid |
| (1Z,19Z)-N5N-dimethylpentacosa-I6,19-dien-8-amine | cationic lipid |
| (20Z)-N,N-dimethylheptacos-20-en-I 0-amine | cationic lipid |
| (20Z)-N,N-dimethylnonacos-20-en-I 0-amine | cationic lipid |
| (20Z,23Z)-N,N-dimethylnonacosa-20,23-dien-10-amine | cationic lipid |
| (20Z,23Z)-N-ethyl-N-methylnonacosa-20,23-dien-I0-amine | cationic lipid |
| (21Z,24Z)-N,N-dimethyltriaconta-21,24-dien-9-amine | cationic lipid |
| (22Z)-N,N-dimethylhentriacont-22-en-I0-amine | cationic lipid |
| (22Z,25Z)-N,N-dimethylhentriaconta-22,25-dien-10-amine | cationic lipid |
| (24Z)-N,N-dimethyltritriacont-24-en-I0-amine | cationic lipid |
| (2R)-1-[(3,7-dimethyloctyl)oxy]-N,N-dimethyl-3-[(9Z,12Z)-octadeca-9,12-dien-1-yloxy]propan-2-amine | cationic lipid |

TABLE 1-continued

| Excipients | |
|---|---|
| Excipient | Example Category |
| (2R)-N,N-dimethyl-H(1-metoyloctyl)oxy]-3-[(9Z,12Z)-octadeca-9,12-dien-1-yloxy]propan-2-amine | cationic lipid |
| (2S)-1-(heptyloxy)-N,N-dimethyl-3-[(9Z,12Z)-octadeca-9,12-dien-1-yloxy]propan-2-amine | cationic lipid |
| (2S)-1-(hexyloxy)-3-[(11Z,14Z)-icosa-11,14-dien-1-yloxy]-N,N-dimethylpropan-2-amine | cationic lipid |
| (2S)-1-(hexyloxy)-N,N-dimethyl-3-[(9Z,12Z)-octadeca-9,12-dien-1-yloxy]propan-2-amine | cationic lipid |
| (2S)-1-[(11Z,14Z)-icosa-11,14-dien-1-yloxy]-N,N-dimethyl-3-(pentyloxy)propan-2-amine | cationic lipid |
| (2S)-1-(13Z)-docos-13-en-1-yloxy]-3-(hexyloxy)-N,N-dimethylpropan-2-amine | cationic lipid |
| (2S)-1-[(13Z,16Z)-docosa-13,16-dien-1-yloxy]-3-(hexyloxy)-N,N-dimethylpropan-2-amine | cationic lipid |
| (2S)-N,N-dimethyl-1-[(6Z,9Z,12Z)-octadeca-6,9,12-trien-1-yloxy]-3-(octyloxy)propan-2-amine | cationic lipid |
| (2S)-N,N-dimethyl-1-[(9Z,12Z)-octadeca-9,12-dien-1-yloxy]-3-[(5Z)-oct-5-en-1-yloxy]propan-2-amine | cationic lipid |
| 1,2-dilinolenyloxy-3-dimethylaminopropane (DLenDMA) | cationic lipid |
| 1,2-distearloxy-N,N-dimethylaminopropane (DSDMA) | cationic lipid |
| 1-[(11Z,14Z)-icosa-11,14-dien-1-yloxy]-N,N-dimethy1-3-(octyloxy)propan-2-amine | cationic lipid |
| 1-[(11Z,14Z)-I-nonylicosa-11,14-dien-I-yl] pyrrolidine | cationic lipid |
| 1-[(13Z)-docos-13-en-1-yloxy]-N,N-dimethyl-3-(octyloxy)propan-2-amine | cationic lipid |
| 1-[(13Z,16Z)-docosa-I3,16-dien-I-yloxy]-N,N-dimethyl-3-(octyloxy)propan-2-amine | cationic lipid |
| 1-[(1R,2S)-2-heptylcyclopropyl]-N,N-dimethyloctadecan-9-amine | cationic lipid |
| 1-[(1S,2R)-2-decylcyclopropyl]-N,N-dimethylpentadecan-6-amine | cationic lipid |
| 1-[(1S,2R)-2-hexylcyclopropyl]-N,N-dimethylnonadecan-10-amine | cationic lipid |
| 1-[(9Z)-hexadec-9-en-1-yloxy]-N,N-dimethyl-3-(octyloxy)propan-2-amine | cationic lipid |
| 1-{2-[(9Z,12Z)-octadeca-9,12-dien-1-yloxy]-1-[(octyloxy)methyl]ethyl}azetidine | cationic lipid |
| 1-{2-[(9Z,12Z)-octadeca-9,12-dien-1-yloxy]-1-[(octyloxy)methyl]ethyl}pyrrolidine | cationic lipid |
| cationic lipid | cationic lipid |
| CLI-CLXXIX of International Publication No. WO2008103276 | cationic lipid |
| DLin-DMA | cationic lipid |
| DODMA | cationic lipid |
| formula CLI-CLXXIX of U.S. Pat. No. 7,893,302 | cationic lipid |
| formula CLI-CLXXXXII of U.S. Pat. No. 7,404,969 | cationic lipid |
| formula I-VI of United States Patent Publication No. US20100036115 | cationic lipid |
| N,N-dimethyl-1-(octyloxy)-3-({8-[(1S,2S)-2-{[(1R,2R)-2-pentylcyclopropyl]methyl}cyclopropyl]octyl}oxy)propan-2-amine | cationic lipid |
| N,N-dimethyl-1-{[8-(2-oc1ylcyclopropyl)octyl]oxy}-3-(octyloxy)propan-2-amine | cationic lipid |
| N,N-dimethyl-21-[(IS,2R)-2-octylcyclopropyl]henicosan-I0-amine | cationic lipid |
| N,N-dimethyl-3-{7-[(1S,2R)-2-octylcyclopropyl]heptyl}dodecan-1-amine | cationic lipid |
| N,N-dimethylheptacosan-10-amine | cationic lipid |
| N,N-dimethyl-I-[(IS,2R)-2-octylcyclopropyl]eptadecan-8-amine | cationic lipid |
| N,N-dimethyl-I-[(IS,2R)-2-octylcyclopropyl]77onadecane77-8-amine | cationic lipid |
| R-N,N-dimethyl-1-[(9Z,12Z)-octadeca-9,12-dien-1-yloxy]-3-(octyloxy)propan-2-amine | cationic lipid |
| S-N,N-dimethyl-1-[(9Z,12Z)-octadeca-9,12-dien-1-yloxy]-3-(octyloxy)propan-2-amine | cationic lipid |
| N,N-dimethyl-[(IR,2S)-2-undecylcyclopropyl]77onadecane77-5-amine | cationic lipid |
| N,N-dimethyl-1-(nonyloxy)-3-[(9Z,12Z)-octadeca-9,12-dien-1-yloxy]propan-2-amine | cationic lipid |
| N,N-dimethyl-1-[(1S,2R)-2-octylcyclopropyl]77onadecane-10-amine | cationic lipid |
| N,N-dimethyl-1-[(1S,2R)-2-octylcyclopropyl]77onadecane-8-amine | cationic lipid |
| N,N-dimethyl-1-[(1S,2S)-2-{[(IR,2R)-2-pentylcyclopropyl]methyl}cyclopropyl]77onadecane-10-amine | cationic lipid |
| N,N-dimethyl-1-[(9Z)-octadec-9-en-1-yloxy]-3-(octyloxy)propan-2-amine | cationic lipid |
| Behentrimonium | Cationic conditioners |
| Polyquaternium-10 | Cationic conditioners |
| Polyquaternium-7 | Cationic conditioners |
| Quaternium-31 | Cationic conditioners |
| Rice quat | Cationic conditioners |
| Guar gum | Cationic conditioners |
| Cetrimonium chloride | Cationic conditioners |
| coating agents | coating agent |
| poly(alkyl)(meth)acrylate | coating agent |
| poly(ethylene-co-vinyl acetate) | coating agent |
| zein | coating agent |
| apocarotenal | Colorant |
| apocarotenal derivative | Colorant |
| astaxanthin | Colorant |
| astaxanthin derivative | Colorant |
| bixin | Colorant |
| canthaxanthin | Colorant |
| canthaxanthin derivative | Colorant |
| capsanthin | Colorant |
| capsanthin derivative | Colorant |
| capsorubin derivative | Colorant |
| capsorubin occurring in paprika oleoresin | Colorant |
| carotinoids | Colorant |

TABLE 1-continued

| Excipients | |
|---|---|
| Excipient | Example Category |
| Chromium oxide green | Colorant |
| colorant | Colorant |
| crocin | Colorant |
| crocin derivative | Colorant |
| dyes | Colorant |
| FD&C Blue No. 2 (indigotine) | Colorant |
| FD&C colorant | Colorant |
| FD&C Red No. 3 (erythrosine) | Colorant |
| FD&C Red No. 40 (allura red AC) | Colorant |
| food coloring | Colorant |
| inks | Colorant |
| Iron oxide black | Colorant |
| Iron oxide brown | Colorant |
| Iron oxide red | Colorant |
| Iron oxide yellow | Colorant |
| Blue No. 1 | Colorant |
| Carbon black | Colorant |
| Red no. 28 | Colorant |
| Red no. 40 | Colorant |
| Red no. 6 | Colorant |
| Red no. 7 | Colorant |
| Violet no. 2 | colorant |
| Yellow no. 5 | Colorant |
| Caramel colorant | Colorant |
| Mica beige | Colorant |
| Mica Blackstar red | Colorant |
| Mica Bordeaux | Colorant |
| Mica bronze | Colorant |
| Mica carmine red | Colorant |
| Mica cinnamon | Colorant |
| Mica diamond | Colorant |
| Mica silver | Colorant |
| Mica gold | Colorant |
| Mica copper | Colorant |
| Mica green | Colorant |
| Mica violet | Colorant |
| Mica light blue | Colorant |
| Mica luster black | Colorant |
| Mica magenta | Colorant |
| Mica majestic green | Colorant |
| Mica patina silver | Colorant |
| Mica pearl white | Colorant |
| Mica pink camel | Colorant |
| Mica purple sky | Colorant |
| Mica red | Colorant |
| Mica sand gold | Colorant |
| Mica Sappan red | Colorant |
| Mica sugar blush | Colorant |
| Mica walnut brown | Colorant |
| lutein | Colorant |
| lutein derivative | Colorant |
| lycopene | Colorant |
| pigments | Colorant |
| rhodoxanthin | Colorant |
| rubixanthin | Colorant |
| saffron | Colorant |
| saffron derivative | Colorant |
| turmeric | Colorant |
| Ultramarine blue | Colorant |
| Ultramarine pink | Colorant |
| violaxanthin | Colorant |
| β-carotene | Colorant |
| β-carotene derivative | Colorant |
| Aluminum chloride | drying agent |
| Aluminum chlorohydrate | drying agent |
| Aluminum zirconium chlorohydrate | drying agent |
| Liquid soy lecithin | Emulsifier/water-in-oil |
| Solid soy lecithin | Emulsifier/water-in-oil |
| Honey | Emulsifier/water-in-oil |
| Beeswax | Emulsifier/water-in-oil |
| Gylceryl stearate | Emulsifier/water-in-oil |
| Sorbitan stearate | Emulsifier/water-in-oil |
| Polyglyceryl oleate | Emulsifier/water-in-oil |
| Glycol stearate | Emulsifier/water-in-oil |
| Glycol distearate | Emulsifier/water-in-oil |
| Glyceryl oleate | Emulsifier/water-in-oil |

TABLE 1-continued

| Excipients | |
|---|---|
| Excipient | Example Category |
| Laureth-3 | Emulsifier/water-in-oil |
| Shea Butter glycerides | Emulsifier/water-in-oil |
| Sorbitan oleate | Emulsifier/water-in-oil |
| Ceteareth-20 | Emulsifier/water-in-oil |
| Gum Arabic | Emulsifier/water-in-oil |
| PEG-7 Glyceryl Cocoate | Emulsifier/water-in-oil |
| PEG-40 Hydrogenated Castor Oil | Emulsifier/water-in-oil |
| Polysorbate 20 | Emulsifier/oil-in water |
| Polysorbate 60 | Emulsifier/oil-in water |
| Polysorbate 80 | Emulsifier/oil-in water |
| PEG-150 Distearate | Emulsifier/oil-in water |
| Cetearyl Alcohol | Emulsifier/oil-in water |
| Ceteareth-25 | Emulsifier/oil-in water |
| Stearic Acid | Emulsifier/oil-in water |
| Glyceryl Stearate Citrate | Emulsifier/oil-in water |
| Stearyl Alcohol | Emulsifier/oil-in water |
| Oleic Acid | Emulsifier/liquid |
| Myristic Acid | Emulsifier/solid |
| PEG-150 Distearate | Emulsifier/solid |
| Brassica alcohol | Emulsifier/solid |
| Brassica glycerides | Emulsifier/solid |
| Lanolin wax | Emulsifier/solid |
| Alginate | Emulsifier/solid |
| Cetyl alcohol | Emulsifier |
| Cetyl Phosphate | Emulsifier |
| Potassium cetyl phosphate | Emulsifier |
| Butyl stearate | Emulsifier |
| Ceteareth-10 | Emulsifier |
| Ceteareth-3 | Emulsifier |
| Ceteareth-30 | Emulsifier |
| Ceteareth-5 | Emulsifier |
| Ceteth-10 | Emulsifier |
| Ceteth-2 | Emulsifier |
| Ceteth-20 | Emulsifier |
| Ceteth-5 | Emulsifier |
| Ceteareth-12 | Emulsifier |
| Ethylene glycol distearate | Emulsifier |
| Ethylene glycol monostearate | Emulsifier |
| Glycereth-26 | Emulsifier |
| Glycereth-7 | Emulsifier |
| Glyceryl dilaurate | Emulsifier |
| Glyceryl monoisostearate | Emulsifier |
| Isocetyle alcohol | Emulsifier |
| Isostearic acid | Emulsifier |
| Isostearyl alcohol | Emulsifier |
| Laureth-10 | Emulsifier |
| Laureth-12 | Emulsifier |
| Laureth-2 | Emulsifier |
| Laureth-23 | Emulsifier |
| Laureth-30 | Emulsifier |
| Laureth-4 | Emulsifier |
| Laureth-7 | Emulsifier |
| Laureth-9 | Emulsifier |
| Lauryl alcohol | Emulsifier |
| Nonoxynol-10 | Emulsifier |
| Nonoxynol-12 | Emulsifier |
| Nonoxynol-9 | Emulsifier |
| Octoxynol-12 | Emulsifier |
| Oleth-10 | Emulsifier |
| Oleth-2 | Emulsifier |
| Oleth-20 | Emulsifier |
| Oleth-5 | Emulsifier |
| Palmitic acid | Emulsifier |
| PEG-100 Stearate | Emulsifier |
| PEG-12 Dilaurate | Emulsifier |
| PEG-12 Dioleate | Emulsifier |
| PEG-12 distearate | Emulsifier |
| PEG-12 laurate | Emulsifier |
| PEG-12 Oleate | Emulsifier |
| PEG-12 stearate | Emulsifier |
| PEG-15 castor oil | Emulsifier |
| PEG-4 oleate | Emulsifier |
| PEG-22 Oleate | Emulsifier |
| PEG-20 stearate | Emulsifier |
| PEG-25 castor oil | Emulsifier |
| PEG-30 castor oil | Emulsifier |

TABLE 1-continued

| Excipients | |
|---|---|
| Excipient | Example Category |
| PEG-30 glyceryl cocoate | Emulsifier |
| PEG-30 glyceryl Laurate | Emulsifier |
| PEG-300 monooleate | Emulsifier |
| PEG-32 stearate | Emulsifier |
| PEG-4 dilaurate | Emulsifier |
| PEG-4 laurate | Emulsifier |
| PEG-40 castor oil | Emulsifier |
| PEG-40 stearate | Emulsifier |
| PEG-5 castor oil | Emulsifier |
| PEG-60 Castor oil | Emulsifier |
| PEG-608 dilaurate | Emulsifier |
| PEG-8 dioleate | Emulsifier |
| PEG-8 laurate | Emulsifier |
| PEG-8 stearate | Emulsifier |
| PPG-11 stearyl ether | Emulsifier |
| PPG-15 stearyl ether | Emulsifier |
| PPG-2 myristyl ether propionate | Emulsifier |
| PPG-3 myristyl ether | Emulsifier |
| Propylene glycol stearate | Emulsifier |
| Sorbitan laurate | Emulsifier |
| Sorbitan palmitate | Emulsifier |
| Sorbitan sesquioleate | Emulsifier |
| Steareth-1 | Emulsifier |
| Steareth-10 | Emulsifier |
| Steareth-2 | Emulsifier |
| Steareth-20 | Emulsifier |
| Steareth-21 | Emulsifier |
| Steareth-4 | Emulsifier |
| Trideceth-10 | Emulsifier |
| Trideceth-3 | Emulsifier |
| Polyethylene 2H | Emulsifier |
| Glycol stearate | Emulsifier |
| PEG-50 stearate | Emulsifier |
| Calcium stearoyl lactylate | Emulsifier |
| Stearyl stearate | Emulsifier |
| Isocetyl stearate | Emulsifier |
| PEG-35 Castor Oil | Emulsifier |
| Propylene glycol ricinoleate | Emulsifier |
| Sorbitan trioleate | Emulsifier |
| Sorbitan tristearate | Emulsifier |
| Polysorbate 40 | Emulsifier |
| Polysorbate 85 | Emulsifier |
| Poloxamer 407NF | Emulsifier |
| Oleth-10 phosphate | Emulsifier |
| Polyethylene 3H | Emulsifier |
| Avocado butter | Emollient |
| Cocoa butter | Emollient |
| Green tea butter | Emollient |
| Mango butter | Emollient |
| Orange peel butter | Emollient |
| Shea butter glycerides | Emollient |
| Shea butter | Emollient |
| Almond oil | Emollient |
| Apricot kernel oil | Emollient |
| Argan oil | Emollient |
| Avocado oil | Emollient |
| Baobab oil | Emollient |
| Camelina oil | Emollient |
| Carrot oil | Emollient |
| Castor oil | Emollient |
| Citronella oil | Emollient |
| Coconut oil | Emollient |
| Cranberry seed oil | Emollient |
| Grape seed oil | Emollient |
| Hemp seed oil | Emollient |
| Jojoba oil | Emollient |
| Macadamia nut oil | Emollient |
| Meadowfoam seed oil | Emollient |
| Oat emollient | Emollient |
| Red raspberry seed oil | Emollient |
| Rose hip oil | Emollient |
| Sesame seed oil | Emollient |
| Squalane light | Emollient |
| Sunflower oil | Emollient |
| C12-15 Alkyl benzoate | Emollient |
| Cetyl palmitate | Emollient |

TABLE 1-continued

| Excipients | |
|---|---|
| Excipient | Example Category |
| Isolanolin | Emollient |
| Isododecane | Emollient |
| Isoeicosane | Emollient |
| Isopropyl myristate | Emollient |
| Mineral oil | Emollient |
| Octyldodecanol | Emollient |
| Polyisobutene 250 | Emollient |
| Polyisobutene 1200 | Emollient |
| Stearyl palmitate | Emollient |
| Sucrose cocoate | Emollient |
| Triglyceride | Emollient |
| Caprylyl glycol | Emollient |
| Jojoba gel | Emollient |
| Polyamide 3 | Emollient |
| Myristyl Myristate | Emollient |
| Isohexadecane | Emollient |
| Ethylhexyl palmitate | Emollient |
| Methyl gluceth1-0 | Emollient |
| Cholesterol | Emollient |
| Hectorite gel | Emollient |
| Butylene glycol | Emollient |
| Ethylhexyl olivate | Emollient |
| Tribehenin | Emollient |
| Marula tetradecane | Emollient |
| Diisooctyl succinate | Emollient |
| Pentylene glycol | Emollient |
| Oleic acid | Emollient |
| Cetearyl octanoate | Emollient |
| Cetyl octanoate | Emollient |
| Decyl oleate | Emollient |
| Diisopropyl adipate | Emollient |
| Diisopropyl sebacate | Emollient |
| Dioctyl adipate | Emollient |
| Dioctyl sebacate | Emollient |
| Isopropyl isostearate | Emollient |
| Isopropyl lanolate | Emollient |
| Isopropyl palmitate | Emollient |
| Lanolin oil | Emollient |
| Myristyl lactate | Emollient |
| Myristyl stearate | Emollient |
| Octyl pelargonate | Emollient |
| Octyle stearate | Emollient |
| PEG-60 lanolin | Emollient |
| PEG-775 lanolin | Emollient |
| PPG-12 PEG-50 Lanolin | Emollient |
| Stearamidopropyl dimethylamine lactate | Emollient |
| Stearyl octanoate | Emollient |
| Triisostearyl citrate | Emollient |
| Choleth 24 ceteth 24 | Emollient |
| PEG-20 hydrogenated lanolin | Emollient |
| PEG-24 Hydrogenated lanolin | Emollient |
| PEG-50 shea butter | Emollient |
| PEG-160m | Emollient |
| PEG-23m | Emollient |
| PEG-40 lanolin | Emollient |
| PEG-5m | Emollient |
| PEG-90m | Emollient |
| PEG-9m | Emollient |
| Shorea stenoptera butter | Emollient |
| Octyldodecyl neopentanoate | Emollient |
| Dioctyl Maleate | Emollient |
| Spent grain wax | Emollient |
| Seaweed oil | Emollient |
| Adipic Acid | Emollient |
| Neopentyl glycol | Emollient |
| Diisoamyl sebacate | Emollient |
| Quinoa milk | Emollient |
| AHA fruit acid | Exfoliant |
| Amber powder | Exfoliant |
| Bacillus ferment | Exfoliant |
| Bamboo stem powder | Exfoliant |
| Salicylic Acid | Exfoliant |
| Citric acid | Exfoliant |
| Glycolic acid | Exfoliant |
| Jojoba castor beads | Exfoliant |
| Jojoba pearls | Exfoliant |

TABLE 1-continued

| Excipients | |
|---|---|
| Excipient | Example Category |
| Mango fruit extract | Exfoliant |
| Olive seed powder | Exfoliant |
| Pumpkin puree | Exfoliant |
| Rice bran beads | Exfoliant |
| Sand | Exfoliant |
| Silica | Exfoliant |
| Tomato fruit extract | Exfoliant |
| Lactic acid | Exfoliant |
| Urea | Exfoliant |
| Walnut shell powder | Exfoliant |
| Yogurt filtrate | Exfoliant |
| Cream soda flavor | Flavor |
| Crème-de-coco flavor | Flavor |
| Vanilla flavor | Flavor |
| Peppermint oil | Flavor |
| Sweet orange essence | Flavor |
| Blood orange | Fragrance |
| Citrus | Fragrance |
| Clean linen | Fragrance |
| Coconut | Fragrance |
| Coconut lime verbena | Fragrance |
| Coral reef | Fragrance |
| Lemon verbena | Fragrance |
| Mandarin berry | Fragrance |
| Mangosteen | Fragrance |
| Natural rose | Fragrance |
| Neroli | Fragrance |
| Patchouli | Fragrance |
| Pineapple lily | Fragrance |
| Pink grapefruit | Fragrance |
| Passion fruit | Fragrance |
| White peach and ginger | Fragrance |
| White tea | Fragrance |
| Lavender | Fragrance |
| Menthol | Fragrance |
| Sweet fennel | Fragrance |
| Sweet orange | Fragrance |
| Tea tree | Fragrance |
| flowability agents | flowability agent |
| 1-dodecylazacyclo-heptan-2-one | gelling agent |
| 2-pyrrolidone | gelling agent |
| acacia | gelling agent |
| alginic acid | gelling agent |
| alpha-cyclodextrin | gelling agent |
| beeswax | gelling agent |
| bentonite | gelling agent |
| benzyl alcohol | gelling agent |
| beta-cyclodextrin | gelling agent |
| caprolactam | gelling agent |
| CARBOPOL ® (also known as carbomer) | gelling agent |
| carboxymethyl cellulose | gelling agent |
| castor oil | gelling agent |
| corn oil | gelling agent |
| cottonseed oil | gelling agent |
| cremaphor RH 40 | gelling agent |
| cremaphor RH 60 | gelling agent |
| d-alpha-tocopherol | gelling agent |
| di-fatty acid ester of PEG 1750 | gelling agent |
| di-fatty acid ester of PEG 300 | gelling agent |
| di-fatty acid ester of PEG 400 | gelling agent |
| dimethyl sulfoxide | gelling agent |
| dimethylacetamide (DMA) | gelling agent |
| dimethylformamide | gelling agent |
| distearoylphosphatidylglycerol | gelling agent |
| ethanol | gelling agent |
| ethyl acetate | gelling agent |
| ethylcellulose | gelling agent |
| gamma-cyclodextrin | gelling agent |
| gelatin | gelling agent |
| Gellucire 44/14 | gelling agent |
| glycerin | gelling agent |
| glycerol | gelling agent |
| glycerol formal | gelling agent |
| glycerophosphate | gelling agent |
| hydrogenated soy phosphatidylcholine | gelling agent |
| hydrogenated soybean oil | gelling agent |

TABLE 1-continued

| Excipients | |
|---|---|
| Excipient | Example Category |
| hydrogenated vegetable oils | gelling agent |
| hydroxy ethyl cellulose | gelling agent |
| hydroxyethyl cellulose | gelling agent |
| hydroxypropyl beta-cyclodextrin | gelling agent |
| hydroxypropyl cellulose | gelling agent |
| hydroxypropyl-beta-cyclodextrin | gelling agent |
| kolliphor 124 | gelling agent |
| kolliphor 181 | gelling agent |
| kolliphor 188 | gelling agent |
| kolliphor 407 | gelling agent |
| kolliphor EL (cremaphor EL) | gelling agent |
| kolliphor RH60 | gelling agent |
| Labrafil M-1944CS | gelling agent |
| Labrafil M-2125CS | gelling agent |
| Labrasol | gelling agent |
| L-alpha-dimyristoylphosphatidylcholine | gelling agent |
| L-alphadimyristoylphosphatidylglycerol | gelling agent |
| magnesium aluminum silicate | gelling agent |
| medium chain triglyceride | gelling agent |
| medium-chain diglyceride | gelling agent |
| medium-chain mono-glyceride | gelling agent |
| medium-chain triglyceride of coconut oil | gelling agent |
| medium-chain triglyceride of palm seed oil | gelling agent |
| methyl acetate | gelling agent |
| methylcellulose | gelling agent |
| mono-fatty acid ester of PEG 1750 | gelling agent |
| mono-fatty acid ester of PEG 300 | gelling agent |
| mono-fatty acid ester of PEG 400 | gelling agent |
| N-methyl-2-pyrrolidone | gelling agent |
| oleic acid | gelling agent |
| olive oil | gelling agent |
| peanut oil | gelling agent |
| PEG 1000 succinate | gelling agent |
| PEG 1750 | gelling agent |
| PEG 300 | gelling agent |
| PEG 300 caprylic/capric glyceride (Softigen 767) | gelling agent |
| PEG 300 linoleic glyceride (Labrafil M-2125CS) | gelling agent |
| PEG 300 oleic glyceride (Labrafil M-1944CS) | gelling agent |
| PEG 400 | gelling agent |
| PEG 400 caprylic/capric glyceride (Labrasol) | gelling agent |
| PEG 4000 (PEG 4 kDa) | gelling agent |
| peppermint oil | gelling agent |
| poloxamer | gelling agent |
| poloxamer-188 | gelling agent |
| poloxamer-407 | gelling agent |
| polyoxyl 40 stearate (PEG 1750 monosterate) | gelling agent |
| polyoxyl 8 stearate (PEG 400 monosterate) | gelling agent |
| polysorbate 20 | gelling agent |
| polysorbate-80 (tween-80) | gelling agent |
| polysorbate-SO | gelling agent |
| polyvinyl alcohol | gelling agent |
| polyvinyl pyrrolidone | gelling agent |
| polyvinyl pyrrolidone-12 | gelling agent |
| polyvinyl pyrrolidone-17 | gelling agent |
| propylene carbonate | gelling agent |
| propylene glycol | gelling agent |
| safflower oil | gelling agent |
| sesame oil | gelling agent |
| sodium alginate | gelling agent |
| Softigen 767 | gelling agent |
| solutol HS 15 | gelling agent |
| sorbitan monooleate | gelling agent |
| sorbitan monooleate (Span 20) | gelling agent |
| sorbitol | gelling agent |
| soybean oil | gelling agent |
| sulfobutylether-beta-cyclodextrin | gelling agent |
| sulfo-butylether-beta-cyclodextrin | gelling agent |
| tetrahydrofuran | gelling agent |
| tragacanth | gelling agent |
| transcutol | gelling agent |
| triacetin | gelling agent |
| triethanolamine | gelling agent |
| triethylamine | gelling agent |
| xanthan gum | gelling agent |
| (50:50, Poly(DI-Lactic-Co-Glycolic Acid) | general |
| (50:50, Polyacrylic Acid (250000 Mw) | general |

TABLE 1-continued

| Excipients | |
|---|---|
| Excipient | Example Category |
| 1,2,6-Hexanetriol | general |
| 1,2-Dimyristoyl-Sn-Glycero-3-(Phospho-S-(1-Glycerol) | general |
| 1,2-Dimyristoyl-Sn-Glycero-3-Phosphocholine | general |
| 1,2-Dioleoyl-Sn-Glycero-3-Phosphocholine | general |
| 1,2-Dipalmitoyl-Sn-Glycero-3-(Phospho-Rac-(1-Glycerol)) | general |
| 1,2-Distearoyl-Sn-Glycero-3-(Phospho-Rac-(1-Glycerol) | general |
| 1,2-Distearoyl-Sn-Glycero-3-Phosphocholine | general |
| 1-O-Tolylbiguanide | general |
| 2-Ethyl-1,6-Hexanediol | general |
| Acetic Acid | general |
| Acetic Anhydride | general |
| Acetone | general |
| Acetone Sodium Bisulfite | general |
| Acetylated Lanolin Alcohol | general |
| Acetylated Monoglyceride | general |
| Acetylcysteine | general |
| Acetyltryptophan (DL−) | general |
| Acrylates Copolymer | general |
| Acrylic Acid-Isooctyl Acrylate Copolymer | general |
| Acrylic Adhesive 788 | general |
| Activated Charcoal | general |
| Adcote 72A103 | general |
| Adhesive Tape | general |
| Adipic Acid | general |
| Aerotex Resin 3730 | general |
| Alanine | general |
| albumin | general |
| Albumin Aggregated | general |
| Albumin Colloidal | general |
| Albumin Human | general |
| Alcohol | general |
| Alfadex | general |
| Alkyl Ammonium Sulfonic Acid Betaine | general |
| Alkyl Aryl Sodium Sulfonate | general |
| Allantoin | general |
| Allyl Alpha-lonone | general |
| Almond Oil | general |
| Alpha Terpineol | general |
| Alpha-Tocopherol (DL−) | general |
| Alpha-Tocopherol Acetate (DL−) | general |
| Aluminum Acetate | general |
| Aluminum Chlorhydroxy Allantoinate | general |
| Aluminum Hydroxide | general |
| Aluminum Hydroxide - Sucrose | general |
| Aluminum Hydroxide Gel | general |
| Aluminum Hydroxide Gel F 500 | general |
| Aluminum Hydroxide Gel F 5000 | general |
| Aluminum Monostearate | general |
| Aluminum Oxide | general |
| Aluminum Polyester | general |
| Aluminum Silicate | general |
| Aluminum Starch Octenylsuccinate | general |
| Aluminum Stearate | general |
| Aluminum Subacetate | general |
| Aluminum Sulfate Anhydrous | general |
| Amerchol C | general |
| Amerchol-Cab | general |
| Aminomethylpropanol | general |
| Ammonia | general |
| Ammonia Solution | general |
| Ammonium Acetate | general |
| Ammonium Hydroxide | general |
| Ammonium Lauryl Sulfate | general |
| Ammonium Nonoxynol-4 Sulfate | general |
| Ammonium Salt Of C-12-C-15 Linear Primary Alcohol Ethoxylate | general |
| Ammonium Sulfate | general |
| Ammonyx | general |
| Amphoteric-2 | general |
| Amphoteric-9 | general |
| Anethole | general |
| Anhydrous Citric Acid | general |
| Anhydrous Dextrose | general |
| Anhydrous Lactose | general |
| Anhydrous Trisodium Citrate | general |
| Aniseed Oil | general |
| Anoxid Sbn | general |

TABLE 1-continued

| Excipients | |
|---|---|
| Excipient | Example Category |
| Antifoam | general |
| Antipyrine | general |
| Apaflurane | general |
| Apricot Kernel Oil Peg-6 Esters | general |
| Aquaphor | general |
| Arginine | general |
| Arlacel | general |
| Ascorbic Acid | general |
| Ascorbyl Palmitate | general |
| Aspartic Acid | general |
| Bacteriostatic | general |
| Balsam Peru | general |
| Barium Sulfate | general |
| Beheneth-10 | general |
| Benzalkonium Chloride | general |
| Benzenesulfonic Acid | general |
| Benzethonium Chloride | general |
| Benzododecinium Bromide | general |
| Benzoic Acid | general |
| Benzyl Benzoate | general |
| Benzyl Chloride | general |
| Betadex | general |
| Bibapcitide | general |
| Bismuth Subgallate | general |
| Boric Acid | general |
| Brocrinat | general |
| Butane | general |
| Butyl Alcohol | general |
| Butyl Ester Of Vinyl Methyl Ether/Maleic Anhydride Copolymer (125000 Mw) | general |
| Butyl Stearate | general |
| Butylated Hydroxyanisole | general |
| Butylated Hydroxytoluene | general |
| Butylene Glycol | general |
| Butylparaben | general |
| Butyric Acid | general |
| C20-40 Pareth-24 | general |
| Caffeine | general |
| Calcium | general |
| Calcium Carbonate | general |
| Calcium Chloride | general |
| Calcium Gluceptate | general |
| Calcium Hydroxide | general |
| Calcium Lactate | general |
| Calcobutrol | general |
| Caldiamide Sodium | general |
| Caloxetate Trisodium | general |
| Calteridol Calcium | general |
| Canada Balsam | general |
| Caprylic/Capric Triglyceride | general |
| Caprylic/Capric/Stearic Triglyceride | general |
| Captan | general |
| Captisol | general |
| Caramel | general |
| Carbomer 1342 | general |
| Carbomer 1382 | general |
| Carbomer 934 | general |
| Carbomer 934p | general |
| Carbomer 940 | general |
| Carbomer 941 | general |
| Carbomer 980 | general |
| Carbomer 981 | general |
| Carbomer Homopolymer Type B (Allyl Pentaerythritol Crosslinked) | general |
| Carbomer Homopolymer Type C (Allyl Pentaerythritol Crosslinked) | general |
| Carbon Dioxide | general |
| Carboxy Vinyl Copolymer | general |
| Carboxymethylcellulose (CMC) | general |
| Carboxymethylcellulose Sodium | general |
| Carboxypolymethylene | general |
| Carrageenan | general |
| Carrageenan Salt | general |
| Cedar Leaf Oil | general |
| Cellobiose | general |
| Cellulose | general |
| Cerasynt-Se | general |
| Ceresin | general |
| Ceteareth-12 | general |

TABLE 1-continued

| Excipients | |
|---|---|
| Excipient | Example Category |
| Ceteareth-15 | general |
| Ceteareth-30 | general |
| Cetearyl Alcohol/Ceteareth-20 | general |
| Cetearyl Ethylhexanoate | general |
| Ceteth-10 | general |
| Ceteth-2 | general |
| Ceteth-20 | general |
| Ceteth-23 | general |
| Cetostearyl Alcohol | general |
| Cetrimonium Chloride | general |
| Cetyl Alcohol | general |
| Cetyl Esters Wax | general |
| Cetyl Palmitate | general |
| Cetylpyridinium Chloride | general |
| Chlorobutanol | general |
| Chlorobutanol Hemihydrate | general |
| Chlorocresol | general |
| Chloroutanol anhydrous | general |
| Chloroxylenol | general |
| Cholesterol | general |
| Choleth | general |
| Choleth-24 | general |
| Citrate | general |
| Citric Acid | general |
| citric acid (hydrous) | general |
| Citric Acid Monohydrate | general |
| Cocamide Ether Sulfate | general |
| Cocamine Oxide | general |
| Coco Betaine | general |
| Coco Diethanolamide | general |
| Coco Monoethanolamide | general |
| Cocoa Butter | general |
| Coco-Glycerides | general |
| Coconut Oil | general |
| Coconut Oil glycerides | general |
| Cocoyl Caprylocaprate | general |
| Cola Nitida Seed Extract | general |
| Collager | general |
| Colloidal | general |
| Coloring Suspension | general |
| Corn | general |
| Cream Base | general |
| Creatine | general |
| Creatinine | general |
| Cresol | general |
| Croscarmelose Sodium | general |
| Crospovidone | general |
| Cupric Sulfate | general |
| Cupric Sulfate Anhydrous | general |
| Cyclomethicone | general |
| Cyclomethicone/Dimethicone Copolyol | general |
| Cysteine | general |
| Cysteine (DL−) | general |
| Cysteine Hydrochloride | general |
| Cysteine Hydrochloride Anhydrous | general |
| D&C Red No. 28 | general |
| D&C Red No. 33 | general |
| D&C Red No. 36 | general |
| D&C Red No. 39 | general |
| D&C Yellow No. 10 | general |
| Dalfampridine | general |
| Daubert 1-5 Pestr (Matte) 164z | general |
| Decyl Methyl Sulfoxide | general |
| Dehydag Wax Sx | general |
| Dehydrated | general |
| Dehydroacetic Acid | general |
| Dehymuls E | general |
| Denatonium Benzoate | general |
| Denatured | general |
| Dental | general |
| Deoxycholic Acid | general |
| Dextran | general |
| Dextran 40 | general |
| Dextrin | general |
| Dextrose | general |
| Dextrose Monohydrate | general |

TABLE 1-continued

| Excipients | |
|---|---|
| Excipient | Example Category |
| Dextrose Solution | general |
| Diatrizoic Acid | general |
| Diazolidinyl Urea | general |
| Dichlorobenzyl Alcohol | general |
| Dichlorodifluoromethane | general |
| Dichlorotetrafluoroethane | general |
| Diethanolamine | general |
| Diethyl Pyrocarbonate | general |
| Diethyl Sebacate | general |
| Diethylene Glycol Monoethyl Ether | general |
| Diethylhexyl Phthalate | general |
| Dihydroxyaluminum Aminoacetate | general |
| Diisopropanolamine | general |
| Diisopropyl Adipate | general |
| Diisopropyl Dilinoleate | general |
| Dimethicone 350 | general |
| Dimethicone Copolyol | general |
| Dimethicone Mdx4-4210 | general |
| Dimethicone Medical Fluid 360 | general |
| Dimethyl Isosorbide | general |
| Dimethylaminoethyl Methacrylate - Butyl Methacrylate -- Methyl Methacrylate Copolymer | general |
| Dimethyldioctadecylammonium Bentonite | general |
| Dimethylsiloxane/Methylvinylsiloxane Copolymer | general |
| Dinoseb Ammonium Salt | general |
| Dipalmitoylphosphatidylglycerol (DL−) | general |
| Dipropylene Glycol | general |
| Disodium Cocoamphodiacetate | general |
| Disodium Laureth Sulfosuccinate | general |
| Disodium Lauryl Sulfosuccinate | general |
| Disodium Sulfosalicylate | general |
| Disofenin | general |
| Divinylbenzene Styrene Copolymer | general |
| Dmdm Hydantoin | general |
| Docosanol | general |
| Docusate Sodium | general |
| Duro-Tak 280-2516 | general |
| Duro-Tak 387-2516 | general |
| Duro-Tak 80-1196 | general |
| Duro-Tak 87-2070 | general |
| Duro-Tak 87-2194 | general |
| Duro-Tak 87-2287 | general |
| Duro-Tak 87-2296 | general |
| Duro-Tak 87-2888 | general |
| Duro-Tak 87-2979 | general |
| Edetate Calcium Disodium | general |
| Edetate Disodium | general |
| Edetate Disodium Anhydrous | general |
| Edetate Sodium | general |
| Edetic Acid | general |
| Egg | general |
| Egg Phospholipid | general |
| Entsufon | general |
| Entsufon Sodium | general |
| Epilactose | general |
| Epitetracycline Hydrochloride | general |
| Essence Bouquet 9200 | general |
| Ethanolamine Hydrochloride | general |
| Ethoxylated | general |
| Ethyl Ester Terminated | general |
| Ethyl Oleate | general |
| Ethylene Glycol | general |
| Ethylene Vinyl Acetate Copolymer | general |
| Ethylenediamine | general |
| Ethylenediamine Dihydrochloride | general |
| Ethylenediaminetetracetic acid (EDTA) | general |
| Ethylene-Propylene Copolymer | general |
| Ethylene-Vinyl Acetate Copolymer (28% Vinyl Acetate) | general |
| Ethylene-Vinyl Acetate Copolymer (9% Vinylacetate) | general |
| Ethylhexyl Hydroxystearate | general |
| Ethylparaben | general |
| Eucalyptol | general |
| Exametazime | general |
| F&C Red No. 40 | general |
| Fat (Edible) | general |
| Fat (Hard) | general |

TABLE 1-continued

| Excipients | |
|---|---|
| Excipient | Example Category |
| Fatty Acid | general |
| Fatty Acid Ester | general |
| Fatty Acid Pentaerythriol Ester | general |
| Fatty Alcohol | general |
| Fatty Alcohol Citrate | general |
| FD&C Blue No. 1 (brilliant blue FCF) | general |
| FD&C Green No. 3 (fast green FCF) | general |
| FD&C Red No. 4 | general |
| FD&C Yellow No. 10 (Delisted) | general |
| FD&C Yellow No. 5 (tartrazine) | general |
| FD&C Yellow No. 6 (sunset yellow) | general |
| Ferric Chloride | general |
| Ferric Oxide | general |
| Flavor 89-186 | general |
| Flavor 89-259 | general |
| Flavor Df-119 | general |
| Flavor Df-1530 | general |
| Flavor Enhancer | general |
| Flavor FIG. 827118 | general |
| Flavor Raspberry Pfc-8407 | general |
| Flavor Rhodia Pharmaceutical No. Rf 451 | general |
| Fluorochlorohydrocarbon | general |
| Formaldehyde | general |
| Formaldehyde Solution | general |
| Fractionated Coconut Oil | general |
| Fragrance 3949-5 | general |
| Fragrance 520a | general |
| Fragrance 6.007 | general |
| Fragrance 91-122 | general |
| Fragrance 9128-Y | general |
| Fragrance 93498g | general |
| Fragrance Balsam Pine No. 5124 | general |
| Fragrance Bouquet 10328 | general |
| Fragrance Chemoderm 6401-B | general |
| Fragrance Chemoderm 6411 | general |
| Fragrance Cream No. 73457 | general |
| Fragrance Cs-28197 | general |
| Fragrance Felton 066m | general |
| Fragrance Firmenich 47373 | general |
| Fragrance Givaudan Ess 9090/1c | general |
| Fragrance H-6540 | general |
| Fragrance Herbal 10396 | general |
| Fragrance Nj-1085 | general |
| Fragrance P O FI-147 | general |
| Fragrance Pa 52805 | general |
| Fragrance Pera Derm D | general |
| Fragrance Rbd-9819 | general |
| Fragrance Shaw Mudge U-7776 | general |
| Fragrance Tf 044078 | general |
| Fragrance Ungerer Honeysuckle K 2771 | general |
| Fragrance Ungerer N5195 | general |
| Fructose | general |
| Gadolinium Oxide | general |
| Galactose | general |
| Gamma Cyclodextrin | general |
| Gelatin (Crosslinked) | general |
| Gelfoam Sponge | general |
| Gellan Gum (Low Acyl) | general |
| Gelva 737 | general |
| Gentisic Acid | general |
| Gentisic Acid Ethanolamide | general |
| Glacial acetic acid | general |
| Gluceptate Sodium | general |
| Gluceptate Sodium Dihydrate | general |
| Gluconolactone | general |
| Glucuronic Acid | general |
| Glutamic Acid (DL−) | general |
| Glutathione | general |
| Glycerol Ester Of Hydrogenated Rosin | general |
| Glyceryl Citrate | general |
| Glyceryl Isostearate | general |
| Glyceryl Laurate | general |
| Glyceryl Monostearate | general |
| Glyceryl Oleate | general |
| Glyceryl Oleate/Propylene Glycol | general |
| Glyceryl Palmitate | general |

TABLE 1-continued

| Excipients | |
|---|---|
| Excipient | Example Category |
| Glyceryl Ricinoleate | general |
| Glyceryl Stearate | general |
| Glyceryl Stearate -- Laureth-23 | general |
| Glyceryl Stearate/Peg Stearate | general |
| Glyceryl Stearate/Peg-100 Stearate | general |
| Glyceryl Stearate/Peg-40 Stearate | general |
| Glyceryl Stearate-Stearamidoethyl Diethylamine | general |
| Glyceryl Trioleate | general |
| Glycine | general |
| Glycine Hydrochloride | general |
| Glycol Distearate | general |
| Glycol Stearate | general |
| Guanidine Hydrochloride | general |
| Guar Gum | general |
| Hair Conditioner (18n195-1m) | general |
| Heptane | general |
| Hetastarch | general |
| Hexylene Glycol | general |
| High Density Polyethylene | general |
| Histidine | general |
| Human Albumin Microspheres | general |
| Hyaluronate Sodium | general |
| Hydrocarbon | general |
| Hydrocarbon Gel | general |
| Hydrochloric Acid | general |
| Hydrocortisone | general |
| Hydrogel Polymer | general |
| Hydrogen Peroxide | general |
| Hydrogenated Castor Oil | general |
| Hydrogenated coconut oil | general |
| Hydrogenated Coconut Oil Glyceride | general |
| Hydrogenated palm kernel oil | general |
| Hydrogenated Palm Kernel Oil glyceride | general |
| Hydrogenated Palm Oil | general |
| Hydrogenated Palm/Palm Kernel Oil Peg-6 Ester | general |
| Hydrogenated Polybutene 635-690 | general |
| Hydrogenated Soy | general |
| Hydrogenated soy phosphotidylcholine | general |
| Hydroxide lon | general |
| Hydroxyethylpiperazine Ethane Sulfonic Acid | general |
| Hydroxymethyl Cellulose | general |
| Hydroxyoctacosanyl Hydroxystearate | general |
| Hydroxypropyl Methylcellulose 2906 | general |
| Hydroxypropyl-B-cyclodextrin | general |
| Hypromellose | general |
| Hypromellose 2208 (15000 Mpa · S) | general |
| Hypromellose 2910 (15000 Mpa · S) | general |
| Imidurea | general |
| Iodine | general |
| Iodoxamic Acid | general |
| Iofetamine Hydrochloride | general |
| Irish Moss Extract | general |
| Isobutane | general |
| Isoceteth-20 | general |
| Isoleucine | general |
| Isooctyl Acrylate | general |
| Isopropyl Alcohol | general |
| Isopropyl Isostearate | general |
| Isopropyl Myristate | general |
| Isopropyl Palmitate | general |
| Isopropyl Stearate | general |
| Isostearic Acid | general |
| Isostearyl Alcohol | general |
| Isotonic Sodium Chloride Solution | general |
| Jelene | general |
| Kaolin | general |
| Kathon Cg | general |
| Kathon Cg II | general |
| Lactate | general |
| Lactic Acid | general |
| Lactic Acid (DL−) | general |
| Lactobionic Acid | general |
| Lactose | general |
| Lactose hydrous | general |
| Lactose Monohydrate | general |
| Laneth | general |

TABLE 1-continued

| Excipients | |
|---|---|
| Excipient | Example Category |
| Lanolin | general |
| Lanolin (ethoxylated) | general |
| Lanolin (hydrogenated) | general |
| Lanolin Alcohol | general |
| Lanolin Anhydrous | general |
| Lanolin Cholesterol | general |
| Lanolin Nonionic Derivatives | general |
| Lauralkonium Chloride | general |
| Lauramine Oxide | general |
| Laurdimonium Hydrolyzed Animal Collagen | general |
| Laureth Sulfate | general |
| Laureth-2 | general |
| Laureth-23 | general |
| Laureth-4 | general |
| Lauric Diethanolamide | general |
| Lauric Myristic Diethanolamide | general |
| Lauroyl Sarcosine | general |
| Lauryl Lactate | general |
| Lauryl Sulfate | general |
| Lavandula Angustifolia Flowering Top | general |
| Lecithin | general |
| Lecithin (hydrogenated) | general |
| Lecithin Unbleached | general |
| Lemon Oil | general |
| Leucine | general |
| Levulinic Acid | general |
| Lidofenin | general |
| Light Mineral Oil | general |
| Light Mineral Oil (85 Ssu) | general |
| Limonene (+/−) | general |
| Lipocol Sc-15 | general |
| Lysine | general |
| Lysine Acetate | general |
| Lysine Monohydrate | general |
| Magnesium Aluminum Silicate Hydrate | general |
| Magnesium Chloride | general |
| Magnesium Nitrate | general |
| Magnesium Stearate | general |
| Maleic Acid | general |
| Maltitol | general |
| Maltodextrin | general |
| Mannitol | general |
| Mannose | general |
| Maprofix | general |
| Mebrofenin | general |
| Medical Adhesive Modified S-15 | general |
| Medical Antiform A-F Emulsion | general |
| Medium Chain | general |
| Medronate Disodium | general |
| Medronic Acid | general |
| Meglumine | general |
| Melezitose | general |
| Menthol | general |
| Metacresol | general |
| Metaphosphoric Acid | general |
| Methanesulfonic Acid | general |
| Methionine | general |
| Methyl Alcohol | general |
| Methyl Gluceth-10 | general |
| Methyl Gluceth-20 | general |
| Methyl Gluceth-20 Sesquistearate | general |
| Methyl Glucose Sesquistearate | general |
| Methyl Laurate | general |
| Methyl Pyrrolidone | general |
| Methyl Salicylate | general |
| Methyl Stearate | general |
| Methylboronic Acid | general |
| Methylcellulose (4000 Mpa · S) | general |
| Methylchloroisothiazolinone | general |
| Methylene Blue | general |
| Methylisothiazolinone | general |
| Methylparaben | general |
| Microcrystalline | general |
| Microcrystalline Wax | general |
| Mineral Oil | general |
| Monostearyl Citrate | general |

TABLE 1-continued

| Excipients | |
|---|---|
| Excipient | Example Category |
| Monothioglycerol | general |
| Multisterol Extract | general |
| Myristyl Alcohol | general |
| Myristyl Lactate | general |
| Myristyl-.Gamma.-Picolinium Chloride | general |
| N-(Carbamoyl-Methoxy Peg-40)-1,2-Distearoyl-Cephalin Sodium | general |
| N,N-Dimethylacetamide | general |
| Niacinamide | general |
| Nioxime | general |
| Nitric Acid | general |
| Nitrogen | general |
| Nonoxynol Iodine | general |
| Nonoxynol-15 | general |
| Nonoxynol-9 | general |
| Norflurane | general |
| Oatmeal | general |
| Octadecene-1/Maleic Acid Copolymer | general |
| Octanoic Acid | general |
| Octisalate | general |
| Octoxynol-1 | general |
| Octoxynol-40 | general |
| Octoxynol-9 | general |
| Octyldodecanol | general |
| Octylphenol Polymethylene | general |
| Oleth-10/Oleth-5 | general |
| Oleth-2 | general |
| Oleth-20 | general |
| Oleyl Alcohol | general |
| Oleyl Oleate | general |
| Oxidronate Disodium | general |
| Oxyquinoline | general |
| Palm Kernel Oil | general |
| Palm Kernel Oil Glyceride | general |
| Palmitamine Oxide | general |
| Parabens | general |
| Paraffin | general |
| Parfum ǀ 45/3 | general |
| Peanut Oil (Refined) | general |
| Pectir | general |
| Peg 6-32 Stearate/Glycol Stearate | general |
| Peg Vegetable Oil | general |
| Peg-100 Stearate | general |
| Peg-12 Glyceryl Laurate | general |
| Peg-120 Glyceryl Stearate | general |
| Peg-120 Methyl Glucose Dioleate | general |
| Peg-15 Cocamine | general |
| Peg-150 Distearate | general |
| Peg-2 Stearate | general |
| Peg-20 Sorbitan Isostearate | general |
| Peg-22 Methyl Ether/Dodecyl Glycol Copolymer | general |
| Peg-25 Propylene Glycol Stearate | general |
| Peg-4 Dilaurate | general |
| Peg-4 Laurate | general |
| Peg-40 Castor Oil | general |
| Peg-40 Sorbitan Diisostearate | general |
| Peg-45/Dodecyl Glycol Copolymer | general |
| Peg-5 Oleate | general |
| Peg-50 Stearate | general |
| Peg-54 Hydrogenated Castor Oil | general |
| Peg-6 Isostearate | general |
| Peg-60 Castor Oil | general |
| Peg-60 Hydrogenated Castor Oil | general |
| Peg-7 Methyl Ether | general |
| Peg-75 Lanolin | general |
| Peg-8 Laurate | general |
| Peg-8 Stearate | general |
| Pegoxol 7 Stearate | general |
| Pentadecalactone | general |
| Pentaerythritol Cocoate | general |
| Pentasodium Pentetate | general |
| Pentetate Calcium Trisodium | general |
| Pentetic Acid | general |
| Perflutren | general |
| Perfume 25677 | general |
| Perfume Bouquet | general |
| Perfume E-1991 | general |

TABLE 1-continued

| Excipients | |
|---|---|
| Excipient | Example Category |
| Perfume Gd 5604 | general |
| Perfume Tana 90/42 Scba | general |
| Perfume W-1952-1 | general |
| Petrolatum | general |
| Petroleum Distillate | general |
| Phenol | general |
| Phenol (Liquefied) | general |
| Phenonip | general |
| Phenoxyethanol | general |
| Phenylalanine | general |
| Phenylethyl Alcohol | general |
| Phenylmercuric Acetate | general |
| Phenylmercuric Nitrate | general |
| Phosphate buffer | general |
| Phosphate buffered saline | general |
| Phosphate salts | general |
| Phosphatidyl Glycerol | general |
| Phospholipid | general |
| Phospholipid (Egg) | general |
| Phospholipon 90g | general |
| Phosphoric Acid | general |
| Pine Needle Oil (Pinus Sylvestris) | general |
| Piperazine Hexahydrate | general |
| Plastibase-50w | general |
| Polacrilin | general |
| Polidronium Chloride | general |
| Poloxamer 124 | general |
| Poloxamer 181 | general |
| Poloxamer 182 | general |
| Poloxamer-188 | general |
| Poloxamer 237 | general |
| Poloxamer-407 | general |
| Poly(Bis(P-Carboxyphenoxy) Propane Anhydride): Sebacic Acid | general |
| Poly(Dimethylsiloxane/Methylvinylsiloxane/Methylhydrogensiloxane) Dimethylvinyl Or Dimethylhydroxy Or Trimethyl Endblocked | general |
| Poly(Dl-Lactic-Co-Glycolic Acid) | general |
| Polybutene (1400 Mw) | general |
| Polycarbophil | general |
| Polyester Polyamine Copolymer | general |
| Polyester Rayon | general |
| Polyethylene Glycol 1000 | general |
| Polyethylene Glycol 1450 | general |
| Polyethylene Glycol 1500 | general |
| Polyethylene Glycol 1540 | general |
| Polyethylene Glycol 200 | general |
| Polyethylene Glycol 300 | general |
| Polyethylene Glycol 300-1600 | general |
| Polyethylene Glycol 3350 | general |
| Polyethylene Glycol 400 (PEG 400) | general |
| Polyethylene Glycol 4000 (PEG 4000, PEG 4 kDa) | general |
| Polyethylene Glycol 540 | general |
| Polyethylene Glycol 600 | general |
| Polyethylene Glycol 6000 | general |
| Polyethylene Glycol 8000 | general |
| Polyethylene Glycol 900 | general |
| Polyethylene High Density Containing Ferric Oxide Black (<1%) | general |
| Polyethylene Low Density Containing Barium Sulfate (20-24%) | general |
| Polyethylene T | general |
| Polyethylene Terephthalate | general |
| Polyglactin | general |
| Polyglyceryl-3 Oleate | general |
| Polyglyceryl-4 Oleate | general |
| Polyhydroxyethyl Methacrylate | general |
| Polyisobutylene | general |
| Polyisobutylene (1100000 Mw) | general |
| Polyisobutylene (35000 Mw) | general |
| Polyisobutylene 178-236 | general |
| Polyisobutylene 241-294 | general |
| Polyisobutylene 35-39 | general |
| Polyisobutylene Low Molecular Weight | general |
| Polyisobutylene Medium Molecular Weight | general |
| Polyisobutylene/Polybutene Adhesive | general |
| Polylactide | general |
| Polyo | general |
| Polyoxyethylene | general |
| Polyoxyethylene Alcohol | general |

TABLE 1-continued

| Excipients | |
|---|---|
| Excipient | Example Category |
| Polyoxyethylene Fatty Acid Ester | general |
| Polyoxyethylene Propylene | general |
| Polyoxyl 20 Cetostearyl Ether | general |
| Polyoxyl 32 Palmitostearate | general |
| Polyoxyl 35 Castor Oil | general |
| Polyoxyl 40 Hydrogenated Castor Oil | general |
| Polyoxyl 40 Stearate | general |
| Polyoxyl 400 Stearate | general |
| Polyoxyl 6 | general |
| Polyoxyl Distearate | general |
| Polyoxyl Glyceryl Stearate | general |
| Polyoxyl Lanolin | general |
| Polyoxyl Palmitate | general |
| Polyoxyl Stearate | general |
| Polyoxypropylene 1800 | general |
| Polypropylene | general |
| Polypropylene Glycol | general |
| Polyquaternium-10 | general |
| Polyquaternium-7 (70/30) Acrylamide/Dadmac | general |
| Polysiloxane | general |
| Polysorbate 40 | general |
| Polysorbate 60 | general |
| Polysorbate 65 | general |
| Polyurethane | general |
| Polyvinyl Acetate | general |
| Polyvinyl Chloride | general |
| Polyvinyl Chloride-Polyvinyl Acetate Copolymer | general |
| Polyvinylpyridine | general |
| Poppy Seed Oil | general |
| Potash | general |
| Potassium Acetate | general |
| Potassium Alum | general |
| Potassium Bicarbonate | general |
| Potassium Bisulfite | general |
| Potassium Chloride | general |
| Potassium Citrate | general |
| Potassium Hydroxide | general |
| Potassium Metabisulfite | general |
| Potassium Phosphate (Dibasic) | general |
| Potassium Phosphate (Monobasic) | general |
| Potassium Soap | general |
| Povidone | general |
| Povidone Acrylate Copolymer | general |
| Povidone Hydrogel | general |
| Povidone K17 | general |
| Povidone K25 | general |
| Povidone K29/32 | general |
| Povidone K30 | general |
| Povidone K90 | general |
| Povidone K90f | general |
| Povidone/Eicosene Copolymer | general |
| Ppg-12/Smdi Copolymer | general |
| Ppg-15 Stearyl Ether | general |
| Ppg-20 Methyl Glucose Ether Distearate | general |
| Ppg-26 Oleate | general |
| Pregelatinized | general |
| Product Wat | general |
| Proline | general |
| Promulgen D | general |
| Promulgen G | general |
| Propane | general |
| Propellant A-46 | general |
| Propyl Gallate | general |
| Propylene Glycol Diacetate | general |
| Propylene Glycol Dicaprylate | general |
| Propylene Glycol Monolaurate | general |
| Propylene Glycol Monopalmitostearate | general |
| Propylene Glycol Palmitostearate | general |
| Propylene Glycol Ricinoleate | general |
| Propylene Glycol/Diazolidinyl Urea/Methylparaben/Propylparben | general |
| Propylparaben | general |
| Protamine Sulfate | general |
| Protein Hydrolysate | general |
| Pvm/Ma Copolymer | general |
| Quaternium-15 | general |
| Quaternium-15 Cis-Form | general |

TABLE 1-continued

| Excipients | |
|---|---|
| Excipient | Example Category |
| Quaternium-52 | general |
| Ra-2397 | general |
| Ra-3011 | general |
| Raffinose | general |
| Saccharin | general |
| Saccharin Sodium | general |
| Saccharin Sodium Anhydrous | general |
| Sd Alcohol 3a | general |
| Sd Alcohol 40 | general |
| Sd Alcohol 40-2 | general |
| Sd Alcohol 40b | general |
| Sepineo P 600 | general |
| Serine | general |
| Shea Butter | general |
| Silastic Brand Medical Grade Tubing | general |
| Silastic Medical Adhesive | general |
| Silica | general |
| Silicon | general |
| Silicon Dioxide | general |
| Silicone | general |
| Silicone Adhesive 4102 | general |
| Silicone Adhesive 4502 | general |
| Silicone Adhesive Bio-Psa Q7-4201 | general |
| Silicone Adhesive Bio-Psa Q7-4301 | general |
| Silicone Emulsion | general |
| Silicone Type A | general |
| Silicone/Polyester Film Strip | general |
| Simethicone | general |
| Simethicone Emulsion | general |
| Sipon Ls 20np | general |
| Soda Ash | general |
| Sodium Acetate | general |
| Sodium Acetate Anhydrous | general |
| Sodium Alkyl Sulfate | general |
| Sodium Ascorbate | general |
| Sodium Benzoate | general |
| Sodium Bicarbonate | general |
| Sodium Bisulfate | general |
| Sodium Borate | general |
| Sodium Borate Decahydrate | general |
| Sodium Carbonate | general |
| Sodium Carbonate Decahydrate | general |
| Sodium Carbonate Monohydrate | general |
| Sodium Cetostearyl Sulfate | general |
| Sodium Chlorate | general |
| Sodium Chloride | general |
| Sodium Chloride Injection | general |
| Sodium Cholesteryl Sulfate | general |
| Sodium Citrate | general |
| Sodium Citrate Dihydrate | general |
| Sodium Cocoyl Sarcosinate | general |
| Sodium Desoxycholate | general |
| Sodium Dithionite | general |
| Sodium Dodecylbenzenesulfonate | general |
| Sodium Formaldehyde Sulfoxylate | general |
| Sodium Gluconate | general |
| Sodium Hydroxide | general |
| Sodium Hypochlorite | general |
| Sodium lodide | general |
| Sodium Lactate | general |
| Sodium Lactate (L−) | general |
| Sodium Laureth-2 Sulfate | general |
| Sodium Laureth-3 Sulfate | general |
| Sodium Laureth-5 Sulfate | general |
| Sodium Lauroyl Sarcosinate | general |
| Sodium Lauryl Sulfate | general |
| Sodium Lauryl Sulfoacetate | general |
| Sodium Metabisulfite | general |
| Sodium Phosphate | general |
| Sodium Phosphate (Dibasic) | general |
| Sodium Phosphate (Dibasic, Anhydrous) | general |
| Sodium Phosphate (Dibasic, Dihydrate) | general |
| Sodium Phosphate (Dibasic, Dodecahydrate) | general |
| Sodium Phosphate (Dibasic, Heptahydrate) | general |
| Sodium Phosphate (Monobasic) | general |
| Sodium Phosphate (Monobasic, Anhydrous) | general |

TABLE 1-continued

| Excipients | |
|---|---|
| Excipient | Example Category |
| Sodium Phosphate (Monobasic, Dihydrate) | general |
| Sodium Phosphate (Monobasic, Monohydrate) | general |
| Sodium Phosphate Dihydrate | general |
| Sodium Polyacrylate (2500000 Mw) | general |
| Sodium Pyrophosphate | general |
| Sodium Pyrrolidone Carboxylate | general |
| Sodium Starch Glycolate | general |
| Sodium Succinate Hexahydrate | general |
| Sodium Sulfate | general |
| Sodium Sulfate Anhydrous | general |
| Sodium Sulfate Decahydrate | general |
| Sodium Sulfite | general |
| Sodium Sulfosuccinated Undecyclenic Monoalkylolamide | general |
| Sodium Tartrate | general |
| Sodium Thioglycolate | general |
| Sodium Thiomalate | general |
| Sodium Thiosulfate | general |
| Sodium Thiosulfate Anhydrous | general |
| Sodium Trimetaphosphate | general |
| Sodium Xylenesulfonate | general |
| Somay 44 | general |
| Sorbic Acid | general |
| Sorbitan | general |
| Sorbitan Isostearate | general |
| Sorbitan Monolaurate | general |
| Sorbitan Monopalmitate | general |
| Sorbitan Monostearate | general |
| Sorbitan Sesquioleate | general |
| Sorbitan Trioleate | general |
| Sorbitan Tristearate | general |
| Sorbitol Solution | general |
| Sorbose | general |
| Soybean | general |
| Soybean Flour | general |
| Spearmint Oil | general |
| Spermaceti | general |
| Squalane | general |
| Stabilized Oxychloro Complex | general |
| Stannous 2-Ethylhexancate | general |
| Stannous Chloride | general |
| Stannous Chloride Anhydrous | general |
| Stannous Fluoride | general |
| Stannous Tartrate | general |
| Starch | general |
| Starch 1500 | general |
| Stearalkonium Chloride | general |
| Stearalkonium Hectorite/Propylene Carbonate | general |
| Stearamidoethyl Diethylamine | general |
| Steareth-10 | general |
| Steareth-100 | general |
| Steareth-2 | general |
| Steareth-20 | general |
| Steareth-21 | general |
| Steareth-40 | general |
| Stearic Acid | general |
| Stearic Diethanolamide | general |
| Stearoxytrimethylsilane | general |
| Steartrimonium Hydrolyzed Animal Collagen | general |
| Stearyl Alcohol | general |
| Styrene/Isoprene/Styrene Block Copolymer | general |
| Succimer | general |
| Succinic Acid | general |
| Sucralose | general |
| Sucrose | general |
| Sucrose Distearate | general |
| Sucrose Polyester | general |
| Sugar | general |
| Sulfacetamide Sodium | general |
| Sulfobutylether.Beta.-Cyclodextrin | general |
| Sulfur Dioxide | general |
| Sulfuric Acid | general |
| Sulfurous Acid | general |
| Surfactol Qs | general |
| Tagatose (D−) | general |
| Talc | general |
| Tall Oil | general |

TABLE 1-continued

| Excipients | |
|---|---|
| Excipient | Example Category |
| Tallow Glycerides | general |
| Tartaric Acid (DL−) | general |
| Tenox | general |
| Tenox-2 | general |
| Tert-Butyl Alcohol | general |
| Tert-Butyl Hydroperoxide | general |
| Tert-Butylhydroquinone | general |
| Tetrakis(2-Methoxyisobutylisocyanide)Copper(I) Tetrafluoroborate | general |
| Tetrapropyl Orthosilicate | general |
| Tetrofosmin | general |
| Theophylline | general |
| Thimerosal | general |
| Threonine | general |
| Thymol | general |
| Tir | general |
| Titanium Dioxide | general |
| Tocopherol | general |
| Tocophersolan | general |
| Trehalose | general |
| Tricaprylin | general |
| Trichloromonofluoromethane | general |
| Trideceth-10 | general |
| Triethanolamine Lauryl Sulfate | general |
| Trifluoroacetic Acid | general |
| Triglycerides | general |
| Trihalose | general |
| Trihydroxystearin | general |
| Trilaneth-4 Phosphate | general |
| Trilaureth-4 Phosphate | general |
| Trisodium Citrate Dihydrate | general |
| Trisodium Hedta | general |
| Triton 720 | general |
| Triton X-200 | general |
| Trolamine | general |
| Tromantadine | general |
| Tromethamine | general |
| Tryptophan | general |
| Tyloxapol | general |
| Tyrosine | general |
| Undecylenic Acid | general |
| Union 76 Amsco-Res 6038 | general |
| Urea | general |
| Valine | general |
| Vegetable Oil | general |
| Vegetable Oil Glyceride | general |
| Versetamide | general |
| Viscarin | general |
| Viscose/Cotton | general |
| Vitamin E | general |
| Water | general |
| Wax | general |
| Wecobee F | general |
| White | general |
| White Ceresin Wax | general |
| White Soft | general |
| White Wax | general |
| Zinc | general |
| Zinc Acetate | general |
| Zinc Carbonate | general |
| Zinc Chloride | general |
| Zinc Oxide | general |
| Hydrogenated polydecene | Hair conditioner |
| Stearalkonium chloride | Hair conditioner |
| PPG-12/SMDI copolymer | Hair conditioner |
| Acacia mlk | Humectant |
| Adipic acid and neopentyl glycol | Humectant |
| Algae extract | Humectant |
| Arnica extract | Humectant |
| Baobab extract | Humectant |
| Benzylsulfonyl D-seryl homophenylalanine amidinobenzamide acetate | Humectant |
| Butylene glycol | Humectant |
| Calendula Extract | Humectant |
| Hyaluronate gel | Humectant |
| Caprylyl glycol | Humectant |
| Ceramide | Humectant |
| Coconut water | Humectant |

TABLE 1-continued

| Excipients | |
|---|---|
| Excipient | Example Category |
| Coenzyme Q10 | Humectant |
| Cotton milk | Humectant |
| Collagen protein | Humectant |
| Colloidal oatmeal | Humectant |
| Elastin protein | Humectant |
| Ethoxydiglycol | Humectant |
| Glycoprotein | Humectant |
| Hexanediol | Humectant |
| Honey extract | Humectant |
| Hyaluronic acid | Humectant |
| Jojoba extract | Humectant |
| Keratin protein | Humectant |
| Lacto-ceramide | Humectant |
| Laurocapram | Humectant |
| Nigari | Humectant |
| Lychee extract | Humectant |
| Marshmallow root extract | Humectant |
| Methyl Gluceth-10 | Humectant |
| Methyl gluceth-20 | Humectant |
| Mexican giant hyssop extract | Humectant |
| Milk protein | Humectant |
| Nori comlex | Humectant |
| Oat amino acid | Humectant |
| Oat milk | Humectant |
| Olive milk | Humectant |
| Pearl powder | Humectant |
| Pantylene glycol | Humectant |
| Phospholipid jojoba milk | Humectant |
| Phytantriol | Humectant |
| Potassium lactate | Humectant |
| Propanediol | Humectant |
| Quinoa protein and Propylene glycol | Humectant |
| Quinoa milk | Humectant |
| Rhubarb root extract | Humectant |
| Sodium PCA | Humectant |
| Sodium hyaluronate and glycosaminoglycans | Humectant |
| Sodium lactate | Humectant |
| Sorbitol | Humectant |
| Soybean oil | Humectant |
| Sucrose propoate | Humectant |
| Tara gum gel | Humectant |
| Urea | Humectant |
| 3-glyceryl ascorbate | Humectant |
| Tetrahexyldecyl ascorbate | Humectant |
| dl-alpha tocopherol | Humectant |
| dl-alpha tocopheryl acetate | Humectant |
| Wheat milk | Humectant |
| Wheat protein | Humectant |
| Witch hazel extract | Humectant |
| Lecithin | Humectant |
| Panthenol | Humectant |
| Pro-vitamin B5 | Humectant |
| Glycerin | Humectant |
| Glycerol | Humectant |
| Aloe Vera | Humectant |
| Aloe vera palmitate | Humectant |
| Sorbitol | Humectant |
| Urea | Humectant |
| Alpha-hydroxy acids | Humectant |
| Sodium pyroglutamate | Humectant |
| N-acetyl-ethanolamine | Humectant |
| Sodium lactate | Humectant |
| Isopropanol | Humectant |
| Polyalkylene glycols | Humectant |
| Ethylene glycol | Humectant |
| Hexylene glycol | Humectant |
| Butylene glycol | Humectant |
| Dipropylene glycol | Humectant |
| Triethylene glycol | Humectant |
| 1,3-propanediol | Humectant |
| Polyethylene glycol | Humectant |
| Synthetic alcohol | Humectant |
| Glyceryl Coconate | Humectant |
| Hydroxystearate | Humectant |
| Myristate | Humectant |
| Oleate | Humectant |

TABLE 1-continued

| Excipients | |
|---|---|
| Excipient | Example Category |
| AHA Fruit acids | Hydroxy Acids |
| Citric acid | Hydroxy Acids |
| Glycolic acid | Hydroxy Acids |
| Lactic acid | Hydroxy Acids |
| Salicylic acid | Hydroxy Acids |
| DSPC | lipid nanoparticle |
| lipid nanoparticle | lipid nanoparticle |
| PEG-DMG 2000 (1,2-dimyristoyl-sn-glycero-3-phophoethanolamine-N-methoxy(polyethylene glycol)-2000) | lipid nanoparticle |
| 1,2-dilauroyl-sn-glycero-3-phosphocholine (DLPC) | lipids |
| 1,2-dimyristoyl-sn-glycero-3-phosphocholine (DMPC)phosphatidylinositol | lipids |
| 1,2-diolecyl-sn-glycero-3-phophoethanolamine (DOPE) | lipids |
| 1,2-dioleoyl-sn-glycero-3-phosphocholine (DOPC) | lipids |
| diglyceride | lipids |
| dilinoleoylphosphatidylcholine | lipids |
| dioleoylphosphatidylcholine | lipids |
| dipalmitoylphosphatidylcholine | lipids |
| distearoylphosphatidylcholine | lipids |
| fats | lipids |
| lysolipids | lipids |
| lysophosphatidylethanolamine | lipids |
| lysophospholipid | lipids |
| monoglyceride | lipids |
| mono-myristoyl-phosphatidylethanolamine (MMPE) | lipids |
| mono-oleoyl-phosphatidic acid (MOPA) | lipids |
| mono-oleoyl-phosphatidylethanolamine (MOPE) | lipids |
| mono-oleoyl-phosphatidylglycerol (MOPG) | lipids |
| mono-oleoyl-phosphatidylserine (MOPS) | lipids |
| palmitoyloleoyl | lipids |
| palmitoyloleoyl phosphatidylcholine | lipids |
| palmitoyl-oleoyl-phosphatidylethanolamine (POPE) | lipids |
| phosphatidic acid | lipids |
| phosphatidylcholines | lipids |
| phosphatidylethanolamine | lipids |
| phosphatidylserine | lipids |
| phosphotidylglycerol | lipids |
| sterol | lipids |
| 1,2-dilinoleyloxy-3-dimethylaminopropane (DLin-DMA) | liposomes |
| 1,2-dioleyloxy-N,N-dimethylaminopropane (DODMA) liposomes | liposomes |
| 2,2-dilinoleyl-4-(2-dimethylaminoethyl)-[1,3]-dioxolane (Dlin-KC2-DMA) | liposomes |
| DiLa2 liposomes from Marina Biotech (Bothell, WA) | liposomes |
| hyaluronan-coated liposomes | liposomes |
| liposome | liposomes |
| MC3 | liposomes |
| neutral DOPC (1,2-dioleoyl-sn-glycero-3-phosphocholine) based liposome | liposomes |
| SMARTICLES ® (Marina Biotech, Bothell, WA) | liposomes |
| stabilized nucleic acid lipid particle (SNALP) | liposomes |
| stabilized plasmid-lipid particles (SPLP) | liposomes |
| Coenzyme Q10 | Liposomes |
| Lacto-ceramide | Liposomes |
| retinol | liposomes |
| alkali salt | lubricant |
| alkaline earth salt | lubricant |
| aqueous solution | lubricant |
| calcium stearate | lubricant |
| fumed silica | lubricant |
| high molecular weight polyalkylene glycol | lubricant |
| high molecular weight polyethylene glycol | lubricant |
| hyaluronic acid | lubricant |
| hydrogenated vegetable oil | lubricant |
| hydrous magnesium silicate | lubricant |
| lipids | lubricant |
| lubricants | lubricant |
| lubricin | lubricant |
| micelle | lubricant |
| microsphere | lubricant |
| monoester of propylene glycol | lubricant |
| oils | lubricant |
| polymer | lubricant |
| saturated fatty acid containing about 16-20 carbon atoms | lubricant |
| saturated fatty acid containing about 8-22 carbon atoms | lubricant |
| solvents | lubricant |
| stearate salts | lubricant |
| transition metal salt | lubricant |
| vegetable oil derivative | lubricant |
| acrylic acid | nanoparticles |

TABLE 1-continued

| Excipients | |
|---|---|
| Excipient | Example Category |
| acrylic polymer | nanoparticles |
| amino alkyl methacrylate copolymer | nanoparticles |
| anhydride-modified material | nanoparticles |
| anhydride-modified phytoglycogen beta-dextrin | nanoparticles |
| carbon nanoparticles | nanoparticles |
| ceramic silicon carbide nanoparticle | nanoparticles |
| cerium oxide nanoparticle | nanoparticles |
| curcumin nanoparticle | nanoparticles |
| cyanoethyl methacrylate | nanoparticles |
| Dlin-KC2-DMA | nanoparticles |
| Dlin-MC3-DMA | nanoparticles |
| ethoxyethyl methacrylate | nanoparticles |
| glycogen-type material | nanoparticles |
| gold nanoparticle | nanoparticles |
| iron nanoparticles | nanoparticles |
| iron oxide nanoparticle | nanoparticles |
| magnetic nanoparticle | nanoparticles |
| methacrylic acid | nanoparticles |
| methacrylic acid copolymer | nanoparticles |
| methyl methacrylate copolymer | nanoparticles |
| nanodiamond | nanoparticles |
| nickel nanoparticle | nanoparticles |
| phytoglycogen beta-dextrin | nanoparticles |
| phytoglycogen octenyl succinate | nanoparticles |
| platinum nanoparticles | nanoparticles |
| poly(4-hydroxy-L-proline ester) | nanoparticles |
| poly(acrylic acid) | nanoparticles |
| poly(ethylene imine) | nanoparticles |
| poly(L-lactide-co-L-lysine) | nanoparticles |
| poly(methacrylic acid) | nanoparticles |
| poly(orthoesters) | nanoparticles |
| poly(serine ester) | nanoparticles |
| polyacetal | nanoparticles |
| polyacrylate | nanoparticles |
| polycyanoacrylate | nanoparticles |
| polyester | nanoparticles |
| polyether | nanoparticles |
| polyethylene | nanoparticles |
| polyhydroxyacid | nanoparticles |
| polylysine | nanoparticles |
| polymer coated iron oxide nanoparticle | nanoparticles |
| polymeric mycelle | nanoparticles |
| polymethacrylate | nanoparticles |
| polyphosphazene | nanoparticles |
| polypropylfumerate | nanoparticles |
| polyureas | nanoparticles |
| protein filled nanoparticle | nanoparticles |
| silica nanoparticle | nanoparticles |
| silicon dioxide crystalline nanoparticle | nanoparticles |
| silver nanoparticles | nanoparticles |
| silver oxide nanoparticle | nanoparticles |
| titanium dioxide nanoparticle | nanoparticles |
| natural polymers | natural polmers |
| natural rubbers | natural polymers |
| Tee tree essential oil | Natural antimicrobials |
| Caprylyl glycol | Natural antimicrobials |
| Caprylic acid | Natural antimicrobials |
| Honeysuckle | Natural antimicrobials |
| Potassium sorbate | Natural antimicrobials |
| Citric acid | Natural antimicrobials |
| Sorbic acid | Natural antimicrobials |
| Caprylhydroxamic acid | Natural antimicrobials |
| Radish root ferment filtrate | Natural antimicrobials |
| Hexanediole | Natural antimicrobials |
| Aloe vera | Nourishing agents |
| Avocado butter | Nourishing agents |
| Baobab protein extract | Nourishing agents |
| Cocoa butter | Nourishing agents |
| Colloidal oatmeal | Nourishing agents |
| Elastin protein | Nourishing agents |
| Green tea butter | Nourishing agents |
| Hemp seed oil | Nourishing agents |
| Jojoba oil | Nourishing agents |
| Keratin protein | Nourishing agents |
| Lacto-ceramide | Nourishing agents |
| Lupine protein | Nourishing agents |

TABLE 1-continued

| Excipients | |
|---|---|
| Excipient | Example Category |
| Macadamia nut oil | Nourishing agents |
| Milk protein | Nourishing agents |
| Oat amino acids | Nourishing agents |
| Orange peel butter | Nourishing agents |
| d-panthenol | Nourishing agents |
| Quinoa protein | Nourishing agents |
| Sunflower oil | Nourishing agents |
| Wheat protein | Nourishing agents |
| Zinc ricinoleate | Odor neutralizer |
| Cottonseed oil | Natural Oils |
| Eucalyptus oil | Natural Oils |
| Borage oil | Natural Oils |
| Black cumin oil | Natural Oils |
| Evening primrose oil | Natural Oils |
| Grapefruit seed oil | Natural Oils |
| Hazelnut oil | Natural Oils |
| Kukui nut oil | Natural Oils |
| Peach kernel oil | Natural Oils |
| Olive oil | Natural Oils |
| Pecan oil | Natural Oils |
| Perilla seed oil | Natural Oils |
| Rice bran oil | Natural Oils |
| Safflower oil | Natural Oils |
| Pistachio oil | Natural Oils |
| Pumpkin seed oil | Natural Oils |
| Wheat germ oil | Natural Oils |
| Pomegranate seed oil | Natural Oils |
| Canola oil | Natural Oils |
| Flax seed oil | Natural Oils |
| Soybean oil | Natural Oils |
| Cherry kernel oil | Natural Oils |
| ceramic | other |
| cobalt-chromium-molydenum composite | other |
| duck's feet collagen | other |
| ionic liquids | other |
| magnesium oxide | other |
| melanin | other |
| metal scaffold | other |
| nano-hydroxyapatite | other |
| poly(α-ester) | other |
| SBA15 | other |
| Argireline | Peptides |
| Hexa peptide | Peptides |
| Penta peptide | Peptides |
| Glycan booster peptide | Peptides |
| LiPeptide | Peptides |
| Palmitoyl isoleucine | Peptides |
| Palmitoyl peptide | Peptides |
| Palmitoyl tripeptide-38 | Peptides |
| dipeptide | Peptides |
| tripeptide | Peptides |
| Bismuth oxychloride | Pearlizer |
| Glycol stearate | Pearlizer |
| Triethanolamine | pH adjuster |
| Citric Acid | pH adjuster |
| Sodium gluconate | pH adjuster |
| Magnesium hydroxide | pH adjuster |
| Acrylate copolymer | Polymer |
| alginate | polymers |
| alkyl cellulose | polymers |
| amber | polymers |
| bacterial cellulose | polymers |
| bioplastic | polymers |
| bioresorbable polymer matrix | polymers |
| carbohydrate polymers | polymers |
| Carbomer 940 | Polymer |
| Carbomer 980 | Polymer |
| cellulose acetate | polymers |
| cellulose ester | polymers |
| cellulose ether | polymers |
| chitin | polymers |
| chitosan | polymers |
| copolymers of acrylic and methacrylic acid esters | polymers |
| derivatized cellulose | polymers |
| elastin | polymers |
| ethylene vinyl acetate polymer (EVA) | polymers |

TABLE 1-continued

| Excipients | |
|---|---|
| Excipient | Example Category |
| EUDRAGIT ® RL | polymers |
| EUDRAGIT ® RS | polymers |
| fibrin | polymers |
| genetically modified bioplastics | polymers |
| glycogen | polymers |
| high-density polyethylene (HDPE) | polymers |
| hydroxypropyl methylcellulose (HPMC) | polymers |
| hydroxyalkyl celluloses | polymers |
| hydroxypropyl ethylcellulose (HEC) | polymers |
| hydroxypropyl methacrylate (HPMA) | polymers |
| hydroxypropylcellulose | polymers |
| Iso-dimethicone copolymer | polymers |
| keratins | polymers |
| lignin | polymers |
| lipid-derived polymer | polymers |
| low-density polyethylene (LDPE) | polymers |
| methacrylates | polymers |
| natural rubber | polymers |
| neoprene | polymers |
| nitro cellulose | polymers |
| nucleic acid | polymers |
| nylon | polymers |
| nylon 6 | polymers |
| nylon 6.6 | polymers |
| nylone | polymers |
| phenol formaldehyde resin | polymers |
| poloxamer | polymers |
| poly(butyl(meth)acrylate) | polymers |
| poly(butyric acid) | polymers |
| poly(caprolactone) (PCL) | polymers |
| poly(D,L-lactide) (PDLA) | polymers |
| poly(D,L-lactide-co-caprolactone) | polymers |
| poly(D,L-lactide-co-caprolactone-co-glycolide) | polymers |
| poly(D,L-lactide-co-PPO-co-D,L-lactide) | polymers |
| poly(ester amides) | polymers |
| poly(ester ethers) | polymers |
| poly(ethyl(meth)acrylate) | polymers |
| poly(ethylene terephthalate) | polymers |
| poly(glycolic acid) (PGA) | polymers |
| poly(hexyl(meth)acrylate) | polymers |
| poly(hydroxy acids) | polymers |
| poly(isobutyl acrylate) | polymers |
| poly(isobutyl(meth)acrylate) | polymers |
| poly(isodecyl(meth)acrylate) | polymers |
| poly(isopropyl acrylate) | polymers |
| poly(lactic acid) (PLA) | polymers |
| poly(lactic acid-co-glycolic acid) (PLGA) | polymers |
| poly(lactide-co-caprolactone) | polymers |
| poly(lactide-co-glycolide) | polymers |
| poly(lauryl(meth)acrylate) | polymers |
| poly(L-lactic acid) (PLLA) | polymers |
| poly(L-lactic acid-co-glycolic acid) (PLLGA) | polymers |
| poly(L-lactide) (PLLA) | polymers |
| poly(methyl acrylate) | polymers |
| poly(methyl(meth)acrylate) (PMMA) | polymers |
| poly(octadecyl acrylate) | polymers |
| poly(ortho)esters | polymers |
| poly(phenyl(meth)acrylate) | polymers |
| poly(valeric acid) | polymers |
| poly(vinyl acetate) | polymers |
| polyacrylonitrile | polymers |
| polyalkyl cyanoacralate | polymers |
| polyalkylene | polymers |
| polyalkylene glycol | polymers |
| polyalkylene oxide | polymers |
| polyalkylene terephthalate | polymers |
| polyamide | polymers |
| polyamino acid | polymers |
| polyanhydride | polymers |
| polyaniline | polymers |
| polycaprolactone | polymers |
| polycarbonate | polymers |
| polydioxanone | polymers |
| polydioxanone copolymer | polymers |
| polyethtylene glycol diglycidi ester | polymers |
| polyethylene glycol | polymers |

TABLE 1-continued

| Excipients | |
|---|---|
| Excipient | Example Category |
| polyethylene oxide | polymers |
| polyethyleneglycol | polymers |
| polyglycolide | polymers |
| polyhydroxyalkanoate | polymers |
| polyhydroxybutyrate (also known as polyhydroxyalkanoate) | polymers |
| polyhydroxyurethane | polymers |
| polyisoprene | polymers |
| polyketal | polymers |
| polylactic acid | polymers |
| poly-L-glutamic acid | polymers |
| poly-L-lysine (PLL) | polymers |
| polymer of acrylic acid | polymers |
| polyorthoester | polymers |
| polyoxymethylene | polymers |
| polypeptides | polymers |
| polyphosphoester | polymers |
| polypropylene fumarate | polymers |
| polysaccharide | polymers |
| polystyrene | polymers |
| polytetrafluoroethylene | polymers |
| polyvinyl butyral | polymers |
| polyvinyl ester | Polymers |
| polyvinyl ether | Polymers |
| polyvinyl halides such as poly(vinyl chloride) (PVC) | Polymers |
| Polyvinylpyrrolidone (PVP) | Polymer |
| poyphosphazene | Polymers |
| quarternary ammonium chitosan | Polymers |
| shellac | Polymers |
| sodium carboxymethylcellulose | Polymers |
| synthetic polyether | Polymers |
| synthetic rubber | Polymers |
| thermoplastic polyurethane | Polymers |
| trimethylene carbonate | Polymers |
| ultra-high-molecular-weight-polyethylene (UHMWPE) | Polymers |
| wool | Polymers |
| β-keratin | Polymers |
| alkylparaben | Preservative |
| amino acids | Preservative |
| Antioxidant | Preservative |
| Benzylalcohol-DHA | Preservative |
| BHA | Preservative |
| BHT | Preservative |
| calcium propionate | Preservative |
| Caprylyl gycol | Preservative |
| disodium EDTA | Preservative |
| DMDM hydantoin | Preservative |
| Diazolidinyl urea | Preservative |
| gluconolactone | Preservative |
| glutaraldehyde | Preservative |
| Hexylene glycol | Preservative |
| Imidazolidinyl urea | Preservative |
| lodopropynyl butylcarbamate | Preservative |
| magnesium chloride hexahydrate | Preservative |
| m-cresol | Preservative |
| methyl paraben | Preservative |
| o-cresol | Preservative |
| p-cresol | Preservative |
| Paraben-DU | Preservative |
| Phenoxyethanol | Preservative |
| phenylmercuric nitrite | Preservative |
| Phenylpropanol EHG | Preservative |
| potassium hydrogen sulfite | Preservative |
| potassium sorbate | Preservative |
| preservative | Preservative |
| propyl paraben | Preservative |
| selenium | Preservative |
| sodium dehydroacetate | Preservative |
| sodium nitrate | Preservative |
| sodium nitrite | Preservative |
| sulfites | Preservative |
| triclosan | Preservative |
| vitamin A | Preservative |
| vitamin C | Preservative |
| Baobab protein | Proteins |
| Barley quat | Proteins |
| Collagen protein | Proteins |

TABLE 1-continued

| Excipients | |
|---|---|
| Excipient | Example Category |
| Collagen solution | Proteins |
| Elastin protein | Proteins |
| glycoproteins | Proteins |
| Jojoba protein | Proteins |
| Keratin protein | Proteins |
| Lupine protein | Proteins |
| Milk protein | Proteins |
| Natto gum phytocollagen | Proteins |
| Oat amino acid | Proteins |
| Palmitoyl isoleucine | Proteins |
| Quinoa protein | Proteins |
| Rice quat | Proteins |
| Rice protein | Proteins |
| Sericin protein | Proteins |
| Soy protein | Proteins |
| Soy-rice peptides | Proteins |
| Chitosan | Scalp treatment |
| Menthyl lactate crystals | Scalp treatment |
| Quassia vinegar | Scalp treatment |
| Oat milk | Scalp treatment |
| St. John's bread seed extract | Scalp treatment |
| Superoxide dismutase | Scalp treatment |
| Rice protein and extract | Scalp treatment |
| Oat protein | Scalp treatment |
| Cereal protein | Scalp treatment |
| Cotton milk | Scalp treatment |
| Nori complex | Scalp treatment |
| Hydrogenated polydecene | Skin conditioner |
| Stearalkonium chloride | Skin conditioner |
| PPG-12/SDMI copolymer | Skin conditioner |
| Aminopropyl kojyl phosphate | Skin lightener |
| Ascorbyl 3-aminopropyl dihydrogen phospate | Skin lightener |
| Kojic dipalmitate | Skin lightener |
| Saphora japonica | Skin lightener |
| Thymus hydrosylate | Skin lightener |
| Bearberry leaves | Skin lightener |
| Undecylenoyl phenylalanine | Skin lightener |
| Menthol crystal | Skin protectants |
| Peppermint oil | Skin protectants |
| Allantoin | Skin protectants |
| Colloidal oatmeal | Skin protectants |
| Kaolin | Skin protectants |
| Malt extract | Skin protectants |
| Mineral oil | Skin protectants |
| Dimethicone | Skin protectants |
| Petrolatum | Skin protectants |
| Acetyl tyrosine and riboflavin | Skin regulator |
| Alpine willowherb extract | Skin regulator |
| Charcoal powder | Skin regulator |
| Dead sea mud | Skin regulator |
| Inositol | Skin regulator |
| Kaolin | Skin regulator |
| Kaolin clay | Skin regulator |
| Lotus flower extract | Skin regulator |
| Round leaf buchu extract | Skin regulator |
| Sebum-REG | Skin regulator |
| Sulphur mud | Skin regulator |
| Sulphur solution | Skin regulator |
| Amodimethicone | Silicones |
| Cyclomethicone | Silicones |
| cyclopentasiloxane | Silicones |
| cyclohexasiloxane | Silicones |
| cyclotetrasiloxane | Silicones |
| Dimethicone 500 | Silicones |
| Dimethicone fluid | Silicones |
| Dimethicone satin | Silicones |
| dimethyconol | Silicones |
| Iso-dimethicone copolymer | Silicones |
| Nonoxynol-10 | Silicones |
| PEG-8 dimethicone | Silicones |
| Polymethylsilsesquiozane | Silicones |
| Polysilicone-11 | Silicones |
| Silicone gel | Silicones |
| Silicone resin | Silicones |
| Tallowtrimonium chloride | Silicones |
| Vitamin C in Silicone | Silicones |

TABLE 1-continued

| Excipients | |
|---|---|
| Excipient | Example Category |
| Dimethicone Satin | Silicone conditioners |
| Dimethicone 500 | Silicone conditioners |
| Iso-dimethicone copolymer | Silicone conditioners |
| Amodimethicone | Silicone conditioners |
| Cyclomethicone | Silicone conditioners |
| Silicone gel | Silicone conditioners |
| PEG-dimethicone | Silicone conditioners |
| Aloe vera palmitate | Solvents |
| Butylene glycol | Solvents |
| C12-15 Alkyl Benzoate | Solvents |
| Ethoxydiglycol | Solvents |
| Ethylhexyl palmitate | Solvents |
| Glycerin | Solvents |
| Isododecane | Solvents |
| lohexadecane | Solvents |
| IsoLanolin | Solvents |
| Isopropyl myristate | Solvents |
| Lavender hydrosol | Solvents |
| Nigari (liquid minerals) | Solvents |
| Mineral oil | Solvents |
| Neroli hydrosol | Solvents |
| Octyldodecanol | Solvents |
| PEG-40 Hydrogenated castor oil | Solvents |
| Pentylene glycol | Solvents |
| Propanediol | Solvents |
| Propylene glycol | Solvents |
| Rose hydrosol | Solvents |
| Rosa centifolia Flower extract | Skin soothing agents |
| Spent grain wax | Skin soothing agents |
| Marine seaweed extract | Skin soothing agents |
| False daisy extract | Skin soothing agents |
| Lotus flower extract | Skin soothing agents |
| Natural flavonoid complex | Skin soothing agents |
| Kola nut extract | Skin soothing agents |
| Guarana extract | Skin soothing agents |
| Mate extract | Skin soothing agents |
| EDTA | Stabilizer |
| BHT | Stabilizer |
| Sodium gluconate | Stabilizer |
| Alpha olefin sulfonate | Surfactants |
| Ammonium laureth sulfate | Surfactants |
| Ammonium lauryl sulfate | Surfactants |
| Castile soap | Surfactants |
| Cocamidopropyl hydroxysultaine | Surfactants |
| Cocamidopropylamine oxide | Surfactants |
| Coco betain | Surfactants |
| Coco glucose | Surfactants |
| Decyl glucoside sodium lauroyl lactylate | Surfactants |
| Disodium cocoamphodipropionate | Surfactants |
| Disodium coco-glucoside citrate | Surfactants |
| Isostearyl lactate | Surfactants |
| Lauramine oxide | Surfactants |
| Lauryl glucose | Surfactants |
| Myristic acid | Surfactants |
| PEG-15 cocamine | Surfactants |
| PEG-15 tallow amine | Surfactants |
| PEG-2 cocoamine | Surfactants |
| PEG-5 cocoamine | Surfactants |
| PEG-5 hydrogenated tallow amine | Surfactants |
| Polyglucose | Surfactants |
| SM Cocoyl taurate | Surfactants |
| Sodium behenoyl lactylate | Surfactants |
| Sodium cocoamphoacetate | Surfactants |
| Sodium cocoyl isethionate | Surfactants |
| Sodium isostearoyl lactylate | Surfactants |
| Sodium lauroamphoacetate | Surfactants |
| Sodium lauroyl lactylate | Surfactants |
| Sodium lauryl sulfate | Surfactants |
| Sodium myreth sulfate | Surfactants |
| Sodium stearoyl lactylate | Surfactants |
| Sulfosuccinate | Surfactants |
| Tallow amine | Surfactants |
| TEA-lauryl sulfate | Surfactants |
| acesulfame potassium | sweetner |
| advantame | sweetner |
| artificial sweetener | sweetner |

TABLE 1-continued

| Excipients | |
|---|---|
| Excipient | Example Category |
| aspartame | sweetner |
| brazzein | sweetner |
| curculin | sweetner |
| cyclamates | sweetner |
| erythritol | sweetner |
| glucose | sweetner |
| glycyrrhizin | sweetner |
| hydrogenated starch hydrolysate | sweetner |
| inulin | sweetner |
| ismalt | sweetner |
| isomaltooligosaccharide | sweetner |
| isomaltulose | sweetner |
| lactitol | sweetner |
| lead acetate | sweetner |
| mabinlin | sweetner |
| miraculin | sweetner |
| mogroside | sweetner |
| monantin | sweetner |
| nectame | sweetner |
| osladin | sweetner |
| pentadin | sweetner |
| polydextrose | sweetner |
| psicose | sweetner |
| stevia | sweetner |
| sweetener | sweetner |
| tagatose | sweetner |
| thaumatin | sweetner |
| xylitol | sweetner |
| xylose | sweetner |
| elastomer | synthetic polymer |
| synthetic fiber | synthetic polymer |
| synthetic polymer | synthetic polymer |
| thermoplastic | synthetic polymer |
| thermoset | synthetic polymer |
| Arrowroot starch | Texturizer/filler |
| Bentonite | Texturizer/filler |
| Bismuth Oxychloride | Texturizer/filler |
| Charcoal powder | Texturizer/filler |
| Colloidal oatmeal | Texturizer/filler |
| Dead sea mud | Texturizer/filler |
| HP starch | Texturizer/filler |
| Kaolin clay | Texturizer/filler |
| Magnesium aluminum sulfate | Texturizer/filler |
| Magnesium hydroxide | Texturizer/filler |
| Magnesium stearate | Texturizer/filler |
| Mica powder | Texturizer/filler |
| Mica spheres | Texturizer/filler |
| Polymethylsilsesquioxane | Texturizer/filler |
| Rice starch | Texturizer/filler |
| Silica | Texturizer/filler |
| Silky talc | Texturizer/filler |
| Sulphur mud | Texturizer/filler |
| Talo | Texturizer/filler |
| Tapioca starch | Texturizer/filler |
| Zinc oxide | Texturizer/filler |
| C18-22 hydroxyalkyl hydroxypropyl guar | Thickener |
| Maltodextrin | Thickener |
| Glucose-D | Thickener |
| Glocose-SORB | Thickener |
| Hectorite Gel | Thickener |
| Gum Arabic | Thickener |
| Stearyl palmitate | Thickener |
| HP starch | Thickener |
| Tapioca starch | Thickener |
| Acrylate copolymer | Thickener |
| Carbomer 940 | Thickener |
| Cetyl alcohol | Thickener |
| Guar gum, cationic | Thickener |
| HE-cellulose | Thickener |
| Hydroxystearic acid | Thickener |
| Polyamide | Thickener |
| PVP | Thickener |
| Sorbitol | Thickener |
| Xanthan gum | Thickener |
| Synthetic wax | Thickener |
| Castor wax | Thickener |

TABLE 1-continued

| Excipients | |
|---|---|
| Excipient | Example Category |
| Hydroxypropyl guar | Thickener |
| Hydroxypropyl methylcellulose | Thickener |
| Trihydroxystearin | Thickener |
| Magnesium aluminum silicate | Thickener |
| Caesalpinia spinosa gum | Thickener |
| Brassica alcohol | Thickener |
| Carbomer 980 | Thickener |
| Silica dimethyl silylate | Thickener |
| Sodium stearate | Thickener |
| Sodium polyacrylate | Thickener |
| polybutene | Thickener |
| Polyhydroxystearic acid | Thickener |
| Bentonite | Thickener |
| Stearyl alcohol | Thickener |
| Tribehenin | Thickener |
| Lanolin wax | Thickener |
| Arrowroot starch | Thickener |
| Rice starch | Thickener |
| Beeswax | Thickener |
| Avobenzone | UVA filter |
| Oxybenzone | UVA filter |
| Benzophenone-4 | UVA filter |
| Homosalate | UVB filter |
| Octisalate | UVB filter |
| Octocrylene | UVB filter |
| Octyl dimethylpaba | UVB filter |
| OM-Cinnamate | UVB filter |
| Polysilicone-15 | UVB filter |
| Titanium Dioxide | UVB filter |
| Zinc Oxide | UVB filter |
| Ethyl panthenol | Vitamins |
| Niacin | Vitamins |
| Retinyl acetate | Vitamins |
| Retinol | Vitamins |
| Vitamin E | Vitamins |
| Vitamin F | Vitamins |
| Bees wax | Waxes |
| Candelilla wax | Waxes |
| Carnauba wax | Waxes |
| Castor wax | Waxes |
| Lanolin alcohol | Waxes |
| Lauryl laurate | Waxes |
| Ozokerite wax | Waxes |
| PEG-8 beeswax | Waxes |
| Polyhydroxystearic acid | Waxes |
| Sunflower wax | Waxes |
| Tribehenin | Waxes |
| Non-polymeric diol | Demulcent |
| Non-polymeric glycol | Demulcent |
| Cellulose derivative | Demulcent |
| Dextran 70 | Demulcent |
| Cationic cellulose derivative | Demulcent |

Some excipients may include pharmaceutically acceptable excipients. The phrase "pharmaceutically acceptable" as used herein, refers to suitability within the scope of sound medical judgment for contacting subject (e.g., human or animal) tissues and/or bodily fluids with toxicity, irritation, allergic response, or other complication levels yielding reasonable benefit/risk ratios. As used herein, the term "pharmaceutically acceptable excipient" refers to any ingredient, other than active agents, that is substantially nontoxic and non-inflammatory in a subject. Pharmaceutically acceptable excipients may include, but are not limited to, solvents, dispersion media, diluents, inert diluents, buffering agents, lubricating agents, oils, liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of pharmaceutical compositions.

In one embodiment, the excipient is sorbitol.

In one embodiment, the excipient is mannitol.

Polymers

In some embodiments, excipients may include polymers. As used herein, the term "polymer" refers to any substance formed through linkages between similar modules or units. Individual units are referred to herein as "monomers." Common polymers found in nature include, but are not limited to, carbon chains (e.g., lipids), polysaccharides, nucleic acids, and proteins. In some embodiments, polymers may be synthetic (e.g., thermoplastics, thermosets, elastomers, and synthetic fibers), natural (e.g., chitosan, cellulose, polysaccharides, glycogen, chitin, polypeptides, β-keratins, nucleic acids, natural rubber, etc.), or a combination thereof. In some embodiments, polymers may be irradiated. Non limiting examples of polymers include ethylcellulose and co-polymers of acrylic and methacrylic acid esters (EUDRAGIT® RS or RL), alginates, sodium carboxymethylcellulose, carboxypolymethylene, hydroxypropyl methylcellulose, hydroxypropyl cellulose, collagen, hydroxypropyl ethylcellulose, hydroxyethylcellulose, methylcellulose, xanthan gum, polyethylene oxide, polyethylene glycol, polysiloxane, polyphosphazene, low-density polyethylene (LDPE), high-density polyethylene (HDPE), polyvinyl chloride, polystyrene, nylon, nylon 6, nylon 6.6, polytetrafluoroethylene, thermoplastic polyurethanes, polycaprolactone, polyamide, polycarbonate, chitosan, cellulose, polysaccharides, glycogen, starch, chitin, polypeptides, keratins, β-keratins, nucleic acids, natural rubber, hyaluronan, polylactic acid, methacrylates, polyisoprene, shellac, amber, wool, synthetic rubber, silk, phenol formaldehyde resin, neoprene, nylon, polyacrylonitrile, silicone, polyvinyl butyral, polyhydroxybutyrate (also known as polyhydroxyalkanoate), polyhydroxyurethanes, bioplastics, genetically modified bioplastics, lipid-derived polymers, lignin, carbohydrate polymers, ultra-high-molecular-weight-polyethylene (UHMWPE), gelatin, dextrans, and polyamino acids.

Specific non-limiting examples of specific polymers include, but are not limited to poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly (vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho) esters, poly(butyric acid), poly(valeric acid), poly(lactide-co-caprolactone), and trimethylene carbonate, polyvinylpyrrolidone. In some embodiments, polymer excipients may include any of those presented in Table 1, above.

Particles

In some embodiments, excipients may include particles. Such particles may be of any size and shape, depending on the nature of associated SBPs. In some embodiments, excipient particles are nanoparticles. Non-limiting examples of nanoparticles include gold nanoparticles, silver nanoparticles, silver oxide nanoparticles, iron nanoparticles, iron oxide nanoparticles, platinum nanoparticles, silica nanoparticles, titanium dioxide nanoparticles, magnetic nanoparticles, cerium oxide nanoparticles, protein filled nanoparticles, carbon nanoparticles, nanodiamonds, curcumin nanoparticles, polymeric micelles, polymer coated iron oxide nanoparticles, ceramic silicon carbide nanoparticles, nickel nanoparticles, and silicon dioxide crystalline nanoparticles.

In some embodiments, nanoparticles may include carbohydrate nanoparticles. Carbohydrate nanoparticles may include carbohydrate carriers. As a non-limiting example, carbohydrate carriers may include, but are not limited to, anhydride-modified or glycogen-type materials, phytoglycogen octenyl succinate, phytoglycogen beta-dextrin, or anhydride-modified phytoglycogen beta-dextrin. (See e.g., International Publication Number WO2012109121, the contents of which are herein incorporated by reference in their entirety).

In some embodiments, excipient nanoparticles may include lipid nanoparticles. Lipid nanoparticle excipients may be carriers in some embodiments. In some embodiments, lipid nanoparticles may be formulated with cationic lipids. In some embodiments, cationic lipids may be biodegradable cationic lipids. Such cationic lipids may be used to form rapidly eliminated lipid nanoparticles. Cationic lipids may include, but are not limited, DLinDMA, DLin-KC2-DMA, and DLin-MC3-DMA. Biodegradable lipid nanoparticles may be used to avoid toxicity associated with accumulation of more stable lipid nanoparticles in plasma and tissues over time.

In some embodiments, nanoparticles include polymeric matrices. As used herein, the term "polymeric matrix" refers to a network of polymer fibers that are bound together to form a material. The polymer fibers may be uniform or may include different lengths or monomer subunits. In some embodiments, polymer matrices may include one or more of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), or combinations thereof.

In some embodiments, polymers include diblock copolymers. As used herein, the term "diblock copolymer" refers to polymers with two different monomer chains grafted to form a single chain. Diblock polymers may be designed to aggregate in different ways, including aggregation as a particle. In some embodiments, diblock copolymers include polyethylene glycol (PEG) in combination with polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), or poly(4-hydroxy-L-proline ester).

In some embodiments, nanoparticles include acrylic polymers. As used herein, the term "acrylic polymer" refers to a polymer made up of acrylic acid monomers or derivatives or variants of acrylic acid. Monomers included in acrylic polymers may include, but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), and polycyanoacrylates.

In some embodiments, particle excipients may include any of those presented in Table 1, above.

Lipids

In some embodiments, excipients include lipids. As used herein, the term "lipid" refers to members of a class of organic compounds that include fatty acids and various derivatives of fatty acids that are soluble in organic solvents, but not in water. Examples of lipids include, but are not limited to, fats, triglycerides, oils, waxes, sterols (e.g. cholesterol, ergosterol, hopanoids, hydroxysteroids, phytosterol, and steroids), stearin, palmitin, triolein, fat-soluble vitamins (e.g., vitamins A, D, E, and K), monoglycerides (e.g. monolaurin, glycerol monostearate, and glyceryl hydroxystearate), diglycerides (e.g. diacylglycerol); phospholipids, glycerophospholipids (e.g., phosphatidic acid, phosphatidylethanolamine, phosphatidylcholine, phosphatidylserine, phosphoinositides), sphingolipids (e.g., sphingomyelin), and phosphosphingolipids. In some embodiments, lipids may include, but are not limited to, any of those listed (e.g., fats and fatty acids) in Table 1, above.

In some embodiments, lipid excipients include amphiphilic lipids (e.g., phospholipids). As used herein, the term "amphiphilic lipid" refers to a class of lipids with both hydrophilic and hydrophobic domains. Amphiphilic lipids may be used to prepare vesicles as these molecules typically form layers along water: lipid interfaces. Non-limiting examples of amphiphilic lipids include, but are not limited to, phospholipids, phosphatidylcholines, phosphatidylethanolamines, palmitoyl-oleoyl-phosphatidylethanolamine (POPE), phosphatidylserines, phosphotidylglycerols, lysophospholipids such as lysophosphatidylethanolamines, mono-oleoyl-phosphatidylethanolamine (MOPE), monomyristoyl-phosphatidylethanolamine (MMPE), lysolipids, mono-oleoyl-phosphatidic acid (MOPA), mono-oleoyl-phosphatidylserine (MOPS), mono-oleoyl-phosphatidylglycerol (MOPG), palmitoyloleoyl phosphatidylcholine, lysophosphatidylethanolamine, dipalmitoylphosphatidylcholine, dioleoylphosphatidylcholine; distearoylphosphatidylcholine, dilinoleoylphosphatidylcholine, 1,2-dioleoyl-sn-glycero-3-phosphocholine (DOPC), 1,2-dioleoyl-sn-glycero-3-phophoethanolamine (DOPE), 1,2-dilauroyl-sn-glycero-3-phosphocholine (DLPC), 1,2-dimyristoyl-sn-glycero-3-phosphocholine (DMPC) phosphatidylinositol, phosphatidic acid, palmitoyloleoyl phosphatidylcholine, lysophosphatidylethanolamines, monoglycerides, diglycerides, triglycerides.

Lipid Vesicles

In some embodiments, excipients may include lipid vesicles or components of lipid vesicles. As used herein, the term "lipid vesicle" refers to a particle enveloped by an amphiphilic lipid membrane. Examples of lipid vesicles include, but are not limited to, liposomes, lipoplexes, and lipid nanoparticles. SBPs may include lipid vesicles as cargo or payloads. In some embodiments, SBPs are or encompassed by lipid vesicles. Such lipid vesicles may be used to deliver SBPs as a payload. Such SBPs may themselves include cargo or payload. As used herein, the term "liposome" refers generally to any vesicle that includes a phospholipid bilayer and aqueous core. Liposomes may be artificially prepared and may be used as delivery vehicles. Liposomes can be of different sizes. Multilamellar vesicles (MLVs) may be hundreds of nanometers in diameter and contain two or more concentric bilayers separated by narrow aqueous compartments. Small unicellular vesicles (SUVs) may be smaller than 50 nm in diameter. Large unilamellar vesicles (LUVs) may be between 50 and 500 nm in diameter. Liposomes may include opsonins or ligands to improve liposome attachment to unhealthy tissue or to activate events (e.g., endocytosis). Liposome core pH may be modulated to improve payload delivery. In some embodiments, lipid vesicle excipients may include, but are not limited to, any of those listed in Table 1, above.

In some embodiments, liposomes may include 1,2-dioleyloxy-N,N-dimethylaminopropane (DODMA) liposomes, DiLa2 liposomes (Marina Biotech, Bothell, WA), 1,2-dilinoleyloxy-3-dimethylaminopropane (DLin-DMA) liposomes, 2,2-dilinoleyl-4-(2-dimethylaminoethyl)-[1,3]-dioxolane (DLin-KC2-DMA) liposomes, and MC3 liposomes (e.g., see US Publication Number US20100324120, the contents of which are herein incorporated by reference in their entirety). In some embodiments, liposomes may include small molecule drugs (e.g., DOXIL® from Janssen Biotech, Inc., Horsham, PA).

Liposomes may be formed from the synthesis of stabilized plasmid-lipid particles (SPLP) or stabilized nucleic acid lipid particle (SNALP) that have been previously described and shown to be suitable for delivery of oligonucleotides in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles *Hum Gene Ther.* 2008 19:125-132). These liposomes are designed for the delivery of DNA, RNA, and other oligonucleotide constructs, and they may be adapted for the delivery of SBPs with oligonucleotides. These liposome formulations may be composed of 3 to 4 lipid components in addition to SBPs. As an example, a liposome may contain 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearyloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, SBPs may be encapsulated within liposomes and/or contained in an encapsulated aqueous liposome core. In another embodiment, SBPs may be formulated in an oil-in-water emulsion where the emulsion particle comprises an oil core and a cationic lipid which can interact with SBPs, anchoring them to emulsion particles (e.g., see International Publication. Number WO2012006380, the contents of which are herein incorporated by reference in their entirety. In another embodiment, SBPs may be formulated in lipid vesicles which may have crosslinks between functionalized lipid bilayers (e.g., see United States Publication Number US20120177724, the contents of which are herein incorporated by reference in their entirety).

In some embodiments, lipid vesicles may include cationic lipids selected from one or more of formula CLI-CLXXIX of International Publication Number WO2008103276; formula CLI-CLXXIX of U.S. Pat. No. 7,893,302; formula CLI-CLXXXXII of U.S. Pat. No. 7,404,969; and formula I-VI of United States Publication Number US20100036115, the contents of each of which are herein incorporated by reference in their entirety. As non-limiting examples, cationic lipids may be selected from (20Z,23Z)—N,N-dimethylnonacosa-20,23-dien-10-amine, (17Z,20Z)—N,N-dimethylhexacosa-17,20-dien-9-amine, (1Z,19Z)—N5N-dimethylpentacosa-| 6, 19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14, 17-dien-6-amine, (15Z,18Z)—N,N-dimethyltetracosa-15, 18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12, 15-dien-1-amine, (13Z,16Z)—N,N-dimethyl-3-nonyldocosa-13,16-dien-1-amine, N,N-dimethyl-|-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl] methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl] heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy) propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9, 12-dien-1-yloxy]-1-[(octyloxy)methyl] ethyl}azetidine, (2S)-1-(hexyloxy)-N,N-dimethyl-3-[(9Z,12Z)-octadeca-9, 12-dien-1-yloxy]propan-2-amine, (2S)-1-(heptyloxy)-N,N-dimethyl-3-[(9Z,12Z)-octadeca-9, 12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11, 14-dien-1-yloxy]-N,N-dimethyl-3-(pentyloxy)propan-2-amine, (2S)-1-(hexyloxy)-3-[(11Z,14Z)-icosa-11, 14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-octylcyclopropyl)octyl]oxy}-3-(octyloxy)propan-2-amine, (11E,20Z,23Z)—N,N-dimethylnonacosa-11,20,2-trien-10-amine, or pharmaceutically acceptable salts or stereoisomers thereof.

In some embodiments, lipids may be cleavable lipids. Such lipids may include any of those described in International Publication Number WO2012170889, the contents of which are herein incorporated by reference in their entirety. In some embodiments, SBPs may be formulated with at least one of the PEGylated lipids described in International Publication Number WO2012099755, the contents of which are herein incorporated by reference in their entirety.

In some embodiments, excipients include lipid nanoparticles. As used herein, the term "lipid nanoparticle" or "LNP" refers to a tiny colloidal particle of solid lipid and surfactant, typically ranging in size of from about 10 nm in diameter to about 1000 nm in diameter. LNPs may contain PEG-DMG 2000 (1,2-dimyristoyl-sn-glycero-3-phophoethanolamine-N-[methoxy (polyethylene glycol)-2000). In some embodiments, LNPs may contain PEG-DMG 2000, a cationic lipid known in the art and at least one other component. LNPs may contain PEG-DMG 2000, a cationic lipid known in the art, DSPC and cholesterol. As a non-limiting example, LNPs may contain PEG-DMG 2000, DLin-DMA, DSPC, and cholesterol.

In some embodiments, excipients may include DiLa2 liposomes (Marina Biotech, Bothell, WA), SMARTICLES® (Marina Biotech, Bothell, WA), neutral DOPC (1,2-dioleoyl-sn-glycero-3-phosphocholine) based liposomes, and hyaluronan-coated liposomes (Quiet Therapeutics, Israel).

In some embodiments, excipients may include lipidoids. As used herein, the term "lipidoid" refers to any non-lipid material that mimics lipid properties. The synthesis of lipidoids may be carried out as described by others (e.g., see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci U SA. 2010 107: 1864-1869; and Siegwart et al., Proc Natl Acad Sci USA. 2011 108: 12996-3001, the contents of each of which are herein incorporated by reference in their entireties). Lipidoids may be included in complexes, micelles, liposomes, or particles. In some embodiments, SBPs may include lipidoids.

In some embodiments, lipidoids may be combined with lipids to form particles. Such lipids may include cholesterol. Some lipidoids may be combined with PEG (e.g., C14 alkyl chain length). As another example, formulations with certain lipidoids, include, but are not limited to, C12-200 and may contain a combination of lipidoid, disteroylphosphatidyl choline, cholesterol, and PEG-DMG.

Coating Agents

In some embodiments, excipients may include coating agents. Polymers are commonly used as coating agents and may be layered over SBPs. Non-limiting examples of polymers for use as coating agents include polyethylene glycol, methylcellulose, hypromellose, ethylcellulose, gelatin, hydroxypropyl cellulose, titanium dioxide, zein, poly(alkyl) (meth)acrylate, poly(ethylene-co-vinyl acetate), and combinations thereof. In some embodiments, coating agents may include one or more compounds listed in Table 1, above.

Bulking Agents

In some embodiments, excipients include bulking agents. As used herein, the term "bulking agent" refers to a substance that adds weight and volume to a composition. Examples of bulking agents include, but are not limited to, lactose, sorbitol, sucrose, mannitol, lactose USP, Starch 1500, microcrystalline cellulose, Avicel, dibasic calcium phosphate dehydrate, sucrose, tartaric acid, citric acid, fumaric acid, succinic acid, malic acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, sodium carboxymethylcellulose, and combinations thereof. In some embodiments, bulking agents may include any of those presented in Table 1, above.

Lubricants

In some embodiments, excipients may include lubricants. As used herein, the term "lubricant" refers to any substance used to reduce friction between two contacting materials. Lubricants may be natural or synthetic. Lubricants may comprise oils, lipids, microspheres, polymers, water, aqueous solutions, liposomes, solvents, alcohols, micelles, stearate salts, alkali, alkaline earth, and transition metal salts thereof (e.g., calcium, magnesium, or zinc), stearic acid, polyethylene oxide, talc, hydrogenated vegetable oil, and vegetable oil derivatives, fumed silica, silicones, high molecular weight polyalkylene glycol (e.g. high molecular weight polyethylene glycol), monoesters of propylene glycol, saturated fatty acids containing about 8-22 carbon atoms and/or 16-20 carbon atoms, and any other component known to one skilled in the art. Other examples of lubricants include, but are not limited to, hyaluronic acid, magnesium stearate, calcium stearate, and lubricin. In some embodiments, lubricant excipients may include any of those presented in Table 1, above.

Sweeteners and Colorants

In some embodiments, excipients may include sweeteners and/or colorants. As used herein, a "sweetener" refers to a substance that adds a sweet taste to or improves the sweetness of a composition. Sweeteners may be natural or artificial. Non-limiting examples of sweeteners include glucose, aspartame, sucralose, neotame, acesulfame potassium, saccharin, advantame, cyclamates, sorbitol, xylitol, lactitol, xylose, stevia, lead acetate, mogrosides, brazzein, curculin, erythritol, glycyrrhizin, glycerol, hydrogenated hydrolysates, inulin, isomalt, isomaltooligosaccharide, isomaltulose, mabinlin, maltodextrin, miraculin, monantin, osladin, pentadin, polydextrose, psicose, tagatose, thaumatin, mannitol, lactose, and sucrose. In some embodiments, sweetener excipients may include any of those presented in Table 1, above.

As used herein, the term "colorant" refers to any substance that adds color to a composition (e.g., a dye). Non-limiting examples of colorants include dyes, inks, pigments, food coloring, turmeric, titanium dioxide, carotinoids (e.g., bixin, β-carotene, apocarotenals, canthaxanthin, saffron, crocin, capsanthin and capsorubin occurring in paprika oleoresin, lutein, astaxanthin, rubixanthin, violaxanthin, rhodoxanthin, lycopene, and derivatives thereof), and FD&C colorants [e.g., FD&C Blue No. 1 (brilliant blue FCF); FD&C Blue No. 2 (indigotine); FD&C Green No. 3 (fast green FCF); FD&C Red No. 40 (allura red AC); FD&C Red No. 3 (erythrosine); FD&C Yellow No. 5 (tartrazine); and FD&C Yellow No. 6 (sunset yellow)]. In some embodiments, colorant excipients may include any of those presented in Table 1, above.

Preservatives

In some embodiments, excipients may include preservatives. As used herein a "preservative" is any substance that protects against decay, decomposition, or spoilage. Preservatives may be natural or synthetic. They may be antimicrobial preservatives, which inhibit the growth of bacteria or fungi, including mold, or antioxidants such as oxygen absorbers, which inhibit the oxidation of food constituents. Common antimicrobial preservatives include calcium propionate, sodium nitrate, sodium nitrite, sulfites (sulfur dioxide, sodium bisulfite, potassium hydrogen sulfite, etc.) and disodium EDTA. Antioxidants include BHA and BHT. Other preservatives include formaldehyde (usually in solution), glutaraldehyde (kills insects), vitamin A, vitamin C, vitamin E, selenium, amino acids, methyl paraben, propyl paraben, potassium sorbate, sodium chloride, ethanol, phenol, m-cresol, p-cresol, o-cresol, chlorocresol, benzyl alcohol, phenylmercuric nitrite, phenoxyethanol, methylchloroisothiazolinone, chlorobutanol, magnesium chloride (e.g., hexahydrate), alkylparaben (methyl, ethyl, propyl, butyl and the like), benzalkonium chloride, benzethonium chloride, sodium dehydroacetate, thimerosal, and combinations thereof. Preservatives may also be a stabilizer. Stabilizers comprise a variety of compounds that are able to maintain the function and activity of other ingredients such as, for example, active ingredients, fragrances and essential oils. In this group there are also several agents that are used for stabilizing the pH value thereby avoiding excessive acidity or alkalinity. A balanced pH value is particularly important for creating stable emulsions. In some embodiments, preservative excipients may include any of those presented in Table 1, above.

Flowability Agents

In some embodiments, excipients may include flowability agents. As used herein, the term "flowability agent" refers to a substance used to reduce viscosity and/or aggregation in a composition. Flowability agents are particularly useful for the formulation of powders, particles, solutions, gels, polymers, and any other form of matter capable of flow from one area to another. Flowability agents have been used to improve powder flowability for the manufacture of therapeutics, as taught in Morin et al. (2013) AAPS PharmSciTech 14 (3): 1158-1168, the contents of which are herein incorporated by reference in their entirety. In some embodiments, flowability agents are used to modulate SBP viscosity. In some embodiments, flowability agents may be lubricants. Non-limiting examples of flowability agents include magnesium stearate, stearic acid, hydrous magnesium silicate, and any other lubricant used to promote flowability known to one skilled in the art. In some embodiments, flowability agent excipients may include any of those presented in Table 1, above.

Gelling Agents

In some embodiments, excipients may include gelling agents. As used herein, the term "gelling agent" refers to any substance that promotes viscosity and/or polymer cross-linking in compositions. Non-limiting examples of gelling agents include glycerol, glycerophosphate, sorbitol, hydroxyethyl cellulose, carboxymethyl cellulose, triethylamine, triethanolamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol formal, hydroxypropyl beta-cyclodextrin, kolliphor 124, kolliphor 181, kolliphor 188, kolliphor 407, kolliphor EL (cremaphor EL), cremaphor RH 40, cremaphor RH 60, d-alpha-tocopherol, PEG 1000 succinate, polysorbate 20, polysorbate-80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil, beeswax, d-alpha-tocopherol, oleic acid, medium-chain mono- and diglycerides, alpha-cyclodextrin, beta-cyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alphadimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), PEG 4000 (PEG 4 kDa), polyoxyl 8 stearate (PEG 400 monosterate), polysorbate 20, polysorbate-SO, polyvinyl pyrrolidone, polyvinyl pyrrolidone-12, polyvinyl pyrrolidone-17, propylene carbonate, propylene glycol, solutol HS 15, sorbitan monooleate (Span 20), sulfobutylether-beta-cyclodextrin, transcutol, triacetin, 1-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, and glycerin. Additional examples of gelling agents include acacia, alginic acid, bentonite, CARBOPOLS® (also known as carbomers), carboxymethyl cellulose, ethylcellulose, gelatin, hydroxy ethyl cellulose, hydroxypropyl cellulose, magnesium aluminum silicate, methylcellulose, poloxamers, polyvinyl alcohol, sodium alginate, tragacanth, and xanthan gum. In some embodiments, gelling agent excipients may include any of those presented in Table 1, above.

PEGs which may be used as gelling agents and/or excipients may be selected from a variety of chain lengths and molecular weights. These compounds are typically prepared through ethylene oxide polymerization. In some embodiments, PEGs may have a molecular weight of from about 300 g/mol to about 100,000 g/mol. In some embodiments, PEGs may have a molecular weight of from about 3600 g/mol to about 4400 g/mol. In some embodiments, PEGs with a molecular weight of from about 300 g/mol to about 3000 g/mol, from about 350 g/mol to about 3500 g/mol, from about 400 g/mol to about 4000 g/mol, from about 450 g/mol to about 4500 g/mol, from about 500 g/mol to about 5000 g/mol, from about 550 g/mol to about 5500 g/mol, from about 600 g/mol to about 6000 g/mol, from about 650 g/mol to about 6500 g/mol, from about 700 g/mol to about 7000 g/mol, from about 750 g/mol to about 7500 g/mol, from about 800 g/mol to about 8000 g/mol, from about 850 g/mol to about 8500 g/mol, from about 900 g/mol to about 9000 g/mol, from about 950 g/mol to about 9500 g/mol, from about 1000 g/mol to about 10000 g/mol, from about 1100 g/mol to about 12000 g/mol, from about 1200 g/mol to about 14000 g/mol, from about 1300 g/mol to about 16000 g/mol, from about 1400 g/mol to about 18000 g/mol, from about 1500 g/mol to about 20000 g/mol, from about 1600 g/mol to about 22000 g/mol, from about 1700 g/mol to about 24000 g/mol, from about 1800 g/mol to about 26000 g/mol, from about 1900 g/mol to about 28000 g/mol, from about 2000 g/mol to about 30000 g/mol, from about 2200 g/mol to about 35000 g/mol, from about 2400 g/mol to about 40000 g/mol, from about 2600 g/mol to about 45000 g/mol, from about 2800 g/mol to about 50000 g/mol, from about 3000 g/mol to about 55000 g/mol, from about 10000 g/mol to about 60000 g/mol, from about 13000 g/mol to about 65000 g/mol, from about 16000 g/mol to about 70000 g/mol, from about 19000 g/mol to about 75000 g/mol, from about 22000 g/mol to about 80000 g/mol, from about 25000 g/mol to about 85000 g/mol, from about 28000 g/mol to about 90000 g/mol, from about 31000 g/mol to about 95000 g/mol, or from about 34000 g/mol to about 100000 g/mol are utilized.

Demulcents

In some embodiments, excipients may include demulcents. As used herein, the term "demulcent" refers to a substance that relieves irritation or inflammation of the mucous membranes by forming a protective film. Demulcents may include non-polymeric demulcents and polymer demulcents. Non-limiting examples of non-polymeric demulcents include glycerin, gelatin, propylene glycol, and other non-polymeric diols and glycols. Non-limiting examples of polymer demulcents include polyvinyl alcohol (PVA), povidone or polyvinyl pyrrolidone (PVP), cellulose derivatives, polyethylene glycol (e.g., PEG 300, PEG 400), polysorbate 80, and dextran (e.g., dextran 70). Specific cellulose derivatives may include hydroxypropyl methyl cellulose, carboxymethyl cellulose, carboxymethylcellulose sodium, methyl cellulose, hydroxyethyl cellulose, hypromellose, and cationic cellulose derivatives. In some embodiments, demulcent excipients may include any of those presented in Table 1, above.

Humectants

In some embodiments, excipients may include humectants. As used herein, the term "humectant" refers to a substance that prevents the loss of moisture; humectants may also be known as a moisturizer. Humectants are important cosmetic ingredients as they prevent the loss of moisture from the skin or hair. Humectants may also actively attract moisture to the skin or hair. Humectants are used in hair care products, because the attracted moisture can affect and expand the hair shaft resulting in more volume for the hair. In embodiments, humectants and moisturizers may include any of those presented in Table 1, above.

Emulsifiers

In some embodiments, excipients may include emulsifiers. As used herein, emulsifiers act to improve mixing of oils and aqueous (water-based) substances to create a homogenous mixture. Water/oil emulsifiers may be used as the sole or additional emulsifier in cosmetic and pharmaceutical formulations, such as ointments, creams, lotions, salves, as well as in cleaning agents such as soaps, shampoos, and bath lotions. Emulsifiers may also provide specific textures to mixtures, such as what is known as silky or velvety. In embodiments, emulsifiers may include any of those presented in Table 1, above.

Hydroxy Acids

In some embodiments, excipients may include hydroxy acids, also known as alpha and beta hydroxy acids or AHAs. As used herein, hydroxy acids may act as a physical or chemical exfoliant. Hydroxy acids cause cells of the epidermis to detach from one another, which allows dead skin cells to slough off. The removal of dead skin often allows for the regrowth of new skin cells. Hydroxy acids may improve the appearance of the skin, including reduction of wrinkles, roughness, and variable pigmentation of the skin. Hydroxy acids often require a long-term approach to creating visible results. Hydroxy acids often work best at concentrations of between 5% to 8% and at a pH of 3 to 4. Beta hydroxy acids, such as salicylic acid are topical exfoliants that affect the appearance of photodamaged skin by reducing fine wrinkles and discoloration. In embodiments, hydroxy acids may include any of those presented in Table 1, above.

Anti-Aging Agents

In some embodiments, excipients may include anti-aging agents. As used herein, anti-aging agents are any substance that may improve the appearance, objectively or subjectively, of the skin. Because anti-aging agents may be widely classified, their mode of action varies. They may act as a moisturizer or humectant, have antioxidant properties, exfoliant properties, replenish depleted components, and provide general stimulation of the skin. In embodiments, anti-aging agents may include any of those presented in Table 1, above.

Anti-Dark Circles Agents

In some embodiments, excipients may include anti-dark circles agents. As used herein, anti-dark circles agents may be any substance that either lightens the skin or reduces dark colors in the skin around the eyes. Dark circles under the eyes are often the result of blood vessels that have become engorged with blood. Because the skin around the eyes is relatively thinner compared to other skin on the face and body. Dark circles are caused by pigments from hemoglobin, which are more easily visible through the thin skin. Anti-dark circles agents reduce the appearance of the pigments. In embodiments, anti-dark circles agents may include any of those presented in Table 1, above.

Antioxidants

In some embodiments, excipients may include antioxidants. As used herein, antioxidants may be any substance that interrupts oxidation reactions and prevents the effects of oxygen radicals or peroxides. Oxidation reactions and peroxides may damage the integrity and function of the skin cells. Antioxidants prevent the degradation of natural substances and ingredients such as lipids, sugars, and proteins. Antioxidants also protect skin cells from excess damage and may slow down visible signs of aging. Antioxidants may improve subjective qualities of the by reducing fine lines and wrinkles, improving age spots, and general aesthetics of the skin. In embodiments, antioxidants may include any of those presented in Table 1, above.

Anti-Wrinkle Agents

In some embodiments, excipients may include anti-wrinkle agents. As used herein, antioxidants may be any substance that interrupts oxidation reactions and prevents the effects of oxygen radicals or peroxides. Oxidation reactions and peroxides may damage the integrity and function of the skin cells. Antioxidants prevent the degradation of natural substances and ingredients such as lipids, sugars, and proteins. Antioxidants also protect skin cells from excess damage and may slow down visible signs of aging. Antioxidants may improve subjective qualities of the by reducing fine lines and wrinkles, improving age spots, and general aesthetics of the skin. In embodiments, antioxidants may include any of those presented in Table 1, above.

Hair Repair Agents

In some embodiments, excipients may include hair repair agents. As used herein, hair repair agents may be any substance that generally supports or repairs hair. Hair repair agents that are able to protect the hair shaft or follicle. The mechanisms of action may include forming a protective film around the hair shaft and filling in broken cuticles or split ends. Hair repair agents may also include substances that correct or moisturize a dry scalp and hydrate hair follicles. These agents may help the hair retain moisture and provide shine and softness to hair. In embodiments, hair repair agents may include any of those presented in Table 1, above.

Liposomes

In some embodiments, excipients may include liposomes. As used herein, liposomes may be any substance that generally supports or repairs hair or skin. Liposomes are nano-sized particles resembling biomembranes and have a very high affinity for the skin. They can easily penetrate through the hard keratin layer of the skin. Based on this feature, active ingredients can be incorporated into liposomes to enhance their absorption by the skin and thus their efficacy. Liposome-encapsulation largely reduces the amount of the active ingredient required for effectiveness as compared to non-encapsulated, pure active ingredients. Examples of such encapsulated functional ingredients include coenzyme Q10 and ceramides. In embodiments, liposomes may include any of those presented in Table 1, above.

Skin Regulators

In some embodiments, excipients may include skin regulators. As used herein, skin regulators may be any substance that generally supports or repairs skin. Sebaceous glands secrete an oily substance called sebum (tallow) that is made of fat (lipids) and the debris of dead fat-producing cells. In the glands, sebum is produced within specialized cells and is released as these cells burst. Sebum is odorless, but its bacterial breakdown can produce odors. Hyperactive sebaceous glands produce too much sebum which is the cause of oily hair or skin and is also involved in skin problems such as blemished skin and dry and itchy scalp. Therefore, an important part of treating these conditions is the reduction of the sebum production. In embodiments, skin regulators may include any of those presented in Table 1, above.

Nourishing Agents

In some embodiments, excipients may include nourishing agents. As used herein, nourishing agents may be any substance that generally supports or repairs skin or hair. Nourishing agents include a wide range of different ingredients with various properties. Typically, proteins, natural butters, certain oils and other natural components (e.g. oatmeal) are widely used to nourish and replenish the skin. In embodiments, nourishing agents may include any of those presented in Table 1, above.

Peptides

In some embodiments, excipients may include peptides. As used herein, peptides may be any substance that generally supports or repairs skin or hair. Peptides are segments of proteins and occur in a wide variety in the body exerting many important physiological functions. When applied topically to skin peptides have been shown to have various benefits including (e.g. anti-aging activity). Today, dozens of peptides are used in skin care products and there are many more currently in development. Even though peptides consist of natural components (amino acids) most peptides that are used in personal care products are synthetic. Peptides are extremely hydrophilic (water-soluble) and therefore easy to use in cosmetic formulas. However, peptides are relatively heat sensitive. In order to be functional, peptides must be stable in their base formula, they must be paired with a specific carrier that enhances their absorption into the skin, and they must be able to reach their target cell groups without breaking down. Because peptides are small, they can penetrate the skin's protective barriers to get to the deeper layers of the dermis. In embodiments, peptides may include any of those presented in Table 1, above.

Proteins

In some embodiments, excipients may include proteins. As used herein, proteins may be any substance that generally supports or repairs skin or hair. Both animals and plants give suitable proteinaceous materials for the preparation of cosmetic ingredients. Proteins from fungi and algae, however, are also increasingly being used as protein sources. High-protein plants most commonly used as starting material for producing vegetable proteins are wheat and corn gluten, soy, rice and oat protein concentrates, and defatted oil seeds (peanuts, almond, sunflower). Among the large variety of vegetable proteins wheat gluten and soy globulins are by far of the widest use. Wheat gluten (often just called wheat protein) is a unique cereal protein of high elasticity when hydrated. Soy proteins are useful due to their gelling and emulsifying effects. To make proteins suitable to be incorporated into water-based cosmetic products, they need to be converted into soluble form. This is usually done by hydrolyzation, a process where the protein is cut into smaller parts. In embodiments, proteins may include any of those presented in Table 1, above.

Soothing Agents

In some embodiments, excipients may include soothing agents. As used herein, soothing agents may be any substance that generally supports or repairs skin or hair. There are a variety of ingredients that have properties able to soothe irritated and stressed skin. Typical examples include are *Aloe vera*, allantoin and rose hip oil which all are widely used in skin care preparations for sensitive or irritated skin. Many of these agents like provitamin B5 and hyaluronic acid have also rejuvenating effects of the skin. Such ingredients are therefore often used in after-peeling treatments, anti-aging formulations and in all treatments aiming to provide smoothness & softening to the skin. In embodiments, soothing agents may include any of those presented in Table 1, above.

Self-Tanners

In some embodiments, excipients may include self-tanners. As used herein, self-tanners may be any substance that generally supports or repairs skin or hair According to the American Academy of Dermatology the most effective sunless tanning product available today is dihydroxyacetone (DHA). As the colorless sugar interacts with the dead skin cells located in the outer layer of the epidermis, a color change occurs which usually lasts about seven to ten days from the initial application. Self-tanners should not be confused with bronzers which can be found in powder or cream form and, unlike self-tanners, can be instantly removed with soap and water. Erythrulose is another self-tanning agent that produces in combination with DHA a natural, deep & even tan without stripes (DHA alone may create an orange tone & stripes). Erythrulose prolongs the tan & leaves the skin less dry. In embodiments, self-tanners may include any of those presented in Table 1, above.

Skin Lightening Agents

In some embodiments, excipients may include skin lightening agents. As used herein, skin lightening agents may be any substance that generally supports or affects skin. Skin may appear darker than normal and may be blotchy, uneven areas, or patches of brown to gray discoloration or freckling. Skin pigmentation disorders occur because the body produces either too much or too little melanin, a pigment produced by melanocytes. Increased melanin production, also known as hyperpigmentation, is often referred to as melasma (general term describing darkening of the skin), chloasma (discolorations caused by hormones) or solar lentigines (darkened spots on the skin caused by the sun). In addition, hyperpigmentation can be caused by skin damage, such as remnants of blemishes, wounds or rashes. Skin-lighteners (like bearberry leaves extract and undecylenoyl phenylalanine) inhibit melanin tyrosinase or melanotropin and reduce or block some amount of melanin production. Many treatments use a combination of topical lotions or gels containing melanin-inhibiting ingredients along with a sunscreen, and a prescription retinoid. Depending on how the skin responds to these treatments exfoliants, either in the form of topical cosmetic or chemical peels, and lasers may be used. In embodiments, skin lightening agents may include any of those presented in Table 1, above.

Vitamins

In some embodiments, excipients may include vitamins. As used herein, vitamins may be any substance that generally supports or affects skin or hair. For years vitamins have been recognized as extremely valuable ingredients in all kinds of cosmetics. Vitamins offer various benefits to the skin as suppression of pigmentation & bruising, anti-aging and anti-wrinkle effects, and antioxidant effects. The antioxidant effect is particularly appreciated since free radicals generated by UV light or pollutants are effectively neutralized and no longer able to damage skin cells. Vitamins can therefore significantly improve the performance of cosmetic and personal care products. The most widely used vitamins in cosmetics are vitamin A, vitamin C, vitamin E and provitamin B5. In embodiments, vitamins may include any of those presented in Table 1, above.

Botanical Extracts

In some embodiments, excipients may include botanical extracts. As used herein, botanical extracts may be any substance that generally supports or affects skin or hair. For years botanical extracts have been recognized as extremely valuable ingredients in all kinds of cosmetics. Botanical extracts offer various benefits to the skin and hair. Botanical extracts may be produced by extracting chemical constituents from their inert herb fibers using a solvent. Botanical extracts can be incorporated into cosmetics or other products such as moisturizers, foaming agents, or after-sun products. In embodiments, botanical extracts may include any of those presented in Table 1, above.

Anti-Acne Agents

In some embodiments, excipients may include anti-acne agents. As used herein, anti-acne agents may be any substance that generally supports or affects skin. Acne vulgaris is an inflammatory disease of the skin, caused by excessive secretion of oils from the sebaceous glands accompanies the plugging of the pores with naturally occurring dead skin cells (corneocytes) blocking hair follicles. Acne can be treated with vitamin A derivatives (tretinoin), and exfoliating and anti-inflammatory agents. The basic principle is to increase skin cell turnover promoting the extrusion of the plugged material in the follicle. Common exfoliating agents include salicylic acid which induce peeling of the top layer of skin preventing a build-up of dead skin cells and blocking pores. It also helps to unblock already clogged pores. In embodiments, anti-acne agents may include any of those presented in Table 1, above.

Anti-Dandruff Agents

In some embodiments, excipients may include anti-dandruff agents. As used herein, anti-dandruff agents may be any substance that generally supports or affects skin or hair. Dandruff is the shedding of dead skin cells from the scalp. The signs and symptoms of dandruff are an itchy scalp and flakiness, and sometimes also red and greasy patches of skin and a tingly feeling on the skin. Dandruff can have several causes, including dry skin, seborrhoeic dermatitis, not cleaning/scrubbing often enough, shampooing too often, psoriasis, eczema, sensitivity to hair care products, or a yeast-like fungus. Dry skin is the most common cause of flaking dandruff. A number of antifungal treatments have been found to be effective including ketoconazole, zinc pyrithione and selenium disulfide. Other effective anti-dandruff agents include salicylic acid, sulfur, and coal tar. In embodiments, anti-acne agents may include any of those presented in Table 1, above.

Antiperspirants and Deodorants

In some embodiments, excipients may include antiperspirants. As used herein antiperspirants may be any substance that generally supports or affects skin or hair. Antiperspirants prevent odor and reduce sweat produced sweat glands. Antiperspirants-classified as drugs by the FDA—are typically applied to the underarms and attempt to stop or significantly reduce perspiration and thus reduce the moist climate in which bacteria thrive. Aluminum chloride, aluminum chlorohydrate, and aluminum zirconium compounds are the most widely used antiperspirants. Aluminium-based complexes react with the electrolytes in the sweat to form a gel plug in the duct of the sweat gland. The plugs prevent the gland from excreting liquid and are removed over time by the natural sloughing of the skin. Antiperspirants are often combined with deodorants which only reduce body odor but do not inhibit sweat. Deodorants like Zinc Ricinoleate do not reduce sweat production but only neutralize bad odors. Deodorants are not classified as OTC active ingredients. In embodiments, antiperspirants may include any of those presented in Table 1, above.

Skin Protectants

In some embodiments, excipients may include skin protectants. As used herein skin protectants may be any substance that generally supports or affects skin. Skin protectants may be used for the treatment of minor cuts, scrapes, minor burns, chapped skin and lips, and rashes due to poison ivy, poison oak, poison sumac, and insect bites. In embodiments, skin protectants may include any of those presented in Table 1, above.

Sunscreens

In some embodiments, excipients may include sunscreens. As used herein sunscreens may be any substance that generally supports or affects skin. Ultraviolet (UV) radiation is known to produce erythema and pigmentation on the skin. When directly exposed to the sun, there is 10 to 100 times more exposure of UVA than UVB. UVB (considered the Burning Ray) has an immediate, harmful impact on the skin within minutes. UVA (considered the Aging Ray), which you do not feel, has been shown to damage the skin by penetration deeply into the dermis able of producing premature aging, and wrinkles. Sunscreens are inactive ingredients that are able, however, to avoid chemically or physically UV radiations (UVA and UVB) to penetrate the skin layers. Chemical sunscreens act by absorbing UV-light. Physical sunscreens reflect or scatter light in both the visible and UV-spectrum. Effectiveness of sunscreens depends upon their UV-absorption, concentration, formulation, and ability to withstand swimming or sweating. In embodiments, sunscreens may include any of those presented in Table 1, above.

Surfactants or Soaps

In some embodiments, excipients may include surfactants or soaps. As used herein surfactants or soaps may be any substance that generally supports, cleans, or affects skin or hair. Surfactants cleanse and build foam by acting at the surface between fat and water (surface-active agents or surfactants). They are able of being mixed with water and fat of the skin, allowing dirt to be removed. Based on their cleansing power surfactants are classified into primary and secondary or co-surfactants. Based on the chemical structure there are anionic, amphoteric, non-ionic, and quaternary agents. Surfactants form the base of all personal cleansing products and can also have wetting, conditioning, defatting, emulsifying, & thickening effects. Surfactants are also very useful for homemade soaps (particularly liquid soaps) to improve lathering and decrease harshness. They are added to the oil-lye mixture during the boiling procedure. Surfactants greatly accelerate and improve the soap making process. In embodiments, surfactants or soaps may include any of those presented in Table 1, above.

Exfoliants

In some embodiments, excipients may include exfoliants. As used herein exfoliants may be any substance that generally supports or affects skin or hair. Exfoliants (or abrasives) are compounds able to slough away the top layer of dead epidermis cells of the skin, thereby leaving the skin appear smoother, fresher and less wrinkled (peelings). The result of exfoliation is to promote blood circulation in the skin and to increase the turnover of surface skin cells. Exfoliation can be achieved either mechanically by scrubbing the skin with cleansers containing small, hard particles (scrubs) or also chemically by applying cleansers containing active ingredients with a peeling effect (e.g. alpha-hydroxy acids, beta-hydroxy acids and others). In embodiments, exfoliants may include any of those presented in Table 1, above.

Quaternary and Cationic Conditioners

In some embodiments, excipients may include quaternary and cationic conditioners. As used herein quaternary and cationic conditioners may be any substance that generally supports or affects skin or hair. Quaternary conditioners are special cationic surfactants (quaternary ammonium compounds) carrying positive electrical charges, thereby neutralizing the negative charges of the hair that occur especially on areas where there is weathering. The effect is a reduction of static electricity on the hair and the 'fly away' associated with it. Not only does this improve the shine and luster of the hair, the change in the hair surface enhances the depth and life of the hair color too. Conditioners also improve detangling and combing the hair, both wet and dry hair. In embodiments, quaternary and cationic conditioners may include any of those presented in Table 1, above.

Emollients

In some embodiments, excipients may include emollients. As used herein emollients may be any substance that generally supports or affects skin or hair. Emollients include a large variety of compounds with softening and smoothing properties. As compared to plant oils, specialty emollients are resistant to oxidation and can therefore not spoil and need no antioxidants for preservation. In addition, most specialty emollients show very good spreadability on the skin and provide a satiny, smooth and non-greasy feel to the skin. Typically, they are non-comedogenic, non-allergic and non-irritant. There are several kinds of natural (vegetable) butters which are extracted from various plants, trees, roots, or seeds. They all consist of solid or semi-solid fat oils (i.e. they remain solid at room temperature) making them excellent emollients, softeners and protecting agents. Their composition of oils, fatty acids and active ingredients, however, is quite different so that each butter additionally has different properties as, for example, anti-inflammatory, soothing, moisturizing or antioxidant activities. Natural oils are vegetable oils that consist of aethereal salts of glycerin with a large number of organic acids such as stearic acid, oleic acid, and palmitic acid forming stearin, olein and palmitin, respectively. Stearin and palmitin prevail in the solid oils and fats, while olein is dominant in the liquid oils. Natural oils are excellent emollients leaving the skin soft and smooth. While penetrating the skin many oils have also effective nourishing and revitalizing effects. Natural oils are used in a wide variety of cosmetic products including personal care and makeup products. Silicones (occur in nature as silicates in sand) are polymers with unique properties and have numerous benefits in all aspects of personal care. They are superb emollients providing great slip and can feel like silk on the skin. Silicones also act as skin protectant, conditioner, pearlizer, film-former, moisturizer, thickener, and emulsifier. As silicones are very mild, they are often used to reduce irritation of harsh surfactants. In embodiments, emollients may include any of those presented in Table 1, above.

Fragrances

In some embodiments, excipients may include fragrances. As used herein fragrances may be any substance that generally applies a smell to, or otherwise affects, skin or hair. Most fragrances are a blend of natural oils and specific aroma compounds which make it possible at all to create stable fragrances and scents. Fragrances can be used in practically all personal care products. They may be undiluted, full-strength oils or water-based mixtures that have not been cut with solvents or the fragrances may be diluted with a solvent. The level of fragrance needed, varies according to the product type. Typically, a face cream may contain only 0.01% fragrance by weight, while a soap bar might range from 0.5-3.0% fragrance. In embodiments, fragrances may include any of those presented in Table 1, above.

Texturizers, Fillers, and Pearlizers

In some embodiments, excipients may include texturizers and fillers. As used herein texturizers and fillers may be any substance that generally affects skin or hair. Texturizers are primarily composed of natural minerals and crystals (e.g. silicates, bismuth, magnesium and others). They are fine powders with effective thickening, filling and stabilizing properties for cosmetic products. They are widely used as basic components in all kinds of makeup products including foundations, face powders, lipsticks, eye shadows, mascara, makeup remover, and more. In addition, some texturizers provide special effects such as emulsifying (e.g. magnesium stearate) or pearlizing effects (e.g. bismuth oxychloride). Pearlizers are cosmetic ingredients used to obtain luster and shimmering effects in cosmetic products. Generally, the luster effect is achieved by microfine crystalline compounds (e.g. pearlescent pigments or special chemical molecules) able the reflect light waves. Pearlizers are very often used to provide a luxurious character to a cosmetic product. Pearlizers used in personal care products as shampoos and shower gels often have also thickening and emulsifying effects. In embodiments, texturizers and fillers may include any of those presented in Table 1, above.

Thickeners

In some embodiments, excipients may include thickeners. As used herein thickeners may be any substance that may be added to cosmetics or other products, or generally affects skin or hair. Thickeners are used very often in various cosmetic products. They enhance the consistency, volume and viscosity of cosmetic products, thereby providing more stability and better performance. While some thickeners have also emulsifying or gelling properties, the majority of thickeners have the ability to retain water on the skin and act therefore as moisturizers. Thickeners can be completely natural like waxes but also synthetic or semi-synthetic. They are derived from various sources and consist of very different molecular structures including polysaccharides, proteins, polymers, alcohols, silicones or waxes. Waxes are complex mixtures of alcohols, fatty acids and esters. They are harder, less greasy and more brittle than fats, and are very resistant to moisture, oxidation and microbial degradation. Waxes very useful cosmetic ingredients based on their various advantageous properties. Generally, waxes have protecting, film-forming, emollient and thickening effects. They provide stability of cosmetic products and enhance their viscosity and consistency. Both natural and synthetic polymers gained rapidly significance in professional cosmetics formulation due to their large variety of functions and generally very good tolerability by skin and hair. Based on the structure they can be used as thickeners, gel builders, fixatives, styling agents, conditioners, pearlizers, emollients, and film-formers. In embodiments, thickeners may include any of those presented in Table 1, above.

Solvents

In some embodiments, excipients may include solvents. As used herein solvents may be any substance that generally can be added to cosmetics or other consumer products, or may otherwise affect skin or hair. Since many ingredients are not or only poorly soluble in water, special solvents may be necessary to bring such ingredients into solution. Special solvents may also be necessary to disperse and wet pigments. Typical solvents for dissolving water-soluble ingredients include glycerin, propanediol 1,3 and propylene glycol. In embodiments, solvents may include any of those presented in Table 1, above.

pH Adjusters

In some embodiments, excipients may include pH adjusters. As used herein pH may be any substance that generally can be added to cosmetics or other consumer products, or may otherwise affect skin or hair. pH adjusters are ingredients used to adjust the pH (acidity or alkalinity) of a finished product. The optimum pH for most products is between 4.5 and 7. The ingredients used in a formula sometimes combine to form too acidic or too alkaline of a solution for the skin or scalp. A pH adjuster is then used to either raise or lower the pH to be less irritating to the skin. In embodiments, pH adjusters may include any of those presented in Table 1, above.

Formats

SBPs may include or be prepared to conform to a variety of formats relating to consumer or personal care. In some embodiments, such formats include formulations of processed silk with various excipients and/or cargo. Examples of personal care compositions contain silk fibroin are disclosed in U.S. Patent Publication 2015/0079012, which is incorporated by reference, in its entirety. In some embodiments, SBP formats include, but are not limited to, gels, hydrogels, drops, creams, microspheres, implants, solutions, pastes, lotions, ointments and salves, oils, liquids, serums, shampoos, sprays and aerosols, foams, sticks, balms, and scrubs. The silk fibroin-based compositions and emulsion compositions described herein can be formulated to any form desirable for a specific application. For example, the composition can be formulated to form a gel or hydrogel, a paste, a lotion, a cream, an ointment, an oil, a liquid, a serum, a shampoo, a foam or mousse, a spray, an aerosol, a stick, a balm, a bar, a scrub, or any combinations thereof. In some embodiments, the formats are formulated with a therapeutic agent or other excipient, as listed in Table 1.

Gels

At the most basic level, gels are active ingredients, such as SBP, suspended in a base of water and a thickening agent, such as xanthan gum. Gels tend to be lighter and less moisturizing than creams or lotions, making them a suitable option for certain types of skin, such as oily or acne-prone. Cooling, refreshing and more readily absorbed than many other topical formulations, gels are often used to deliver active ingredients in anti-cellulite products and in products designed for use around the delicate eye area. In addition to the eye and face area, gels may be used in other areas of the body and on other membranes, such as vaginal and mucosal.

Hydrogels

In some embodiments, SBP formulations include gels or hydrogels. As used herein, the term "gel" refers to a dispersion of liquid molecules in a solid medium. Gels in which the dispersed liquid molecules include water are referred to herein as "hydrogels." In addition to the eye and face area, hydrogels may be used in other areas of the body and on other membranes, such as vaginal and mucosal. Gels in which the dispersed liquid molecules include an organic phase are referred to herein as "organogels." The solid medium may include polymer networks. Hydrogels may be formed with silk of any grade (e.g. grade 3, grade 4, grade 5, and grade 6; A, B, C; or any other relative classifications commonly used in the art).

In some embodiments, SBP gels or hydrogels are prepared with processed silk. In processed silk gels, polymer networks may include silk fibroin. In some embodiments, gels are prepared with one or more therapeutic agents. In some embodiments, gels include one or more excipients. The excipients may be selected from any of those described herein. In some embodiments, excipients may include salts. In some embodiments, the excipients may include gelling agents. In some embodiments, gels are prepared with one or more therapeutic agents, biological agents, proteins, small molecules, and/or polymers. In some embodiments, gels may be prepared by mixing a solution comprising processed silk with a gelling agent. The gelling agent may be in a second solution. In some embodiments, the therapeutic agent may be in solution with processed silk. In some embodiments, the therapeutic agent may be in solution with the gelling agent. In some embodiments, a stock solution of therapeutic agent may be used to dissolve processed silk for the preparation of a hydrogel. The ratio of the solution comprising processed silk to the gelling agent or solution comprising the gelling agent may be from about 5:1 to about 4.5:1, from about 4.5:1 to about 4:1, from about 4:1 to about 3.5:1, from about 3.5:1 to about 3:1, from about 3:1 to about 2.5:1, from about 2.5:1 to about 2:1, from about 2:1 to about 1.5:1, from about 1.5:1 to about 1:1, from about 1:1 to about 1:1.5, from about 1:1.5 to about 1:2, from about 1:2 to about 1:2.5, from about 1:2.5 to about 1:3, from about 1:3 to about 1:3.5, from about 1:3.5 to about 1:4, from about 1:4 to about 1:4.5, or from about 1:4.5 to about 1:5.

Gel preparation may require varying temperatures and incubation times for gel polymer networks to form. In some embodiments, SBP formulations are heated to 37° C. to prepare gels. In some embodiments, SBP formulations are incubated at 4° C. to prepare gels. In some embodiments, SBP formulations are incubated for from about 2 hours to about 36 hours or more to promote gel formation. In some embodiments, gel formation requires mixing with one or more gelling agents or excipients. Mixing may be carried out under various temperatures and lengths of time to allow gel polymer networks to form. Gel formation may require homogenous dispersion of gelling agents or excipients. In some embodiments, SBP formulations used to prepare gels include silk fibroin. Gel formation for processed silk gels may require incubation at 37° C. for up to 24 hours. Gel formation for processed silk gels may require incubation at 4° C. for up to 24 hours. Some gels may be stored for later use or processing. In some embodiments, gels are stored at 4° C.

In some embodiments, processed silk gels include one or more excipients and/or gelling agents at a concentration of from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

In some embodiments, processed silk gels (e.g., hydrogels or organogels) include silk fibroin at a concentration of from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

Silk fibroin included may be from a silk fibroin preparation with an average silk fibroin molecular weight or range of molecular weights of from about 3.5 kDa to about 10 kDa, from about 5 kDa to about 20 kDa, from about 10 kDa to about 30 kDa, from about 15 kDa to about 40 kDa, from about 20 kDa to about 50 kDa, from about 25 kDa to about 60 kDa, from about 30 kDa to about 70 kDa, from about 35 kDa to about 80 kDa, from about 40 kDa to about 90 kDa, from about 45 kDa to about 100 kDa, from about 50 kDa to about 110 kDa, from about 55 kDa to about 120 kDa, from about 60 kDa to about 130 kDa, from about 65 kDa to about 140 kDa, from about 70 kDa to about 150 kDa, from about 75 kDa to about 160 kDa, from about 80 kDa to about 170 kDa, from about 85 kDa to about 180 kDa, from about 90 kDa to about 190 kDa, from about 95 kDa to about 200 kDa, from about 100 kDa to about 210 kDa, from about 115 kDa to about 220 kDa, from about 125 kDa to about 240 kDa, from about 135 kDa to about 260 kDa, from about 145 kDa to about 280 kDa, from about 155 kDa to about 300 kDa, from about 165 kDa to about 320 kDa, from about 175 kDa to about 340 kDa, from about 185 kDa to about 360 kDa, from about 195 kDa to about 380 kDa, from about 205 kDa to about 400 kDa, from about 215 kDa to about 420 kDa, from about 225 kDa to about 440 kDa, from about 235 kDa to about 460 kDa, or from about 245 kDa to about 500 kDa.

In some embodiments, hydrogels include one or more therapeutic agents at a concentration of from about 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

Gelling agents may be used to facilitate sol-gel transition. As used herein, the term "sol-gel transition" refers to the shift of a formulation from a solution to a gel. In some embodiments, the use of gelling agents may be carried out according to any of such methods described in International Publication No. WO2017139684, the contents of which are herein incorporated by reference in their entirety. Gelling agents may be water-soluble, waxy solids. In some embodiments, gelling agents may be water-soluble and hygroscopic in nature. In some embodiments, gelling agents may include polar molecules. Gelling agents may have net positive, net negative, or net neutral charges at a physiological pH (e.g., pH of about 7.4). Some gelling agents may be amphipathic. Additional examples of gelling agents include oils (e.g., castor, corn oil, cottonseed oil, olive oil, peanut oil, peppermint oil, safflower oil, sesame oil, soybean oil, hydrogenated vegetable oil, hydrogenated soybean oil, and medium-chain triglycerides of coconut oil and/or palm seed oil), emulsifiers [e.g., polyoxyl 40 stearate (PEG 1750 monosterate), polyoxyl 8 stearate (PEG 400 monosterate), polysorbate 20, polysorbate 80, polysorbate-SO, or poloxamer], surfactants (e.g., polysorbate, poloxamer, sodium dodecyl sulfate, Triton X100, or tyloxapol), and suspending agents (e.g., polyvinyl pyrrolidone, polyvinyl pyrrolidone-12, polyvinyl pyrrolidone-17, hydroxyethyl cellulose, or carboxymethyl cellulose). Any gelling agent listed in Table 1 may be used.

In some embodiments, gel formation is induced by applying one or more of the following to processed silk preparations: ultrasound, sonication, shear forces, temperature change (e.g., heating), addition of precipitants, modulation of pH, changes in salt concentration, chemical cross-linking, chemical modification, seeding with preformed hydrogels, increasing silk fibroin concentration, modulating osmolarity, use of electric fields, or exposure to electric currents. In some embodiments, methods of inducing gel formation may include, but are not limited to any of those described in International Patent Application Publication No. WO2005012606 or United States Patent Publication No. US2011/0171239, the contents of each of which are herein incorporated by reference in their entirety.

In some embodiments, processed silk gel preparation may be carried with the aid of sonication. As used herein, the term "sonication" refers to a process of agitation using sound energy. Sonication conducted at frequencies greater than 20 KHz is referred to as ultrasonication. Sonication may aid in gel formation by dispersing and/or agitating polymer components within a solution to foster an arrangement that favors polymer network formation. The polymer network may include silk fibroin. In some embodiments, the use of sonication for gel preparation may be carried out according to any of the methods described in Zhao et al. (2017) Materials Letters 211:110-113 or Mao et al. (2017) Colloids Surf B Biointerfaces 160:704-714), the contents of each of which are herein incorporated by reference in their entirety.

In some embodiments, processed silk gel formation may be carried out using shear forces. As used herein, the term "shear forces" refers to unaligned forces that apply pressure to two or more different parts of an object or medium from different and/or opposing directions. Shear forces are distinct from compression forces, which are directed toward each other. Shear forces may be applied during processed silk gel preparation using a syringe, tubing, needle, or other apparatus capable of increasing shear forces. Processed silk preparation may be pushed through a syringe, tubing, needle, or other apparatus to generate shear forces. The use of shear forces in gel formation may include any of those described in United States Patent Publication No. US2011/0171239, the contents of which are herein incorporated by reference in their entirety.

In some embodiments, changes in temperature may be used to aid in processed silk gel formation. Changes in temperature may be used to disperse or align polymer components in an arrangement that promotes gel polymer network formation. The polymer components may include silk fibroin. In some embodiments, gel formation may be carried out by raising or lowering the temperature of a processed silk preparation to from about 0° C. to about 5° C., from about 2° C. to about 6° C., from about 4° C. to about 12° C., from about 8° C. to about 16° C., from about 10° C. to about 26° C., from about 15° C. to about 28° C., from about 20° C. to about 32° C., from about 25° C. to about 34° C., from about 30° C. to about 45° C., from about 35° C. to about 55° C., from about 37° C. to about 65° C., from about 40° C. to about 75° C., from about 50° C. to about 100° C., from about 60° C. to about 120° C., from about 70° C. to about 140° C., from about 80° C. to about 160° C., or from about 100° C. to about 300° C. In some embodiments, one or more excipients or gelling agents may be included to lower the temperature necessary for gel formation to occur. Such embodiments may be employed to protect temperature-sensitive components embedded within gels. In some embodiments, gel formation is carried out at 4° C. Glycerol, polyethylene glycol (PEG), and/or polymers of PEG (e.g., PEG400) may be included in SBP formulations as excipients to lower the temperature necessary to form a gel. The gel may be a silk fibroin gel. Excipient concentration may be about 30% (w/v). Silk fibroin concentration may be from about 2% to about 30%.

In some embodiments, gel formation is carried out by applying an electric current, also referred to as "electrogelation." Electrogelation may be carried out according to any of the methods presented in International Publication No. WO2010036992, the contents of which are herein incorporated by reference in their entirety. In some embodiments, a reverse voltage may be applied to reverse gel formation and regenerate a processed silk solution.

In some embodiments, gel formation is carried out by modulating the pH of processed silk preparations. Gel formation through pH modulation may be carried out according to the methods described in International Patent Application Publication No. WO2005012606, United States Patent Publication No. US2011/0171239, and Dubey et al. (2017) Materials Chemistry and Physics 203:9-16, the contents of each of which are herein incorporated by reference in their entirety.

In some embodiments, gel formation is carried out in association with modulating the osmolarity of a processed silk preparation. As used herein, the term "osmolarity" or "osmotic concentration" refers to the number of osmoles of solute in solution on a per liter basis (Osm/L). Unlike molarity, which is a measure of the number of moles solute per liter of solvent (M), osmolarity factors in the effect of ions on osmotic pressure. For example, a 1 M solution of NaCl would have an osmolarity of 2 Osm/L while a 1 M solution of $MgCl_2$ would have an osmolarity of 3 Osm/L. Hypo- or hyper-osmotic formulations can lead to local tissue damage and reduced biocompatibility. In some embodiments, the osmolarity of processed silk gels is modulated by controlling the type, molecular weight, and/or concentration of excipients included. Osmolarity may be modulated by varying the concentration and/or molecular weight of salts used in processed silk preparations. In some embodiments, osmolarity is reduced by using lower molecular weight gelling agents. For example, 4 kDa PEG may be used in place of PEG400. The use of Poloxamer-188 at 10% (w/v) may reduce osmolarity in comparison to lower molecular weight species such as glycerol. In some embodiments, sodium chloride may be added to increase osmolarity. In some embodiments, osmolarity is adjusted to fall between 280 and 320 mOsm/L.

In some embodiments, gel formation is carried out through seeding. As used herein when referring to gel formation, "seeding" refers to a process of inducing gel formation using a small amount of pre-formed gel. Seeding may promote gel formation by encouraging polymer network formation to build off of the pre-formed gel introduced. In some embodiments the gel includes silk fibroin. Seeding with a pre-formed silk fibroin hydrogel may be used to promote transition of a silk fibroin solution into a silk fibroin gel. In some embodiments, seeding reduces the need for gelling agents and/or excipients to form gels.

In some embodiments, gel formation is carried out using chemical cross-linking. As used herein, the term "chemical cross-linking" refers to a process of forming covalent bonds between chemical groups from different molecules or between chemical groups present on different parts of the same molecule. In some embodiments, chemical cross-linking may be carried out by contacting SBP formulations with ethanol. Such methods may be carried out according to those described in Shi et al. (2017) Advanced Material 29 (29): 1701089, the contents of which are herein incorporated by reference in their entirety. In some embodiments, cross-linking may be carried out using enzymes. Methods of enzyme cross-linking using horse radish peroxidase may include any of those described in McGill et al. (2017) Acta Biomaterialia 63:76-84 or Guo et al. (2017) Biomaterials 145:44-55, the contents of each of which are herein incorporated by reference in their entirety. In some embodiments, chemical cross-linking may be photo-initiated, as disclosed in International Publication No. WO2017123383 and in Zhang et al. (2017) Fibers and Polymers 18 (10): 1831-1840, the contents of each of which are herein incorporated by reference in their entirety.

In some embodiments, other chemical modifications may be used during processed silk gel preparation. Some chemical modifications may be used to induce silk fibroin β-sheet conformations. In some embodiments, this process involves contact with a chemical. Chemicals may include, but are not limited to, ethanol. In some embodiments, silk fibroin may be chemically crosslinked with other materials during gel preparation. Such materials may include other peptides (e.g., see Guo et al. (2017) Biomaterials 145:44-55, the contents of which are herein incorporated by reference in their entirety). In some embodiments, processed silk gels are prepared by formation of internal chemical cross-links. These crosslinks may be dityrosine crosslinks (e.g., see International Patent Application Publication No. WO2017123383, the contents of which are herein incorporated by reference in their entirety). In some embodiments, photosensitive materials may be used to promote chemical modifications. Such materials may include riboflavin (e.g., see International Publication No. WO2017123383). In some embodiments, processed silk gels may be functionalized with particles. These particles may be microspheres and/or nanospheres (e.g., see Ciocci et al. (2017) Int J Biol Macromol S0141-8130 (17): 32839-8, the contents of which are herein incorporated by reference in their entirety).

In some embodiments, the SBPs are prepared as hydrogels. In some embodiments, the hydrogels have a concentration between about 3% (w/v) to about 15% (w/v) silk fibroin. In some embodiments the silk fibroin has a boiling time of 90 mb, 120 mb, or 480 mb. In some embodiments, the hydrogels are prepared from silk fibroin lyophilized in phosphate buffer. In some embodiments, the hydrogels have trace amounts of phosphate salts (e.g. potassium phosphate dibasic and potassium phosphate monobasic). In some embodiments, the hydrogels comprise between about 10% (w/v) to about 50% (w/v) excipient. In some embodiments, the excipient is poloxamer-188 (P188), in some embodiments, the excipient is glycerol. In some embodiments, the excipient is PEG 4000 (PEG 4 kDa) and the formulation may optionally include hydrochloric acid. In some embodiments, the excipient is PEG400 and the formulation may optionally include hydrochloric acid. In some embodiments, the hydrogels comprise 15 mM hydrochloric acid. In some embodiments, the formulations are as described in Table 2. In the sample named 90mb; hyd; 5% SFf; 10% P188f, "90mb" refers to silk degummed with a 90-minute boil, "hyd" refers to the formulation of the sample as a hydrogel, "5% SFf" refers to a formulation with 5% (w/v) silk fibroin, and "40% Glycf" refers to a formulation with 40% (w/v) glycerol.

Drops

In some embodiments, SBP formulations include drops. As used herein, the term drops refers to a solution of liquid molecules that may have wetting properties or are intended to spread out to cover a location. In some embodiments, SBP drops are prepared with processed silk. In processed silk drops, polymer networks may include silk fibroin. In some embodiments, drops are prepared with one or more therapeutic agents. In some embodiments, drops include one or more excipients. The excipients may be selected from any of those described herein. In some embodiments, excipients may include salts. In some embodiments, the excipients may include gelling agents. In some embodiments, drops are prepared with one or more therapeutic agents, biological agents, proteins, small molecules, and/or polymers. In some embodiments, drops may be prepared by mixing a solution comprising processed silk with other soluble or liquid constituents. In some embodiments, the therapeutic agent may be in solution with processed silk. In some embodiments, a stock solution of therapeutic agent may be used to dissolve processed silk for the preparation of drops. The ratio of the solution comprising processed silk to the solution comprising other liquid ingredients may be from about 5:1 to about 4.5:1, from about 4.5:1 to about 4:1, from about 4:1 to about 3.5:1, from about 3.5:1 to about 3:1, from about 3:1 to about 2.5:1, from about 2.5:1 to about 2:1, from about 2:1 to about 1.5:1, from about 1.5:1 to about 1:1, from about 1:1 to about 1:1.5, from about 1:1.5 to about 1:2, from about 1:2 to about 1:2.5, from about 1:2.5 to about 1:3, from about 1:3 to about 1:3.5, from about 1:3.5 to about 1:4, from about 1:4 to about 1:4.5, or from about 1:4.5 to about 1:5

Creams and Spreadable Formats

In some embodiments, SBP formats and formulations include creams or moisturizers. As used herein, the term cream refers to a thick mixture of various ingredients. Creams may be semisolid dosage forms containing more than 20% water or volatile components. Creams may also contain one or more therapeutic agent, including SBPs, dissolved in a suitable cream base. Creams may have four main ingredients: water, oil, emulsifier, and a thickening agent, in addition to an active ingredient, such as silk fibroin. In some embodiments, SBP creams are prepared with processed silk or silk fibroin. The ratio of the cream comprising processed silk to the other ingredients may be from about 5:1 to about 4.5:1, from about 4.5:1 to about 4:1, from about 4:1 to about 3.5:1, from about 3.5:1 to about 3:1, from about 3:1 to about 2.5:1, from about 2.5:1 to about 2:1, from about 2:1 to about 1.5:1, from about 1.5:1 to about 1:1, from about 1:1 to about 1:1.5, from about 1:1.5 to about 1:2, from about 1:2 to about 1:2.5, from about 1:2.5 to about 1:3, from about 1:3 to about 1:3.5, from about 1:3.5 to about 1:4, from about 1:4 to about 1:4.5, or from about 1:4.5 to about 1:5.

Related to creams, ointments and salves may have a greater concentration of oil or other skin protectant relative to water. Ointments may have up to 80% of oil or other non-water-soluble component, the remaining portion comprising water, an emulsifier, a thickening agent, and an active ingredient like silk fibroin.

Pastes, although spreadable like a gel, cream, or ointment, only contain three main ingredients: oil, water and powder. Pastes may be thicker than other spreadable formats. Pastes may contain silk fibroin or other SBPs.

Lotions are low-viscosity topical preparations intended for application to the skin intended to simply moisturize the skin or to treat or prevent skin diseases and irritations. In addition to the eye and face area, gels may be used in other areas of the body and on other membranes, such as vaginal and mucosal. Compared to other topical and spreadable formats, lotions may have a higher water content. Shampoos may be considered lotions due to the viscosity. Most lotions are oil-in-water emulsions using a substance such as cetearyl alcohol to keep the emulsion together, but water-in-oil lotions are also formulated. The key components of a skin care lotion, cream or gel emulsion (that is mixtures of oil and water) are the aqueous and oily phases, an emulgent to prevent separation of these two phases, and, if used, the drug substance or substances. A wide variety of other ingredients such as fragrances, glycerol, petroleum jelly, dyes, preservatives, proteins and stabilizing agents are commonly added to lotions.

Foams and Aerosols

Foaming cosmetic compositions for personal cleansing and cosmetic purposes must satisfy a number of criteria including good cleansing power and foaming properties. Ideal cosmetic cleansers should cleanse the skin or hair gently, without causing irritation, without dehydrating the skin, and without leaving the skin feeling taut after use. Ideal cosmetic cleansers should also condition the skin. Most lathering soaps, liquids, gels and bars fail in one or more of these respects. For example, good foaming cleansers tend to be harsh to the skin. This occurs because the surfactant systems that provide good lathering performance, while being effective cleansers, also tend to dehydrate the skin and remove lipids from the skin. The skin becomes dry due to the hygroscopic effect of the surfactants, which remove water from the skin. The skin becomes tight, or taut due to the emulsification effects of the surfactants. The surfactants emulsify natural oils in the skin, which are then washed away when the cleansing composition is rinsed off.

In order to provide high quality lather or foam, conventional skin cleansing products based on surfactant cleansers typically contain from greater than 10% to about 20% of surfactants, typically including relatively high levels of anionic surfactants. Lather is produced as a result of physical agitation, e.g. rubbing with ones hands or mechanical devises (e.g., sponges and washcloths), on the skin. The high levels of surfactants used in these products have substantial dehydration and delipidization effects on the skin. Even products that contain humectants and emollients to compensate for this typically are not completely effective at restoring the skin to its original condition. It would be desirable to provide a foaming cleansing product which could restore the skin to its original levels of hydration and lipids. It is an additional object of this invention to provide such a product. The addition of silk fibroin to foams can assist in maintaining the effectiveness of the foam yet reducing the drying or stripping properties.

Sticks and Solids

There are a range of cosmetic products known which are available on the market in stick form, such as lip sticks, deodorant sticks, personal care sticks, etc. All of these sticks have in common the fact that they are essentially developed on a wax basis in order to achieve the appropriate stability at ambient temperature.

One embodiment of this aspect and other aspects described herein, the humectant agent comprises glycerin. While glycerin (also known as glycerol) has been previously used in a silk fibroin composition (e.g., described in the International Patent Application No. WO 2010/042798, the entirety of which is incorporated herein by reference), it was mainly incorporated as a plasticizer, at a glycerin: silk weight ratio up to 1:1, to make silk materials (e.g., a silk film) more flexible. The '798 patent application does not describe a composition comprising glycerin and silk fibroin in a weight ratio greater than 1:1, or a composition comprising silk fibroin and glycerin in an amount greater than 50% (w/w) as described herein. The inventors have discovered inter alia that the gels formed from a mixture of glycerin and silk fibroin in a ratio greater than 1:1 (e.g., glycerin: silk ration=˜4:1) differ from the silk fibroin-based materials described in the '798 patent application (i.e., a silk fibroin-based material formed from the same components but with a ratio of glycerin to silk fibroin no more than 1:1). For example, unlike flexible silk fibroin films described in the '798 patent applications, the compositions described herein have a gel-consistency with silk fibroin maintained in dominant random-coil content, which likely contributes to its flowability. Accordingly, in some embodiments of this aspect and other aspects described herein, glycerin can be present in an amount of at least about 50% (w/v or w/w), at least about 60% (w/v or w/w), at least about 70% (w/v or w/w), at least about 80% (w/v or w/w), at least about 90%

(w/v or w/w) or higher (excluding 100%). In some embodiments, glycerin can be present in an amount of about 50% (w/v or w/w) to about 99% (w/v or w/w).

In some embodiments of this aspect and other aspects described herein, the silk fibroin can be present in an amount of about 1% (w/v or w/w) to about 30% (w/v or w/w), or about 1% (w/v or w/w) to about 10% (w/v or w/w).

In some embodiments of this aspect and other aspects described herein, the silk fibroin and the humectant agent can be present in any ratio, provided that the amount of the humectant agent is more than that of the silk fibroin. For example, the silk fibroin and the humectant agent can be present in a volume ratio of about 1:1.1 to about 1:100, or about 1:2 to about 1:100, or about 1:2 to about 1:10, or about 1:2 to about 1:8. Stated another way, the silk fibroin and the humectant agent can be present in a weight/mass ratio of about 1:1.1 to 1:1000, about 1:5 to about 1:750, or about 1:10 to about 1:500.

In some embodiments of this aspect and other aspects described herein, the volume or weight ratio of the silk fibroin to the humectant agent can be adjusted to yield a translucent composition. Accordingly, in some embodiments, the composition described herein can be translucent.

In some embodiments of this aspect and other aspects described herein, the volume or weight ratio of the silk fibroin to the humectant can be adjusted to yield a flowable or spreadable composition. Accordingly, in some embodiments, the composition described herein can be flowable or readily spreadable on a surface.

In some embodiments of this aspect and other aspects described herein, the volume or weight ratio of the silk fibroin to the humectant can be adjusted to yield a composition that does not shear-thicken or precipitate when exposed to shear. Accordingly, in some embodiments, the composition described herein can be resistant to shear-thickening or does not readily form precipitates or particulates when exposed to shear. In some embodiments, the composition described herein can be shear-thinning when exposed to shear. In some embodiments, the composition described herein can substantially maintain their viscosity or rheology when exposed to shear.

The compositions described herein are distinct from a composition comprising silk fibroin without a humectant agent. For example, silk fibroin protein may form a gel in the absence of a humectant, the resulting gel contains a prominent beta-sheet content, as opposed to more random coil conformation maintained in the silk fibroin-based gels comprising a humectant. Thus, in some embodiments, the composition described herein can have a larger amount of silk fibroin in random coil conformation, as compared to a composition comprising the silk fibroin in the absence of the humectant agent. For example, the amount of silk fibroin in random coil conformation can be at least about 10% or more, larger than when the humectant agent is absent.

In some embodiments, the composition described herein can have a smaller amount of silk fibroin in beta-sheet conformation, as compared to a composition comprising silk fibroin in the absence of the humectant agent. For example, the amount of silk fibroin in beta sheet conformation can be at least about 10% or more, smaller than when the humectant agent is absent.

In some embodiments, the composition described herein does not have a peak in the amide II region (e.g., between ~1475 cm-1 and ~1560 cm-1), as determined in a Fourier Transform Infrared Spectroscopy (FTIR) spectrum.

In some embodiments, the composition described herein can be used to form an aqueous-based phase, which can then be mixed with an oil-based phase or a wax-based phase to form an emulsion. The inventors have discovered that when an aqueous mixture of a humectant (e.g., glycerin) and silk fibroin was added to an oil-based solution, the silk fibroin plays a role in emulsifying the oil and aqueous phases. For example, addition of soy lecithin alone is not a sufficient emulsifier to emulsify the aqueous and oil phases. The use of hydrolyzed silk fibroin or water in place of silk fibroin resulted in phase separation, even in the presence of soy lecithin. Thus, soy lecithin alone is not sufficient to stabilize an emulsion, e.g., an oil-in-water emulsion where it contains hydrolyzed silk, but not silk fibroin. Only when silk fibroin was mixed with the aqueous and oil phases did the ingredients form a single-phase gel. Thus, in some embodiments, silk fibroin can act as an emulsifying agent in the compositions described herein and/or aid in an emulsification process, allowing aqueous and oil phases to mix and form a single-phase gel (e.g., a flowable single-phase gel). This has not been previously reported for silk fibroin, and, without wishing to be bound by theory, the ability of silk fibroin to act as an emulsifying agent can be in part due to the protein having both hydrophilic and hydrophobic regions.

Accordingly, in another aspect, an emulsion composition comprising silk fibroin is also provided herein. The emulsion composition comprises an aqueous-based phase, and an oil-based phase and/or a wax-based phase, wherein the aqueous-based phase comprises silk fibroin and a humectant agent described herein. In some embodiments, the emulsion composition can further comprise any natural or synthetic emulsifier known in the art, including, for example, liquid soy lecithin, solid soy lecithin, honey, beeswax, cetyl alcohol, or any combinations thereof.

In some embodiments, the oil-based phase can comprise a carrier oil. For example, a carrier oil can be a synthetic or natural oil derived from seeds, nuts, fruits, flowers, planti-based materials, or any combinations thereof. In some embodiments, the wax-based phase can comprise, e.g., but not limited to, butters, wax, paraffin wax, paraffin oil, petrolatum, or any combinations thereof.

While the humectant agent can be present in any appropriate amount in the aqueous-based phase, in some embodiments, the humectant agent can be present in an amount of at least about 50% (w/v or w/w), at least about 60% (w/v or w/w), at least about 70% (w/v or w/w), at least about 80% (w/v or w/w), at least about 90% (w/v or w/w) or higher (excluding 100%) of the aqueous-based phase. In some embodiments, the humectant agent can be present in an amount of about 50% (w/v or w/w) to about 99% (w/v or w/w) of the aqueous-based phase.

In some embodiments where glycerin is a selected humectant agent, glycerin can be present in an amount of at least about 50% (w/v or w/w), at least about 60% (w/v or w/w), at least about 70% (w/v or w/w), at least about 80% (w/v or w/w), at least about 90% (w/v or w/w) or higher (excluding 100%) of the aqueous-based phase. In some embodiments, glycerin can be present in an amount of about 50% (w/v or w/w) to about 99% (w/v or w/w) of the aqueous-based phase.

In some embodiments, the silk fibroin can be present in an amount of about 1% (w/v or w/w) to about 30% (w/v or w/w), or about 1% (w/v or w/w) to about 10% (w/v or w/w) of the aqueous-based phase.

In some embodiments, the silk fibroin and the humectant agent in the aqueous-based phase can be in any ratio, provided that the amount of the humectant agent is more than that of the silk fibroin. For example, in the aqueous-based phase, the silk fibroin and the humectant agent can be present in a volume ratio of about 1:1.1 to about 1:100, or about 1:2 to about 1:100, or about 1:2 to about 1:10, or about 1:2 to about 1:8. Stated another way, the silk fibroin and the humectant agent can be present in a weight/mass ratio of about 1:1.1 to 1:1000, about 1:5 to about 1:750, or about 1:10 to about 1:500 in the aqueous-based phase.

The ratio of the aqueous-based phase to the oil-based phase can vary to form different types of emulsion compositions, e.g., water-in-oil compositions or oil-in-water compositions. Accordingly, the ratio of the aqueous-based phase to the oil-based phase can vary from about 1:100 to about 100:1.

In some embodiments, the emulsion composition can comprise at least one or more additives. For example, at least one additive can be present in the aqueous-based phase. Additionally, or alternatively, the oil-based phase can comprise at least one or more additives.

Compositions of various aspects described herein are versatile and can be adapted for various applications, e.g., personal care, skin care, body care, wound healing, or any applications where a flowable or spreadable composition is desirable. Accordingly, in some embodiments, the silk fibroin-based composition and/or the emulsion composition described herein can further comprise an additive, e.g., to suit the need of an application. Examples of an additive include, but are not limited to, aqueous-soluble components, oil-soluble components, wax-soluble components, essential oils, emulsifiers, surfactants, flavors, fragrance, nutraceuticals, vitamins, therapeutic agents, cosmeceuticals, preservatives, botanical extracts or distillates, antioxidants, antibacterial agents, anti-inflammatory agents, cosmetically-acceptable agents, skin-lightening agents, skin-evening agents, anti-reddening agents, viscosity modifiers, emollients, active agents, nano- or micro-particles, photothermal elements (e.g., gold nanoparticles), wound healing-promoting agents, and any combinations thereof.

One of skill in the art can determine appropriate additives and amounts thereof based on different applications. In one embodiment, the composition can be formulated for use in a personal care product (e.g., a cosmetic, skincare, body care, or hair product). In one embodiment, the composition can be formulated for use in a food product.

In various embodiments of any aspects described herein, the composition can maintain stable (e.g., no brittle gel formation; or no precipitate formation when the composition is exposed to shear) for at least about 1 month or longer at room temperature or higher. In some embodiments, the composition can maintain stable (e.g., no brittle gel formation; or no precipitate formation when the composition is exposed to shear) for at least about 1 year or longer at room temperature or higher.

The silk fibroin-based compositions and the emulsion compositions described herein can be formulated to any form desirable for a specific application. For example, the composition can be formulated to form a gel or hydrogel, a paste, a lotion, a cream, an ointment, an oil, a liquid, a serum, a shampoo, a foam or mousse, a spray, an aerosol, a stick, a balm, a bar, a scrub, or any combinations thereof.

In some embodiments, the silk fibroin-based compositions and the emulsion compositions can be translucent. In some embodiments, the silk fibroin-based compositions and the emulsion compositions can be flowable. In some embodiments, the silk fibroin-based compositions and the emulsion compositions do not precipitate when exposed to shear.

Methods for producing one or more embodiments of a silk fibroin-based composition and/or an emulsion composition are also provided herein. Accordingly, in one aspect, compositions produced by the methods described herein are provided. In one embodiment, the composition is formulated for use in a personal care product (e.g., a cosmetic, skincare, body care, or hair product). In another embodiment, the composition is formulated for use in a food product.

The method of producing a silk fibroin-based composition and/or an emulsion composition described herein comprises mixing a silk fibroin solution and a humectant agent in a volume ratio of about 1:2 to about 1:100. In some embodiments, the volume ratio of the silk fibroin solution to the humectant agent can be about 1:2 to about 1:10. The humectant agent can be powder, a liquid, a solution, or a suspension. Where the humectant agent is powder, the d silk fibroin solution and the humectant agent can be mixed in a weight or mass ratio of about 1:1.1 to about 1:1000, about 1:5 to about 1:750, or about 1:10 to about 1:500.

The rate and/or degree of gelation can be controlled by varying the volume or weight/mass ratio of a silk fibroin solution to a humectant agent. By way of example only, when the volume ratio of the silk fibroin solution to glycerin (an example of a humectant agent) is about 1:4, a gel can be formed within seconds, whereas a ratio of 1:8 can form a gel within about 15 minutes. In addition, the 1:4 silk: glycerin formulations can have a more viscous texture, as compared to 1:8 silk: glycerin formulations.

Any desirable concentration of the silk fibroin solution can be used to produce a composition of various aspects described herein. In some embodiments, the silk fibroin solution can have a concentration of about 1% (w/v or w/w) to about 30% (w/v or w/w). In some embodiments, the silk fibroin solution can have a concentration of about 1% (w/v or w/w) to about 10% (w/v or w/w).

In some embodiments where the silk fibroin solution has a concentration of about 7% (w/v), it can be desirable to maintain the volume ratio of the silk fibroin solution to glycerin at about 1:4 to about 1:8. The inventors have discovered that silk fibroin maintains a random coil configuration at these ratios. If the amount of glycerin is too high relative to the silk fibroin solution (e.g., a silk: glycerin ratio of about 1:10), the mixture of the silk fibroin solution and glycerin does not appear to form a gel. However, if the amount of glycerin is too low relative to the silk fibroin solution (e.g., a silk: glycerin ratio of about 1:2), the relatively-high concentration of the silk fibroin solution can allow formation of beta sheet structures in small regions within the solution, resulting in precipitation of the protein, especially when exposed to shear forces (such as those produced by rubbing the composition on a skin surface).

In some embodiments, the method can further comprise mixing at least one or more additive with the humectant agent and the silk fibroin solution. In some embodiments, the aqueous soluble additive can be mixed with the humectant agent prior to mixing with the silk fibroin solution. In some embodiments, the additive mixed with the humectant agent and/or the silk fibroin solution can be aqueous-soluble.

In some embodiments, the method can further comprise mixing the mixture comprising the silk fibroin solution and the humectant agent with an oil-based phase described herein, for example, to form an emulsion. In some embodiments, the oil-based phase can further comprise a carrier oil and optionally any art-recognized emulsifier. Any carrier oils known in the art, e.g., for use in formulating personal care products, skin care products, body care products, hair products, and/or aromatherapy products, can be used herein. Examples of carrier oils include, without limitations, a synthetic or natural oil derived from seeds, nuts, fruits, flowers, planti-based materials, or any combinations thereof. An appropriate ratio of the carrier oil to the emulsifier can be readily determined by a skilled artisan for different emulsion compositions forms. By way of example only, the volume ratio of the carrier oil to the emulsifier can range from about 2:1 to about 100:1. In some embodiments, the oil-based phase can further comprise an additive described herein.

Yet another aspect provides a method using any compositions of various aspects described herein. The method comprises applying on a target surface one or more embodiments of silk fibroin-based compositions and/or emulsion compositions described herein. The compositions described herein can be applied to a target surface by any means known in the art, e.g., rubbing, spreading, gliding, painting, spraying, extruding, massaging, brushing, smoothing, rolling, or any combinations thereof, depending on the format of the compositions described herein.

By way of example only, when the compositions described herein is flowable or spreadable (e.g., in a form of a serum, a lotion, or a cream), the compositions can be applied on a target surface, e.g., by rubbing, spreading, massaging, smoothing, or any combinations thereof. In other embodiments where the composition and/or emulsion compositions is a solid, e.g., balm, or a stick, the compositions and/or emulsion compositions described herein can be applied by rubbing, rolling, gliding, or any combinations thereof.

Any target surface can be amenable to the application of the compositions described herein. In some embodiments, the target surface can be skin or hair of a subject. In some embodiments, the target surface can be a wound. In some embodiments, the target surface can be a surface of food, for example, where the composition can be used as an edible food-decorating material, e.g., in a form of ink, gel, or paste.

In some embodiments, the method can further comprise maintaining the composition at room temperature for at least about 1 month or longer, wherein the composition remains stable thereafter.

Formulations

In some embodiments, SBPs may be formulations. As used herein, the term "formulation" refers to a mixture of two or more components or the process of preparing such mixtures. In some embodiments, the formulations are low cost and eco-friendly. In some embodiments, the preparation or manufacturing of formulations is low cost and eco-friendly. In some embodiments, the preparation or manufacturing of formulations is scalable. In some embodiments, SBPs are prepared by extracting silk fibroin via degumming silk yarn. In some embodiments, the yarn is medical grade. In some embodiments the yarn may be silk sutures. The extracted silk fibroin may then be dissolved in a solvent (e.g. water, aqueous solution, organic solvent). The dissolved silk fibroin may then be dried (e.g., oven dried, air dried, or freeze-dried). In some embodiments, dried silk fibroin is formed into formats described herein. In some embodiments, that format is a solution. In some embodiments, that format is a hydrogel. In some embodiments, formulations include one or more excipients, carriers, additional components, and/or therapeutic agents to generate SBPs. In some embodiments, formulations of processed silk are prepared during the manufacture of SBPs. In some embodiments, the silk is graded from 3-6, wherein the higher graded silk denotes higher quality silk. Grades of silk may vary in several properties, including, but not limited to, color, number of knots, lustrousness, and cleanliness. In some embodiments, the silk is grade 3 (grade AAA). In some embodiments, the silk is grade 4 (grade AAAA). In some embodiments, the silk is grade 5 (grade AAAAA). In some embodiments, the silk is grade 6 (grade AAAAAA). Formulations, preparations, and SBPs of the present disclosure may use silk of any grade. In some embodiments, properties of SBPs and ocular SBPs may not be affected or altered by the grade of silk (e.g. clarity, solubility, rheology, viscosity, hydrogel formation, and SEC results). In some embodiments, properties of SBPs and ocular SBPs may be affected or altered by the grade of silk (e.g. clarity, solubility, rheology, viscosity, hydrogel formation, and SEC results).

Formulation components and/or component ratios may be modulated to affect one or more SBP properties, effects, and/or applications. Variations in the concentration of silk fibroin, choice of excipient, the concentration of excipient, the osmolarity of the formulation, and the method of formulation represent non-limiting examples of differences in formulation that may alter properties, effects, and applications of SBPs. In some embodiments, the formulation of SBPs may modulate their mechanical properties. Examples of mechanical properties that may be modulated include, but are not limited to, mechanical strength, tensile strength, elongation capabilities, elasticity, compressive strength, stiffness, shear strength, toughness, torsional stability, temperature stability, moisture stability, viscosity, and reeling rate.

Cargo

In some embodiments, SBPs and SBP formulations are or include cargo. As used herein, the term "cargo" refers to any substance that is embedded in, enclosed within, attached to, or otherwise associated with a carrier. SBP formulations may be carriers for a large variety of cargo. Such cargo may include, but are not limited to, compounds, compositions, therapeutic agents, biological agents, materials, cosmetics, devices, agricultural compositions, particles, lipids, liposomes, sweeteners, colorants, preservatives, carbohydrates, small molecules, supplements, tranquilizers, ions, metals, minerals, nutrients, pesticides, herbicides, fungicides, and cosmetics.

In some embodiments, the cargo is or includes a payload. As used herein, the term "payload" refers to cargo that is delivered from a source or carrier to a target. Payloads may be released from SBP formulations, where SBP formulations serve as a carrier. Where SBPs are the payload, the SBPs may be released from a source or carrier. In some embodiments, payloads remain associated with carriers upon delivery. Payloads may be released in bulk or may be released over a period of time, also referred to herein as the "delivery period." In some embodiments, payload release is by way of controlled release. As used herein, the term "controlled release" refers to distribution of a substance from a source or carrier to a surrounding area, wherein the distribution occurs in a manner that includes or is affected by some manipulation, some property of the carrier, or some carrier activity.

In some embodiments, controlled release may include a steady rate of release of payload from carrier. In some embodiments, payload release may include an initial burst, wherein a substantial amount of payload is released during an initial release period followed by a period where less payload is released. As used herein, the term "initial burst" refers to a rate of payload release from a source or depot over an initial release period (e.g., after administration or other placement, for example in solution during experimental analysis) that is higher than rates during one or more subsequent release periods. In some embodiments, release rate slows over time. Payload release may be measured by assessing payload concentration in a surrounding area and comparing to initial payload concentration or remaining payload concentration in a carrier or source area. Payload release rate may be expressed as a quantity or mass of payload released over time (e.g., mg/min). Payload release rate may be expressed as a percentage of payload released from a source or carrier over a period of time (e.g., 5%/hour). Controlled release of a payload that extends the delivery period is referred to herein as "sustained release." Sustained release may include delivery periods that are extended over a period of hours, days, months, or years.

Some controlled release may be mediated by interactions between payload and carrier. Some controlled release is mediated by interactions between payload or carrier with surrounding areas where payload is released. With sustained payload release, payload release may be slowed or prolonged due to interactions between payload and carrier or payload and surrounding areas where payload is released. Payload release from SBPs may be controlled by SBP viscosity. Where the SBP includes processed silk gel, gel viscosity may be adjusted to modulate payload release.

In some embodiments, payload delivery periods may be from about 1 second to about 20 seconds, from about 10 seconds to about 1 minute, from about 30 seconds to about 10 minutes, from about 2 minutes to about 20 minutes, from about 5 minutes to about 30 minutes, from about 15 minutes to about 1 hour, from about 45 minutes to about 2 hours, from about 90 minutes to about 5 hours, from about 3 hours to about 20 hours, from about 10 hours to about 50 hours, from about 24 hours to about 100 hours, from about 48 hours to about 2 weeks, from about 72 hours to about 4 weeks, from about 1 week to about 3 months, from about 1 month to about 6 months, from about 3 months to about 1 year, from about 9 months to about 2 years, or more than 2 years.

In some embodiments, payload release may be consistent with near zero-order kinetics. In some embodiments, payload release may be consistent with first-order kinetics. In some embodiments, payload release may be modulated based on the density, loading, molecular weight, and/or concentration of the payload. Where the carrier is an SBP, payload release may be modulated by one or more of SBP drying method, silk fibroin molecular weight, and silk fibroin concentration.

In some embodiments, SBP formulations maintain and/or improve cargo stability, purity, and/or integrity. For example, SBP formulations may be used to protect therapeutic agents or macromolecules during lyophilization. The maintenance and/or improvement of stability during lyophilization may be determined by comparing SBP cargo stability to formulations lacking processed silk or to standard formulations in the art.

Viscosity

In some embodiments, SBPs may be formulated to modulate SBP viscosity. The viscosity of a composition (e.g., a solution, a gel or hydrogel) provided herein can be determined using a rotational viscometer or rheometer. Additional methods for determining the viscosity of a composition and other rheological properties may include any of those known in the art. In some embodiments, the SBP viscosity may be controlled via the concentration of processed silk. In some embodiments, the SBP viscosity may be controlled via the molecular weight of processed silk. In some embodiments, the SBP viscosity may be controlled via the boiling time or mb of the processed silk. In some embodiments, the SBP viscosity may be altered by the incorporation of stressed silk. In some embodiments, SBP viscosity is altered by the incorporation of an excipient. In some embodiments, SBP viscosity may be altered by the incorporation of an excipient that is a gelling agent. In some embodiments, the identity of the excipient (e.g., PEG or poloxamer) may be altered to modulate SBP viscosity. In some embodiments, the viscosity of SBPs may be tuned for the desired application (e.g., drug delivery system, surgical implant, lubricant, etc.). In some embodiments, the viscosity of SBPs is tunable between 1-1000 centipoise (cP). In some embodiments, the viscosity of an SBP is tunable from about 0.0001 to about 1000 Pascal seconds (Pa*s). In some embodiments, the viscosity of an SBP is from about 1 cP to about 10 cP, from about 2 cP to about 20 cP, from about 3 cP to about 30 cP, from about 4 cP to about 40 cP, from about 5 cP to about 50 cP, from about 6 cP to about 60 cP, from about 7 cP to about 70 cP, from about 8 cP to about 80 cP, from about 9 cP to about 90 cP, from about 10 cP to about 100 cP, from about 100 cP to about 150 cP, from about 150 cP to about 200 cP, from about 200 cP to about 250 cP, from about 250 cP to about 300 cP, from about 300 cP to about 350 cP, from about 350 cP to about 400 cP, from about 400 cP to about 450 cP, from about 450 cP to about 500 cP, from about 500 cP to about 600 cP, from about 550 cP to about 700 cP, from about 600 cP to about 800 cP, from about 650 cP to about 900 cP, or from about 700 cP to about 1000 cP. In some embodiments, the viscosity of an SBP is from about 0.0001 Pa*s to about 0.001 Pa*s, from about 0.001 Pa*s to about 0.01 Pa*s, from about 0.01 Pa*s to about 0.1 Pa*s, from about 0.1 Pa*s to about 1 Pa*s, from about 1 Pa*s to about 10 Pa*s, from about 2 Pa*s to about 20 Pa*s, from about 3 Pa*s to about 30 Pa*s, from about 4 Pa*s to about 40 Pa*s, from about 5 Pa*s to about 50 Pa*s, from about 6 Pa*s to about 60 Pa*s, from about 7 Pa*s to about 70 Pa*s, from about 8 Pa*s to about 80 Pa*s, from about 9 Pa*s to about 90 Pa*s, from about 10 Pa*s to about 100 Pa*s, from about 100 Pa*s to about 150 Pa*s, from about 150 Pa*s to about 200 Pa*s, from about 200 Pa*s to about 250 Pa*s, from about 250 Pa*s to about 300 Pa*s, from about 300 Pa*s to about 350 Pa*s, from about 350 Pa*s to about 400 Pa*s, from about 400 Pa*s to about 450 Pa*s, from about 450 Pa*s to about 500 Pa*s, from about 500 Pa*s to about 600 Pa*s, from about 550 Pa*s to about 700 Pas, from about 600 Pa*s to about 800 Pa*s, from about 650 Pa*s to about 900 Pa*s, or from about 700 Pa*s to about 1000 Pa*s.

Interfacial Viscosity

In some embodiments, silk fibroin may preferentially partition to the air-water interface when in solution. Similar to a surfactant, hydrophobic regions of hydrophobic proteins (e.g. silk fibroin) may exclude themselves from solution. The protein may migrate to the air-water boundary, resulting in an increase in the local concentration at this interface. This increase in the local concentration of a high molecular weight, hydrophobic protein may lead to an increase in local viscosity, as described in Sharma et al. (2011) Soft Matter 7 (11): 5150-5160 and in Jaishankar et al. (2011) Soft Matter 7:7623-7634, the contents of each of which are herein incorporated by reference in their entirety. This effect is termed "interfacial viscosity". In some embodiments, processed silk may demonstrate the effects of interfacial viscosity. In some embodiments, the interfacial viscosity is independent of the concentration of processed silk. As long as there is sufficient protein in solution to create a film at the air-water interface, the viscosity of this film will increase to a similar effect.

This phenomenon may be observed with the use of a rotational rheometer fit with a cone and plate configuration. This setup allows for an air-water interface located at the edges of the cone and plate. If protein migrates and leads to local concentration build-up at the edges of the plate, increasing shear viscosity will be observed due the increased local viscosity on the torque of the rotating cone spindle. Viscosity may increase with decreasing shear rate, as the decreasing shear allows for more efficient stacking of proteins, increased protein concentration, and more stable film of protein at the air-water interface.

Incorporation of a surfactant, a molecule that can better and more efficiently associate to the air-water interface, may block the hydrophobic protein association and may negate increase in viscosity due to the protein buildup at the boundary. When a competing surfactant is added to the formulations, preventing the silk fibroin from partitioning this interface, the viscosity may be reduced; formulations may have shear viscosity properties similar to controls (without silk fibroin).

In some embodiments, the viscosity of an SBP as measured by a rotational rheometer fit with a cone and plate configuration may be the interfacial viscosity. Unlike the rotational rheometer, a capillary rheometer has a very low air-water interface. This may greatly reduce if not eliminate interfacial viscosity effects that are observed using other rheologic methods (cone and plate rotational rheology). In some embodiments, the viscosity of an SBP may be measured by a capillary rheometer to measure the viscosity without measuring the interfacial viscosity. In some embodiments, the viscosity of an SBP may be measured with a surfactant incorporated to negate the effects of interfacial viscosity.

Stress Resistance

In some embodiments, SBPs may be formulated to modulate SBP resistance to stress. Resistance to stress may be measured using one or more rheological measurements. Such measurements may include, but are not limited to tensile elasticity, shear or rigidity, volumetric elasticity, and compression. Additional rheological measurements and properties may include any of those taught in Zhang et al. (2017) Fiber and Polymers 18 (10): 1831-1840; McGill et al. (2017) Acta Biomaterialia 63:76-84; and Choi et al. (2015) In-Situ Gelling Polymers, Series in BioEngineering doi. 10.1007/978-981-287-152-7_2, the contents of each of which are herein incorporated by reference in their entirety. In some embodiments, stress resistance may be modulated through incorporation of excipients (e.g., PEG or poloxamer). In some embodiments, SBP stress-resistance properties may be modulated to suit a specific application (e.g., lubricant, etc.).

Concentrations and Ratios of SBP Components

SBPs may include formulations of processed silk with other components (e.g., excipients and cargo), wherein each SBP component is present at a specific concentration, ratio, or range of concentrations or ratios, depending on SBP format and/or application. In some embodiments, the concentration of processed silk (e.g. silk fibroin) or other SBP component (e.g., excipient or cargo) is present in SBPs and SBP formulations at a concentration of from about 0.0001% (w/v) to about 0.001% (w/v), from about 0.001% (w/v) to about 0.01% (w/v), from about 0.01% (w/v) to about 1% (w/v), from about 0.05% (w/v) to about 2% (w/v), from about 1% (w/v) to about 5% (w/v), from about 2% (w/v) to about 10% (w/v), from about 4% (w/v) to about 16% (w/v), from about 5% (w/v) to about 20% (w/v), from about 8% (w/v) to about 24% (w/v), from about 10% (w/v) to about 30% (w/v), from about 12% (w/v) to about 32% (w/v), from about 14% (w/v) to about 34% (w/v), from about 16% (w/v) to about 36% (w/v), from about 18% (w/v) to about 38% (w/v), from about 20% (w/v) to about 40% (w/v), from about 22% (w/v) to about 42% (w/v), from about 24% (w/v) to about 44% (w/v), from about 26% (w/v) to about 46% (w/v), from about 28% (w/v) to about 48% (w/v), from about 30% (w/v) to about 50% (w/v), from about 35% (w/v) to about 55% (w/v), from about 40% (w/v) to about 60% (w/v), from about 45% (w/v) to about 65% (w/v), from about 50% (w/v) to about 70% (w/v), from about 55% (w/v) to about 75% (w/v), from about 60% (w/v) to about 80% (w/v), from about 65% (w/v) to about 85% (w/v), from about 70% (w/v) to about 90% (w/v), from about 75% (w/v) to about 95% (w/v), from about 80% (w/v) to about 96% (w/v), from about 85% (w/v) to about 97% (w/v), from about 90% (w/v) to about 98% (w/v), from about 95% (w/v) to about 99% (w/v), from about 96% (w/v) to about 99.2% (w/v), from about 97% (w/v) to about 99.5% (w/v), from about 98% (w/v) to about 99.8% (w/v), from about 99% (w/v) to about 99.9% (w/v), or greater than 99.9% (w/v).

In some embodiments, the concentration of processed silk (e.g. silk fibroin) or other SBP component (e.g., excipient or cargo) may be present in SBPs or SBP formulations at a concentration of from about 0.0001% (v/v) to about 0.001% (v/v), from about 0.001% (v/v) to about 0.01% (v/v), from about 0.01% (v/v) to about 1% (v/v), from about 0.05% (v/v) to about 2% (v/v), from about 1% (v/v) to about 5% (v/v), from about 2% (v/v) to about 10% (v/v), from about 4% (v/v) to about 16% (v/v), from about 5% (v/v) to about 20% (v/v), from about 8% (v/v) to about 24% (v/v), from about 10% (v/v) to about 30% (v/v), from about 12% (v/v) to about 32% (v/v), from about 14% (v/v) to about 34% (v/v), from about 16% (v/v) to about 36% (v/v), from about 18% (v/v) to about 38% (v/v), from about 20% (v/v) to about 40% (v/v), from about 22% (v/v) to about 42% (v/v), from about 24% (v/v) to about 44% (v/v), from about 26% (v/v) to about 46% (v/v), from about 28% (v/v) to about 48% (v/v), from about 30% (v/v) to about 50% (v/v), from about 35% (v/v) to about 55% (v/v), from about 40% (v/v) to about 60% (v/v), from about 45% (v/v) to about 65% (v/v), from about 50% (v/v) to about 70% (v/v), from about 55% (v/v) to about 75% (v/v), from about 60% (v/v) to about 80% (v/v), from about 65% (v/v) to about 85% (v/v), from about 70% (v/v) to about 90% (v/v), from about 75% (v/v) to about 95% (v/v), from about 80% (v/v) to about 96% (v/v), from about 85% (v/v) to about 97% (v/v), from about 90% (v/v) to about 98% (v/v), from about 95% (v/v) to about 99% (v/v), from about 96% (v/v) to about 99.2% (v/v), from about 97% (v/v) to about 99.5% (v/v), from about 98% (v/v) to about 99.8% (v/v), from about 99% (v/v) to about 99.9% (v/v), or greater than 99.9% (v/v).

In some embodiments, the concentration of processed silk (e.g. silk fibroin) or other SBP component (e.g., excipient or cargo) may be present in SBPs and SBP formulations at a concentration of from about 0.0001% (w/w) to about 0.001% (w/w), from about 0.001% (w/w) to about 0.01% (w/w), from about 0.01% (w/w) to about 1% (w/w), from about 0.05% (w/w) to about 2% (w/w), from about 1% (w/w) to about 5% (w/w), from about 2% (w/w) to about 10% (w/w), from about 4% (w/w) to about 16% (w/w), from about 5% (w/w) to about 20% (w/w), from about 8% (w/w) to about 24% (w/w), from about 10% (w/w) to about 30% (w/w), from about 12% (w/w) to about 32% (w/w), from about 14% (w/w) to about 34% (w/w), from about 16% (w/w) to about 36% (w/w), from about 18% (w/w) to about 38% (w/w), from about 20% (w/w) to about 40% (w/w), from about 22% (w/w) to about 42% (w/w), from about 24% (w/w) to about 44% (w/w), from about 26% (w/w) to about 46% (w/w), from about 28% (w/w) to about 48% (w/w), from about 30% (w/w) to about 50% (w/w), from about 35%

(w/w) to about 55% (w/w), from about 40% (w/w) to about 60% (w/w), from about 45% (w/w) to about 65% (w/w), from about 50% (w/w) to about 70% (w/w), from about 55% (w/w) to about 75% (w/w), from about 60% (w/w) to about 80% (w/w), from about 65% (w/w) to about 85% (w/w), from about 70% (w/w) to about 90% (w/w), from about 75% (w/w) to about 95% (w/w), from about 80% (w/w) to about 96% (w/w), from about 85% (w/w) to about 97% (w/w), from about 90% (w/w) to about 98% (w/w), from about 95% (w/w) to about 99% (w/w), from about 96% (w/w) to about 99.2% (w/w), from about 97% (w/w) to about 99.5% (w/w), from about 98% (w/w) to about 99.8% (w/w), from about 99% (w/w) to about 99.9% (w/w), or greater than 99.9% (w/w).

In one embodiment, the concentration of processed silk or other SBP component (e.g., excipient or cargo) is present in SBPs and SBP formulations at a concentration of 1% (w/v).

In one embodiment, the concentration of processed silk or other SBP component (e.g., excipient or cargo) is present in SBPs at a concentration of 2% (w/v).

In one embodiment, the concentration of processed silk or other SBP component (e.g., excipient or cargo) is present in SBPs at a concentration of 3% (w/v).

In one embodiment, the concentration of processed silk or other SBP component (e.g., excipient or cargo) is present in SBPs at a concentration of 4% (w/v).

In one embodiment, the concentration of processed silk or other SBP component (e.g., excipient or cargo) is present in SBPs at a concentration of 5% (w/v).

In one embodiment, the concentration of processed silk or other SBP component (e.g., excipient or cargo) is present in SBPs at a concentration of 6% (w/v).

In one embodiment, the concentration of processed silk or other SBP component (e.g., excipient or cargo) is present in SBPs at a concentration of 10% (w/v).

In one embodiment, the concentration of processed silk or other SBP component (e.g., excipient or cargo) is present in SBPs at a concentration of 20% (w/v).

In one embodiment, the concentration of processed silk or other SBP component (e.g., excipient or cargo) is present in SBPs at a concentration of 30% (w/v).

In one embodiment, the concentration of processed silk or other SBP component (e.g., excipient or cargo) is present in SBPs at a concentration of 16.7% (w/w).

In one embodiment, the concentration of processed silk or other SBP component (e.g., excipient or cargo) is present in SBPs at a concentration of 20% (w/w).

In one embodiment, the concentration of processed silk or other SBP component (e.g., excipient or cargo) is present in SBPs at a concentration of 23% (w/w).

In one embodiment, the concentration of processed silk or other SBP component (e.g., excipient or cargo) is present in SBPs at a concentration of 25% (w/w).

In one embodiment, the concentration of processed silk or other SBP component (e.g., excipient or cargo) is present in SBPs at a concentration of 27.3% (w/w).

In one embodiment, the concentration of processed silk or other SBP component (e.g., excipient or cargo) is present in SBPs at a concentration of 28.6% (w/w).

In one embodiment, the concentration of processed silk or other SBP component (e.g., excipient or cargo) is present in SBPs at a concentration of 33.3% (w/w).

In one embodiment, the concentration of processed silk or other SBP component (e.g., excipient or cargo) is present in SBPs at a concentration of 40% (w/w).

In one embodiment, the concentration of processed silk or other SBP component (e.g., excipient or cargo) is present in SBPs at a concentration of 50% (w/w).

In some embodiments, the concentration of processed silk (e.g., silk fibroin) or other SBP component (e.g., excipient or cargo) may be present in SBPs and SBP formulations at a concentration of from about 0.01 pg/mL to about 1 pg/mL, from about 0.05 pg/mL to about 2 pg/mL, from about 1 pg/mL to about 5 pg/mL, from about 2 pg/mL to about 10 pg/mL, from about 4 pg/mL to about 16 pg/mL, from about 5 pg/mL to about 20 pg/mL, from about 8 pg/mL to about 24 pg/mL, from about 10 pg/mL to about 30 pg/mL, from about 12 pg/mL to about 32 pg/mL, from about 14 pg/mL to about 34 pg/mL, from about 16 pg/mL to about 36 pg/mL, from about 18 pg/mL to about 38 pg/mL, from about 20 pg/mL to about 40 pg/mL, from about 22 pg/mL to about 42 pg/mL, from about 24 pg/mL to about 44 pg/mL, from about 26 pg/mL to about 46 pg/mL, from about 28 pg/mL to about 48 pg/mL, from about 30 pg/mL to about 50 pg/mL, from about 35 pg/mL to about 55 pg/mL, from about 40 pg/mL to about 60 pg/mL, from about 45 pg/mL to about 65 pg/mL, from about 50 pg/mL to about 75 pg/mL, from about 60 pg/mL to about 240 pg/mL, from about 70 pg/mL to about 350 pg/mL, from about 80 pg/mL to about 400 pg/mL, from about 90 pg/mL to about 450 pg/mL, from about 100 pg/mL to about 500 pg/mL, from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 μg/mL to about 1 g/mL, from about 0.05 μg/mL to about 2 μg/mL, from about 1 μg/mL to about 5 μg/mL, from about 2 μg/mL to about 10 μg/mL, from about 4 μg/mL to about 16 μg/mL, from about 5 μg/mL to about 20 g/mL, from about 8 μg/mL to about 24 μg/mL, from about 10 μg/mL to about 30 μg/mL, from about 12 μg/mL to about 32 μg/mL, from about 14 jug/mL to about 34 μg/mL, from about 16 μg/mL to about 36 μg/mL, from about 18 μg/mL to about 38 μg/mL, from about 20 μg/mL to about 40 μg/mL, from about 22 μg/mL to about 42 μg/mL, from about 24 μg/mL to about 44 μg/mL, from about 26 μg/mL to about 46 μg/mL, from about 28 μg/mL to about 48 μg/mL, from about 30 μg/mL to about 50 μg/mL, from about 35 μg/mL to about 55 μg/mL, from about 40 μg/mL to about 60 μg/mL, from about 45 μg/mL to about 65 μg/mL, from about 50 μg/mL to about 75 μg/mL, from about 60 μg/mL to about 240 μg/mL, from about 70 g/mL to about 350 μg/mL, from about 80 μg/mL to about 400 g/mL, from about 90 μg/mL to about 450 μg/mL, from about 100 μg/mL to about 500 μg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 1 g/mL to about 5 g/mL, from about 2 g/mL to about 10 g/mL, from about 4 g/mL to about 16 g/mL, or from about 5 g/mL to about 20 g/mL.

In one embodiment, the concentration of processed silk (e.g., silk fibroin) or other SBP component (e.g., excipient or cargo) is present in SBPs at a concentration of 5 mg/mL.

In one embodiment, the concentration of processed silk (e.g., silk fibroin) or other SBP component (e.g., excipient or cargo) is present in SBPs at a concentration of 2.5 mg/mL.

In one embodiment, the concentration of processed silk (e.g., silk fibroin) or other SBP component (e.g., excipient or cargo) is present in SBPs at a concentration of 1.25 mg/mL.

In one embodiment, the concentration of processed silk (e.g., silk fibroin) or other SBP component (e.g., excipient or cargo) is present in SBPs at a concentration of 0.625 mg/mL.

In one embodiment, the concentration of processed silk (e.g., silk fibroin) or other SBP component (e.g., excipient or cargo) is present in SBPs at a concentration of 0.3125 mg/mL.

In some embodiments, the concentration of processed silk (e.g., silk fibroin) or other SBP component (e.g., excipient or cargo) is present in SBPs and SBP formulations at a concentration of from about 0.01 pg/kg to about 1 pg/kg, from about 0.05 pg/kg to about 2 pg/kg, from about 1 pg/kg to about 5 pg/kg, from about 2 pg/kg to about 10 pg/kg, from about 4 pg/kg to about 16 pg/kg, from about 5 pg/kg to about 20 pg/kg, from about 8 pg/kg to about 24 pg/kg, from about 10 pg/kg to about 30 pg/kg, from about 12 pg/kg to about 32 pg/kg, from about 14 pg/kg to about 34 pg/kg, from about 16 pg/kg to about 36 pg/kg, from about 18 pg/kg to about 38 pg/kg, from about 20 pg/kg to about 40 pg/kg, from about 22 pg/kg to about 42 pg/kg, from about 24 pg/kg to about 44 pg/kg, from about 26 pg/kg to about 46 pg/kg, from about 28 pg/kg to about 48 pg/kg, from about 30 pg/kg to about 50 pg/kg, from about 35 pg/kg to about 55 pg/kg, from about 40 pg/kg to about 60 pg/kg, from about 45 pg/kg to about 65 pg/kg, from about 50 pg/kg to about 75 pg/kg, from about 60 pg/kg to about 240 pg/kg, from about 70 pg/kg to about 350 pg/kg, from about 80 pg/kg to about 400 pg/kg, from about 90 pg/kg to about 450 pg/kg, from about 100 pg/kg to about 500 pg/kg, from about 0.01 ng/kg to about 1 ng/kg, from about 0.05 ng/kg to about 2 ng/kg, from about 1 ng/kg to about 5 ng/kg, from about 2 ng/kg to about 10 ng/kg, from about 4 ng/kg to about 16 ng/kg, from about 5 ng/kg to about 20 ng/kg, from about 8 ng/kg to about 24 ng/kg, from about 10 ng/kg to about 30 ng/kg, from about 12 ng/kg to about 32 ng/kg, from about 14 ng/kg to about 34 ng/kg, from about 16 ng/kg to about 36 ng/kg, from about 18 ng/kg to about 38 ng/kg, from about 20 ng/kg to about 40 ng/kg, from about 22 ng/kg to about 42 ng/kg, from about 24 ng/kg to about 44 ng/kg, from about 26 ng/kg to about 46 ng/kg, from about 28 ng/kg to about 48 ng/kg, from about 30 ng/kg to about 50 ng/kg, from about 35 ng/kg to about 55 ng/kg, from about 40 ng/kg to about 60 ng/kg, from about 45 ng/kg to about 65 ng/kg, from about 50 ng/kg to about 75 ng/kg, from about 60 ng/kg to about 240 ng/kg, from about 70 ng/kg to about 350 ng/kg, from about 80 ng/kg to about 400 ng/kg, from about 90 ng/kg to about 450 ng/kg, from about 100 ng/kg to about 500 ng/kg, from about 0.01 μg/kg to about 1 μg/kg, from about 0.05 μg/kg to about 2 μg/kg, from about 1 μg/kg to about 5 μg/kg, from about 2 μg/kg to about 10 μg/kg, from about 4 μg/kg to about 16 μg/kg, from about 5 μg/kg to about 20 μg/kg, from about 8 μg/kg to about 24 μg/kg, from about 10 μg/kg to about 30 μg/kg, from about 12 μg/kg to about 32 μg/kg, from about 14 μg/kg to about 34 μg/kg, from about 16 μg/kg to about 36 μg/kg, from about 18 μg/kg to about 38 μg/kg, from about 20 μg/kg to about 40 μg/kg, from about 22 μg/kg to about 42 μg/kg, from about 24 μg/kg to about 44 μg/kg, from about 26 μg/kg to about 46 μg/kg, from about 28 μg/kg to about 48 μg/kg, from about 30 μg/kg to about 50 μg/kg, from about 35 μg/kg to about 55 μg/kg, from about 40 μg/kg to about 60 μg/kg, from about 45 μg/kg to about 65 μg/kg, from about 50 μg/kg to about 75 μg/kg, from about 60 μg/kg to about 240 μg/kg, from about 70 μg/kg to about 350 μg/kg, from about 80 μg/kg to about 400 μg/kg, from about 90 μg/kg to about 450 μg/kg, from about 100 μg/kg to about 500 μg/kg, from about 0.01 mg/kg to about 1 mg/kg, from about 0.05 mg/kg to about 2 mg/kg, from about 1 mg/kg to about 5 mg/kg, from about 2 mg/kg to about 10 mg/kg, from about 4 mg/kg to about 16 mg/kg, from about 5 mg/kg to about 20 mg/kg, from about 8 mg/kg to about 24 mg/kg, from about 10 mg/kg to about 30 mg/kg, from about 12 mg/kg to about 32 mg/kg, from about 14 mg/kg to about 34 mg/kg, from about 16 mg/kg to about 36 mg/kg, from about 18 mg/kg to about 38 mg/kg, from about 20 mg/kg to about 40 mg/kg, from about 22 mg/kg to about 42 mg/kg, from about 24 mg/kg to about 44 mg/kg, from about 26 mg/kg to about 46 mg/kg, from about 28 mg/kg to about 48 mg/kg, from about 30 mg/kg to about 50 mg/kg, from about 35 mg/kg to about 55 mg/kg, from about 40 mg/kg to about 60 mg/kg, from about 45 mg/kg to about 65 mg/kg, from about 50 mg/kg to about 75 mg/kg, from about 60 mg/kg to about 240 mg/kg, from about 70 mg/kg to about 350 mg/kg, from about 80 mg/kg to about 400 mg/kg, from about 90 mg/kg to about 450 mg/kg, from about 100 mg/kg to about 500 mg/kg, from about 0.01 g/kg to about 1 g/kg, from about 0.05 g/kg to about 2 g/kg, from about 1 g/kg to about 5 g/kg, from about 2 g/kg to about 10 g/kg, from about 4 g/kg to about 16 g/kg, or from about 5 g/kg to about 20 g/kg, from about 10 g/kg to about 50 g/kg, from about 15 g/kg to about 100 g/kg, from about 20 g/kg to about 150 g/kg, from about 25 g/kg to about 200 g/kg, from about 30 g/kg to about 250 g/kg, from about 35 g/kg to about 300 g/kg, from about 40 g/kg to about 350 g/kg, from about 45 g/kg to about 400 g/kg, from about 50 g/kg to about 450 g/kg, from about 55 g/kg to about 500 g/kg, from about 60 g/kg to about 550 g/kg, from about 65 g/kg to about 600 g/kg, from about 70 g/kg to about 650 g/kg, from about 75 g/kg to about 700 g/kg, from about 80 g/kg to about 750 g/kg, from about 85 g/kg to about 800 g/kg, from about 90 g/kg to about 850 g/kg, from about 95 g/kg to about 900 g/kg, from about 100 g/kg to about 950 g/kg, or from about 200 g/kg to about 1000 g/kg.

Appearance: Transparent, Opaque, Translucent

In some embodiments, the appearance of SBPs described in the present disclosure may be tuned for the application for which they were designed. In some embodiments, SBPs may be transparent. In some embodiments, SBPs may be translucent. In some embodiments, SBPs may be opaque. In some embodiments, SBP preparation methods may be used to modulate clarity, as taught in International Patent Application Publication No. WO2012170655, the contents of which are herein incorporated by reference in their entirety. In some embodiments, the incorporation of excipients may be used to tune the clarity of processed silk preparations. In some embodiments, the excipient is sucrose. In some embodiments, the sucrose may also increase protein reconstitution during lyophilization. In some embodiments, sucrose may improve processed silk hydrogel clarity (optical transparency).

The optical clarity of an SBP may be measured by any method known to one of skill in the art. SBPs may be determined to be optically clear because silk materials may be naturally optically clear, as described in Lawrence et al. (2009) Biomaterials 30 (7): 1299-1308, the contents of which are herein incorporated by reference in their entirety. In some embodiments, the optical clarity of an SBP is measured by absorbance. As used herein, the term "absorbance" refers to a measurement of a substance's ability to take in light. Absorbance may be measured at any wavelength. In some embodiments, the absorbance of an SBP is measured from 200 nm-850 nm. The absorbance of an SBP may optionally be converted to transmittance. As used herein, the term "transmittance" refers to a measurement of the amount of light that has passed through a substance unchanged, without absorbance, reflection, or scattering. Transmittance may be determined by the ratio of the intensity of transmitted light to the ratio of the intensity of the incident light. In some embodiments, an SBP absorbs light at around 280 nm, which is the range of light absorbed for a protein. Said SBP may be otherwise determined to be optically clear. In some embodiments, the optical clarity of an SBP is measured with any of the methods described in Toytziaridis et al. (2016) International Journal of Molecular Sciences 17:1897, the contents of which are herein incorporated by reference in their entirety.

In some embodiments, optically transparent SBPs may be used for ocular applications, e.g., treatment of ocular conditions, diseases, and/or indications.

Combinations

In some embodiments, SBP formulations are presented in a combinatorial format. A combinatorial format may consist of two or more different materials that have been combined to form a single composition. In some embodiments, two or more SBPs of different formats (e.g. rod, hydrogel etc.) are combined to form a single composition (e.g., see European Publication Number EP3212246, the contents of which are herein incorporated by reference in their entirety). In some embodiments, one or more SBP is combined with a different material (e.g. a polymer, a mat, a particle, a microsphere, a nanosphere, a metal, a scaffold, etc.) to form a single composition (e.g., see International Publication Number WO2017179069, the contents of which are herein incorporated by reference in their entirety. In some embodiments, combinatorial formats are prepared by formulating two or more SBPs of different formats as a single composition (e.g., see Kambe et al. (2017) Materials (Basel) 10 (10): 1153, the contents of which are herein incorporated by reference in their entirety). In some embodiments, combinatorial formats are prepared by formulating two or more SBPs of different formats, along with another material, as a single composition (e.g., see International Publication Number WO2017177281, the contents of which are herein incorporated by reference in their entirety). In some embodiments, combinatorial formats include adding one or more SBPs to a first SBP of a different format (e.g., see European Patent Number EP3212246, the contents of which are herein incorporated by reference in their entirety). In some embodiments, combinatorial formats include adding one or more SBPs to a first composition comprising a different material (e.g., see Jiang et al. (2017) J Biomater Sci Polym Ed 15:1-36, the contents of which are herein incorporated by reference in their entirety). In some embodiments, the combinatorial formats are prepared by adding one or more materials to one or more first formed SBPs (e.g., see Babu et al. (2017) J Colloid Interface Sci 513:62-72, the contents of which are herein incorporated by reference in their entirety).

In some embodiments, SBP formulations may be administered in combination with other therapeutic agent and/or methods of treatment, e.g., with known pharmaceuticals and/or known therapeutic methods, such as, for example, those which are currently employed for treating these disorders. For example, SBP formulations used to treat cancer may be administered in combination with other anti-cancer treatments (e.g., biological, chemotherapy, or radiotherapy treatments).

Distribution

SBP components may be distributed equally or unequally, depending on format and application. Non-limiting examples of unequal distribution include component localization in SBP regions or compartments, on SBP surfaces, etc. In some embodiments, components include cargo. Such cargo may include payloads, for example, therapeutic agents. In some embodiments, therapeutic agents are present on the surface of an SBP (e.g., see Han et al. (2017) Biomacromolecules 18 (11): 3776-3787; Ran et al. (2017) Biomacromolecules 18 (11): 3788-3801, the contents of each of which are herein incorporated by reference in their entirety). In some embodiments, components (e.g., therapeutic agents) are homogenously mixed with processed silk to generate a desired distribution (e.g., see United States Publication No. US20170333351; Sun et al. (2017) Journal of Materials Chemistry B 5:8770-8779; and Du et al. (2017) Nanoscale Res Lett 12 (1): 573, the contents of each of which are herein incorporated by reference in their entirety). In some embodiments, components (e.g., therapeutic agents) are encapsulated in SBPs (e.g., see Shi et al. (2017) Nanoscale 9:14520, the contents of which are herein incorporated by reference in their entirety).

Rods

In some embodiments, SBP formulation includes rods. As used herein when referring to SBPs, the term "rod" refers to an elongated format, typically cylindrical, that may have blunted or tapered ends. Rods may be suitable for implantation or similar administration methods as it may be possible to deliver rods by injection. Rods may also be obtained simply by passing suitably viscous SBP formulations through a needle, cannula, tube, or opening. In some embodiments, rods are prepared by one or more of injection molding, heated or cooled extrusion, extrusion through a coating agent, milling with a therapeutic agent, and combining with a polymer followed by extrusion.

In some embodiments, SBP rods include processed silk (e.g., silk fibroin) rods. Some rods may include coterminous luminal cavities in whole or in part running through the rod. Rods may be of any cross-sectional shape, including, but not limited to, circular, square, oval, triangular, irregular, or combinations thereof.

In some embodiments, rods are prepared from silk fibroin preparations. The silk fibroin preparations may include lyophilized silk fibroin. The lyophilized silk fibroin may be dissolved in water to form silk fibroin solutions used in rod preparation. Silk fibroin solutions may be prepared as stock solutions to be combined with additional components prior to rod preparation. In some embodiments silk fibroin stock solutions have a silk fibroin concentration of between 10% (w/v) and 40% (w/v). In some embodiments, the silk fibroin stock solution for the preparation of silk fibroin rods has a concentration of at least 10% (w/v), at least 20% (w/v), at least 30% (w/v), at least 40% (w/v), or at least 50% (w/v).

In some embodiments, silk fibroin stock solution prepared for rod formation are mixed with one or more other components intended to be include in the final processed silk rods. Examples of such other components include, but are not limited to, excipients, salts, therapeutic agents, biological agents, proteins, small molecules, and polymers. In some embodiments, processed silk rods may include between 20 to 55% (w/w) silk fibroin. In some embodiments, processed silk rods may include between 40 to 80% (w/w) therapeutic agent. In some embodiments, processed silk rods may include 35% (w/w) silk fibroin and 65% (w/w) therapeutic agent. In some embodiments, processed silk rods may include 30% (w/w) silk fibroin and 70% (w/w) therapeutic agent. In some embodiments, processed silk rods may include 40% (w/w) silk fibroin and 60% (w/w) therapeutic agent. In some embodiments, processed silk rods may include 26% (w/w) silk fibroin and 74% (w/w) therapeutic agent. In some embodiments, processed silk rods may include 37% (w/w) silk fibroin and 63% (w/w) therapeutic agent. In some embodiments, processed silk rods may include 33% (w/w) silk fibroin and 66% (w/w) therapeutic agent. In some embodiments, processed silk rods may include 51% (w/w) silk fibroin and 49% (w/w) therapeutic agent. In some embodiments, silk fibroin may be included at a concentration (w/w) of 0.01% to about 1%, from about 0.05% to about 2%, from about 0.1% to about 30%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 96%, from about 32% to about 97%, from about 34% to about 98%, from about 36% to about 98.5%, from about 38% to about 99%, from about 40% to about 99.5%, from about 42% to about 99.6%, from about 44% to about 99.7%, from about 46% to about 99.8%, or from about 50% to about 99.9%.

In some embodiments, processed silk rods are prepared by extrusion. As used herein, the term "extrusion" refers to a process by which a substance is forced through an opening, tube, or passage. In some embodiments, processed silk rods are formed by extruding SBP formulations through a needle or cannula. SBP formulations used for rod formation may have varying levels of viscosity. Preparation viscosity may depend on the presence and/or identity of excipients present. In some embodiments, SBP formulations may include compounds or compositions intended to be embedded in rods prepared by extrusion. Excipients, compounds, or compositions included in SBP formulations used for extrusion may include, but are not limited to, salts, therapeutic agents, biological agents, proteins, small molecules, and polymers. Extrusion may be carried out manually or by an automated process.

In some embodiments, extrusion may be carried out using a syringe. The syringe may be fitted with a needle, tube, or cannula. The needle, tube, or cannula may have a sharpened end or a blunt end. The needle may have a diameter of from about 0.1 mm to about 0.3 mm, from about 0.2 mm to about 0.7 mm, from about 0.4 mm to about 1.1 mm, from about 0.6 mm to about 1.5 mm, from about 0.8 mm to about 1.9 mm, from about 1 mm to about 2.3 mm, from about 1.2 mm to about 2.7 mm, from about 1.6 mm to about 3.1 mm, or from about 2 mm to about 3.5 mm. SBP formulations may be used to fill tubes, wherein the SBP formulations are incubated in the tubes for various periods of time under various conditions (e.g., various temperatures). In some embodiments, tubing filled with processed silk preparation may be incubated at 37° C. for from about 2 hours to about 36 hours or more. In some embodiments, processed silk filled tubing is incubated for 24 hours. In some embodiments, SBP formulations remain in tubing after the 37° C. incubation. In some embodiments, SBP formulations are removed from the tubing after the incubation at 37° C. SBP formulations removed from tubing may maintain a rod-shaped format. Such preparations may be dried after removal from tubing. In some embodiments, SBP formulations may be encased in tubing while drying. Rods may be dried by one or more of freeze-drying, oven drying, and air drying. Some SBP formulations may be removed tubing after drying.

Tubing used for extrusion may be composed of various materials. In some embodiments, tubing is made from one or more of silicone, polyetheretherketone (PEEK), polytetrafluoroethylene (PTFE), amorphous fluoroplastics, fluorinated ethylene propylene, perfluoroalkoxy copolymers, ethylene-tetrafluoroethylene, polyolefins, and nylon.

In some embodiments, rods may have a diameter of from about 0.05 μm to about 10 μm, from about 1 μm to about 20 μm, from about 2 μm to about 30 μm, from about 5 μm to about 40 μm, from about 10 μm to about 50 μm, from about 20 μm to about 60 μm, from about 30 μm to about 70 μm, from about 40 μm to about 80 μm, from about 50 μm to about 90 μm, from about 0.05 mm to about 2 mm, from about 0.1 mm to about 3 mm, from about 0.2 mm to about 4 mm, from about 0.5 mm to about 5 mm, from about 1 mm to about 6 mm, from about 2 mm to about 7 mm, from about 5 mm to about 10 mm, from about 8 mm to about 16 mm, from about 10 mm to about 50 mm, from about 20 mm to about 100 mm, from about 40 mm to about 200 mm, from about 60 mm to about 300 mm, from about 80 mm to about 400 mm, from about 250 mm to about 750 mm, or from about 500 mm to about 1000 mm. In some embodiments, rods include a diameter of at least 0.5 μm, at least 1 μm, at least 10 μm, at least 100 μm, at least 500 μm, at least 1 mm, at least 10 mm, or at least 100 mm. In one embodiment, the rods have a diameter of 1 mm. In another embodiment, the rods have a diameter of 0.5 mm. In another embodiment, the rods have a diameter of 400 μm. In another embodiment, the rods have a diameter of 430 μm.

In some embodiments, the rods described herein may have a density of from about 0.01 μg/mL to about 1 g/mL, from about 0.05 μg/mL to about 2 μg/mL, from about 1 μg/mL to about 5 μg/mL, from about 2 μg/mL to about 10 μg/mL, from about 4 μg/mL to about 16 μg/mL, from about 5 μg/mL to about 20 μg/mL, from about 8 μg/mL to about 24 μg/mL, from about 10 μg/mL to about 30 μg/mL, from about 12 μg/mL to about 32 μg/mL, from about 14 μg/mL to about 34 μg/mL, from about 16 μg/mL to about 36 μg/mL, from about 18 μg/mL to about 38 μg/mL, from about 20 μg/mL to about 40 μg/mL, from about 22 μg/mL to about 42 μg/mL, from about 24 μg/mL to about 44 μg/mL, from about 26 μg/mL to about 46 μg/mL, from about 28 μg/mL to about 48 μg/mL, from about 30 μg/mL to about 50 μg/mL, from about 35 μg/mL to about 55 μg/mL, from about 40 μg/mL to about 60 μg/mL, from about 45 μg/mL to about 65 μg/mL, from about 50 μg/mL to about 75 μg/mL, from about 60 μg/mL to about 240 μg/mL, from about 70 μg/mL to about 350 μg/mL, from about 80 μg/mL to about 400 μg/mL, from about 90 μg/mL to about 450 μg/mL, from about 100 μg/mL to about 500 μg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 1 g/mL to about 5 g/mL, from about 2 g/mL to about 10 g/mL, from about 4 g/mL to about 16 g/mL, or from about 5 g/mL to about 20 g/mL.

Gels and Hydrogels

In some embodiments, SBP formulations include gels or hydrogels. As used herein, the term "gel" refers to a dispersion of liquid molecules in a solid medium. Gels in which the dispersed liquid molecules include water are referred to herein as "hydrogels." Gels in which the dispersed liquid molecules include an organic phase are referred to herein as "organogels." The solid medium may include polymer networks. Hydrogels may be formed with silk of any grade (e.g. grade 3, grade 4, grade 5, and/or grade 6).

In some embodiments, SBP gels or hydrogels are prepared with processed silk. In processed silk gels, polymer networks may include silk fibroin. In some embodiments, gels are prepared with one or more therapeutic agents. In some embodiments, gels include one or more excipients. The excipients may be selected from any of those described herein. In some embodiments, excipients may include salts. In some embodiments, the excipients may include gelling agents. In some embodiments, gels are prepared with one or more therapeutic agents, biological agents, proteins, small molecules, and/or polymers. In some embodiments, gels may be prepared by mixing a solution comprising processed silk with a gelling agent. The gelling agent may be in a second solution. In some embodiments, the therapeutic agent may be in solution with processed silk. In some embodiments, the therapeutic agent may be in solution with the gelling agent. In some embodiments, a stock solution of therapeutic agent may be used to dissolve processed silk for the preparation of a hydrogel. The ratio of the solution comprising processed silk to the gelling agent or solution comprising the gelling agent may be from about 5:1 to about 4.5:1, from about 4.5:1 to about 4:1, from about 4:1 to about 3.5:1, from about 3.5:1 to about 3:1, from about 3:1 to about 2.5:1, from about 2.5:1 to about 2:1, from about 2:1 to about 1.5:1, from about 1.5:1 to about 1:1, from about 1:1 to about 1:1.5, from about 1:1.5 to about 1:2, from about 1:2 to about 1:2.5, from about 1:2.5 to about 1:3, from about 1:3 to about 1:3.5, from about 1:3.5 to about 1:4, from about 1:4 to about 1:4.5, or from about 1:4.5 to about 1:5.

Gel preparation may require varying temperatures and incubation times for gel polymer networks to form. In some embodiments, SBP formulations are heated to 37° C. to prepare gels. In some embodiments, SBP formulations are incubated at 4° C. to prepare gels. In some embodiments, SBP formulations are incubated for from about 2 hours to about 36 hours or more to promote gel formation. In some embodiments, gel formation requires mixing with one or more gelling agents or excipients. Mixing may be carried out under various temperatures and lengths of time to allow gel polymer networks to form. Gel formation may require homogenous dispersion of gelling agents or excipients. In some embodiments, SBP formulations used to prepare gels include silk fibroin. Gel formation for processed silk gels may require incubation at 37° C. for up to 24 hours. Gel formation for processed silk gels may require incubation at 4° C. for up to 24 hours. Some gels may be stored for later use or processing. In some embodiments, gels are stored at 4° C.

In some embodiments, processed silk gels include one or more excipients and/or gelling agents at a concentration of from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

In some embodiments, processed silk gels (e.g., hydrogels or organogels) include silk fibroin at a concentration of from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

Silk fibroin included may be from a silk fibroin preparation with an average silk fibroin molecular weight or range of molecular weights of from about 3.5 kDa to about 10 kDa, from about 5 kDa to about 20 kDa, from about 10 kDa to about 30 kDa, from about 15 kDa to about 40 kDa, from about 20 kDa to about 50 kDa, from about 25 kDa to about 60 kDa, from about 30 kDa to about 70 kDa, from about 35 kDa to about 80 kDa, from about 40 kDa to about 90 kDa, from about 45 kDa to about 100 kDa, from about 50 kDa to about 110 kDa, from about 55 kDa to about 120 kDa, from about 60 kDa to about 130 kDa, from about 65 kDa to about 140 kDa, from about 70 kDa to about 150 kDa, from about 75 kDa to about 160 kDa, from about 80 kDa to about 170 kDa, from about 85 kDa to about 180 kDa, from about 90 kDa to about 190 kDa, from about 95 kDa to about 200 kDa, from about 100 kDa to about 210 kDa, from about 115 kDa to about 220 kDa, from about 125 kDa to about 240 kDa, from about 135 kDa to about 260 kDa, from about 145 kDa to about 280 kDa, from about 155 kDa to about 300 kDa, from about 165 kDa to about 320 kDa, from about 175 kDa to about 340 kDa, from about 185 kDa to about 360 kDa, from about 195 kDa to about 380 kDa, from about 205 kDa to about 400 kDa, from about 215 kDa to about 420 kDa, from about 225 kDa to about 440 kDa, from about 235 kDa to about 460 kDa, or from about 245 kDa to about 500 kDa.

In some embodiments, hydrogels include one or more therapeutic agents at a concentration of from about 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

Gelling agents may be used to facilitate sol-gel transition. As used herein, the term "sol-gel transition" refers to the shift of a formulation from a solution to a gel. In some embodiments, the use of gelling agents may be carried out according to any of such methods described in International Publication No. WO2017139684, the contents of which are herein incorporated by reference in their entirety. Gelling agents may be water-soluble, waxy solids. In some embodiments, gelling agents may be water-soluble and hygroscopic in nature. In some embodiments, gelling agents may include polar molecules. Gelling agents may have net positive, net negative, or net neutral charges at a physiological pH (e.g., pH of about 7.4). Some gelling agents may be amphipathic. Additional examples of gelling agents include oils (e.g., castor, corn oil, cottonseed oil, olive oil, peanut oil, peppermint oil, safflower oil, sesame oil, soybean oil, hydrogenated vegetable oil, hydrogenated soybean oil, and medium-chain triglycerides of coconut oil and/or palm seed oil), emulsifiers [e.g., polyoxyl 40 stearate (PEG 1750 monosterate), polyoxyl 8 stearate (PEG 400 monosterate), polysorbate 20, polysorbate 80, polysorbate-SO, or poloxamer], surfactants (e.g., polysorbate, poloxamer, sodium dodecyl sulfate, Triton X100, or tyloxapol), and suspending agents (e.g., polyvinyl pyrrolidone, polyvinyl pyrrolidone-12, polyvinyl pyrrolidone-17, hydroxyethyl cellulose, or carboxymethyl cellulose). Any gelling agent listed in Table 1 may be used.

In some embodiments, gel formation is induced by applying one or more of the following to processed silk preparations: ultrasound, sonication, shear forces, temperature change (e.g., heating), addition of precipitants, modulation of pH, changes in salt concentration, chemical cross-linking, chemical modification, seeding with preformed hydrogels, increasing silk fibroin concentration, modulating osmolarity, use of electric fields, or exposure to electric currents. In some embodiments, methods of inducing gel formation may include, but are not limited to any of those described in International Patent Application Publication No. WO2005012606 or United States Patent Publication No. US2011/0171239, the contents of each of which are herein incorporated by reference in their entirety.

In some embodiments, processed silk gel preparation may be carried with the aid of sonication. As used herein, the term "sonication" refers to a process of agitation using sound energy. Sonication conducted at frequencies greater than 20 KHz is referred to as ultrasonication. Sonication may aid in gel formation by dispersing and/or agitating polymer components within a solution to foster an arrangement that favors polymer network formation. The polymer network may include silk fibroin. In some embodiments, the use of sonication for gel preparation may be carried out according to any of the methods described in Zhao et al. (2017) Materials Letters 211:110-113 or Mao et al. (2017) Colloids Surf B Biointerfaces 160:704-714), the contents of each of which are herein incorporated by reference in their entirety.

In some embodiments, processed silk gel formation may be carried out using shear forces. As used herein, the term "shear forces" refers to unaligned forces that apply pressure to two or more different parts of an object or medium from different and/or opposing directions. Shear forces are distinct from compression forces, which are directed toward each other. Shear forces may be applied during processed silk gel preparation using a syringe, tubing, needle, or other apparatus capable of increasing shear forces. Processed silk preparation may be pushed through a syringe, tubing, needle, or other apparatus to generate shear forces. The use of shear forces in gel formation may include any of those described in United States Patent Publication No. US2011/0171239, the contents of which are herein incorporated by reference in their entirety.

In some embodiments, changes in temperature may be used to aid in processed silk gel formation. Changes in temperature may be used to disperse or align polymer components in an arrangement that promotes gel polymer network formation. The polymer components may include silk fibroin. In some embodiments, gel formation may be carried out by raising or lowering the temperature of a processed silk preparation to from about 0° C. to about 5° C., from about 2° C. to about 6° C., from about 4° C. to about 12° C., from about 8° C. to about 16° C., from about 10° C. to about 26° C., from about 15° C. to about 28° C., from about 20° C. to about 32° C., from about 25° C. to about 34° C., from about 30° C. to about 45° C., from about 35° C. to about 55° C., from about 37° C. to about 65° C., from about 40° C. to about 75° C., from about 50° C. to about 100° C., from about 60° C. to about 120° C., from about 70° C. to about 140° C., from about 80° C. to about 160° C., or from about 100° C. to about 300° C. In some embodiments, one or more excipients or gelling agents may be included to lower the temperature necessary for gel formation to occur. Such embodiments may be employed to protect temperature-sensitive components embedded within gels. In some embodiments, gel formation is carried out at 4° C. Glycerol, polyethylene glycol (PEG), and/or polymers of PEG (e.g., PEG400) may be included in SBP formulations as excipients to lower the temperature necessary to form a gel. The gel may be a silk fibroin gel. Excipient concentration may be about 30% (w/v). Silk fibroin concentration may be from about 2% to about 30%.

In some embodiments, gel formation is carried out by applying an electric current, also referred to as "electrogelation." Electrogelation may be carried out according to any of the methods presented in International Publication No. WO2010036992, the contents of which are herein incorporated by reference in their entirety. In some embodiments, a reverse voltage may be applied to reverse gel formation and regenerate a processed silk solution.

In some embodiments, gel formation is carried out by modulating the pH of processed silk preparations. Gel formation through pH modulation may be carried out according to the methods described in International Patent Application Publication No. WO2005012606, United States Patent Publication No. US2011/0171239, and Dubey et al. (2017) Materials Chemistry and Physics 203:9-16, the contents of each of which are herein incorporated by reference in their entirety.

In some embodiments, gel formation is carried out in association with modulating the osmolarity of a processed silk preparation. As used herein, the term "osmolarity" or "osmotic concentration" refers to the number of osmoles of solute in solution on a per liter basis (Osm/L). Unlike molarity, which is a measure of the number of moles solute per liter of solvent (M), osmolarity factors in the effect of ions on osmotic pressure. For example, a 1 M solution of NaCl would have an osmolarity of 2 Osm/L while a 1 M solution of $MgCl_2$ would have an osmolarity of 3 Osm/L. Hypo- or hyper-osmotic formulations can lead to local tissue damage and reduced biocompatibility. In some embodiments, the osmolarity of processed silk gels is modulated by controlling the type, molecular weight, and/or concentration of excipients included. Osmolarity may be modulated by varying the concentration and/or molecular weight of salts used in processed silk preparations. In some embodiments, osmolarity is reduced by using lower molecular weight gelling agents. For example, 4 kDa PEG may be used in place of PEG400. The use of Poloxamer-188 at 10% (w/v) may reduce osmolarity in comparison to lower molecular weight species such as glycerol. In some embodiments, sodium chloride may be added to increase osmolarity. In some embodiments, osmolarity is adjusted to fall between 280 and 320 mOsm/L.

In some embodiments, gel formation is carried out through seeding. As used herein when referring to gel formation, "seeding" refers to a process of inducing gel formation using a small amount of pre-formed gel. Seeding may promote gel formation by encouraging polymer network formation to build off of the pre-formed gel introduced. In some embodiments the gel includes silk fibroin. Seeding with a pre-formed silk fibroin hydrogel may be used to promote transition of a silk fibroin solution into a silk fibroin gel. In some embodiments, seeding reduces the need for gelling agents and/or excipients to form gels.

In some embodiments, gel formation is carried out using chemical cross-linking. As used herein, the term "chemical cross-linking" refers to a process of forming covalent bonds between chemical groups from different molecules or between chemical groups present on different parts of the same molecule. In some embodiments, chemical cross-linking may be carried out by contacting SBP formulations with ethanol. Such methods may be carried out according to those described in Shi et al. (2017) Advanced Material 29 (29): 1701089, the contents of which are herein incorporated by reference in their entirety. In some embodiments, cross-linking may be carried out using enzymes. Methods of enzyme cross-linking using horse radish peroxidase may include any of those described in McGill et al. (2017) Acta Biomaterialia 63:76-84 or Guo et al. (2017) Biomaterials 145:44-55, the contents of each of which are herein incorporated by reference in their entirety. In some embodiments, chemical cross-linking may be photo-initiated, as disclosed in International Publication No. WO2017123383 and in Zhang et al. (2017) Fibers and Polymers 18 (10): 1831-1840, the contents of each of which are herein incorporated by reference in their entirety.

In some embodiments, other chemical modifications may be used during processed silk gel preparation. Some chemical modifications may be used to induce silk fibroin β-sheet conformations. In some embodiments, this process involves contact with a chemical. Chemicals may include, but are not limited to, ethanol. In some embodiments, silk fibroin may be chemically crosslinked with other materials during gel preparation. Such materials may include other peptides (e.g., see Guo et al. (2017) Biomaterials 145:44-55, the contents of which are herein incorporated by reference in their entirety). In some embodiments, processed silk gels are prepared by formation of internal chemical cross-links. These crosslinks may be dityrosine crosslinks (e.g., see International Patent Application Publication No. WO2017123383, the contents of which are herein incorporated by reference in their entirety). In some embodiments, photosensitive materials may be used to promote chemical modifications. Such materials may include riboflavin (e.g., see International Publication No. WO2017123383). In some embodiments, processed silk gels may be functionalized with particles. These particles may be microspheres and/or nanospheres (e.g., see Ciocci et al. (2017) Int J Biol Macromol S0141-8130 (17): 32839-8, the contents of which are herein incorporated by reference in their entirety).

In some embodiments, the SBPs are prepared as hydrogels. In some embodiments, the hydrogels have a concentration between about 3% (w/v) to about 15% (w/v) silk fibroin. In some embodiments the silk fibroin has a boiling time of 90 mb, 120 mb, or 480 mb. In some embodiments, the hydrogels are prepared from silk fibroin lyophilized in phosphate buffer. In some embodiments, the hydrogels have trace amounts of phosphate salts (e.g. potassium phosphate dibasic and potassium phosphate monobasic). In some embodiments, the hydrogels comprise between about 10% (w/v) to about 50% (w/v) excipient. In some embodiments, the excipient is poloxamer-188 (P188), in some embodiments, the excipient is glycerol. In some embodiments, the excipient is PEG 4000 (PEG 4 kDa) and the formulation may optionally include hydrochloric acid. In some embodiments, the excipient is PEG400 and the formulation may optionally include hydrochloric acid. In some embodiments, the hydrogels comprise 15 mM hydrochloric acid. In some embodiments, the formulations are as described in Table 2. In the sample named 90mb; hyd; 5% SFf; 10% P188f, "90mb" refers to silk degummed with a 90-minute boil, "hyd" refers to the formulation of the sample as a hydrogel, "5% SFf" refers to a formulation with 5% (w/v) silk fibroin, and "40% Glycf" refers to a formulation with 40% (w/v) glycerol.

TABLE 2

Hydrogel formulations

| Sample | Boil Time (mb) | [Silk] (%) | Excipient | [Excipient] (%) | Sample Name |
|---|---|---|---|---|---|
| 1 | 90 | 5 | P188 | 10 | 90 mb; hyd; 10% st; 5% SFf; 10% P188f |
| 2 | 90 | 5 | PEG 4 kDa | 40 | 90 mb; hyd; 10% st; 5% SFf; 40% PEG4kf |
| 3 | 90 | 5 | Glycerol | 40 | 90 mb; hyd; 10% st; 5% SFf; 40% Glycf |
| 4 | 90 | 10 | P188 | 10 | 90 mb; hyd; 20% st; 10% SFf; 10% P188f |
| 5 | 90 | 10 | PEG 4 kDa | 40 | 90 mb; hyd; 20% st; 10% SFf; 40% PEG4kf |
| 6 | 90 | 10 | Glycerol | 40 | 90 mb; hyd; 20% st; 10% SFf; 40% Glycf |
| 7 | 480 | 5 | P188 | 10 | 480 mb; hyd; 10% st; 5% SFf; 10% P188f |
| 8 | 480 | 5 | PEG 4 kDa | 40 | 480 mb; hyd; 10% st; 5% SFf; 40% PEG4kf |
| 9 | 480 | 5 | Glycerol | 40 | 480 mb; hyd; 10% st; 5% SFf; 40% Glycf |
| 10 | 480 | 10 | P188 | 10 | 480 mb; hyd; 120% st; 0% SFf; 10% P188f |
| 11 | 480 | 10 | PEG 4 kDa | 40 | 480 mb; hyd; 20% st; 10% SFf; 40% PEG4kf |
| 12 | 480 | 10 | Glycerol | 40 | 480 mb; hyd; 20% st; 10% SFf; 40% Glycf |
| 13 | 480 | 15 | P188 | 10 | 480 mb; hyd; 30% st; 15% SFf; 10% P188f |
| 14 | 480 | 15 | PEG 4 kDa | 40 | 480 mb; hyd; 30% st; 15% SFf; 40% PEG4kf |
| 15 | 480 | 15 | Glycerol | 40 | 480 mb; hyd; 30% st; 15% SFf; 40% Glycf |

In some embodiments, SBP gels or hydrogels have sufficient internal strength to maintain themselves as a cohesive matrix without the need for mechanical reinforcement. The cohesive property of SBP gels or hydrogels may be tuned according to their intended applications. As a non-limiting example, SBP gels or hydrogels may be capable of tolerating physiological concentrations of ionized salt without breakdown of the gel.

Solutions

In some embodiments, SBPs, SBP formulations are or include solutions. As used herein, the term "solution" refers to a dispersion of molecules or solute in a liquid medium or solvent. In some embodiments, the solute is a processed silk or an SBP. In some embodiments, the solvent is water. In some embodiments, the solvent is an aqueous buffer. Non-limiting examples of buffer include citrate buffer, phosphate buffer, phosphate buffer saline, borate buffer, sodium borate, glycine-HCl, sodium acetate, citrate buffered saline, Tris buffer, HEPES buffer, MOPS buffer, and cacodylate buffer. In some embodiments, SBP formulations may be prepared as a solution, as taught in International Patent Application Publication No. WO2005012606 and Cheng et al. (2015) J. App. Polym. Sci. 132 (22): 41959. In some embodiments, an SBP is prepared as a solution using any of the methods described herein. In some embodiments, the solution is prepared by dissolving processed silk in water or buffer. In some embodiments the solution is mixed to facilitate dissolution. In some embodiments, the solution is heated to facilitate dissolution. In some embodiments, solutions are prepared with one or more therapeutic agents. In some embodiments, solutions include one or more excipients. The excipients may be selected from any of those described herein. In some embodiments, excipients may include salts. In some embodiments, the excipients may be any of those described in Table 1. In some embodiments, solutions are prepared with one or more therapeutic agents, biological agents, proteins, small molecules, and/or polymers. In some embodiments, a stock solution of the therapeutic agent may be used to dissolve processed silk in the preparation of a solution. In some embodiments, a stock solution of the therapeutic agent may be mixed with a stock solution of processed silk to prepare the SBP. In some embodiments, a solution may be diluted to obtain additional solutions with processed silk at varying concentrations.

In some embodiments, processed silk solutions include one or more excipients at a concentration of from about 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

In some embodiments, processed silk solutions include silk fibroin at a concentration of 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v). Silk fibroin included may be from a silk fibroin preparation with an average silk fibroin molecular weight or range of molecular weights of from about 3.5 kDa to about 10 kDa, from about 5 kDa to about 20 kDa, from about 10 kDa to about 30 kDa, from about 15 kDa to about 40 kDa, from about 20 kDa to about 50 kDa, from about 25 kDa to about 60 kDa, from about 30 kDa to about 70 kDa, from about 35 kDa to about 80 kDa, from about 40 kDa to about 90 kDa, from about 45 kDa to about 100 kDa, from about 50 kDa to about 110 kDa, from about 55 kDa to about 120 kDa, from about 60 kDa to about 130 kDa, from about 65 kDa to about 140 kDa, from about 70 kDa to about 150 kDa, from about 75 kDa to about 160 kDa, from about 80 kDa to about 170 kDa, from about 85 kDa to about 180 kDa, from about 90 kDa to about 190 kDa, from about 95 kDa to about 200 kDa, from about 100 kDa to about 210 kDa, from about 115 kDa to about 220 kDa, from about 125 kDa to about 240 kDa, from about 135 kDa to about 260 kDa, from about 145 kDa to about 280 kDa, from about 155 kDa to about 300 kDa, from about 165 kDa to about 320 kDa, from about 175 kDa to about 340 kDa, from about 185 kDa to about 360 kDa, from about 195 kDa to about 380 kDa, from about 205 kDa to about 400 kDa, from about 215 kDa to about 420 kDa, from about 225 kDa to about 440 kDa, from about 235 kDa to about 460 kDa, or from about 245 kDa to about 500 kDa.

In some embodiments, processed silk solutions include one or more therapeutic agents at a concentration of from about 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v). In some embodiments, the solutions have a concentration between about 0.25% (w/v) to about 2% (w/v) silk fibroin. In some embodiments the silk fibroin has a boiling time of 90 mb, 120 mb, or 480 mb. In some embodiments, the solutions are prepared from silk fibroin lyophilized in phosphate buffer. In some embodiments, the solutions have trace amounts of phosphate salts (e.g. potassium phosphate dibasic and potassium phosphate monobasic). In some embodiments, the solutions are formulated with one or more therapeutic agents. In some embodiments, one or more therapeutic agents may be a biological agent. In some embodiments, the biological agent is a protein.

In some embodiments, the solutions have a concentration between about 0.25% (w/v) to about 2% (w/v) silk fibroin. In some embodiments the silk fibroin has a boiling time of 90 mb, 120 mb, or 480 mb. In some embodiments, the solutions are prepared from silk fibroin lyophilized in phosphate buffer. In some embodiments, the solutions have trace amounts of phosphate salts (e.g. potassium phosphate dibasic and potassium phosphate monobasic). In some embodiments, the solutions are formulated with one or more therapeutic agents. In some embodiments, one or more therapeutic agents may be a biological agent. In some embodiments, the biological agent is a protein.

In some embodiments, silk fibroin may be prepared as a stock solution.

In one embodiment, the silk fibroin stock solution has a concentration of 10% (w/v).

In one embodiment, the silk fibroin stock solution has a concentration of 20% (w/v).

In one embodiment, the silk fibroin stock solution has a concentration of 30% (w/v).

In one embodiment, the silk fibroin stock solution has a concentration of 40% (w/v).

In one embodiment, the silk fibroin stock solution has a concentration of 50% (w/v).

In some embodiments, processed silk formulations may be prepared as solutions. In these solutions, the processed silk may be silk fibroin. Silk fibroin may be degummed with any minute boil (mb) described herein, including, but not limited to, 15, 30, 60, 90, 120 and 480 mb. These solutions may be prepared in water. These solutions may also be prepared with any buffer or excipient described herein, including, but not limited to, phosphate buffer (PB), borate buffer (DED), and propylene glycol (PG). Buffers and excipients may be present at any concentration described herein (e.g. 10 mM PB). Phosphate buffer may be prepared as 10 mM PB. Borate buffer (DED) may be prepared as 6 mg/mL boric acid, 0.45 mg/mL sodium borate, 3.4 mg/mL sodium chloride, 1.4 mg/mL potassium chloride, 0.06 mg/mL magnesium chloride, and 0.06 mg/mL calcium chloride, pH 7.3. In some embodiments, the solutions may comprise 1% PG. In some embodiments, the solution has a pH between 7.0 and 8.0. In some embodiments, the solution has a pH of 7.3. In some embodiments, the solution has a pH of 7.4. In some embodiments, these solutions may comprise silk fibroin at a concentration of from about 0.01% to about 30% (w/v). In some embodiments, these solutions may comprise silk fibroin at a concentration of from about 0.01% to about 0.1%, about 0.1% to about 1%, about 1% to about 2%, about 2% to about 3%, about 3% to about 4%, about 4% to about 5%, about 5% to about 10%, about 10% to about 15%, about 15% to about 20%, or about 20% to about 30% (w/v) silk fibroin.

In some embodiments, the solution comprises 1% (w/v) silk fibroin.

In some embodiments, the solution comprises 2% (w/v) silk fibroin.

In some embodiments, the solution comprises 3% (w/v) silk fibroin.

In some embodiments, the solution comprises 1% (w/v) silk fibroin and 1% (w/v) PG.

In some embodiments, the solutions may be any of those described in Table 3.

TABLE 3

Solution formulations

| Sample No. | Description | Silk % | Buffer |
|---|---|---|---|
| 82-1 | 3% Water, Baseline | 3 | Water |
| 82-2 | 3% PB, Baseline | 3 | 10 mM PB |
| 82-3 | 3% DED, Baseline | 3 | DED |
| 82-4 | 1% PBS, Baseline | 1 | PBS |
| 82-5 | 1% DED, Baseline | 1 | DED |
| 82-6 | 1% PBS + PG, Baseline | 1 | PBS + 1% PG |
| 82-7 | 1% DED + PG, Baseline | 1 | DED + 1% PG |
| 83-1 | 0.5% SF in 10 mM phosphate, pH 7.4 | 5 | 10 mM PB |

TABLE 3-continued

| Solution formulations | | | |
|---|---|---|---|
| Sample No. | Description | Silk % | Buffer |
| 83-2 | 1% SF in 10 mM phosphate, pH 7.4 | 10 | 10 mM PB |
| 83-3 | 2.5% SF in 10 mM phosphate, pH 7.4 | 25 | 10 mM PB |
| 83-4 | 5% SF in 10 mM phosphate, pH 7.4 | 50 | 10 mM PB |
| 83-5 | 5% SF, 10 mM sucrose in 10 mM phosphate, pH 7.4 | 50 | 10 mM PB + 10 mM sucrose |
| 83-6 | 5% SF, 50 mM sucrose in 10 mM phosphate, pH 7.4 | 50 | 10 mM PB + 50 mM sucrose |
| 83-7 | 5% SF, 100 mM sucrose in 10 mM phosphate, pH 7.4 | 50 | 10 mM PB + 100 mM sucrose |
| 83-8 | 5% SF, 150 mM sucrose in 10 mM phosphate, pH 7.4 | 50 | 10 mM PB + 150 mM sucrose |
| 83-9 | 5% SF, 10 mM trehalose in 10 mM phosphate, pH 7.4 | 50 | 10 mM PB + 10 mM trehalose |
| 83-10 | 5% SF, 50 mM trehalose in 10 mM phosphate, pH 7.4 | 50 | 10 mM PB + 50 mM trehalose |
| 83-11 | 5% SF, 100 mM trehalose in 10 mM phosphate, pH 7.4 | 50 | 10 mM PB + 100 mM trehalose |
| 83-12 | 5% SF, 150 mM trehalose in 10 mM phosphate, pH 7.4 | 50 | 10 mM PB + 150 mM trehalose |

Particles

In some embodiments, SBP formulation include SBP particles. As used herein, the term "particle" refers to a minute portion of a substance. SBP particles may include particles of processed silk. Processed silk particles may include silk fibroin particles. Silk fibroin particles may be tiny clusters of silk fibroin or they may be arranged as more ordered structures. Particles may vary in size. Processed silk particles may be visible or may be too tiny to view easily with the naked eye. Particles with a width of from about 0.1 μm to about 100 μm are referred to herein as "microparticles." Particles with a width of about 100 nm or less are referred to herein as "nanoparticles." Microparticles and nanoparticles that are spherical in shape are termed microspheres and nanospheres, respectively. Processed silk particle preparations may include particles with uniform width or with ranges of widths. In some embodiments, processed silk particle preparations include average particle widths of or ranges of particle widths of from about 10 nm to about 25 nm, from about 20 nm to about 50 nm, from about 30 nm to about 75 nm, from about 40 nm to about 80 nm, from about 50 nm to about 100 nm, from about 0.05 μm to about 10 μm, from about 1 μm to about 20 μm, from about 2 μm to about 30 μm, from about 5 μm to about 40 μm, from about 10 μm to about 50 μm, from about 20 μm to about 60 μm, from about 30 μm to about 70 μm, from about 40 μm to about 80 μm, from about 50 μm to about 90 μm, from about 0.05 mm to about 2 mm, from about 0.1 mm to about 3 mm, from about 0.2 mm to about 4 mm, from about 0.5 mm to about 5 mm, from about 1 mm to about 6 mm, from about 2 mm to about 7 mm, from about 5 mm to about 10 mm, from about 10 nm to about 100 μm, from about 10 μm to about 10 mm, from about 50 nm to about 500 μm, from about 50 μm to about 5 mm, from about 100 nm to about 10 mm, or from about 1 μm to about 10 mm. In some embodiments, processed silk particle preparations include average particle widths of at least 10 nm, at least 100 nm, at least 0.5 μm, at least 1 μm, at least 10 μm, at least 100 μm, at least 500 μm, at least 1 mm, or at least 10 mm.

Processed silk particles may be formed through spraying of a processed silk preparation. In some embodiments, electrospraying is used. Electrospraying may be carried out using a coaxial electrospray apparatus (e.g., see Cao et al. (2017) Scientific Reports 7:11913, the contents of which are herein incorporated by reference in their entirety). In some embodiments, silk fibroin microspheres or nanospheres may be obtained by electrospraying a silk fibroin preparation into a collector and flash freezing the sprayed particles (e.g., see United States Publication No. US2017/0333351, the contents of which are herein incorporated by reference in their entirety). The flash frozen silk fibroin particles may then be lyophilized. In some embodiments, processed silk particles may be prepared using centrifugal washing, followed by lyophilization, as taught in United States Publication No. US2017/0340575, the contents of which are herein incorporated by reference in their entirety. In some embodiments, processed silk microspheres may be formed through the use of a microfluidic device (e.g., see Sun et al. (2017) Journal of Materials Chemistry B 5:8770-8779, the contents of which are herein incorporated by reference in their entirety). In some embodiments, microspheres are formed via coagulation in a methanol bath, as taught in European Patent No. EP3242967, the contents of which are herein incorporated by reference in their entirety.

Devices

In some embodiments, SBP formulations may be included as or in device components. As used herein, the term "device" refers to any article constructed or modified to suit a particular purpose. Devices may be designed for a variety of purposes, including, but not limited to, therapeutic applications, material science applications, and agricultural applications. In some embodiments, SBPs are embedded or incorporated into devices. Some devices include SBPs as coatings or lubricants. In some embodiments, devices include implants, patches, mesh, sponges, grafts, insulators, pipes, prosthetics, resistors, bedding, blankets, liners, ropes, plugs, fillers, electronic devices, mechanical devices, medical devices, surgical devices, veterinary devices, and agricultural devices. Additional devices are described herein.

In some embodiments, SBPs may be or may be included in therapeutic devices. In some embodiments, therapeutic devices may be coated with SBPs described herein. Some therapeutic devices may include therapeutic agents. In some embodiments, the use of SBPs within therapeutic devices may enable the delivery of therapeutic agents via such therapeutic devices. Some therapeutic devices may include synthetic materials. In some embodiments, therapeutic devices include, but are not limited to, artificial blood vessels, artificial organ, bandage, cartilage replacement, filler, hemostatic sponge, implant, silk contact lens, contact lens solution, stem cell, surgical mesh, surgical suture, tissue replacement, vascular patch, wound dressing, antenna, applier, assembly, balloon, barrier, biosensor, biotransducer, cable assembly, caliper, capacitor, carrier, clamp, connector, corneal implant, coronary stent, cryotome, degradable device, delivery device, dermatome, detector, diagnostic device, dilator, diode, discharge device, display technology, distractor, drill bit, electronic device, graft, grasper, harmonic scalpel, hemostatic device, imaging apparatus, implant, implant for continuous drug delivery, integrated circuit, intraocular lens, lancet, LIGASURE™, liner, magnetic or inductive device, magnetic resonance imaging apparatus, mechanical assembly, medical device, memristor, module, needle, nerve stimulator, network, neurostimulator, occluder, optoelectronic device, pacemaker, patch, pen, piezoelectric device, pin, pipe, plate, positioner, power source, probe, prosthesis, prosthetic, protection device, removable device, resistor, retractor, rod, rongeur, rope, ruler, scalpel, scope, screw, semiconductor, sensor, solution, specula, stent, stent, stereotactic device, suction tip, suction tube, surgical device, surgical mesh, surgical scissor, surgical staple, suture, switch, temperature sensor, terminal, tie, tip, transducer, transistor, tube, ultrasound tissue disruptor, vacuum tube, vacuum valve, ventilation system, water balloon, wire, bleb, gel, gel that hardens after implantation, implant, lacrimal plug, lens, plug, punctal plug, rod, slurry, slurry that hardens after implantation, and solids.

Solid Implants

In some embodiments, SBP formulations may be included as or in solid implants. SBP solid implants may be prepared by gelation of processed silk followed by drying and/or injection molding. Methods of drying may include any of those described herein, such as heat, air drying or lyophilization. The drying process may induce beta-sheet formation. Density of the SBP formulation is properly controlled during this process. SBP formulations may also be formatted as a film that is applied to the exterior of a solid implant. Alternatively, SBP formulations may be included into solid implants by spray-drying, spray-coating, and/or milling.

Solid implants prepared with SBP formulations may be of any size and shape. As a non-limiting example, solid implants may be shaped as forceps, speculum, bands, stoppers, screws, tubes, rods, cones, cylinders, teardrops, etc. Solid implants prepared with SBP formulations may be prepared via aqueous processing. The pH of solid implants prepared with SBP formulations may be controlled during preparation and degradation. Solid implants prepared with SBP formulations may comprise a hydrophobic matrix. Solid implants prepared with SBP formulations prepared with high loading of active pharmaceutical ingredient (e.g. at least 50% (w/w). Delivery of the active pharmaceutical ingredient may be sustained (e.g. for weeks to months). Solid implants prepared with SBP formulations may be biocompatible and/or biodegradable Controlled Release In some embodiments, SBP formulations and related methods described herein be may be used for controlled release of therapeutic agents. As used herein, the term "controlled release" refers to regulated movement of factors from specific locations to surrounding areas. In some embodiments, the specific location is a depot. Controlled release of factors from depots may be regulated by interactions between therapeutic agents and depot components. Such interactions may, for example, modulate therapeutic agent diffusion rate and/or affect therapeutic agent stability and/or degradation. In some embodiments, the depot is an SBP formulation. In some embodiments, factors subject to controlled release from depots are SBP formulations. In some embodiments, therapeutic agents are subject to controlled release from SBP depots.

In some embodiments, SBP formulations may control payload release by extending payload half-life. As used herein, the term "half-life" refers to the length of time necessary for levels of a factor to be reduced (e.g., through clearance or degradation) by 50%. In some embodiments, SBP depots may be used for therapeutic agents, wherein release is facilitated by diffusion. In some embodiments, SBP formulations may be lyophilized together with therapeutic agents. In some embodiments, combined lyophilization may induce further interactions between therapeutic agents and SBP formulations. These interactions may be maintained through SBP preparation and support extended payload release. Payload release may be dependent on SBP degradation and/or dissolution. In some embodiments, SBP β-sheet content is increased (e.g., via water annealing), thereby increasing SBP insolubility in water. Such SBPs may exhibit increased payload release periods. In some embodiments, these SBP formulations may include therapeutic agent stabilizing properties to extend administration periods and/or therapeutic agent half-life.

In some embodiments, methods of increasing payload half-life using SBPs may include any of those described in United States Patent Publication US20100028451, the contents of which are herein incorporated by reference in their entirety. Methods of improving payload half-life may be carried out in vitro or in vivo. In some embodiments, SBP-based methods of improving payload half-life may enable therapeutic indication treatment with fewer doses and/or treatments. Such methods may include any of those described in International Patent Application Publication No. WO2017139684, the contents of which are herein incorporated by reference in their entirety. In some embodiments, payload half-life may be extended by from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 100%, from about 32% to about 105%, from about 34% to about 110%, from about 36% to about 115%, from about 38% to about 120%, from about 40% to about 125%, from about 42% to about 130%, from about 44% to about 135%, from about 46% to about 140%, from about 48% to about 145%, from about 50% to about 150%, from about 60% to about 175%, from about 70% to about 200%, from about 80% to about 225%, from about 90% to about 250%, from about 100% to about 275%, from about 110% to about 300%, from about 120% to about 325%, from about 130% to about 350%, from about 140% to about 375%, from about 150% to about 400%, from about 170% to about 450%, from about 190% to about 500%, from about 210% to about 550%, from about 230% to about 600%, from about 250% to about 650%, from about 270% to about 700%, from about 290% to about 750%, from about 310% to about 800%, from about 330% to about 850%, from about 350% to about 900%, from about 370% to about 950%, from about 390% to about 1000%, from about 410% to about 1050%, from about 430% to about 1100%, from about 450% to about 1500%, from about 480% to about 2000%, from about 510% to about 2500%, from about 540% to about 3000%, from about 570% to about 3500%, from about 600% to about 4000%, from about 630% to about 4500%, from about 660% to about 5000%, from about 690% to about 5500%, from about 720% to about 6000%, from about 750% to about 6500%, from about 780% to about 7000%, from about 810% to about 7500%, from about 840% to about 8000%, from about 870% to about 8500%, from about 900% to about 9000%, from about 930% to about 9500%, from about 960% to about 10000%, or more than 10000%.

Ocular SBPs

SBPs described herein may include ocular SBPs. As used herein, the term "ocular SBP" refers to an SBP used in any application related to the eye. Ocular SBPs may be used in therapeutic applications. Such therapeutic applications may include treating or otherwise addressing one or more ocular indications.

In further embodiments, ocular SBPs may be prepared as eye drops for the treatment of dry eye disease, as described in U.S. Pat. No. 9,394,355, the contents of which are hereby incorporated by reference in their entirety, or formulated for the treatment of corneal injury, as described in International Patent Application Publication Nos. WO2017200659 and WO2018031973; Abdel-Naby et al. (2017) Invest Ophthalmol Vis Sci; 58 (3): 1425-1433; and Abdel-Naby et al. (2017) PLOS One; 12 (11): e0188154, the contents of each of which are hereby incorporated by reference in their entirety.

Ocular SBPs may be prepared in a variety of formats. Some ocular SBPs are in the form of a hydrogel. These hydrogels may vary in viscosity and appear runny. Other ocular SBPs may be in the form of a solution. Some ocular SBPs may be devices. These devices may include medical devices. In some embodiments, solutions may include silk fibroin micelles, as described in Wongpanit et al. (2007) Macromolecular Bioscience 7:1258-1271, the contents of which are herein incorporated by reference in their entirety. Silk fibroin micelles may be of any size (e.g. between 100 to 200 nm). In some embodiments, ocular SBPs may act as demulcents. The ocular SBPs described herein may relieve irritation or inflammation of the mucous membranes by forming a protective film. In some embodiments, the ocular SBPs of the present disclosure may contain one or more demulcents (e.g. propylene glycol, gelatin, glycerin, carboxymethylcellulose, Dextran 70, methylcellulose, PEG 300, PEG 400, hydroxyethyl cellulose, hydroxypropyl methylcellulose, povidone, polyvinyl alcohol, and polysorbate 80). This film may mimic a mucous membrane. In some embodiments, ocular SBPs may act as a surfactant.

Ocular SBPs may include ocular therapeutic agents. Ocular therapeutic agents may be delivered to subject eyes by release from SBPs while SBPs are in contact with the eyes. Release of ocular therapeutic agents from SBPs may be modulated by one or more of silk fibroin concentration, silk fibroin molecular weight, SBP volume, method used to dry SBPs, ocular therapeutic agent molecular weight, and inclusion of at least one excipient. The ocular therapeutic agents may include any of those described herein. In some embodiments, ocular therapeutic agents include one or more of processed silk, biological agents, small molecules, analgesics, proteins, anti-inflammatory agents, steroids, opiates, sodium channel blockers (e.g. lidocaine and proparacaine), ciclosporin, corticosteroids, tetracyclines, fatty acids, NSAIDs, and VEGF-related agents. Ocular therapeutic agent proteins may include, but are not limited to, lysozyme, bovine serum albumin (BSA), bevacizumab, or VEGF-related agents. NSAIDs may include, but are not limited to, aspirin, carprofen, celecoxib, deracoxib, diclofenac, diflunisal, etodolac, fenoprofen, firocoxib, flurbiprofen, ibuprofen, indomethacin, ketoprofen, ketorolac, mefenamic acid, meloxicam, nabumetone, naproxen, oxaprozin, piroxicam, robenacoxib, salsalate, sulindac, and tolmetin. In some embodiments, the SBPs stabilize ocular therapeutic agents included. Ocular SBPs may include ocular therapeutic agent concentrations [expressed as percentage of ocular therapeutic agent weight contributing to total SBP volume] of from about 0.0001% (w/v) to about 98% (w/v). For example, SBPs may include ocular therapeutic agents at a concentration of from about 0.0001% (w/v) to about 0.001% (w/v), from about 0.001% (w/v) to about 0.01% (w/v), from about 0.01% (w/v) to about 1% (w/v), from about 0.05% (w/v) to about 2% (w/v), from about 1% (w/v) to about 5% (w/v), from about 2% (w/v) to about 10% (w/v), from about 4% (w/v) to about 16% (w/v), from about 5% (w/v) to about 20% (w/v), from about 5% (w/v) to about 85% (w/v), from about 8% (w/v) to about 24% (w/v), from about 10% (w/v) to about 30% (w/v), from about 12% (w/v) to about 32% (w/v), from about 14% (w/v) to about 34% (w/v), from about 15% (w/v) to about 95% (w/v), from about 16% (w/v) to about 36% (w/v), from about 18% (w/v) to about 38% (w/v), from about 20% (w/v) to about 40% (w/v), from about 22% (w/v) to about 42% (w/v), from about 24% (w/v) to about 44% (w/v), from about 26% (w/v) to about 46% (w/v), from about 28% (w/v) to about 48% (w/v), from about 30% (w/v) to about 50% (w/v), from about 35% (w/v) to about 55% (w/v), from about 40% (w/v) to about 60% (w/v), from about 45% (w/v) to about 65% (w/v), from about 50% (w/v) to about 70% (w/v), from about 55% (w/v) to about 75% (w/v), from about 60% (w/v) to about 80% (w/v), from about 65% (w/v) to about 85% (w/v), from about 70% (w/v) to about 90% (w/v), from about 75% (w/v) to about 95% (w/v), from about 80% (w/v) to about 96% (w/v), from about 85% (w/v) to about 97% (w/v), from about 90% (w/v) to about 98% (w/v), from about 95% (w/v) to about 99% (w/v), from about 96% (w/v) to about 99.2% (w/v), or from about 97% (w/v) to about 98% (w/v).

Ocular SBPs may have a pH from about 3 to about 10. In some embodiments, the pH is from about 3 to about 6, from about 6 to about 8, or from about 8 to about 10. In some embodiments, the pH of the SBP is about 7.4.

In some embodiments, the ocular SBP is a solution. In some embodiments the ocular SBP is a hydrogel. In some embodiments, the SBP comprises from about 0.0001% to about 35% (w/v) of silk fibroin. In some embodiments the silk fibroin may be included at a concentration (w/w or w/v) of from about 0.0001% to about 0.001%, from about 0.001% to about 0.01%, from about 0.01% to about 1%, from about 0.05% to about 2%, from about 0.1% to about 30%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 96%, from about 32% to about 97%, from about 34% to about 98%, from about 36% to about 98.5%, from about 38% to about 99%, from about 40% to about 99.5%, from about 42% to about 99.6%, from about 44% to about 99.7%, from about 46% to about 99.8%, or from about 50% to about 99.9%.

Ocular SBPs may include one or more excipients. The excipients may include any of those described herein. In some embodiments, the excipients include one or more of sucrose, lactose, phosphate salts, sodium chloride, potassium phosphate monobasic, potassium phosphate dibasic, sodium phosphate dibasic, sodium phosphate monobasic, polysorbate 80, phosphate buffer, phosphate buffered saline, sodium hydroxide, sorbitol, mannitol, lactose USP, Starch 1500, microcrystalline cellulose, potassium chloride, sodium borate, boric acid, sodium borate decahydrate, magnesium chloride hexahydrate, calcium chloride dihydrate, sodium hydroxide, Avicel, dibasic calcium phosphate dehydrate, tartaric acid, citric acid, fumaric acid, succinic acid, malic acid, hydrochloric acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, and sodium carboxymethylcellulose. In some embodiments, excipients may include phosphate buffered saline. In some embodiments, excipients may include phosphate buffer. In some embodiments, excipients may include sucrose. In some embodiments, excipients may include boric acid, sodium borate decahydrate, sodium chloride, potassium chloride, magnesium chloride hexahydrate, calcium chloride dihydrate, sodium hydroxide, and hydrochloric acid. SBPs may include at least one excipient at a concentration of from about 0.0001% to about 50% (w/w or w/v). In some embodiments, SBPs include at least one excipient at a concentration of from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 96%, from about 32% to about 97%, from about 34% to about 98%, from about 36% to about 98.5%, from about 38% to about 99%, from about 40% to about 99.5%, from about 42% to about 99.6%, from about 44% to about 99.7%, from about 46% to about 99.8%, or from about 50% to about 99.9%.

In some embodiments, less than 1% of silk fibroin in an ocular SBP aggregates In some embodiments, less than 0.1% of silk fibroin in an ocular SBP aggregates.

Ocular SBPs may be hydrogels. Such SBPs may include at least one excipient selected from one or more of sorbitol, triethylamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol, glycerol formal, hydroxypropyl beta-cyclodextrin, kolliphor 124, kolliphor 181, kolliphor 188, kolliphor 407, kolliphor EL (cremophor EL), cremophor RH 40, cremophor RH 60, dalpha-tocopherol, PEG 1000 succinate, polysorbate 20, polysorbate 80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, medium chain triglycerides of coconut oil, medium chain triglycerides of palm seed oil, beeswax, d-alpha-tocopherol, oleic acid, medium-chain mono-glycerides, medium-chain di-glycerides, alpha-cyclodextrin, betacyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alpha-dimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), polyoxyl 8 stearate (PEG 400 monosterate), polysorbate 20, polysorbate 80, polyvinyl pyrrolidone, propylene carbonate, propylene glycol, solutol HS15, sorbitan monooleate (Span 20), sulfobutylether-beta-cyclodextrin, transcutol, triacetin, I-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, glycerin, and PEG 4 kDa. The SBPs may have an osmolarity of from about 1 mOsm to about 10 mOsm, from about 2 mOsm to about 20 mOsm, from about 3 mOsm to about 30 mOsm, from about 4 mOsm to about 40 mOsm, from about 5 mOsm to about 50 mOsm, from about 6 mOsm to about 60 mOsm, from about 7 mOsm to about 70 mOsm, from about 8 mOsm to about 80 mOsm, from about 9 mOsm to about 90 mOsm, from about 10 mOsm to about 100 mOsm, from about 15 mOsm to about 150 mOsm, from about 25 mOsm to about 200 mOsm, from about 35 mOsm to about 250 mOsm, from about 45 mOsm to about 300 mOsm, from about 55 mOsm to about 350 mOsm, from about 65 mOsm to about 400 mOsm, from about 75 mOsm to about 450 mOsm, from about 85 mOsm to about 500 mOsm, from about 125 mOsm to about 600 mOsm, from about 175 mOsm to about 700 mOsm, from about 225 mOsm to about 800 mOsm, from about 275 mOsm to about 285 mOsm, from about 280 mOsm to about 900 mOsm, or from about 325 mOsm to about 1000 mOsm.

In some embodiments, the viscosity and/or complex viscosity of SBPs is tunable between 1-1000 centipoise (cP). In some embodiments, the viscosity of an SBP is tunable from about 0.0001 to about 1000 Pascal seconds (Pa*s). In some embodiments, the viscosity of an SBP is from about 1 cP to about 10 cP, from about 2 cP to about 20 cP, from about 3 cP to about 30 cP, from about 4 cP to about 40 cP, from about 5 cP to about 50 cP, from about 6 cP to about 60 cP, from about 7 cP to about 70 cP, from about 8 cP to about 80 cP, from about 9 cP to about 90 cP, from about 10 cP to about 100 cP, from about 100 cP to about 150 cP, from about 150 cP to about 200 cP, from about 200 cP to about 250 cP, from about 250 cP to about 300 cP, from about 300 cP to about 350 cP, from about 350 cP to about 400 cP, from about 400 cP to about 450 cP, from about 450 cP to about 500 cP, from about 500 cP to about 600 cP, from about 550 cP to about 700 cP, from about 600 cP to about 800 cP, from about 650 cP to about 900 cP, from about 700 cP to about 1000 cP, from about 1000 cP to about 5000 cP, from about 5000 cP to about 10000 cP, from about 10000 cP to about 20000 cP, from about 20000 cP to about 30000 cP, from about 30000 cP to about 40000 cP, from about 40000 cP to about 50000 cP, from about 50000 cP to about 60000 cP, from about 60000 cP to about 80000 cP, from about 80000 cP to about 90000 cP, or from about 90000 cP to about 100000 cP. In some embodiments, the viscosity of an SBP is from about 0.0001 Pa*s to about 0.001 Pa*s, from about 0.001 Pa*s to about 0.01 Pas, from about 0.01 Pas to about 0.1 Pa*s, from about 0.1 Pa*s to about 1 Pa*s, from about 1 Pa*s to about 10 Pass, from about 2 Pa*s to about 20 Pa*s, from about 3 Pa*s to about 30 Pa*s, from about 4 Pas to about 40 Pa*s, from about 5 Pa*s to about 50 Pa*s, from about 6 Pa*s to about 60 Pa*s, from about 7 Pa*s to about 70 Pa*s, from about 8 Pa*s to about 80 Pa*s, from about 9 Pa*s to about 90 Pa*s, from about 10 Pa*s to about 100 Pa*s, from about 100 Pa*s to about 150 Pa*s, from about 150 Pa*s to about 200 Pa*s, from about 200 Pa*s to about 250 Pa*s, from about 250 Pa*s to about 300 Pa*s, from about 300 Pa*s to about 350 Pa*s, from about 350 Pa*s to about 400 Pa*s, from about 400 Pa*s to about 450 Pa*s, from about 450 Pa*s to about 500 Pa*s, from about 500 Pa*s to about 600 Pa*s, from about 550 Pa*s to about 700 Pa*s, from about 600 Pa*s to about 800 Pa*s, from about 650 Pa*s to about 900 Pa*s, from about 700 Pa*s to about 1000 Pa*s, from about 1000 Pa*s to about 2500 Pa*s, from about 2500 Pa*s to about 5000 Pa*s, from about 5000 Pa*s to about 7500 Pa*s, from about 7500 Pa*s to about 10000 Pass, from about 10000 Pa*s to about 20000 Pa*s, from about 20000 Pa*s to about 30000 Pa*s, from about 30000 Pa*s to about 40000 Pa*s, or from about 40000 Pa*s to about 50000 Pa*s. In some embodiments, the SBP formulations may shear thin or display shear thinning properties. As used herein, the term "shear thinning" refers to a decrease in viscosity at increasing shear rates. As used herein, the term "shear rate" refers to the rate of change in the ratio of displacement of material upon the application of a shear force to the height of the material. This ratio is also known as strain.

In some embodiments, the storage modulus and/or the loss modulus (G' and G" respectively) of SBPs is tunable between 0.0001-20000 Pascals (Pa). In some embodiments, the storage modulus and/or the loss modulus of SBPs is from about 0.0001 Pa to about 0.001 Pa, from about 0.001 Pa to about 0.01 Pa, from about 0.01 Pa to about 0.1 Pa, from about 0.1 Pa to about 1 Pa, from about 1 Pa to about 10 Pa, from about 2 Pa to about 20 Pa, from about 3 Pa to about 30 Pa, from about 4 Pa to about 40 Pa, from about 5 Pa to about 50 Pa, from about 6 Pa to about 60 Pa, from about 7 Pa to about 70 Pa, from about 8 Pa to about 80 Pa, from about 9 Pa to about 90 Pa, from about 10 Pa to about 100 Pa, from about 100 Pa to about 150 Pa, from about 150 Pa to about 200 Pa, from about 200 Pa to about 250 Pa, from about 250 Pa to about 300 Pa, from about 300 Pa to about 350 Pa, from about 350 Pa to about 400 Pa, from about 400 Pa to about 450 Pa, from about 450 Pa to about 500 Pa, from about 500 Pa to about 600 Pa, from about 550 Pa to about 700 Pa, from about 600 Pa to about 800 Pa, from about 650 Pa to about 900 Pa, from about 700 Pa to about 1000 Pa, from about 1000 Pa to about 1500 Pa, from about 1500 Pa to about 2000 Pa, from about 2000 Pa to about 2500 Pa, from about 2500 Pa to about 3000 Pa, from about 3000 Pa to about 3500 Pa, from about 3500 Pa to about 4000 Pa, from about 4000 Pa to about 4500 Pa, from about 4500 Pa to about 5000 Pa, from about 5000 Pa to about 5500 Pa, from about 5500 Pa to about 6000 Pa, from about 6000 Pa to about 6500 Pa, from about 6500 Pa to about 7000 Pa, from about 7000 Pa to about 7500 Pa, from about 7500 Pa to about 8000 Pa, from about 8000 Pa to about 8500 Pa, from about 8500 Pa to about 9000 Pa, from about 9000 Pa to about 9500 Pa, from about 9500 Pa to about 10000 Pa, from about 10000 Pa to about 11000 Pa, from about 11000 Pa to about 12000 Pa, from about 12000 Pa to about 13000 Pa, from about 13000 Pa to about 14000 Pa, from about 14000 Pa to about 15000 Pa, from about 15000 Pa to about 16000 Pa, from about 16000 Pa to about 17000 Pa, from about 17000 Pa to about 18000 Pa, from about 18000 Pa to about 19000 Pa, or from about 19000 Pa to about 20000 Pa.

In some embodiments, the phase angle of SBPs is tunable between 1°-90°). In some embodiments, the phase angle of SBPs is from about 1° to about 2°, from about 2° to about 3°, from about 3° to about 4°, from about 4° to about 5°, from about 5° to about 6°, from about 6° to about 7°, from about 7° to about 8°, from about 8° to about 9°, from about 9° to about 10°, from about 10° to about 15°, from about 15° to about 20°, from about 20° to about 25°, from about 25° to about 30°, from about 30° to about 35°, from about 35° to about 40°, from about 40° to about 45°, from about 45° to about 50°, from about 50° to about 55°, from about 55° to about 60°, from about 60° to about 65°, from about 65° to about 70°, from about 70° to about 75°, from about 75° to about 80°, from about 80° to about 85°, or from about 85° to about 90°.

In some embodiments, ocular SBPs may demonstrate the effects of interfacial viscosity. In some embodiments, the processed silk of an ocular SBP may migrate to the air-water boundary. In some embodiments this migration may result in an increase in the local concentration at this interface and ultimately generate the effects of interfacial viscosity. The effects of interfacial viscosity may be independent of the concentration of processed silk. In some embodiments, the effects of interfacial viscosity may be mitigated through the incorporation of a surfactant. The surfactant may be any surfactant described herein. In some embodiments, the surfactant is polysorbate 80. In some embodiments, the SBPs are topical ocular drops. In some embodiments these topical ocular drops show the effects of interfacial viscosity, as the thin tear film allows for a large air-water interface. In some embodiments, the processed silk in the ocular SBP and/or topical ocular drops may migrate to the air-water interface. In some embodiments, the ocular SBP and/or topical ocular drops create a viscous film-like layer at the tear film surface. In some embodiments, the effects interfacial viscosity in an ocular SBP and/or topical ocular drops may prevent evaporation of tears. In some embodiments, the effects interfacial viscosity in an ocular SBP and/or topical ocular drops may extend silk residence dwell time on the surface of the eye. In some embodiments, the effects of interfacial viscosity of an ocular SBP and/or topical ocular drops may lead to a reduction in the frequency of application. In some embodiments, ocular SBPs and/or topical ocular drops may have viscosities similar to that of saline (1 cP). In some embodiments, ocular SBPs and/or topical ocular drops may have viscosities similar to that of saline at high shear rates (e.g. greater than or equal to 500 1/s). These shear rates may be similar or identical to those produced during blinking. In some embodiments, the ocular SBPs and/or topical ocular drops may not elicit any unwanted effects with comfort due to the effects of interfacial viscosity.

In some embodiments, ocular SBPs may comprise a solution with a demulcent. In some embodiments, the demulcent is propylene glycol. In some embodiments, ocular SBPs may comprise a solution with 0.001%-10% propylene glycol. In some embodiments, ocular SBPs may comprise a solution with 1% propylene glycol.

In some embodiments, ocular SBPs may comprise a solution in borate (DED) buffer.

In some embodiments, ocular SBPs may comprise a solution in borate (DED) buffer with 1% 480 mb silk fibroin at pH 7.5 with an osmolarity of 150 mOsm/L. These ocular SBPs may be prepared with silk fibroin lyophilized in 50 mM sucrose.

In some embodiments, ocular SBPs may comprise a solution in borate (DED) buffer with 1% 120 mb silk fibroin at pH 7.5 with an osmolarity of 150 mOsm/L. These ocular SBPs may be prepared with silk fibroin lyophilized in 50 mM sucrose.

In some embodiments, ocular SBPs may comprise a solution in borate (DED) buffer with 1% 480 mb silk fibroin at pH 7.5 with an osmolarity of 150 mOsm/L and 1% propylene glycol. These ocular SBPs may be prepared with silk fibroin lyophilized in 50 mM sucrose.

In some embodiments, the ocular SBP may be formulated for topical administration. In some embodiments, ocular SBPs may be formulated for ocular administration. In some embodiments, ocular SBPs are formulated for intraocular administration. In some embodiments, ocular SBPs are formulated for one or more of intravitreal administration, intraretinal administration, intracorneal administration, intrascleral administration, lacrimal administration, punctal administration, administration to the anterior sub-Tenon's, suprachoroidal administration, administration to the posterior sub-Tenon's, subretinal administration, administration to the fornix, administration to the lens, administration to the anterior segment, administration to the posterior segment, macular administration, and intra-aqueous humor administration. Ocular SBPs may be biocompatible, well tolerated, and/or non-immunogenic. Ocular SBPs may be administered as eye drops. Ocular SBPs may be administered as sprays. Ocular SBPs may be biocompatible. Ocular SBPs may be tolerable.

In some embodiments, ocular SBPs may be used as artificial tears. In some embodiments, ocular SBPs may be used in the management of glaucoma. In some aspects, the ocular SBPs useful for the management of glaucoma may be in the format of drops. Eye drops used in managing glaucoma help the eye's fluid to drain better and decrease the amount of fluid made by the eye which decreases eye pressure. Ocular SBPs formatted as eye drops may include prostaglandin analogs, beta blockers, alpha agonists, and carbonic anhydrase inhibitors.

In some embodiments, SBPs formatted as drops may be used to treat ocular allergies. Drops may contain histamine antagonists or nonsteroidal anti-inflammatory drug (NSAIDs), which suppress the optical mast cell responses to allergens including (but not limited to) aerosolized dust particles.

In some embodiments, SBPs formatted as drops may be used to treat conjunctivitis or pink eye. In some embodiments ocular SBPs comprising antibiotics as therapeutic agents may be prescribed when the conjunctivitis is caused by bacteria. In some embodiments, pharmaceutical compositions comprising ocular SBPs may be prepared as artificial tears to help dilute irritating allergens present in the tear film.

In some embodiments, ocular SBPs formatted as drops may include mydriatics, an agent that causes pupil dilation. Mydriatics include but are not limited to phenylephrine, cyclopentolate, tropicamide, hydroxyamphetamine/tropicamide, atropine, cyclopentolate/phenylephrine ophthalmic, homatropine ophthalmic, and scopolamine. Such SBPs may be used in the treatment of ocular indications or in preparation for the diagnosis of ocular conditions.

In some embodiments, ocular SBPs formatted as solutions may be used as contact lens solution. Contact lens solutions are solutions used for the storage of contact lenses in between use of said contact lenses. Contact lenses may be used for vision correction and/or for cosmetic purposes. In some embodiments, the anti-microbial and/or bacteriostatic properties of an SBP may enable the storage of contact lenses while prohibiting the growth of microbes and/or bacteria.

In some embodiments, the ocular SBPs of the present disclosure are biocompatible in the ocular space. In some embodiments, administration of the ocular SBP does not cause local inflammation in the ocular space. In some embodiments, ocular SBP is tolerable in the ocular space. In some embodiments, the retinal tissue remains normal after the administration of the ocular SBP. In some embodiments, the SBPs are biocompatible and tolerable in the ocular space for at least 1 day, at least 3 days, at least 1 week, at least 2 weeks, at least 1 month, at least 3 months, at least 4 months, at least 6 months, or at least 1 year.

In some embodiments, the present disclosure provides methods of treating subjects by contacting them with ocular SBPs. The subjects may have, may be suspected of having, and/or may be at risk for developing one or more ocular indications. Such ocular indications may include any of those described herein. In some embodiments, ocular indications include dry eye disease. In some embodiments, ocular indications include one or more of an infection, refractive errors, age related macular degeneration, cystoid macular edema, cataracts, diabetic retinopathy (proliferative and non-proliferative), glaucoma, amblyopia, strabismus, color blindness, cytomegalovirus retinitis, keratoconus, diabetic macular edema (proliferative and non-proliferative), low vision, ocular hypertension, retinal detachment, eyelid twitching, inflammation, uveitis, bulging eyes, dry eye disease, floaters, xerophthalmia, diplopia, Graves' disease, night blindness, eye strain, red eyes, nystagmus, presbyopia, excess tearing, retinal disorder, conjunctivitis, cancer, corneal ulcer, corneal abrasion, snow blindness, scleritis, keratitis, Thygeson's superficial punctate keratopathy, corneal neovascularization, Fuch's dystrophy, keratoconjunctivitis sicca, iritis, cyclitis, cycloplegia, chorioretinal inflammation (e.g. chorioretinitis, choroiditis, retinitis, retinochoroiditis, pars planitis, Harada's disease, aniridia, macular scars, solar retinopathy, choroidal degeneration, choroidal dystrophy, choroideremia, gyrate atrophy, choroidal hemorrhage, choroidal detachment, retinoschisis, hypertensive retinopathy, Bull's eye maculopathy, epiretinal membrane, peripheral retinal degeneration, hereditary retinal dystrophy, retinitis pigmentosa, retinal hemorrhage, retinal vein occlusion, and separation of retinal layers.

In some embodiments, the present disclosure provides methods of delivering ocular therapeutic agents to subjects by contacting subject eyes with ocular SBPs. Such ocular SBPs may be prepared by combining processed silk with ocular therapeutic agents. The SBPs may be prepared as solutions. The SBPs may be prepared by dissolving processed silk in water or buffer. In some embodiments, the processed silk is silk fibroin. In some embodiments, the processed silk is prepared by degummed degumming for a boiling time selected from a 30-minute boil, a 60-minute boil, a 90-minute boil, a 120-minute boil, and a 480-minute boil. In some embodiments the processed silk is freeze dried in phosphate buffer. In some embodiments, the processed silk is freeze dried with sucrose. In some embodiments, the SBP is stressed. In some embodiments, the SBP is stressed by one or more methods including heating to 60° C. and autoclaving. In some embodiments, the SBP contains phosphate salts. In some embodiments, the SBP is formulated as a hydrogel. In some embodiments the SBP is formulated as a solution. In some embodiments, the SBP solution comprises phosphate buffered saline and trace amounts of phosphate buffer. In some embodiments, the SBP solution comprises sucrose, phosphate buffered saline and/or trace amounts of phosphate buffer.

In some embodiments, the viscosity of an ocular SBP may be tuned by preparation with silk fibroin of different boiling times. In some embodiments, a preparation of an ocular SBP from silk fibroin with a longer boiling time (e.g. 480 mb) may increase the viscosity of the SBP. In some embodiments, a preparation of an ocular SBP from silk fibroin with a shorter boiling time (e.g. 30 mb) may increase the viscosity of the SBP. In some embodiments, the viscosity of an ocular SBP may be tuned by preparation with different concentrations of silk fibroin. In some embodiments, a preparation of an ocular SBP with a lower concentration of silk fibroin may increase the viscosity of the SBP. In some embodiments, a preparation of an ocular SBP with a silk fibroin concentration of below 1% (w/v) may increase viscosity. In some embodiments, a preparation of an ocular SBP with a concentration between 0.005% and 0.5% (w/v) may increase viscosity. In some embodiments, both the boiling time of silk fibroin and the concentration of silk fibroin may be used to tune the viscosity of the SBP. In some embodiments, the viscosity of an ocular SBP may be tuned by preparation with stressed silk fibroin. In some embodiments, both the preparation of an SBP with stressed silk and the concentration of silk fibroin may be used to tune the viscosity of the SBP.

In some embodiments, the shear storage modulus and/or the shear loss modulus of an ocular SBP are tuned by the concentration of silk fibroin. In some embodiments, the shear storage modulus and/or the shear loss modulus of an ocular SBP are tuned by preparation with stressed silk fibroin. In some embodiments, both the preparation of an SBP with stressed silk and the concentration of processed silk may be used to tune the shear storage modulus and the shear loss modulus of the SBP. In some embodiments, the phase angle of the ocular SBP is tuned by preparation with stressed silk fibroin. In some embodiments, the phase angle of the ocular SBP is tuned by the concentration of processed silk.

In some embodiments, the viscosity of an ocular SBP may remain consistent across a range of silk fibroin concentrations. In some embodiments the viscosity of an ocular SBP may remain within 50%, 40%, 30% 20%, 10%, 5%, or 1% upon dilution. An ocular SBP may be diluted between 0 and 20-fold while maintaining a consistent viscosity.

In some embodiments, the ocular SBPs shear thin, or demonstrate shear thinning properties. In some embodiments, the ocular SBPs demonstrate greater shear thinning than commercially available treatments for dry eye disease. In some embodiments, the ocular SBPs of the present disclosure have a higher viscosity at a lower shear rate. In some embodiments, the ocular SBPs of the present disclosure have the viscosity of a gel at a lower shear rate. In some embodiments, the higher viscosity at a lower shear rate tunes the residence time of the SBP. In some embodiments, the residence time is increased. In some embodiments, the ocular SBPs of the present disclosure have a lower viscosity at a higher shear rate. In some embodiments, the ocular SBPs of the present disclosure have the viscosity of a fluid (e.g. liquid) at a higher shear rate. In some embodiments, the lower viscosity at a higher shear rate increases the comfort in the eye. In some embodiments, the shear thinning of tolerable ocular SBPs promotes differentiation.

In some embodiments, the ocular SBPs of the present disclosure are used to treat a subject. In some embodiments, ocular SBPs are used to treat a subject by contacting the subject with an ocular SBP. In some embodiments, the subject has an ocular indication. In some embodiments, the ocular condition is dry eye disease (DED). In some embodiments, the ocular SBP is administered for ocular lubrication. In some embodiments, the ocular SBP acts as artificial tears and/or a tear replacement. In some embodiments, the ocular SBP alleviates the symptoms of DED after administration. These symptoms may include, but are not limited to, ocular discomfort, dryness, grittiness, and pain. These symptoms may be associated with any grade of DED, including mild, moderate, and/or severe DED. In some embodiments, administration of an ocular SBP of the present disclosure may reduce signs of DED. These signs include, but are not limited to, ocular surface staining and/or tear film break-up time. In some embodiments, the ocular SBP improves comfort in the eye. In some embodiments, the ocular SBP is a hydrogel. In some embodiments, the ocular SBP is a solution. In some embodiments, the ocular SBP is hydrophobic. In some embodiments, the ocular SBP is administered to the eye. In some embodiments, the ocular SBP is administered via topical administration. In some embodiments, the ocular SBP is administered as drops. In some embodiments, the ocular SBP is administered as a spray. In some embodiments, the ocular SBP adheres to the ocular surface. In some embodiments, the ocular SBP adheres to the ocular surface in a manner similar to a mucin layer. In some embodiments, the hydrophobicity of the ocular SBP may improve tear film formation and enhance tear production. In some embodiments, the hydrophobicity of the ocular SBP may prevent evaporation. In some embodiments, the residence time of an ocular SBP will be analyzed after ocular SBP administration, using any method known to one skilled in the art. In some embodiments, the efficacy of an ocular SBP will be analyzed after ocular SBP administration, using any method known to one skilled in the art. In some embodiments, the pharmacokinetics of an ocular SBP will be analyzed after ocular SBP administration, using any method known to one skilled in the art. In some embodiments, the irritability of an ocular SBP will be analyzed after ocular SBP administration, using any method known to one skilled in the art. In some embodiments, the use of an ocular SBP to treat irritation will be analyzed after ocular SBP administration, using any method known to one skilled in the art. In some embodiments, the toxicity of an ocular SBP will be analyzed after ocular SBP administration, using any method known to one skilled in the art.

In some embodiments, the ocular SBP has a surface tension similar to that of water. In some embodiments, the ocular SBP has a surface tension similar to that of human tears. In some embodiments, the surfactant properties of ocular SBPs reduce surface tension to magnitude similar to human tears. Human tears have been reported to have a surface tension of 43.6 mN/m, as described in Sweeney et al. (2013) Experimental Eye Research 117:28-38. In some embodiments, ocular SBPs have a surface tension of about 40-50 mN/m.

Ocular SBPs with a surface tension similar to human tears may allow optimal spreading and tear reformation after blinking. In some embodiments, the surface tension of an ocular SBP may be optimizing to allow for improved spreading and/or tear reformation following blinking. In some embodiments, the surface tension of the ocular SBP may be controlled by the concentration of processed silk. In some embodiments, the surfactant and/or demulcent properties of an ocular SBP may reduce surface tension and provide optimal spreading and/or coating of the ocular surface. In some embodiments, the spreading and/or wetting capabilities of an ocular SBP may be modulated via the surface tension of the ocular SBP. In some embodiments, spreading and/or wetting is improved in ocular SBPs with lower surface tension. In some embodiments, the coating of the ocular surface may be improved in ocular SBPs with lower surface tension.

In some embodiments, ocular SBPs may display a coefficient of friction lower than that of water, as measured by the experimental sliding speeds. In some embodiments, the coefficient of friction of an ocular SBP is slightly lower than that of water. In some embodiments, the ocular SBP is more lubricating that water. In some embodiments, the ocular SBP is slightly more lubricating that water.

In some embodiments, silk fibroin solutions described herein may be prepared by dissolving lyophilized processed silk. That processed silk may be silk fibroin. Silk fibroin may be lyophilized in water, phosphate buffer, sucrose, and any other cryoprotectant and/or buffer described herein. In some embodiments, the formulations with lower molecular weight silk fibroin (480 mb) may be more viscous than the formulations with higher molecular weight silk fibroin (120 mb). Preparation from silk fibroin lyophilized in PB may not affect the viscosity of the formulations.

In some embodiments, silk fibroin may be conjugated with a fluorescent label (e.g. fluorescein isothiocyanate (FITC)). Conjugation may be performed by any method known to one of skill in the art. In some embodiments, the silk fibroin may be conjugated to FITC by mixing the two components together in a sodium bicarbonate solution at a basic pH (e.g. 9.0). The reaction may be performed under light protection at room temperature for at least 1 hour, 2 hours, 3 hours, 4 hours, 5 hours, 6 hours, or overnight. The resulting labeled silk fibroin (FITC-SF) may be dialyzed to remove any impurities. The FITC-SF may be stored at 4° C. until use.

In some embodiments, FITC-SF may be added to solutions of silk fibroin. In the resulting solution, FITC-SF may comprise at 10%, 20%, 30%, or 40% of the total silk fibroin in solution. The total concentration of silk fibroin, with and without FITC-SF, may be any concentration described herein. In some embodiments, formulations of silk fibroin solutions may comprise 1% (w/v) silk fibroin of which 10%, 20%, 30%, or 40% of the total silk fibroin is FITC-SF. In some embodiments, formulations with higher percentages of FITC-SF may have lower complex viscosities. In some embodiments, formulations comprising silk fibroin in which 30% of the silk fibroin is FITC-SF have the most similar rheological properties to solutions of unlabeled silk fibroin.

In some embodiments, silk fibroin solutions may be prepared in any buffer described herein. In some embodiments, silk fibroin solutions may be prepared in a borate (DED) buffer. This buffer may comprise 6 mg/mL boric acid, 0.45 mg/mL sodium borate, 3.4 mg/mL sodium chloride, 1.4 mg/mL, potassium chloride, 0.06 mg/mL magnesium chloride, and 0.06 mg/mL calcium chloride, pH 7.3. Silk fibroin solutions may further comprise polyethylene glycol (PG). PG may be present at any concentration described herein. In some embodiments, silk solutions comprise 1% PG. In some embodiments, G' and G" may be measured to be lower for formulations with higher molecular weight silk fibroin. G' and G" may also be increased by the preparation from silk fibroin lyophilized in PB or formulations with PG. The phase angle may be higher for formulations with higher molecular weight silk fibroin.

The irritability and/or tolerability of any silk fibroin solution described herein may be analyzed after administration to the eye of a subject. In some embodiments, topical administration of the solution of silk fibroin may be well tolerated for at least 1 hour, 2 hours, 1 day, 2 days, 3 days, 4 days, 5 days, 6 days, 1 week, 2 weeks, 3 weeks, or 1 month. In some embodiments, no deleterious effects (e.g. to the corneal surface) are detected after administration of an ocular SBP.

In some embodiments, the silk fibroin solutions described herein may be stable under storage. Storage conditions may include, but are not limited to, 4° C., room temperature, and 40° C. Silk fibroin solutions may be stable under the storage conditions for at least 1 hour, 2 hours, 1 day, 2 days, 3 days, 4 days, 5 days, 6 days, 1 week, 2 weeks, 3 weeks, 1 month, 6 months, 1 year, 2 years, 3 years, 4 years, 5 years, or 10 years. In some embodiments, an ocular SBP may have a shelf life of least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 14 weeks, at least 4 months, at least 18 weeks, at least 5 months, at least 22 weeks, at least 6 months, at least 7 months, at least 8 months, at least 9 months, at least 10 months, at least 11 months, at least a year, at least 2 years, at least 3 years, at least 4 years, at least 5 years, or more than 5 years. In some embodiments, ocular SBPs may have a shelf life of about 1 year at room temperature. In some embodiments, ocular SBPs may have a shelf life of about 2 years at room temperature. In some embodiments, ocular SBPs may have a shelf life of about 3 years at room temperature. In some embodiments, ocular SBPs may have a shelf life of about 4 years at room temperature. In some embodiments, ocular SBPs may have a shelf life of about 5 years at room temperature.

In some embodiments, ocular SBPs may be prepared to have desired residence time for their intended use. As used herein, the term "residence time" refers to the average length of time during which a substance (e.g., SBPs) is in a given location or condition. In some embodiments, enhanced residence time may enable convenient dosing for patients, as described in Zhu et al. (2008) Optometry and Vision Science 85 (8): E715-E725, the contents of which are herein incorporated by reference in their entirety. The residence time may be modulated via the viscosity of the SBP. In some embodiments the viscosity is about 10-100 cP. In some embodiments, the viscosity is about 20-80 cP. In some embodiments, the viscosity is about 30-60 cP. In some embodiments, higher viscosity of an ocular SBP may lead to a longer residence time of said ocular SBP, as described in Zhu et al. (2007) Current Eye Research 32 (3): 177-179, the contents of which are herein incorporated by reference in their entirety. These longer residence times may improve the symptoms benefit of an ocular indication (e.g. DED). In some embodiments, residence time of ocular SBP formulations described herein may vary from a few hours to several weeks. For example, residence time of SBP formulations may be about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 day, about 2 days, about 3 days, about 4 days, about 5 days, about 6 days, about 1 week, about 2 weeks, about 3 weeks, about 4 weeks, one month, 2 months, 6 months, 1 year, or longer than two years. In some embodiments, residence time of ocular SBP may be from about 4 hours to about 10 hours, from about 8 hours to about 12 hours, from about 10 hours to about 14 hours, from about 12 hours to about 16 hours, from about 15 hours to about 20 hours, from about 18 hours to about 22 hours, from about 20 to about 25 hours, from about 22 hours to about 26 hours, from about 24 hour to about 30 hours, from about 20 hour to about 28 hours, or from about 30 hours to about 40 hours. In one embodiment, residence time of an ocular SBP is about 24 hours. In some embodiments, sustained viscosity of an ocular SBP upon dilution may enable longer residence times and enhanced retention.

In some embodiments, ocular SBPs may be prepared to have desired degradation time for their intended use. As used herein, the term “degradation time” refers to the amount of time required for a substance to break down. In some embodiments, degradation times of ocular SBP formulations described herein may vary from a few hours to several weeks. For example, degradation time of ocular SBP formulations may be about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 day, about 2 days, about 3 days, about 4 days, about 5 days, about 6 days, about 1 week, about 2 weeks, about 3 weeks, about 4 weeks, one month, 2 months, 6 months, 1 year, or longer than two years. In some embodiments, degradation time of ocular SBPs may be from about 4 hours to about 10 hours, from about 8 hours to about 12 hours, from about 10 hours to about 14 hours, from about 12 hours to about 16 hours, from about 15 hours to about 20 hours, from about 18 hours to about 22 hours, from about 20 to about 25 hours, from about 22 hours to about 26 hours, from about 24 hour to about 30 hours, from about 20 hour to about 28 hours, or from about 30 hours to about 40 hours.

Delivery

SBPs may be delivered to cells, tissues, organs and/or organisms in naked form. As used herein in, “naked” delivery refers to delivery of an active agent with minimal or with no additional formulation or modification. Naked SBPs may be delivered to cells, tissues, organs and/or organisms using routes of administration known in the art and described herein. In some embodiments, naked delivery may include formulation in a simple buffer such as saline or PBS.

In some embodiments, SBPs may be prepared with one or more cell penetration agents, pharmaceutically acceptable carriers, delivery agents, bioerodible or biocompatible polymers, solvents, and/or sustained-release delivery depots. SBPs may be delivered to cells using routes of administration known in the art and described herein. In some embodiments, SBPs may be formulated for direct delivery to organs or tissues in any of several ways in the art including, but not limited to, direct soaking or bathing, via a catheter, by gels, powder, ointments, creams, gels, lotions, and/or drops, or by using substrates (e.g., fabric or biodegradable materials) coated or impregnated with SBPs.

Routes of Delivery

In some embodiments, SBP formulations may be administered by any route to achieve a therapeutically effective outcome.

These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intra-arterial (into an artery), intramuscular (into a muscle), intracranial (into the heart), intraosseous infusion (into the bone marrow), intrathecal (into the spinal canal), intraperitoneal, (infusion or injection into the peritoneum), intrasinal infusion, intravitreal, (through the eye), intravenous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

As a non-limiting example, the SBP is in the form of a hydrogel and the route of delivery is topical.

In one embodiment, the amount of the SBP in the formulation can be optimized for a particular Cmax value. When used for delivery (e.g., oral delivery) for small molecules or biologics, the Cmax may be decreased.

Detectable Agents and Labels

In some embodiments, SBP formulations may include detectable labels. As used herein, the term "detectable label" refers to any incorporated compound or entity that facilitates some form of identification. Detectable labels may include, but are not limited to various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}$F, $^{67}$Ga, $^{81}$mKr, $^{82}$Rb, $^{111}$In, $^{123}$I, $^{133}$Xe, $^{201}$Tl, $^{125}$I, $^{35}$S, $^{14}$C, $^{3}$H, or $^{99}$mTc (e.g., as pertechnetate (technetate (VII), $TcO^{4-}$)), contrast agents (e.g., gold, gold nanoparticles, gadolinium, chelated Gd, iron oxides, superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl) maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[1,3-dihydro-1,1-dimethyl-3-(3-sulfopropyl)-2H-benz [e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,ndiethylethanamine (1:1) (IR144); 5-chloro-2-[2-[3-[(5-chloro-3-ethyl-2 (3H)-benzothiazolylidene)ethylidene]-2-(diphenylamino)-1-cyclopenten-1-yl]ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (CIBACRON™ Brilliant Red 3B-A); rhodamine and derivatives (e.g., 6-carboxy-Xrhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable labels may include non-detectable precursors that becomes detectable upon activation (e.g., fluorogenic tetrazine-fluorophore constructs, tetrazine-BODIPY FL, tetrazine-Oregon Green 488, or tetrazine-BODIPY TMR-X) or enzyme activatable fluorogenic agents (e.g., PROSENSE® (VisEn Medical)). In vitro assays in which enzyme labeled compositions can be used include, but are not limited to, enzyme linked immunosorbent assays (ELISAs), immunoprecipitation assays, immunofluorescence, enzyme immunoassays (EIA), radioimmunoassays (RIA), and Western blot analysis.

In some embodiments, SBP formulations may include may fluorescein isothiocyanate (FITC) as a detectable label. In some embodiments, FITC is conjugated to processed silk. In some embodiments, the processed silk conjugated to FITC is silk fibroin. Conjugation of FITC to silk fibroin may be performed using the standard isothiocyanate coupling protocol. FITC can be attached to silk fibroin via the amine group. The labeled silk fibroin may be purified from the unconjugated fluorescein by gel filtration. The final ratio of labeled and unlabeled silk fibroin can be determined by measuring the absorbance at 280 nm and at 495 nm.

SBP formulations may contain both labeled SBP and free (unlabeled) SBP. In some embodiments, the ratio of labeled SBP to free (unlabeled) SBP may be about 50:1, about 20:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 7:3, about 2.5:1, about 2:1, about 1.5:1, about 1:1, about 1:1.5, about 1:2, about 1:2.5, about 3:7, about 1:3, about 1:3.5, about 1:4, about 1:4, about 1:4.5, about 1:5, about 1:5.5, about 1:6, about 1:7, about 1:7.5, about 1:8, about 1:8.5, about 1:9, about 1:9.5, about 1:10, about 1:20, or about 1:50. In some embodiments, the ratio of labeled SBP to free (unlabeled) SBP may be from about 10:1 to about 7:1, from about 8:1 to about 5:1, from about 6:1 to about 4:1, from about 5:1 to about 3:1, from about 4:1 to about 2:1, from about 3:1 to about 1.5:1, from about 2:1 to about 1:1, from about 1:1 to about 1:2, from about 1:1.5 to about 1:3, about 1:2 to about 1:4, from about 1:3 to about 1:5, from about 1:4 to about 1:6, from about 1:5 to about 1:8, or from about 1:7 to about 1:10.

In one embodiment, the SBP formulation contains 1% silk fibroin, wherein the ratio of FITC labeled silk fibroin and unlabeled silk fibroin is 4:6.

In one embodiment, the SBP formulation contains 1% silk fibroin, wherein the ratio of FITC labeled silk fibroin and unlabeled silk fibroin is 3:7.

In one embodiment, the SBP formulation contains 1% silk fibroin, wherein the ratio of FITC labeled silk fibroin and unlabeled silk fibroin is 2:8.

In one embodiment, the SBP formulation contains 1% silk fibroin, wherein the ratio of FITC labeled silk fibroin and unlabeled silk fibroin is 1:9.

Depot Administration

In some embodiments, SBPs may be administered by or be used to administer therapeutic agents by depot administration. As used herein, the term "depot" refers to a concentration of one or more agents in a particular region or in association with a composition or device. With depot administration, the one or more agents exit or diffuse from the concentration into surrounding areas. Agents administered by depot administration may be SBPs. In some embodiments, SBPs are depots for therapeutic agents, wherein the therapeutic agents exit or diffuse from the SBPs. In some embodiments, depots are solutions. In some embodiments, depots are gels or hydrogels. In some embodiments, depots are eye drops. In some embodiments, depot administration of an SBP may reduce the number of times a therapeutic agent needs to be administered. In some embodiments, depot administration of an SBP may replace oral administration of a therapeutic agent.

In some embodiments, SBP depots may be used for controlled release of therapeutic agents, wherein release is facilitated by diffusion. Such methods may include any of those described in United States Patent Publication Number US20170333351, the contents of which are herein incorporated by reference in their entirety. Therapeutic agent diffusion may be slowed (i.e., controlled) by SBP depots leading to extended release periods. Extended therapeutic agent release periods may enable longer administration periods. In some embodiments, administration periods are extended by from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 100%, from about 32% to about 105%, from about 34% to about 110%, from about 36% to about 115%, from about 38% to about 120%, from about 40% to about 125%, from about 42% to about 130%, from about 44% to about 135%, from about 46% to about 140%, from about 48% to about 145%, from about 50% to about 150%, from about 60% to about 175%, from about 70% to about 200%, from about 80% to about 225%, from about 90% to about 250%, from about 100% to about 275%, from about 110% to about 300%, from about 120% to about 325%, from about 130% to about 350%, from about 140% to about 375%, from about 150% to about 400%, from about 170% to about 450%, from about 190% to about 500%, from about 210% to about 550%, from about 230% to about 600%, from about 250% to about 650%, from about 270% to about 700%, from about 290% to about 750%, from about 310% to about 800%, from about 330% to about 850%, from about 350% to about 900%, from about 370% to about 950%, from about 390% to about 1000%, from about 410% to about 1050%, from about 430% to about 1100%, from about 450% to about 1500%, from about 480% to about 2000%, from about 510% to about 2500%, from about 540% to about 3000%, from about 570% to about 3500%, from about 600% to about 4000%, from about 630% to about 4500%, from about 660% to about 5000%, from about 690% to about 5500%, from about 720% to about 6000%, from about 750% to about 6500%, from about 780% to about 7000%, from about 810% to about 7500%, from about 840% to about 8000%, from about 870% to about 8500%, from about 900% to about 9000%, from about 930% to about 9500%, from about 960% to about 10000%, In some embodiments, the controlled release of a therapeutic agent for the treatment of a condition, disease, or indication may be facilitated by the degradation and/or dissolution of SBPs. Such methods may be carried according to those described in International Patent Application Publication Nos. WO2013126799, WO2017165922, and U.S. Pat. No. 8,530,625, the contents of each of which are herein incorporated by reference in their entirety. SBP degradation and/or dissolution may expose increasing amounts of therapeutic agents over time for treatment of therapeutic indications.

In some embodiments, therapeutic agent release from SBPs may be monitored via high performance liquid chromatography (HPLC), ultra-performance liquid chromatography (UPLC), and/or other methods known to those skilled in the art.

SBP hydrogels may be used to extend payload release periods (e.g., as shown for extended release of small molecule in International Patent Application Publication No. WO2017139684, the contents of which are herein incorporated by reference in their entirety. In some embodiments, SBP hydrogels are used to provide extended release of therapeutic agents (e.g., biological agents). Hydrogel networks may stabilize such agents and support their release as the hydrogel degrades. This effect serves to extend agent release and may be modulated by varying factors including processed silk molecular weight, concentration, excipient type, pH, and temperature. In some embodiments, processed silk molecular weight, concentration, excipient type, pH, and processing temperature used to prepare SBPs may be modulated to achieve desired payload release periods for specific therapeutic agents.

In some embodiments, SBPs may be lyophilized together with therapeutic agents. In some embodiments, combined lyophilization may induce further interactions between therapeutic agents and SBPs. These interactions may be maintained through SBP preparation and support extended payload release. Payload release may be dependent on SBP degradation and/or dissolution. In some embodiments, SBP β-sheet content is increased (e.g., via water annealing), thereby increasing SBP insolubility in water. Such SBPs may exhibit increased payload release periods. In some embodiments, these SBPs may include therapeutic agent stabilizing properties to extend administration periods and/or therapeutic agent half-life.

In some embodiments, SBPs described herein maintain and/or improve the controlled delivery of a therapeutic agent. In some embodiments, SBPs lengthen payload release period and/or administration period by at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. In some embodiments, SBPs lengthen payload release period and/or administration period by at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, or at least 3 months.

In some embodiments, SBPs may be used to modulate depot release of therapeutic agents. Some SBPs may release therapeutic agents according to near zero-order kinetics. In some embodiments, SBPs may release therapeutic agents according to first-order kinetics. In some embodiments, therapeutic agent release rate may be modulated by preparing SBP depots with modification of one or more of density, loading, drying method, silk fibroin molecular weight, and silk fibroin concentration.

In some embodiments, SBPs are prepared to release from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 100% of the total amount of therapeutic or macromolecular therapeutic agent to be delivered.

II. Therapeutic Applications

In some embodiments, SBP formulations may be used in a variety of therapeutic applications. As used herein, the term "therapeutic application" refers to any method related to restoring or promoting the health, nutrition, and/or well-being of a subject; supporting or promoting reproduction in a subject; or treating, preventing, mitigating, alleviating, curing, or diagnosing a disease, disorder, or condition. As used herein, the term "condition" refers to a physical state of wellbeing. Therapeutic applications may include, but are not limited to, medical applications, surgical applications, and veterinary applications. As used herein, the term "medical application" refers to any method or use that involves treating, diagnosing, and/or preventing disease according to the science of medicine. "Surgical applications" refer to methods of treatment and/or diagnosis that involve operation on a subject, typically requiring incision and the use of instruments. "Veterinary applications" refer to therapeutic applications where the subject is a non-human animal. In some embodiments, therapeutic applications may include, but are not limited to, experimental, diagnostic, or prophylactic applications. In some embodiments, therapeutic applications include preparation and/or use of therapeutic devices. As used herein, the term "therapeutic device" refers to any article prepared or modified for therapeutic use.

SBP formulations used for therapeutic applications may include or may be combined with one or more pharmaceutical compositions, implants, therapeutic agents, coatings, excipients, or devices. In some embodiments, SBP formulations facilitate the delivery and/or controlled release of therapeutic agent payloads. In some embodiments, SBP formulations described herein may be used to stabilize therapeutic agents. Some SBP formulations may be used as tools, materials, or devices in therapeutic applications. Such SBP formulations may include, but are not limited to, delivery vehicles, and scaffolds. In some embodiments, therapeutic applications utilizing SBP formulations may include gene therapy. As used herein, the term "gene therapy" refers to the use of genetic transplantation to address disease and/or genetic disorders. In some embodiments, therapeutic applications utilizing SBP formulations may include gene editing. As used herein, the term "gene editing" refers to any process used to alter a DNA gene sequence at the level of individual nucleotides. In some embodiments, therapeutic applications utilizing SBP formulations may include immunotherapy. As used herein, the term "immunotherapy" refers to treatment of a disease, condition, or indication by modulating the immune system. In some embodiments, therapeutic applications utilizing SBP formulations may include diagnostic applications. In some embodiments, SBP formulations are used as diagnostic tools. In some embodiments, therapeutic applications utilizing SBP formulations may include tissue engineering. In some embodiments, therapeutic applications utilizing SBP formulations may include cell culture. In some embodiments, therapeutic applications utilizing SBP formulations may include surgical applications (e.g. incorporation into surgical tools, devices, and fabrics). In some embodiments, SBP formulations may be or may be included in therapeutic devices. In some embodiments, therapeutic devices may be coated with SBP formulations described herein.

Therapeutic applications of the present disclosure may be applied to a variety of subjects. As used herein, the term "subject" refers to any entity to which a particular process or activity relates to or is applied. Subjects of therapeutic applications described herein may be human or non-human. Human subjects may include humans of different ages, genders, races, nationalities, or health status. Non-human subjects may include non-human animal subjects (also simply referred to herein as "animal subjects"). Animal subjects may be non-human vertebrates or invertebrates. Some animal subjects may be wild type or genetically modified organisms (e.g., transgenic). In some embodiments, subjects include patients. As used herein, the term "patient" refers to a subject seeking treatment, in need of treatment, requiring treatment, receiving treatment, expecting treatment, or who is under the care of a trained (e.g., licensed) professional for a particular disease, disorder, and/or condition.

In some embodiments, SBP formulations may be used to address one or more therapeutic indications. As used herein, the term "therapeutic indication" refers to a disease, disorder, condition, or symptom that may be cured, reversed, alleviated, stabilized, improved, or otherwise addressed through some form of therapeutic intervention (e.g., administration of a therapeutic agent or method of treatment). As a non-limiting example, the therapeutic indication is ophthalmology, ophthalmology-related disease and/or disorder, otology, or an otology-related disease and/or disorder. As a non-limiting example, the ophthalmology-related disease and/or disorder is dry eye disease.

SBP formulation treatment of therapeutic indications may include contacting subjects with SBPs. SBP formulations may include therapeutic agents (e.g., any of those described herein) as cargo or payloads for treatment. In some embodiments, payload release may occur over a period of time (the "payload release period"). The payload release rate and/or length of the payload release period may be modulated by SBP components or methods of preparation.

In some embodiments, ocular SBPs may be used as an anti-inflammatory treatment for dry eye disease, as described in Kim et al. (2017) Scientific Reports 7:44364, the contents of which are herein incorporated by reference in their entirety. It has been demonstrated that the administration of 0.1 to 0.5% silk fibroin solutions in a mouse model of dry eye disease enhances corneal smoothness and tear production, while reducing the amount of inflammatory markers detected.

Therapeutic Agents

In some embodiments, therapeutic applications involve the use of SBP formulations that are therapeutic agents or are combined with one or more therapeutic agents. As used herein, the term "therapeutic agent" refers to any substance used to restore or promote the health and/or wellbeing of a subject and/or to treat, prevent, alleviate, cure, or diagnose a disease, disorder, or condition. Examples of therapeutic agents include, but are not limited to, adjuvants, analgesic agents, antiallergic agents, antiangiogenic agents, antiarrhythmic agents, antibacterial agents, antibiotics, antibodies, anticancer agents, anticoagulants, antidementia agents, antidepressants, antidiabetic agents, antigens, antihypertensive agents, anti-infective agents, anti-inflammatory agents, antioxidants, antipyretic agents, anti-rejection agents, antiseptic agents, antitumor agents, antiulcer agents, antiviral agents, biological agents, birth control medication, carbohydrates, cardiotonics, cells, chemotherapeutic agents, cholesterol lowering agents, cytokines, endostatins, enzymes, fats, fatty acids, genetically engineered proteins, glycoproteins, growth factors, health supplements, hematopoietics, herbal preparations, hormones, hypotensive diuretics, immunological agents, inorganic synthetic pharmaceutical drugs, ions, lipoproteins, metals, minerals, nanoparticles, naturally derived proteins, NSAIDs, nucleic acids, nucleotides, organic synthetic pharmaceutical drugs, oxidants, peptides, pills, polysaccharides, proteins, protein-small molecule conjugates or complexes, psychotropic agents, small molecules, sodium channel blockers, statins, steroids, stimulants, therapeutic agents for osteoporosis, therapeutic combinations, thrombopoietics, tranquilizers, vaccines, vasodilators, VEGF-related agents, veterinary agents, viruses, virus particles, and vitamins. In some embodiments, SBP therapeutics and methods of delivery may include any of those taught in International Publication Numbers WO2017139684, WO2010123945, WO2017123383, or United States Publication Numbers US20170340575, US20170368236, and US20110171239 the contents of each of which are herein incorporated by reference in their entirety. In some embodiments, SBPs may be used to encapsulate, store, stabilize, preserve, and/or release, in a controlled manner, therapeutic agents. For example, using silk fibroin micrococoons as delivery vehicles for small molecules has been described in Shimanovich et al. (Shimanovich et al. (2015) Nature Communications 8:15902, the contents of which are herein incorporated by reference in their entirety). In some embodiments, SBP formulations may be prepared with therapeutic agents selected from any of those listed in Table 4. In the Table, example categories are indicated for each therapeutic agent. These categories are not limiting and each therapeutic agent may fall under multiple categories (e.g., any of the categories of therapeutic agents described herein).

TABLE 4

| Therapeutic agents | |
|---|---|
| Agent | Category |
| opium | analgesic agent |
| opiate | analgesic agent |
| doxycycline monohydrate | antibacterial agent |
| tigecycline | antibacterial agent |
| doxycycline hyclate | antibacterial agent |
| vibramycin | antibacterial agent |
| doxycycline hydrochloride hemiethanolate hemihydrate | antibacterial agent |
| doxycycline calcium | antibacterial agent |
| abciximab | antibody |
| adalimumab | antibody |
| adalimumab-atto | antibody |
| alefacept | antibody |
| alemtuzumab | antibody |
| antibody fragment | antibody |
| antibody-drug conjugate | antibody |
| atezolizumab | antibody |
| basiliximab | antibody |
| belimumab | antibody |
| bezlotoxumab | antibody |
| bivalent antibody | antibody |
| canakinumab | antibody |
| certolizumab pegol | antibody |
| cetuximab | antibody |
| daclizumab | antibody |
| denosumab | antibody |
| efalizumab | antibody |
| golimumab | antibody |
| inflectra | antibody |
| ipilimumab | antibody |
| ixekizumab | antibody |
| monoclonal antibody | antibody |
| monovalent antibody | antibody |
| multivalent antibody | antibody |
| natalizumab | antibody |
| nivolumab | antibody |
| obiltoxaxamab | antibody |
| olaratumab | antibody |
| omalizumab | antibody |
| palivizumab | antibody |
| panitumumab | antibody |
| pembrolizumab | antibody |
| polyclonal antibody | antibody |
| reslizumab | antibody |
| rituximab | antibody |
| secukinumab | antibody |

TABLE 4-continued

| Therapeutic agents | |
|---|---|
| Agent | Category |
| tocilizumab | antibody |
| trastuzumab | antibody |
| ustekinumab | antibody |
| autoantigen | antigen |
| endogenous antigen | antigen |
| exogenous antigen | antigen |
| neoantigen | antigen |
| tumor antigen | antigen |
| viral antigen | antigen |
| exogenous antigen | antigen |
| endogenous antigen | antigen |
| autoantigen | antigen |
| neoantigen | antigen |
| viral antigen | antigen |
| tumor antigen | antigen |
| xenogenus (heterologous) antigen | antigen |
| autologous antigen | antigen |
| idiotypic antigen | antigen |
| allogenic (homologous) antigen | antigen |
| epitope | antigen |
| tumor-specific antigen | antigen |
| tumor-associated antigen | antigen |
| neo-epitope | antigen |
| allergen | antigen |
| superantigen | antigen |
| tolerogen | antigen |
| immunoglobulin-binding protein | antigen |
| t-dependent antigen | antigen |
| t-independent antigen | antigen |
| immunodominant antigen | antigen |
| COX-1 inhibitor | anti-inflammatory agent |
| COX-2 inhibitor | anti-inflammatory agent |
| bisbiguanides polymeric quaternary ammonium compound | antiseptic agent |
| chlorhexidine | antiseptic agent |
| chlorinated phenol | antiseptic agent |
| ethanol | antiseptic agent |
| hydrogen peroxide | antiseptic agent |
| lower alcohol | antiseptic agent |
| peroxides | antiseptic agent |
| propanol | antiseptic agent |
| quaternary amine surfactant | antiseptic agent |
| silver complex | antiseptic agent |
| small molecule quaternary ammonium compound | antiseptic agent |
| 5-FU Enhancer | anticancer agent |
| 9-AC | anticancer agent |
| abraxane | anticancer agent |
| actinomycin | anticancer agent |
| AG2037 | anticancer agent |
| AG3340 | anticancer agent |
| Aggrecanase Inhibitor | anticancer agent |
| alitretinoin | anticancer agent |
| alkylating agent | anticancer agent |
| Aminoglutethimide | anticancer agent |
| Amsacrine (m-AMSA) | anticancer agent |
| anthracycline | anticancer agent |
| antimicrobial peptide | anticancer agent |
| Asparaginase | anticancer agent |
| Azacitidine | anticancer agent |
| azathioprine | anticancer agent |
| Batimastat (BB94) | anticancer agent |
| BAY 12-9566 | anticancer agent |
| BCH-4556 | anticancer agent |
| bexarotene | anticancer agent |
| Bis-Naphtalimide | anticancer agent |
| bleomycin | anticancer agent |
| Busulfan | anticancer agent |
| Capecitabine | anticancer agent |
| Carboplatin | anticancer agent |
| Carmustaine + Polifepr Osan | anticancer agent |
| cdk4/cdk2 inhibitor | anticancer agent |
| chlorambucil | anticancer agent |
| CI-994 | anticancer agent |
| Cisplatin | anticancer agent |
| Cladribine | anticancer agent |
| CS-682 | anticancer agent |
| cyclophosphamide | anticancer agent |

TABLE 4-continued

| Therapeutic agents | |
|---|---|
| Agent | Category |
| cytarabine | anticancer agent |
| Cytarabine HCl | anticancer agent |
| cytoskeletal disruptor | anticancer agent |
| D2163 | anticancer agent |
| dacarbazine | anticancer agent |
| Dactinomycin | anticancer agent |
| daunorubicin | anticancer agent |
| Daunorubicin HCl | anticancer agent |
| DepoCyt | anticancer agent |
| Dexifosamide | anticancer agent |
| Docetaxel | anticancer agent |
| Dolastain | anticancer agent |
| Doxifluridine | anticancer agent |
| Doxorubicin | anticancer agent |
| DX8951f | anticancer agent |
| E 7070 | anticancer agent |
| EGFR | anticancer agent |
| Epirubicin | anticancer agent |
| epothilone | anticancer agent |
| erlotinib | anticancer agent |
| Estramustine phosphate sodium | anticancer agent |
| Etoposide (VP16-213) | anticancer agent |
| Farnesyl Transferase Inhibitor | anticancer agent |
| FK 317 | anticancer agent |
| Flavopiridol | anticancer agent |
| Floxuridine | anticancer agent |
| Fludarabine | anticancer agent |
| Fluorouracil (5-FU) | anticancer agent |
| Flutamide | anticancer agent |
| Fragyline | anticancer agent |
| gefitinib | anticancer agent |
| Gemcitabine | anticancer agent |
| Hexamethylmelamine (HMM) | anticancer agent |
| histone deacetylase inhibitor | anticancer agent |
| hydroxyurea | anticancer agent |
| Hydroxyurea (hydroxycarbamide) | anticancer agent |
| darubicin | anticancer agent |
| Ifosfamide | anticancer agent |
| imatinib | anticancer agent |
| Interferon Alfa-2a | anticancer agent |
| Interferon Alfa-2b | anticancer agent |
| Irinotecan | anticancer agent |
| ISI 641 | anticancer agent |
| kinase inhibitor | anticancer agent |
| Krestin | anticancer agent |
| Lemonal DP 2202 | anticancer agent |
| Leuprolide acetate (LHRH-releasing factor analogue) | anticancer agent |
| Levamisole | anticancer agent |
| LiGLA (lithium-gamma linolenate) | anticancer agent |
| Lodine Seed | anticancer agent |
| Lometexol | anticancer agent |
| Lomustine (CCNU) | anticancer agent |
| Marimistat | anticancer agent |
| mechlorethamine | anticancer agent |
| Mechlorethamine HCl (nitrogen mustard) | anticancer agent |
| Megestrol acetate | anticancer agent |
| Meglamine GLA | anticancer agent |
| melphalan | anticancer agent |
| Mercaptopurine | anticancer agent |
| Mesna | anticancer agent |
| methotrexate | anticancer agent |
| methyl glyoxal bis-guanylhydrazone (MGBG) | anticancer agent |
| Mitoguazone (methyl-GAG | anticancer agent |
| Mitotane (o.p'-DDD) | anticancer agent |
| Mitoxantrone HCl | anticancer agent |
| mitozantrone | anticancer agent |
| MMI 270 | anticancer agent |
| MMP | anticancer agent |
| MTA/LY 231514 | anticancer agent |
| MTX | anticancer agent |
| nitrosourea | anticancer agent |
| nucleotide analogue | anticancer agent |
| nucleotide precursor analogue | anticancer agent |
| ODN 698 | anticancer agent |
| OK-432 | anticancer agent |
| Oral Platinum | anticancer agent |

TABLE 4-continued

| Therapeutic agents | |
|---|---|
| Agent | Category |
| Oral Taxoid | anticancer agent |
| oxaliplatin | anticancer agent |
| paclitaxel | anticancer agent |
| PARP Inhibitor | anticancer agent |
| PD 183805 | anticancer agent |
| Pentostatin (2' deoxycoformycin) | anticancer agent |
| PKC 412 | anticancer agent |
| platinum based chemotherapeutic | anticancer agent |
| Plicamycin | anticancer agent |
| Procarbazine HCl | anticancer agent |
| PSC 833 | anticancer agent |
| Ralitrexed | anticancer agent |
| RAS Farnesyl Transferase Inhibitor | anticancer agent |
| RAS Oncogene Inhibitor | anticancer agent |
| retinoids | anticancer agent |
| romidepsin | anticancer agent |
| Semustine (methyl-CCNU) | anticancer agent |
| Streptozocin | anticancer agent |
| Suramin | anticancer agent |
| tafluposide | anticancer agent |
| Tamoxifen citrate | anticancer agent |
| taxane | anticancer agent |
| Taxane Analog | anticancer agent |
| taxotere | anticancer agent |
| Temozolomide | anticancer agent |
| Teniposide (VM-26) | anticancer agent |
| Thioguanine | anticancer agent |
| Thiotepa | anticancer agent |
| tioguanine | anticancer agent |
| topoisomerase I inhibitor | anticancer agent |
| topoisomerase II inhibitor | anticancer agent |
| Topotecan | anticancer agent |
| tretinoin | anticancer agent |
| Tyrosine Kinase | anticancer agent |
| UFT (Tegafur/Uracil) | anticancer agent |
| Valrubicin | anticancer agent |
| vemurafenib | anticancer agent |
| vinblastine | anticancer agent |
| Vinblastine sulfate | anticancer agent |
| vinca alkaloid | anticancer agent |
| vinca alkaloid derivative | anticancer agent |
| vincristine | anticancer agent |
| vindesine | anticancer agent |
| Vindesine sulfate | anticancer agent |
| vinorelbine | anticancer agent |
| vismodegib | anticancer agent |
| vorinostat | anticancer agent |
| VX-710 | anticancer agent |
| VX-853 | anticancer agent |
| YM 116 | anticancer agent |
| ZD 0101 | anticancer agent |
| ZD 0473/Anormed | anticancer agent |
| ZD 1839 | anticancer agent |
| ZD 9331 | anticancer agent |
| 2-dimensional tissue | biological |
| 3-dimensional tissue | biological |
| adenovirus | biological |
| adipose tissue-derived mesenchymal stem cell | biological |
| bacteria | biological |
| bone mesenchymal stem cell | biological |
| cardiac mesenchymal stem cell | biological |
| cells | biological |
| chicken dorsal root ganglion | biological |
| complex carbohydrate | biological |
| deoxyribonucleic acid | biological |
| embryonic stem cell | biological |
| fibroblast | biological |
| fungi | biological |
| gene | biological |
| hematopoietic stem cell | biological |
| human corneal epithelial cell | biological |
| human corneal stromal stem cell | biological |
| human small intestinal enteroids | biological |
| lentivirus | biological |
| limbal epithelial stem cell | biological |
| lipids | biological |

TABLE 4-continued

| Therapeutic agents | |
|---|---|
| Agent | Category |
| macromolecule | biological |
| mesenchymal stem cell | biological |
| microbe | biological |
| microbiome | biological |
| microorganism | biological |
| neural stem cells | biological |
| oligonucleotide | biological |
| oral keratinocyte | biological |
| organ | biological |
| organism | biological |
| periodontal ligament stem cells | biological |
| polymer | biological |
| probiotic | biological |
| proteins | biological |
| ribonucleic acid | biological |
| spore | biological |
| stem cell | biological |
| symbiote | biological |
| T cell | biological |
| tissue | biological |
| transfected fibroblast | biological |
| vesicle | biological |
| viral particle | biological |
| virus | biological |
| abequose | carbohydrate |
| arabinose | carbohydrate |
| cellobiose | carbohydrate |
| derivative of a monosaccharide | carbohydrate |
| disaccharide | carbohydrate |
| fructose | carbohydrate |
| fucose | carbohydrate |
| galactosamine | carbohydrate |
| galactose | carbohydrate |
| glucosamine | carbohydrate |
| glucose | carbohydrate |
| glucuronic acid | carbohydrate |
| iduronic acid | carbohydrate |
| lactose | carbohydrate |
| maltose | carbohydrate |
| mannose | carbohydrate |
| monosaccharide | carbohydrate |
| muramic acid | carbohydrate |
| N-acetylgalactosamine | carbohydrate |
| N-acetylglucosamine | carbohydrate |
| N-acetylmuramic acid | carbohydrate |
| N-acetylneuraminic acid | carbohydrate |
| oligosaccharide | carbohydrate |
| rhamnose | carbohydrate |
| ribose | carbohydrate |
| sialic acid | carbohydrate |
| sucrose | carbohydrate |
| trehalose | carbohydrate |
| xylose | carbohydrate |
| adipose tissue-derived mesenchymal stem cell | cell |
| periodontal ligament stem cell | cell |
| human small intestinal enteroid | cell |
| oral keratinocyte | cell |
| fibroblast | cell |
| transfected fibroblast | cell |
| 2-dimensional tissue | cell |
| 3-dimensional tissue | cell |
| T cell | cell |
| embryonic stem cell | cell |
| neural stem cell | cell |
| mesenchymal stem cell | cell |
| hematopoietic stem cell | cell |
| osteoblast | cell |
| osteoclast | cell |
| osteocyte | cell |
| neuron | cell |
| glial cell | cell |
| chondrocyte | cell |
| photoreceptor cell | cell |
| cone cell | cell |
| rod cell | cell |
| corneal cell | cell |

TABLE 4-continued

| Therapeutic agents | |
|---|---|
| Agent | Category |
| keratocyte | cell |
| corneal endothelial cell | cell |
| brain-derived neurotrophic factor (BDNF) | cytokine |
| cardiotrophin 1 (CTF1) | cytokine |
| cardiotrophin-like cytokine factor 1 (CLCF1) | cytokine |
| cell signal molecule | cytokine |
| chemokine | cytokine |
| ciliary neurotrophic factor (CNTF) | cytokine |
| erythropoietin (EPO) | cytokine |
| fibroblast growth factor acidic (FGFa) | cytokine |
| fibroblast growth factor basic (FGFb) | cytokine |
| IL- 18 | cytokine |
| IL-10 | cytokine |
| IL-11 | cytokine |
| IL-12 | cytokine |
| IL-13 | cytokine |
| IL-14 | cytokine |
| IL-15 | cytokine |
| IL-16 | cytokine |
| IL-17 | cytokine |
| IL-19 | cytokine |
| IL-1α | cytokine |
| IL-1β | cytokine |
| IL-2 | cytokine |
| IL-20 | cytokine |
| IL-21 | cytokine |
| IL-22 | cytokine |
| IL-23 | cytokine |
| IL-27 | cytokine |
| IL-3 | cytokine |
| IL-4 | cytokine |
| IL-5 | cytokine |
| IL-6 | cytokine |
| IL-7 | cytokine |
| IL-8 | cytokine |
| IL-9 | cytokine |
| interferon | cytokine |
| interferon-α1 | cytokine |
| interleukin | cytokine |
| interleukin-1 receptor antagonist (IL-1RA) | cytokine |
| keratinocyte growth factor 1 | cytokine |
| keratinocyte growth factor 2 (KGF) | cytokine |
| kit ligand/stem cell factor (KITLG) | cytokine |
| leptin (LEP) | cytokine |
| leukemia inhibitory factor (LIF) | cytokine |
| lymphokine | cytokine |
| matrix metalloproteinase (MMP) | cytokine |
| monokine | cytokine |
| nerve growth factor (NGF) | cytokine |
| oncostatin M (OSM) | cytokine |
| prolactin (PRL) | cytokine |
| TGFβ | cytokine |
| tissue inhibitor of metalloproteinase (TIMP) | cytokine |
| transforming growth factor (TGF) α (TGFα) | cytokine |
| tumor necrosis factor α (TNFα) | cytokine |
| diacylglycerol | fat |
| diglycerides | fat |
| ergosterol | fat |
| fat-soluble vitamin | fat |
| glycerol monostearate | fat |
| glycerophospholipid | fat |
| glyceryl hydroxystearate | fat |
| hopanoid | fat |
| hydroxysteroid | fat |
| monoglyceride | fat |
| monolaurin | fat |
| oil | fat |
| palmitin | fat |
| phosphatidic acid | fat |
| phosphatidylcholine | fat |
| phosphatidylethanolamine | fat |
| phosphatidylserine | fat |
| phosphoinositides | fat |
| phospholipids | fat |
| phosphosphingolipids | fat |
| phytosterol | fat |

TABLE 4-continued

| Therapeutic agents | |
|---|---|
| Agent | Category |
| sphingolipid | fat |
| sphingomyelin | fat |
| stearin | fat |
| sterol | fat |
| triglyceride | fat |
| triolein | fat |
| wax | fat |
| fatty acid | fatty acid |
| essential fatty acid | fatty acid |
| omega-3 fatty acid | fatty acid |
| lineoleic acid | fatty acid |
| omega-6 fatty acid | fatty acid |
| docosahexaenoic acid | fatty acid |
| arachidonic acid | fatty acid |
| omega-9 fatty acid | fatty acid |
| Hexadecatrienoic acid (HTA) | fatty acid |
| α-Linolenic acid (ALA) | fatty acid |
| Stearidonic acid (SDA) | fatty acid |
| Eicosatrienoic acid (ETE) | fatty acid |
| Eicosatetraenoic acid (ETA) | fatty acid |
| Eicosapentaenoic acid (EPA) | fatty acid |
| Heneicosapentaenoic acid (HPA) | fatty acid |
| Docosapentaenoic acid (DPA), | fatty acid |
| Clupanodonic acid | fatty acid |
| Docosahexaenoic acid (DHA) | fatty acid |
| Tetracosapentaenoic acid | fatty acid |
| Tetracosahexaenoic acid (Nisinic acid) | fatty acid |
| 5-Dodecenoic acid | fatty acid |
| 7-Tetradecenoic acid | fatty acid |
| 9-Hexadecenoic acid | fatty acid |
| 11-Octadecenoic acid | fatty acid |
| 13-Eicosenoic acid | fatty acid |
| 15-Docosenoic acid | fatty acid |
| 17-Tetracosenoic acid | fatty acid |
| Linoleic acid (LA) | fatty acid |
| Gamma-linolenic acid (GLA) | fatty acid |
| Calendic acid | fatty acid |
| Eicosadienoic acid | fatty acid |
| Dihomo-gamma-linolenic acid (DGLA) | fatty acid |
| Arachidonic acid (AA, ARA) | fatty acid |
| Docosadienoic acid | fatty acid |
| Adrenic acid | fatty acid |
| Osbond acid | fatty acid |
| Tetracosatetraenoic acid | fatty acid |
| Tetracosapentaenoic acid | fatty acid |
| oleic acid | fatty acid |
| elaidic acid | fatty acid |
| gondoic acid | fatty acid |
| mead acid | fatty acid |
| erucic acid | fatty acid |
| nervonic acid | fatty acid |
| ximenic acid | fatty acid |
| bone morphogenic protein | protein |
| bone morphogenic-like protein | protein |
| epidermal growth factor | protein |
| fibroblast growth factor | protein |
| insulin like growth factor I | protein |
| insulin like growth factor II | protein |
| transforming growth factor | protein |
| biotin (vitamin B7) | health supplement |
| iodine | health supplement |
| niacin (vitamin B3) | health supplement |
| pantothenic acid (vitamin B5) | health supplement |
| phosphorus | health supplement |
| riboflavin (vitamin B2) | health supplement |
| selenium | health supplement |
| thiamine (vitamin B1) | health supplement |
| vanadium | health supplement |
| vitamin A | health supplement |
| vitamin B | health supplement |
| vitamin B12 | health supplement |
| vitamin B6 | health supplement |
| vitamin B9 | health supplement |
| vitamin C | health supplement |
| vitamin D | health supplement |
| vitamin E | health supplement |

TABLE 4-continued

| Therapeutic agents | |
|---|---|
| Agent | Category |
| vitamin K | health supplement |
| allspice berry essential oil | herbal preparation |
| angelica seed essential oil | herbal preparation |
| anise seed essential oil | herbal preparation |
| basil | herbal preparation |
| basil essential oil | herbal preparation |
| bay essential oil | herbal preparation |
| bay laurel | herbal preparation |
| bay laurel essential oil | herbal preparation |
| bergamot essential oil | herbal preparation |
| blood orange essential oil | herbal preparation |
| borage | herbal preparation |
| camphor essential oil | herbal preparation |
| caraway | herbal preparation |
| caraway seed essential oil | herbal preparation |
| cardamom seed essential oil | herbal preparation |
| carrot seed essential oil | herbal preparation |
| cassia essential oil | herbal preparation |
| catnip | herbal preparation |
| catnip essential oil | herbal preparation |
| cedarwood essential oil | herbal preparation |
| celery seed essential oil | herbal preparation |
| chamomile german essential oil | herbal preparation |
| chamomile roman essential oil | herbal preparation |
| chervil | herbal preparation |
| chives | herbal preparation |
| cilantro | herbal preparation |
| cinnamon bark essential oil | herbal preparation |
| cinnamon leaf essential oil | herbal preparation |
| citronella essential oil | herbal preparation |
| clary sage essential oil | herbal preparation |
| clove bud essential oil | herbal preparation |
| cold infusion | herbal preparation |
| compresses | herbal preparation |
| cordial | herbal preparation |
| coriander seed essential oil | herbal preparation |
| cumin | herbal preparation |
| cypress essential oil | herbal preparation |
| decoctions | herbal preparation |
| dill | herbal preparation |
| elemi essential oil | herbal preparation |
| epazote | herbal preparation |
| essential oils | herbal preparation |
| eucalyptus essential oil | herbal preparation |
| fennel | herbal preparation |
| fennel essential oil | herbal preparation |
| fir needle essential oil | herbal preparation |
| flower essence | herbal preparation |
| frankincense essential oil | herbal preparation |
| garlic | herbal preparation |
| geranium essential oil | herbal preparation |
| ginger essential oil | herbal preparation |
| granule | herbal preparation |
| grapefruit pink essential oil | herbal preparation |
| helichrysum essential oil | herbal preparation |
| herbal wine | herbal preparation |
| hop essential oil | herbal preparation |
| hyssop essential oil | herbal preparation |
| jasmine absolute oil | herbal preparation |
| juniper berry essential oil | herbal preparation |
| labdanum essential oil | herbal preparation |
| lavender | herbal preparation |
| lavender absolute oil | herbal preparation |
| lemon balm | herbal preparation |
| lemon essential oil | herbal preparation |
| lemon verbena | herbal preparation |
| lemongrass | herbal preparation |
| lemongrass essential oil | herbal preparation |
| lime essential oil | herbal preparation |
| lovage | herbal preparation |
| magnolia essential oil | herbal preparation |
| mandarin essential oil | herbal preparation |
| margoram essential oil | herbal preparation |
| marjoram | herbal preparation |
| Melissa essential oil | herbal preparation |
| mints | herbal preparation |

TABLE 4-continued

| Therapeutic agents | |
|---|---|
| Agent | Category |
| mugward essential oil | herbal preparation |
| myrrh essential oil | herbal preparation |
| myrtle essential oil | herbal preparation |
| nasturtium | herbal preparation |
| neroli essential oil | herbal preparation |
| niaouli essential oil | herbal preparation |
| nutmeg essential oil | herbal preparation |
| ointment | herbal preparation |
| orange sweet essential oil | herbal preparation |
| oregano | herbal preparation |
| oregano essential oil | herbal preparation |
| palmarosa essential oil | herbal preparation |
| parsley | herbal preparation |
| patchouli essential oil | herbal preparation |
| pennyroyal essential oil | herbal preparation |
| pepper black essential oil | herbal preparation |
| peppermint essential oil | herbal preparation |
| petitgram essential oil | herbal preparation |
| pine needle essential oil | herbal preparation |
| pink lotus absolute oil | herbal preparation |
| poultice | herbal preparation |
| radiata essential oil | herbal preparation |
| ravensara essential oil | herbal preparation |
| rose absolute oil | herbal preparation |
| rose essential oil | herbal preparation |
| rosemary | herbal preparation |
| rosemary essential oil | herbal preparation |
| rosewood essential oil | herbal preparation |
| sage | herbal preparation |
| sage essential oil | herbal preparation |
| salad burnet | herbal preparation |
| salve | herbal preparation |
| sambac absolute oil | herbal preparation |
| sandalwood essential oil | herbal preparation |
| savory | herbal preparation |
| scented geranium | herbal preparation |
| sitz bath | herbal preparation |
| soak | herbal preparation |
| sorrel | herbal preparation |
| spearmint essential oil | herbal preparation |
| spikenard essential oil | herbal preparation |
| spruce essential oil | herbal preparation |
| star anise essential oil | herbal preparation |
| suppository | herbal preparation |
| sweet annie essential oil | herbal preparation |
| syrup | herbal preparation |
| tangerine essential oil | herbal preparation |
| tarragon | herbal preparation |
| tea | herbal preparation |
| tea tree essential oil | herbal preparation |
| thyme | herbal preparation |
| thyme red essential oil | herbal preparation |
| tincture | herbal preparation |
| verbena essential oil | herbal preparation |
| vetiver essential oil | herbal preparation |
| white lotus absolute oil | herbal preparation |
| wintergreen essential oil | herbal preparation |
| wormwood essential oil | herbal preparation |
| yarrow essential oil | herbal preparation |
| ylang essential oil | herbal preparation |
| 3-ketodesogestrel | hormone |
| allopregnanolone | hormone |
| androgen | hormone |
| androstenediol | hormone |
| androstenedione | hormone |
| chlormadinone acetate | hormone |
| cholesterol | hormone |
| conjugated estrogen | hormone |
| dehydroepiandrosterone | hormone |
| dexamethasone | hormone |
| dihydrotestosterone | hormone |
| drospirorenone | hormone |
| estradiol ester | hormone |
| estradiols | hormone |
| estriol | hormone |
| estriol succinate | hormone |

TABLE 4-continued

| Therapeutic agents | |
|---|---|
| Agent | Category |
| estrogen | hormone |
| estrone | hormone |
| estrone sulfate | hormone |
| ethinyl estradiol | hormone |
| gestodene | hormone |
| glucocoriticoid | hormone |
| levonorgestrel | hormone |
| mestranol | hormone |
| mineralocorticoid | hormone |
| norethisterone acetate | hormone |
| norgestrel | hormone |
| polyestriol phosphate | hormone |
| progesterone | hormone |
| progestogen | hormone |
| testosterone | hormone |
| calcium oxide | ion, metal, or mineral |
| iron oxide | ion, metal, or mineral |
| phosphorus oxide | ion, metal, or mineral |
| iodine oxide | ion, metal, or mineral |
| magnesium oxide | ion, metal, or mineral |
| zinc oxide | ion, metal, or mineral |
| selenium oxide | ion, metal, or mineral |
| copper oxide | ion, metal, or mineral |
| manganese oxide | ion, metal, or mineral |
| chromium oxide | ion, metal, or mineral |
| molybdenum oxide | ion, metal, or mineral |
| gold oxide | ion, metal, or mineral |
| potassium oxide | ion, metal, or mineral |
| nickel oxide | ion, metal, or mineral |
| silicon oxide | ion, metal, or mineral |
| vanadium oxide | ion, metal, or mineral |
| tin oxide | ion, metal, or mineral |
| calcium | ion, metal, or mineral |
| chloride | ion, metal, or mineral |
| chromium | ion, metal, or mineral |
| copper | ion, metal, or mineral |
| gold | ion, metal, or mineral |
| iron | ion, metal, or mineral |
| magnesium | ion, metal, or mineral |
| manganese | ion, metal, or mineral |
| metal oxide | ion, metal, or mineral |
| molybdenum | ion, metal, or mineral |
| nickel | ion, metal, or mineral |
| potassium | ion, metal, or mineral |
| silicon | ion, metal, or mineral |
| silver | ion, metal, or mineral |
| silver oxide | ion, metal, or mineral |
| tin | ion, metal, or mineral |
| zinc | ion, metal, or mineral |
| nano-hydroxyapatite | nanoparticle |
| acetominophen | NSAID |
| carprofen | NSAID |
| deracoxib | NSAID |
| fenoprofen | NSAID |
| firocoxib, | NSAID |
| flurbirofen | NSAID |
| mefenamic acid | NSAID |
| meloxicam | NSAID |
| robenacoxib | NSAID |
| aptamer | nucleic acid |
| antisense nucleic acid | nucleic acid |
| small interfering RNA (siRNA) | nucleic acid |
| exon skipping nucleic acid | nucleic acid |
| RNA editing nucleic acid | nucleic acid |
| microRNA therapeutic inhibitor (antimiR) | nucleic acid |
| microRNA therapeutic inhibitor mimic (promiR) | nucleic acid |
| long non-coding RNA modulator | nucleic acid |
| mRNA | nucleic acid |
| plasmid | nucleic acid |
| DNA aptamer | nucleic acid |
| deoxyribonucleic acidzyme | nucleic acid |
| RNA aptamer | nucleic acid |
| RNA decoy | nucleic acid |
| antisense DNA | nucleic acid |
| antisense RNA | nucleic acid |
| ribozyme | nucleic acid |

TABLE 4-continued

| Therapeutic agents | |
|---|---|
| Agent | Category |
| micro ribonucleic acid | nucleic acid |
| fomivirsen | nucleic acid |
| viral nucleic acid | nucleic acid |
| Gendicine (Shenzhen SiBiono GeneTech) | nucleic acid |
| Advexin (Introgen) | nucleic acid |
| nucleic acid vaccines | nucleic acid |
| fomivirsen sodium (Isis Pharmaceuticals) | nucleic acid |
| MG98 | nucleic acid |
| ISIS 5132 | nucleic acid |
| DNAzyme | nucleic acid |
| 2,5-diketopiperazine | oxidant or antioxidant |
| antioxidant | oxidant or antioxidant |
| melanin | oxidant or antioxidant |
| oxidants | oxidant or antioxidant |
| quarternary ammonium chitosan | oxidant or antioxidant |
| ion | oxidant or antioxidant |
| mineral | oxidant or antioxidant |
| vitamin | oxidant or antioxidant |
| protein | oxidant or antioxidant |
| hydrogen peroxide | oxidant or antioxidant |
| ozone | oxidant or antioxidant |
| nitric acid | oxidant or antioxidant |
| sulfuric acid | oxidant or antioxidant |
| oxygen | oxidant or antioxidant |
| sodium perborate | oxidant or antioxidant |
| nitrous oxide | oxidant or antioxidant |
| potassium nitrate | oxidant or antioxidant |
| sodium bismuthate | oxidant or antioxidant |
| hypochlorite | oxidant or antioxidant |
| bleach | oxidant or antioxidant |
| halogen | oxidant or antioxidant |
| Cl2 | oxidant or antioxidant |
| F2 | oxidant or antioxidant |
| endogenous oxidant | oxidant or antioxidant |
| exogenous oxidant | oxidant or antioxidant |
| hydroxide | oxidant or antioxidant |
| singlet oxygen | oxidant or antioxidant |
| superoxide anion | oxidant or antioxidant |
| hydroxy one radical | oxidant or antioxidant |
| reactive oxygen species | oxidant or antioxidant |
| vitamin A | oxidant or antioxidant |
| beta-carotene | oxidant or antioxidant |
| carotenoid | oxidant or antioxidant |
| vitamin C | oxidant or antioxidant |
| ascorbic acid | oxidant or antioxidant |
| vitamin E | oxidant or antioxidant |
| tocopherol | oxidant or antioxidant |
| tocotrienol | oxidant or antioxidant |
| selenium | oxidant or antioxidant |
| glutatione peroxidase | oxidant or antioxidant |
| zinc | oxidant or antioxidant |
| catalase | oxidant or antioxidant |
| superoxide dismutase | oxidant or antioxidant |
| copper | oxidant or antioxidant |
| manganese | oxidant or antioxidant |
| glutathione | oxidant or antioxidant |
| polyphenol | oxidant or antioxidant |
| tirilazad | oxidant or antioxidant |
| allupurinol | oxidant or antioxidant |
| acetylcysteine | oxidant or antioxidant |
| lipoic acid | oxidant or antioxidant |
| carotene | oxidant or antioxidant |
| ubiquinol | oxidant or antioxidant |
| BHA | oxidant or antioxidant |
| BHT | oxidant or antioxidant |
| Anidulafungin | peptide |
| Atosiban acetate | peptide |
| Bacitracin | peptide |
| Bivalirudin | peptide |
| Bortezomib | peptide |
| Buserelin | peptide |
| Calcitonin | peptide |
| Captopril | peptide |
| Carbetocin acetate | peptide |
| Caspofungin | peptide |
| Cetrorelix acetate | peptide |

TABLE 4-continued

| Therapeutic agents | |
|---|---|
| Agent | Category |
| Colistin | peptide |
| cyclic dipeptide | peptide |
| cyclic peptide | peptide |
| Cyclosporine | peptide |
| Daptomycin | peptide |
| Degarelix acetate | peptide |
| Enalapril maleate | peptide |
| Enfuvirtide | peptide |
| Eptifibatide | peptide |
| Exenatide | peptide |
| Glutathione | peptide |
| Goserelin | peptide |
| Human calcitonin | peptide |
| lanreotide acetate | peptide |
| Icatibant acetate | peptide |
| Lepirudin | peptide |
| Liraglutide | peptide |
| Lisinopril | peptide |
| Lypressin | peptide |
| Nafarelin acetate | peptide |
| Nesiritide | peptide |
| Oxytocin | peptide |
| RGD peptide | peptide |
| r-hirudin | peptide |
| Salmon calcitonin | peptide |
| Saralasin acetate | peptide |
| Somatostatin acetate | peptide |
| Spaglumat magnesium | peptide |
| Thymalfasin | peptide |
| Tirofiban | peptide |
| Vapreotide acetate | peptide |
| Ziconotide | peptide |
| adrenocorticotropic hormone (ACTH) | protein |
| Alpha interferon | protein |
| antibody | protein |
| Anakinra | protein |
| antigen | protein |
| Beta interferon | protein |
| Bone morphogenetic protein (BMP) | protein |
| bone-morphogenic protein 2 | protein |
| chimeric protein | protein |
| Coagulation Factor IX | protein |
| Colony stimulating growth factor (CSF) | protein |
| Desmopressin | protein |
| Etanercept | protein |
| Factor IX | protein |
| Factor VII | protein |
| Factor VIII | protein |
| Follicle stimulating hormone (FSH) | protein |
| Gamma interferon | protein |
| gastrin prolactin | protein |
| Granulocyte colony-stimulating factor (G-CSF) | protein |
| Granulocyte macrophage colony stimulating factor (GM-CSF) | protein |
| growth hormone (GH) | protein |
| Human chorionic gonadotropin (HCG) | protein |
| infliximab | protein |
| insulin | protein |
| Insulin glargine | protein |
| Insulin-like growth factor (IGF) | protein |
| kallikrein | protein |
| kerantinocyte growth factor (KGF) | protein |
| Luteinizing hormone (LH) | protein |
| Macrophage colony stimulating factor (M-CSF) | protein |
| Neurotrophic growth factor (NGF) | protein |
| obesity protein (leptin) | protein |
| Octreotide | protein |
| Osteoprotegerin (OPG) | protein |
| pancreatic RNAase | protein |
| Pegfilgrastim | protein |
| peptides | protein |
| platelet activating factor acetyl hydrolase | protein |
| Platelet-derived growth factor (PDGF) | protein |
| processed silk | protein |
| sericin | protein |
| silk | protein |
| silk fibroin | protein |

TABLE 4-continued

| Therapeutic agents | |
|---|---|
| Agent | Category |
| Stem cell factor (SCF) | protein |
| streptokinase | protein |
| Superoxide dismutase (SOD) | protein |
| synthetic protein | protein |
| thrombopoietin | protein |
| Thyroid stimulating hormone (TSH) | protein |
| tissue plasminogen activator (TPA) | protein |
| Tumor necrosis factor (TNF) | protein |
| tumor necrosis factor binding protein (TNFbp) | protein |
| urokinase | protein |
| Vascular endothelial growth factor (VEGF) | protein |
| antibacterial agent | small molecule |
| antifungal agent | small molecule |
| antimalarial agent | small molecule |
| antiseptic | small molecule |
| nonsteroidal anti-inflammatory drugs (NSAIDs) | small molecule |
| stimulant | small molecule |
| tranquilizers | small molecule |
| acetaminophen | small molecule - analgesic agent |
| alcohols | small molecule - analgesic agent |
| alcuronium | small molecule - analgesic agent |
| alfentanyl | small molecule - analgesic agent |
| amethocaine | small molecule - analgesic agent |
| amobarbital | small molecule - analgesic agent |
| anileridine | small molecule - analgesic agent |
| atracurium | small molecule - analgesic agent |
| bupivacaine | small molecule - analgesic agent |
| buprenorphine | small molecule - analgesic agent |
| butorphanol | small molecule - analgesic agent |
| cannabinoid | small molecule - analgesic agent |
| cannabis | small molecule - analgesic agent |
| cisatracurium | small molecule - analgesic agent |
| cocaine | small molecule - analgesic agent |
| codiene | small molecule - analgesic agent |
| COX-2 inhibitor | small molecule - analgesic agent |
| decamethonium | small molecule - analgesic agent |
| diacetyl morphine | small molecule - analgesic agent |
| diamorphine | small molecule - analgesic agent |
| diazepam | small molecule - analgesic agent |
| dibucaine | small molecule - analgesic agent |
| doxacurium | small molecule - analgesic agent |
| etomidate | small molecule - analgesic agent |
| fentanyl | small molecule - analgesic agent |
| gallamine | small molecule - analgesic agent |
| hydrocodone | small molecule - analgesic agent |
| hydromorphone | small molecule - analgesic agent |
| ketamine | small molecule - analgesic agent |
| levobupivacaine | small molecule - analgesic agent |
| levorphanol | small molecule - analgesic agent |
| lidocaine | small molecule - analgesic agent |
| lorazepam | small molecule - analgesic agent |
| meperidine (pethidine) | small molecule - analgesic agent |
| mepivacaine | small molecule - analgesic agent |
| methadone | small molecule - analgesic agent |
| methohexital | small molecule - analgesic agent |
| metocurine | small molecule - analgesic agent |
| midazolam | small molecule - analgesic agent |
| morphine | small molecule - analgesic agent |
| morphine glucuronide | small molecule - analgesic agent |
| morphine sulfate | small molecule - analgesic agent |
| nalbuphine | small molecule - analgesic agent |
| NSAID | small molecule - analgesic agent |
| opioid agonist | small molecule - analgesic agent |
| opioid antagonist | small molecule - analgesic agent |
| opioids | small molecule - analgesic agent |
| oxycodone | small molecule - analgesic agent |
| oxymorphone | small molecule - analgesic agent |
| pancuronium | small molecule - analgesic agent |
| pentazocine | small molecule - analgesic agent |
| pipecuronium | small molecule - analgesic agent |
| prilocaine | small molecule - analgesic agent |
| procaine | small molecule - analgesic agent |
| propoxyphene | small molecule - analgesic agent |
| rapacuronium | small molecule - analgesic agent |
| remifentanil | small molecule - analgesic agent |
| rocuronium | small molecule - analgesic agent |

TABLE 4-continued

| Therapeutic agents | |
|---|---|
| Agent | Category |
| ropivacaine | small molecule - analgesic agent |
| succinylcholine | small molecule - analgesic agent |
| sufentanil | small molecule - analgesic agent |
| thiamylal | small molecule - analgesic agent |
| thiopental | small molecule - analgesic agent |
| tubocurarine | small molecule - analgesic agent |
| vecuronium | small molecule - analgesic agent |
| amikacin | small molecule - antibacterial agent |
| amoxicillin | small molecule - antibacterial agent |
| ampicillin | small molecule - antibacterial agent |
| azithromycin | small molecule - antibacterial agent |
| azlocillin | small molecule - antibacterial agent |
| aztreonam | small molecule - antibacterial agent |
| capreomycin | small molecule - antibacterial agent |
| carbenicillin | small molecule - antibacterial agent |
| cefaclor | small molecule - antibacterial agent |
| cefadroxil | small molecule - antibacterial agent |
| cefalexin | small molecule - antibacterial agent |
| cefalotin | small molecule - antibacterial agent |
| cefamandole | small molecule - antibacterial agent |
| cefazolin | small molecule - antibacterial agent |
| cefdinir | small molecule - antibacterial agent |
| cefditoren | small molecule - antibacterial agent |
| cefepime | small molecule - antibacterial agent |
| cefixime | small molecule - antibacterial agent |
| cefoperazone | small molecule - antibacterial agent |
| cefotaxime | small molecule - antibacterial agent |
| cefoxitin | small molecule - antibacterial agent |
| cefpodoxime | small molecule - antibacterial agent |
| cefprozil | small molecule - antibacterial agent |
| ceftaroline fosamil | small molecule - antibacterial agent |
| ceftazidime | small molecule - antibacterial agent |
| ceftibuten | small molecule - antibacterial agent |
| ceftizoxime | small molecule - antibacterial agent |
| ceftobiprole | small molecule - antibacterial agent |
| ceftriaxone | small molecule - antibacterial agent |
| cefuroxime | small molecule - antibacterial agent |
| cilastatin | small molecule - antibacterial agent |
| ciprofolaxin | small molecule - antibacterial agent |
| clarithromycin | small molecule - antibacterial agent |
| clindamycin | small molecule - antibacterial agent |
| clofazimine | small molecule - antibacterial agent |
| cloxacillin | small molecule - antibacterial agent |
| cycloserine | small molecule - antibacterial agent |
| dalbavancin | small molecule - antibacterial agent |
| dapsone | small molecule - antibacterial agent |
| demeclocycline | small molecule - antibacterial agent |
| dicloxacillin | small molecule - antibacterial agent |
| dirithromycin | small molecule - antibacterial agent |
| doripenem | small molecule - antibacterial agent |
| doxycycline | small molecule - antibacterial agent |
| enoxacin | small molecule - antibacterial agent |
| ertapenem | small molecule - antibacterial agent |
| erythromycin | small molecule - antibacterial agent |
| ethambutol | small molecule - antibacterial agent |
| ethionamide | small molecule - antibacterial agent |
| flucloxacillin | small molecule - antibacterial agent |
| furazolidone | small molecule - antibacterial agent |
| gatifloxacin | small molecule - antibacterial agent |
| geldanamycin | small molecule - antibacterial agent |
| gemifloxacin | small molecule - antibacterial agent |
| gentamicin | small molecule - antibacterial agent |
| grepafloxacin | small molecule - antibacterial agent |
| herbimycin | small molecule - antibacterial agent |
| imipeneum | small molecule - antibacterial agent |
| isoniazid | small molecule - antibacterial agent |
| kanamycin | small molecule - antibacterial agent |
| levofloxacin | small molecule - antibacterial agent |
| linezolid | small molecule - antibacterial agent |
| linomycin | small molecule - antibacterial agent |
| lomefloxacin | small molecule - antibacterial agent |
| loracarbef | small molecule - antibacterial agent |
| mafenide | small molecule - antibacterial agent |
| meropenem | small molecule - antibacterial agent |
| methicillin | small molecule - antibacterial agent |
| mezlocillin | small molecule - antibacterial agent |

TABLE 4-continued

| Therapeutic agents | |
|---|---|
| Agent | Category |
| minocycline | small molecule - antibacterial agent |
| moxifloxacin | small molecule - antibacterial agent |
| nafcillin | small molecule - antibacterial agent |
| nalidixic acid | small molecule - antibacterial agent |
| neomycin | small molecule - antibacterial agent |
| netilmicin | small molecule - antibacterial agent |
| nitrofurantoin | small molecule - antibacterial agent |
| norfloxacin | small molecule - antibacterial agent |
| ofloxacin | small molecule - antibacterial agent |
| oritavancin | small molecule - antibacterial agent |
| oxacillin | small molecule - antibacterial agent |
| oxytetracycline | small molecule - antibacterial agent |
| paromomycin | small molecule - antibacterial agent |
| penicillin | small molecule - antibacterial agent |
| penicillin G | small molecule - antibacterial agent |
| penicillin V | small molecule - antibacterial agent |
| piperacillin | small molecule - antibacterial agent |
| posizolid | small molecule - antibacterial agent |
| pyrazinamide | small molecule - antibacterial agent |
| radezolid | small molecule - antibacterial agent |
| rifampicin | small molecule - antibacterial agent |
| rifaximin | small molecule - antibacterial agent |
| roxithromycin | small molecule - antibacterial agent |
| sparfloxacin | small molecule - antibacterial agent |
| spectinomycin | small molecule - antibacterial agent |
| spiramycin | small molecule - antibacterial agent |
| streptomycin | small molecule - antibacterial agent |
| sulfacetamide | small molecule - antibacterial agent |
| sulfadiazine | small molecule - antibacterial agent |
| sulfadimethoxine | small molecule - antibacterial agent |
| sulfamethizole | small molecule - antibacterial agent |
| sulfamethoxazole | small molecule - antibacterial agent |
| sulfanilimide | small molecule - antibacterial agent |
| sulfasalazine | small molecule - antibacterial agent |
| sulfisoxazole | small molecule - antibacterial agent |
| teicoplanin | small molecule - antibacterial agent |
| telavancin | small molecule - antibacterial agent |
| telithromycin | small molecule - antibacterial agent |
| temafloxacin | small molecule - antibacterial agent |
| temocillin | small molecule - antibacterial agent |
| tetracycline | small molecule - antibacterial agent |
| ticarcillin | small molecule - antibacterial agent |
| tobramycin | small molecule - antibacterial agent |
| torezolid | small molecule - antibacterial agent |
| troleandomycin | small molecule - antibacterial agent |
| trovafloxacin | small molecule - antibacterial agent |
| vancomycin | small molecule - antibacterial agent |
| 5-fluorocytosine | small molecule - antifungal |
| abafungin | small molecule - antifungal |
| albaconazole | small molecule - antifungal |
| amorolfin | small molecule - antifungal |
| amphotericin B | small molecule - antifungal |
| benzoic acid | small molecule - antifungal |
| bifonazole | small molecule - antifungal |
| butenafine | small molecule - antifungal |
| butoconazole | small molecule - antifungal |
| candicidin | small molecule - antifungal |
| caspofungin | small molecule - antifungal |
| ciclopirox | small molecule - antifungal |
| clotrimazole | small molecule - antifungal |
| crystal violet | small molecule - antifungal |
| econazole | small molecule - antifungal |
| efinaconazole | small molecule - antifungal |
| epoxiconazole | small molecule - antifungal |
| fenticonazole | small molecule - antifungal |
| filipin | small molecule - antifungal |
| fluconazole | small molecule - antifungal |
| flucytosine | small molecule - antifungal |
| griseofulvin | small molecule - antifungal |
| haloprogin | small molecule - antifungal |
| hamycin | small molecule - antifungal |
| isavuconazole | small molecule - antifungal |
| isoconazole | small molecule - antifungal |
| itraconazole | small molecule - antifungal |
| ketoconazole | small molecule - antifungal |
| luliconazole | small molecule - antifungal |

TABLE 4-continued

| Therapeutic agents | |
|---|---|
| Agent | Category |
| micafungin | small molecule - antifungal |
| miconazole | small molecule - antifungal |
| naftifine | small molecule - antifungal |
| natamycin | small molecule - antifungal |
| nystatin | small molecule - antifungal |
| omoconazole | small molecule - antifungal |
| oxiconazole | small molecule - antifungal |
| posaconazole | small molecule - antifungal |
| propiconazole | small molecule - antifungal |
| ravuconazole | small molecule - antifungal |
| rimocidin | small molecule - antifungal |
| sertaconazole | small molecule - antifungal |
| sulconazole | small molecule - antifungal |
| terbinafine | small molecule - antifungal |
| terconazole | small molecule - antifungal |
| tioconazole | small molecule - antifungal |
| tolnaftate | small molecule - antifungal |
| undecylenic acid | small molecule - antifungal |
| voriconazole | small molecule - antifungal |
| aminoquinoline | small molecule - antimalarial |
| amodiaquine | small molecule - antimalarial |
| antifolate | small molecule - antimalarial |
| artemether | small molecule - antimalarial |
| artemisinin derivative | small molecule - antimalarial |
| artemotil | small molecule - antimalarial |
| artesunate | small molecule - antimalarial |
| atovaquone | small molecule - antimalarial |
| biguanide | small molecule - antimalarial |
| bisphosphonate | small molecule - antimalarial |
| chloproguanil | small molecule - antimalarial |
| chloroquine | small molecule - antimalarial |
| cinchona alkaloid | small molecule - antimalarial |
| dermaseptin | small molecule - antimalarial |
| DHA-piperaquine | small molecule - antimalarial |
| diaminopyrimidine | small molecule - antimalarial |
| dihydroartemisinin | small molecule - antimalarial |
| doxycillin | small molecule - antimalarial |
| halofantrine | small molecule - antimalarial |
| lumefantrine | small molecule - antimalarial |
| melfoquine | small molecule - antimalarial |
| N-acetyl cysteine | small molecule - antimalarial |
| piperaquine | small molecule - antimalarial |
| primaquine | small molecule - antimalarial |
| proguanil | small molecule - antimalarial |
| pyremethamine | small molecule - antimalarial |
| pyronaridine | small molecule - antimalarial |
| quercitin | small molecule - antimalarial |
| quinidine | small molecule - antimalarial |
| quinine | small molecule - antimalarial |
| sulfadoxine-pyrimethamine | small molecule - antimalarial |
| sulfonamide | small molecule - antimalarial |
| tafenoquine | small molecule - antimalarial |
| trimethoprim | small molecule - antimalarial |
| choline salicylate | small molecule - antipyretic |
| magnesium salicylate | small molecule - antipyretic |
| metamizole | small molecule - antipyretic |
| nimesulide | small molecule - antipyretic |
| phenazone | small molecule - antipyretic |
| salicylate | small molecule - antipyretic |
| sodium salicylate | small molecule - antipyretic |
| aspirin | small molecule - NSAID |
| celecoxib | small molecule - NSAID |
| diclofenac | small molecule - NSAID |
| diflunisal | small molecule - NSAID |
| etodolac | small molecule - NSAID |
| fenoprofen | small molecule - NSAID |
| flurbiprofen | small molecule - NSAID |
| ibuprofen | small molecule - NSAID |
| indomethacin | small molecule - NSAID |
| ketoprofen | small molecule - NSAID |
| ketorolac | small molecule - NSAID |
| mechlofenamic acid | small molecule - NSAID |
| nabumetone | small molecule - NSAID |
| naproxen | small molecule - NSAID |
| oxaprozin | small molecule - NSAID |
| piroxicam | small molecule - NSAID |

TABLE 4-continued

| Therapeutic agents | |
|---|---|
| Agent | Category |
| roficoxib | small molecule - NSAID |
| salsalate | small molecule - NSAID |
| sulindac | small molecule - NSAID |
| tolfenamic acid | small molecule - NSAID |
| tolmetin | small molecule - NSAID |
| sodium channel blocker | sodium channel blocker |
| alkaloid | sodium channel blocker |
| saxitoxin | sodium channel blocker |
| neosaxitoxin | sodium channel blocker |
| tetrodoxin | sodium channel blocker |
| class I antiarrhythmic agent | sodium channel blocker |
| quinidine | sodium channel blocker |
| procainamide | sodium channel blocker |
| disopryamide | sodium channel blocker |
| tocainide | sodium channel blocker |
| mexiletine | sodium channel blocker |
| proparacaine | sodium channel blocker |
| flecainide | sodium channel blocker |
| propafenone | sodium channel blocker |
| moricizine | sodium channel blocker |
| atorvastatin | statin |
| cerivastatin | statin |
| fluvastatin | statin |
| lovastatin | statin |
| mevastatin | statin |
| pitavastatin | statin |
| pravastatin | statin |
| rosuvastatin | statin |
| simvastatin | statin |
| statin | statin |
| steroid | steroid |
| corticosteroid | steroid |
| triamcinolone | steroid |
| cortisone | steroid |
| prednisone | steroid |
| methylprenisolone | steroid |
| prednisolone | steroid |
| betamethasone | steroid |
| dexamethasone | steroid |
| hydrocortisone | steroid |
| deflazacort | steroid |
| fludrocortisone | steroid |
| Anadrol | steroid |
| Anavar | steroid |
| Clenbuterol | steroid |
| Clomid | steroid |
| Cytomel | steroid |
| Deca Durabolin | steroid |
| Dianabol | steroid |
| Equipoise | steroid |
| Halotestin | steroid |
| Human Growth Hormone | steroid |
| Insulin | steroid |
| Lasix | steroid |
| Methyltestosterone | steroid |
| Nolvadex | steroid |
| Omnadren | steroid |
| Primobolan | steroid |
| Sustanon | steroid |
| Cypionate | steroid |
| Enanthate | steroid |
| Propionate | steroid |
| Testosterone | steroid |
| Trenbolone | steroid |
| Winstrol | steroid |
| Flunisolide | steroid |
| Budesonide | steroid |
| Mometasone | steroid |
| Ciclesonide | steroid |
| Fluticasone | steroid |
| Beclomethasone | steroid |
| glutocorticoid | steroid |
| minerolocorticoid | steroid |
| corticosterone | steroid |
| aldosterone | steroid |
| Hydrocortisone | steroid |

TABLE 4-continued

| Therapeutic agents | |
|---|---|
| Agent | Category |
| methylprednisolone | steroid |
| prednisolone | steroid |
| prednisone | steroid |
| triamcinolone | steroid |
| Amcinonide | steroid |
| budesonide | steroid |
| desonide | steroid |
| fluocinolone acetonide | steroid |
| fluocinonide | steroid |
| halcinonide | steroid |
| triamcinolone acetonide | steroid |
| Beclometasone | steroid |
| betamethasone | steroid |
| dexamethasone | steroid |
| fluocortolone | steroid |
| halometasone | steroid |
| mometasone | steroid |
| Alclometasone dipropionate | steroid |
| betamethasone dipropionate | steroid |
| betamethasone valerate | steroid |
| clobetasol propionate | steroid |
| clobetasone butyrate | steroid |
| fluprednidene acetate | steroid |
| mometasone furoate | steroid |
| Ciclesonide | steroid |
| cortisone acetate | steroid |
| hydrocortisone aceponate | steroid |
| hydrocortisone acetate | steroid |
| hydrocortisone buteprate | steroid |
| hydrocortisone butyrate | steroid |
| hydrocortisone valerate | steroid |
| prednicarbate | steroid |
| tixocortol pivalate | steroid |
| 3,4-methylenedioxymethamphetamine | stimulant |
| amphetamines | stimulant |
| caffeine | stimulant |
| ephedrine | stimulant |
| mephedrone | stimulant |
| methamphetamine | stimulant |
| methylenedioxypyrovalerone | stimulant |
| methylphenidate | stimulant |
| nicotine | stimulant |
| phenylpropanolamine | stimulant |
| propylhexedrine | stimulant |
| pseudoephedrine | stimulant |
| imatinib (Gleevac) | therapeutic combination |
| all-trans-retinoic acid | therapeutic combination |
| monoclonal antibody treatment | therapeutic combination |
| gemtuzumab | therapeutic combination |
| ozogamicin | therapeutic combination |
| chemotherapy | therapeutic combination |
| chlorambucil | therapeutic combination |
| prednisone | therapeutic combination |
| prednisolone | therapeutic combination |
| vincristine | therapeutic combination |
| cytarabine | therapeutic combination |
| clofarabine | therapeutic combination |
| farnesyl transferase inhibitor | therapeutic combination |
| decitabine | therapeutic combination |
| inhibitor of MDR1 | therapeutic combination |
| rituximab | therapeutic combination |
| interferon-α | therapeutic combination |
| anthracycline drug | therapeutic combination |
| daunorubicin | therapeutic combination |
| idarubicin | therapeutic combination |
| L-asparaginase | therapeutic combination |
| doxorubicin | therapeutic combination |
| cyclophosphamide | therapeutic combination |
| bleomycin | therapeutic combination |
| fludarabine | therapeutic combination |
| etoposide | therapeutic combination |
| pentostatin | therapeutic combination |
| cladribine | therapeutic combination |
| bone marrow transplant | therapeutic combination |
| stem cell transplant | therapeutic combination |
| radiation therapy | therapeutic combination |

TABLE 4-continued

| Therapeutic agents | |
|---|---|
| Agent | Category |
| anti-metabolite drug | therapeutic combination |
| methotrexate | therapeutic combination |
| 6-mercaptopurine | therapeutic combination |
| acepromazine | tranquilizer |
| alpha blockers | tranquilizer |
| alpha-adrenergic agonist | tranquilizer |
| antihistamine | tranquilizer |
| azapirone | tranquilizer |
| barbiturate | tranquilizer |
| benperidol | tranquilizer |
| benzamidine | tranquilizer |
| benzodiazepine | tranquilizer |
| beta-blocker | tranquilizer |
| bromantane | tranquilizer |
| bromperidol | tranquilizer |
| butyrophenone | tranquilizer |
| carbamates | tranquilizer |
| carpipramine | tranquilizer |
| chlorpromazine | tranquilizer |
| chlorprothixene | tranquilizer |
| clocapramine | tranquilizer |
| clopenthixol | tranquilizer |
| clorotepine | tranquilizer |
| cyamemazine | tranquilizer |
| diphenylbutylpiperidine | tranquilizer |
| dixyrazine | tranquilizer |
| droperidol | tranquilizer |
| emoxypine | tranquilizer |
| fabomotizole | tranquilizer |
| flupentixol | tranquilizer |
| fluphenazine | tranquilizer |
| fluspirilene | tranquilizer |
| gamma aminobutyric acid | tranquilizer |
| haloperidol | tranquilizer |
| inhalants | tranquilizer |
| levomepromazine | tranquilizer |
| loxapine | tranquilizer |
| mebicar | tranquilizer |
| mentyl isovalerate | tranquilizer |
| mesoridazine | tranquilizer |
| molindone | tranquilizer |
| monoamine oxidase inhibitors | tranquilizer |
| moperone | tranquilizer |
| mosapramine | tranquilizer |
| penfluridol | tranquilizer |
| perazine | tranquilizer |
| periciazine | tranquilizer |
| perphenazine | tranquilizer |
| phenothiazine | tranquilizer |
| pimozide | tranquilizer |
| pipamperone | tranquilizer |
| pipotiazine | tranquilizer |
| pregabalin | tranquilizer |
| prochlorperazine | tranquilizer |
| promazine | tranquilizer |
| promethazine | tranquilizer |
| propofol | tranquilizer |
| prothipendyl | tranquilizer |
| racetam | tranquilizer |
| selank | tranquilizer |
| selective serotonin reuptake inhibitors | tranquilizer |
| serotonin-norepinephrine reuptake inhibitor | tranquilizer |
| sulpiride | tranquilizer |
| sultopride | tranquilizer |
| sympatholytic | tranquilizer |
| thioproperazine | tranquilizer |
| thioridazine | tranquilizer |
| thiothixene | tranquilizer |
| thioxanthene | tranquilizer |
| timiperone | tranquilizer |
| tricyclic | tranquilizer |
| trifluoperazine | tranquilizer |
| triflupromazine | tranquilizer |
| veralipride | tranquilizer |
| zuclopenthixol | tranquilizer |

TABLE 4-continued

| Therapeutic agents | |
|---|---|
| Agent | Category |
| 3-(4-Bromo-2,6-difluoro-benzyloxy)-5-[3-(4-pyrrolidin 1-yl-butyl)-ureido]-isothiazole-4-carboxylic acid amide hydrochloride | VEGF-related agent |
| 5-((7-Benzyloxyquinazolin-4-yl)amino)-4-fluoro-2-methyl phenol hydrochloride | VEGF-related agent |
| aflibercept | VEGF-related agent |
| AG-013958 (Pfizer Inc.) | VEGF-related agent |
| Angiogenesis inhibitor | VEGF-related agent |
| angiostatin | VEGF-related agent |
| angiozyme | VEGF-related agent |
| anti-VEGF antibody | VEGF-related agent |
| arresten | VEGF-related agent |
| AVASTIN ® | VEGF-related agent |
| axitinib | VEGF-related agent |
| bevacizumab | VEGF-related agent |
| canstatin | VEGF-related agent |
| cediranib | VEGF-related agent |
| combretastatin | VEGF-related agent |
| Combretastatin A4 Prodrug (CA4P) | VEGF-related agent |
| combstatin | VEGF-related agent |
| endogenous peptide | VEGF-related agent |
| EVIZON ™ (squalamine lactate) | VEGF-related agent |
| Fumagillin | VEGF-related agent |
| Fumagillin analogue | VEGF-related agent |
| glufanide disodium | VEGF-related agent |
| JSM6427 (Jerini AG) | VEGF-related agent |
| LUCENTIS ® | VEGF-related agent |
| MACUGEN ® | VEGF-related agent |
| multitargeted human epidermal receptor (HER) 1/2 and vascular endothelial growth factor receptor (VEGFR) 1/2 receptor family tyrosine kinases inhibitor | VEGF-related agent |
| N-(4-bromo-2-fluorophenyl)-6-methoxy-7-[(I-methylpiperidin-4-y1) methoxy]quinazol in-4-amine | VEGF-related agent |
| N-(4-bromo-2-fluorophenyl)-6-methoxy-7-[(I-methylpiperidin-4-yl) methoxy]quinazol in-4-amine | VEGF-related agent |
| N,2-dimethyl-6-(2-(I-methyl-IH-imidazol-2-yl)thieno[3,2-b]pyridin-7-yloxy)benzo[b]thiophene-3-carboxamide | VEGF-related agent |
| pan-VEGF-R-kinase inhibitor | VEGF-related agent |
| pegaptanib | VEGF-related agent |
| protein kinase inhibitor | VEGF-related agent |
| ranibizumab | VEGF-related agent |
| shark cartilage | VEGF-related agent |
| shark cartilage derivative | VEGF-related agent |
| short interfering RNA (siRNA) | VEGF-related agent |
| siRNA-based VEGFR 1 inhibitor | VEGF-related agent |
| soluble ectodomain of the VEGF receptor | VEGF-related agent |
| sorafenib | VEGF-related agent |
| synthetic peptide | VEGF-related agent |
| thalidomide | VEGF-related agent |
| thalidomide derivative | VEGF-related agent |
| thrombospondin | VEGF-related agent |
| tivozanib | VEGF-related agent |
| toll-like receptor agonist | VEGF-related agent |
| tumstatin | VEGF-related agent |
| tyrosine kinase inhibitor of the RET/PTC oncogenic kinase | VEGF-related agent |
| vatalanib | VEGF-related agent |
| VEGF agonist | VEGF-related agent |
| VEGF antagonist | VEGF-related agent |
| VEGF nucleic acid ligand | VEGF-related agent |
| VEGF therapeutic agent | VEGF-related agent |
| VEGF-R1 inhibitor | VEGF-related agent |
| VEGF-R2 inhibitor | VEGF-related agent |
| VEGFR2-selective monoclonal antibody | VEGF-related agent |
| VEGF-Trap | VEGF-related agent |
| β2-glycoprotein 1 | VEGF-related agent |

Processed Silk

In some embodiments, SBP formulations may include processed silk as an active therapeutic component. The processed silk may include, but is not limited to one or more of silk fibroin, fragments of silk fibroin, chemically altered silk fibroin, and mutant silk fibroin. Therapeutic applications including such SBPs may include any of those taught in International Publication Number WO2017200659; Aykac et al. (2017) Gene s0378-1119 (17) 30865-8; and Abdel-Naby (2017) PLOS One 12 (11): e0188154, the contents of each of which are herein incorporated by reference in their entirety. Processed silk may be administered as a therapeutic agent for treatment of a localized indication or for treatment of an indication further from the SBP application site. In some embodiments, therapeutic agents are combinations of processed silk and some other active component. In some embodiments, therapeutic agent activity requires cleavage or dissociation from silk. Therapeutic agents may include silk fibroin and/or chemically modified silk fibroin. In some embodiments, such therapeutic agents may be used to treat burn injury, inflammation, wound healing, or corneal injury. These and other treatments may be carried out according to any of the methods described in International Publication Number WO2017200659; United States Publication Number US20140235554; Aykac et al. (2017) Gene s0378-1119 (17) 30868-30865; or Abdel-Naby (2017) PLOS One 12 (11): e0188154, the contents of each of which are herein incorporated by reference in their entirety. In some embodiments, SBPs are silk fibroin solutions used to facilitate wound healing, as described in Park et al. (2017) Acta Biomater 67:183-195, the contents of which are herein incorporated by reference in their entirety. These SBPs may enhance wound healing via a nuclear factor kappa enhancer binding protein (NF-κB) signaling pathway. In some embodiments, SBPs are therapeutic agents used to facilitate delivery and/or release of therapeutic agent payloads. Such therapeutic agents and/or methods of use may include, but are not limited to, any of those described in International Publication Number WO2017139684, the contents of which are herein incorporated by reference in their entirety.

Lubricants

In some embodiments, processed silk and/or SBPs may be used as a lubricant. In some embodiments, processed silk may be selected base on or prepared to maximize its use as a lubricant. As used herein, the term "lubricant" refers to a substance that reduces the friction between two or more surfaces. In some embodiments, the surfaces in need of lubrication may be part of a subject. In some embodiments, surfaces in need of lubrication include, but are not limited to, the body, eyes, ears, skin, scalp, mouth, vagina, nose, hands, feet, and lips. In some embodiments, SBPs are used for ocular lubrication. As used herein, the term "ocular lubrication" refers to a method of the reduction of friction and/or irritation in the eye. In some embodiments, processed silk and/or SBPs may be used to reduce friction caused by dryness, as taught in U.S. Pat. No. 9,907,836 (the content of which is herein incorporated by reference in its entirety). This dryness may be dryness in the eye.

In some embodiments, the coefficient of friction of an SBP is approximately that of naturally occurring, biological, and/or protein lubricants (e.g. lubricin). In some embodiments, SBPs may display a coefficient of friction lower than that of water, as measured by the experimental sliding speeds. In some embodiments, the coefficient of friction of an SBP is slightly lower than that of water. In some embodiments, the SBP is more lubricating that water. In some embodiments, the SBP is slightly more lubricating that water. In some embodiments, SBPs may be incorporated into a lubricant. Such methods may include any of those presented in International Patent Application Publication No. WO2013163407, the contents of which are herein incorporated by reference in their entirety. In some embodiments, processed silk and/or SBPs may be used as an excipient. In some embodiments, processed silk and/or SBPs may be used as an excipient to prepare a lubricant.

Lubricants comprising SBPs may be prepared in any format described herein. Non-limiting examples include solutions, gels, hydrogels, creams, drops, and sprays.

In some embodiments, an SBP is a lubricant prepared in the format of a nasal spray.

In some embodiments, an SBP is a lubricant prepared in the format of eye drops.

In some embodiments, an SBP is a lubricant prepared in the format of ear drops.

Biological Agents

In some embodiments, therapeutic agents include biological agents (also referred to as "biologics" or "biologicals"). As used herein, a "biological agent" refers to a therapeutic substance that is or is derived from an organism or virus. Examples of biological agents include, but are not limited to, proteins, organic polymers and macromolecules, carbohydrates, complex carbohydrates, nucleic acids, cells, tissues, organs, organisms, DNA, RNA, oligonucleotides, genes, and lipids. Biological agents may include processed silk. In some embodiments, biological agents may include any of the biologicals and compounds associated with specific categories of biological agents listed in Table 4, above. In some embodiments, biological agents may include any of those taught in International Publication Numbers WO2010123945 or WO2017123383, the contents of each of which are herein incorporated by reference in their entirety.

In some embodiments, SBP formulations may be used to deliver or administer biological agents. In some embodiments, delivery may include controlled release of one or more biological agents. Delivery may be carried out in vivo. In some embodiments, delivery is in vitro. Processed silk may be used to facilitate delivery and/or maintain stability of biological agents.

Antibodies

In some embodiments, SBP formulations may include one or more antibodies. As used herein, the term "antibody" refers to a class of immune proteins that bind to specific target antigens or epitopes. Herein, "antibody" is used in the broadest sense and embraces various natural and derivative formats that include, but are not limited to monoclonal antibodies, polyclonal antibodies, multispecific antibodies (e.g., bispecific antibodies that bind to two different epitopes), antibody conjugates (e.g., antibodies conjugates with therapeutic agents, cytotoxic agents, or detectable labels), antibody variants [e.g., antibody mimetics, chimeric antibodies (e.g., having components from two or more antibody types or species), and synthetic variants], and antibody fragments. Antibodies are typically amino acid-based but may include post-translational or synthetic modifications. In some embodiments, SBPs may be used to facilitate antibody delivery, as taught in International Publication Number WO2017139684 and Guziewicz et al. (2011) Biomaterials 32 (10): 2642-2650, the contents of each of which are herein incorporated by reference in their entirety. In some embodiments, SBPs may be used to improve antibody stability.

In some embodiments, antibodies are VEGF antagonist or agonists. Non-limiting examples of monoclonal antibody therapeutic agents include canakinumab, palivizumab, panitumumab, inflectra, adalimumab-atto, alemtuzumab, nivolumab, ustekinumab, alefacept, ixekizumab, obiltoxaximab, golimumab, pembrolizumab, atezolizumab, tocilizumab, basiliximab, abciximab, denosumab, omalizumab, belimumab, efalizumab, natalizumab, ustekinumab, trastuzumab, bezlotoxumab, adalimumab, rituximab, daclizumab, secukinumab, cetuximab, reslizumab, olaratumab, ipilimumab, ixekizumab, certolizumab pegol, and daclizumab. In some embodiments, antibodies may include, but are not limited to, any of those listed in Table 4, above.

Antigens

In some embodiments, SBP formulations include antigens. As used herein, the term "antigen" refers to any substance capable of provoking an immune response. In some embodiments, antigens include processed silk. In some embodiments, antigens include any of those presented in Table 4, above. In some embodiments, SBPs may be used to facilitate antigen delivery. In some embodiments, SBPs may stabilize included antigens. In some embodiments, SBPs are or are included in vaccines. Vaccines that include processed silk and methods of using such vaccines may include any of those taught in United States Publication Number 20170258889 or in Zhang et al. (2012) PNAS 109 (30): 11981-6 (retracted), the contents of each of which are herein incorporated by reference in their entirety. In some embodiments, formulation of an antigen with processed silk may be used to facilitate the delivery of said antigen in a vaccine, as taught in Zhang et al. (2012) PNAS 109 (30): 11981-6 (retracted).

Carbohydrates

In some embodiments, SBP formulations include carbohydrates. As used herein, the term "carbohydrate" refers to any members of a class of organic compounds that typically have carbon, oxygen, and hydrogen atoms and include, but are not limited to, simple and complex sugars. In some embodiments, carbohydrates may be monosaccharides or derivatives of a monosaccharides (e.g., ribose, glucose, fructose, galactose, mannose, abequose, arabinose, fucose, rhamnose, xylose, glucuronic acid, galactosamine, glucosamine, N-acetylgalactosamine, N-acetylglucosamine, iduronic acid, muramic acid, sialic acid, N-acetylmuramic acid, and N-acetylneuraminic acid). In some embodiments, carbohydrates may include disaccharides (e.g., sucrose, lactose, maltose, trehalose, and cellobiose). In some embodiments, carbohydrates are oligosaccharides or polysaccharides. In some embodiments, incorporation of carbohydrates may be used to stabilize SBPs. Such methods of use may include any of those taught in Li et al. (2017) Biomacromolecules 18 (9): 2900-5, the contents of which are herein incorporated by reference in their entirety. In some embodiments, carbohydrates may include, but are not limited to, any of those listed in Table 4, above.

Cells, Tissues, Microorganisms, and Microbiomes

In some embodiments, SBP formulations include cells, tissues, organs, and/or organisms. In some embodiments, such agents are used for direct treatment. In other embodiments, cell- or tissue-based therapeutic agents are incorporated into SBPs to prepare model systems. Such methods may include any of those taught in International Publication Number WO2017189832; Chen et al. (2017) PLOS One, 12 (11): e0187880; or Chen et al. (2017) Stem Cell Research and Therapy 8:260, the contents of each of which are herein incorporated by reference in their entirety. In some embodiments, incorporated cells are stem cells (e.g., see International Publication Number WO2017189832; Chendang et al. (2017) J Biomaterials and Tissue Engineering 7:858-862; Xiao et al. (2017) Oncotarget 8 (49): 86471-89487; Ciocci et al. (2017) Int J Biol Macromol S0141-8130 (17): 32839-8; Li et al. (2017) Stem Cell Res Ther 8 (1): 256; or Ruan et al. (2017) Biomed Pharmacother 97:600-6, the contents of each of which are herein incorporated by reference in their entirety). Examples of cell- or tissue-based therapeutic agents include, but are not limited to, human corneal stromal stem cells, human corneal epithelial cells, chicken dorsal root ganglions, bone mesenchymal stem cells, limbal epithelial stem cells, cardiac mesenchymal stem cells, adipose tissue-derived mesenchymal stem cells, periodontal ligament stem cells, human small intestinal enteroids, oral keratinocytes, fibroblasts, transfected fibroblasts, any 2-dimensional tissue, and any 3-dimensional tissue, T cells, embryonic stem cells, neural stem cells, mesenchymal stem cells, and hematopoietic stem cells. In some embodiments, cells used as therapeutic agents may include, but are not limited to, any of those listed in Table 4, above.

In some embodiments, therapeutic agents include bacteria or other microorganisms. Such therapeutic agents may be used to alter a microbiome. Examples of bacteria or other microorganisms that may be used as therapeutic agents in SBPs include any of those described in U.S. Pat. Nos. 9,688,967 and 9,688,967; US Publication Numbers US20170136073, US20170128499, US20160206666, US20170067065, and US20170014457; and International Publication Numbers WO2017123676, WO2017123675, WO2017123610, WO2017123592, WO2017123418, WO2016210384, WO2017075485, WO2017023818, WO2016210373, WO2017040719, WO2016210378, and WO2016106343, the contents of each of which are herein incorporated by reference in their entirety.

In some embodiments, SBP formulations include cellular therapeutics, such as bacteria and/or other microorganisms. As used herein, the term "microorganism" refers to a microscopic living thing (e.g. bacteria and/or fungi). In some embodiments, SBPs may be used to deliver cellular therapeutics (e.g., bacteria and/or other microorganisms) to alter or improve the microbiome of a subject or patient. In some embodiments, bacteria and/or other microorganisms used as therapeutic agents may include, but are not limited to, any of those described in U.S. Pat. No. 9,688,967, or 9,688,967; in US Patent Publication Numbers US20170136073, US20170128499, US20160206666, US20170067065, or US20170014457; or in International Publication Numbers WO2017123676, WO2017123675, WO2017123610, WO2017123592, WO2017123418, WO2016210384, WO2017075485, WO2017023818, WO2016210373, WO2017040719, WO2016210378, WO2016200614, WO2017087580, or WO2016106343, the contents of each of which are herein incorporated by reference in their entirety. In some embodiments, said bacteria and/or microorganisms are formulated as a part of SBPs. In some embodiments, the bacteria and/or microorganisms may be supported during delivery using SBPs. In some embodiments, bacteria and/or other microorganisms used as therapeutic agents may be engineered, e.g., by any method described in the U.S. Pat. No. 9,688,967 or 9,487,764; or in International Publication Numbers WO2016200614 and WO2017087580, the contents of each of which are herein incorporated by reference in their entirety.

In some embodiments, SBPs described herein maintain and/or improve the stability of bacteria and/or other microorganisms. The maintenance and/or improvement of stability may be determined by comparing stability with SBP compositions to stability with compositions lacking SBPs or to standard compositions in the art. Maintenance and/or improvement of stability may be found or appreciated where superior or durational benefits are observed with SBPs. In some embodiments, SBPs maintain and/or improve the stability of bacteria and/or other microorganisms that can be used in bacterial or microbial therapy.

In some embodiments, bacteria and/or other microorganisms may be used as biopesticides. As used herein, the term "biopesticide" refers to a composition with a bacteria, microorganisms, or biological cargo used to harm, kill, or prevent the spread of pests. Biopesticides have been used in agricultural development, as described in U.S. Pat. No. 6,417,163, the contents of which are herein incorporated by reference in their entirety. In some embodiments, SBPs that include bacteria, microorganisms, and/or microbiomes, may be used as biopesticides to support agricultural applications.

In some embodiments, bacteria and/or other microorganisms formulated as a part of SBPs may include one or more of the following microbes: *Abiotrophia, Abiotrophia defectiva, Acetanaerobacterium, Acetanaerobacterium elongatum, Acetivibrio, Acetivibrio bacterium, Acetobacterium, Acetobacterium woodii, Acholeplasma, Acidaminococcus, Acidaminococcus fermentans, Acidianus, Acidianus brierieyi, Acidovorax, Acinetobacter, Acinetobacter guillouiae, Acinetobacter junii, Actinobacillus, Actinobacillus M*1933/96/1, *Actinomyces, Actinomyces* ICM34, *Actinomyces* ICM41, *Actinomyces* ICM54, *Actinomyces lingnae, Actinomyces odontolyticus, Actinomyces oral, Actinomyces* ph3, *Adlercreutzia, Adlercreutzia equolifaciens, Adlercreutzia intestinal, Aerococcus, Aeromonas, Aeromonas* 165C, *Aeromonas hydrophila, Aeromonas* RC50, *Aeropyrum, Aeropyrum pernix, agglomerans, Aggregatibacter, Agreia, Agreia bicolorata, Agromonas, Agromonas CS*30, *Akkermansia, Akkermansia muciniphila, Alistipes, Alistipes* ANH, *Alistipes* AP11, *Alistipes bacterium, Alistipes* CCUG, *Alistipes* DJF B185, *Alistipes DSM, Alistipes* EBA6-25cl2, *Alistipes finegoldii, Alistipes indistinctus, Alistipes* JC136, *Alistipes* NML05A004, *Alistipes onderdonkii, Alistipes putredinis, Alistipes* RMA, *Alistipes senegalensis, Alistipes shahii, Alistipes* Smarlab, *Alkalibaculum, Alkaliflexus, Allisonella, Allisonelia histaminiformans, Alloscardovia, Alloscardovia omnicolens, Anaerofilum, Anaerofustis, Anaerofustis stercorihominis, Anaeroplasma, Anaerostipes, Anaerostipes* 08964, *Anaerostipes* 494a, *Anaerostipes* 5_1_63FAA, *Anaerostipes* AIP, *Anaerostipes bacterium, Anaerostipes butyraticus, Anaerostipes caccae, Anaerostipes hadrum, Anaerostipes* IE4, *Anaerostipes indolis, Anaerostipes* ly-2, *Anaerotruncus, Anaerotruncus colihominis, Anaerotruncus* NML, *Aquincola, Arcobacter, Arthrobacter, Arthrobacter* FVi-1, *Asaccharobacter, Asaccharobacter celatus, Asteroleplasma, Atopobacter, Atopobacter phocae, Atopobium, Atopobium parvulum, Atopobium rimae, Bacteriovorax, Bacteroides, Bacteroides* 31SF18, *Bacteroides* 326-8, *Bacteroides* 35AE31, *Bacteroides* 35AE37, *Bacteroides* 35BE34, *Bacteroides* 4072, *Bacteroides* 7853, *Bacteroides acidifaciens, Bacteroides* API, *Bacteroides* AR20, *Bacteroides* AR29, *Bacteroides* B2, *Bacteroides bacterium, Bacteroides barnesiae, Bacteroides* BLBE-6, *Bacteroides* BV-1, *Bacteroides caccae, Bacteroides* CannelCatfish9, *Bacteroides cellulosilyticus, Bacteroides chinchillae, Bacteroides* CIP 103040, *Bacteroides clarus, Bacteroides coprocola, Bacteroides coprophilus, Bacteroides* D8, *Bacteroides* DJF_B097, *Bacteroides* dnLKV2, *Bacteroides* dnLKV7, *Bacteroides* dnLKV9, *Bacteroides dorei, Bacteroides* EBA5-17, *Bacteroides eggerthil, Bacteroides* enrichment, *Bacteroides* F-4, *Bacteroides faecichinchillae, Bacteroides faecis, Bacteroides* fecal, *Bacteroides finegoldii, Bacteroides fragilis, Bacteroides gallinarum, Bacteroides helcogenes, Bacteroides* ici292, *Bacteroides intestinalis, Bacteroides massiliensis, Bacteroides mpnisolate, Bacteroides* NB-8, *Bacteroides* new, *Bacteroides* NLAE-zl-c204, *Bacteroides* NLAE-zl-c205, *Bacteroides* NLAE-zl-c206, *Bacteroides* NLAE-zl-c207, *Bacteroides* NLAE-zl-c211, *Bacteroides* NLAE-zl-c218, *Bacteroides* NLAE-zl-c257, *Bacteroides* NLAE-zl-c260. *Bacteroides* NLAE-zl-c261, *Bacteroides* NLAE-zl-c263. *Bacteroides* NLAE-zl-c308, *Bacteroides* NLAE-zl-c315, *Bacteroides* NLAE-zl-c322, *Bacteroides* NLAE-zl-c324, *Bacteroides* NLAE-zl-c331, *Bacteroides* NLAE-zl-c339, *Bacteroides* NLAE-zl-c36, *Bacteroides* NLAE-zl-c367, *Bacteroides* NLAE-zl-c375, *Bacteroides* NLAE-zl-c376, *Bacteroides* NLAE-zl-c380, *Bacteroides* NLAE-zl-c391, *Bacteroides* NLAE-zl-c459, *Bacteroides* NLAE-zl-c484, *Bacteroides* NLAE-zl-c501, *Bacteroides* NLAE-zl-c504, *Bacteroides* NLAE-zl-c515, *Bacteroides* NLAE-zl-c519, *Bacteroides* NLAE-zl-c532, *Bacteroides* NLAE-zl-c557. *Bacteroides* NLAE-zl-c57, *Bacteroides* NLAE-zl-c574, *Bacteroides* NLAE-zl-c592, *Bacteroides* NLAE-zl-cl3, *Bacteroides* NLAE-zl-cl58, *Bacteroides* NLAE-zl-cl59, *Bacteroides* NLAE-zl-cl61, *Bacteroides* NLAE-zl-cl63, *Bacteroides* NLAE-zl-cl67, *Bacteroides* NLAE-zl-cl72, *Bacteroides* NLAE-zl-cl8, *Bacteroides* NLAE-zl-cl82, *Bacteroides* NLAE-zl-cl90, *Bacteroides* NLAE-zl-cl98, *Bacteroides* NLAE-zl-g209, *Bacteroides* NLAE-zl-g212, *Bacteroides* NLAE-zl-g213, *Bacteroides* NLAE-zl-g218, *Bacteroides* NLAE-zl-g221, *Bacteroides* NLAE-zl-g228, *Bacteroides* NLAE-zl-g234, *Bacteroides* NLAE-zl-g237, *Bacteroides* NLAE-zl-g24, *Bacteroides* NLAE-zl-g245, *Bacteroides* NLAE-zl-g257, *Bacteroides* NLAE-zl-g27, *Bacteroides* NLAE-zl-g285, *Bacteroides* NLAE-zl-g288, *Bacteroides* NLAE-zl-g295, *Bacteroides* NLAE-zl-g296, *Bacteroides* NLAE-zl-g303, *Bacteroides* NLAE-zl-g310, *Bacteroides* NLAE-zl-g312, *Bacteroides* NLAE-zl-9327, *Bacteroides* NLAE-zl-g329, *Bacteroides* NLAE-zl-g336, *Bacteroides* NLAE-zl-g338, *Bacteroides* NLAE-zl-g347, *Bacteroides* NLAE-zl-g356, *Bacteroides* NLAE-zl-g373, *Bacteroides* NLAE-zl-g376, *Bacteroides* NLAE-zl-g380, *Bacteroides* NLAE-zl-g382, *Bacteroides* NLAE-zl-g385, *Bacteroides* NLAE-zl-g4, *Bacteroides* NLAE-zl-g422, *Bacteroides* NLAE-zl-g437, *Bacteroides* NLAE-zl-g454, *Bacteroides* NLAE-zl-g455, *Bacteroides* NLAE-zl-g456, *Bacteroides* NLAE-zl-g458, *Bacteroides* NLAE-zl-g459, *Bacteroides* NLAE-zl-g46, *Bacteroides* NLAE-zl-g461, *Bacteroides* NLAE-zl-g475, *Bacteroides* NLAE-zl-9481, *Bacteroides* NLAE-zl-g484, *Bacteroides* NLAE-zl-g5, *Bacteroides* NLAE-zl-g502, *Bacteroides* NLAE-zl-g515, *Bacteroides* NLAE-zl-g518, *Bacteroides* NLAE-zl-g521, *Bacteroides* NLAE-zl-g54, *Bacteroides* NLAE-zl-g6, *Bacteroides* NLAE-zl-g8, *Bacteroides* NLAE-zl-g80, *Bacteroides* NLAE-zl-g98, *Bacteroides* NLAE-zl-gl l7, *Bacteroides* NLAE-zl-g105, *Bacteroides* NLAE-zl-gl27, *Bacteroides* NLAE-zl-gi36, *Bacteroides* NLAE-zl-gl43, *Bacteroides* NLAE-zl-gl57, *Bacteroides* NLAE-zl-gl67, *Bacteroides* NLAE-zl-gi71, *Bacteroides* NLAE-zl-gl87, *Bacteroides* NLAE-zl-g194, *Bacteroides* NLAE-zl-gl95, *Bacteroides* NLAE-zl-gl99, *Bacteroides* NLAE-zl-h207, *Bacteroides* NLAE-zl-h22, *Bacteroides* NLAE-zl-h250, *Bacteroides* NLAE-zl-h251, *Bacteroides* NLAE-zl-h28, *Bacteroides* NLAE-zl-h313, *Bacteroides* NLAE-zl-h319, *Bacteroides* NLAE-zl-h321, *Bacteroides* NLAE-zl-h328, *Bacteroides* NLAE-zl-h334, *Bacteroides* NLAE-zl-h390, *Bacteroides* NLAE-zl-h391, *Bacteroides* NLAE-zl-h414, *Bacteroides* NLAE-zl-h416, *Bacteroides* NLAE-zl-h419, *Bacteroides* NLAE-zl-h429, *Bacteroides* NLAE-zl-h439, *Bacteroides* NLAE-zl-h444, *Bacteroides* NLAE-zl-h45, *Bacteroides* NLAE-zl-h46, *Bacteroides* NLAE-zl-h462, *Bacteroides* NLAE-zl-h463, *Bacteroides* NLAE-zl-h465, *Bacteroides* NLAE-zl-h468, *Bacteroides* NLAE-zl-h471, *Bacteroides* NLAE-zl-h472, *Bacteroides* NLAE-zl-h474, *Bacteroides* NLAE-zl-h479, *Bacteroides* NLAE-zl-h482, *Bacteroides* NLAE-zl-h49, *Bacteroides* NLAE-zl-h493, *Bacteroides* NLAE-zl-h496, *Bacteroides* NLAE-zl-h497, *Bacteroides* NLAE-zl-h499, *Bacteroides* NLAE-zl-h50, *Bacteroides* NLAE-zl-h531, *Bacteroides* NLAE-zl-h535, *Bacteroides* NLAE-zl-h8, *Bacteroides* NLAE-zl-h/20, *Bacteroides* NLAE-zl-h15, *Bacteroides* NLAE-zl-hi62, *Bacteroides* NLAE-zl-hl7, *Bacteroides* NLAE-zl-hl74, *Bacteroides* NLAE-z-hl8, *Bacteroides* NLAE-zl-h/88, *Bacteroides* NLAE-zl-hi92, *Bacteroides* NLAE-zl-h/94, *Bacteroides* NLAE-zl-hl95, *Bacteroides* NLAE-zl-p208, *Bacteroides* NLAE-zl-p213, *Bacteroides*

NLAE-zl-p228, *Bacteroides* NLAE-zl-p233, *Bacteroides* NLAE-zl-p267, *Bacteroides* NLAE-zl-p278, *Bacteroides* NLAE-zl-p282, *Bacteroides* NLAE-zl-p286, *Bacteroides* NLAE-zl-p295, *Bacteroides* NLAE-zl-p299. *Bacteroides* NLAE-zl-p301, *Bacteroides* NLAE-zl-p302, *Bacteroides* NLAE-zl-p304, *Bacteroides* NLAE-zl-p317, *Bacteroides* NLAE-zl-p319, *Bacteroides* NLAE-zl-p32, *Bacteroides* NLAE-zl-p332, *Bacteroides* NLAE-zl-p349, *Bacteroides* NLAE-zl-p35, *Bacteroides* NLAE-zl-p356, *Bacteroides* NLAE-zl-p370, *Bacteroides* NLAE-zl-p371, *Bacteroides* NLAE-zl-p376, *Bacteroides* NLAE-zl-p395, *Bacteroides* NLAE-zl-p402, *Bacteroides* NLAE-zl-p403, *Bacteroides* NLAE-zl-p409, *Bacteroides* NLAE-zl-p412, *Bacteroides* NLAE-zl-p436, *Bacteroides* NLAE-zl-p438, *Bacteroides* NLAE-zl-p440, *Bacteroides* NLAE-zl-p447, *Bacteroides* NLAE-zl-p448, *Bacteroides* NLAE-zl-p451, *Bacteroides* NLAE-zl-p476, *Bacteroides* NLAE-zl-p478, *Bacteroides* NLAE-zl-p483, *Bacteroides* NLAE-zl-p489, *Bacteroides* NLAE-zl-p493, *Bacteroides* NLAE-zl-p557, *Bacteroides* NLAE-zl-p559, *Bacteroides* NLAE-zl-p564, *Bacteroides* NLAE-zl-p565, *Bacteroides* NLAE-zl-p572, *Bacteroides* NLAE-zl-p573, *Bacteroides* NLAE-zl-p576, *Bacteroides* NLAE-zl-p591, *Bacteroides* NLAE-zl-p592, *Bacteroides* NLAE-zl-p631, *Bacteroides* NLAE-zl-p633, *Bacteroides* NLAE-zl-p696, *Bacteroides* NLAE-zl-p7, *Bacteroides* NLAE-zl-p720, *Bacteroides* NLAE-zl-p730, *Bacteroides* NLAE-zl-p736, *Bacteroides* NLAE-zl-p737, *Bacteroides* NLAE-zl-p754, *Bacteroides* NLAE-zl-p759, *Bacteroides* NLAE-zl-p774, *Bacteroides* NLAE-zl-p828, *Bacteroides* NLAE-zl-p854, *Bacteroides* NLAE-zl-p860, *Bacteroides* NLAE-zl-p886, *Bacteroides* NLAE-zl-p887, *Bacteroides* NLAE-zl-p900, *Bacteroides* NLAE-zl-p909, *Bacteroides* NLAE-zl-p913, *Bacteroides* NLAE-zl-p916, *Bacteroides* NLAE-zl-p920, *Bacteroides* NLAE-zl-p96, *Bacteroides* NLAE-zl-p/04, *Bacteroides* NLAE-zl-pl05, *Bacteroides* NLAE-zl-pl08, *Bacteroides* NLAE-zl-pl32, *Bacteroides* NLAE-zl-p/33, *Bacteroides* NLAE-zl-p/51, *Bacteroides* NLAE-zl-p/57, *Bacteroides* NLAE-zl-p/66, *Bacteroides* NLAE-zl-p/67, *Bacteroides* NLAE-zl-p/71, *Bacteroides* NLAE-zl-pl78, *Bacteroides* NLAE-zl-p/87, *Bacteroides* NLAE-zl-p/91, *Bacteroides* NLAE-zl-p/96, *Bacteroides* nordii, *Bacteroides oleiciplenus, Bacteroides ovatus, Bacteroides paurosaccharolyticus, Bacteroides piebeius, Bacteroides* R6, *Bacteroides rodentium, Bacteroides* S-17, *Bacteroides* S-18, *Bacteroides salyersiae, Bacteroides* SLCI-38, *Bacteroides* Smarlab, *Bacteroides* 'Smarlab, *Bacteroides stercorirosoris, Bacteroides stercoris, Bacteroides* str, *Bacteroides thetaiotaomicron, Bacteroides* TP-5, *Bacteroides uniformis, Bacteroides vulgatus, Bacteroides* WA1, *Bacteroides* WH2, *Bacteroides* WH302, *Bacteroides* WH305, *Bacteroides* X077B42, *Bacteroides* XB12B, *Bacteroides* XB44A, *Bacteroides xylanisolvens, Barnesiella, Barnesiella intestinihominis, Barnesiella* NSB1, *Barnesiella viscericola, Bavariicoccus, Bdellovibrio, Bdellovibrio* oral, *Bergeriella, Bifidobacterium, Bifidobacterium* 103, *Bifidobacterium* 108, *Bifidobacterium* 113, *Bifidobacterium* 120, *Bifidobacterium* 138, *Bifidobacterium* 33, *Bifidobacterium* Acbbto5, *Bifidobacterium adolescentis, Bifidobacterium* Amsbbt/2, *Bifidobacterium angulatum, Bifidobacterium animalis, Bifidobacterium bacterium, Bifidobacterium bifidum, Bifidobacterium* Bisn6, *Bifidobacterium* Bma6, *Bifidobacterium breve, Bifidobacterium catenulatum, Bifidobacterium choerinum, Bifidobacterium coryneforme, Bifidobacterium dentium, Bifidobacterium* DJF_WC44, *Bifidobacterium* F-10, *Bifidobacterium* F-1 l, *Bifidobacterium* group, *Bifidobacterium* hl2, *Bifidobacterium* HMLN1, *Bifidobacterium* HMLN12, *Bifidobacterium* HMLN5, *Bifidobacterium* iarfr2341d, *Bifidobacterium* iarfr642d48, *Bifidobacterium* ici332, *Bifidobacterium indicum, Bifidobacterium kashiwanohense, Bifidobacterium* LISLUCIII-2, *Bifidobacterium longum, Bifidobacterium* M45, *Bifidobacterium merycicum, Bifidobacterium minimum, Bifidobacterium* MSX5B, *Bifidobacterium* oral, *Bifidobacterium* PG12A, *Bifidobacterium* PL1, *Bifidobacterium pseudocatenulatum, Bifidobacterium pseudolongum, Bifidobacterium pullorum, Bifidobacterium ruminantium, Bifidobacterium* S-10, *Bifidobacterium saeculare, Bifidobacterium saguini, Bifidobacterium scardovii, Bifidobacterium simiae, Bifidobacterium* SLPYG-1, *Bifidobacterium* stercoris, *Bifidobacterium* TM-7, *Bifidobacterium* Trm9, *Bilophila, Bilophila* NLAE-zl-h528, *Bilophila wadsworthia, Blautia, Blautia bacterium, Blautia* CE2, *Blautia* CE6, *Blautia coccoides, Blautia* DJF_VR52, *Blautia* DJF_VR67, *Blautia* DJF_VR70kl, *Blautia formate, Blautia glucerasea, Blautia hansenii, Blautia* ici272, *Blautia* IE5, *Blautia* K-I, *Blautia luti, Blautia* M-I, *Blautia mpnisolate, Blautia* NLAE-zl-c25, *Blautia* NLAE-zl-c259, *Blautia* NLAE-zl-c51, *Blautia* NLAE-zl-c520, *Blautia* NLAE-zl-c542, *Blautia* NLAE-zl-c544, *Blautia* NLAE-zl-h27, *Blautia* NLAE-zl-h316, *Blautia* NLAE-zl-h317, *Blautia obeum, Blautia producta, Blautia productus, Blautia schinkii, Blautia* Ser5, *Blautia* Ser8, *Biautia* WAL, *Blautia wexlerae, Blautia* YHC-4, *Brenneria, Brevibacterium, Brochothrix, Brochothrix thermosphacta, Buttiauxella, Buttiauxella* 57916, *Buttiauxella gaviniae, Butyricicoccus, Butyricicoccus bacterium, Butyricimonas, Butyricimonas* 180-3, *Butyricimonas* 214-4, *Butyricimonas bacterium, Butyricimonas* GD2, *Butyricimonas synergistica, Butyricimonas virosa, Butyrivibrio, Butyrivibrio fibrisolvens, Butyrivibrio hungatei, Caldimicrobium, Caidisericum, Campylobacter, Campylobacter coli, Campylobacter hominis, Capnocytophaga, Carnobacterium, Carnobacterium alterfunditum, Caryophanon, Catenibacterium, Catenibacterium mitsuokai, Catonella, Caulobacter, Cellulophaga, Cellulosilyticum, Cetobacterium, Chelatococcus, Chlorobium, Chryseobacterium, Chryseobacterium* A1005, *Chryseobacterium* KJ9C8, *Citrobacter, Citrobacter* 1, *Citrobacter* 191-3, *Citrobacter agglomerans, Citrobacter amalonaticus, Citrobacter ascorbata, Citrobacter bacterium, Citrobacter* BinzhouCLT, *Citrobacter braakii, Citrobacter* enrichment, *Citrobacter* F24, *Citrobacter* F96, *Citrobacter farmeri, Citrobacter freundii, Citrobacter gillenii, Citrobacter* HBKC_SR1, *Citrobacter* HD4.9, *Citrobacter hormaechei, Citrobacter* ka55, *Citrobacter* lapagei, *Citrobacter* LAR-1, *Citrobacter ludwigii, Citrobacter* MEB5, *Citrobacter* MS36, *Citrobacter murliniae, Citrobacter* NLAE-zl-c269, *Citrobacter* P014, *Citrobacter* P042bN, *Citrobacter* P046a, *Citrobacter* P073, *Citrobacter* SR3, *Citrobacter* TI, *Citrobacter* tnt4, *Citrobacter* tnt5, *Citrobacter* trout, *Citrobacter* TSA-1, *Citrobacter werkmanil, Cloacibacillus, Cloacibacillus* adv66, *Cloacibacillus* NLAE-zl-p702, *Cloacibacillus* NML05A017, *Cloacibacterium, Collinsella, Collinsella aerofaciens, Collinsella* A-I, *Collinsella* AUH-Julong21, *Collinsella bacterium, Collinsella* CCUG, *Comamonas, Comamonas straminea, Comamonas testosteroni, Conexibacter, Coprobacillus, Coprobacillus bacterium, Coprobacillus cateniformis, Coprobacillus* TM-40, *Coprococcus, Coprococcus* 14505, *Coprococcus bacterium, Coprococcus catus, Coprococcus comes, Coprococcus eutactus, Coprococcus nexile, Coraliomargarita, Coraliomargarita fucoidanolyticus, Coraliomargarita marisflavi, Corynebacterium, Corynebacterium amycolatum, Corynebacterium durum, Coxiella, Cronobacter, Cronobacter dublinensis, Cronobacter sakazakii, Cronobacter turicensis, Cryptobacterium, Cryptobacterium curtum,*

*Cupriavidus, Cupriavidus eutropha, Dechloromonas, Dechloromonas* HZ, *Desuifobacterium, Desulfobulbus, Desulfopila, Desulfopila* La4.1, *Desulfovibrio, Desulfovibrio* D4, *Desulfovibrio desulfuricans, Desulfovibrio* DSM 12803, *Desulfovibrio* enrichment, *Desulfovibrio fairfieldensis, Desulfovibrio* LNB1, *Desulfovibrio piger, Dialister, Dialister* E2_20, *Dialister* GBA27, *Dialister invisus, Dialister* oral, *Dialister succinatiphilus, Dorea, Dorea* auhjulong64, *Dorea bacterium, Dorea formicigenerans, Dorea longicatena, Dorea mpnisolate, Dysgonomonas, Dysgonomonas gadei, Edwardsiella, Edwardsiella tarda, Eggerthella, Eggerthella* El, *Eggerthella lenta, Eggerthella* MLG043, *Eggerthella* MVA1, *Eggerthella S*6-C1, *Eggerthella* SDG-2, *Eggerthella sinensis, Eggerthella* str, *Enhydrobacter, Enterobacter, Enterobacter* 1050, *Enterobacter* 112, *Enterobacter* 1122, *Enterobacter* 77000, *Enterobacter* 82353, *Enterobacter* 9C, *Enterobacter* A5C, *Enterobacter adecarboxylata, Enterobacter aerogenes, Enterobacter agglomerans, Enterobacter* AJAR-A2, *Enterobacter amnigenus, Enterobacter asburiae, Enterobacter* B 1 (2012), *Enterobacter* B363, *Enterobacter* B509, *Enterobacter bacterium, Enterobacter* Badong3, *Enterobacter* BEC441, *Enterobacter* C8, *Enterobacter cancerogenus, Enterobacter cloacae, Enterobacter* CO, *Enterobacter* core2, *Enterobacter* cowanii, *Enterobacter* dc6, *Enterobacter* DRSBII, *Enterobacter* enrichment, *Enterobacter* FL13-2-1, *Enterobacter* GIST-NKst9, *Enterobacter* GIST-NKstIO, *Enterobacter* GJI-11, *Enterobacter* gx-148, *Enterobacter hormaechei, Enterobacter* I-Bh20-21, *Enterobacter* ICB113, *Enterobacter kobei, Enterobacter* KW14, *Enterobacter ludwigii, Enterobacter* M10_1B, *Enterobacter* M1R3, *Enterobacter* marine, *Enterobacter* NCCP-167, *Enterobacter* of, *Enterobacter oryzae, Enterobacter oxytoca, Enterobacter* P101, *Enterobacter* SEL2, *Enterobacter* SI 1, *Enterobacter* SPh, *Enterobacter* SSASP5, *Enterobacter terrigena, Enterobacter* TNT3, *Enterobacter* TP2MC, *Enterobacter* TS4, *Enterobacter* TSSAS2-48, *Enterobacter* ZYXCA1, *Enterococcus, Enterococcus* 020824/02-A, *Enterococcus* 1275b, *Enterococcus* 16C, *Enterococcus* 48, *Enterococcus* 6114, *Enterococcus* ABRI-INW-H61, *Enterococcus* asini, *Enterococcus avium, Enterococcus azikeevi, Enterococcus bacterium, Enterococcus* BBDP57, *Enterococcus* BPH34, *Enterococcus* Bt, *Enterococcus canis, Enterococcus* casselif avus, *Enterococcus* CmNA2, *Enterococcus* Da-20, *Enterococcus* devriesei, *Enterococcus dispar, Enterococcus* DJF_O30, *Enterococcus* DMB4, *Enterococcus durans, Enterococcus* enrichment, *Enterococcus* F81, *Enterococcus faecalis, Enterococcus faecium, Enterococcus* fcc9, *Enterococcus* fecal, *Enterococcus flavescens, Enterococcus fluvialis, Enterococcus* FR-3, *Enterococcus* FUA3374, *Enterococcus gallinarum, Enterococcus* GSC-2, *Enterococcus* GYPB01, *Enterococcus hermanniensis, Enterococcus hirae, Enterococcus lactis, Enterococcus malodoratus, Enterococcus manure, Enterococcus marine, Enterococcus* MNC1, *Enterococcus moraviensis, Enterococcus* MS2, *Enterococcus mundtii, Enterococcus* NAB 15, *Enterococcus* NBRC, *Enterococcus* NLAE-zl-c434, *Enterococcus* NLAE-zl-g87, *Enterococcus* NLAE-zl-gl06, *Enterococcus* NLAE-zl-h339, *Enterococcus* NLAE-zl-h375, *Enterococcus* NLAE-zl-h381, *Enterococcus* NLAE-zl-h383, *Enterococcus* NLAE-zl-h405, *Enterococcus* NLAE-zl-p401, *Enterococcus* NLAE-zl-p650, *Enterococcus* NLAE-zl-pl 16, *Enterococcus* NLAE-zl-pl48, *Enterococcus pseudoavium, Enterococcus* R-25205, *Enterococcus raffinosus, Enterococcus* rottae, *Enterococcus* RU07, *Enterococcus saccharolyticus, Enterococcus saccharominimus, Enterococcus sanguinicola, Enterococcus* SCA16, *Enterococcus* SCA2, *Enterococcus* SE138, *Enterococcus* SF-1, *Enterococcus sulfureus, Enterococcus* SV6, *Enterococcus* te32a, *Enterococcus* te42a, *Enterococcus* te45r, *Enterococcus* te49a, *Enterococcus* te51a, *Enterococcus* te58r, *Enterococcus* te59r, *Enterococcus* te61r, *Enterococcus* te93r, *Enterococcus* te95a, *Enterococcus* tela, *Enterorhabdus, Enterorhabdus caecimuris, Entomophaga, Erwinia, Erwinia agglomerans, Erwinia enterica, Erwinia rhapontici, Erwinia tasmaniensis, Erysipelotrichaceae incertae sedis, Erysipelotrichaceae incertae sedis aff, Erysipelotrichaceae incertae sedis bacterium, Erysipelotrichaceae incertae sedis biforme, Erysipelotrichaceae incertae sedis* C-I, *Erysipelotrichaceae incertae sedis cylindroides, Erysipelotrichaceae incertae sedis* GK12, *Erysipelotrichaceae incertae sedis innocuum, Erysipelotrichaceae incertae sedis* NLAE-zl-c332, *Erysipelotrichaceae incertae sedis* NLAE-zl-c340, *Erysipelotrichaceae incertae sedis* NLAE-zl-g420, *Erysipelotrichaceae incertae sedis* NLAE-zl-g425, *Erysipelotrichaceae incertae sedis* NLAE-zl-g440, *Erysipelotrichaceae incertae sedis* NLAE-zl-g463, *Erysipelotrichaceae incertae sedis* NLAE-zl-h340, *Erysipelotrichaceae incertae sedis* NLAE-zl-h354, *Erysipelotrichaceae incertae sedis* NLAE-zl-h379, *Erysipelotrichaceae incertae sedis* NLAE-zl-h380, *Erysipelotrichaceae incertae sedis* NLAE-zl-h385, *Erysipelotrichaceae incertae sedis* NLAE-zl-h410, *Erysipelotrichaceae incertae sedis tortuosum, Escherichia/Shigella, Escherichia/Shigella* 29 (2010), *Escherichia/Shigella* 4091, *Escherichia/Shigella* 4104, *Escherichia/Shigella* 8gwl8, *Escherichia/Shigella* A94, *Escherichia/Shigella albertii, Escherichia/Shigella* B-1012, *Escherichia/Shigella* B4, *Escherichia/Shigella bacterium, Escherichia/Shigella* BBDP15, *Escherichia/Shigella* BBDP80, *Escherichia/Shigella boydii, Escherichia/Shigella carotovorum, Escherichia/Shigella* CERAR, *Escherichia/Shigella coli, Escherichia/Shigella* DBC-1, *Escherichia/Shigella* dc262011, *Escherichia/Shigella dysenteriae, Escherichia/Shigella* enrichment, *Escherichia/Shigella escherichia, Escherichia/Shigella* fecal, *Escherichia/Shigella fergusonii, Escherichia/Shigella flexneri, Escherichia/Shigella* GDR05, *Escherichia/Shigella* GDR07, *Escherichia/Shigella* H7, *Escherichia/Shigella* marine, *Escherichia/Shigella* ML2-46, *Escherichia/Shigella* mpnisolate, *Escherichia/Shigella* NA, *Escherichia/Shigella* NLAE-zl-g330, *Escherichia/Shigella* NLAE-zl-g400, *Escherichia/Shigella* NLAE-zl-g441, *Escherichia/Shigella* NLAE-zl-g506, *Escherichia/Shigella* NLAE-zl-h204, *Escherichia/Shigella* NLAE-zl-h208, *Escherichia/Shigella* NLAE-zl-h209, *Escherichia/Shigella* NLAE-zl-h213, *Escherichia/Shigella* NLAE-zl-h214, *Escherichia/Shigella* NLAE-zl-h4, *Escherichia/Shigella* NLAE-zl-h435, *Escherichia/Shigella* NLAE-zl-h81, *Escherichia/Shigella* NLAE-zl-p21, *Escherichia/Shigella* NLAE-zl-p235, *Escherichia/Shigella* NLAE-zl-p237, *Escherichia/Shigella* NLAE-zl-p239, *Escherichia/Shigella* NLAE-zl-p25, *Escherichia/Shigella* NLAE-zl-p252, *Escherichia/Shigella* NLAE-zl-p275, *Escherichia/Shigella* NLAE-zl-p280, *Escherichia/Shigella* NLAE-zl-p51, *Escherichia/Shigella* NLAE-zl-p53, *Escherichia/Shigella* NLAE-zl-p669, *Escherichia/Shigella* NLAE-zl-p676, *Escherichia/Shigella* NLAE-zl-p717, *Escherichia/Shigella* NLAE-zl-p731, *Escherichia/Shigella* NLAE-zl-p826, *Escherichia/Shigella* NLAE-zl-p877, *Escherichia/Shigella* NLAE-zl-p884, *Escherichia/Shigella* NLAE-zl-p/26, *Escherichia/Shigella* NLAE-zl-p/98, *Escherichia/Shigella* NMU-ST2, *Escherichia/Shigella* ocl 82011, *Escherichia/Shigella* of, *Escherichia/Shigella* proteobacterium, *Escherichia/Shigella* QI, *Escherichia/Shigella* sakazakii, *Escheri-*

*chia/Shigella* SF6, *Escherichia/Shigella* sml719, *Escherichia/Shigella* SOD-7317, *Escherichia/Shigella sonnei, Escherichia/Shigella* SW86, *Escherichia/Shigella vuineris, Ethanoligenens, Ethanoligenens harbinense, Eubacterium, Eubacterium* ARC-2, *Eubacterium callanderi, Eubacterium* E-I, *Eubacterium* G3 (2011), *Eubacterium infirmum, Eubacterium limosum, Eubacterium methylotrophicum, Eubacterium* NLAE-zl-p439, *Eubacterium* NLAE-zl-p457, *Eubacterium* NLAE-zl-p458, *Eubacterium* NLAE-zl-p469, *Eubacterium* NLAE-zl-p474, *Eubacterium* oral, *Eubacterium saphenum, Eubacterium sulci, Eubacterium* WAL, *Euglenida, Euglenida longa, Faecalibacterium, Faecalibacterium bacterium, Faecalibacterium canine, Faecalibacterium* DJF VR20, *Faecalibacterium* ic/379, *Faecalibacterium prausnitzii, Filibacter, Filibacter globispora, Flavobacterium, Flavobacterium* SSL03, *Flavonifractor, Flavonifractor* AUH-JLC235, *Flavonifractor* enrichment, *Flavonifractor* NLAE-zl-c354, *Flavonifractor orbiscindens, Flavonifractor plautii, Francisella, Francisella piscicida, Fusobacterium, Fusobacterium nucleatum, Gardnerella, Gardnerella vaginalis, Gemmiger, Gemmiger* DJF_VR33k2, *Gemmiger formicilis, Geobacter*, GHAPRB1, *Gordonibacter, Gordonibacter bacterium, Gordonibacter* intestinal, *Gordonibacter pamelaeae*, Gp2, Gp21, Gp4, Gp6, *Granulicatella, Granulicatella adiacens, Granulicatella* enrichment, *Granulicatella oral, Granulicatella paraadiacens, Haemophilus, Hafnia, Hafnia* 3-12 (2010), *Hafnia alvei, Hafnia* CC16, *Hafnia proteus, Hallea, Hallella, Hallella seregens, Herbaspirillum, Herbaspirillum* 022S4-11, *Herbaspirillum seropedicae, Hespellia, Hespellia porcina, Hespellia stercorisuis, Holdemania, Holdemania* AP2, *Hoidemania filiformis, Howardella, Howardella ureilytica, Hydrogenoanaerobacterium, Hydrogenoanaerobacterium saccharovorans, Hydrogenophaga, Hydrogenophaga bacterium, Ilumatobacter, inulinivorans, Janthinobacterium, Janthinobacterium* C30An7, *Jeotgalicoccus, Klebsiella, Klebsiella aerogenes, Klebsiella bacterium, Klebsiella* E1L1, *Klebsiella* EB2-THQ, *Klebsiella* enrichment, *Klebsiella* F83, *Klebsiella* ggi60e, *Klebsiella* GI-6, *Klebsiella granulomatis, Klebsiella* HaNA20, *Klebsiella* HF2, *Klebsiella* il_3_chl_I, *Klebsiella* KALA-ICIBA17, *Klebsiella* kpu, *Klebsiella* M3, *Klebsiella* MB45, *Klebsiella* milletis, *Klebsiella* NCCP-138, *Klebsiella* okl_1_9_S16, *Klebsiella* okl_1_9_S54, *Klebsiella pianticola, Klebsiella pneumoniae, Klebsiella poinarii, Klebsiella* PSB26, *Klebsiella* RS, *Klebsiella* Sel4, *Klebsiella* SRC_DSD12, *Klebsiella* tdi53s, *Klebsiella* TG-1, *Klebsiella* TPS 5, *Klebsiella variicola, Klebsiella* WB-2, *Klebsiella* Y9, *Klebsiella* zlmy, *Kluyvera, Kluyvera* An5-1, *Kluyvera cryocrescens, Kocuria, Kocuria* 2216.35.31, *Kurthia, Lachnobacterium, Lachnobacterium* C12b, *Lachnospiracea incertae sedis, Lachnospiracea incertae sedis bacterium, Lachnospiracea incertae sedis contortum, Lachnospiracea incertae sedis* Eg2, *Lachnospiracea incertae sedis eligens, Lachnospiracea incertae sedis ethanolgignens, Lachnospiracea incertae sedis galacturonicus, Lachnospiracea incertae sedis gnavus, Lachnospiracea incertae sedis hallii, Lachnospiracea incertae sedis hydrogenotrophica, Lachnospiracea incertae sedis* ID5, *Lachnospiracea incertae sedis intestinal, Lachnospiracea incertae sedis mpnisolate, Lachnospiracea incertae sedis pectinoschiza, Lachnospiracea incertae sedis ramulus, Lachnospiracea incertae sedis rectale, Lachnospiracea incertae sedis* RLB1, *Lachnospiracea incertae sedis rumen, Lachnospiracea incertae sedis* SY8519, *Lachnospiracea incertae sedis torques, Lachnospiracea incertae sedis uniforme, Lachnospiracea incertae sedis ventriosum, Lachnospiracea incertae sedis xylanophilum, Lachnospiracea incertae sedis* ye62, *Lactobacillus, Lactobacillus* 5-1-2, *Lactobacillus* 66c, *Lactobacillus acidophilus, Lactobacillus arizonensis, Lactobacillus* B5406, *Lactobacillus brevis, Lactobacillus casei, Lactobacillus crispatus, Lactobacillus curvatus, Lactobacillus delbrueckii, Lactobacillus fermentum, Lactobacillus gasseri, Lactobacillus helveticus, Lactobacillus hominis, Lactobacillus* ID9203, *Lactobacillus* IDSAc, *Lactobacillus* intestinal, *Lactobacillus johnsonii, Lactobacillus lactis, Lactobacillus manihotivorans, Lactobacillus mucosae, Lactobacillus* NA, *Lactobacillus oris, Lactobacillus* P23. *Lactobacillus* P8, *Lactobacillus paracasei, Lactobacillus paraplantarum, Lactobacillus pentosus, Lactobacillus plantarum, Lactobacillus pontis, Lactobacillus* rennanqilfyl4, *Lactobacillus* rennanqilyf9, *Lactobacillus reuteri, Lactobacillus rhamnosus, Lactobacillus salivarius, Lactobacillus sanfranciscensis, Lactobacillus suntoryeus, Lactobacillus* T3R1C1, *Lactobacillus vaginalis, Lactobacillus zeae, Lactococcus, Lactococcus* 56, *Lactococcus* CR-317S, *Lactococcus* CW-1, *Lactococcus* D8, *Lactococcus* Da-18, *Lactococcus* DAP39, *Lactococcus delbrueckii, Lactococcus* F116, *Lactococcus fujiensis, Lactococcus* G22, *Lactococcus garvieae, Lactococcus lactis, Lactococcus manure, Lactococcus* RT5, *Lactococcus* SXVIII1 (2011), *Lactococcus* TP2MJ, *Lactococcus* TP2ML, *Lactococcus* TP2MN, *Lactococcus* U5-1, *Lactonifactor, Lactonifactor bacterium, Lactonifactor longoviformis, Lactonifactor* NLAE-zl-c533, *Leciercia, Lentisphaera, Leuconostoc, Leuconostoc carnosum, Leuconostoc citreum, Leuconostoc garlicum, Leuconostoc gasicomitatum, Leuconostoc gelidum, Leuconostoc inhae, Leuconostoc lactis, Leuconostoc* MEBE2, *Leuconostoc mesenteroides, Leuconostoc pseudomesenteroides, Limnobacter, Limnobacter* spf3, *Luteolibacter, Luteolibacter bacterium, Lutispora, Marinifilum, Marinobacter, Marinobacter arcticus, Mariprofundus, Marvinbryantia, Megamonas, Megasphaera, Melissococcus, Melissococcus faecalis, Methanobacterium, Methanobacterium subterraneum, Methanobrevibacter, Methanobrevibacter arboriphilus, Methanobrevibacter millerae, Methanobrevibacter olleyae, Methanobrevibacter oralis, Methanobrevibacter* SM9, *Methanobrevibacter smithii, Methanosphaera, Methanosphaera stadtmanae, Methylobacterium, Methyiobacterium adhaesivum, Methylobacterium bacterium, Methylobacterium HEID, Methylobacterium* MP3, *Methylobacterium oryzae, Methylobacterium* PB132, *Methylobacterium* PB20, *Methyiobacterium* PB280, *Methylobacterium* PDD-23b-14, *Methyiobacterium radiotolerans, Methyiobacterium* SKJH-1, *Mitsuokella, Mitsuokella jalaludinii, Morganella, Morganella morganii, Moritelia, Moritella* 2D2, *Moryella, Moryella indoligenes, Moryella naviforme, Mycobacterium, Mycobacterium tuberculosis, Negativicoccus, Nitrosomonas, Nitrosomonas eutropha, Novosphingobium, Odoribacter, Odoribacter laneus, Odoribacter splanchnicus, Olsenella, Olsenelia* 1832, *Olsenella F*0206, *Orbus, Orbus gilliamella, Oribacterium, Oscillibacter, Oscillibacter bacterium, Oscillibacter* enrichment, *Owenweeksia, Oxalobacter, Oxalobacter formigenes, Paludibacter, Pantoea, Pantoea eucalypti, Papillibacter, Papillibacter cinnamivorans, Parabacteroides, Parabacteroides* ASF519, *Parabacteroides* CR-34, *Parabacteroides distasonis, Parabacteroides* DJF B084, *Parabacteroides* DJF B086, *Parabacteroides* dnLKV8, *Parabacteroides* enrichment, *Parabacteroides fecal, Parabacteroides goldsteinii, Parabacteroides gordonii, Parabacteroides johnsonii, Parabacteroides merdae, Parabacteroides mpnisolate, Parabacteroides* NLAE-zl-p340, *Paraeggerthella, Paraeggerthella hongkongensis, Paraeggerthella* NLAE-zlp797, *Paraeggerthelia* NLAE-zl-p896, *Paraprevotella, Paraprevotella clara, Paraprevotella xylaniphila, Parasutterella, Parasutterella excrementihominis, Pectobacterium, Pectobacterium carotovorum, Pectobacterium wasabiae, Pediococcus, Pediococcus* te2r, *Pedobacter, Pedobacter* b3Nlb-b5, *Pedobacter daechungensis, Peptostreptococcus, Peptostreptococcus anaerobius, Peptostreptococcus stomatis, Phascolarctobacterium, Phascolarctobacterium faecium, Photobacterium, Photobacterium MIE, Pilibacter, Planctomyces, Planococcaceae incertae sedis, Planomicrobium, Plesiomonas, Porphyrobacter, Porphyrobacter* KK348, *Porphyromonas, Porphyromonas asaccharolytica, Porphyromonas bennonis, Porphyromonas canine, Porphyromonas somerae, Prevotella, Prevotella bacterium, Prevotella* BI-42, *Prevotella bivia, Prevotella buccalis, Prevotella copri, Prevotella* DJF_B112, *Prevotella* mpnisolate, *Prevotella* oral, *Propionibacterium, Propionibacterium acnes, Propionibacterium freudenreichii, Propionibacterium* LG, *Proteiniborus, Proteiniphilum, Proteus, Proteus* HS7514, *Providencia, Pseudobutyrivibrio, Pseudobutyrivibrio bacterium, Pseudobutyrivibrio fibrisolvens, Pseudobutyrivibrio ruminis, Pseudochrobactrum, Pseudoflavonifractor, Pseudoflavonifractor* asf500, *Pseudoflavonifractor bacterium, Pseudoflavonifractor capillosus, Pseudoflavonifractor* NML, *Pseudomonas, Pseudomonas* 1043, *Pseudomonas* 10569. *Pseudomonas* 11-44, *Pseudomonas* 127 (39-zx), *Pseudomonas* 12A_19, *Pseudomonas* 145 (38zx), *Pseudomonas* 22010, *Pseudomonas* 32010, *Pseudomonas* 34t20. *Pseudomonas* 3C_10, *Pseudomonas* 4-5 (2010), *Pseudomonas* 4-9 (2010), *Pseudomonas* 6-13.J. *Pseudomonas* 63596, *Pseudomonas* 82010, *Pseudomonas* a001-142L, *Pseudomonas aeruginosa, Pseudomonas agarici, Pseudomonas* al 1 1-5, *Pseudomonas* alOl-18-2, *Pseudomonas amspl, Pseudomonas* AU2390, *Pseudomonas* AZ18R1, *Pseudomonas azotoformans, Pseudomonas* B122, *Pseudomonas* B65 (2012), *Pseudomonas bacterium, Pseudomonas* BJSX, *Pseudomonas* BLH-8D5, *Pseudomonas* BWDY-29, *Pseudomonas* CA18, *Pseudomonas* Cantasl2, *Pseudomonas* CB11, *Pseudomonas* CBZ-4, *Pseudomonas cedrina, Pseudomonas* CGMCC, *Pseudomonas* CL16, *Pseudomonas* CNE, *Pseudomonas corrugata, Pseudomonas cuatrocienegasensis, Pseudomonas* CYEB-7, *Pseudomonas* D5, *Pseudomonas* DAP37, *Pseudomonas* DB48, *Pseudomonas deceptionensis, Pseudomonas* Den-05, *Pseudomonas* DF7EH1, *Pseudomonas* DhA-91, *Pseudomonas* DVS14a, *Pseudomonas* DYJK4-9, *Pseudomonas* DZQ5, *Pseudomonas* E11_ICE19B, *Pseudomonas* E2.2, *Pseudomonas* e2-CDC-TB4D2, *Pseudomonas* EM189, *Pseudomonas* enrichment, *Pseudomonas extremorientalis, Pseudomonas* FAIR/BE/F/GH37, *Pseudomonas* FAIR/BE/F/GH39, *Pseudomonas* FAIR/BE/F/GH94, *Pseudomonas* FLM05-3, *Pseudomonas fluorescens, Pseudomonas fragi, Pseudomonas* 'FSL, *Pseudomonas* G1013, *Pseudomonas* gingeri, *Pseudomonas* HC2-2, *Pseudomonas* HC2-4, *Pseudomonas* HC2-5, *Pseudomonas* HC4-8, *Pseudomonas* HC6-6, *Pseudomonas* Hg4-06, *Pseudomonas* HLB8-2, *Pseudomonas* HLS12-1, *Pseudomonas* HSF20-13, *Pseudomonas* HW08, *Pseudomonas* IpA-92, *Pseudomonas* IV, *Pseudomonas* JCM, *Pseudomonas jessenii, Pseudomonas* JSPB5, *Pseudomonas* K3R3.1A, *Pseudomonas* KB40, *Pseudomonas* KB42, *Pseudomonas* KB44, *Pseudomonas* KB63, *Pseudomonas* KB73, *Pseudomonas* KK-21-4, *Pseudomonas* KOPRI, *Pseudomonas* L1R3.5, *Pseudomonas* LAB-27, *Pseudomonas* LAB-44, *Pseudomonas* LcIO-2, *Pseudomonas libanensis, Pseudomonas* Ln5C.7. *Pseudomonas* LS197, *Pseudomonas lundensis, Pseudomonas marginalis, Pseudomonas* MFY143, *Pseudomonas* MFY146, *Pseudomonas* MY 1412, *Pseudomonas* MY1404, *Pseudomonas* MY1416, *Pseudomonas* MY1420, *Pseudomonas* N14zhy, *Pseudomonas* NBRC, *Pseudomonas* NCCP-506, *Pseudomonas* NFU20-14, *Pseudomonas* NJ-22, *Pseudomonas* NJ-24, *Pseudomonas* Nj-3, *Pseudomonas* Nj-55, *Pseudomonas* Nj-56, *Pseudomonas* Nj-59, *Pseudomonas* Nj-60, *Pseudomonas* Nj-62, *Pseudomonas* Nj-70, *Pseudomonas* NP41, *Pseudomonas* OCW4, *Pseudomonas* OW3-15-3-2, *Pseudomonas* P2 (2010), *Pseudomonas* P3 (2010), *Pseudomonas* P4 (2010), *Pseudomonas* PD, *Pseudomonas* PF1B4, *Pseudomonas* PF2M10. *Pseudomonas* PILH1, *Pseudomonas* Pl(2010), *Pseudomonas poae, Pseudomonas proteobacterium, Pseudomonas* ps4-12, *Pseudomonas* ps4-2, *Pseudomonas* ps4-28, *Pseudomonas* ps4-34, *Pseudomonas* ps4-4, *Pseudomonas psychrophila, Pseudomonas putida, Pseudomonas* R-35721, *Pseudomonas* R-37257, *Pseudomonas* R-37265, *Pseudomonas* R-37908, *Pseudomonas* RBE2CD-42, *Pseudomonas* regd9, *Pseudomonas* RKS7-3. *Pseudomonas* S2, *Pseudomonas* seawater, *Pseudomonas* SGb08, *Pseudomonas* SGb396, *Pseudomonas* SGbi20, *Pseudomonas* sgn, *Pseudomonas* 'Shk, *Pseudomonas stutzeri, Pseudomonas syringae, Pseudomonas taetrolens, Pseudomonas tolaasii, Pseudomonas trivialis, Pseudomonas* TUT1023, *Pseudomonas* W15Feb26, *Pseudomonas* W15Feb4, *Pseudomonas* W15Feb6, *Pseudomonas* WD-3, *Pseudomonas* WR4-13, *Pseudomonas* WR7 #2, *Pseudomonas* Y1000, *Pseudomonas* ZS29-8, *Psychrobacter, Psychrobacter* umbi3d, *Pyramidobacter, Pyramidobacter piscolens, Rahnella, Rahnella aquatilis, Rahnella carotovorum, Rahnella* GIST-WP4wl, *Rahnella* LR113, *Rahnella* Z2-S1, *Raistonia, Ralstonia bacterium, Raoultella, Raoultella* B 19, *Raoultella* enrichment, *Raoultella planticola, Raoultella* sv6xvii, *Raoultella* SZ015, RBEICD-48, *Renibacterium, Renibacterium* G20, rennangilfylO, *Rhizobium, Rhizobium leguminosarum, Rhodococcus, Rhodococcus erythropolis, Rhodopirelluia, Riemerella, Riemerella anatipestifer, Rikenella, Robinsoniella, Robinsoniella peoriensis, Roseburia, Roseburia* 11SE37, *Roseburia bacterium, Roseburia cecicola, Roseburia* DJF_VR77, *Roseburia faecis, Roseburia fibrisolvens, Roseburia hominis, Roseburia intestinalis, Rose bacillus, Rothia, Rubritalea, Ruminococcus, Ruminococcus* 25F6, *Ruminococcus albus, Ruminococcus bacterium, Ruminococcus bromil, Ruminococcus callidus, Ruminococcus champanellensis, Ruminococcus* DJF_VR87, *Ruminococcus flavefaciens, Ruminococcus gauvreauii, Ruminococcus lactaris, Ruminococcus* NK3A76, *Ruminococcus* YE71, *Saccharofermentans, Salinicoccus, Salinimicrobium, Salmonella, Salmonella agglomerans, Salmonella bacterium, Salmonella enterica, Salmonella freundii, Salmonella hermannii, Salmonella paratyphi, Salmonella* SL0604, *Salmonella subterranea, Scardovia, Scardovia oral, Schwartzia, Sedimenticola, Sediminibacter, Selenomonas, Selenomonas fecal, Serpens, Serratia, Serratia* 1135, *Serratia* 136-2, *Serratia* 5.1R, *Serratia* AC-CS-1B, *Serratia* AC-CS-B2, *Serratia aquatilis, Serratia bacterium, Serratia* BS26, *Serratia carotovorum, Serratia* DAP6, *Serratia* enrichment, *Serratia* F2, *Serratia ficaria, Serratia fonticola, Serratia grimesii, Serratia* J 145, *Serratia* JM983, *Serratia liquefaciens, Serratia marcescens, Serratia plymuthica, Serratia proteamaculans, Serratia proteolyticus, Serratia* ptz-16s, *Serratia quinivorans, Serratia* SBS, *Serratia* SS22, *Serratia* trout, *Serratia* UA-G004, *Serratia* White, *Serratia* yellow, *Shewanella, Shewanella baltica, Slackia, Slackia intestinal, Slackia isoflavoniconvertens, Slackia* NATTS, *Solibacillus, Solobacterium, Solobacterium moorei, Spartobacteria genera incertae sedis, Sphingobium, Sphingomo-*

*nas, Sporacetigenium, Sporobacter, Sporobacterium, Sporobacterium olearium, Staphylococcus, Staphylococcus epidermidis, Staphylococcus* PCA17, *stellenboschense, Stenotrophomonas, Streptococcus, Streptococcus* 15, *Streptococcus* 1606-02B, *Streptococcus agalactiae, Streptococcus alactolyticus, Streptococcus anginosus, Streptococcus bacterium, Streptococcus bovis, Streptococcus* ChDC, *Streptococcus constellatus, Streptococcus* CR-314S, *Streptococcus criceti, Streptococcus cristatus, Streptococcus downei, Streptococcus dysgalactiae, Streptococcus* enrichment, *Streptococcus equi, Streptococcus equinus, Streptococcus* ES11, *Streptococcus eubacterium, Streptococcus fecal, Streptococcus gallinaceus, Streptococcus gallolyticus, Streptococcus gastrococcus, Streptococcus genomosp, Streptococcus gordonii, Streptococcus infantarius, Streptococcus intermedius, Streptococcus* Je2, *Streptococcus* JS-CD2, *Streptococcus* LRC, *Streptococcus luteciae, Streptococcus lutetiensis, Streptococcus* M09-11185, *Streptococcus mitis, Streptococcus mutans, Streptococcus* NA, *Streptococcus* NLAE-zl-c353, *Streptococcus* NLAE-zl-p68, *Streptococcus* NLAE-zl-p758, *Streptococcus* NLAE-zlp807, *Streptococcus* oral, *Streptococcus oralis, Streptococcus parasanguinis, Streptococcus phocae, Streptococcus pneumoniae, Streptococcus porcinus, Streptococcus pyogenes, Streptococcus* S 16-08, *Streptococcus salivarius, Streptococcus sanguinis, Streptococcus sobrinus, Streptococcus suis, Streptococcus symbiont, Streptococcus thermophilus, Streptococcus* TW1, *Streptococcus vestibularis, Streptococcus warneri, Streptococcus* XJ-RY-3, *Streptomyces, Streptomyces malaysiensis, Streptomyces* MVCS6, *Streptophyta, Streptophyta cordifolium, Streptophyta ginseng, Streptophyta hirsutum, Streptophyta oleracea, Streptophyta sativa, Streptophyta sativum, Streptophyta sativus, Streptophyta tabacum*, Subdivision3 genera incertae *sedis, Subdoligranulum, Subdoligranulum bacterium, Subdoligranulum* ic/393, *Subdoligranulum* ic/395, *Subdoligranulum variabile, Succiniclasticum, Sulfuricella, Sulfuro spirilium, Sutterella, Syntrophococcus, Syntrophomonas, Syntrophomonas bryantii, Syntrophus, Tannerella, Tatumella, Thermo gymnomonas, Thermofilum, Thermogymnomonas, Thermovirga, Thiomonas, Thiomonas* ML1-46, *Thorsellia, Thorsellia carsonella*, TM7 genera *incertae sedis, Trichococcus, Turicibacter, Turicibacter sanguinis, Vagococcus, Vagococcus* bfsl 1-15, *Vampiro vibrio, Vampirovibrio, Varibaculum, Variovorax, Variovorax* KS2D-23, *Veillonella, Veillonella dispar, Veillonella* MSA 12, *Veillonella* OK8, *Veillonella* oral, *Veillonella parvula, Veillonella tobetsuensis, Vibrio, Vibrio* 3C1, *Victivallis, Victivallis vadensis, Vitellibacter, wadsworthensis, Wandonia, Wandonia haliotis, Weissella, Weissella cibaria, Weissella confusa, Weissella oryzae, Yersinia, Yersinia* 9gw38, *Yersinia* A125, *Yersinia aldovae, Yersinia aleksiciae, Yersinia* b702011, *Yersinia bacterium, Yersinia bercovieri, Yersinia enterocolitica, Yersinia frederiksenii, Yersinia intermedia, Yersinia kristensenii, Yersinia* MAC, *Yersinia massiliensis, Yersinia mollaretii, Yersinia nurmii, Yersinia pekkanenii, Yersinia pestis, Yersinia pseudotuberculosis, Yersinia rohdei, Yersinia ruckeri, Yersinia* s4fe31, *Yersinia* sl0fe31, *Yersinia* sl7fe31, and *Yersinia* YEM17B.

The names of the microbes provided herein, may optionally include the strain name.

Cytokines

In some embodiments, SBP formulations include cytokines. As used herein, the term "cytokine" refers to a class of biological signaling molecules produced by cells that regulate cellular activity in surrounding or distant cells. In some embodiments, the cytokine is a lymphokine, monokine, growth factor, colony-stimulating factor (CSF), transforming growth factor (TGF), tumor necrosis factor (TNF), chemokine, and/or interleukin. Examples of cytokines include, but are not limited to, brain-derived neurotrophic factor (BDNF), cardiotrophin-like cytokine factor 1 (CLCF1), ciliary neurotrophic factor (CNTF), cardiotrophin 1 (CTF1), epidermal growth factor (EGF), erythropoietin (EPO), fibroblast growth factor acidic (FGFa), fibroblast growth factor basic (FGFb), granulocyte colony stimulating factor (G-CSF), growth hormone, granulocyte-macrophage colony stimulating factor 2 (GM-CSF), interferon-α1, interleukin (IL)-1 (IL-1), IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-27, interleukin-1 receptor antagonist (IL-1RA), keratinocyte growth factor 1 and 2 (KGF), kit ligand/stem cell factor (KITLG), leptin (LEP), leukemia inhibitory factor (LIF), nerve growth factor (NGF), oncostatin M (OSM), platelet derived growth factors, prolactin (PRL), thrombopoietin (THPO), transforming growth factor (TGF) α (TGFα), TGFβ, tumor necrosis factor α (TNFα), vascular endothelial growth factor (VEGF), tissue inhibitor of metalloproteinase (TIMP), matrix metalloproteinase (MMP), any of the interferons, any of the interleukins, any of the lymphokines, any of the cell signal molecules, and any structural or functional molecule thereof. In some embodiments, cytokines may include, but are not limited to, any of those listed in Table 4, above.

Lipids

In some embodiments, therapeutic agents include lipids. As used herein, the term "lipid" refers to members of a class of organic compounds that include fatty acids and various derivatives of fatty acids that are soluble in organic solvents, but not in water. Examples of lipids include, but are not limited to, fats, triglycerides, oils, waxes, sterols (e.g. cholesterol, ergosterol, hopanoids, hydroxysteroids, phytosterol, and steroids), stearin, palmitin, triolein, fat-soluble vitamins (e.g., vitamins A, D, E, and K), monoglycerides (e.g. monolaurin, glycerol monostearate, and glyceryl hydroxystearate), diglycerides (e.g. diacylglycerol), phospholipids, glycerophospholipids (e.g., phosphatidic acid, phosphatidylethanolamine, phosphatidylcholine, phosphatidylserine, phosphoinositides), sphingolipids (e.g., sphingomyelin), and phosphosphingolipids. In some embodiments, lipids may include, but are not limited to, any of those listed (e.g., fats and fatty acids) in Table 4, above.

Macromolecules

In some embodiments, therapeutic agents include macromolecules, cells, tissues, organs, and/or organisms. Examples of macromolecules include, but are not limited to, proteins, polymers, carbohydrates, complex carbohydrates, lipids, nucleic acids, oligonucleotides, and genes. Macromolecules may be expressed (e.g. expression in *Escherichia coli*) or they may be chemically synthesized (e.g. solid phase synthesis, and/or polymer forming chain reactions).

Nucleic Acids

In some embodiments, SBP formulations include nucleic acids. As used herein, the term "nucleic acid" refers to any polymer of nucleotides (natural or non-natural) or derivatives or variants thereof. Nucleic acids may include deoxyribonucleic acid (DNA) or ribonucleic acid (RNA). In some embodiments, SBP formulations may enhance the stability of the nucleic acid (e.g. RNA), as taught in He et al. (2018) ACS Biomaterials Science and Engineering/4 (5): 1708-1715, the contents of which are herein incorporated by reference in their entirety. In some embodiments, nucleic acids may be polynucleotides or oligonucleotides. Some nucleic acids may include aptamers, plasmids, small interfering RNA (siRNA), microRNAs, or viral nucleic acids. In some embodiments, nucleic acids may encode proteins. In some embodiments, SBPs including therapeutic agent nucleic acids may include any of those described in International Publication Number WO2017123383, the contents of which are herein incorporated by reference in their entirety. In some embodiments, nucleic acids may include, but are not limited to, any of those listed in Table 4, above.

In some embodiments, nucleic acids may include a "CELiD" DNA as described in Li et al. (2013) PLOS One. 8 (8): e69879, the contents of which are herein incorporated by reference in their entirety. CELiD DNA is a eukaryotic vector DNA that includes an expression cassette flanked by adeno-associated virus (AAV) inverted terminal repeats.

Proteins

In some embodiments, SBP formulations may include biological agents that are or include proteins. As used herein, the term "protein" generally refers to polymers of amino acids linked by peptide bonds and embraces "peptides" and "polypeptides." In some SBPs, the biological agent protein included is processed silk. Classes of proteins used as biological agent may include, but are not limited to, antigens, antibodies, antibody fragments, cytokines, peptides, hormones, enzymes, oxidants, antioxidants, synthetic proteins, and chimeric proteins. In some embodiments, proteins include any of those presented in Table 4, above. In some embodiments, proteins are combined with processed silk to improve protein stability.

In some embodiments, SBP formulations include peptides. The term "peptide" generally refers to shorter proteins of about 50 amino acids or less. Peptides with only two amino acids may be referred to as "dipeptides." Peptides with only three amino acids may be referred to as "tripeptides." Polypeptides generally refer to proteins with from about 4 to about 50 amino acids. SBPs that include peptides may include any of those described in International Publication Numbers WO2017123383 and WO2010123945, the contents of each of which are herein incorporated by reference in their entirety. Peptides may be obtained via any method known to those skilled in the art. In some embodiments, peptides may be expressed in culture. In some embodiments, peptides may be obtained via chemical synthesis (e.g. solid phase peptide synthesis). In some embodiments, peptides are used to functionalize SBPs, for example, as taught in International Publication Number WO2010123945.

In some embodiments, SBP formulations are used to facilitate peptide delivery, for example, according to the methods presented in International Publication Number WO2017123383. In some embodiments, peptides include RGD peptides, for example, as taught in Kambe et al. (2017) Materials 10 (10): 1153, the contents of which are herein incorporated by reference in their entirety. Non-limiting examples of peptide therapeutic agents include, but are not limited to, Degarelix acetate, Liraglutide, Cyclosporine, Eptifibatide, Dactinomycin, Spaglumat magnesium, Colistin, Nafarelin acetate, Somatostatin acetate, Buserelin, Enfuvirtide, Octreotide, lanreotide acetate, Caspofungin, Nesiritide, Goserelin, Salmon calcitonin, Lepirudin or r-hirudin, Daptomycin, Exenatide, Carbetocin acetate, Tirofiban, Glutathione, Cetrorelix acetate, Enalapril maleate, Bivalirudin, Vapreotide acetate, Icatibant acetate, Human calcitonin, Oxytocin, Atosiban acetate, Bacitracin, Lypressin, Vancomycin, Captopril, Anidulafungin, Bortezomib, Saralasin acetate, Calcitonin, Thymalfasin, Ziconotide, and Lisinopril. In some embodiments, peptides may include any of those presented in Table 4, above.

Synthetic/Chimeric Proteins

In some embodiments, SBP formulations include synthetic proteins. As used herein, the term "synthetic" refers to any article produced through at least some human manipulation. Synthetic proteins may be identical to proteins found in nature or may have one or more distinguishing features. Distinguishing features may include, but are not limited to, differences in amino acid sequences, incorporation of non-natural amino acids, post-translational modifications, and conjugation to non-protein moieties (e.g., some antibody drug conjugates). Synthetic proteins may be expressed in vitro or in vivo. Synthetic proteins may also be chemically synthesized (e.g. by solid phase peptide synthesis). In some embodiments, synthetic proteins are made from a combination of expression and chemical synthesis (e.g. native chemical ligation or enzyme catalyzed protein ligation).

In some embodiments, synthetic proteins include chimeric or fusion proteins. As used herein, the term "fusion protein" refers to a substance that includes two or more protein components that are conjugated through at least one chemical bond. As used herein, the term "chimeric protein" refers to a protein that includes segments from at least two different sources (e.g., from two different species or two different isotypes or variants from a common species). Chimeric proteins may be produced via the expression of two or more ligated genes encoding different proteins. Chimeric proteins may be produced via chemical synthesis. In some embodiments, chimeric proteins are made from a combination of expression and chemical synthesis (e.g. native chemical ligation or enzyme catalyzed protein ligation). In some embodiments, synthetic proteins or chimeric proteins may include, but are not limited to, any of those listed in Table 4, above.

Viruses and Viral Particles

In some embodiments, SBP formulations include viruses or viral particles. Viruses and viral particles may be used to transfer nucleic acid into cells for genetic manipulation, gene therapy, gene editing, protein expression, or to inhibit protein expression. In some embodiments, SBPs be prepared with viral or viral particle payloads. In some embodiments, payload release may occur over a period of time (the payload release period). The payload release rate and/or length of the payload release period may be modulated by SBP components or methods of preparation. Examples of viruses and viral particles may include, but are not limited to, any of those presented in Table 4, above. In some embodiments, SBP formulations with a virus or viral particle may enhance the stability of said virus or viral particle, as taught in WO2018053524A1, the contents of which are herein incorporated by reference in their entirety.

In some embodiments, the virus or viral particle payloads prepared with SBP formulations may include, but are not limited to, adeno-associated virus, lentivirus, alphavirus, enterovirus, pestivirus, baculovirus, herpesvirus, Epstein Barr virus, papovavirus, poxvirus, vaccinia virus, herpes simplex virus, and/or a viral particle thereof.

Oxidants/Antioxidants

In some embodiments, therapeutic agents include oxidants or antioxidants. As used herein, the term "oxidant" refers to a substance that oxidizes (i.e., strips electrons from) another substance. Inhibitors of oxidation are referred to herein as "antioxidants." The use of oxidants and/or antioxidants as therapeutic agents may include any of the methods taught, for example, in International Publication Number WO2017137937; Min et al. (2017) Int J Biol Macromol s0141-8130 (17): 32855-32856; or Manchineella et al. (2017) European Journal of Organic Chemistry 30:4363-4369, the contents of each of which are herein incorporated by reference in their entirety. Oxidant or antioxidant therapeutic agents may be included in SBPs for treatment of indications requiring localized treatment or for indications requiring activity more distant from an administration site. In some embodiments, incorporation of oxidants or antioxidants may be used to modulate SBPs stability or degradation. In some embodiments, oxidants or antioxidants may be polymers. Such polymers may include quaternary ammonium chitosan and melanin. Examples of such therapeutic agents include those taught in International Publication Number WO2017137937 and Min et al. (2017) Int J Biol Macromol s0141-8130 (17): 32855-32856, the contents of each of which are herein incorporated by reference in their entirety. In some embodiments, oxidants or antioxidants include small molecules, metals, ions, minerals, vitamins, peptides, and/or proteins. In some embodiments, antioxidants include cyclic dipeptides or 2,5-diketopiperazines. Such antioxidants may include any of those taught in Manchineella et al. (2017) European Journal of Organic Chemistry 30:4363-4369, the contents of which are herein incorporated by reference in their entirety. In some embodiments, oxidants or antioxidants may include, but are not limited to, any of those listed in Table 4, above.

Small Molecules

In some embodiments, SBP formulations include small molecule therapeutic agents. As used herein, the term "small molecule" refers to a low molecular weight compound, typically less than 900 Daltons. Many small molecules are able to pass through cell membranes, making them attractive candidates for therapeutic applications. SBPs may be combined with any small molecules to carry out a variety of therapeutic applications. Such small molecules may include small molecule drugs approved for human treatment. Some small molecules may be hydrophobic or hydrophilic. Small molecules may include, but are not limited to, antibacterial agents, antifungal agents, anti-inflammatory agents, non-steroidal anti-inflammatory drugs, antipyretics, analgesics, antimalarial agents, antiseptics, hormones, stimulants, tranquilizers, and statins. In some embodiments, small molecules may include any of those listed in Table 4, above.

In some embodiments, SBP formulations may be used to encapsulate, store and/or release, in a controlled manner, small molecules. For example, using silk fibroin micrococoons as delivery vehicles for small molecules has been described in Shimanovich et al. (Shimanovich et al. (2015) Nature Communications 8:15902, the contents of which are herein incorporated by reference in their entirety).

Angiogenesis Modulators

In some embodiments, therapeutic agents include modulators of angiogenesis. Such therapeutic agents may include vascular endothelial growth factor (VEGF)-related agents. As used herein, the term "VEGF-related agent" refers to any substance that affects VEGF expression, synthesis, stability, biological activity, degradation, receptor binding, cellular signaling, transport, secretion, internalization, concentration, or deposition (e.g., in extracellular matrix).

In some embodiments, VEGF-related agents are angiogenesis inhibitors. In some embodiments, the angiogenesis inhibitor includes any of those taught in International Publication Number WO2013126799, the contents of which are herein incorporated by reference in their entirety. In some embodiments, VEGF-related agents may include antibodies. VEGF-related agents may include VEGF agonists, including, but not limited to, toll-like receptor agonists. In some embodiments, the therapeutic agent is a VEGF antagonist. VEGF agonists or antagonists may be small molecules. In some embodiments, VEGF agonists or antagonists may be macromolecules or proteins. Angiogenesis inhibitors may include, but are not limited to, MACUGEN® or another VEGF nucleic acid ligand; LUCENTIS®, AVASTIN®, or another anti-VEGF antibody; combretastatin or a derivative or prodrug thereof such as Combretastatin A4 Prodrug (CA4P); VEGF-Trap (Regeneron); EVIZON™ (squalamine lactate); AG-013958 (Pfizer, Inc.); JSM6427 (Jerini AG); a short interfering RNA (siRNA) that inhibits expression of one or more VEGF isoforms (e.g., $VEGF_{165}$); an siRNA that inhibits expression of a VEGF receptor (e.g., VEGFRI), endogenous or synthetic peptides, angiostatin, combstatin, arresten, tumstatin, thalidomide, thalidomide derivatives, canstatin, endostatin, thrombospondin, and β2-glycoprotein 1. In some embodiments, VEGF-related agents may include, but are not limited to any of those listed in Table 4, above.

Antibacterial Agents

In some embodiments, therapeutic agents include antibacterial agents. As used herein, the term "antibacterial agent" refers to any substance that harms, kills, or otherwise inhibits the growth and/or reproduction of bacteria. Antibacterial agents may include, but are not limited to, any of those listed in Table 4, above.

Antifungal Agents

In some embodiments, therapeutic agents include antifungal agents. As used herein, the term "antifungal agent" refers to any substance that harms, kills, or otherwise inhibits the growth and/or reproduction of fungi. Antifungal agents may include, but are not limited to, any of those listed in Table 4, above.

Analgesic Agents

In some embodiments, therapeutic agents include analgesic agents. As used herein, the term "analgesic agent" refers to any substance used to reduce or alleviate pain. Analgesic agents may include, but are not limited to, any of those listed in Table 4, above.

Antipyretics

In some embodiments, therapeutic agents include antipyretics. As used herein, the term "antipyretic" refers to any substance used to reduce or alleviate fever. Examples of antipyretics include, but are not limited to, any NSAID, acetaminophen, aspirin and related salicylates (e.g. choline salicylate, magnesium salicylate, and sodium salicylate), ibuprofen, naproxen, ketoprofen, nimesulide, phenazone, metamizole, and nabumetone. In some embodiments, antipyretics may include, but are not limited to, any of those listed in Table 4, above.

Antimalarial Agents

In some embodiments, therapeutic agents include antimalarial agents. As used herein, the term "antimalarial agent" refers to any substance that harms, kills, or otherwise inhibits the growth and/or reproduction of *plasmodium* parasites. Examples of antimalarial agents may include, but are not limited to, any of those listed in Table 4, above.

Antiseptic Agents

In some embodiments, therapeutic agents include antiseptic agents. As used herein, the term "antiseptic agent" refers to any substance that harms, kills, or otherwise inhibits the growth and/or reproduction of microorganisms. Examples of antiseptics include, but are not limited to, iodine, lower alcohols (ethanol, propanol, etc.), chlorhexidine, quaternary amine surfactants, chlorinated phenols, biguanides, bisbiguanides polymeric quaternary ammonium compounds, silver and its complexes, small molecule quaternary ammonium compounds, peroxides, and hydrogen peroxide. In some embodiments, antiseptic agents may include any of those listed in Table 4, above.

Hormones

In some embodiments, therapeutic agents include hormones. As used herein, the term "hormone" refers to a cellular signaling molecule that promotes a response in cells or tissues. Hormones may be produced naturally by cells. In some embodiments, hormones are synthetic. Examples of hormones include, but are not limited to, any steroid, dexamethasone, allopregnanolone, any estrogen (e.g. ethinyl estradiol, mestranol, estradiols and their esters, estriol, estriol succinate, polyestriol phosphate, estrone, estrone sulfate and conjugated estrogens), any progestogen (e.g. progesterone, norethisterone acetate, norgestrel, levonorgestrel, gestodene, chlormadinone acetate, drospirorenone, and 3-ketodesogestrel), any androgen (e.g. testosterone, androstenediol, androstenedione, dehydroepiandrosterone, and dihydrotestosterone), any mineralocorticoid, any glucocoriticoid, cholesterols, and any hormone known to those skilled in the art. In some embodiments, hormones may include, but are not limited to, any of those listed in Table 4, above.

Non-Steroidal Anti-Inflammatory Drugs

In some embodiments, therapeutic agents include nonsteroidal anti-inflammatory drugs. A nonsteroidal anti-inflammatory drug (NSAID) is a class of non-opioid analgesics used to reduce inflammation and associated pain. NSAIDs may include, but are not limited to, any of those listed in Table 4, above. In some embodiments, the NSAID is celecoxib. Some SBPs include gels or hydrogels that are combined with NSAIDs (e.g., celecoxib). Such SBPs may be used as carriers for NSAID payload delivery. NSAID delivery may include controlled release of the NSAID.

Stimulants

In some embodiments, therapeutic agents include stimulants. As used herein, the term "stimulant" refers to any substance that increases subject physiological or nervous activity. Examples of stimulants include, but are not limited to, amphetamines, caffeine, ephedrine, 3,4-methylenedioxymethamphetamine, methylenedioxypyrovalerone, mephedrone, methamphetamine, methylphenidate, nicotine, phenylpropanolamine, propylhexedrine, pseudoephedrine, and cocaine. In some embodiments, stimulants may include, but are not limited to, any of those listed in Table 4, above.

Tranquilizers

In some embodiments, therapeutic agents include tranquilizers. As used herein, the term "tranquilizer" refers to any substance used to lower subject anxiety or tension. Examples of tranquilizers include, but are not limited to, barbiturates, benzodiazepines, carbamates, antihistamines, opioids, antidepressants (e.g. monoamine oxidase inhibitors, tetracyclic antidepressants, tricyclic antidepressants, selective serotonin reuptake inhibitors, and serotonin-norepinephrine reuptake inhibitors), sympatholytics (e.g. alpha blockers, beta-blockers, and alpha-adrenergic agonists), mebicar, fabomotizole, selank, bromantane, emoxypine, azapirones, pregabalin, mentyl isovalerate, propofol, racetams, alcohols, inhalants, any butyrophenone (e.g. benperidol, bromperidol, droperidol, haloperidol, moperone, pipamperone, and timiperone), any diphenylbutylpiperidine (e.g. fluspirilene, penfluridol, and pimozide), any phenothiazine (e.g. acepromazine, chlorpromazine, cyamemazine, dixyrazine, fluphenazine, levomepromazine, levomepromazine, mesoridazine, perazine, periciazine, perphenazine, pipotiazine, prochlorperazine, promazine, promethazine, prothipendyl, thioproperazine, thioridazine, trifluoperazine, and triflupromazine), any thioxanthene (e.g. chlorprothixene, clopenthixol, flupentixol, thiothixene, and zuclopenthixol), any benzamidine (e.g. sulpiride, sultopride, and veralipride), any tricyclic (e.g. carpipramine, clocapramine, clorotepine, loxapine, and mosapramine), gamma aminobutyric acid, and molindone. In some embodiments, tranquilizers may include, but are not limited to, any of those listed in Table 4, above.

Statins

In some embodiments, therapeutic agents include statins. As used herein, the term "statin" refers to a class of compounds that inhibit hydroxy-methylglutaryl-coenzyme A reductase (HMG-COA reductase), a key enzyme in cholesterol biosynthesis. Statins are referred to herein in the broadest sense and include statin derivatives such as ester derivatives or protected ester derivatives. Examples of statins include, but are not limited to, rosuvastatin, pitavastatin, pravastatin, fluvastatin, cerivastatin, atorvastatin, simvastatin, mevastatin, and lovastatin. In some embodiments, statins may include, but are not limited to, any of those listed in Table 4, above.

Anti-Cancer Agents

In some embodiments, therapeutic agents include anticancer agents. As used herein, the term "anticancer agent" refers to any substance used to kill cancer cells or inhibit cancer cell growth and/or cell division. Anticancer agents that target tumor cells are referred to herein as "antitumor agents." Such anticancer agents may reduce tumor mass and/or volume. Anticancer agents that are chemical substances are referred to herein as "chemotherapeutic agents." Examples of antitumor agents include, but are not limited to, busulphan, cisplatin, cyclophosphamide, MTX, daunorubicin, doxorubicin, melphalan, vincristine, vinblastine, chlorabucil, any alkylating agent (e.g. cyclophosphamide, mechlorethamine, chlorambucil, melphalan, dacarbazine, nitrosoureas, and temozolomide), any anthracycline (e.g. daunorubicin, doxorubicin, epirubicin, idarubicin, mitozantrone, and valrubicin), any cytoskeletal disruptors or taxanes (e.g. paclitaxel, docetaxel, abraxane, and taxotere), any epothilones, any histone deacetylase inhibitors (e.g. vorinostat and romidepsin), any topoisomerase I inhibitors (e.g. irinotecan and topotecan), any topoisomerase II inhibitors (e.g. etoposide, teniposide, and tafluposide), kinase inhibitors (e.g. bortezomib, erlotinib, gefitinib, imatinib, vemurafenib, and vismodegib), nucleotide and precursor analogues (e.g. azacitidine, azathioprine, capecitabine, cytarabine, doxifluridine, fluorouracil, gemcitabine, hydroxyurea, mercaptopurine, methotrexate, and tioguanine), antimicrobial peptides (e.g. bleomycin and actinomycin), platinum based chemotherapeutics (e.g. carboplatin, cisplatin, oxaliplatin), retinoids (e.g. tretinoin, alitretinoin, and bexarotene), and vinca alkaloids and derivatives (e.g. vinblastine, vincristine, vindesine, and vinorelbine). In some embodiments, anticancer agents may include, but are not limited to, any of those listed in Table 4, above.

Herbal Preparations

In some embodiments, therapeutic agents include herbal preparations. As used herein, the term "herbal preparation" refers to any substance derived or extracted from vegetation. These preparations may include, but are not limited to, tea, decoctions, cold infusions, tinctures, cordials, herbal wines, granules, syrups, essential oils (e.g. allspice berry essential oil, angelica seed essential oil, anise seed essential oil, basil essential oil, bay laurel essential oil, bay essential oil, bergamot essential oil, blood orange essential oil, camphor essential oil, caraway seed essential oil, cardamom seed essential oil, carrot seed essential oil, cassia essential oil, catnip essential oil, cedarwood essential oil, celery seed essential oil, chamomile german essential oil, chamomile roman essential oil, cinnamon bark essential oil, cinnamon leaf essential oil, citronella essential oil, clary sage essential oil, clove bud essential oil, coriander seed essential oil, cypress essential oil, elemi essential oil, eucalyptus essential oil, fennel essential oil, fir needle essential oil, frankincense essential oil, geranium essential oil, ginger essential oil, grapefruit pink essential oil, helichrysum essential oil, hop essential oil, hyssop essential oil, juniper berry essential oil, labdanum essential oil, lemon essential oil, lemongrass essential oil, lime essential oil, magnolia essential oil, mandarin essential oil, margoram essential oil, Melissa essential oil, mugward essential oil, myrrh essential oil, myrtle essential oil, neroli essential oil, niaouli essential oil, nutmeg essential oil, orange sweet essential oil, oregano essential oil, palmarosa essential oil, patchouli essential oil, pennyroyal essential oil, pepper black essential oil, peppermint essential oil, petitgram essential oil, pine needle essential oil, radiata essential oil, ravensara essential oil, rose essential oil, rosemary essential oil, rosewood essential oil, sage essential oil, sandalwood essential oil, spearmint essential oil, spikenard essential oil, spruce essential oil, star anise essential oil, sweet annie essential oil, tangerine essential oil, tea tree essential oil, thyme red essential oil, verbena essential oil, vetiver essential oil, wintergreen essential oil, wormwood essential oil, yarrow essential oil, ylang essential oil, jasmine absolute oil, lavender absolute oil, pink lotus absolute oil, rose absolute oil, sambac absolute oil, and white lotus absolute oil), flower essences, sitz baths, soaks, pills, suppositories, poultices, compresses, salves, and ointments. Examples of herbs to be incorporated include, but are not limited to, sage, thyme, cumin, basil, bay laurel, borage, caraway, catnip, chervil, chives, cilantro, dill, epazote, fennel, garlic, lavender, lemongrass, lemon balm, lemon verbena, lovage, marjoram, mints, nasturtium, parsley, oregano, rosemary, salad burnet, savory, scented geranium, sorrel, and tarragon. In some embodiments, herbal preparations may include, but are not limited to, any of those listed in Table 4, above.

Health Supplements

In some embodiments, therapeutic agents include health supplements. As used herein, the term "health supplement" refers to any substance used to provide a nutrient, vitamin, or other beneficial compound that is typically lacking from a normal diet or is complimentary to such substances present in a normal diet. Examples of health supplements include, but are not limited to, vitamin A, vitamin B, vitamin C, vitamin D, vitamin E, vitamin K, thiamin, riboflavin, niacin, vitamin B6, vitamin B12, biotin, pantothenic acid, calcium, iron, phosphorus, iodine, magnesium, zinc, selenium, selenium, copper, manganese, chromium, molybdenum, chloride, potassium, nickel, silicon, vanadium, and tin. In some embodiments, health supplements may include, but are not limited to, any of those listed in Table 4, above.

Ions, Metals, Minerals

In some embodiments, therapeutic agents include ions, metals, and/or minerals. Examples include, but are not limited to, calcium, iron, phosphorus, iodine, magnesium, zinc, selenium, selenium, copper, manganese, chromium, molybdenum, gold, silver, chloride, potassium, nickel, silicon, vanadium, and tin. In some embodiments, therapeutic agents include oxides (e.g. silver oxide). In some embodiments, ions, metals, and/or minerals may be present in nanoparticles. Such nanoparticles may include any of those taught in Mane et al. (2017) Scientific Reports 7:15531; and Babu et al. (2017) J Colloid Interface Sci 513:62-72, the contents of each of which are herein incorporated by reference in their entirety. In some embodiments, ions, metals, and/or minerals may include, but are not limited to, any of those listed in Table 4, above.

Vitamins

In some embodiments, therapeutic agents include vitamins or vitamin analogues. As used herein, the term "vitamin" refers to a nutrient that must be obtained through diet (i.e., is not synthesized endogenously or is synthesized endogenously, but in insufficient amounts). Examples of vitamins include, but are not limited to, vitamin A, vitamin B-1, vitamin B-2, vitamin B-3, vitamin B-5, vitamin B-6, vitamin B-7, vitamin B-9, vitamin B-12, vitamin C, vitamin D, vitamin E, and vitamin K. In some embodiments, vitamins may include, but are not limited to, any of those listed in Table 4, above.

Other Therapeutic Agents

Other therapeutic agents may include, but are not limited to, anthocyanidin, anthoxanthin, apigenin, dihydrokaempferol, eriodictyol, fisetin, flavan, flavan-3,4-diol, flavan-3-ol, flavan-4-ol, flavanone, flavanonol, flavonoid, furanoflavonols, galangin, hesperetin, homoeriodictyol, isoflavonoid, isorhamnetin, kaempferol, luteolin, myricetin, naringenin, neoflavonoid, pachypodol, proanthocyanidins, pyranoflavonols, quercetin, rhamnazin, tangeritin, taxifolin, theaflavin, thearubigin, chondrocyte-derived extracellular matrix, macrolide, erythromycin, roxithromycin, azithromycin and clarithromycin. In some embodiments, other therapeutic agents may include, but are not limited to, any of those listed in Table 4, above.

Controlled Degradation

In some embodiments, SBP formulations may be used for controlled degradation, and to modulate the stability and storage of therapeutic agents or other materials (e.g., agricultural compositions, agricultural products, materials, devices, and excipients). As used herein, the term "controlled degradation" refers to regulated loss of structure, function, and/or other physical and chemical properties. Such SBP formulations may be used to stabilize therapeutic agents used in therapeutic applications. In some embodiments, SBP formulations are used to maintain and/or improve the stability of therapeutic agents during storage. In some embodiments SBP formulations may be used to enhance the degradation rate of therapeutic agents. In some embodiments, an SBP formulation may increase the rate of degradation of a therapeutic agent (e.g. a protein) during storage. In some embodiments, preparation of an SBP formulation with a therapeutic agent may increase the rate of degradation of said therapeutic agent (e.g. a protein) during storage.

Use as a Preservation/Stabilizing Agent

In some embodiments, SBP formulations may be used to preserve or stabilize therapeutic agents or other materials (e.g., agricultural compositions, agricultural products, materials, devices, and excipients). Such SBPs may be used to stabilize therapeutic agents used in therapeutic applications. In some embodiments, SBP formulations are used to maintain and/or improve the stability of therapeutic agents during lyophilization. The maintenance and/or improvement of stability during lyophilization may be determined by comparing products lyophilized with SBP formulations to products lyophilized with non-SBP formulation. Maintenance and/or improvement of stability during lyophilization will be found or appreciated by those of skill in the art when products lyophilized with SBP formulations are determined to impart superior or durational benefits over non-SBP formulations or those standard in the art.

In some embodiments, lyophilization may be utilized for long term storage of processed silk formulations. In some embodiments processed silk formulations are stored frozen. In some embodiments, processed silk formulations may be frozen without altering the protein quality. In some embodiments, processed silk formulations may be frozen without altering rheological properties, protein size, and aggregation of said formulations. In some embodiments, processed silk formulations may be prepared as solutions, and then frozen. In some embodiments these solutions may then be thawed. The thawed solutions may exhibit less than 10%, less than 5%, less than 3%, less than 1%, less than 0.1%, less than 0.01%, or less than 0.001% aggregation of protein.

In some embodiments, silk fibroin processing will be more efficient and cheaper if there is no need for lyophilization. In some embodiments, removing a drying condition will require that silk fibroin solutions are stable through a freeze/thaw process. This will allow for aseptic preparation and shipment of drug substance from the manufacturing site to the fill/finish facility. In some embodiments, these silk fibroin solutions may comprise silk fibroin at various concentrations, as well as cryoprotectants (sucrose and trehalose), to improve the freeze-thaw stability of dialyzed drug substance. In some embodiments, these solutions may comprise silk fibroin at a concentration of from about 0.01% to about 0.1%, about 0.1% to about 1%, about 1% to about 2%, about 2% to about 3%, about 3% to about 4%, about 4% to about 5%, about 5% to about 10%, about 10% to about 15%, about 15% to about 20%, or about 20% to about 30% (w/v) silk fibroin. In some embodiments, the cryoprotectant is sucrose or trehalose. Cryoprotectants may be included at a concentration of 0 to about 150 mM. In some embodiments, the rheological properties of the silk fibroin solutions may remain the same following freeze/thaw. In some embodiments, the molecular weight by SEC may not change following freeze/thaw. In some embodiments, the lowest increase in aggregation may be seen in formulations with sucrose as an excipient.

In some embodiments, the SBP formulations maintain and/or improve therapeutic agent stability by at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 14 weeks, at least 4 months, at least 18 weeks, at least 5 months, at least 22 weeks, at least 6 months, at least 7 months, at least 8 months, at least 9 months, at least 10 months, at least 11 months, at least a year, at least 2 years, at least 3 years, at least 4 years, at least 5 years, or more than 5 years.

Ocular Therapeutic Agents

In some embodiments, therapeutic agents include ocular therapeutic agents. As used herein, the term "ocular therapeutic agent" refers to any compound that has a healing, corrective, diagnostic, and/or prophylactic effect and/or elicits a desired biological and/or pharmacological effect on the eye. In some embodiments, ocular therapeutic agents include one or more of processed silk, biological agents, small molecules, proteins, anti-inflammatory agents, steroids, opiates, analgesics, ciclosporin, corticosteroids, tetracyclines, essential fatty acids, sodium channel blockers, nonsteroidal anti-inflammatory drugs, cyclosporine, lifitegrast, and vascular endothelial growth factor-related agents. Ocular therapeutic agent proteins may include, but are not limited to, lysozyme, bovine serum albumin (BSA), bevacizumab, or VEGF-related agents. In some embodiments, ocular therapeutic agents may be used to treat one or more of the ocular therapeutic indications described herein.

Bacteriostatic Agents

In some embodiments, therapeutic agents include bacteriostatic agents. As used herein, the term "bacteriostatic agent" or "bacteriostat" refers to a substance that prevents bacterial reproduction and may or may not kill said bacteria. Bacteriostatic agents prevent the growth of bacteria. Non-limiting examples of bacteriostatic agents include antibiotics, antiseptics, disinfectants, and preservatives. Other non-limiting examples of bacteriostatic agents include tigecycline, trimethoprim, oxazolidinone, tetracyclines, novobiocin, clindamycin, nitrofurantoin, ethambutol, sulfonamides, macrolides, lincosamides, spectinomycin, and chloramphenicol.

Non-Steroidal Anti-Inflammatory Drugs

Therapeutic agents may include nonsteroidal anti-inflammatory drugs. A nonsteroidal anti-inflammatory drug (NSAID) is a class of non-opioid analgesics used to reduce inflammation and associated pain. NSAIDs may include small molecules. NSAIDs may include, but are not limited to, aspirin, carprofen, celecoxib, deracoxib, diclofenac, diflunisal, etodolac, fenoprofen, firocoxib, flurbiprofen, ibuprofen, indomethacin, ketoprofen, ketorolac, mefenamic acid, meloxicam, nabumetone, naproxen, oxaprozin, piroxicam, robenacoxib, salsalate, sulindac, and tolmetin. In some embodiments, NSAIDs may be used to treat one or more of the ocular therapeutic indications described herein. In some embodiments, the NSAID is celecoxib. Some SBPs include gels or hydrogels that are combined with NSAIDs (e.g., celecoxib). Such SBPs may be used as carriers for NSAID payload delivery. NSAID delivery may include controlled release of the NSAID.

Therapeutic Indications

In some embodiments, SBPs are used to address one or more therapeutic indications. As used herein, the term "therapeutic indication" refers to a disease, disorder, condition, or symptom that may be cured, reversed, alleviated, stabilized, improved, or otherwise addressed through some form of therapeutic intervention (e.g., administration of a therapeutic agent or method of treatment).

SBP treatment of therapeutic indications may include contacting subjects with SBPs. SBPs may include therapeutic agents (e.g., any of those described herein) as cargo or payloads for treatment. In some embodiments, payload release may occur over a period of time (the "payload release period"). The payload release rate and/or length of the payload release period may be modulated by SBP components or methods of preparation.

Ocular Indications

In some embodiments, therapeutic indications include ocular indications. As used herein, the term "ocular indication" refers to any therapeutic indication related to the eye. Treatment of such indications in subjects may include contacting subjects with SBPs. SBPs and SBP formulations may include therapeutic agents (e.g., any of those described herein) as cargo or payloads for treatment. In some embodiments, payload release may occur over a period of time (the payload release period). The payload release rate and/or length of the payload release period may be modulated by SBP components or methods of preparation. In some embodiments, SBPs may be provided in the form of a solution or may be incorporated into a solution for ocular administration. Such solutions may be administered topically (e.g., in the form of drops, creams, or sprays) or by injection. In some embodiments, SBPs may be provided in the format of a lens or may be incorporated into lenses that are placed on eye. In some embodiments, SBPs are provided in the form of implants or are incorporated into implants that may be placed around the eye, on a surface of the eye, in a periocular space or compartment, or intraocularly. Implants may be solid or gelatinous (e.g., a gel or slurry) and may be in the form of a bleb, rod, or plug. Some gelatinous implants may harden after application. In some embodiments, implants include punctal plugs. Such plugs may be inserted into tear ducts. In some embodiments, SBPs may be used to repair ocular damage. In some embodiments, the SBP adheres to the ocular surface. In some embodiments, the SBP adheres to the ocular surface in a manner similar to a mucin layer.

Non-limiting examples of ocular indications include infection, refractive errors, age related macular degeneration, cataracts, diabetic retinopathy (proliferative and non-proliferative), cystoid macular edema, glaucoma, amblyopia, strabismus, color blindness, cytomegalovirus retinitis, keratoconus, diabetic macular edema (proliferative and non-proliferative), low vision, ocular hypertension, retinal detachment, eyelid twitching, inflammation, uveitis, bulging eyes, dry eye disease, floaters, xerophthalmia, diplopia, Graves' disease, night blindness, eye strain, red eyes, nystagmus, presbyopia, excess tearing, retinal disorders (e.g. age related macular degeneration), conjunctivitis, cancer, corneal ulcer, corneal abrasion, snow blindness, scleritis, keratitis, Thygeson's superficial punctate keratopathy, corneal neovascularization, Fuch's dystrophy, keratoconjuctitivis sicca, iritis, chorioretinal inflammation (e.g. chorioretinitis, choroiditis, retinitis, retinochoroiditis, pars planitis, and Harada's disease), aniridia, macular scars, solar retinopathy, choroidal degeneration, choroidal dystrophy, choroideremia, gyrate atrophy, choroidal hemorrhage, choroidal detachment, retinoschisis, hypertensive retinopathy, Bull's eye maculopathy, epiretinal membrane, peripheral retinal degeneration, hereditary retinal dystrophy, retinitis pigmentosa, retinal hemorrhage, separation of retinal layers, retinal vein occlusion, and other visual impairments. In some embodiments, ocular indications include inflammation of the eye.

Dry Eye

In one embodiment, the ocular indications which may be treated with the SBPs described herein may be dry eye. "Dry eye", "dry eye syndrome," "dry eye disease", or "DED" is a condition involving a lack of hydration on the eye surface that may be caused by one or more of a variety of factors (e.g., cellular/tissue dysfunction or environmental irritants). After the development of symptoms in a subject or patient, an optometrist and/or ophthalmologist may conduct and ocular exam and test for additional signs in the cornea and tears (e.g. ocular surface staining, corneal fluorescein and conjunctival staining, or tear film break-up time). Symptoms of DED may result from lack of tear production, improper tear or film production, alterations in tear or film composition and/or alteration in tear or film clearance. General symptoms of DED include, but are not limited to, ocular discomfort, dryness, conjunctival redness, grittiness, pain, burning, stinging, and any other symptom described in Moshifar et al. (2014) Clinical Ophthalmology 8:1419-1433, the contents of which are herein incorporated by reference in their entirety.

Symptoms may vary with the severity level of DED, which is graded on a scale of 1-4, as described in Behrens et al. (2006) Cornea 25:900-907, the contents of which are herein incorporated by reference in their entirety. Mild and/or episodic DED (grade 1) has signs and symptoms which may include, but are not limited to, no or episodic mild fatigue, a variable Schirmer score, no to mild conjunctival injection, variable tear film break-up time (TFBUT), no to mild conjunctival staining, variable meibomian gland dysfunction (MGD), no to mild corneal staining, and no to mild corneal/and or tear signs. Mild DED may be caused by environmental stress. Moderate episodic and/or chronic DED (grade 2) has signs and symptoms which may include, but are not limited to, episodic visual symptoms that may annoy and/or limit activity, a Schirmer score of less than 10 mm/5 min, no to mild conjunctival injection, variable conjunctival staining, variable MGD, TFBUT of less than 10 minutes, variable corneal staining, and mild debris with a variable meniscus. Moderate DED may be brought on due to stress. Severe DED (grades 3-4) may be frequent, annoying, chronic, activity limiting, disabling, constant, and brought on without stress. Signs and symptoms of severe DED may include, but are not limited to, conjunctival injection (+/− and +/++), a Schirmer score of less than 5 mm/5 min (in some cases less than 2 mm/5 min), moderate to marked conjunctival staining, frequent MGD (optionally including trichiasis, keratinization, and symblepharon), moderate to marked corneal staining (optionally with severe punctate erosions), a TFBUT of less than 5 minutes (in some cases immediate), filamentary keratitis, mucus clumping, increased tear debris, and ulceration.

After diagnosis of DED, a treatment for DED (e.g. artificial tears) may be administered to the subject. Non-limiting examples of current DED treatments include education, counseling, environmental management, tear supplementation (with or without preservatives), prescription drugs (e.g. cyclosporine and lifitegrast), punctal plugs, and surgery. Side effects of current DED treatments include, but are not limited to, burning, redness, discomfort, discharge, pain, blurring, eye irritation, and changes in taste. Current DED treatments may also require frequent administration, as described in Moshifar et al. (2014) Clinical Ophthalmology 8:1419-1433.

In some embodiments, SBPs used to treat dry eye are provided as or included in solutions or devices. Solutions may include silk fibroin micelles, as described in Wongpanit et al. (2007) Macromolecular Bioscience 7:1258-1271, the contents of which are herein incorporated by reference in their entirety. Solutions and SBPs to treat dry eye may be administered topically (e.g., by cream, spray, microspheres, or drops) or by injection to periocular or intraocular areas. Solutions may include viscous solutions, such as gels or slurries. The viscosity of such a solution may modulate properties of a resulting artificial tear replacement. Low viscosity artificial tear replacements may have shorter residence times and less efficacy. High viscosity artificial tear replacements may result in side effects including, but not limited to, blurred vision and discomfort. Devices for the treatment of DED may include, but are not limited to, solutions, implants, microspheres, hydrogels, lenses, artificial tear replacements, contact lens solution, and plugs. Devices may be hardened structures or gelatinous. In some embodiments, devices are gelatinous or prepared as a slurry, but harden after placement. Devices may include lacrimal or punctal plugs that treat dry eye via tear duct insertion. Punctal plugs may be prepared with or without therapeutic agent payloads.

SBPs used to treat dry eye may include therapeutic agent payloads. The therapeutic agents may include any of those described herein. In some embodiments, therapeutic agents include one or more of cyclosporine, corticosteroids, tetracyclines, lifitegrast, NSAIDs, anti-inflammatory agents, opiates, analgesics, and essential fatty acids. In some embodiments, processed silk is the therapeutic agent. Therapeutic agent release from SBPs may occur over an extended payload release period. The payload release period may be from about 1 hour to about 48 hours, from about 1 day to about 14 days, or from about 1 week to about 52 weeks, or more than 52 weeks.

In some embodiments, ocular SBPs may be used as an anti-inflammatory treatment for dry eye disease, as described in Kim et al. (2017) Scientific Reports 7:44364, the contents of which are herein incorporated by reference in their entirety. It has been demonstrated that the administration of 0.1 to 0.5% silk fibroin solutions in a mouse model of dry eye disease enhances corneal smoothness and tear production, while reducing the amount of inflammatory markers detected. In some embodiments, the SBPs described herein may be used to treat dry eye disease in humans. In some embodiments, the SBPs described herein may be used to treat dry eye disease in non-human primates. In some embodiments, the SBPs described herein may be used to treat dry eye disease in canines (e.g. dogs). In some embodiments, the SBPs described herein may be used to treat dry eye disease in felines (e.g. cats).

Combinations

In some embodiments, SBPs may be administered in combination with other therapeutic agent and/or methods of treatment, e.g., with known pharmaceuticals and/or known therapeutic methods, such as, for example, those which are currently employed for treating these disorders. For example, SBPs used to treat ocular indications may be administered in combination with other therapeutic agents used to treat ocular indications.

Pharmaceutical Compositions

In some embodiments, SBPs are or are included in pharmaceutical compositions. As used herein, the term "pharmaceutical composition" refers to a composition designed and/or used for medicinal purposes (e.g., the treatment of a disease).

In some embodiments, pharmaceutical compositions include one or more excipients and/or one or more therapeutic agents. Excipients and/or therapeutic agents included in pharmaceutical compositions may include, but are not limited to, any of those described herein. Relative amounts of therapeutic agents, excipient, and/or any additional ingredients in pharmaceutical compositions may vary, depending upon the identity, size, and/or condition of subjects being treated and further depending upon routes by which compositions are administered. For example, the compositions may include from about 0.0001% to about 99% (w/v) of a therapeutic agent.

Some excipients may include pharmaceutically acceptable excipients. The phrase "pharmaceutically acceptable" as used herein, refers to suitability within the scope of sound medical judgment for contacting subject (e.g., human or animal) tissues and/or bodily fluids with toxicity, irritation, allergic response, or other complication levels yielding reasonable benefit/risk ratios. As used herein, the term "pharmaceutically acceptable excipient" refers to any ingredient, other than active agents, that is substantially nontoxic and non-inflammatory in a subject. Pharmaceutically acceptable excipients may include, but are not limited to, solvents, dispersion media, diluents, inert diluents, buffering agents, lubricating agents, oils, liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, M D, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of pharmaceutical compositions.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of therapeutic agent or other compound. The amount of therapeutic agent may generally be equal to the dosage of therapeutic agent administered to a subject and/or a convenient fraction of such dosage including, but not limited to, one-half or one-third of such a dosage.

In some embodiments, pharmaceutical compositions may include between 0.0001 to 35% (w/v) silk fibroin. In some embodiments, the pharmaceutical compositions may include silk fibroin in concentrations from about 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 1% (w/v) to about 5% (w/v), from about 5% (w/v) to about 10% (w/v), from about 10% (w/v) to about 20% (w/v), or from about 20% (w/v) to about 35% (w/v).

Dosing

In some embodiments, the present disclosure provides methods of administering pharmaceutical compositions that are or include SBPs to subjects in need thereof. Such methods may include providing pharmaceutical compositions at one or more doses and/or according to a specific schedule. In some embodiments, doses may be determined based on desired amounts of therapeutic agent or SBP to be delivered. Doses may be adjusted to accommodate any route of administration effective for a particular therapeutic application. The exact amount required will vary from subject to subject, depending on the species, age, and general condition of the subject, the severity of the disease, the particular composition, its mode of administration, its mode of activity, and the like. The frequency of dosing required will also vary from subject to subject, depending on the species, age, and general condition of the subject, the severity of the disease, the particular composition, its mode of administration, its mode of activity, and the like.

SBPs may be formulated in dosage unit form. Such forms may allow for ease of administration and uniformity of dosage. Total daily SBP usage may be decided by an attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, pharmaceutical compositions that are or include SBPs may include a therapeutic agent or SBP at a concentration of from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 μg/mL to about 1 μg/mL, from about 0.05 μg/mL to about 2 μg/mL, from about 1 μg/mL to about 5 μg/mL, from about 2 μg/mL to about 10 μg/mL, from about 4 μg/mL to about 16 μg/mL, from about 5 μg/mL to about 20 μg/mL, from about 8 μg/mL to about 24 μg/mL, from about 10 μg/mL to about 30 μg/mL, from about 12 μg/mL to about 32 μg/mL, from about 14 μg/mL to about 34 μg/mL, from about 16 μg/mL to about 36 μg/mL, from about 18 μg/mL to about 38 μg/mL, from about 20 μg/mL to about 40 μg/mL, from about 22 μg/mL to about 42 μg/mL, from about 24 μg/mL to about 44 μg/mL, from about 26 μg/mL to about 46 μg/mL, from about 28 μg/mL to about 48 μg/mL, from about 30 μg/mL to about 50 μg/mL, from about 35 μg/mL to about 55 μg/mL, from about 40 μg/mL to about 60 μg/mL, from about 45 μg/mL to about 65 μg/mL, from about 50 μg/mL to about 75 μg/mL, from about 60 μg/mL to about 240 μg/mL, from about 70 μg/mL to about 350 μg/mL, from about 80 μg/mL to about 400 μg/mL, from about 90 μg/mL to about 450 μg/mL, from about 100 g/mL to about 500 μg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 40 mg/mL to about 100 mg/mL, from about 100 mg/mL to about 200 mg/mL, from about 200 mg/mL to about 300 mg/mL, from about 300 mg/mL to about 400 mg/mL, or more than 400 mg/mL.

In some embodiments, pharmaceutical compositions that are or include SBPs may be administered at a dose that provides subjects with a mass of therapeutic agent or SBP per unit mass of the subject (e.g., mg therapeutic agent or SBP per kg of subject [mg/kg]). In some embodiments, therapeutic agents or SBPs are administered at a dose of from about 1 ng/kg to about 5 ng/kg, from about 2 ng/kg to about 10 ng/kg, from about 4 ng/kg to about 16 ng/kg, from about 5 ng/kg to about 20 ng/kg, from about 8 ng/kg to about 24 ng/kg, from about 10 ng/kg to about 30 ng/kg, from about 12 ng/kg to about 32 ng/kg, from about 14 ng/kg to about 34 ng/kg, from about 16 ng/kg to about 36 ng/kg, from about 18 ng/kg to about 38 ng/kg, from about 20 ng/kg to about 40 ng/kg, from about 22 ng/kg to about 42 ng/kg, from about 24 ng/kg to about 44 ng/kg, from about 26 ng/kg to about 46 ng/kg, from about 28 ng/kg to about 48 ng/kg, from about 30 ng/kg to about 50 ng/kg, from about 35 ng/kg to about 55 ng/kg, from about 40 ng/kg to about 60 ng/kg, from about 45 ng/kg to about 65 ng/kg, from about 50 ng/kg to about 75 ng/kg, from about 60 ng/kg to about 240 ng/kg, from about 70 ng/kg to about 350 ng/kg, from about 80 ng/kg to about 400 ng/kg, from about 90 ng/kg to about 450 ng/kg, from about 100 ng/kg to about 500 ng/kg, from about 0.01 μg/kg to about 1 μg/kg, from about 0.05 μg/kg to about 2 μg/kg, from about 1 μg/kg to about 5 μg/kg, from about 2 μg/kg to about 10 μg/kg, from about 4 μg/kg to about 16 μg/kg, from about 5 μg/kg to about 20 μg/kg, from about 8 μg/kg to about 24 μg/kg, from about 10 μg/kg to about 30 μg/kg, from about 12 μg/kg to about 32 μg/kg, from about 14 μg/kg to about 34 μg/kg, from about 16 μg/kg to about 36 μg/kg, from about 18 μg/kg to about 38 μg/kg, from about 20 μg/kg to about 40 μg/kg, from about 22 μg/kg to about 42 μg/kg, from about 24 μg/kg to about 44 μg/kg, from about 26 μg/kg to about 46 μg/kg, from about 28 μg/kg to about 48 μg/kg, from about 30 μg/kg to about 50 μg/kg, from about 35 μg/kg to about 55 μg/kg, from about 40 μg/kg to about 60 μg/kg, from about 45 μg/kg to about 65 μg/kg, from about 50 μg/kg to about 75 μg/kg, from about 60 μg/kg to about 240 μg/kg, from about 70 μg/kg to about 350 μg/kg, from about 80 μg/kg to about 400 μg/kg, from about 90 μg/kg to about 450 μg/kg, from about 100 μg/kg to about 500 jug/kg, from about 0.01 mg/kg to about 1 mg/kg, from about 0.05 mg/kg to about 2 mg/kg, from about 1 mg/kg to about 5 mg/kg, from about 2 mg/kg to about 10 mg/kg, from about 4 mg/kg to about 16 mg/kg, from about 5 mg/kg to about 20 mg/kg, from about 8 mg/kg to about 24 mg/kg, from about 10 mg/kg to about 30 mg/kg, from about 12 mg/kg to about 32 mg/kg, from about 14 mg/kg to about 34 mg/kg, from about 16 mg/kg to about 36 mg/kg, from about 18 mg/kg to about 38 mg/kg, from about 20 mg/kg to about 40 mg/kg, from about 22 mg/kg to about 42 mg/kg, from about 24 mg/kg to about 44 mg/kg, from about 26 mg/kg to about 46 mg/kg, from about 28 mg/kg to about 48 mg/kg, from about 30 mg/kg to about 50 mg/kg, from about 35 mg/kg to about 55 mg/kg, from about 40 mg/kg to about 60 mg/kg, from about 45 mg/kg to about 65 mg/kg, from about 50 mg/kg to about 75 mg/kg, from about 60 mg/kg to about 240 mg/kg, from about 70 mg/kg to about 350 mg/kg, from about 80 mg/kg to about 400 mg/kg, from about 90 mg/kg to about 450 mg/kg, from about 100 mg/kg to about 500 mg/kg, from about 0.01 g/kg to about 1 g/kg, from about 0.05 g/kg to about 2 g/kg, from about 1 g/kg to about 5 g/kg, or more than 5 g/kg.

In some embodiments, pharmaceutical compositions that are or include SBPs may be administered at a dose sufficient to yield desired therapeutic agent or SBP concentration levels in subject tissue or fluids (e.g., blood, plasma, urine, etc.). In some embodiments, doses are adjusted to achieve subject therapeutic agent or SBP concentration levels in subject tissues or fluids of from about 1 μg/mL to about 5 pg/mL, from about 2 pg/mL to about 10 pg/mL, from about 4 pg/mL to about 16 pg/mL, from about 5 pg/mL to about 20 pg/mL, from about 8 pg/mL to about 24 pg/mL, from about 10 pg/mL to about 30 pg/mL, from about 12 pg/mL to about 32 pg/mL, from about 14 pg/mL to about 34 pg/mL, from about 16 pg/mL to about 36 pg/mL, from about 18 pg/mL to about 38 pg/mL, from about 20 pg/mL to about 40 pg/mL, from about 22 pg/mL to about 42 pg/mL, from about 24 pg/mL to about 44 pg/mL, from about 26 pg/mL to about 46 pg/mL, from about 28 pg/mL to about 48 pg/mL, from about 30 pg/mL to about 50 pg/mL, from about 35 pg/mL to about 55 pg/mL, from about 40 pg/mL to about 60 pg/mL, from about 45 pg/mL to about 65 pg/mL, from about 50 pg/mL to about 75 pg/mL, from about 60 pg/mL to about 240 pg/mL, from about 70 pg/mL to about 350 pg/mL, from about 80 pg/mL to about 400 pg/mL, from about 90 pg/mL to about 450 pg/mL, from about 100 pg/mL to about 500 pg/mL, from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 μg/mL to about 1 μg/mL, from about 0.05 μg/mL to about 2 μg/mL, from about 1 μg/mL to about 5 μg/mL, from about 2 μg/mL to about 10 μg/mL, from about 4 μg/mL to about 16 μg/mL, from about 5 μg/mL to about 20 μg/mL, from about 8 μg/mL to about 24 μg/mL, from about 10 μg/mL to about 30 μg/mL, from about 12 μg/mL to about 32 μg/mL, from about 14 μg/mL to about 34 μg/mL, from about 16 μg/mL to about 36 μg/mL, from about 18 μg/mL to about 38 μg/mL, from about 20 μg/mL to about 40 μg/mL, from about 22 μg/mL to about 42 μg/mL, from about 24 μg/mL to about 44 μg/mL, from about 26 μg/mL to about 46 μg/mL, from about 28 μg/mL to about 48 μg/mL, from about 30 μg/mL to about 50 μg/mL, from about 35 μg/mL to about 55 μg/mL, from about 40 μg/mL to about 60 μg/mL, from about 45 μg/mL to about 65 μg/mL, from about 50 μg/mL to about 75 μg/mL, from about 60 μg/mL to about 240 μg/mL, from about 70 μg/mL to about 350 μg/mL, from about 80 μg/mL to about 400 μg/mL, from about 90 μg/mL to about 450 μg/mL, from about 100 μg/mL to about 500 μg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL.

In some embodiments, pharmaceutical compositions that are or include SBPs are provided in one or more doses and are administered one or more times to subjects. Some pharmaceutical compositions are provided in only a single administration. Some pharmaceutical compositions are provided according to a dosing schedule that include two or more administrations. Each administration may be at the same dose or may be different from a previous and/or subsequent dose. In some embodiments, subjects are provided an initial dose that is higher than subsequent doses (referred to herein as a "loading dose"). In some embodiments, doses are decreased over the course of administration. In some embodiments, dosing schedules include pharmaceutical composition administration from about every 2 hours to about every 10 hours, from about every 4 hours to about every 20 hours, from about every 6 hours to about every 30 hours, from about every 8 hours to about every 40 hours, from about every 10 hours to about every 50 hours, from about every 12 hours to about every 60 hours, from about every 14 hours to about every 70 hours, from about every 16 hours to about every 80 hours, from about every 18 hours to about every 90 hours, from about every 20 hours to about every 100 hours, from about every 22 hours to about every 120 hours, from about every 24 hours to about every 132 hours, from about every 30 hours to about every 144 hours, from about every 36 hours to about every 156 hours, from about every 48 hours to about every 168 hours, from about every 2 days to about every 10 days, from about every 4 days to about every 15 days, from about every 6 days to about every 20 days, from about every 8 days to about every 25 days, from about every 10 days to about every 30 days, from about every 12 days to about every 35 days, from about every 14 days to about every 40 days, from about every 16 days to about every 45 days, from about every 18 days to about every 50 days, from about every 20 days to about every 55 days, from about every 22 days to about every 60 days, from about every 24 days to about every 65 days, from about every 30 days to about every 70 days, from about every 2 weeks to about every 8 weeks, from about every 3 weeks to about every 12 weeks, from about every 4 weeks to about every 16 weeks, from about every 5 weeks to about every 20 weeks, from about every 6 weeks to about every 24 weeks, from about every 7 weeks to about every 28 weeks, from about every 8 weeks to about every 32 weeks, from about every 9 weeks to about every 36 weeks, from about every 10 weeks to about every 40 weeks, from about every 11 weeks to about every 44 weeks, from about every 12 weeks to about every 48 weeks, from about every 14 weeks to about every 52 weeks, from about every 16 weeks to about every 56 weeks, from about every 20 weeks to about every 60 weeks, from about every 2 months to about every 6 months, from about every 3 months to about every 12 months, from about every 4 months to about every 18 months, from about every 5 months to about every 24 months, from about every 6 months to about every 30 months, from about every 7 months to about every 36 months, from about every 8 months to about every 42 months, from about every 9 months to about every 48 months, from about every 10 months to about every 54 months, from about every 11 months to about every 60 months, from about every 12 months to about every 66 months, from about 2 years to about 5 years, from about 3 years to about 10 years, from about 4 years to about 15 years, from about 5 years to about 20 years, from about 6 years to about 25 years, from about 7 years to about 30 years, from about 8 years to about 35 years, from about 9 years to about 40 years, from about 10 years to about 45 years, from about 15 years to about 50 years, or more than every 50 years.

In some embodiments, pharmaceutical compositions that are or include SBPs may be administered at a dose sufficient to provide a therapeutically effective amount of therapeutic agents or SBPs. As used herein, the term "therapeutically effective amount" refers to an amount of an agent sufficient to achieve a therapeutically effective outcome. As used herein, the term "therapeutically effective outcome" refers to a result of treatment where at least one objective of treatment is met. In some embodiments, a therapeutically effective amount is provided in a single dose. In some embodiments, a therapeutically effective amount is administered according to a dosing schedule that includes a plurality of doses. Those skilled in the art will appreciate that in some embodiments, a unit dosage form may be considered to include a therapeutically effective amount of a particular agent or entity if it includes an amount that is effective when administered as part of such a dosage regimen.

Administration

In some embodiments, pharmaceutical compositions that are or include SBPs may be administered according to one or more administration routes. In some embodiments, administration is enteral (into the intestine), transdermal, intravenous bolus, intralesional (within or introduced directly to a localized lesion), intrapulmonary (within the lungs or its bronchi), diagnostic, intraocular (within the eye), transtympanic (across or through the tympanic cavity), intravesical infusion, sublingual, nasogastric (through the nose and into the stomach), spinal, intracartilaginous (within a cartilage), insufflation (snorting), rectal, intravascular (within a vessel or vessels), buccal (directed toward the cheek), dental (to a tooth or teeth), intratesticular (within the testicle), intratympanic (within the aurus media), percutaneous, intrathoracic (within the thorax), submucosal, cutaneous, epicutaneous (application onto the skin), dental intracornal, intramedullary (within the marrow cavity of a bone), intra-abdominal, epidural (into the dura matter), intramuscular (into a muscle), intralymphatic (within the lymph), iontophoresis (by means of electric current where ions of soluble salts migrate into the tissues of the body), subcutaneous (under the skin), intragastric (within the stomach), nasal administration (through the nose), transvaginal, intravenous drip, endosinusial, intraprostatic (within the prostate gland), soft tissue, intradural (within or beneath the dura), subconjunctival, oral (by way of the mouth), peridural, parenteral, intraduodenal (within the duodenum), intracisternal (within the cisterna magna cerebellomedularis), periodontal, periarticular, biliary perfusion, intracoronary (within the coronary arteries), intrathecal (within the cerebrospinal fluid at any level of the cerebrospinal axis), intrameningeal (within the meninges), intracavernous injection (into a pathologic cavity) intracavitary (into the base of the penis), intrabiliary, subarachnoid, intrabursal, ureteral (to the ureter), intratendinous (within a tendon), auricular (in or by way of the ear), intracardiac (into the heart), enema, intraepidermal (to the epidermis), intraventricular (within a ventricle), intramyocardial (within the myocardium), intratubular (within the tubules of an organ), vaginal, sublabial, intracorporus cavernosum (within the dilatable spaces of the corporus cavernosa of the penis), intradermal (into the skin itself), intravitreal (through the eye), perineural, cardiac perfusion, irrigation (to bathe or flush open wounds or body cavities), in ear drops, endotracheal, intraosseous infusion (into the bone marrow), caudal block, intrauterine, transtracheal (through the wall of the trachea), intra-articular, intracorneal (within the cornea), endocervical, extracorporeal, intraspinal (within the vertebral column), transmucosal (diffusion through a mucous membrane), topical, photopheresis, oropharyngeal (directly to the mouth and pharynx), occlusive dressing technique (topical route administration which is then covered by a dressing which occludes the area), transplacental (through or across the placenta), intrapericardial (within the pericardium), intraarterial (into an artery), interstitial, intracerebral (into the cerebrum), intracerebroventricular (into the cerebral ventricles), peridural, intrapleural (within the pleura), infiltration, intrabronchial, intrasinal (within the nasal or periorbital sinuses), intraductal (within a duct of a gland), transdermal (diffusion through the intact skin for systemic distribution), intracaudal (within the cauda equine), nerve block, retrobulbar (behind the pons or behind the eyeball), intravenous (into a vein), intraamniotic, conjunctival, intrasynovial (within the synovial cavity of a joint), gastroenteral, intraluminal (within a lumen of a tube), intrathecal (into the spinal canal), electro-osmosis, intraileal (within the distal portion of the small intestine), intraesophageal (to the esophagus), extra-amniotic administration, hemodialysis, intragingival (within the gingivae), intratumor (within a tumor), eye drops (onto the conjunctiva), laryngeal (directly upon the larynx), urethral (to the urethra), intravaginal administration, intramyocardial (entering the myocardium), intraperitoneal (infusion or injection into the peritoneum), respiratory (within the respiratory tract by inhaling orally or nasally for local or systemic effect), intradiscal (within a disc), ophthalmic (to the external eye), and/or intraovarian (within the ovary).

In some embodiments, pharmaceutical compositions that are or include SBPs may be administered by auricular administration, intraarticular administration, intramuscular administration, intrathecal administration, extracorporeal administration, buccal administration, intrabronchial administration, conjunctival administration, cutaneous administration, dental administration, endocervical administration, endosinusial administration, endotracheal administration, enteral administration, epidural administration, intra-abdominal administration, intrabiliary administration, intrabursal administration, oropharyngeal administration, interstitial administration, intracardiac administration, intracartilaginous administration, intracaudal administration, intracavernous administration, intracerebral administration, intracorporus cavernosum, intracavitary administration, intracorneal administration, intracisternal administration, cranial administration, intracranial administration, intradermal administration, intralesional administration, intratympanic administration, intragingival administration, intraovarian administration, intraocular administration, intradiscal administration, intraductal administration, intraduodenal administration, ophthalmic administration, intradural administration, intraepidermal administration, intraesophageal administration, nasogastric administration, nasal administration, laryngeal administration, intraventricular administration, intragastric administration, intrahepatic administration, intraluminal administration, intravitreal administration, intravesicular administration, intralymphatic administration, intramammary administration, intramedullary administration, intrasinal administration, intrameningeal administration, intranodal administration, intraovarian administration, intrapulmonary administration, intrapericardial administration, intraperitoneal administration, intrapleural administration, intrapericardial administration, intraprostatic administration, intrapulmonary administration, intraluminal administration, intraspinal administration, intrasynovial administration, intratendinous administration, intratesticular administration, subconjunctival administration, intracerebroventricular administration, epicutaneous administration, intravenous administration, retrobulbar administration, periarticular administration, intrathoracic administration, subarachnoid administration, intratubular administration, periodontal administration, transtympanic administration, transtracheal administration, intratumor administration, vaginal administration, urethral administration, intrauterine administration, oral administration, gastroenteral administration, parenteral administration, sublingual administration, ureteral administration, percutaneous administration, peridural administration, transmucosal administration, perineural administration, transdermal administration, rectal administration, soft tissue administration, intraarterial administration, subcutaneous administration, topical administration, extra-amniotic administration, insufflation, enema, eye drops, ear drops, or intravesical infusion. In some embodiments, the SBPs described herein may be administered via injection. Injection site reactions may be monitored via any method known to one skilled in the art.

In some embodiments, SBPs may be administered for localized treatment (e.g., see United States Publication Numbers US20170368236 and US20110171239, the contents of each of which are herein incorporated by reference in their entirety). In some embodiments, SBPs may be administered for treatment of areas located further away from administration sites (e.g., see Aykac et al. (2017) Gene s0378-1119 (17) 30868-30865, the contents of which are herein incorporated by reference in their entirety).

In some embodiments, administration includes ocular administration. As used herein, the term "ocular administration" refers to delivery of an agent to an eye. Ocular administration may include, but is not limited to, topical administration (e.g., using eye drops, ointments, sprays, or creams), intraocular administration, intravitreal administration, intraretinal administration, intracorneal administration, intrascleral administration, lacrimal administration, punctal administration, administration to the anterior sub-Tenon's, suprachoroidal administration, administration to the posterior sub-Tenon's, subretinal administration, administration to the fornix, administration to the lens, administration to the anterior segment, administration to the posterior segment, macular administration, and intra-aqueous humor administration. Administration may include intravitreal injection.

In some embodiments, the SBPs described herein may be administered as an eye drop. In some embodiments, the SBPs described herein may be administered as a spray. In some embodiments, the SBPs described herein may be administered by injection. In some embodiments, the SBPs described herein may be administered by lens application. In some embodiments, the SBPs described herein may be administered as a plug. In some embodiments, the SBPs are administered as a lacrimal plug. In some embodiments, the SBPs are administered as a punctal plug.

In some embodiments, SBP administration or SBP-based therapeutic agent administration occurs over a period of time, referred to herein as the "administration period." During administration periods, administration may be continuous or may be separated into two or more administrations. In some embodiments, administration periods may be from about 1 min to about 30 min, from about 10 min to about 45 min, from about 20 min to about 60 min, from about 40 min to about 90 min, from about 2 hours to about 10 hours, from about 4 hours to about 20 hours, from about 6 hours to about 30 hours, from about 8 hours to about 40 hours, from about 10 hours to about 50 hours, from about 12 hours to about 60 hours, from about 14 hours to about 70 hours, from about 16 hours to about 80 hours, from about 18 hours to about 90 hours, from about 20 hours to about 100 hours, from about 22 hours to about 120 hours, from about 24 hours to about 132 hours, from about 30 hours to about 144 hours, from about 36 hours to about 156 hours, from about 48 hours to about 168 hours, from about 2 days to about 10 days, from about 4 days to about 15 days, from about 6 days to about 20 days, from about 8 days to about 25 days, from about 10 days to about 30 days, from about 12 days to about 35 days, from about 14 days to about 40 days, from about 16 days to about 45 days, from about 18 days to about 50 days, from about 20 days to about 55 days, from about 22 days to about 60 days, from about 24 days to about 65 days, from about 30 days to about 70 days, from about 2 weeks to about 8 weeks, from about 3 weeks to about 12 weeks, from about 4 weeks to about 16 weeks, from about 5 weeks to about 20 weeks, from about 6 weeks to about 24 weeks, from about 7 weeks to about 28 weeks, from about 8 weeks to about 32 weeks, from about 9 weeks to about 36 weeks, from about 10 weeks to about 40 weeks, from about 11 weeks to about 44 weeks, from about 12 weeks to about 48 weeks, from about 14 weeks to about 52 weeks, from about 16 weeks to about 56 weeks, from about 20 weeks to about 60 weeks, from about 2 months to about 6 months, from about 3 months to about 12 months, from about 4 months to about 18 months, from about 5 months to about 24 months, from about 6 months to about 30 months, from about 7 months to about 36 months, from about 8 months to about 42 months, from about 9 months to about 48 months, from about 10 months to about 54 months, from about 11 months to about 60 months, from about 12 months to about 66 months, from about 2 years to about 5 years, from about 3 years to about 10 years, from about 4 years to about 15 years, from about 5 years to about 20 years, from about 6 years to about 25 years, from about 7 years to about 30 years, from about 8 years to about 35 years, from about 9 years to about 40 years, from about 10 years to about 45 years, from about 15 years to about 50 years, or more than 50 years.

III. Agricultural Applications and Products

In some embodiments, SBP formulations are prepared for use in agriculture. As used herein, the term "agriculture" refers to the cultivation of plants and animals to produce products useful for individual, communal, industrial, or commercial purposes. SBPs may be agricultural compositions. In some embodiments, SBPs may include an agricultural composition. As used herein, the term "agricultural composition" refers to any substance used in or produced by agriculture. In some embodiments, SBPs may be used to improve the growth, production, the shelf-life and stability of agricultural products. As used herein, the term "agriculture product" refers to any product of agriculture (e.g., food, medicines, materials, biofuels, etc.). In some embodiments, SBP formulations may be used in a variety of agricultural applications (e.g., agricultural SBP formulations). As used herein, the term "agricultural application" refers to any method used to improve, promote or increase the production of products obtained through the cultivation of plants and animals, for the benefit of individuals, communities, or commercial entities.

In some embodiments, agricultural compositions described herein are used for agricultural and environmental development. In some embodiments, SBP formulations may be used to improve the growth and production of agricultural products. These agricultural products may be plants, animals, plant agricultural products, or animal agricultural products. In some embodiments, SBP formulation administration may result in increased weight, biomass, growth, offspring production, product levels, and/or product size of one or more agricultural products. In some embodiments, the agricultural SBP formulations may include soil or locus stabilizers.

Cargo

In some embodiments, agricultural SBP formulations are used to facilitate delivery of cargo that enhance agricultural product health, yield, half-life and/or stability. In some embodiments, SBP formulations may be the cargos. In some embodiments, cargos may include, but are not limited to, therapeutic agents, small molecules, chemicals, nutrients, micronutrients, macronutrients, pest control agents, pesticides, antibiotics, antifungal, fungicide, virus, virus fragment, virus particle, herbicide, insecticide, fertilizers, pH modulators, soil stabilizers, and flowability agents. In some embodiments, the efficacy of the cargo is improved by formulation within an agricultural SBP formulations. In some embodiments, agricultural SBP formulations may encapsulate cargo for extended and/or controlled release.

In some embodiments, cargos for use in SBP formulations may be selected from any of those listed in Table 5.

TABLE 5

| Cargo | |
|---|---|
| Payload | Category |
| amikacin | antibiotic |
| amoxicillin | antibiotic |
| ampicillin | antibiotic |
| azithromycin | antibiotic |
| azlocillin | antibiotic |
| aztreonam | antibiotic |
| capreomycin | antibiotic |
| carbenicillin | antibiotic |
| cefaclor | antibiotic |
| cefadroxil | antibiotic |
| cefalexin | antibiotic |
| cefalothin | antibiotic |
| cefamandole | antibiotic |
| cefazolin | antibiotic |
| cefdinir | antibiotic |
| cefditoren | antibiotic |
| cefepime | antibiotic |
| cefixime | antibiotic |
| cefoperazone | antibiotic |
| cefotaxime | antibiotic |
| cefoxitin | antibiotic |
| cefpodoxime | antibiotic |
| cefprozil | antibiotic |
| ceftaroline fosamil | antibiotic |
| ceftazidime | antibiotic |
| ceftibuten | antibiotic |
| ceftizoxime | antibiotic |
| ceftobiprole | antibiotic |
| ceftriaxone | antibiotic |
| cefuroxima | antibiotic |
| cilastatin | antibiotic |
| ciprofolaxin | antibiotic |
| clarithromycin | antibiotic |
| clindamycin | antibiotic |
| clofazimine | antibiotic |
| cloxacillin | antibiotic |
| cycloserine | antibiotic |
| dalbavancin | antibiotic |
| dapsone | antibiotic |
| daptomycin | antibiotic |
| demeclocycline | antibiotic |
| dicloxacillin | antibiotic |
| dirithromycin | antibiotic |
| doripenem | antibiotic |
| doxycycline | antibiotic |
| enoxacin | antibiotic |
| ertapenem | antibiotic |
| ethambutol | antibiotic |
| ethionamide | antibiotic |
| flucloxacillin | antibiotic |
| furazolidone | antibiotic |
| gatifloxacin | antibiotic |
| geldanamycin | antibiotic |
| gemifloxacin | antibiotic |
| gentamicin | antibiotic |
| grepafloxacin | antibiotic |
| herbimycin | antibiotic |
| imipeneum | antibiotic |
| isoniazid | antibiotic |
| kanamycin | antibiotic |
| levofloxacin | antibiotic |
| linezolid | antibiotic |
| linomycin | antibiotic |
| lomefloxacin | antibiotic |
| loracarbef | antibiotic |
| mafenide | antibiotic |
| meropenem | antibiotic |
| methicillin | antibiotic |
| mezlocillin | antibiotic |
| minocycline | antibiotic |
| moxifloxacin | antibiotic |
| nafcillin | antibiotic |
| nalidixic acid | antibiotic |
| neomycin | antibiotic |
| netilmicin | antibiotic |
| nitrofurantoin | antibiotic |
| norfloxacin | antibiotic |
| ofloxacin | antibiotic |
| oritavancin | antibiotic |
| oxacillin | antibiotic |
| oxytetracycline | antibiotic |
| paromomycin | antibiotic |
| penicillin G | antibiotic |
| penicillin V | antibiotic |
| piperacillin | antibiotic |
| posizolid | antibiotic |
| pyrazinamide | antibiotic |
| radezolid | antibiotic |
| rifampicin | antibiotic |
| rifaximin | antibiotic |
| roxithromycin | antibiotic |
| sparfloxacin | antibiotic |
| spectinomycin | antibiotic |
| spiramycin | antibiotic |
| sulfacetamide | antibiotic |
| sulfadiazine | antibiotic |
| sulfadimethoxine | antibiotic |
| sulfamethizole | antibiotic |
| sulfamethoxazole | antibiotic |
| sulfanilimide | antibiotic |
| sulfasalazine | antibiotic |
| sulfisoxazole | antibiotic |
| teicoplanin | antibiotic |
| telavancin | antibiotic |
| telithromycin | antibiotic |
| temafloxacin | antibiotic |
| temocillin | antibiotic |
| ticarcillin | antibiotic |
| tobramycin | antibiotic |
| torezolid | antibiotic |
| troleandomycin | antibiotic |
| trovafloxacin | antibiotic |
| vancomycin | antibiotic |
| erythromycin | antibiotic; endoparasiticide |
| penicillin | antibiotic; endoparasiticide |
| streptomycin | antibiotic; endoparasiticide |
| tetracycline | antibiotic; endoparasiticide |
| 5-fluorocytosine | antifungal |
| abafungin | antifungal |
| albaconazole | antifungal |
| allylamine | antifungal |
| amorolfin | antifungal |
| amphotericin B | antifungal |
| anidulafungin | antifungal |
| aurone | antifungal |
| balsam | antifungal |

TABLE 5-continued

| Cargo | |
|---|---|
| Payload | Category |
| benzoic acid | antifungal |
| bifonazole | antifungal |
| butenafine | antifungal |
| butoconazole | antifungal |
| candicidin | antifungal |
| caspofungin | antifungal |
| ciclopirox | antifungal |
| clotrimazole | antifungal |
| crystal violet | antifungal |
| echinocandin | antifungal |
| econazole | antifungal |
| efinaconazole | antifungal |
| epoxiconazole | antifungal |
| fenticonazole | antifungal |
| filipin | antifungal |
| fluconazole | antifungal |
| flucytosine | antifungal |
| griseofulvin | antifungal |
| haloprogin | antifungal |
| hamycin | antifungal |
| imidazole | antifungal |
| isavuconazole | antifungal |
| isoconazole | antifungal |
| itraconazole | antifungal |
| ketoconazole | antifungal |
| luliconazole | antifungal |
| micafungin | antifungal |
| miconazole | antifungal |
| miltefosine | antifungal |
| naftitine | antifungal |
| natamycin | antifungal |
| nystatin | antifungal |
| omoconazole | antifungal |
| orotomide | antifungal |
| oxiconazole | antifungal |
| polyene antifungal | antifungal |
| posaconazole | antifungal |
| propiconazole | antifungal |
| ravuconazole | antifungal |
| rimocidin | antifungal |
| sertaconazole | antifungal |
| sulconazole | antifungal |
| terbinafine | antifungal |
| terconazole | antifungal |
| thiazole | antifungal |
| tioconazole | antifungal |
| tolnaftate | antifungal |
| triazole | antifungal |
| undecylenic acid | antifungal |
| voriconazole | antifungal |
| bacterial cell | biologic |
| microbiome | biologic |
| microorganism | biologic |
| rhizobia bacteria | biologic |
| symbiote | biologic |
| virus | biologic |
| virus fragment | biologic |
| virus particle | biologic |
| fungicide | biologic; pesticide |
| Pour-Ons | ectoparasiticide |
| Sprays | ectoparasiticide |
| Dips | ectoparasiticide |
| Ear Tags | ectoparasiticide |
| Collars | ectoparasiticide |
| Oral Tablets | ectoparasiticide |
| Other Ectoparasiticides | ectoparasiticide |
| Spot-Ons | ectoparasiticide |
| ectoparaciticide | ectoparasiticide |
| pyrethroid | ectoparasiticide |
| carbamate | ectoparasiticide |
| water-insoluble organo-phospphorus compound | ectoparasiticide |
| benzoyl urea | ectoparasiticide |
| formamidine | ectoparasiticide |
| triazine | ectoparasiticide |
| avermectin | ectoparasiticide |
| milbemycin | ectoparasiticide |
| flumethrin | ectoparasiticide |
| alphamethrin | ectoparasiticide |
| pirimphos methyl | ectoparasiticide |
| pirimphos ethyl | ectoparasiticide |
| mylbemycin | ectoparasiticide |
| moxidectin | ectoparasiticide; endoparasiticide |
| ivermectin | ectoparasiticide; endoparasiticide; insecticide |
| doramectin | ectoparasiticide; endoparasiticide; insecticide |
| abamectin | ectoparasiticide; insecticide |
| pyrethrin | ectoparasiticide; insecticide |
| cyhalothrin | ectoparasiticide; insecticide |
| amitraz | ectoparasiticide; insecticide |
| deltamethrin | ectoparasiticide; insecticide |
| diazinon | ectoparasiticide; insecticide |
| macrocyclic lactones | endecticide |
| benzimidazole | endecticide |
| pro-benzimidazole | endecticide |
| imidazothiazole | endecticide |
| tetrahydropyrimidine | endecticide |
| organophosphate | endecticide |
| Endoparasiticide | endoparasiticide |
| Oral Liquids | endoparasiticide |
| Oral Solids | endoparasiticide |
| Injectables | endoparasiticide |
| Feed Additives | endoparasiticide |
| Endectocides | endoparasiticide |
| Tetramisole | endoparasiticide |
| dexamisole | endoparasiticide |
| Milbemycin oxime | endoparasiticide |
| Nemadectin | endoparasiticide |
| Albendazole | endoparasiticide |
| Clorsulon | endoparasiticide |
| Cydectin | endoparasiticide |
| Diethylcarbamazine | endoparasiticide |
| Febantel | endoparasiticide |
| Fenbendazole | endoparasiticide |
| Haloxon | endoparasiticide |
| Levamisole | endoparasiticide |
| Mebendazole | endoparasiticide |
| Morantel | endoparasiticide |
| Oxyclozanide | endoparasiticide |
| Oxibendazole | endoparasiticide |
| Oxfendazole | endoparasiticide |
| Oxamniquine | endoparasiticide |
| Pyrantel | endoparasiticide |
| Praziquantel | endoparasiticide |
| Thiabendazole | endoparasiticide |
| cyclosporin | endoparasiticide |
| sulfonamide | endoparasiticide |
| cephalosporin | endoparasiticide |
| cephamycin | endoparasiticide |
| aminoglucosid | endoparasiticide |
| trimethoprim | endoparasiticide |
| dimetridazole | endoparasiticide |
| framycetin | endoparasiticide |
| fruazolidone | endoparasiticide |
| pleuromutilin | endoparasiticide |
| a compound active against protozoa | endoparasiticide |
| piperazine | endoparasiticide; endecticide |
| emamectin | endoparasiticide; insecticide |
| eprinomectin | endoparasiticide; insecticide |
| milbemectin | endoparasiticide; insecticide |
| permethrin | endoparasiticide; insecticide |
| selamectin | endoparasiticide; insecticide |
| trichlorfon | endoparasiticide; insecticide |
| ammonium nitrate | fertilizer |
| binary fertilizer | fertilizer |
| compound fertilizer | fertilizer |
| diammonium phosphate | fertilizer |
| fertilizer | fertilizer |
| monoammonium phosphate | fertilizer |
| multinutrient fertilizer | fertilizer |
| natural fertilizer | fertilizer |

TABLE 5-continued

| Cargo | |
|---|---|
| Payload | Category |
| nitrogen fertilizer | fertilizer |
| NK fertilizer | fertilizer |
| NP fertilizer | fertilizer |
| NPK fertilizer | fertilizer |
| organic fertilizer | fertilizer |
| phosphate fertilizer | fertilizer |
| PK fertilizer | fertilizer |
| potassium fertilizer | fertilizer |
| single-nutrient fertilizer | fertilizer |
| superphosphate | fertilizer |
| synthetic fertilizer | fertilizer |
| urea | fertilizer |
| binapacryl | fungicide |
| Bisphenol A | fungicide |
| copper 8-hydroxyquinoline | fungicide |
| copper sulfate | fungicide |
| mercuric chloride | fungicide |
| phenol | fungicide |
| phenylmercuric oleate | fungicide |
| tributyltin chloride | fungicide |
| tributyltin triacetate | fungicide |
| pentachlorophenol | fungicide; insecticide |
| Bupirimate | fungicide; pesticide |
| Captan | fungicide; pesticide |
| Carbendazim | fungicide; pesticide |
| Chloranil | fungicide; pesticide |
| antibiotic | general |
| fertilizer | general |
| nutrient | general |
| pH modulator | general |
| small molecule | general |
| soil stabilizer | general |
| therapeutic agent | general |
| 2,4,5-T | herbicide |
| 2,4-D | herbicide |
| atrazine | herbicide |
| chlorophenoxy acid | herbicide |
| cynazine | herbicide |
| glyphosate | herbicide |
| hexazinone | herbicide |
| MCPA | herbicide |
| metribuzin | herbicide |
| organic phosphorus herbicide | herbicide |
| silvex | herbicide |
| simazine | herbicide |
| triazine herbicide | herbicide |
| bromacil | herbicide; pesticide |
| Chloramben | herbicide; pesticide |
| Chlorfenac | herbicide; pesticide |
| Chlorsulfuron | herbicide; pesticide |
| Abscisic acid | hormone |
| Auxins | hormone |
| Cytokinins | hormone |
| Ethylene | hormone |
| Gibberellins | hormone |
| steroid | hormone |
| dexamethasone | hormone |
| allopregnanolone | hormone |
| estrogen | hormone |
| ethinylestradiol | hormone |
| mestranol | hormone |
| estradiols | hormone |
| estriol | hormone |
| estriolsuccinate | hormone |
| polyestriolphosphate | hormone |
| estrone | hormone |
| estronesulfate | hormone |
| conjugatedestrogens | hormone |
| progesterone | hormone |
| norethisteroneacetate | hormone |
| norgestrel | hormone |
| levonorgestrel | hormone |
| gestodene | hormone |
| chlormadinoneacetate | hormone |
| drospirorenone | hormone |
| 3-ketodesogestrel | hormone |

TABLE 5-continued

| Cargo | |
|---|---|
| Payload | Category |
| androgen | hormone |
| testosterone | hormone |
| androstenediol | hormone |
| androstenedione | hormone |
| dehydroepiandrosterone | hormone |
| dihydrotestosterone | hormone |
| anymineralocorticoid | hormone |
| anyglucocorticoid | hormone |
| cholesterols | hormone |
| 1,2-dichloropropane | insecticide |
| acephate | insecticide |
| acetamiprid | insecticide |
| acethion | insecticide |
| acetoprole | insecticide |
| acrinathrin | insecticide |
| acrylonitrile | insecticide |
| alanycarb | insecticide |
| aldicarb | insecticide |
| aldnrn | insecticide |
| aldoxycarb | insecticide |
| allethrin | insecticide |
| allosamidin | insecticide |
| allyxycarb | insecticide |
| alpha-cypermethrin | insecticide |
| amidithion | insecticide |
| aminocarb | insecticide |
| amiton | insecticide |
| anabasine | insecticide |
| athidathion | insecticide |
| azadirachtin | insecticide |
| azamethiphos | insecticide |
| azinphos-ethyl | insecticide |
| azinphos-methyl | insecticide |
| azothoate | insecticide |
| barium hexafluorosilicate | insecticide |
| barthrin | insecticide |
| bendiocarb | insecticide |
| benfuracarb | insecticide |
| bensultap | insecticide |
| beta-cyfluthrin | insecticide |
| beta-cypermethrin | insecticide |
| bifenthrin | insecticide |
| bioallethrin | insecticide |
| bioethanomethrin | insecticide |
| biopermethrin | insecticide |
| bioresmethrin | insecticide |
| bistrifluron | insecticide |
| borax | insecticide |
| botanical insecticide | insecticide |
| bromfenvinfos | insecticide |
| bromo-DDT | insecticide |
| bromophos-ethyl | insecticide |
| bufencarb | insecticide |
| buprofezin | insecticide |
| butacarb | insecticide |
| butathiofos | insecticide |
| butocarboxim | insecticide |
| butonate | insecticide |
| butoxycarboxim | insecticide |
| cadusafos | insecticide |
| calcium arsenate | insecticide |
| calcium polysulfide | insecticide |
| camphechlor | insecticide |
| carbanolate | insecticide |
| carbofuran | insecticide |
| carbon disulfide | insecticide |
| carbon tetrachloride | insecticide |
| carbosulfan | insecticide |
| cartap | insecticide |
| chlorbicyclen | insecticide |
| chlordane | insecticide |
| chlordecone | insecticide |
| chlorethoxyfos | insecticide |
| chlorfenapyr | insecticide |
| chlorfenvinphos | insecticide |
| chlorfluazuron | insecticide |

TABLE 5-continued

| Cargo | |
|---|---|
| Payload | Category |
| chlormephos | insecticide |
| chloroform | insecticide |
| chloropicrin | insecticide |
| chlorphoxim | insecticide |
| chlorprazophos | insecticide |
| chlorpyrifos-methyl | insecticide |
| chlorthiophos | insecticide |
| chromafenozide | insecticide |
| cinerin I | insecticide |
| cinerin II | insecticide |
| cismethrin | insecticide |
| cloethocarb | insecticide |
| closantel | insecticide |
| clothianidin | insecticide |
| copper acetoarsenite | insecticide |
| copper arsenate | insecticide |
| coumaphos | insecticide |
| coumithoate | insecticide |
| crotamiton | insecticide |
| crotoxyphos | insecticide |
| crufomate | insecticide |
| cryolite | insecticide |
| cyanofenphos | insecticide |
| cyanophos | insecticide |
| cyanthoate | insecticide |
| cyclethrin | insecticide |
| cycloprothrin | insecticide |
| cyfluthrin | insecticide |
| cypermethrin | insecticide |
| cyphenothrin | insecticide |
| cyromazine | insecticide |
| cythioate | insecticide |
| DDT | insecticide |
| decarbofuran | insecticide |
| demephion | insecticide |
| demephion-O | insecticide |
| demephion-S | insecticide |
| demeton | insecticide |
| demeton-methyl | insecticide |
| demeton-O | insecticide |
| demeton-O-methyl | insecticide |
| demeton-S | insecticide |
| demeton-S-methyl | insecticide |
| demeton-S-methylsulphon | insecticide |
| diafenthiuron | insecticide |
| dialifos | insecticide |
| dicapthon | insecticide |
| dichlofenthion | insecticide |
| dichlorvos | insecticide |
| dicresyl | insecticide |
| dicrotophos | insecticide |
| dicyclanil | insecticide |
| dieldrin | insecticide |
| diflubenzuron | insecticide |
| dilor | insecticide |
| dimefox | insecticide |
| dimetan | insecticide |
| dimethoate | insecticide |
| dimethrin | insecticide |
| dimethylvinphos | insecticide |
| dimetilan | insecticide |
| dinex | insecticide |
| dinoprop | insecticide |
| dinosam | insecticide |
| dinotefuran | insecticide |
| diofenolan | insecticide |
| dioxabenzofos | insecticide |
| dioxacarb | insecticide |
| dioxathion | insecticide |
| disulfoton | insecticide |
| dithicrofos | insecticide |
| d-limonene | insecticide |
| ecdysterone | insecticide |
| empenthrin | insecticide |
| endosulfan | insecticide |
| endothion | insecticide |

TABLE 5-continued

| Cargo | |
|---|---|
| Payload | Category |
| endrin | insecticide |
| epofenonane | insecticide |
| esfenvalerate | insecticide |
| etaphos | insecticide |
| ethiofencarb | insecticide |
| ethion | insecticide |
| ethiprole | insecticide |
| ethoate-methyl | insecticide |
| ethoprophos | insecticide |
| ethyl formate | insecticide |
| ethylene dibromide | insecticide |
| ethylene dichloride | insecticide |
| ethylene oxide | insecticide |
| etofenprox | insecticide |
| etrimfos | insecticide |
| famphur | insecticide |
| fenamiphos | insecticide |
| fenazaflor | insecticide |
| fenchlorphos | insecticide |
| fenethacarb | insecticide |
| fenfluthrin | insecticide |
| fenitrothion | insecticide |
| fenobucarb | insecticide |
| fenoxacrim | insecticide |
| fenoxycarb | insecticide |
| fenpirithrin | insecticide |
| fenpropathrin | insecticide |
| fensulfothion | insecticide |
| fenthion | insecticide |
| fenthion-ethyl | insecticide |
| fenvalerate | insecticide |
| fipronil | insecticide |
| flonicamid | insecticide |
| flucofuron | insecticide |
| flucycloxuron | insecticide |
| flucythrinate | insecticide |
| flufenerim | insecticide |
| flufenoxuron | insecticide |
| flufenprox | insecticide |
| fluvalinate | insecticide |
| fonofos | insecticide |
| formetanate | insecticide |
| formothion | insecticide |
| formparanate | insecticide |
| fosmethilan | insecticide |
| fospirate | insecticide |
| fosthietan | insecticide |
| furathiocarb | insecticide |
| furethrin | insecticide |
| gamma-cyhalothrin | insecticide |
| halfenprox | insecticide |
| halofenozide | insecticide |
| heptachlor | insecticide |
| heptenophos | insecticide |
| heterophos | insecticide |
| hexaflumuron | insecticide |
| hydramethylnon | insecticide |
| hydrogen cyanide | insecticide |
| hydroprene | insecticide |
| hyquincarb | insecticide |
| imidacloprid | insecticide |
| imiprothrin | insecticide |
| indoxacarb | insecticide |
| isazofos | insecticide |
| isobenzan | insecticide |
| sodrir | insecticide |
| isofenphos | insecticide |
| isoprocarb | insecticide |
| isoprothiolane | insecticide |
| isothioate | insecticide |
| isoxathion | insecticide |
| isoxazole | insecticide |
| jasmolin I | insecticide |
| jasmolin II | insecticide |
| jodfenphos | insecticide |
| juvenile hormone I | insecticide |

TABLE 5-continued

| Cargo | |
|---|---|
| Payload | Category |
| juvenile hormone II | insecticide |
| juvenile hormone III | insecticide |
| kelevan | insecticide |
| kinoprene | insecticide |
| lambda-cyhalothrin | insecticide |
| lead arsenate | insecticide |
| leptophos | insecticide |
| lirimfos | insecticide |
| lufenuron | insecticide |
| lythidathion | insecticide |
| malathion | insecticide |
| malonoben | insecticide |
| mazidox | insecticide |
| mecarbam | insecticide |
| mecarphon | insecticide |
| menazon | insecticide |
| mephosfolan | insecticide |
| mercurous chloride | insecticide |
| mesulfenfos | insecticide |
| methacrifos | insecticide |
| methamidophos | insecticide |
| methidathion | insecticide |
| methiocarb | insecticide |
| methocrotophos | insecticide |
| methomyl | insecticide |
| methoprene | insecticide |
| methoxychlor | insecticide |
| methoxyfenozide | insecticide |
| methyl bromide | insecticide |
| methylchloroform | insecticide |
| methylene chloride | insecticide |
| metofluthrin | insecticide |
| metolcarb | insecticide |
| metoxadiazone | insecticide |
| mevinphos | insecticide |
| mexacarbate | insecticide |
| mipafox | insecticide |
| mirex | insecticide |
| monocrotophos | insecticide |
| morphothion | insecticide |
| naftalofos | insecticide |
| naled | insecticide |
| naphthalene | insecticide |
| nicotine | insecticide |
| nifluridide | insecticide |
| nitenpyram | insecticide |
| nithiazine | insecticide |
| nitrilacarb | insecticide |
| novaluron | insecticide |
| noviflumuron | insecticide |
| omethoate | insecticide |
| oxamyl | insecticide |
| oxydemeton-methyl | insecticide |
| oxydeprofos | insecticide |
| oxydisulfoton | insecticide |
| para-dichlorobenzene | insecticide |
| parathion | insecticide |
| parathion-methyl | insecticide |
| penfluron | insecticide |
| phenkapton | insecticide |
| phenothrin | insecticide |
| phenthoate | insecticide |
| phorate | insecticide |
| phosalone | insecticide |
| phosfolan pirimetaphos | insecticide |
| phosmet | insecticide |
| phosnichlor | insecticide |
| phosphamidon | insecticide |
| phosphine | insecticide |
| phoxim | insecticide |
| phoxim-methyl | insecticide |
| pirimicarb | insecticide |
| pirimiphos-ethyl | insecticide |
| pirimiphos-methyl | insecticide |
| potassium arsenite | insecticide |
| potassium thiocyanate | insecticide |

TABLE 5-continued

| Cargo | |
|---|---|
| Payload | Category |
| pp'-DDT | insecticide |
| prallethrin | insecticide |
| precocene I | insecticide |
| precocene II | insecticide |
| precocene III | insecticide |
| primidophos | insecticide |
| profenofos | insecticide |
| profluthrin | insecticide |
| promacyl | insecticide |
| promecarb | insecticide |
| propaphos | insecticide |
| propetamphos | insecticide |
| propoxur | insecticide |
| prothidathion | insecticide |
| prothiofos | insecticide |
| prothoate | insecticide |
| protrifenbute | insecticide |
| pyraclofos | insecticide |
| pyrazophos | insecticide |
| pyresmethrin | insecticide |
| pyrethrin I | insecticide |
| pyrethrin II | insecticide |
| pyridaben | insecticide |
| pyridalyl | insecticide |
| pyridaphenthion | insecticide |
| pyrimidifen | insecticide |
| pyrimitate | insecticide |
| pyriproxyfen | insecticide |
| quassia | insecticide |
| quinalphos | insecticide |
| quinalphos-methyl | insecticide |
| quinothion | insecticide |
| rafoxanide | insecticide |
| resmethrin | insecticide |
| rotenone | insecticide |
| ryania | insecticide |
| sabadilla | insecticide |
| schradan | insecticide |
| silafluofen | insecticide |
| sodium arsenite | insecticide |
| sodium fluoride | insecticide |
| sodium hexafluorosilicate | insecticide |
| sodium thiocyanate | insecticide |
| sophamide | insecticide |
| spinosad | insecticide |
| spiromesifen | insecticide |
| sulcofuron | insecticide |
| sulfluramid | insecticide |
| sulfotep | insecticide |
| sulfuryl fluoride | insecticide |
| sulprofos | insecticide |
| tau-fluvalinate | insecticide |
| tazimcarb | insecticide |
| tebufenozide | insecticide |
| tebufenpyrad | insecticide |
| tebupirimfos | insecticide |
| teflubenzuron | insecticide |
| tefluthrin | insecticide |
| temephos | insecticide |
| terallethrin | insecticide |
| terbufos | insecticide |
| tetrachloroethane | insecticide |
| tetrachlorvinphos | insecticide |
| tetramethrin | insecticide |
| theta-cypermethrin | insecticide |
| thiacloprid | insecticide |
| thiamethoxam | insecticide |
| thicrofos | insecticide |
| thiocarboxime | insecticide |
| thiocyclam | insecticide |
| thiodicarb | insecticide |
| thiofanox | insecticide |
| thiometon | insecticide |
| thiosultap | insecticide |
| thuringiensin | insecticide |
| tolfenpyrad | insecticide |

TABLE 5-continued

| Cargo | |
|---|---|
| Payload | Category |
| tralomethrin | insecticide |
| transfluthrin | insecticide |
| transpermethrin | insecticide |
| triarathene | insecticide |
| triazamate | insecticide |
| triazophos | insecticide |
| trichlormetaphos-3 | insecticide |
| trichloronat | insecticide |
| trifenofos | insecticide |
| triflumuron | insecticide |
| trimethacarb | insecticide |
| triprene | insecticide |
| vamidothion | insecticide |
| vaniliprole | insecticide |
| xylylcarb | insecticide |
| zeta-cypermethrin | insecticide |
| zolaprofos | insecticide |
| α-ecdysone | insecticide |
| bromophos | insecticide; pesticide |
| chlordimeform | insecticide; pesticide |
| Carbaryl | insecticide; pesticide |
| Carbophenothion | insecticide; pesticide |
| Chlorpyrifos | insecticide; pesticide |
| amino acid | macronutrient |
| amylopectin | macronutrient |
| amylose | macronutrient |
| arachidic acid | macronutrient |
| behenic acid | macronutrient |
| butyric acid | macronutrient |
| capric acid | macronutrient |
| capricic acid | macronutrient |
| caprylic acid | macronutrient |
| carbohydrate | macronutrient |
| cerotic acid | macronutrient |
| cervonic acid | macronutrient |
| clupanodonic acid | macronutrient |
| eicosen | macronutrient |
| erucic acid | macronutrient |
| essential fatty acid | macronutrient |
| fat | macronutrient |
| fructose | macronutrient |
| galactose | macronutrient |
| glucose | macronutrient |
| heptadecanoic acid | macronutrient |
| lactose | macronutrient |
| lauric acid | macronutrient |
| lignoceric acid | macronutrient |
| linoleic acid | macronutrient |
| Macronutrient | macronutrient |
| maltose | macronutrient |
| margaric acid | macronutrient |
| monounsaturated fat | macronutrient |
| myristic acid | macronutrient |
| myristol | macronutrient |
| nervonic acid | macronutrient |
| oleic acid | macronutrient |
| palmitic acid | macronutrient |
| palmitoyl | macronutrient |
| pentadecanoic acid | macronutrient |
| polyunsaturated fat | macronutrient |
| protein | macronutrient |
| ribose | macronutrient |
| saturated fat | macronutrient |
| stearic acid | macronutrient |
| steridonic acid | macronutrient |
| sucrose | macronutrient |
| timnodonic acid | macronutrient |
| α-linoleic acid | macronutrient |
| calcium | micronutrient |
| chloride | micronutrient |
| chromium | micronutrient |
| copper | micronutrient |
| iodine | micronutrient |
| iron | micronutrient |
| magnesium | micronutrient |
| manganese | micronutrient |

TABLE 5-continued

| Cargo | |
|---|---|
| Payload | Category |
| mineral | micronutrient |
| molybdenum | micronutrient |
| nickel | micronutrient |
| phosphorus | micronutrient |
| potassium | micronutrient |
| selenium | micronutrient |
| silicon | micronutrient |
| tin | micronutrient |
| vanadium | micronutrient |
| vitamin | micronutrient |
| vitamin A | micronutrient |
| vitamin B-1 | micronutrient |
| vitamin B-12 | micronutrient |
| vitamin B-2 | micronutrient |
| vitamin B-3 | micronutrient |
| vitamin B-5 | micronutrient |
| vitamin B-6 | micronutrient |
| vitamin B-7 | micronutrient |
| vitamin B-9 | micronutrient |
| vitamin C | micronutrient |
| vitamin D | micronutrient |
| vitamin E | micronutrient |
| vitamin K | micronutrient |
| zinc | micronutrient |
| adhesive | pest control agent |
| allomone | pest control agent |
| anti-disease agent | pest control agent |
| antifeedant | pest control agent |
| antifungal | pest control agent |
| behavior-modifying compound | pest control agent |
| bird repellent | pest control agent |
| black pepper | pest control agent |
| caffeine | pest control agent |
| capsaicin | pest control agent |
| capsaicin oleoresin | pest control agent |
| catnip oil | pest control agent |
| chemosterilant | pest control agent |
| chili powder | pest control agent |
| complex sugar | pest control agent |
| dill | pest control agent |
| ginger | pest control agent |
| gum | pest control agent |
| herbicide | pest control agent |
| insect attractant | pest control agent |
| insect repellent | pest control agent |
| insecticide | pest control agent |
| kairomone | pest control agent |
| mammal repellent | pest control agent |
| mating disrupter | pest control agent |
| monoterpenoid | pest control agent |
| paprika | pest control agent |
| pest control agent | pest control agent |
| pesticide | pest control agent |
| phenolic compound | pest control agent |
| pheromone | pest control agent |
| red pepper | pest control agent |
| acaricide | pesticide |
| algicide | pesticide |
| avicide | pesticide |
| Bacillus thuringiensis endotoxin polypeptide | pesticide |
| bactericide | pesticide |
| Bis(p-chlorophenoxy)methane | pesticide |
| Bitertanol | pesticide |
| Bromadiolone | pesticide |
| Bromethalinlin | pesticide |
| Bromopropylate | pesticide |
| Busulfan | pesticide |
| Butrylin | pesticide |
| Cambendazole | pesticide |
| Candicidin | pesticide |
| Candidin | pesticide |
| Chloramphenacol | pesticide |
| Chlorbetamide | pesticide |
| Chlorothion | pesticide |
| Chlorphenesin | pesticide |

TABLE 5-continued

| Cargo | |
|---|---|
| Payload | Category |
| molluscicide | pesticide |
| nematicide | pesticide |
| rodenticide | pesticide |
| virucide | pesticide |
| biopolymer | soil stabilizer |
| chemical | soil stabilizer |
| co-polymer | soil stabilizer |
| enzyme | soil stabilizer |
| fiber reinforcement agent | soil stabilizer |
| flowability agent | soil stabilizer |
| hydrophilic agent | soil stabilizer |
| hydrophobic agent | soil stabilizer |
| ionic stabilizer | soil stabilizer |
| polymer | soil stabilizer |
| resin | soil stabilizer |
| salt | soil stabilizer |
| surfactant | soil stabilizer |
| chelated micronutrient | therapeutic agent |
| microbe | therapeutic agent |
| non-chelated micronutrient | therapeutic agent |
| probiotic | therapeutic agent |

In one embodiment, the cargo for use in SBP formulations may be hormone analogue such as, but not limited to, Deslorelin.

Coating

In some embodiments, agricultural SBP formulations may include one or more coatings. As used herein, the term "coating" refers to any substance that is applied to the surface of another substance. In some embodiments, the coating may be functional, decorative or both. Coatings may be applied to completely cover the surface. Coating may also be applied to partially cover the surface. In some embodiments, coatings may include processed silk. In some aspects, the coating may be an SBP formulation. Coatings may also include but are not limited to any of the cargos described in Table 5. In some embodiments, the coating may be a plant coating. In some embodiments, the coating may be a seed coating. In some embodiments, the coating may be a leaf coating. In some embodiments, agricultural compositions described herein, such as coatings, may be able to penetrate plants, leaves, seeds, roots, and/or any other part of the plant described herein. In some embodiments, the SBP coating may be used for one or more applications, including, but not limited to, protection of a seed, plant, planting substrate, agricultural product, or device; fertilizing and/or promoting germination of a coated seed or plant; encasing a payload; delivering a payload; modulating nutrient and/or water uptake; stabilizing a payload; and/or controlling the release of a payload. In some embodiments, SBP coatings may be applied to a fruit or a vegetable to prevent spoilage.

Silk fibroin and SBP may also be used to label or write on certain products, like pharmaceuticals or other edible or ingestible products. Silk fibroin or SBP may be an edible ink. A method for labeling products is disclosed in U.S. Patent Publication 2011/0135697 the contents of which are incorporated by reference in its entirety. ilk fibroin is a unique biopolymer that can be reconfigured from its native or synthesized states in various shapes and conformations. Silk fibroin protein has recently found uses well beyond textile and medical suture applications that have been the main modes of utilization in the past. For example, the generation of hydrogels (WO2005/012606; PCT/US08/65076; PCT/US08/65076), ultrathin films (WO2007/016524), thick films, conformal coatings (WO2005/000483; WO2005/123114), microspheres (PCT/US2007/020789), 3D porous matrices (WO2004/062697), combinations of the films, microspheres and porous matrices (PCT/US09/44117), solid blocks (WO2003/056297), microfluidic devices (PCT/US07/83646; PCT/US07/83634), electro-optical devices (PCT/US07/83639), and fibers with diameters ranging from the nanoscale (WO2004/0000915) to several centimeters (U.S. Pat. No. 6,902,932.) have been explored with implications in biomaterials and regenerative medicine (WO2006/042287; U.S. patent application Ser. No. 11/407,373; PCT/US08/55072), the contents of which are incorporated by reference, in their entirety. The holograph of the present invention may be used in conjunction with any of the above applications. The toughness of this natural fiber, unmatched in nature, confers impressive mechanical properties (both tensile and compressive) to silk-based materials which rival, if not exceed, most organic counterparts such as Kevlar or other polymeric materials.

Silk fibroin can be formed easily into mechanically robust films of thermodynamically stable beta-sheets, with control of thicknesses from a few nanometers to hundreds of micrometers or more. These films may be formed by casting of purified silk fibroin solution which crystallizes upon exposure to air, humidity or dry nitrogen gas, as some examples, without the need for exogenous crosslinking reactions or post processing crosslinking for stabilization. The resulting hardened silk has mechanical properties, surface quality and transparency which are suited for use as optical substrates. See, e.g., PCT/US07/83600; PCT/US07/83620; PCT/US07/83605, the contents of which are incorporated by reference in their entirety.

Food labeling provides a particularly suitable application of the present invention. For example, not only could a spinach bag carry the silk hologram label, the spinach itself might be labeled with the edible microrelief. Because the label is small and edible, it need not be removed before cooking or consumption. Fruits such as apples and tomatoes may bear a label, or may be surrounded by a microrelief-bearing silk film. In that regard, fruit can be dipped or otherwise introduced into silk fibroin solution, then dried by air or gas. Such process might provide both stability to the food product as well authentication regarding origin and whether the food is certified organic. Silk labels, unlike current paper-based labels, may themselves be certified organic. Silk fibroin produced by silkworms, such as *Bombyx mori*, is the most common and represents an earth-friendly, renewable resource. Silkworm cocoons are commercially available from silkworms fed on U.S. Dept. of Agriculture Certified Organic mulberry leaves. Additionally, vegetarian or "peace silk", from cocoons from which silk moths emerge, yield silk fibroin suitable for use in the silk holograms of the instant invention. The organic silk fibroin may be prepared from organic-fed silkworm cocoons using water- and salts-based techniques disclosed, for example, in U.S. patent application Ser. No. 11/247,358, WO/2005/012606, and PCT/US07/83605. Hence, the edible hologram label that identifies a food as certified organic may itself, when organic silk standards are finalized, be certified organic.

Agricultural Products

In some embodiments, agricultural SBP formulations may include one or more agricultural products. These agricultural products may be plants, animals, plant agricultural products, and animal agricultural products.

In some embodiments, agricultural SBP formulations may include plants. The methods and SBPs of the present disclosure may have applications in plants. In some embodiments, SBPs will serve as agricultural composition to facilitate the production of plants. In some embodiments the plants are agricultural plants i.e., plants for farming purposes. In some embodiments, the plants are silvicultural plants, i.e. plants for the controlling the growth, health, establishment, composition, and quality of forests. In some embodiments, the plants are ornamental plants. In some embodiments, the plants are edible plants. In some embodiments, the plants are horticultural plants. In some embodiments, the plants are natural or wild-type plants. In other embodiments, the plants are genetically modified plants. In some aspects, the plants are medicinal plants. In some embodiments, the agricultural products may be portions of plants.

In some embodiments, agricultural products may include animals and/or animal agricultural products. In some embodiments, the animals used with agricultural compositions of the present disclosure include but are not limited to cows, bulls, sheep, goat, bison, turkey, buffalo, pigs, poultry, horses, alpaca, llama, camels, rabbits, guinea pigs, fish, shrimps, crustaceans, mollusks, insects, silk worms, bees, and crickets.

In some embodiments, the agricultural SBP formulations may be or may include one or more animal agricultural products. Animal agricultural products may include, but are not limited to milk, butter, cheese, yogurt, whey, curds, meat, oil, fat, blood, amino acids, hormones, enzymes, wax, feathers, fur, hide, bones, gelatin, horns, ivory, wool, venom, tallow, silk, sponges, manure, eggs, pearl culture, honey, and food dye. In some embodiments, the animal agricultural product is a dairy product. Non-limiting examples of dairy products include milk, cream, cheese, clotted cream, sour cream, gelato, ghee, infant formula, powdered milk, butter, crème fraiche, ice cream, yoghurt, curds, whey, custard, dulce de leche, evaporated milk, eggnog, frozen yoghurt, frozen custard, buttermilk, formula, casein, condensed milk, cottage cheese, and cream cheese.

Pest Control Agent

In some embodiments, agricultural SBP formulations may include pest control agents. In some aspects, the SBPs may be a pest control agent. As used herein, the term "pest" refers to any organism that harms, irritates, causes discomfort, or generally annoys another organism. In some embodiments, the pest control agent may optionally include a pesticide. In some embodiments, pesticides used in agricultural compositions may be selected from any of those listed in Table 5. Pesticides may include, but are not limited to parasiticides, insecticides, herbicides, antifungal or fungicide, anti-disease agents, behavior-modifying compounds, adhesives (e.g. gums), acaricide, algicide, avicide, bactericide, molluskicide, biocides, miticides, nematicide, rodenticide, and a virucide.

Biological Systems

In some embodiments, agricultural SBP formulations described herein include biological systems. As used herein, the term "biological system" refers to a network of interrelated substances and/or organisms. These biological systems may include systems of symbiotes, microbiomes and/or probiotics. The compositions provided herein may include a SBPs and an active amount of beneficial microbes/probiotics. In some embodiments, SBP formulations may be used as stabilizers in the microbial compositions. In some embodiments, these microbiomes or symbiotes may incorporate species of fungi or bacteria. In some embodiments, the fungi are from the *Aspergillus* genus. In some embodiments, the bacteria are from the *Streptomyces* genus. In some embodiments, SBP biological systems may be used as biopesticides. As used herein, the term "biopesticide" refers to a composition with a bacteria, microorganism, or biological cargo that displays pesticidal activity. In some embodiments, SBP biological systems may be applied as a coating to a plant. The coating may be applied to the whole plant, or to any part of the plant described in the present disclosure. In some embodiments, the coating may be applied to a seed.

In some embodiments, the biological systems may be used to enable nitrogen fixation. These microbes, microorganisms, and/or microbiomes may incorporate *rhizobia* bacteria. *Rhizobia* bacteria enable nitrogen fixation in plants that do not independently fix nitrogen, such as legumes (Zahran et al. (1999) Microbiology and Molecular Biology Reviews 63 (4): 968-989, the contents of which are herein incorporated by reference in its entirety). In some embodiments, the biological systems described herein deliver *rhizobia* bacteria for the growth and production of other plants. In some embodiments, the SBP agricultural compositions described herein may be formulated with the nutrients needed to promote the growth of *rhizobia* bacteria. The beneficial microbe and/or probiotic can be any beneficial microbe and/or probiotic known in the art.

In some embodiments, SBP biological systems formulations may include microbes, microorganisms, and/or microbiomes that promote plant growth. SBP biological systems may include one or more microbes, microorganisms and/or microbiomes that promote plant growth. Such microbes, microorganisms, and/or microbiomes may include, but are not limited to, *Algoriphagus ratkowskyi, Altererythrobacter luteolus, Alternaria thalictrigena, Arthrobacter agilis, Arthrobacter arilaitensis, Arthrobacter aurescens, Arthrobacter citreus, Arthrobacter crystallopoeietes, Arthrobacter globiformis, Arthrobacter humicola, Arthrobacter oryzae, Arthrobacter oxydans, Arthrobacter pascens, Arthrobacter ramosus, Arthrobacter tumbae, Aspergillus fumigatiaffinis, Bacillus aquimaris, Bacillus benzoevorans, Bacillus cibi, Bacillus herbersteinensis, Bacillus idriensis, Bacillus licheniformis, Bacillus niacin, Bacillus psychordurans, Bacillus simplex, Bacillus simplex* 11, *Bacillus simplex* 237, *Bacillus simplex* 30N-5, *Bacillus subtilis* 30VD-1, *Bartonella elizabethae, Citricoccus alkalitolerans, Citricoccus nitrophenolicus, Cladosporium sphaerospermum, Curtobacterium flaccumfaciens, Exiguobacterium aurantiacum, Fusarium equiseti, Fusarium oxysporum, Georgenia ruanii, Halomonas aquamarina, Kocuria rosea, Massilia timonae, Mesorhizobium loti, Microbacterium aerolatum, Microbacterium oxydans, Microbacterium paludicola, Microbacterium paraoxydans, Microbacterium phyllosphaerae, Microbacterium testaceum, Micrococcus luteus, Mycobacterium sacrum, Nocardiopsis quinghaiensis, Oceanobacillus picturae, Ochroconis sp., Olivibacter soli, Paenibacillus tundrae, Penicillium chrysogenum, Penicillium commune, Phoma betae, Planococcus maritimus, Planococcus psychrotoleratus, Planomicrobium koreense, Planomicrobium okeanokoites, Promicromonospora kroppenstedtii, Pseudomonas brassicacearum, Pseudomonas fluorescens. Pseudomonas frederiksbergensis, Pseudomonas fulva, Pseudomonas geniculata, Pseudomonas gessardii, Pseudomonas libanensis, Pseudomonas mosselii, Pseudomonas plecoglossicida, Pseudomonas putida, Pseudomonas stutzeri, Pseudomonas syringae, Rhodococcus jostil, Sinorhizobium medicae, Sinorhizobium meliloti, Staphylococcus succinus, Stenotrophomonas maltophilia, Stenotrophomonas rhizophila, Streptomyces althioticus, Streptomyces azureus, Streptomyces bottropensis, Streptomyces candidus, Streptomyces chryseus, Streptomyces cirratus, Streptomyces coeruleofuscus, Streptomyces durmitorensis, Streptomyces flaveus, Strepto-*

*myces fradeiae, Streptomyces griseoruber, Streptomyces griseus, Streptomyces halstedii, Streptomyces marokkonensis, Streptomyces olivoviridis, Streptomyces peucetius, Streptomyces phaeochromogenes, Streptomyces pseudogriseolus, Terribacillus halophilus, Virgibacillus halodenitrificans*, and *Williamensia muralis*. In further embodiments, such plant growth-promoting microbes, microorganisms, and/or microbiomes may be selected from any of those microbial isolates described in US Publication Number US20140342905, and International Publication Number WO2014201044, the contents of which are hereby incorporated by reference in their entirety.

In some embodiments, the SBP biological system formulations contains a mixture of two or more microbes and/or microorganisms. In some embodiments, the mixture might be a mixture of generic microbes. In some embodiments, formulation with one or more microbes enhances the viability of said microbes. In some embodiments, the SBP biological system may also include one or more excipients (e.g. sugar, mannitol, trehalose, buffer salts, PEGs, Poloxamer-188, Poloxamer-407, glycerol, HPMC, HEC, CMC, glycerol formal, propylene glycol, propylene carbonate, sorbitol, and/or polysorbate-80). The excipients may be included at concentrations between 0.1%-50% (w/w or w/v). The concentration of processed silk may be any of those described in the present disclosure. The SBP biological systems may be made from processed silk prepared with any boiling time described in the present disclosure (e.g. 90mb, 120mb, and 480mb) and one or more microbes. In some embodiments, the pH of the SBP biological system is between about 4 and about 6. In some embodiments, the osmolarity of the SBP biological system is between about 200 mOsm/L to about 400 mOsm/L. The osmolarity may also be from about 290 mOsm/L to about 320 mOsm/L.

In some embodiments, the SBP biological system formulations may be prepared as a solution. These solutions may be made from processed silk prepared with any boiling time described in the present disclosure (e.g. 90mb, 120mb, and 480mb) and the bacteria. The solutions may be prepared with any concentration of processed silk described herein (e.g. 0.5%, 1%, 5%). The solutions may be prepared with any solvent and/or buffer described in the present disclosure.

In some embodiments, the SBP biological system formulations may be prepared as a lyophilized powder. These powders may be prepared from processed silk prepared with any boiling time described in the present disclosure (e.g. 90mb, 120mb, and 480mb) and the bacteria. The processed silk may be mixed with one or more microbes and then lyophilized. The lyophilized powder may be prepared from solutions of any concentration of processed silk described herein (e.g. 0.5%, 1%, 5%). The lyophilized powder may be prepared from processed silk formulated with a sugar (e.g. sugar, mannitol, or trehalose) to aid in the stability of bacteria. The lyophilized silk may be reconstituted in a solvent (e.g. water or buffer). The lyophilized powder may be reconstituted in any solvent and/or buffer described in the present disclosure.

In some embodiments, the SBP biological system formulations may be prepared as insoluble powder, particles, cakes and/or films. To prepare the powder, particles, cakes and/or films, gels and/or other SBP formulations may be formed and then dried. In some embodiments, the gels and/or other SBP formulations may be lyophilized to form cakes and/or films. Powders, particles, cakes and films may also utilize excipients (e.g. gelling agents) as well as sonication, or pH changes to induce beta-sheet formation prior to or during drying or lyophilization. These excipients may be powders under typical environmental conditions (e.g. MW PEG's, Poloxamer-188, etc.). The total solid content of the powders, particles, cakes and/or films may be between 3-40% (w/w or w/v). The solid content included buffer, silk, and any excipients included.

In some embodiments, the SBP biological systems formulations may be insoluble. These SBP biological system formulations may be lyophilized powders. The SBP biological system formulations may also be prepared by milling insoluble solids (e.g. cakes or films) into a powder. In some embodiments, the SBP biological system formulations may be digested. In some embodiments, insoluble SBP biological system formulations are formulated for spray drying. The total solid content of the formulations for spray drying may be between 5-40% (w/w or w/v). The solid content included buffer, silk, and any excipients included.

Agricultural Therapeutic Agent

In some embodiments, agricultural applications involve the use of SBP formulations which can be agricultural therapeutic agents or are combined with one or more agricultural therapeutic agents. Examples of SBP therapeutic agents include, but are not limited to, adjuvants, analgesic agents, antiallergic agents, antiangiogenic agents, antiarrhythmic agents, antibacterial agents, antibiotics, antibodies, anticancer agents, anticoagulants, antidementia agents, antidepressants, antidiabetic agents, antigens, antihypertensive agents, anti-infective agents, anti-inflammatory agents, antioxidants, antipyretic agents, anti-rejection agents, antiseptic agents, antitumor agents, antiulcer agents, antiviral agents, biological agents, birth control medication, carbohydrates, cardiotonics, cells, chemotherapeutic agents, cholesterol lowering agents, cytokines, endostatins, enzymes, fats, fatty acids, genetically engineered proteins, glycoproteins, growth factors, health supplements, hematopoietics, herbal preparations, hormones, hypotensive diuretics, immunological agents, inorganic synthetic pharmaceutical drugs, ions, lipoproteins, metals, minerals, nanoparticles, naturally derived proteins, NSAIDs, nucleic acids, nucleotides, organic synthetic pharmaceutical drugs, oxidants, peptides, pills, polysaccharides, proteins, protein-small molecule conjugates or complexes, psychotropic agents, small molecules, sodium channel blockers, statins, steroids, stimulants, therapeutic agents for osteoporosis, therapeutic combinations, thrombopoietics, tranquilizers, vaccines, vasodilators, VEGF-related agents, veterinary agents, viruses, virus particles, and vitamins. In some embodiments, SBP therapeutics and methods of delivery may include any of those taught in International Patent Publication Numbers WO2017139684, WO2010123945, WO2017123383, or United States Publication Numbers US20170340575, US20170368236, and US20110171239 the contents of each of which are herein incorporated by reference in their entirety. In some embodiments, the agricultural therapeutic agent may be a pest control agent. In some embodiments, examples of pest control agents that may be useful as agricultural therapeutic agent include, but are not limited to parasiticides, insecticides, antifungal or fungicide, anti-disease agents, acaricide, algicide, avicide, bactericide, nematicide, and a virucide.

In some embodiments, the subject in the context of an agricultural therapeutic agent may refer to one or more plants.

In some embodiments, the subject in the context of an agricultural therapeutic agent may refer to one or more non-human animals.

In some embodiments, the agricultural therapeutic agent may be nucleic acids. Nucleic acids may include DNA and/or RNA. In some embodiments, nucleic acids may be polynucleotides or oligonucleotides. Exemplary nucleic acids may include, but are not limited to, aptamers, plasmids, siRNA, microRNAs, or viral nucleic acids. In some embodiments, nucleic acids may encode a therapeutic peptide or protein, such as any one of those described herein. In some embodiments, SBPs may be used to improve the stability of composition comprising the nucleic acids. In some embodiments, SBPs may be used to facilitate the delivery of the nucleic acids to a plant.

Agriculture Devices

In some embodiments, agricultural SBP formulations may be or may include may be used to improve the growth and production of agricultural products by utilizing said composition with an agricultural device. An agricultural device is a device or machine that assists in agricultural production. The agricultural SBP formulations may comprise any format described in the present disclosure (e.g. hydrogel). In some embodiments, SBP formulations may be utilized as an agricultural device, as taught in in United States Patent Publication US20030198659 (the contents of which are herein incorporated by reference in its entirety). In some embodiments, SBP formulations may comprise one or more components of an agricultural device. In some embodiments, SBP formulations may be used in conjunction with another agricultural device. Agricultural devices that may incorporate SBP formulations include, but are not limited to, agricultural equipment, crop storage devices (e.g. bale bags), landscaping fabrics (e.g. polypropylene and burlap blankets), and pest control devices. In one embodiments, the agricultural equipment may comprise a silk-coated microporous pipeline, as taught in Chinese Patent Publication, CN102407193, the contents of which are herein incorporated by reference in their entirety.

In some embodiments, SBP formulations are or are used with agricultural devices used for pest control and are referred to as pest control agents. In some embodiments, SBPs that include one or more pest control agents are used as coatings to coat agricultural pest control devices. Devices may be carriers used to spread pest control agents included in carrier coatings. The carriers may be seeds. SBP seed coatings (e.g., seed coating compositions) provided herein may offer advantages with respect to the variety of cargo that can be formulated (small molecules, proteins, DNA, microbes, viruses), the ability to tailor the release rate of the cargo, stabilization of the cargo, efficient seed coating, break-down into non-toxic peptides, and/or a significantly reduced propensity to produce dust that can contaminate surrounding environments. The latter property, along with the controlled and delayed release of the active ingredient significantly reduces the contamination of surrounding environments by the active ingredient. These properties will likely mitigate the collateral damage to important pollinator populations. In addition, the compositions (e.g., seed coating compositions) provided herein impart advantages vs. seed flow and plantability that are due to the physical properties of silk fibroin such as a very low coefficient of friction.

In some embodiments, SBP formulation agricultural devices described herein may be used in the field of animal husbandry. In some embodiments, SBP formulation agricultural devices described herein may be include a component or the whole of animal housing in the field of animal husbandry. SBP formulations may be used in animal housing applications to provide optimal temperature, humidity, radiation, air flow, precipitation and light required to keep the animal safe, healthy and comfortable.

Animals require healthy environments that permit the production, and quality of the non-human animals, as well as that of the animal agricultural products. Examples of animal housing include, but are not limited to, blankets, bedding, clothing, footwear (e.g. horseshoes), feeding equipment (e.g. bowls and water bottles), brushes, bandages, barns, coops, cages, stalls, liners, enclosures, ropes, ties, pens, flooring, shelters, sheds, stalls, ventilations systems, and wires.

In some embodiments, SBP formulation agricultural devices may be used to aid the health and production of animals. In some embodiments, SBP formulations may be used in the treatment of mastitis. Transition from the dry period prior to lactation to lactation is a high-risk period for agricultural animals such as cows. During the period, the mammary gland (udder) may become infected with bacteria resulting in inflammation. In some embodiments, SBPs may be used in the treatment of mastitis. SBP formulations may be or may include antibiotics effective against one or more mastitis causing bacteria. SBP formulations may also be formatted into plugs and inserted into the teat canal (e.g., a teat sealant). In some embodiments, SBP formulations may be prepared as solutions and injected into the teat canal by an injection apparatus (e.g., a syringe, a needle, etc.). Formation of the plug may occur during injection and/or after injection. In some embodiments, SBP formulations may be formatted into films that is applied to the exterior of the teats. SBPs may be useful, both in treating and preventing mastitis. In some embodiments, SBP formulations may be used as a form of birth control, to regulate the production of animals, such as cows In some embodiments, SBP formulations may be or may include hormones and/or birth control agents. SBP formulations may be prepared as implants or depots and injected into the subject (cattle).

Aquaculture Products

In some embodiments, agricultural SBP formulations may be used in the preparation of aquaculture products. As used herein, the term "aquaculture" generally refers to the farming of aquatic animals (e.g., fish, crustaceans, mollusks) or the cultivation of aquatic plants (e.g., algae). As a non-limiting example, agricultural SBP formulations may be used in the preparation of aquaculture feeds for various aquatic animals including, but not limited to, carp, salmon, catfish, tilapia, cod, trout, milkfish, eel, shrimp, crawfish, crab, oyster, mussel, clam, jellyfish, sea cucumbers and sea urchins.

In some embodiments silk fibroin or SBP may be added to fish feed or food pellets. The method and formulation for aquaculture food is discussed in U.S. Pat. No. 10,265,366, the contents of which are hereby incorporated by reference in its entirety. Fish pellets are commonly either pressed or extruded. The main raw materials are ground and mixed. Microingredients are added to the mixer. The homogenous mix is conditioned by adding water and steam to the mass in a preconditioner. This starts a cooking process in the starch fraction (the binding component). The mass is fed into a pellet mill. The mass is forced through the mill's die and the strings are broken into pellets on the outside of the die. The moisture content is low and drying of the feed is not necessary. Additional oil may be sprayed onto the surface of pellets, but as the pellets are rather compact, the total lipid content rarely exceeds 24%. The added oil may be fish oil or vegetable oils, for example rape seed oil or soy oil, or a mixture of vegetable oils or a mixture of fish oil and vegetable oils. After oil coating, the pellets are cooled in a cooler and bagged. Alternatively, silk fibroin or SBP may be added to the mixture of the raw materials so that the SBP is incorporated into the substance of the feed, which may improve the consistency of the feed and prevent dissolution in water. SBP in the feed may also improve oil uptake, but making the feed more water insoluble, thus preventing the oil from leaching away from the feed. SBP may also be used to coat the exterior of the pellets, in lieu of or in addition to the oil spray or coating. An SBP coating on the exterior of the pellets may help prevent dissolution in water prior to being eaten by fish. The exterior SBP coating may also prevent sticking or clumping of the pellets after manufacturing.

As used herein, the term "coating" means a partial or complete covering, typically on a core, that covers at least a portion of a surface, for example a surface of a core. In one example, a core may be partially covered with a coating such that only part of the core is covered, and part of the core is not covered and is thus exposed. In another example, the core may be completely covered with a coating such that the entire core is covered and thus not exposed, as discussed in U.S. Patent Publication 2012/0021094, which is incorporated by reference in its entirety. Therefore, a coating may cover from a negligible amount up to the entire surface. A coating can also be coated onto other coatings such that a layering of coatings can be present. For example, a core can be completely coated with coating A, and coating A can be completely coated with coating B, such that coating A and coating B each form a layer. When used herein, unless specifically stated, a coating means a coating that comprises SBP and/or another substance.

In an embodiment, the surfaces of the preformed pellets may be sprayed with a settable gel mixture of 1 percent by weight of sodium alginate along with SBP in warm water. The amount of SBP mixed with sodium alginate may be between 1% and 5%, 5% and 10%, 10% and 15%, 15% and 20%, 20% and 25%, 25% and 30%, 30% and 35%, 35% and 40%, 40% and 45%, 45% and 50%, 50% and 55%, 55% and 60%, 60% and 65%, 65% and 70%, 70% and 75%, 75% and 80%, 80% and 85%, 85% and 90%, 90% and 95%, or 95% and 99%. The amount of such settable gel material sprayed onto the surface of the pellets should be approximately 5 percent of the weight of the pellets. Such spraying may be accomplished while the pellets are free-falling or are being transported by a conveyor. Immediately thereafter the pellets are sprayed with gel-setting material which may be 10 percent by weight aqueous solution of calcium chloride. The amount of such gel-setting material sprayed onto the pellets may be approximately 5 percent of the weight of the pellets. Following the two pellet-spraying operations, the pellets may be passed through a drying atmosphere to facilitate setting of the coating. It is also within the scope of this invention to modify the SBP or silk fibroin, along with other materials and ingredients, to a consistency that is suitable for applying to feed using techniques such as, but not limited to panning, spray coating, powder coating, anti-caking, electrostatic, glazing, or extrusion. In some embodiments, methods for coating pellets may utilize different processing equipment, such as rotary tumblers, rotating screws, vibratory trays, fluidizing mixers, and spray nozzles or anything commonly known in the art.

After spray coating, specialized drying may be used to induce a more insoluble coating. The temperature and humidity may be changed to affect the insoluble coating. Post treatment with a solvent, such as methanol or ethanol, ammonium sulfate solution, low pH solution, or a combination thereof may induce an increase in β-sheets formation in the silk coating, thus increasing the water insolubility. Additionally, water annealing, which is discussed in detail in PCT Publication WO2012/170655, which is herein incorporated by reference in its entirety, to increase the β-sheet formation in the silk may be used to prepare and creating the coating. Spraying silk fibroin mixed with other volatile additives may also create a coating with increase water insolubility. The relationship between water annealing. β-sheet formation, and hydrophobicity or water insolubility is discussed in Jin et al., Water Stable Silk Films with Reduced β-Sheet Content. Advanced Functional Materials. 2005 15 (8): 1241-7, which is incorporated herein by reference in its entirety. U.S. Pat. No. 9,381,642, which is herein incorporated by reference in its entirety, discusses methods for cold spraying, ethanol and water annealing to modulate silk stability. Cold ethanol mixed with silk fibroin may be volatile enough to vaporize. WO2013/155404, WO2014/145002, WO2013/071107, each of which is herein incorporated by reference in their entirety, discuss the induction of β-sheet formation and modulation.

For extruded fish pellets, the main raw materials are ground and mixed. Micro ingredients are added to the mixer. The homogenous mix is conditioned by adding water and steam to the mass in a preconditioner. Additional oil may also be added to the mass at this stage. This starts a cooking process in the starch fraction (the binding component). The mass is fed into an extruder. The extruder may be of the single screw or the twin-screw type. Due to the rotational movement of the mass in the extruder, the mass is further mixed. Additional oil, water and steam may be added to the mass in the extruder. At the end of the extruder, the mass has a temperature above 100° C. and a pressure above ambient pressure. The mass is forced through the openings in the extruder's die plate. Due to the relief in temperature and pressure, some of the moisture will evaporate immediately (flash off) and the extruded mass becomes porous. The strings are cut into pellets by a rotating knife. The water content is rather high (18-28%) and the pellets are therefore immediately dried to approximately 10% water content in a dryer. After the dryer, more oil may be added to the feed by spraying oil onto the surface of the feed, or by dipping the feed in oil. It is advantageous to add the oil to the feed in a closed vessel where the air pressure is below ambient (vacuum coating) so that the porous feed pellets absorb more oil. Feed containing more than 40% lipid may be produced this way. After the coater, the feed is cooled and bagged. Oil may be added at several places in the process as explained above, and may be fish oil or vegetable oils, by example rape seed oil or soy oil, or a mixture of vegetable oils or a mixture of fish oil and vegetable oils. Alternatively, silk fibroin or SBP may be added to the mixture of the raw materials so that the SBP is incorporated into the substance of the feed, which may aid in binding the pellet, induce gelation, and increase water insolubility, which may lead to reduction in dissolution. SBP may also be used to coat the exterior of the pellets, in lieu of or in addition to the oil spray or coating. The SBP on the exterior of the pellets may help prevent loss of oil and prevent dissolution in water prior to being eaten by fish. The exterior SBP coating may also prevent sticking or clumping of the pellets after manufacturing.

Delivery

In some embodiments, the delivery of the agricultural SBP formulations described herein may occur through controlled release. In some embodiments, the agricultural SBP formulations may be utilized for the local delivery of cargo. In some embodiments, the agent may be a chemical for use in any one agricultural applications described in the present disclosure. In some embodiments, SBP formulations described herein may enable the controlled delivery of cargos that have a shorter half-life when delivered without SBP formulations, therein enhancing the time for which the therapeutic agent may be effective, as taught in United States Patent Publication US20100028451, the contents of which are herein incorporated by reference in its entirety. In some embodiments, SBP formulations may enhance the residence time of a cargo. In some embodiments the SBP formulation delivery may be targeting to the entire plant, or animal; or it may be targeted to a portion of the plant or animal. In some embodiments, the portion of the plant may be leaf, root, bark, phloem, seed, and/or fruit.

In some embodiments, the controlled release of the SBP formulations for agricultural applications may be facilitated by diffusion of SBP formulations into the surrounding environment. This phenomenon has been observed in pharmaceutical compositions for animal subjects, as taught in United States Patent Publication No. US20170333351, the contents of which are herein incorporated by reference in its entirety. In some embodiments, the controlled release of SBPs for an agricultural application may be facilitated by the degradation and/or dissolution of SBPs. The degradation and/or dissolution has been employed for pharmaceutical compositions for animal subjects, as taught in International Patent Publications WO2013126799, WO2017165922, and U.S. Pat. No. 8,530,625, the contents of each of which are herein incorporated by reference in their entirety. In some embodiments, both the diffusion and the degradation and/or dissolution of SBPs may facilitate the controlled release of the agricultural compositions for agricultural applications.

Applications

In some embodiments, the agricultural SBP formulations may be used to increase biomass, increase product yield, and/or enhance offspring production of plants, plant agricultural products, animals, and animal agricultural products. In some embodiments, SBPs may be used in the field of farming. As used herein, "farming" refers to the technique of growing crops, or keeping animals for food and materials. Agricultural SBP formulations may be used in arable farming to grow crops, and/or pastoral farming SBP formulations may be utilized to improve one or more aspects of farming such as, but not limited to, plant growth, yield, reproduction, soil properties, weed control, pest control, disease control, product preservation, and/or treatment, environmental factors such as controlling access to water, air, and/or sunlight. In some embodiments, SBPs may be used to mitigate crop damage. In some embodiments, the agricultural SBP formulations of the present disclosure may be used to tune properties of soil. In some embodiments, the agricultural SBP formulations of the present disclosure are used as agents of weed control. In some embodiments, seeds may be treated with agricultural SBP formulations to increase germination, seedling vigor, and seedling size. In some aspects, seeds may be treated with agricultural SBP formulations to increase seed storage, and shelf life of the seed, such that the seedlings produced upon germination of stored seeds are superior to seeds that stored without SBPs. In some embodiments, the agricultural SBP formulations described herein may be used to enhance plant germination. As used herein, the term "germination" refers to growth from a seed or spore. In some embodiments, agricultural products may be treated with agricultural SBP formulations to improve preservation, the shelf life, the physical appearance, and/or freshness of the agricultural products. In some aspects, agricultural products may be treated with SBPs to preserve the products such that they are superior in agricultural SBP formulations and appearance to products untreated agricultural products. In some embodiments, SBPs described herein may be used to control the access of the plant, animal or agricultural product to environmental factors such as water, air and/or sunlight. In some embodiments, agricultural SBP formulations may be used to modulate different aspects of the environment such as, but are not limited to, water, air, humidity, and light.

In some embodiments, the agricultural SBP formulations of the present disclosure may be or may include photodegradable film. Agricultural SBP formulations may be prepared to be photosensitive or may include photosensitive agents that degrade upon exposure to light, (see Chinese Patent Publication CN105199353 and International Patent Publication WO2017123383; the contents of each of which are herein incorporated by reference in their entirety). Photosensitive agents may be chemicals, small molecules, or a drug. Photodegradable SBPs may be prepared in any format (e.g. films, microspheres, nanospheres, and any format described in the present disclosure).

Animals

In some embodiments, agricultural SBP formulations may be used to improve characteristics of animal, and/or increase the yield and quality of animal agricultural products. In some embodiments, the agricultural products include, but are not limited to, milk, butter, cheese, yogurt, whey, curds, meat, oil, fat, blood, amino acids, hormones, enzymes, wax, feathers, fur, hide, bones, gelatin, horns, ivory, wool, venom, tallow, silk, sponges, manure, eggs, pearl culture, honey, and food dye.

In some embodiments, agricultural SBP formulations of the present disclosure may be used in animal agricultural products to facilitate the release of fragrance, flavor, or other compounds responsible for odor and/or flavor, as taught in United States Patent Publication No. US20150164117, the contents of which are herein incorporated by reference in their entirety.

In some embodiments, agricultural SBP formulations may incorporate animal feed or beverage. In some embodiments, agricultural SBP formulations may include health supplements, produce supplements, hormone supplements, and/or agricultural therapeutic agents to improve the health and viability of the animals. In some embodiments, agricultural SBP formulations may include animal feed such as forage, fodder, or a combination of forage and fodder. Examples of forage include, but are not limited to, plant derived material (e.g. leaves and stems), hay, grass, silage, herbaceous legumes, tree legumes, and crop residue. Examples of fodder include, but are not limited to, hay, straw, silage, compressed and pelleted feeds, oils, mixed rations, fish meal, meat and bone meal, molasses, oligosaccharides, seaweed, seeds, grains (e.g. maize, soybeans, wheat, oats, barley, rise, peanuts, corn, and sorghum), crop residues (e.g. stover, copra, straw, chaff, and sugar beet waste), sprouted grains and legumes, brewer's spent grains, yeast extract, compounded feeds (e.g. meal type, pellets, nuts, cakes, and crumbles), cut grass and other forage plants, bran, concentrate mix, oilseed prescake (e.g. cottonseed, safflower, soybean peanut, and groundnut), horse gram, clipping waste, and legumes.

In some embodiments, agricultural SBP formulations described herein may be used to improve the yield of animal agricultural products by improving the health of non-human animals. In some embodiments, SBPs described herein may be used to improve the production capabilities of non-human animals. In some embodiments, SBPs described herein may be used to improve the breeding of non-human animals. In some embodiments, SBPs described herein may be used to improve the health, production, breeding, or a combination thereof in non-human animals.

In some embodiments, agricultural SBP formulations of this disclosure may be used to deliver health supplements to a non-human animal. These health supplements may improve the health of said non-human animals. SBPs may deliver said health supplements as a payload. SBPs may be incorporated into the feed, housing, or any other component or tool of animal husbandry that would enable the delivery of the payload. Examples of health supplements include, but are not limited to, vitamin A, vitamin B, vitamin C, vitamin D, vitamin E, vitamin K, thiamin, riboflavin, niacin, vitamin B6, vitamin B12, biotin, pantothenic acid, calcium, iron, phosphorus, iodine, magnesium, zinc, selenium, selenium, copper, manganese, chromium, molybdenum, chloride, potassium, nickel, silicon, vanadium, and tin.

In some embodiments, agricultural SBP formulations of this disclosure may be used to deliver supplements to a non-human animal that improve the yield and/or quality of the animal agricultural products. These health supplements may improve the production capabilities of said non-human animals. SBPs may include said supplements as a payload. Examples of supplements include, but are not limited to, vitamins, minerals, ions, nutrients, and hormones. In some embodiments, the SBPs may be used to stimulate animal appetite.

In some embodiments, agricultural SBP formulations of this disclosure may be used to deliver hormones to a non-human animal. SBPs may deliver said hormones as a payload. Examples of hormones include, but are not limited to, any steroid, dexamethasone, allopregnanolone, any estrogen (e.g. ethinyl estradiol, mestranol, estradiols and their esters, estriol, estriol succinate, polyestriol phosphate, estrone, estrone sulfate and conjugated estrogens), any progestogen (e.g. progesterone, norethisterone acetate, norgestrel, levonorgestrel, gestodene, chlormadinone acetate, drospirorenone, and 3-ketodesogestrel), any androgen (e.g. testosterone, androstenediol, androstenedione, dehydroepiandrosterone, and dihydrotestosterone), any mineralocorticoid, any glucocoriticoid, cholesterols, and any hormone known to those skilled in the art. In some embodiments, any of the hormones described herein.

In some embodiments, agricultural SBP formulations of this disclosure may be used to deliver birth control agents to a non-human animal. These agents of disease control may improve the health, growth, and/or increase the yield of the agricultural product from said non-human animals. SBPs may be or may include birth control as cargo. SBPs may be incorporated into the feed, housing, or any other component or tool of animal husbandry that would enable the delivery of the payload. In some embodiments, SBPs may be used in conjunction with other forms of birth control, such as surgical procedures (e.g. spaying and neutering). Examples of birth control agents, include, but are not limited to, pills, ointments, implants, surgical procedures, hormones, patches, barriers, and injections.

In one embodiment, agricultural SBP formulations may be used to deliver birth control agents to cattle. Cattle birth control is important for producers to maintain herd genetic traits, reduce disease transmission, as well as eliminating the need for separate breeding pastures. The SBPs may provide controlled release of the birth control agent to the cattle. The birth control agents may include, but are not limited to, gonadorelin, gonadorelin acetate, progesterone, dinoprost tromethamine, and cloprostenol sodium, and any combination thereof.

Pest Control

In some embodiments, agricultural SBP formulations may be used in pest control of plants, animals, plant agricultural products, and/or animal agricultural products. agricultural SBP formulations may be or may include pest control agents described herein. In some embodiments, agricultural SBP formulations pest control devices may be used in pest control. Pest control agents and devices described herein may be applied directly to the pest; a pest susceptible surface such as the locus or planting substrate where the plant is growing e.g. soil; a pest habitat and/or the animal affected by the pest. In some embodiments, SBPs may be used to reduce the drift of a pest control agent to a surrounding environment.

Disease Control

In some embodiments, agricultural SBP formulations may be useful in disease control of plants, and/or animals. In some embodiments, disease may be caused by disease agents. As used herein, the term “disease agent” refers to any biological pathogen that causes a disease. In some embodiments, the disease agent may be a parasite.

In some embodiments, the agricultural SBP formulations of the present disclosure may be used to treat plant diseases. In some embodiments, the present disclosure relates to the use SBPs as a matrix for formulations of disease inhibitory agents. In some embodiments, formulations of silk fibroin containing active ingredients with the ability to prevent the infection of plants, or of controlling disease in plants already infected with disease. More specifically, compositions including a silk fibroin and an inhibitory agent (e.g., 10 antibiotics with the ability to prevent the infection of citrus trees with Las, or of controlling citrus greening in citrus trees already infected with Las). In some embodiments, the agricultural SBP formulations may be or may include therapeutic agents and/or agricultural therapeutic agents to enable disease control. SBPs offer advantages for treating plant disease in their ability to tune the release rate, stabilization, and are biodegradable.

In some embodiments, hydrogels or other formats of agricultural SBP formulations described herein may be utilized to inject and form drug depots in the phloem, and provide effective and long-term treatment of affected plants or agricultural products, or protection of susceptible plants and agricultural products.

In some embodiments, agricultural SBP formulations of this disclosure may be used to deliver agents of disease control to a non-human animal. These agents of disease control may improve the health of said non-human animals. Agricultural SBP formulations may deliver said agents of disease control as a payload. SBPs may be incorporated into the feed, housing, or any other component or tool of animal husbandry that would enable the delivery of the payload. In some embodiments, SBPs for disease control may be administered to treat a disease. In some embodiments, SBPs for disease control may be administered as a prophylactic to prevent the onset and/or spread of disease. Examples of agents of disease control include, but are not limited to, biologics, small molecules, vitamins, minerals, herbal preparations, health supplements, ions, metals, carbohydrates, fats, hormones, proteins, peptides, antibiotics and other anti-infective agents, hematopoietics, thrombopoietics, agents, antidementia agents, antiviral agents, antiangiogenic proteins (e.g. endostatin), antitumoral agents (chemotherapeutic agents), antipyretics, analgesics, anti-inflammatory agents, anti-infective, antiulcer agents, antiallergic agents, antidepressants, psychotropic agents, cardiotonics, antiarrhythmic agents, vasodilators, antihypertensive agents such as hypotensive diuretics, antidiabetic agents, anti-rejection agents, anticoagulants, cholesterol lowering agents, therapeutic agents for osteoporosis, bone morphogenic proteins, bone morphogenic-like proteins, enzymes, vaccines, immunological agents and adjuvants, naturally derived proteins, genetically engineered proteins, chemotherapeutic agents, cytokines, growth factors (e.g. epidermal growth factor, fibroblast growth factor, insulin like growth factor I and II, transforming growth factors, and vascular endothelial growth factors), nucleotides and nucleic acids, steroids carbohydrates and polysaccharides, glycoproteins, lipoproteins, viruses and virus particles, conjugates or complexes of small molecules and proteins, or mixtures thereof, and organic or inorganic synthetic pharmaceutical drugs.

IV. Material Science Applications

In some embodiments, SBP formulations may be prepared for use in one or more material science (MS) applications (e.g., MS SBP formulations). As used herein, the term "material science application" refers to any method related to development, production, synthesis, use, degradation, or disposal of materials. As used herein, the term "material" refers to a substance or chemical substance that may be used for the fabrication, production, and/or manufacture of an article. MS SBP formulations may be materials or may be combinations of processed silk with one or more materials. Examples of materials include, but are not limited to, adhesives, aquaculture products, biomaterials, composting agents, conductors, devices, electronics, emulsifiers, fabrics, fibers, fillers, films, filters, food products, heaters, insulators, lubricants, membranes, metal replacements, micelles, microneedles, microneedle arrays, microspheres, nanofibers, nanomaterials, nanoparticles, nanospheres, paper, paper additives, particles, plastics, plastic replacements, polymers, sensors, solar panels, spheres, sun screens, taste-masking agents, textiles, thickening agents, topical creams or ointments, optical devices, vasolines, and composites thereof. In some embodiments, materials comprising SBPs described herein may be used as a plastic, plastic supplement, or a plastic replacement, as taught in Yu et al. and Chantawong et al. (Yu et al. (2017) Biomed Mater Res A doi. 10.1002/jbm.a.36297; Chantawong et al. (2017) Mater Sci Mater Med 28 (12): 191), the contents of which are herein incorporated by reference in their entirety.

Consumer Products

In some embodiments, MS SBP formulations or materials comprising SBP formulations may be used to produce or may be incorporated into consumer products. As used herein, the term "consumer products" refers to goods or merchandise purchasable by the public. Consumer products may include, but are not limited to, agricultural products, therapeutic products, veterinary products, and products for household use. Non-limiting examples of consumer products include cleaning supplies, sponges, brushes, cloths, protectors, sealant, adhesives, lubricants, protectants, labels, paint, clothing, insulators, devices, bandages, screens, electronics, batteries, and surfactants.

In any embodiment of consumer products, for personal or non-personal use, the following are non-limiting examples of suitable ranges for various parameters in and for preparation of the silk products of the present disclosure. The silk products of the present disclosure may include one or more, but not necessarily all, of these parameters and may be prepared using various combinations of ranges of such parameters.

In an embodiment, the percent silk in the product is less than 60%. In an embodiment, the percent silk in the product is less than 25%. In an embodiment, the percent silk in the product is less than 20%. In an embodiment, the percent silk in the product is less than 19%. In an embodiment, the percent silk in the product is less than 18%. In an embodiment, the percent silk in the product is less than 17%. In an embodiment, the percent silk in the product is less than 16%. In an embodiment, the percent silk in the product is less than 15%. In an embodiment, the percent silk in the product is less than 14%. In an embodiment, the percent silk in the product is less than 13%. In an embodiment, the percent silk in the product is less than 12%. In an embodiment, the percent silk in the product is less than 11%. In an embodiment, the percent silk in the product is less than 10%. In an embodiment, the percent silk in the product is less than 9%. In an embodiment, the percent silk in the product is less than 8%. In an embodiment, the percent silk in the product is less than 7%. In an embodiment, the percent silk in the product is less than 6%. In an embodiment, the percent silk in the product is less than 5%. In an embodiment, the percent silk in the product is less than 4%. In an embodiment, the percent silk in the product is less than 3%. In an embodiment, the percent silk in the product is less than 2%. In an embodiment, the percent silk in the product is less than 1%. In an embodiment, the percent silk in the product is less than 0.9%. In an embodiment, the percent silk in the product is less than 0.8%. In an embodiment, the percent silk in the product is less than 0.7%. In an embodiment, the percent silk in the product is less than 0.6%. In an embodiment, the percent silk in the product is less than 0.5%. In an embodiment, the percent silk in the product is less than 0.4%. In an embodiment, the percent silk in the product is less than 0.3%. In an embodiment, the percent silk in the product is less than 0.2%. In an embodiment, the percent silk in the product is less than 0.1%. In an embodiment, the percent silk in the product is greater than 0.1%. In an embodiment, the percent silk in the product is greater than 0.2%. In an embodiment, the percent silk in the product is greater than 0.3%. In an embodiment, the percent silk in the product is greater than 0.4%. In an embodiment, the percent silk in the product is greater than 0.5%. In an embodiment, the percent silk in the product is greater than 0.6%. In an embodiment, the percent silk in the product is greater than 0.7%. In an embodiment, the percent silk in the product is greater than 0.8%. In an embodiment, the percent silk in the product is greater than 0.9%. In an embodiment, the percent silk in the product is greater than 1%. In an embodiment, the percent silk in the product is greater than 2%. In an embodiment, the percent silk in the product is greater than 3%. In an embodiment, the percent silk in the product is greater than 4%. In an embodiment, the percent silk in the product is greater than 5%. In an embodiment, the percent silk in the product is greater than 6%. In an embodiment, the percent silk in the product is greater than 7%. In an embodiment, the percent silk in the product is greater than 8%. In an embodiment, the percent silk in the product is greater than 9%. In an embodiment, the percent silk in the product is greater than 10%. In an embodiment, the percent silk in the product is greater than 11%. In an embodiment, the percent silk in the product is greater than 12%. In an embodiment, the percent silk in the product is greater than 13%. In an embodiment, the percent silk in the product is greater than 14%. In an embodiment, the percent silk in the product is greater than 15%. In an embodiment, the percent silk in the product is greater than 16%. In an embodiment, the percent silk in the product is greater than 17%. In an embodiment, the percent silk in the product is greater than 18%. In an embodiment, the percent silk in the product is greater than 19%. In an embodiment, the percent silk in the product is greater than 20%. In an embodiment, the percent silk in the product is greater than 25%. In an embodiment, the percent silk in the product is between 0.1% and 30%. In an embodiment, the percent silk in the product is between 0.1% and 25%. In an embodiment, the percent silk in the product is between 0.1% and 20%. In an embodiment, the percent silk in the product is between 0.1% and 15%. In an embodiment, the percent silk in the product is between 0.1% and 10%. In an embodiment, the percent silk in the product is between 0.1% and 9%. In an embodiment, the percent silk in the product is between 0.1% and 8%. In an embodiment, the percent silk in the product is between 0.1% and 7%. In an embodiment, the percent silk in the product is between 0.1% and 6.5%. In an embodiment, the percent silk in the product is between 0.1% and 6%. In an embodiment, the percent silk in the product is between 0.1% and 5.5%. In an embodiment, the percent silk in the product is between 0.1% and 5%. In an embodiment, the percent silk in the product is between 0.1% and 4.5%. In an embodiment, the percent silk in the product is between 0.1% and 4%. In an embodiment, the percent silk in the product is between 0.1% and 3.5%. In an embodiment, the percent silk in the product is between 0.1% and 3%. In an embodiment, the percent silk in the product is between 0.1% and 2.5%. In an embodiment, the percent silk in the product is between 0.1% and 2.0%. In an embodiment, the percent silk in the product is between 0.1% and 2.4%. In an embodiment, the percent silk in the product is between 0.5% and 5%. In an embodiment, the percent silk in the product is between 0.5% and 4.5%. In an embodiment, the percent silk in the product is between 0.5% and 4%. In an embodiment, the percent silk in the product is between 0.5% and 3.5%. In an embodiment, the percent silk in the product is between 0.5% and 3%. In an embodiment, the percent silk in the product is between 0.5% and 2.5%. In an embodiment, the percent silk in the product is between 1 and 4%. In an embodiment, the percent silk in the product is between 1 and 3.5%. In an embodiment, the percent silk in the product is between 1 and 3%. In an embodiment, the percent silk in the product is between 1 and 2.5%. In an embodiment, the percent silk in the product is between 1 and 2.4%. In an embodiment, the percent silk in the product is between 1 and 2%. In an embodiment, the percent silk in the product is between 20% and 30%. In an embodiment, the percent silk in the product is between 0.1% and 10%. In an embodiment, the percent silk in the product is between 1% and 10%. In an embodiment, the percent silk in the product is between 2% and 10%. In an embodiment, the percent silk in the product is between 0.1% and 6%. In an embodiment, the percent silk in the product is between 6% and 10%. In an embodiment, the percent silk in the product is between 6% and 8%. In an embodiment, the percent silk in the product is between 6% and 9%. In an embodiment, the percent silk in the product is between 10% and 20%. In an embodiment, the percent silk in the product is between 11% and 19%. In an embodiment, the percent silk in the product is between 12% and 18%. In an embodiment, the percent silk in the product is between 13% and 17%. In an embodiment, the percent silk in the product is between 14% and 16%. In an embodiment, the percent silk in the product is about 1%. In an embodiment, the percent silk in the product is about 1.5%. In an embodiment, the percent silk in the product is about 2%. In an embodiment, the percent silk in the product is about 2.4%. In an embodiment, the percent silk in the product is 3%. In an embodiment, the percent silk in the product is 3.5%. In an embodiment, the percent silk in the product is about 4%. In an embodiment, the percent silk in the product is about 4.5%. In an embodiment, the percent silk in the product is about 5%. In an embodiment, the percent silk in the product is about 5.5%. In an embodiment the percent silk in the product is about 6%. In an embodiment, the percent silk in the product is about 6.5%. In an embodiment, the percent silk in the product is about 7%. In an embodiment, the percent silk in the product is about 7.5%. In an embodiment, the percent silk in the product is about 8%. In an embodiment, the percent silk in the product is about 8.5%. In an embodiment, the percent silk in the product is about 9%. In an embodiment, the percent silk in the product is about 9.5%. In an embodiment, the percent silk in the product is about 10%.

Personal Use

Compositions of various aspects described herein are versatile and can be adapted for various applications, e.g., personal care (e.g., cosmetic, skin care, body care, hair care), therapeutic use (e.g., wound healing), or any applications where a flowable or spreadable composition is desirable. By the term "personal care" is meant any substance or product applied to a human body for improving appearance, providing protection from Surrounding environment, cleansing, odor control and/or general aesthetics. Nonlimiting examples of personal care applications include leave-on skin lotions and creams, shampoos, hair conditioners, hair serum, shower cream or gels, antiperspirants, deodorants, dental products such as toothpaste, shave creams, depilatories, cosmetic products (e.g., lipsticks, foundations, mascara), sunless tanners and sunscreen lotions. Accordingly, the silk fibroin-based compositions and the emulsion compositions described herein can be formulated to any form desirable for a specific application or provide a desired characteristic of the product, such as matte, sticky, smooth, hard, waxy, or other characteristics. For example, the composition can be formulated to form a gel or hydrogel, a paste, a lotion, a cream, an ointment, an oil, a liquid, a serum, a shampoo, a foam or mousse, a spray, an aerosol, a stick, a balm, a bar, a scrub, or any combinations thereof.

In some embodiments, SBP or silk fibroin could be used a nutritional or neutraceutical protein supplement or protein source. As a nutritional supplement, the SBP or fibroin could take the form of a powder, a pill or capsule, a liquid, or any other format that allows for consumption. In some embodiments, SBP or silk fibroin may be useful as a laxative or stool softener. The silk-product may take the form of a particle or gel that carries water to the lower gastrointestinal system. The silk product may also be used in oral, vaginal, or rectal applications to assist in wound protection or healing in salivary or mucosal tissue.

Cosmetics

In some embodiments, MS SBP formulations are or used in the preparation of cosmetics. In some embodiments, SBPs are active substances in said cosmetics, e.g., as taught in U.S. Pat. No. 6,280,747 and United States Publication Number US20040170590, the contents of each of which are herein incorporated by reference in their entirety. In some embodiments, SBPs are added as a thickening agent, e.g., as taught in United States Publication Number US20150079012, the contents of which are herein incorporated by reference in their entirety. In some embodiments, cosmetics may incorporate SBPs for stabilization and/or preservation of cosmetic components (e.g., see Li et al. (2017) Biomacromolecules 19 (9): 2900-2905, the contents of which are herein incorporated by reference in their entirety). In some embodiments, MS SBP formulations may be incorporated into cosmetics as a lubricant. In some embodiments, MS SBP formulations may be used as a plastic replacement in the preparation of cosmetics. As a non-limiting example, MS SBP formulations may be formatted as microbeads to be used in replacement of plastic microbeads in facial scrubs and toothpastes. Examples of cosmetics include, but are not limited to, shampoos, conditioners, lotions, foundations, concealers, eye shadows, powders, lipsticks, lip glosses, ointments, mascara, gels, sprays, eye liners, liquids, solids, eyebrow mascaras, eyebrow gels, hairspray, moisturizers, dyes, minerals, perfumes, colognes, rouges, natural cosmetics, synthetic cosmetics, soaps, cleansers, deodorants, creams, towelettes, bath oils, bath salts, body butters, nail polish, hand sanitizer, primers, plumpers, balms, contour powders, bronzers, setting sprays, and setting powders.

Sunscreen

In some embodiments, SBP and silk fibroin formulations may be used in the formulation, production, and/or manufacture of sunscreens. The percentage of volume of SBP or silk fibroin may vary based on the desired effect, desired consistency, or desired characteristic of the final product, such as matte, sticky, smooth, hard, waxy, or other characteristics. SBP or silk fibroin may take the place of other, less-desirable, non-active ingredients in sunscreen. Personal care compositions described herein can also comprise an organic sunscreen. Suitable sunscreens can have UVA absorbing properties, UVB absorbing properties or a mixture thereof. The exact amount of the sunscreen active will vary depending upon the desired Sun Protection Factor, i.e., the "SPF of the composition as well as the desired level of UV protection. SPF is a commonly used measure of photoprotection of a sunscreen against erythema. The SPF is defined as a ratio of the ultraviolet energy required to produce minimal erythema on protected skin to that required to produce the same minimal erythema on unprotected skin in the same individual. Amounts of the sunscreen may comprise from about 2% to about 20%, and specifically from about 4% to about 14% by weight of the personal care composition. Suitable sunscreens include, but are not limited to, those approved for use in the United States, Japan, Europe and Australia. The compositions described herein can comprise an SPF of about 2 to about 100, or about 4 about 70, or about 4 to about 30.

The personal care compositions described herein can include one or more UVA absorbing Sunscreen actives that absorb UV radiation having a wavelength of from about 320 nm to about 400 nm. Suitable UVA absorbing sunscreen actives are selected from dibenzoylmethane derivatives, anthranilate derivatives such as methylanthranilate and homomethyl, 1-N-acetylanthranilate, and mixtures thereof. Examples of dibenzoylmethane sunscreen actives are described in sunscreens: Development, Evaluation, and Regulatory Aspects edited by N. J. Lowe and N. A. Shaath, Marcel Dekker, Inc (1990). The UVA absorbing sunscreen active may be present in an amount to provide broad spectrum UVA protection either independently, or in combination with, other UV protective actives which may be present in the composition. Suitable UVA sunscreen actives are dibenzoyl methane sunscreen actives and their derivatives. They include, but are not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4-methoxydibenzoylmethane, 2-methyl-5-isopropyl-4'-methoxydibenzoylmethane, 2-methyl-5-tert-butyl-4'-methoxy dibenzoylmethane, 2,4-dimethyl-4-methoxydibenzoylmethane, 2,6-dimethyl-4-tert-butyl-4-methoxydibenzoylmethane, and mixtures thereof. In one embodiment, the dibenzoyl sunscreen actives include those selected from 4-(1,1-dimethylethyl)-4'-methoxydibenzoylmethane, 4-isopropyldibenzoylmethane, and mixtures thereof. In another embodiment, the sunscreen active is 4-(1,1-dimethylethyl)-4'-methoxydibenzoylmethane. The sunscreen active 4-(1,1-dimethylethyl)-4-methoxydibenzoylmethane, which is also known as butyl methoxydibenzoylmethane or AVobenzone, is commercially available under the names of PARSOLOR) 1789 from Givaudan Roure (International) S. A. and EUSOLEXR, 9020 from Merck & Co., Inc. The sunscreen 4-isoproplydibenzoyl methane, which is also known as isopropyldibenzoyl methane, is commercially available from Merck under the name of EUSOLEXOR) 8020. The personal care compositions described herein can further include one or more UVB Sunscreen actives that absorb UV radiation having a wavelength of from about 290 nm to about 320 nm. The compositions comprise an amount of the UVB sunscreen active that which is safe and effective to provide UVB protection either independently, or in combination with, other UV protective actives which may be present in the compositions. The compositions may comprise from about 0.1% to about 20%, specifically from about 0.1% to about 12%, and more specifically from about 0.5% to about 8% by weight of each UVB absorbing organic sunscreen, or as mandated by the relevant regulatory authority(s). A variety of UVB sunscreen actives are suitable for use herein. Non-limiting examples of such organic sunscreen actives are described in U.S. Pat. No. 5,087,372 to Haffey et al; and U.S. Pat. Nos. 5,073,371 and 5,073,372 to Turner et al, the contents of which are incorporated in their entirety. Still other useful sunscreens are those disclosed in U.S. Pat. No. 4,937,370, to Sabatelli; and U.S. Pat. No. 4,999,186, to Sabatelli et al., the contents of which are incorporated by reference in their entirety. Preferred UVB sunscreen actives are selected from 2-ethylhexyl-2-cyano-3-2-ethylhexyl N,N-dimethyl-paminobenzoate, p-aminobenzoic acid, oxybenzone, homomethyl salicylate, octyl salicylate, 4,4'-methoxy-t-butyldibenzoylmethane, 4-isopropyldibenzoylmethane, 3-benzylidene camphor, 3-(4-methylbenzylidene) camphor, 3-diphenylacrylate, 2-phenyl-benzimidazole-5-sulphonic acid (PBSA), cinnamate esters and their derivatives such as 2-ethylhexyl p-methoxycinnamate and octyl-p-methoxycinnamate, salicylate esters and their derivatives such as TEA triethanolamine salicylate, ethylhexylsaliycyilate, octyldimethyl para aminobenzoic acid PABA, camphor derivatives and their derivatives, and mixtures thereof. Examples of organic sunscreen actives are 2-ethylhexyl-2-cyano-3,3-diphenylacrylate, 2-phenyl-benzimidazole-5-sulphonic acid (PBSA), octyl-p-methoxycinnamate, and mixtures thereof. Salt and acid neutralized forms of the acidic sunscreens are also useful herein.

An agent may also be added to any of the compositions described herein to stabilize the UVA sunscreen to prevent it from photo-degrading on exposure to UV radiation and thereby maintaining its UVA protection efficacy. A wide range of compounds have been cited as providing these stabilizing properties and should be chosen to complement both the UVA sunscreen and the composition as a whole. Suitable stabilizing agents include, but are not limited to, those described in U.S. Pat. Nos. 5,972,316; 5,968,485; 5,935,556; 5,827,508 and Published International Application WO 00/06110, all of which are incorporated by reference in their entirety. Examples of stabilizing agents for use in the present invention include 2-ethylhexyl-2-cyano-3,3-diphenylacrylate, ethyl-2-cyano-3,3-diphenylacrylate, 2-ethyl hexyl-3,3-diphenylacrylate, ethyl-3,3-bis(4-methoxyphenyl) acrylate, diethylhexyl 2.6 napthalate and mixtures thereof (Symrise Chemical Company). An agent may also be added to any of the personal care compositions described herein to improve the skin substantivity of those compositions, particularly to enhance their resistance to being washed off by water or rubbed off. Examples include, but are not limited to, acrylates/C12-22 alkylmethacrylate copolymer, acrylate/acrylate copolymer, dimethicone, dimethiconol, graft-copoly(dimethylsiloxane/il-butyl methacrylate), lauryl dimethicone, PVP/Hexadecane copolymer, PVP/Eicosene copolymer, tricontanyl PVP and trimethoxysiloxysiliacate. In addition to the organic sunscreens, personal care compositions described herein can additionally comprise inorganic physical sunblocks. Non-limiting examples of suitable physical sunblocks are described in CTFA International Cosmetic Ingredient Dictionary, 6th Edition, 1995, pp. 1026 28 and 1103, Sayre, R. M. et al., "Physical Sunscreens", J. Soc. Cosmet. Chem. Vol 41, no 2, pp. 103-109 (1990) and Lowe et al., as per above. Specific examples of inorganic physical sunblocks are Zinc oxide and titanium dioxide and mixtures thereof. When used, the physical sunblocks are present in an amount such that the present compositions are transparent on the skin (i.e., non-whitening), from about 0.5% to about 20%, or from about 0.51% to about 10%, or from about 0.5% to 5% by weight of the composition. When titanium dioxide is used, it can have an anatase, rutile or amorphous structure. Manufacturers of micronized grade titanium dioxide and zinc oxide for sunscreen use include, but are not limited to Tayca Corporation, Uniqema, Shinetsu Chemical Corporation, Ken McGee, Nanophase, Nanosource, Sachtleben, Elementis, and BASF Corporation, as well as their distribution agents and those companies that further process the material for Sun screen use. Physical sunblock particles, e.g., titanium dioxide and zinc oxide, can be uncoated or coated with a variety of materials including but not limited to amino acids, aluminum compounds such as alumina, aluminum stearate, aluminum laurate, and the like; carboxylic acids and their salts e.g., stearic acid and its salts; phospholipids, such as lecithin; organic silicon compounds; inorganic silicon compounds such as silica and silicates and mixtures thereof. The personal care compositions described herein can comprise from about 0.1% to about 25%, or from about 0.1% to about 7% or from about 0.5% to about 5% by weight of an inorganic sunscreen. In some embodiments, sunscreens may be comprised of a formulation having zinc (or a derivative thereof such as zinc oxide), a non-photosensitive carrier oil, silk fibroin or SBP, and glycerol.

Antiperspirants and Deodorants

Antiperspirants are popular personal care products used to prevent or eliminate perspiration and body odor caused by perspiration. Antiperspirant products, including for example sticks, emulsions, and roll-on antiperspirants are desired by a large majority of the population because of the presence of active antiperspirant compounds that minimize or prevent the secretion of perspiration by blocking or plugging ducts of sweat-secreting glands, such as those located at the underarms. Antiperspirants typically comprise an active antiperspirant compound in a carrier that permits the antiperspirant product to be applied to the skin by swiping or rubbing the stick across the skin, typically of the underarm. Upon application, the carrier coats the skin or evaporates, releasing the active antiperspirant compound from the antiperspirant product upon exposure to moisture to form plugs in the sweat ducts. SBP or silk fibroin may be incorporated into the formulation to achieve desired results or provide a desired characteristic of the product, such as matte, sticky, smooth, hard, waxy, or other characteristics. The incorporated silk may be at different percentages based on resultant effects. SBP or silk fibroin may be used as the base formulation excipient, in order to induce gelation and aid in formulation properties. Formulation properties may include lubrication as well as carriers in the overall formulation. SBP or fibroin may also mechanically block the sweat glands.

Active antiperspirant compounds reduce underarm wetness and odor by migrating into openings of the sweat gland ducts and reacting with proteins therein to form antiperspirant plugs, which mechanically prevent sweat from escaping the ducts. Two types of sweat glands are present in the underarm region. The first type of sweat gland, apocrine sweat glands, terminate and secrete at the top of hair follicles.

As such, active antiperspirant compounds should migrate into the hair follicle to access the apocrine sweat gland duct and block secretion. However, underarm hair can partially block the duct opening, making it more difficult for the active antiperspirant compound to enter and migrate into the duct. The second type of sweat gland, eccrine sweat glands, open directly onto the skin. Eccrine sweat is responsible for the largest volume of sweat that causes underarm wetness. As with apocrine glands, active antiperspirant compounds migrate into the eccrine gland openings and form plugs, which reduce underarm wetness.

In one embodiment, an antiperspirant composition in accordance with the present disclosure includes a water-soluble active antiperspirant compound. Active antiperspirant compounds contain at least one active ingredient, for example metal salts, that, as noted above, are thought to reduce perspiration by diffusing through the sweat ducts of apocrine glands and eccrine glands and hydrolyzing in the sweat ducts, where they combine with proteins to form an amorphous metal hydroxide agglomerate, plugging the sweat ducts so perspiration cannot diffuse to the skin surface. Some active antiperspirant compounds that may be used in the antiperspirant product include astringent metallic salts, for example inorganic and organic salts of aluminum, zirconium, and zinc, including tetra- and octa-salts, as well as mixtures thereof. Exemplary compounds include aluminum-containing and/or zirconium-containing salts or materials, such as aluminum halides, aluminum chlorohydrates, aluminum hydroxyhalides, zirconyl oxyhalides, zirconyl hydroxyhalides, and mixtures thereof. Exemplary aluminum salts include those having the general formula $Al_2(OH)_aCl_bx(H_2O)$, wherein a is from 2 to about 5; a and b total to about 6; x is from 1 to about 6; and wherein a, b, and x may have non-integer values. Exemplary zirconium salts include those having the general formula $ZrO(OH)_{2-a}Cl_ax(H_2O)$, wherein a is from about 1.5 to about 1.87, x is from about 1 to about 7, and wherein a and x may both have non-integer values. Exemplary zirconium salts are those complexes that additionally contain aluminum and glycine, commonly known as ZAG complexes. These ZAG complexes contain aluminum chlorohydroxide and zirconyl hydroxy chloride conforming to the above-described formulas. Examples of active antiperspirant compounds suitable for use in the various embodiments contemplated herein include aluminum dichlorohydrate, aluminum-zirconium octachlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum-zirconium trichlorohydrate, aluminum zirconium tetrachlorohydrate, aluminum zirconium pentachlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, zirconium chlorohydrate, aluminum chloride, aluminum sulfate buffered, and the like, and mixtures thereof. In one embodiment, the active antiperspirant compound is aluminum zirconium pentachlorohydrex glycine complex or aluminum zirconium trichlorohydrex glycine complex. In a further embodiment, the antiperspirant product comprises an active antiperspirant compound in an amount of about 8 to about 30 wt. % (USP). As used herein, weight percent (USP) or wt. % (USP) of an antiperspirant salt is calculated as anhydrous weight percent in accordance with the U.S.P. method, as is well known in the art. This calculation excludes any bound water and glycine. In yet another embodiment, the antiperspirant composition includes about 20-25 wt. % aluminum zirconium pentachlorohydrex glycine complex or aluminum zirconium trichlorohydrex glycine complex. SBP or silk fibroin may be used as the base formulation excipient, as a gel, used to prevent, reduce, or stop sweat. SBP or fibroin may also mechanically block the sweat glands.

In one embodiment, an antiperspirant composition in accordance with the present disclosure further includes at least one structurant and/or gellant (hereinafter referred collectively as "structurant") that facilitates the solid consistency of the antiperspirant stick product. Naturally-occurring or synthetic waxy materials or combinations thereof can be used as such structurants. Suitable structurants, including waxes and gellants, are often selected from fatty alcohols often containing from 12 to 30 carbons, such as stearyl alcohol, behenyl alcohol and sterols such as lanosterol. As used herein, the term "fatty" means a long chain aliphatic group, such as at least 8 or 12 linear carbons, which is frequently not branched (linear) and is typically saturated, but which can alternatively be branched and/or unsaturated. It is possible for the fatty acid to contain a hydroxyl group, as in 12-hydroxystearic acid, for example as part of a gellant combination, and to employ amido or ester derivates thereof.

Other structurants can comprise hydrocarbon waxes such as paraffin waxes, microcrystalline waxes, ceresin, squalene, and polyethylene waxes. Other suitable structurants are waxes derived or obtained from plants or animals such as hydrogenated castor oil, hydrogenated soybean oil, carnabau, spermacetti, candelilla, beeswax, modified beeswaxes, and Montan wax and individual waxy components thereof. In an exemplary embodiment, a mixture of wax structurants may be employed. Suitable mixtures of structurants can reduce the visibility of active antiperspirant compounds deposited on the skin and result in either a soft solid or a firm solid. In an exemplary embodiment, the surfactant(s) comprise about 10 to about 35 wt. % of the total antiperspirant composition. In a preferred embodiment, the antiperspirant composition comprises a mixture of stearyl alcohol and hydrogenated castor oil. In another exemplary embodiment, the antiperspirant composition comprises about 12 to about 25 wt. % stearyl alcohol and about 1.5 to about 7 wt. % hydrogenated castor oil. In yet another exemplary embodiment, the antiperspirant composition comprises about 15-22 wt. % stearyl alcohol and about 2.8 wt. % hydrogenated castor oil.

In one embodiment, an antiperspirant composition in accordance with the present disclosure further includes a high refractive index (R.I.) hydrophobic compound. As used herein, the term "high refractive index" means a refractive index of no less than about 1.4. The high R.I. hydrophobic compound also facilitates the minimization and/or prevention of a white residue on the skin by masking the active antiperspirant salt that stays upon the skin upon evaporation of the carrier. Examples of high R.I. hydrophobic compounds for use in the antiperspirant products include PPG-14 butyl ether, C12-C15 alkyl benzoate, such as Finsolv TN® available from Innospec of the United Kingdom, and phenyl dimethicone. In a preferred embodiment, the antiperspirant composition comprises PPG-14 butyl ether and, in a more preferred embodiment, the antiperspirant composition comprises PPG-14 butyl ether in an amount of about 5 to about 15 wt. % of the total antiperspirant composition. In a most preferred embodiment, the antiperspirant product comprises about 9 to about 11 wt. % PPG-14 butyl ether.

In one exemplary embodiment, the antiperspirant product includes one or more suspending agents, including silk fibroin, that facilitate suspension of the active antiperspirant compound in the antiperspirant product, thereby minimizing the amount of active antiperspirant compound that settles out of the antiperspirant product during manufacture. Suitable suspending agents include clays and silicas. Examples of suitable silicas include fumed silicas and silica derivatives, such as silica dimethyl silylate. Suitable clays include bentonites, hectorites and colloidal magnesium aluminum silicates. In one exemplary embodiment, the antiperspirant product includes about 0.2 to about 2.5 wt. % suspending agents. In another exemplary embodiment, the antiperspirant product comprises a mixture of silica and silica dimethyl silylate. In a further embodiment, the antiperspirant product comprises from about 0.1-0.5 wt. % silica and from about 0.1 to about 2 wt. % silica dimethyl silylate. In another yet another embodiment, the antiperspirant product does not use suspending agents, but comprises high melting point waxes to prevent settling of the active ingredients. Examples of suitable high melting point waxes include hydrogenated castor oils and polyethylenes having various melting points above 65° C.

In addition to the compounds identified above, the antiperspirant product may include additives, such as those used in conventional antiperspirants. These additives include, but are not limited to, fragrances, including encapsulated fragrances, dyes, pigments, preservatives, antioxidants, moisturizers, and the like. These ingredients can be included in the antiperspirant product in an amount of 0 to about 20 wt. %. In an exemplary embodiment, the antiperspirant product includes myristyl myristate, which provides a conditioning effect to the skin.

The antiperspirant product, in one embodiment, further includes a hydrophobic carrier. Exemplary hydrophobic carriers include liquid siloxanes and particularly volatile polyorganosiloxanes, that is, liquid materials having a measurable vapor pressure at ambient conditions. The polyorganosiloxanes can be linear or cyclic or mixtures thereof. The linear volatile silicones generally have viscosities of less than about 5 centistokes at 25° C., while the cyclic volatile silicones have viscosities under 10 centistokes. Exemplary siloxanes include cyclomethicones, which have from about 3 to about 6 silicon atoms, such as cyclotetramethicone, cyclopentamethicone, and cyclohexamethicone, and mixtures thereof. The carrier also may include, additionally or alternatively, nonvolatile silicones such as dimethicone and dimethicone copolyols, which have from about 2 to about 9 silicon atoms. Examples of suitable dimethicone and dimethicone copolyols include polyalkyl siloxanes, polyalkylaryl siloxanes, and polyether siloxane copolymers.

In one embodiment, the antiperspirant product further includes a hair minimizing compound. As set forth above, the hair minimizing compound serves to minimize the hair in, for example, the underarm area of the user, thereby allowing the active antiperspirant compound easier access to the sweat gland duct and further reducing the aggressiveness of shaving required. Exemplary hair minimizing compounds include, but are not limited to, urea, salicylic acid, and *Salix alba* (willow) bark extract. Further hair minimizing compounds that may be employed with active antiperspirant compounds include, but are not limited to, *Myrica cerifera* (bayberry) leaf extract, dihydromyricetin, *Cymnema sylvestre* leaf extract, *Jserenoa serrulata* (saw palmetto) fruit extract, *Epilobium angustifolium* (fireweed) extract, *Cucurbita pepo* (pumpkin) seed extract, *Iarrea divaricata* (chaparral) extract, palmatine, subtilisin, hydrolyzed soy protein, nordihydroguaiaretic acid, acetyl glucosamine, and oleanolic acid. A particular hair minimizing compound known in the art is Pilinhib™, manufactured by Cognis Corporation, which includes propylene glycol, hydrolyzed soy protein, *Hypericum performatum* extract, *Hamaelis virginiana* extract, *Arnica montana* flower extract, urea, willow bark extract, menthol, and salicylic acid. The hair minimizing compound may be added to the antiperspirant composition in an amount between about 0.1-20% by weight, about 0.5-10% by weight, or about 1-5% by weight of the total antiperspirant composition.

In one embodiment, the antiperspirant composition further includes a skin lubricating compound. As set forth above, the skin lubricating compound serves to reduce the aggressiveness and increase the ease with which the user shave, and further to reduce skin abrasion during shaving, thereby minimizing the number of antiperspirant plugs removed during shaving. Exemplary skin lubricating compounds include emollients, which serve to soften or smooth the user's skin prior to and after shaving. In an exemplary embodiment, skin lubricating compounds include, but are not limited to, silk powder or *Aloe vera*. Exemplary skin lubricating compounds further include slip modifiers, which are compounds used to enhance the flow properties of other compounds but do not react chemically with the compounds to which they are added. Numerous slip modifying compounds are known in the art, and include quaternary ammonium compounds (including salts), synthetic polymers (including salts), glycosaminoglycans, fatty esters, hydrocarbons, i.e., oils and waxes, silicone polymers, siloxanes and silanes, soaps, and fatty esters. The skin lubricating compound may be added to the antiperspirant composition in an amount between about 1-20% by weight, about 1-10% by weight, or about 1-5% by weight of the total antiperspirant composition.

Lip Balms and Lip Sticks

Lip balms are used primarily for their moisturizing and hydrating effects and (when sunscreen active ingredients are incorporated) for their sunscreen effects. Lip sticks are often used to add color to lips but may also moisturize and hydrate. Common product positionings revolve around botanical and herbal content and vitamin and/or mineral content. As with lipsticks, relatively few ingredient types are required to prepare a stable and superior-performing product, although proper selection and processing are critical for optimal effect. The typical components of a lip balm: Emollient Carriers 40-85%, Flavor 0-0.5%, Waxes 10-20%, Active Ingredients 0-50%, Preservatives 0-0.3%, Photostabilizers 0-6%, Antioxidants 0-0.1%. SBP or silk fibroin may be added to the formulation at any percentage that can affect the user or provide a desired characteristic of the product, such as matte, sticky, smooth, hard, waxy, or other characteristics.

Emollient carriers (which, when solid sunscreen active ingredients are incorporated, are also sunscreen solvents) are the largest component by weight. Their proper selection contributes the product's unique feel and delivery characteristics and also affects the physical and photochemical stability of the product. The most commonly utilized emollient carriers are *Ricinus communis* (Castor) Seed Oil, Butyrospermum Parkii (Shea) Butter, Petrolatum, Octyldodecanol, Mineral Oil (*Paraffinum liquidum*), *Simmondsia chinensis* (Jojoba) Seed Oil and Lanolin. It is obvious from this list that lip balms aren't greening as rapidly or extensively as some other personal care product segments. There are several reasons for this: the superior moisturization and occlusivity of certain petroleum-(and animal-) derived ingredients, the tastelessness of many petroleum-derived products, and the greater oxidation resistance of the saturated hydrocarbon products. Waxes are used to provide structure. A range of waxes is necessary so the lip balm provides the desired pay-off and feel while also maintaining stick integrity at high, moderate and low temperatures. The more commonly utilized waxes include a lower melting point, softer wax, Beeswax (*Cera alba*), a hard and higher melting point wax, *Euphorbia cerifera* (*Candelilla*) Wax (*Candelilla cera*), and a high melting point, brittle wax, *Copernicia cerifera* (Carnauba) Wax (*Copernicia cerifera cera*). The most commonly used sunscreen active ingredients (UV filters) used in lip balms are Ethylhexyl Methoxycinnamate (Octinoxate), Titanium Dioxide, Butyl Methoxydibenzoylmethane (Avobenzone), and Benzophenone-3 (Oxybenzone). These represent the best balance between high and broad spectrum UV absorbance (or scattering) and low bitterness among authorized UV filters.

When photolabile UVA-absorbing Avobenzone is included in a lip balm to impart broad spectrum UV protection, incorporation of Ethylhexyl Methoxycrylene and/or Polyester-25 (if Octinoxate is also present), Undecylcrylene Dimethicone and/or Polyester-8 is recommended to photostabilize the Avobenzone and so retain the lip balm's broad spectrum UV protection through prolonged sun exposure.

Because some fraction of the lip balm is inevitably going to be ingested, it is important to select a flavor/fragrance that is toxicologically benign, both topically and orally, and that conforms to regulatory requirements for lip care products. An increasing number of geopolitical zones are requiring the declaration of flavor/fragrance ingredients that are known sensitizers. Commonly listed ones in lip balms include Linalool, Benzyl Benzoate, Citral, Geraniol and Citronellol. Some lip balm ingredients have a taste (in addition to any odor) and, unfortunately, that taste is often perceived as bitter. A masking agent may be included towards reducing the lip balm's bitterness. Most frequently used is saccharin or sodium saccharin.

There is a secondary effect from certain preservatives that may be of benefit in lip balms. Specifically, the most commonly utilized preservatives for lip balms are parabens, and parabens (at sufficient concentration) have a numbing effect on the tongue. Including parabens in a lip balm may help mitigate the bitterness of the formulation. Antioxidants are particularly valuable in lip care products since the tongue and nose are very sensitive to peroxidation products. It is therefore important, with respect to both product esthetics and shelf life, to include antioxidants in lip care products when unsaturated materials (whether from botanical sources or synthetic flavor or fragrance compounds) are present. The most commonly utilized antioxidants in lip balms are Tocopheryl Acetate and Tocopherol, with lesser use of BHT and Ascorbyl Palmitate.

Fragrances, Perfumes, and Flavorings

In some embodiments, the silk fibroin and SBP and compositions described herein can be used in flavor compositions, such as in U.S. Patent Publication 2015/0164117, which is incorporated by reference in its entirety, and provide a desired characteristic of the product, such as matte, sticky, smooth, hard, waxy, or other characteristics. A flavor composition or flavoring delivery composition refers to a silk-based matrix encapsulating one or more oil droplets, wherein said one or more oil droplets comprises at least one flavoring substance. As used herein interchangeably herein, the terms "flavor or "flavoring substance' are understood as meaning a substance having a sensory impression of a food or another Substance. In some embodiments, flavors or flavoring substances can encompass odor-releasing substances described herein as certain substances can comprise aroma and flavor properties. The flavors or flavoring substances can be incorporated in the oil phase (e.g., oil droplets) of the compositions or the silk particles described herein. The compositions and/or the silk particles described herein can be used to stabilize and/or control release of the flavors of flavoring substances.

In some embodiments, the silk-based material can form a particle. In a particular aspect, provided herein is a silk particle comprising silk fibroin and at least one or more oil droplets encapsulated therein, wherein the oil droplets are loaded with at least one odor-releasing and/or flavoring substance. The silk particle comprises (a) an aqueous phase comprising silk fibroin, and (b) an oil phase comprising an odor releasing Substance and/or flavoring substance, wherein the aqueous phase encapsulates the oil phase (or stated another way, the oil phase is dispersed in the aqueous phase). In some embodiments, the oil phase can exclude a liposome. The size of the silk particle can vary based on the needs of various applications, e.g., cosmetics or food applications. Thus, the silk particle can be of any size. For example, the size of the silk particle can range from about 10 nm to about 10 mm, or from about 50 nm to about 5 mm. In Some embodiments, the size of the silk particle can range from about 10 nm to about 1000 nm, or from about 10 nm to about 500 nm, or form about 20 nm to about 250 nm. In some embodiments, the size of the silk particle can range from about 1 um to about 1000 um, or from about 5 um to about 500 um, or form about 10 um to about 250 um. In some embodiments, the size of the silk particle can range from about 0.1 mm to about 10 mm, or from about 0.5 mm to about 10 mm, from about 0.5 mm to about 8 mm, or from about 1 mm to about 5 mm. As noted above, the oil phase can form a single or a plurality of (e.g., at least two or more) droplets of any size and/or shape in the silk particle. The size and/or shape of the oil droplets can vary with a number of factors including, e.g., silk solution concentration, silk processing, and/or size of the silk particle. In some embodiments, the size of the droplets can be in a range of about 1 nm to about 1000 μm, or about 5 nm to about 500 μm. In some embodiments, the size of the oil compartments or droplets can be in range of about 1 nm to about 1000 nm, or about 2 nm to about 750 nm, or about 5 nm. to about 500 nm, or about 10 nm to about 250 nm. In some embodiments, the size of the oil compartments or droplets can be in a range of about 1 μm to about 1000 μm, or about 5 μm to about 750 μm, or about 10 μm to about 500 μm, or about 25 μm to about 250 μm. The silk particle described herein can incorporate at least one or more of the features described for any embodiment of the silk-based emulsion compositions described above.

As described herein can be used in odor-releasing compositions. An odor-releasing composition refers to a composition comprising at least one odor-releasing substance as described herein. As used herein, the term "odor-releasing substance' refers to a molecule, composition, or a component thereof capable of imparting to an ambient surrounding an odor, including, but not limited to pleasant, and savory smells and, thus, also encompass scents or odors that function as insecticides, insect repellants, air fresheners, deodorants, aromacology, aromatherapy, or any other odor that acts to condition, modify, or otherwise charge the atmosphere or to modify the environment. It should be understood that perfumes, fragrance, aromatic materials, and/or scents, e.g., used in fragrance preparations, foods, cosmetics, personal care products, etc., are thus encompassed herein. In some embodiments, an odor-releasing substance can encompass natural perfumes extracted from natural matter, such as fruits, plants, flowers, e.g., rose essential oil and peppermint essential oil, and synthetic perfumes artificially prepared, such as limonene and linalool. Aromatic plant parts, such as fruits, herbs, and trees, (including dried plant parts such as potpourri) can also be encompassed herein. In some embodiments, the odor-releasing substance can be a volatile oil. The term "volatile oil" means an oil (or a non-aqueous medium) that can evaporate on contact with the skin in less than one hour at room temperature and atmospheric pressure. In some embodiments, the volatile oil can be a volatile fragrance oil, which is liquid at room temperature, e.g., having a non-zero vapor pressure, at room temperature and atmospheric pressure, for example, having a vapor pressure ranging from 0.13 Pa to 40,000 Pa (10 to 300 mmHg), from 1.3 Pa to 13,000 Pa (0.01 to 100 mmHg) or from 1.3 Pa to 1300 Pa (0.01 to 10 mmHg). The odor-releasing substance can be incorporated in the oil phase of the compositions or the silk particles described herein. The compositions and/or the silk particles described herein can be used to stabilize and/or control release of the odor-releasing substance. In some embodiments, odor-releasing substances can encompass flavors or flavoring substances described herein as certain substances can comprise aroma and flavor properties.

The fragrance compositions described herein can be used as a fragrance component in fragrance products such as perfume, eau de parfum, eau de toilette, cologne, etc.; in skin-care preparation, face washing cream, vanishing cream, cleansing cream, cold cream, massage cream, milky lotion, toilet water, liquid foundation, pack, makeup remover, etc.; in make-up cosmetic, foundation, face powder, pressed powder, talcum powder, lipstick, rouge, lip cream, cheek rouge, eye liner, mascara, eye shadow, eyebrow pencil, eye pack, nail enamel, enamel remover, etc.; in hair cosmetic, pomade, brilliantine, set lotion, hair stick, hair solid, hair oil, hair treatment, hair cream, hair tonic, hair liquid, hair spray, hair growth agent, hair dye, etc.; in suntan cosmetic, suntan product, sunscreen product, etc.; in medicated cosmetic, antiperspirant, after shave lotion and gel, permanent wave agent, medicated soap, medicated shampoo, medicated skin cosmetic, etc.; in hair-care product, shampoo, rinse, rinse-in shampoo, conditioner, treatment, hair pack, etc.; in soap, toilet soap, bath soap, perfumed soap, transparent soap, synthetic soap, etc.; as body cleaner, body soap, body shampoo, hand soap, etc.; and, in bath preparation, bath preparations (e.g. bath salt, bath tablet and bath liquid), foam bath (e.g. bubble bath), bath oils (e.g. bath perfume and bath capsule), milk bath, bath jelly, bath cube, etc.; in detergent, heavy-duty detergent for clothing, light-duty detergent for clothing, liquid detergent, washing soap, compact detergent, soap powder, etc.; in fabric softener, softener, furniture care, etc.; in cleaning agent, cleanser, house cleaner, toilet cleaner, bath cleaner, glass cleaner, mold remover, cleaner for waste pipe, etc.; in cleaner for kitchen, soap for kitchen, synthetic soap for kitchen, cleaner for dishes, etc.; in bleaching agent, oxidation type bleaching agent (e.g. chlorine-based bleaching agent or oxygen-based bleaching agent), reduction type bleaching agent (e.g. sulfur-based bleaching agent), optical bleaching agent, etc.; in aerosol, spray type, powder spray type, etc.; in deodoranti-aromatic, solid type, gel type, liquid type, etc.; in other articles of manufactures, tissue paper, toilet paper, etc.; and in some embodiments of the personal care compositions described herein. The amount of incorporation of the odor-releasing composition into a product of interest and/or personal care compositions can range from 0.001 to 50% by weight, and more preferably from 0.01 to 20% by weight. In some embodiments, at least one fixing agent can be added into the fragrance composition. There can be used, for example, but not limited to, ethylene glycol, propylene glycol, dipropylene glycol, glycerine, hexylene glycol, benzyl benzoate, triethyl citrate, diethyl phthalate, Hercolyn, medium chain fatty acid triglyceride, and medium chain fatty acid diglyceride.

Creams and Spreadable Formats

In some embodiments, SBP formats and formulations include creams or moisturizers. As used herein, the term cream refers to a thick mixture of various ingredients. Creams may be semisolid dosage forms containing more than 20% water or volatile components. Creams may also contain one or more therapeutic agent, including SBPs, dissolved in a suitable cream base. Creams may have four main ingredients: water, oil, emulsifier, and a thickening agent, in addition to an active ingredient, such as silk fibroin. In some embodiments, SBP creams are prepared with processed silk or silk fibroin. The ratio of the cream comprising processed silk to the other ingredients may be from about 5:1 to about 4.5:1, from about 4.5:1 to about 4:1, from about 4:1 to about 3.5:1, from about 3.5:1 to about 3:1, from about 3:1 to about 2.5:1, from about 2.5:1 to about 2:1, from about 2:1 to about 1.5:1, from about 1.5:1 to about 1:1, from about 1:1 to about 1:1.5, from about 1:1.5 to about 1:2, from about 1:2 to about 1:2.5, from about 1:2.5 to about 1:3, from about 1:3 to about 1:3.5, from about 1:3.5 to about 1:4, from about 1:4 to about 1:4.5, or from about 1:4.5 to about 1:5.

Related to creams, ointments and salves may have a greater concentration of oil or other skin protectant relative to water. Ointments may have up to 80% of oil or other non-water-soluble component, the remaining portion comprising water, an emulsifier, a thickening agent, and an active ingredient like silk fibroin.

Pastes, although spreadable like a gel, cream, or ointment, only contain three main ingredients: oil, water and powder. Pastes may be thicker than other spreadable formats. Pastes may contain silk fibroin or other SBPs. Examples of pastes may include diaper creams, which may include zinc, inclusive of derivatives thereof, such as zinc oxide. In some embodiments, zinc may comprise 40-50% or more of the total volume of the diaper cream, which may help to treat and prevent diaper rash. Diaper creams may include other emulsion and emollient excipients to create a desired thickness and spreadability.

Lotions are low-viscosity topical preparations intended for application to the skin intended to simply moisturize the skin or to treat or prevent skin diseases and irritations. Compared to other topical and spreadable formats, lotions may have a higher water content. Shampoos may be considered lotions due to the viscosity. Most lotions are oil-in-water emulsions using a substance such as cetearyl alcohol to keep the emulsion together, but water-in-oil lotions are also formulated. The key components of a skin care lotion, cream or gel emulsion (that is mixtures of oil and water) are the aqueous and oily phases, an emulgent to prevent separation of these two phases, and, if used, the drug substance or substances. A wide variety of other ingredients such as fragrances, glycerol, petroleum jelly, dyes, preservatives, proteins and stabilizing agents are commonly added to lotions.

Silk fibroin-based lotions may be combined with benzalkonium to create a hand sanitizer. Silk fibroin based lotions may be combined with different active ingredients to act as an insect repellent.

Wound Healing and Dressing

In some embodiments, a topical formulation of silk fibroin or other SBP composition discussed herein wherein the topical formulation is administered with (or via) a wound dressing. Wound dressings include, but are not limited to gauzes, bandages, sutures, transparent film dressings, hydrogels, polyurethane foam dressings, hydrocolloids and alginates. In certain instances, wound dressings promote wound healing. In some instances, wound dressings reduce or inhibit aberrant wound healing and may prevent complications, such as infection. Silk fibroin or SBP may be combined with any excipient discussed above or in Table 1, to further encourage would healing and overall health, or provide a desired characteristic of the product, such as matte, sticky, smooth, hard, waxy, or other characteristics.

In some embodiments, the formulations and compositions disclosed herein are administered as a dermal paint, which includes silk fibroin or SBP. As used herein, paints (also known as film formers) are solutions comprised of a solvent, a monomer or polymer, an active agent, and optionally one or more pharmaceutically acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent which may be lost and correspondingly increases the amount delivered to the affected area of the skin of an individual. By way of nonlimiting example, paints include collodions (e.g. Flexible Collodion, USP), and solutions comprising saccharide siloxane copolymers and a cross linking agent. Collodions are ethyl ether/ethanol solutions containing pyroxylin (a nitrocellulose). After application, the ethyl ether/ethanol solution evaporates leaving behind a thin film of pyroxylin and silk. In solutions comprising saccharide siloxane copolymers, the saccharide siloxane copolymers form the coating after evaporation of the solvent initiates the cross linking of the saccharide siloxane copolymers.

Hair and Skin Cleaning Products

In some embodiments, silk fibroin-based compositions and/or emulsion compositions described herein can be further formulated accordingly for different types of personal care compositions. In one embodiment, the silk fibroin-based compositions and/or emulsion compositions described herein can be adapted to form a hair care composition in a form selected from the group consisting of shampoo, conditioner, anti-dandruff treatments, styling aids, styling conditioner, hair repair or treatment serum, lotion, cream, pomade, and chemical treatments. In another embodiment, the styling aids are selected from the group consisting of spray, mousse, rinse, gel, foam and a combination thereof. In another embodiment, the chemical treatments are selected from the group consisting of permanent waves, relaxers, and permanent, semi-permanent, and temporary color treatments and combinations thereof. The amount or percentage of silk fibroin or SBP can be amended to reflect an intended effect on the skin or hair or provide a desired characteristic of the product, such as matte, sticky, smooth, hard, waxy, or other characteristics.

In another embodiment, the silk fibroin-based compositions and/or emulsion compositions described herein can be adapted to form a skin care composition in a form selected from the group consisting of moisturizing body wash, body wash, antimicrobial cleanser, skin protectant treatment, body lotion, facial cream, moisturizing cream, facial cleansing emulsion, surfactanti-based facial cleanser, facial exfoliating gel, facial toner, exfoliating cream, facial mask, after shave balm and sunscreen. The amount or percentage of silk fibroin or SBP can be amended to reflect an intended effect on the skin or hair. The method of producing a silk fibroin-based composition and/or an emulsion composition described herein comprises mixing a silk fibroin solution and a humectant agent in a volume ratio of about 1:2 to about 1:100. In some embodiments, the volume ratio of the silk fibroin solution to the humectant agent can be about 1:2 to about 1:10. The humectant agent can be powder, a liquid, a solution, or a suspension. Where the humectant agent is powder, the non-hydrolyzed silk fibroin solution and the humectant agent can be mixed in a weight or mass ratio of about 1:1.1 to about 1:1000, about 1:5 to about 1:750, or about 1:10 to about 1:500.

Contact Lens Solution

Contact lenses are safely used by millions of people every day, but they require reasonable upkeep and care. Oil, debris, makeup, and microorganisms can all accumulate on them over time, and these in turn can irritate the eyes. Because contacts sit directly on the surface of your eyes, a lens that is not properly cleaned and disinfected can increase the risk of eye infection. A good cleansing regimen will include some type of contact solution and/or related products and must include cleaning, disinfecting, rinsing, and properly storing the lenses. Some of the cleaning regimens may be multistep and others may be "all-in-one," but it is important to understand the role of different solutions and not confuse their use contexts.

Contact solution is a commercially prepared chemical solution for cleaning and disinfecting contact lenses. There are many types and brands, but most of them contain some kind of preservative, a binding agent, a buffer, and a surfactant or wetting agent. Many different formulations of contact solution exist in the market, but none include silk fibroin or other SBP. These elements effectively remove any buildup that has formed on the lenses without scratching them and condition the lenses so that they are moist and wet on the surface of your eyes. Lenses can safely be stored in contact solution when not in use, where they will be kept sterile and hydrated.

Saline solution is a simple, PH-balanced saltwater solution that can be used to rinse off your lenses before inserting them. It is important to note that saline solution does not contain any cleansing agents, however, so it should never be used to try to clean, disinfect, or store your lenses. In the early days of contacts use, it was common to have multiple steps involved in lens care, including separate solutions and products to rinse, clean, disinfect, neutralize, and remove proteins. Today, many people use a single, multipurpose contact solution that can perform all the steps in one go and eliminates the need for a saline solution rinse. The multipurpose solution appears to save both time and money, but it may not be suitable for everyone. Including a percentage of silk fibroin or other SBP may have a positive effect on the contact lens and the wearer's comfort or provide a desired characteristic of the product, such as matte, sticky, smooth, hard, waxy, or other characteristics. In some embodiments for contact solution, the SBP or silk fibroin may increase the residence of the solution on the eye.

Surfactant Materials

In some embodiments, MS SBP formulations may be used as a surfactant. In some embodiments, SBP materials may reduce the surface tension of liquids. In some embodiments, the SBP materials may be used to tune the surface tension of liquids. In some embodiments, the SBP may be a surfactant. In some embodiments, the surfactant may be prepared from SBPs. In some embodiments, silk is used in the preparation of surfactant using any of the methods described in Chinese patent publication CN105380891, the contents of which are herein incorporated by reference in their entirety. In some embodiments, SBP surfactants may be more environmentally friendly than existing surfactants. In some embodiments, MS SBP formulations have the surface tension of water. In some embodiments, SBPs have the surface tension of tears.

Lubricant

In some embodiments, MS SBP formulations may be used as lubricants, to reduce friction between two or more surfaces. In some embodiments, the SBP is a lubricant. In some embodiments, the SBP is an excipient in a lubricant. In some embodiments, the SBP is prepared from processed silk, oils, water, and other materials as described in Chinese Patent Publication Number CN101725049, the contents of which are herein incorporated by reference in their entirety. Lubricants can be prepared from SBPs in many formats, including, but not limited to, capsules, coatings, emulsions, fibers, films, foams, gels, grafts, hydrogels, membranes, microspheres, nanoparticles, nanospheres, organogels, particles, powders, rods, scaffolds, sheets, solids, solutions, sponges, sprays, suspensions, and vapors. In some embodiments, an SBP lubricant may comprise silk microspheres. In some embodiments, the microspheres may be prepared with a phospholipid coating as described in United States Patent Application Publication Number US20150150993A1, the contents of which are herein incorporated by reference in their entirety. In some embodiments, the lubricants may be used on a material surface, non-limiting examples of which include gears, machinery, vacuums, plastics, threads, wood, furniture, and other items. In some embodiments, the lubricants may be used on a biological surface, non-limiting examples of which include bones, joints, eyes, and mucosal membranes. In some embodiments, the coefficient of friction of an SBP is approximately that of naturally occurring, biological and/or protein lubricants (e.g. lubricin). In some embodiments, SBPs may be incorporated into a lubricant. Such methods may include any of those presented in International Publication No. WO2013163407, the contents of which are herein incorporated by reference in their entirety. In some embodiments, processed silk and/or SBPs may be used as an excipient to prepare a lubricant.

Surface Coatings and Treatments

In some embodiments, MS SBP formulations may be used as a clear gel or a glass coating to protect and treat the surface of the substrate. In some embodiments the SBP is a glass coating which is an optically clear silk fibroin hydrogel, or an optically clear silk fibroin film. In some embodiments the SBP is an anti-fog coating, which can be used on eyeglasses, mirrors, automotive and aerospace glass, medical devices, and other products where a clear or reflective surface is needed.

Device Materials

In some embodiments, MS SBP formulations may be used in the fabrication, production, and/or manufacture of a device, e.g., as taught in European Patent Number EP2904133, U.S. Pat. No. 9,802,374, and United States Patent Application Publication Number US20170312387, the contents of each of which are herein incorporated by reference in their entirety. In some embodiments, the device is a medical device (e.g. surgical devices, implants, dental devices, dental implants, diagnostic device, hospital equipment, etc.). In some embodiments, the device is an electronic device (e.g. diagnostic device, hospital equipment, implants, etc.).

In some embodiments, SBP formulations and silk fibroin may be used to manufacture silk microneedles.

The term "medical device" refers to any device, product, equipment or material having surfaces that contact tissue, blood, or other bodily fluids of a subject in the course of their use or operation. Exemplary medical devices include, but are not limited to, absorbable and nonabsorbable sutures, access ports, amniocentesis needles, arterial catheters, arteriovenous shunts, artificial joints, artificial organs, artificial urinary sphincters, bandages, biliary stents, biopsy needles, blood collection tubes, blood filters, blood oxygenators, blood pumps, blood storage bags, bolts, brain and nerve stimulators, calipers, cannulas, cardiac defibrillators, cardioverter defibrillators, castings, catheter introducers, catheter sheaths s, catheters, chemical sensors, clips or fasteners, contraceptive devices, coronary stents, dialysis catheters, dialysis devices, dilators, drain tubes, drainage tubes, drug infusion catheters and guidewires, electrodes, endoscopes, endotracheal tubes, feminine hygiene products, fetal monitors, Foley catheters, forceps, gastroenteric tubes, genitourinary implants, guide wires, halo systems, heart valves, hearing aids, hydrocephalus shunts, implants, infusion needles, inserters, intermittent urinary catheters, intraurethral implants, introducers, introducer needles, irrigators, joint prostheses, knives, long-term central venous catheters, long-term tunneled central venous catheters, long-term urinary devices, monitors, nails, nasogastric tubes, needles, neurological stents, nozzles, nuts, obdurators, orthopedic implants, orthopedic devices, osteoports, pacemaker capsules, pacemaker leads, pacemakers, patches, penile prostheses, peripheral venous catheters, peripherally insertable central venous catheters, peritoneal catheters, peritoneal dialysis catheters, personal hygiene items, pins, plates, probes, prostheses, pulmonary artery Swan-Ganz catheters, pulse generators, retractors, rods, scaffolding, scalpels, screws, sensors, short-term central venous catheters, shunts, small joint replacements, specula, spinal stimulators, stents, stints, stylets, suture needles, suturing materials, syringes, temporary joint replacements, tissue bonding urinary devices, tracheostomy devices, transducers, trocars, tubes, tubing, urethral inserts, urinary catheters, urinary dilators, urinary sphincters, urological stents, valves, vascular catheters, vascular catheter ports, vascular grafts, vascular port catheters, vascular stents, wire guides, wires, wirings, wound drains, wound drain tubes, and wound dressings.

In some embodiments, the medical device may be an ocular device, such as, but not limited to, contact lens (hard or soft), intraocular lens, corneal onlay, ocular inserts, artificial cornea and membranes, eye bandages, and eyeglasses.

In some embodiments, the medical device may be a dental device, such as, but not limited to, dental flossers, dental flossing devices, dental threaders, dental stimulators, dental picks, dental massagers, proxy brushes, dental tapes, dental fillings, dental implants, orthodontic arch wire, and other orthodontic devices or prostodontic devices.

In some embodiments, the device may be any one of the following devices: audio players, bar code scanners, cameras, cell phones, cellular phones, car audio systems, communication devices, computer components, computers, credit cards, depth finders, digital cameras, digital versatile discs (DVDs), electronic books, electronic games and game systems, emergency locator transmitters (ELTs), emergency position-indicating radio beacons (EPIRBs), fish finders, global positioning system (GPS), home security systems, image play back devices, media players, mobile computers, mobile phones, MP3 players, music players, notebook computers, pagers, palm pilots, personal computers, personal digital assistants (PDAs), personal locator beacons, portable books, portable electronic devices, portable game consoles, radar displays, radios, remote control device, satellite phones, smart cards, smartphones, speakers, tablets, telephones (e.g. cellular and standard), televisions, video cameras, video players, automobiles, boats, and aircraft.

In some embodiments, MS SBP formulations are used as, or incorporated into, the coating materials of a device. In some embodiments, the coating may be functional, decorative or both. Coatings may be applied to completely cover the surface. Coating may also be applied to partially cover the surface. Devices coated with SBPs may be more biocompatible and/or less-immunogenic. Sutures or other implantable devices may be made completely of, or coated with, silk fibroin or MS SBP to reduce the immunogenicity.

Antibiotic Materials

In some embodiments, MS SBP formulations may be used as materials due to their antibiotic properties. Such methods may include any of those described in European Patent Number EP3226835 and Mane et al. (2017) Scientific Reports 7:15531, the contents of each of which are herein incorporated by reference in their entirety. These antibiotic properties may be a general property of SBPs. In some embodiments, SBPs materials with antibiotic properties may include antibiotic cargo. In some embodiments, SBP materials may include antibiotic wound-healing materials (e.g., see Babu et al. (2017) J Colloid Interface Sci 513:62-72, the contents of which are herein incorporated by reference in their entirety).

Synthetic Materials

In some embodiments, MS SBP formulations are combined with synthetic materials. Such SBPs may be used to form scaffolds (e.g., see Lo et al. (2017) J Tissue Eng Regen Med doi. 10.1002/term.2616, the contents of which are herein incorporated by reference in their entirety). In some embodiments, SBPs described herein are utilized to coat other materials. Such SBPs may include any of those described in Ai et al. (2017) International Journal of Nanomedicine 12:7737-7750, the contents of which are herein incorporated by reference in their entirety. In some embodiments, SBPs include plastics (e.g. thermoplastics, bioplastics, polyethylene, ultra-high-molecular-weight polyethylene, polypropylene, polystyrene, and polyvinyl chloride). In some embodiments, SBPs include plastic replacements. In some embodiments, SBPs include electronic materials or insulators.

In some embodiments, SBPs include polyolefins, polymers, and/or particles. In some embodiments, SBP materials may be prepared and used according to the methods of preparation and use described in European Patent Numbers EP3226835, EP3242967, and EP2904133, United States Publication Numbers US20170333351 and US20170340575, and Cheng et al. (2017) ACS Appl Mater Interfaces doi. 10.1021/acsami.7b13460, the contents of each of which are herein incorporated by reference in their entireties.

In some embodiments, MS SBP formulations may be used as a plastic replacement in various products. Conventional plastic is made from petroleum products, primarily oil. It does not biodegrade and is harmful to the environment. MS SBP formulations are an attractive alternative to synthetic plastics due to their biocompatibility and biodegradability. As a non-limiting example, SBPs may be used as a plastic replacement in the production of water bottles and food containers. As another non-limiting example, MS SBP formulations may be used as a plastic replacement in the preparation of coating materials on a fabric or a cloth. Coatings used on apparels, such as a waterproof jacket or athletic shirt, are generally made of synthetic polymers and may release micro-plastic particles into water during a wash cycle. Using MS SBP formulations in replacement of synthetic polymers may help eliminate this problem.

Nanomaterials

In some embodiments, MS SBP formulations include nanomaterials (e.g. nanoparticles, nanofibrils, nanostructures, and nanofibers), as taught in International Patent Application Publication No. WO2017192227, Xiong et al., and Babu et al. (Xiong et al. (2017) ACS Nano 11 (12): 12008-12019; Babu et al. (2017) J Colloid Interface Sci 513:62-72), the contents of each of which are herein incorporated by reference in their entirety. In some embodiments, the nanoparticles may include excipients. In some embodiments, the nanoparticles may include, but are not limited to, any of those excipients listed in Table 1, above.

Thickening Agents

In some embodiments, MS SBP formulations may be or may be combined with thickening agents. As used herein, the term "thickening agent" refers to a substance used to increase viscosity of another material, typically without altering any properties of the other material. In some embodiments, SBP thickening agents may be used in paints, inks, explosives, cosmetics, foods, or beverages.

In some embodiments, SBP thickening agents may be used in products for human consumption (e.g., as taught in United States Publication No. US20150079012, the contents of which are herein incorporated by reference in their entirety). SBP biocompatibility, biodegradability, and low toxicity make SBPs attractive tools for thickening materials designed for human consumption. In some embodiments, SBP thickening agents may be used to increase the viscosity of a food item. Examples of food items include, but are not limited to, puddings, soups, sauces, gravies, yogurts, oatmeals, chilis, gumbos, chocolates, and stews. In some embodiments, SBP thickening agents may be used to increase the viscosity of beverages. Examples of beverages include, but are not limited to, shakes, drinkable yogurts, milks, creams, sports drinks, protein shakes, diet supplement beverages, and coffee creamers.

In some embodiments, SBP thickening agents may be added to cosmetics (e.g., as taught in United States Publication Number US20150079012, the contents of which are herein incorporated by reference in their entirety. Such cosmetic products may include, but are not limited to, shampoos, conditioners, lotions, foundations, concealers, eye shadows, powders, lipsticks, lip glosses, ointments, mascara, gels, sprays, eye liners, liquids, solids, eyebrow mascaras, eyebrow gels, hairspray, moisturizers, dyes, minerals, perfumes, colognes, rouges, natural cosmetics, synthetic cosmetics, soaps, cleansers, deodorants, creams, towelettes, bath oils, bath salts, body butters, nail polish, hand sanitizer, primers, plumpers, balms, contour powders, bronzers, setting sprays, and setting powders.

Military Applications

In some embodiments, SBP formulations may be used in military applications. For example, SBP formulations may be incorporated in military fabrics. Such fabrics may be used in items such as, but not limited to, ponchos, tents, uniforms, vests, backpacks, personal protective equipment (PPE), linings, cords, ropes, and cables, webbings, straps and sheaths, helmet coverings, flags, bedsheets and mattress fabrics, ribbons, hats, gloves, masks, boots, suits and belts. As another example, SBP formulations may be used in the manufacture of a military device or gear. Non-limiting examples of military devices or gears include goggles, sunglasses, telescopes, binoculars, monoculars, flashlight, torches, watches, compasses, whistle, shields, knee caps, water bottles, flasks, and cameo face paint.

The details of one or more embodiments of the disclosure are set forth in the accompanying description above. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

Commercial Applications

In some embodiments, SBP formulations may be used in commercial applications, or other non-personal use. For example, SBP may be formulated to be a hard-plastic replacement. SBP as a solid, formable, moldable or 3D-printable material may be used in material such as toys, home goods, furniture, electronics (as a dielectric), building material, pulp replacement for paper, bottles, straws, epoxies, sealants, or another substrate. In some embodiments, the SBP or silk fibroin used in commercial applications may be non-virgin, or recycled silk. In some embodiments, SBP or silk fibroin may be added to other products, such as paint or cement, to provide textural, structural, or visual characteristics. In other embodiments, SBP or silk fibroin may be added to soils or other potting-media to affect water retention or dispersion.

Solid Silk Structures

Creating different levels of structures using silk fibroin is discussed by Qi et al., A Review of Structure Construction of Silk Fibroin Biomaterials from Single Structures to Multi-Level Structures, *Int. J. Mol. Sci.* 2017, 18, 237, which is incorporated by reference herein in its entirety. Silk fibroin materials can take the form of several structures: particulate, film, three-dimensional, and multi-level structures. Multi-level structures include various combinations of the lesser structures.

Particulate structures can be created using different processes, such as self-assembly, freezing, phase separation, and milling. Self-assembly can be used to prepare silk fibroin micro- and nanoparticles. Hydrophilic (Tyr, Ser) and hydrophobic (Gly, Ala) chain segments in silk fibroin can be arranged alternately allowing silk fibroin molecules to form micelles via a self-assembly mechanism. Adding methanol and quenching below the freezing point, self-assembly is initiated, producing 0.2 to 1.5 μm silk fibroin microspheres. Microsphere size is controlled by the concentration of silk fibroin, the freezing temperature, and the amount of ethanol added to the mixture. The addition of poly vinyl alcohol (PVA) may improve the texture of silk fibroin particles. During the freezing process, PVA forms a hydrogel network to restrain the nucleation of silk fibroin. Regular and smooth silk fibroin particles are formed under the influence of PVA, unlike the unpredictable structures of silk fibroin particles produced without PVA.

Phase separation of silk fibroin solution by salting out is simple. Silk fibroin particles obtained using potassium phosphate has controllable sizes ranging from 500 nm to 2 μm, as discussed by Lammel et al., Controlling silk fibroin particle features from drug delivery, *Biomaterials* 2010, 31, 4583-4591. The secondary structure and the zeta potential (the potential difference between the dispersion medium and the stationary layer of fluid attached to the particle) of the silk fibroin particles are affected by the pH value of the potassium phosphate solution. A lower and narrower molecular weight distribution of silk fibroin could promote the formation of silk fibroin microspheres with smoother surfaces and shapes, as discussed by Zeng et al. Controlling silk fibroin microspheres via molecular weight distribution. *Mater. Sci. Eng.,* 2015, 50, 226-233, which is incorporated by reference herein in its entirety. Other methods for silk fibroin micro and nanoparticle preparation include desolvation, spray drying, laminar jet break-up capillary microdot, and electrospray.

Silk fibroin can be prepared as films or mats. Silk fibroin films can be prepared by casting aqueous fibroin solutions into different shapes and molds. Films or mats may be cast by allowing silk fibroin solution to dry or evaporate over a smooth, flat plate. A vertical deposition method is also available to produce films. A glass coverslip can be inserted vertically in silk fibroin solution in an oven at 50. Because of the lateral capillary force and surface tension drive between the fibroin solution and the glass coverslip, silk fibroin solution can be deposited on the glass coverslip and dried to obtain a transparent silk fibroin film. A layered silk fibroin mat may demonstrate high elastic modulus and tensile strength because of the self-reinforcing structure of multiple layered deposits. The stability of silk fibroin films used as biomaterial is significant; this property can be improved by stretching, water annealing, slow-drying, and alcohol immersion. Methanol or ethanol are most often used to prepare water-insoluble silk fibroin films with increased β-sheet content. Silk fibroin films treated with methanol showed high oxygen and water vapor permeability, as well as good mechanical properties. Ethanol concentration may influence the surface properties of the films. When less than 80% ethanol is used to treat the silk fibroin film, the outermost layer of fibroin film looked like jelly, while after treatment with great than 90% ethanol, the film surface is harder. A glucose oxidase (GOD)-immobilized silk fibroin membrane, which can be physically stretched in an apparatus with Clark-type oxygen electrode to induce structural transition from the random coil (silk I) to β-sheet (silk II) without chemical treatments. Silk fibroin films treated with these techniques exhibit slow biodegradation due to their high β-sheet content. Water-stable fibroin films with reduced β-sheet content may be prepared by water annealing. After being annealed in water for 24 h, the silk fibroin films formed stable Silk I structure and did not transform to Silk II with methanol or stretching treatment. Water-annealed silk fibroin films are more transparent and could avoid cracks induced by methanol treatment. Water-insoluble silk fibroin films with a silk I structure may be made by very slow drying; the resulting films have a faster enzymatic degradation rate and better mechanical ductility.

Electrospinning is the most commonly used technique to prepare silk fibroin mats due to its flexibility and versatility. The morphology and secondary structure of silk fibroin mats can be adjusted by tuning the electrospinning voltage, silk fibroin concentration, flow rate, and receive distance. At low silk fibroin concentrations, clustered or beaded fibers may occur in the collector. The best electrospinning conditions have been widely investigated to obtain optimal silk fibroin mats. In general, silk fibroin has been electrospun with spinning solvents such as polyethylene oxide (PEO), hexafluoroisopropanol (HFIP), hexafluoroacetone (HFA), and formic acid, which can decrease biocompatibility. silk fibroin mats may be made by an electrospinning process using a highly concentrated, all-aqueous silk fibroin solution. Electrospun silk fibroin mats exhibit belt-like fibers, with a breaking stress and strain of 1.49 MPa and 1.63%, respectively. An electrospinning method can be used to easily prepare composite silk fibroin mats with unique functions. Cellulose nanowhiskers (CNWs) may be added to the silk fibroin solution to reinforce the mats with twice the tensile strength and Young's modulus. Additionally, doping of Ag and $TiO_2$ nanoparticles may improve the antibacterial property of silk fibroin mats. silk fibroin mats coated with silver nanoparticles (AgNPs) were revealed to have effective antibacterial activity with a relatively low concentration of ionic silver compared with commercial wound dressing and has potential commercial application as antimicrobial wound dressings.

Three-dimensional structures of silk fibroin usually exist as hydrogels and sponge materials. Hydrogels possess an interconnected network structure with high water content. The gelation of silk fibroin can be induced by sonication, vortex, heating, solvent treatment, photo-crosslinking, and electrogelation. The rate of the gelation process may be controlled by temperature, pH, fibroin concentration, and addition of other compounds. Faster silk fibroin gelation may be produced by higher concentration, lower pH values, higher temperature, and the addition of $Ca^{2+}$. During the sol-gel transition process of silk fibroin, secondary structural changes occur from a random coil state to a β-sheet conformation. Another method to fabricate highly tunable elastic silk fibroin hydrogels is via enzymatically covalent crosslinking of tyrosine residues in silk fibroin generated by horseradish peroxidase (HRP) and hydrogen peroxide. The new hydrogels can bear shear strains approximatively 100%, compressive strains greater than 70%, and show stiffness between 200 and 10,000 Pa, which include numerous properties of native soft tissues. The HRP silk fibroin hydrogels exhibit controllable kinetics and can maintain high resilience and resistance to fatigue under different molecular weights and solvent compositions. An all-aqueous processing technique may be used to fabricate porous silk fibroin scaffolds without the addition of organic solvents. Aqueous-derived silk fibroin sponges exhibited a more uniform and highly interconnected morphology, as well as a faster degradation rate in the presence of protease, compared with hexaflouroisopropanol-derived sponges.

Another method is freeze-thaw, which formed silk fibroin porous sponges via the addition of organic solvents such as methanol, ethanol, and propanol. A mixed solution can be frozen and then immersed in buffer solution or water to remove the solvents. Silk fibroin sponges made by this method has good tensile strength and compressive modulus due to the existence of silk II crystalline structures induced by organic solvents. Salt-leaching and freeze-drying methodologies may be used to prepare silk fibroin scaffolds with high-concentration aqueous solutions. Sodium chloride particles (500-1000 μm) can be used as porogens added into silk fibroin solution and then extracted by distilled water. Next, the scaffolds may be frozen at −80° C. for one day and then freeze-dried. Prepared silk fibroin scaffolds possess high porosity and interconnectivity with homogeneous macro/microporous structures. Importantly, after in vitro degradation for 30 days, the silk fibroin scaffolds can maintain their original structure and morphology integrity, as well as their mechanical properties. Therefore, the silk fibroin scaffolds showed potential use in meniscus and cartilage regeneration. Silk fibroin as three-dimensional structures are ideal material for tissue engineering because 3D structure biomaterials mimic the in vivo physiological environment more closely than 2D structures. Silk fibroin hydrogels can be used in cell encapsulation.

Photolithography is a widely used and traditional method for fabricating micropatterning silk fibroin biomaterials. The photolithography technique is based on a photomask with micro/nanoscale patterns and photoresist. The photoresist is spin-coated on a substrate and then the photomask covers on the photoresist. Because of the photo-sensitive property of photoresist, regions exposed to certain light source through the photomask will be decomposed. In this manner, the patterns of the mask are transferred to the substrate. Pure silk fibroin as a positive-tone photoresist in lithography does not require photoinitiators, and water may be the only chemical used. Silk fibroin solution may be first spin-coated onto the silica substrate, then the silk fibroin film is illuminated by ArF excimer laser through a patterned Cr mask. After developing the exposed area with distilled water, the patterned silk fibroin film shows diffracted colors with a minimum line width of 1 μm. Another technique is soft lithography, which is based on molding and printing with an elastomeric stamp to realize pattern transfer from the template. Compared to traditional photolithography technique, soft lithography is highly effective, convenient, and inexpensive. Polydimethylsiloxane (PDMS) is commonly used as the elastomeric stamp mold. The electron beam lithography technique uses a focused electron beam to expose the resist on the substrate, which can produce nanometer scale patterns under the control of computer. The fabrication of linewidths as small as 5-7 nm using 100 keV electron beam lithography, is possible. Scanning probe lithography (SPL) is a high-resolution patterning technique that uses a tip to image features on a substrate. Atomic force microscopy (AFM), a type of SPL, has been reported to directly deposit the relatively hydrophobic silk fibroin onto mica under liquid. The AFM tip produced silk fibroin micropatterns on mica in both contact and tapping modes.

Three-dimensional printing (3DP) is a rapid prototyping (RP) technology that utilizes computer-aided design (CAD) model for layer-by-layer fabrication of 3D objects. Traditional methods of fabricating biomaterials fail to control their structures and internal geometry. The use of 3DP allows accurate, computer-controlled repetition of desired internal architectures and structures. Three-dimensional printing has been used as an emerging technology in engineering, manufacturing, art, and many other areas. In recent years, 3DP has been applied in the field of biomaterials to meet the need for organs and tissues. In one embodiment, concentrated silk fibroin solution (28-30 wt %) may be used as ink in the 3D direct writing of microperiodic scaffolds. The ink may be deposited through a fine nozzle to form a precisely controlled complex array with 5 μm diameter silk fibers, in a layer-by-layer sequence. Alternative silk fibroin 3D structures also may be obtained, such as square lattice and circular web.

Three-dimensional silk/hydroxyapatite (HA) scaffolds with gradient pore spacings ranging from 200 μm to 750 μm may be developed by direct-write printing using silk fibroin ink containing HA particles. The multi-level scaffolds may be printed in the form of a 3D lattice composed of interconnected silk/HA filaments. Printed silk fibroin may be nests in circular arrays with diameters of 70-100 μm and modified with ionic pairing to form silk II secondary structure. Due to its unparalleled advantages, 3D printing will play an important role in future fabrication of biomaterials. With the aid of CAD modelling, virtually any structure can be printed. Currently, silk fibroin 3D printing focuses on single structure construction and rapid modeling of silk fibroin. However, as 3DP techniques mature, more attention will be directed to the construction of multi-level structures with excellent multifunctionality.

Gelation

Silk fibroin gelation can be used to prepare hydrogels. Hydrogels having variable structural characteristics and mechanical properties (e.g., elasticity, viscoelasticity, equilibrium modulus) can be created by tuning factors involved in the gelation process. Factors affecting the rate of gelation and properties of hydrogels formed include, for example, temperature (gelation rate being directly proportional to temperature), pH (inversely proportional), fibroin concentration (directly proportional), and addition of other compounds (e.g. Ca2+, hydroxy propyl methyl cellulose (HPMC)), and fibroin molecular weight (directly proportional).

In some embodiments, sonication or ultrasonication may be used to cross link silk fibroin to form hydrogels as described by Wang, Xiaoqin, et al. "Sonication-induced gelation of silk fibroin for cell encapsulation." Biomaterials 29.8 (2008): 1054-1064; the contents of which are incorporated by reference in their entirety. Such hydrogels are useful in, for example, replacing petroleum-based chemicals for use in encapsulation materials, including, e.g., controlled-release capsules for hydrophobic and hydrophilic drugs. Wang et al show that silk fibroin gelation can be rapidly induced by sonication, and that structural parameters of the resultant hydrogel are tunable by adjusting concentrations of starting materials. The hydrogels may be used as encapsulating material for culturing human bone marrow derived mesenchymal stem cells (hMSCs), demonstrating their utility as vectors for delivery of cell-based or other pharmaceutical compositions to, e.g., human subjects.

Similar to sonication-based methods, alternative mechanical perturbations can be used to induce silk fibroin gelation. Such perturbations include, without limitation, vortexing, pressurizing, and heating, as well as combinations thereof. Yucel, Tuna, Peggy Cebe, and David L. Kaplan. "Vortex-induced injectable silk fibroin hydrogels." Biophysical journal 97.7 (2009): 2044-2050; incorporated by reference in its entirety.

Solvent and non-solvent-based treatments can be used to induce silk fibroin gelation. Solvent-based treatments include, for example, treatment with methanol as a solvent, ethanol as a solvent, and/or propanol as a solvent. Non-solvent based methods include using non-solvent-induced phase separation according to methods described by Kasoju, Naresh, et al. "Silk fibroin gelation via non-solvent induced phase separation." Biomaterials science 4.3 (2016): 460-473; the contents of which are incorporated by reference herein in their entirety. Kasoju et al show that reconstituted silk fibroin combined with methanol in final concentrations of 2.5% w/v and 12.5% v/v, respectively, formed a hydrogel which, after freeze-drying, provided favorable structural characteristics tunable based on temperature, time, and other factors. The resultant hydrogels and porous foams may be used to replace petroleum-based chemicals for use in encapsulation materials, including, e.g., controlled-release capsules for hydrophobic and hydrophilic drugs.

Covalent cross-linking for silk fibroin gelation can also be achieved using photo-crosslinking as described in Int'l Pat. App. Pub. No. WO 2017/123383, which is incorporated by reference in its entirety, and which describes methods of exposing silk fibroin and a flavin compound, e.g., riboflavin, to a source of light to form dityrosine crosslinks. Other forms of covalent cross-linking include those described in Int'l Pat. App. No. WO 2015/054125, which is incorporated by reference in its entirety, and which describes gelation by sonication, enzymatic cross-linking, and addition of, e.g., poloxamer to achieve dityrosine bonds. Relatedly, Partlow et al generated highly tunable elastic silk fibroin hydrogels using enzymatic covalent cross linking of tyrosine residues treated with horse radish peroxidase (HRP) and hydrogen peroxide (Partlow, B. P et al. Highly Tunable Elastomeric Silk Biomaterials. Adv. Funct. Mater. 2014, 24, 4615-4624; incorporated by reference in its entirety).

Electrogelation can be used in some embodiments to solidify silk fibroin in accordance with the disclosure of Int'l Pat. App. Pub. No. WO 2012/087823, which is incorporated by reference in its entirety. Porogens, including salts such as sodium chloride, can be introduced into the gelation process to form porous solids. Porogen size and concentration can be adjusted to tune pore size and porosity.

Additives

In some embodiments, silk solids and methods, processes, or system for making silk solids as described herein can involve one or more additive. The one or more additive can be introduced, for example, into the silk fibroin material or other starting materials (e.g., solvents, fillers, etc.), or into a solidified or gelated silk product. In some embodiments, the one or more additive facilitates the solidification of silk fibroin and/or reinforces the solid structure of the gelated or solidified silk fibroin form. Such additives include, but are not limited to plastics such as acrylics, polyesters, silicones, polyurethanes, and halogenated plastics. Plastic additives also include, but are not limited to polyamides, polycarbonates, polyethylene (high-density polyethylene, low-density polyethylene, polyethylene terephthalate), polypropylene, polystyrene, polyvinyl chloride, acrylonitrile butadiene styrene, polyepoxide (epoxy), polymethyl methacrylate, methyl acrylate (also useful in manufacturing methods for silk-based solids, discussed below), polytetrafluoroethylene, phenolics or phenol formaldehyde, melamine formaldehyde, urea-formaldehyde (UF), polyether ether ketone (PEEK), maleimide, bismaleimide, polyimide, plastarch materials, polylactic acid (PLA), furan, silicone poly, polysulfone, polydiketoenamine, and combinations thereof.

Various carbohydrates and polysaccharides may also be useful as additives that facilitate the solidification of silk fibroin and/or reinforce the solid structure of the gelated or solidified silk fibroin form. Examples of carbohydrates and polysaccharides include, but are not limited to erythrose, threose, ribose, arabinose, xylose, lyxose, ribulose, xylulose, allose, altrose, glucose, mannose, gulose, idose, galactose, galactosamine, N-acetylgalactose, glucosamine, N-acetylglucosamine, sialic acid, talose, psicose, fructose, sorbose, tagatose, fucose, fuculose, rhamonse, sedoheptulose, octose, sulfoquinovose, nonose, and combinations thereof. Plant starches useful as additives include, but are not limited to cellulose, cornstarch, arrowroot starch, barley starch, cassava starch, maize starch, millet starch, rice starch, tapioca starch, sago starch, sorghum starch, sweet potato starch, wheat starch, soy starch, and the like, and combinations thereof. Additional additives include agar or agaropectin (a branched and sulfated (or pyruvated) polymer consisting of heterogeneous smaller molecules). Animal-based carbohydrates include chitin and chitosan. The carbohydrates and polysaccharides provided can be useful as fillers, solidifiers, gelation promoters, and/or as structural reinforcers which function to resist degradation or collapse of the silk-based solids described herein. Some additives that can be used in the silk solids described herein include those described, for example, in US Pat. App. Pub. No. 2013/0186303, incorporated by reference in its entirety.

Plasticizers are materials that can soften and loosen a polymer structure by reducing the intermolecular forces and increasing the intermolecular mobility of the polymer. In some embodiments, one or more plasticizers can be used in the formation of silk fibroin solids as described herein. Example plasticizers include, but are not limited to low molecular weight polymers, oligomers, copolymers, small organic molecules, low molecular weight polyols, glycol ethers, poly(propylene glycol), polyethylene glycols (low molecular weight and high molecular weight), citrate ester-type plasticizers, triacetin, propylene glycol, sugar alcohols, glycerin, urea, urea derivatives, ethylene glycols, glycerols, 1,2-butylene glycol, 2,3-butylene glycol, styrene glycol, diethylene triethylene glycol, tetraethylene glycol, hexane triol, mannitol, sorbitol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate, allyl glycolate, polyethers, polyols, ureas, sorbitol, and combinations thereof.

In some embodiments, additives can include certain materials added to enhance properties of bioplastics, including those derived from coconut/coconut shells/husks, eggs/eggshells, clams/clam shells, wood, pulp, paper, sawdust, collagen, and gelatin.

In some embodiments, acids can be additives in the gelation and/or solidification of silk fibroin. Acids useful in the compositions, processes, and systems described herein include, for example, carboxylic acid, formic acid, acetic acid, propionic acid, oxalic acid, malonic acid, succinic acid, glutaric acid, adipic acid, maleic acid, malic acid, oleic acid, salicylic acid, gallic acid, citric acid, lactic acid, tartaric acid (e.g., dextro-tartaric acid, mesa-tartaric acid, etc.), glycolic acid, trifluoroacetic acid, benzoic acid, 4-hydroxybenzoic acid, aminobenzoic acid, and p-toluenesulfonic acid. In some embodiments, phenols can be additives in the gelation and/or solidification of silk fibroin. Phenols useful in the compositions, processes, and systems described herein include, for example, pyrogallol, benzene-1,2,3-triol, and catechol (benzenediol). In still other embodiments, anhydrides can be additives in the gelation and/or solidification of silk fibroin. Anhydrides useful in the compositions, processes, and systems described herein include, for example, acetic anhydride, succinic anhydride, and trifluoroacetic anhydride.

Other agents useful as additives in the compositions, processes, and systems described herein include dispersion aids, melt stabilizers, processing stabilizers, heat stabilizers, light stabilizers, antioxidants, heat aging stabilizers, whitening agents, anti-blocking agents, bonding agents, and lubricants.

In some embodiments, water repellent agents can be additives in the gelation and/or solidification of silk fibroin. Water repellent agents useful in the compositions, processes, and systems described herein include, for example, parylene, polydimethylsiloxane, polyethylene, polyvinyl, polypropylene, polyester, latex, oils, organic solvents, waxes, lipids, esters of fatty acids, esters of sterols, long chain alcohols, myricyl palmitate, cetyl palmitate, lanolin, candelilla wax, ouricury wax, sugarcane wax, retamo wax, jojoba oil, and paraffin.

Manufacturing

Silk fibroin solids can be prepared, for example, from silk protein concentrates using the methods described in WO 2018/229341, incorporated by reference in its entirety. Silk fibroin solids can alternatively be prepared using the composite, mixing, heating, and/or cross-linking methodologies described in WO 2016/156930, incorporated by reference in its entirety. In some embodiments, the solids described herein are produced using a method of layering composites, e.g., dried carbohydrate layers alternating with lyophilized, dried, gelated, or solidified silk fibroin layers consistent with the manufacturing methods described in WO 2012/030805, incorporated by reference in its entirety. In some embodiments, silk fibroin can be used to manufacture particulate structures, films, 3-dimensional shaped structures, and multi-level structures as described, for example, in Qi, Yu, et al. "A review of structure construction of silk fibroin biomaterials from single structures to multi-level structures." International journal of molecular sciences 18.3 (2017): 237; incorporated by reference in its entirety. In some embodiments, silk fibroin can be used to manufacture silk-cellulose composites in accordance with Mohammadi, Pezhman, et al. "Biomimetic composites with enhanced toughening using silk-inspired triblock proteins and aligned nanocellulose reinforcements." Science advances 5.9 (2019): eaaw2541, incorporated by reference herein in its entirety.

In some embodiments, silk solids as described herein can be useful in micropatterning, photolithography, and similar manufacturing applications, including soft lithography and scanning probe lithography. In some embodiments, silk solids can be used as a photoresist in photolithography, photoengraving techniques, and related techniques.

In some embodiments, silk solids can be used to create hard or firm solids, for example, using the methods described in WO 2019/106129, incorporated by reference in its entirety. For example, injection molding of silk-based resins can be used to form hard solids. The resins can be processed using dry-mixing and/or extrusion prior to injection molding. Alternatively, additive manufacturing processes can be employed to form silk-based solids. Additive manufacturing describes techniques wherein a solid is constructed additively by deposition of new material onto a substrate or previously deposited material by repeated solidification of a thin liquid layer or droplet onto the substrate or previously solidified liquid layer or droplet, or by repeated printing with a thermoplastic polymeric material on a substrate or on a previously printed plastics material, or by repeated soldering in an additive fashion of plastics material e.g. by use of laser. Additive manufacturing methods include, for example, photopolymerization additive manufacturing, thermoplastic additive manufacturing, powder-based additive manufacturing, and granulate-based additive manufacturing. In some embodiments, 3-D printing is used as an additive manufacturing process.

Applications and Advantages

Silk fibroin, with its superior mechanical properties, including tensile and compressive properties, can be engineered to take on various solid shapes and conformations that match or improve on the mechanical properties of most other organic or polymeric materials (WO 2012/087823; incorporated by reference in its entirety). Solid conformations that can be prepared using silk fibroin include, for example, hydrogels (WO 2005/012606; WO 2008/150861; incorporated by reference in their entirety), laminates (WO 2012/030805; incorporated by reference in its entirety), ultrathin films (WO 2007/016524; incorporated by reference in its entirety), thick films, conformal coatings (WO 2005/000483; WO 2005/123114; incorporated by reference in their entirety), microspheres (WO 2008/118133; incorporated by reference in its entirety), 3D porous matrices (WO 2004/062697; incorporated by reference in its entirety), solid blocks (WO 2003/056297; incorporated by reference in its entirety), microfluidic devices (WO 2008/127405; WO 2008/127403; incorporated by reference in their entirety), electro-optical devices (WO 2008/140562; incorporated by reference in its entirety), and fibers with diameters ranging from the nano scale (WO 2004/0000915; incorporated by reference in its entirety) to several centimeters (U.S. Pat. No. 6,902,932; incorporated by reference in its entirety) (see also WO 2006/042287; U.S. Pat. App. Pub. No. 20070212730; WO 2008/106485; incorporated by reference in their entirety).

The silk fibroin solids described herein and produced using the methods and systems described herein can be environmentally friendly substitutes for petroleum-based chemicals. Their manufacture and use can have a reduced carbon footprint as compared with petroleum-based chemicals. Products made using the solids described herein can be recycled and/or biodegradable. These economic and environmental advantages can be achieved without compromising characteristics consumers expect of conventional plastics, including, for example, desirable flexibility, heat resistance, gloss, strength, and durability characteristics. Like conventional plastics, the solids described herein can further have permanence in form, e.g., they will not undergo chemical change when heated, allowing them to be molded and shaped, or in some instances remolded and reshaped. The solids described herein can be resistant to degradation by, e.g., sunlight or ultra-violet radiation, water or dampness, bacteria, enzymes, and wind abrasion. The solids described herein can also be resistant to other forms of degradation, including biodegradation, rodent attack, pest attack, and insect attack. Thus, the silk fibroin solids described herein and produced using the methods and systems described herein can be used as a substitute for petroleum-based products in the manufacture of a variety of consumer products, including:

- medical devices and sterile materials, including textiles, filters, biomedical coatings, wound dressings, drug release materials, biological scaffolds, and adhesives, and the like;
- toiletries such as brushes and brush bristles (toothbrushes, hairbrushes, etc.), dental floss, disposable wipes, absorptive materials, and the like;

ocular aides such as eyeglasses, eyeglass frames, and contact lenses, and other wearable devices such as watches, bracelets, rings, bands, and the like;

food-related and/or packaging materials, such as bags (reusable bags, disposable bags, packaging bags, refuse/waste bags, grocery bags, etc.), bottles, jars, jugs, containers, caps, straws, reusable storage containers, food covering films and sheets, tableware, food trays, cutting boards, food-prep surfaces, silverware, disposable dishes, disposable utensils, cutlery, ventilated food storage containers (hard containers, flexible containers), disposable cups or containers, and microwaveable materials, microwaveable surfaces, microwaveable containers, and microwaveable packaging, and the like;

non-food-related packaging materials and containers, such as clamshell packaging, foam peanuts, electronic equipment cases (e.g. external, superficial, and/or structural components of computers, monitors, printers, keyboards, and the like), detergent bottles, shampoo bottles, shopping bags, compost bags, trash bin liners, single-use disposable packaging materials, and foam packaging materials, and the like;

components of electronics and appliances, such as mobile phone bodies and parts, fluorescent light diffusers, compact discs, cassette boxes, refrigerator liners, electrical wire/cable insulation, dielectrics, laptop frames and cases, and the like;

home improvement materials and products, such as outdoor furniture, siding, floor tiles, shower curtains, window frames, flooring, light covers, electrical outlet or switch coverings and housings, and the like, piping, guttering, drainage components, tubing, insulation foams, cushion foams, and the like;

automotive or vehicular materials and products, such as fenders, bumpers, compressive materials, cushion materials, and targeted destructive zones, or crumple zones, and the like;

toys or play-related items, such as stackable or interconnecting blocks, dolls, games, puzzles, action figures, and the like;

agricultural materials and products, such as plant containers, biodegradable pots, mulches, mulch films, turf layers, turf protectants or barriers, and the like; and other consumer products and materials, including, for example, credit cards, surface coatings, printing rollers, adhesives, heat-resistant coatings, low-friction coatings, sealants, industrial paints, filtration membranes, filtration media, gun frames, picture frames, chairs, pens, protective materials, armor materials (armor, riot shields, vehicular armor, personal armor (KEVLAR substitutes), fishing line, twines, ropes, chords, brushes, bristles, and etc.

V. Textiles

The present disclosure includes methods of preparing processed silk and SBTs, different forms of SBTs, and a variety of applications for utilizing processed silk and SBTs alone or in combination with various fibers, compositions, articles and devices.

Silk-Based Textiles

As used herein, the term "silk-based product" or "SBP" refers to any compound, mixture, or other entity that is made up of or that is combined with processed silk. The term, "Silk-based textile" or "SBT" as used herein refers to any textile that is made up of or includes or is combined with SBP. In some embodiments, SBPs may be SBTs. In some embodiments, SBT may be composition may be SBPs included and/or combined with textiles. In one embodiment, SBPs may be included in SBT during the preparation of the textiles. In some embodiments, SBPs may be combined with SBTs after the preparation of the textiles. The term, "textile" as used herein refers to a material that includes one or more connected fibers and/or yarns. As used herein, the term "fiber" refers to a filament whose length exceeds its diameter. Fibers may vary in length and width and may include, but are not limited to, yarns, strings, threads, and nanofibers. The term, "processed silk," as used herein, refers to any forms of silk harvested, obtained, synthesized, formatted, manipulated, or altered through at least one human intervention. In some embodiments, SBTs may be prepared from SBPs. In some embodiments, SBPs may be or may include textiles. In some embodiments, SBTs may be or may include SBPs and textiles,

Recycled Silk-Based Textiles and Recycled Silk-Based Products

In some embodiments, SBTs and/or SBPs produced by methods described herein may be used as a source of silk and are herein referred "recycled silk-based textiles" or "RSBT" and recycled silk-based products" or "RSBPs". RSBT and/or RSBPs may be used as a silk source prior to intended application and/or following the intended application.

In some embodiments, RSBTs may be used as silk source. Non-limiting examples of RSBTs and/or RSBPs articles such as apparel, footwear, containers, bags, personal protection equipment textiles, furnishings, sporting goods, transportation textiles, infrastructure construction articles, geotextiles, industrial textiles, therapeutic textiles, agrotextiles, consumer products and/or consumer textiles.

Recycling products and materials has the potential to reduce the impact of SBT and/or SBP production and use on the environment. Natural fibers may take hundreds of years to decompose in landfills. They may release methane and CO2 gas into the atmosphere. Additionally, synthetic fibers may not to decompose in landfills, and/or may release toxic substances into groundwater and surrounding soil. Recycling therefore has the potential to decrease landfill space requirements, reduce consumption of energy and water, and minimize pollution.

In some embodiments, the RSBTs and/or RSBPs may be substantially homogeneous or heterogeneous. RSBTs and/or RSBPs utilized as silk source may include greater than 90; greater than 80%; greater than 70%; greater than 60%; greater than 50% %; greater than 40%; greater than 30%, greater than 20%, greater than 10%, greater than 5%, greater than 4%, greater than 3%, greater than 2%, or greater than 1% processed silk. RSBTs and/or RSBPs may also include silk produced by silk producers and/or synthetic silk.

In some embodiments, RSBT may be or may include commercially available fabrics which may be prepared by methods known in the art. Commercially available fabrics may include but are not limited to charmeuse (silk satin), silk gauze, fuji silk, silk noil, silk shantung, tussah silk, silk organza, silk broadcloth, silk brocade, four-ply silk, silk/metal tissue, peau de soie (duchess datin), habutai silk/habotai silk, silk pongee, china silk, spun silk, watered silk, tulle, gazar, faille, Thai silk, and/or Indian silks (e.g. matka silk, surah, Garad silk, Jamawar, Banarasi/Benarasi silk, Bangalore silk, Angora silk, Pochampally/Pochampalli silk, Mysore silk, Sournachuri silk, Kosa silk, Muga silk, Dharamavaram silk, Narayanpet silk, Pat/Paat silk, Kanchipuram silk, Bhagalpuri silk, Uppada silk).

In some embodiments, recycled silk-based textiles may include textile blends. As used herein, the term "textile blend" as used herein refers to textiles that include or a prepared as a combination of two or more types of fibers. In some embodiments, textile blend may include silk fiber. The percentage of silk fiber in a textile blend may be greater than 90; greater than 80%; greater than 70%; greater than 60%; greater than 50% %; greater than 40%; greater than 30%, greater than 20%, greater than 10%, greater than 5%, greater than 4%, greater than 3%, greater than 2%, and/or greater than 1% processed silk. Table 6 provides examples of textile blends that include silk fibers.

TABLE 6

Textile blends with silk fiber

| Name | Fiber components |
|---|---|
| — | Cotton, silk |
| — | Silk, wool |
| — | Art, silk |
| — | Khadi, silk |
| — | Silk, cashmere |
| — | Silk, linen |
| — | Silk, bamboo |
| — | Silk, nylon, viscose |
| Batiste | Cotton, silk, polyester |
| Broadcloth | Cotton, silk, rayon, polyester |
| Challis | Cotton, silk, wool, rayon |
| Charmeuse | Silk, polyester, rayon |
| Chiffon | Silk, polyester |
| Crepe | Silk, rayon, cotton, wool, polyester |
| Crepe de Chine | Silk, polyester, rayon, nylon, acetate |
| Damask | Wool, cotton, linen, silk, polyester |
| Dupioni | Silk, polyester |
| Faille | Silk, cotton, wool |
| Gauze | Cotton, wool, silk, poly/blends |
| Georgette | Silk, polyester, rayon |
| Jersey | Cotton, wool, rayon, poly/blends, silk |
| Khadi Silk | Cotton and silk (handspun) |
| Lace | Cotton, nylon, polyester, silk |
| Satin | Silk, rayon, acetate, nylon, polyester, cotton, wool |
| Suiting | Wool, cashmere, silk, rayon, polyester |
| Taffeta | Silk, polyester, rayon, nylon, acetate |
| Tweed | Wool, silk, polyester, blends |
| Twill | Cotton, wool, silk, poly/blends |
| Velvet | Silk, rayon, polyester |

In some embodiments, RSBTs and/or RSBPs may include one or more formats such as but not limited to from the group consisting of yarns, fibers, sheets, textile, discs, nanofibers, particles, cylinders, nanoparticles, solutions, gels, hydrogels, organogels, powders, solids, threads, spuns, mats, films, foams, suspensions, sprays, membranes, rods, tubes, microspheres, nanospheres, cones, patches, sponges, scaffolds, capsules, nets, grafts, vapors, emulsions, tablets, and/or adhesives. RSBTs may be prepared from articles and/or compositions that include SBTs. Such as but not limited to apparel, apparel accessories, footwear, bags, personal protection equipment, furnishings, sporting goods, therapeutic textiles, agrotextiles, articles used in infrastructure construction, geotextiles, and/or industrial textiles.

SBT Waste and SBP Waste

In some embodiments SBT waste and/or SBP waste may be used as a source of silk. As used herein, any material that is deemed unusable for its intended purpose may be referred to as a "waste." "SBT waste" and "SBP waste" respectively may be defined as waste generated during the preparation/production, use or disposal of SBTs and SBPs respectively.

In some embodiments, SBT waste and/or SBP waste may be pre-consumer waste such as but not limited to (i) defective cocoons (ii) waste and by-products generated during processing methods described herein (iii) scrap and surplus.

SBT waste and/or SBP waste may be defective cocoons. As used herein, "defective cocoon" refers to a cocoon that may have one or more characteristics such as but not limited to double cocoon, dead cocoon, an outside discolored cocoon, an abnormally shaped cocoon, a flimsy cocoon, a cocoon with thin ends, and/or a pierced cocoon. In some embodiments, a defective cocoon may be a double cocoon which includes a cocoon spun by two worms. In some embodiments, a defective cocoon may be a dead cocoon wherein the pupa is dead and sticks to the inside shell of the cocoon. In some embodiments, a defective cocoon may be an outside discolored cocoon which may be identified by a rusty color spot on the cocoon shell which may be caused by absorption of intestinal fluid/urine of the mature worm. In some embodiments, a defective cocoon may be a flimsy cocoon wherein the cocoon may be loosely spun by the pupa in layers and has a low silk content. In some embodiments, a defective cocoon may be a thin-end cocoon wherein one or both ends of the cocoon may be very thin. In some embodiments, a defective cocoon may be a pierced cocoon caused by the emergence of the moth from the cocoon, emergence of parasite (e.g. Uzi) or damage caused by pests such as beetles.

SBT waste and/or SBP waste may also include waste and/or by-products generated during processing methods described herein. In some embodiments, broken, kinked, tangled silk fibers, yarns, and/or threads may be used as a silk source. In some aspects, raw silk fibers obtained from the outer and/or inner layers extracted from the cocoon may be used as silk source. In one embodiment, SBT waste may be threads and/or yarn that cannot be reeled continuously.

In some embodiments, SBT waste and/or SBP waste may include materials left over from the production of SBPs and SBTs described herein. SBT waste and/or SBP waste may also include defective, damaged and/or non-functional textiles and products that do not behave as expected. SBTs and/or SBPs generated in surplus of their demand, and/or are no longer of use to a consumer may also considered as waste.

In one embodiment, SBP waste may be a solution.

In one embodiment, SBP waste may be a precipitate.

In some embodiments, SBT waste and/or SBP waste may be post-consumer waste which may include waste generated by (i) wear and tear (ii) outdated and/or (iii) post-consumer use (iv) damaged/degraded. In some embodiments, SBTs and/or SBPs that may be subject to consumer use may suffer wear and tear and/or no longer satisfy their intended purpose and may be considered as SBT waste and/or SBP waste. Materials, textiles, devices, articles prepared with or including SBTs and/or SBPs may no longer be popular with the consumer and/or may not be considered attractive resulting in the discontinuation of their use thereby generating SBT waste and/or SBP waste. In some embodiments, the silk source may be SBT waste and/or SBP waste generated by the completion of the intended use of the textile and/or product. SBTs and/or SBPs damaged or degraded as a result of consumer use may also be considered SBT waste and SBP waste respectively.

Upstream Silk-Based Textile Processing

Various processing methods may be used to obtain specific forms or formats of processed silk. Such processing methods may include, but are not limited to, acidifying, air drying, alkalinizing, annealing, autoclaving, chemical cross-linking, chemical modification, concentration, cross-linking, degumming, dissolving, dry spinning, drying, electrifying, electrospinning, electro spraying, emulsifying, encapsulating, extraction, extrusion, gelation, harvesting, heating, lyophilization, molding, oven drying, pH alteration, precipitation, purification, shearing, sonication, spinning, spray drying, spray freezing, spraying, vapor annealing, vortexing, and water annealing. The processing steps may be used to prepare final SBTs and/or SBPs or they may be used to generate processed silk preparations. As used herein, the term "processed silk preparation" is generally used to refer to processed silk or compositions that include processed silk that may be prepared for or obtained during or after one or more processing steps. Processed silk preparations may be SBTs and/or, may be components of SBTs and/or, or may be used as a starting or intermediate composition in the preparation of SBPs. Processed silk preparations may include other components related to processing (e.g., solvents, solutes, impurities, catalysts, enzymes, intermediates, etc.). Processed silk preparations that include silk fibroin may be referred to as silk fibroin preparations. In some embodiments, processed silk manufacturing is simple, scalable, and/or cost effective.

In some embodiments, processed silk may be prepared as, provided as, or included in a yarn, thread, string, a nanofiber, a particle, a nanoparticle, a microsphere, a nanosphere, a powder, a solution, a gel, a hydrogel, an organogel, a mat, a film, a foam, a membrane, a rod, a tube, a patch, a sponge, a scaffold, a capsule, an excipient, an implant, a solid, a coating, and/or a graft.

In some embodiments, the compositions may be prepared to be sterile. As used herein, the term "sterile" refers to something that is aseptic. In some embodiments, SBTs and/or SBPs may be prepared from sterile materials. In some embodiments, SBTs and/or SBPs may be prepared and then sterilized. In some embodiments, processed silk is degummed and then sterilized. In some embodiments, processed silk is sterilized and then degummed. Processed silk, SBTs and/or SBPs may be sterilized via gamma radiation, autoclave (e.g., autoclave sterilization), filtration, electron beam, and any other method known to those skilled in the art.

In some embodiments, processed silk may be stored frozen or dried to a stable soluble form. Processed silk may be frozen with cryoprotectants. Cryoprotectants may include, but are not limited to, phosphate buffer, sucrose, histidine, and any other cryoprotectant known to one of skill in the art. In some embodiments, SBTs and/or SBPs may be stored frozen or dried to a stable soluble form. In some embodiments, the SBTs and/or SBPs may be solutions.

In some embodiments, preparation of processed silk, SBTs and/or SBP compositions may be scaled up for manufacturing at a large scale. In some embodiments, production of processed silk and/or SBP compositions may be accomplished with automated machinery.

Any of the methods known in the art and/or described herein may be used to extract silk fibroin. The yield of silk fibroin from extraction may be, but is not limited to, 1%, 2%, 3%, 4%, 5%, 5.8, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99%.

In some embodiments, any of the processing methods described herein may be performed as a batch processing and/or as continuous processing. As used herein, the term "batch processing" may be defined as processing method that includes a sequence of one or more steps that may be performed in a defined order. A finite quantity of the product is produced at the end of the sequence, which may be repeated in order to produce another finite quantity of the product. As used herein, the term "continuous processing" may be defined as processing that may involve moving a single work unit at a time between every step of the process without any breaks in time, substance, sequence or extend. In some embodiments, any of the processing methods may be used in conjunction with solvent recovery. As used herein, the term "solvent recovery" may be defined as the process of extracting useful materials from waste and/or by-product solvents generated during the process of manufacturing SBTs and/or SBPs.

Harvesting Silk

Harvesting from Silk Producers

In some embodiments, processed silk may be harvested from silk producer cocoons (including defective cocoons). Cocoons may be prepared by cultivating silkworm moths and allowing them to pupate. Once fully formed, cocoons may be treated to soften sericin and allow for unwinding of the cocoon to form raw silk fiber. The treatment may include treatment with hot air, steam, and/or boiling water. Raw silk fibers may be produced by unwinding multiple cocoons simultaneously. The resulting raw silk fibers include both silk fibroin and sericin. Subsequent processing may be carried out to remove sericin from the raw silk fibers or from later forms of processed silk or SBPs. In some embodiments, raw silk may be harvested directly from the silk glands of silk producers. Raw silk may be harvested from wild type or GMO silk producers.

Harvesting Silk from RSBT, SBT Waste, RSBP and SBP Waste

In some embodiments, processed silk may be harvested from recycled and waste SBT/SBPs. Recycled and waste SBT/SBPs may be collected and sorted using criteria such as but not limited to weight, size, components and/or composition. Manual sorting and visual inspection may be employed to sort based on physical attributes such as state, form, and color. Techniques and equipment that enable automated sorting may also be employed. In some embodiments, sorting may be performed using radio frequency identification (RFID) technology. Recycled and waste SBT/SBPs may include chips encoding information that may be useful in sorting such as composition and/or fiber identity. In some embodiments, recycled and waste SBT/SBPs may be sorted based on their silk fibroin content. In some embodiments, silk fibroin content may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99%.

In some embodiments, physical and mechanical processing may be included in the process of harvesting silk from recycled and/or waste SBT/SBP silk sources. Mechanical processing may include methods and steps wherein recycled and waste may be transformed to a secondary material without changing basic structure. Such processes may also involve the removal of non-silk fibroin components such as but not limited to buttons, zippers, closures, and/or tags. Mechanical processing methods may also include sizing or comminution methods such as such as shredding, extruding silk fibers, pulling, grinding, cutting, and/or tearing. In some embodiments, mechanical processing methods may include carding. As used herein, "carding" refers to the process of untangling, separating and organizing fibers. Carding may also involve willowing. As used herein, the term "willowing" may be defined as a process wherein the fibers may be loosened and separated. In some embodiments, carding may include the process of opening. As used herein, the term "opening" refers to the methods wherein recycled and/or waste SBT/SBP silk sources are blended together to achieve a uniform consistency and/or are broken down in smaller tufts of fibers. In one embodiment, carding processing methods may be combined with one or more methods designed to remove colorants from recycled and/or waste SBT/SBP silk sources.

In one embodiment, processed silk obtained after carding may be mixed with other fibers prior to further processing.

In some embodiments, chemical processing may be included in the process of harvesting silk from recycled and/or waste SBT/SBP silk sources. Chemical processing may include aqueous washing, oxidation/reduction, treatment with swelling agents, organic solvents, enzymatic treatment, extrusion after chemical processing.

In some embodiments, chemical processing may include aqueous washing. The washing step may facilitate the removal of contaminants such as soils, deodorant, lanolin, silicone, and cationic softeners as well as stripping various product/and or textile treatments, such as but not limited to optical brighteners, and/or moisture wicking enhancers. Aqueous washing may be performed at high temperature such as but not limited to 100° C., 110° C., 120° C., 130° C., 140° C., 150° C., 160° C., 170° C., 180° C., 190° C., 200° C. The high temperature aqueous washing may be conducted in a closed vessel batch system with circulation or agitation or mixing of the hot aqueous media. Pressure conditions in a closed vessel system, as described, may range from 100 kPa to about 2000 kPa, depending on the temperature of the aqueous media, with higher pressure conditions accompanying higher temperature media.

In some embodiments, chemical processing may include treatment with an oxidative or reducing agent. The treatment may occur in an aqueous solution. Duration of the treatment with the oxidative or reducing agent may depend on time required to remove materials such as but not limited to dyes, finishes, and contaminants. Suitable oxidative and/or reducing agents include peroxide compositions (e.g. hydrogen peroxide, sodium peroxide) and perborate (sodium perborate. Additional oxidative and/or reducing agents that may be used include agents such as but not limited to per carbonate compositions; per acetic acid compositions; potassium permanganate; persulfate compositions; ozone; sodium chloride; calcium oxychloride; sodium hypochlorite, calcium hypochlorite; lithium hypochlorite; chloramine; isocynual trichloride; sulphur dioxide; sodium hydrosulfite; sulphoxylates; acidic sodium sulphite; sodium bisulphite; sodium meta bisulphite; TAED (tetra-acetyl-ethylene-diamine)oxi; and sodium hydrosulfite. The oxidizing/reducing agent may be evacuated following a suitable residence time and optional rinsing of solids within an aqueous solution may be implemented. Rinsing may be implemented at ambient temperatures with a rinse solution removed following a suitable residence time. The oxidizing/reducing agent may be neutralized, following this treatment. In some embodiments, multiple cycles may be implemented using different oxidative and reducing agents using different concentrations of agents, pH, temperature and/or residence time.

In some embodiments, chemical processing may include treatment with one or more swelling agents such as but not limited to an ionic liquid. Swelling agents may include hydroxides such as of Ca, Mg, Na, K, and/or Li. Swelling agents suitable for use as reagents may alternatively or additionally include one or more of the following agents: [AMIM]Cl I-Allyl-3-methylimidazolium chloride; [BzPy]Cl Benzylpyridinium chloride; [BMIM]Ace I-Butyl-3-methylimidazolium acesulphamate; [BMIM]DBP I-Butyl-3-methylimidazolium dibutylphosphate; [BMIM]Cl I-Butyl-3-methylimidazolium chloride; [BMIM]PF6 I-Butyl-3-methylimidazolium hexafluorophosphate; [BMIM]BF4 1-Buty 1-3-methy limidazolium tetrafluoro borate; [BMPy]Cl I-Butyl-3-methylpyridinium chloride; [DBNH]AcO 1,8-Diazabicyclo [5.4.0]undec-7-enium acetate; [DBNH]EtCOO 1,8-Diazabicyclo [5.4.0]undec-7-enium propionate; [DMIM]DEP 1,3-Dimethylimidazolium diethylphosphate; [DMIM]DMP 1,3-Dimethylimidazolium dimethylphosphate; [EMBy]D EP 1-Ethyl-3-methy Ibutylpyridinium diethyl phosphate; [EMIM]AcO I-Ethyl-3-methylimidazolium acetate; [EMIM]Br I-Ethyl-3-methylimidazolium bromide; [EMIM]D BP 1-Ethy 1-3-methy limidazolium dibutylphosphate; [EMIM]DEP I-Ethyl-3-methylimidazolium diethylphosphate; [EMIM]DMP I-Ethyl-3-methylimidazolium dimethyl phosphate; [EMIM]MeSO4 1-Ethy 1-3-methy limidazolium methanesulphonate; [HPy]Cl 1-Hexylpyridinium chloride; [E (OH) MIM]AcO I-Hydroxyethyl-3-methylimidazolium acetate; [DBNMe]DMP I-Methyl-1,8-diazabicyclo [5.4.0]undec-7-enium dimethylphosphate; [P4444]OH Tetrabutylphosphonium hydroxide; [TMGH]AcO 1,1,3,3-Tetramethylguanidinium acetate; [TMGH]n-PrCOO 1,1,3,3-Tetramethylguanidinium butyrate; [TMGH]COO 1,1,3,3-Tetramethylguanidinium formiate; TMGH]EtCOO 1,1,3,3-Tetramethylguanidinium propionate; [P8881]AcO Trioctylmethylphosphonium acetate; and HEMA Tris-(2-hydroxyethyl)methylammonium methylsulphate.

In some embodiments, chemical processing may include treatment with an organic solvent such as but not limited to Acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxy-, ethane (glyme, DME), dimethyl-, formamide (DMF), dimethyl sulfoxide (DMSO), 1,4-dioxane, ethanol, ethyl acetate, ethylene glycol, glycerin, heptane, Hexamethylphosphoramide, (HMPA), Hexamethylphosphorous, triamide (HMPT), hexane, methanol, methyl t-butyl, ether (MTBE), methylene chloride, N-methyl-2-pyrrolidinone, (NMP), nitromethane, pentane, Petroleum ether (ligroine), 1-propanol, 2-propanol, pyridine, tetrahydrofuran (THF), toluene, triethyl amine, water, water, heavy, o-xylene, m-xylene, or p-xylene.

In some embodiments, chemical processing may include enzymatic treatment. Due to their high specificity, enzymes allow step-wise recovery of the components of blended materials. Enzymatic hydrolysis may be utilized to degrade materials in a blend such as but not limited to cotton, wool, polyester. When the recycled and/or waste SBT/SBP silk sources include cellulose, enzymatic treatments may be employed to increase solubility and/or reduce reaction times in processing. Enzymes may include endoglucanases (e.g. Cel 5A, Cel 7B, Cel 12A, Cel 45, Cel 61A); Cellobiohydrolases (e.g. Cel 6A, Cel 7A); LMPO/GH61; cellulases. Enzymatic treatment may be carried out at a pH such as but not limited to 4, 5, 6, 7, 8 or 9. Duration of the enzymatic treatment may be related to the concentration of the enzyme substrate present in the silk source.

In some embodiments, chemical processing may be performed to remove colorants from recycled and/or waste SBT and/or SBP silk sources. In some embodiments, the chemical processing methods may include any of the methods utilized for extraction of sericin and/or degumming. In some embodiments, removal of colorants from recycled and/or waste SBT and/or SBP sources may include treatment with degumming agents and/or degumming solutions such as but not limited to water, alcohols, soaps, acids, alkaline solutions, and enzyme solutions. In some embodiments, degumming solutions used for chemical processing may include salt-containing alkaline solutions. Colorants may be removed from SBT and/or SBP recycled and/or waste sources by boiling in degumming agents and/or solutions. The duration and/or temperature of boiling may be varied depending on the amount of colorant present in the silk source.

In some embodiments, chemical processing may involve the dissolution of the recycled and/or waste SBT/SBP silk sources silk with the aid of a chaotropic agent. Non-limiting examples of chaotropic agents include, but are not limited to, sodium dodecyl sulfate, ethanol, methanol, phenol, 2-propanol, thiourea, urea, n-butanol, and any other chemicals capable of solubilizing silk. In some embodiments, the chaotropic agent is a salt, including, but not limited to, zinc chloride, calcium nitrate, lithium perchlorate, lithium acetate, sodium thiocyanate, calcium thiocyanate, magnesium thiocyanate, calcium chloride, magnesium chloride, guanidinium chloride, lithium bromide, lithium thiocyanate, copper salts, and other salts capable of solubilizing silk.

Following chemical processing, the recycled and/or waste SBT/SBP silk sources may be subject to a dissolving step which includes treatment with reagents that promote molecular separation of the processed silk such as but not limited to silk fibers. Processed silk may be separated by sedimentation, size exclusion or filtration steps. Suitable methods for separation may depend on the types and levels of contaminants/constituents remaining. In some embodiments, a cascade of progressively smaller pore size filtration stages may follow preliminary separation by gravitation or centrifugation. Separated byproducts may be isolated and purified.

In some embodiments, material recycling may be included in the process of harvesting silk from recycled and/or waste SBT/SBP. As used herein, material recycling refers to the recovery of processed silk from recycled and/or waste SBT/SBP in a format that is suitable and ready for preparation of SBTs/SBPS described herein without additional processing steps. For example, silk fibers, silk threads, and/or silk yarns extracted from recycled and waste SBT/SBPs may be used without further physical, mechanical, or chemical processing of the recycled or waste materials.

Extraction of Sericin/Degumming

In some embodiments, SBTs and/or SBPs may be prepared by degumming. In some embodiments, sericin may be removed from processed silk, a process referred to herein as "degumming." The processed silk may include raw silk, which includes sericin secreted during cocoon formation. Methods of degumming may include heating (e.g., boiling) in a degumming solution. As used herein, the term "degumming solution" refers to a composition used for sericin removal that includes at least one degumming agent. As used herein, a "degumming agent" refers to any substance that may be used for sericin removal. Heating in degumming solution may reduce or eliminate sericin from processed silk. In some embodiments, heating in degumming solution includes boiling. Heating in degumming solution may be followed by rinsing to enhance removal of sericin that remains after heating. In some embodiments, raw silk is degummed before further processing or utilization in SBPs. In other embodiments, raw silk is further processed or otherwise incorporated into a SBP prior to degumming. Such methods may include any of those presented in European Patent No. EP2904134 or United States Publication No. US2017031287, the contents of each of which are herein incorporated by reference in their entirety. In one embodiment, SBT waste and/or SBP waste may be processed using processing methods described in Mollahosseini, et al. (2019). Recycling of waste silk fibers towards silk fibroin fibers with different structures through wet spinning technique. Journal of Cleaner Production. 236. 117653. 10.1016/j.jclepro.2019.117653. (the contents of which are herein incorporated by reference in their entirety).

Reeling and Silk Throwing

In some embodiments, SBPs and/or SBTs may be prepared by reeling and/or silk throwing. As used herein "reeling" refers to the process of unwinding the cocoon to release silk filaments. In some embodiments, silk filaments from more than one cocoon may be joined, twisted and combined with a number of similarly twisted filaments. Raw silk obtained by the process of reeling may herein be referred to as "reeled silk". Reeling may be performed using methods and/or machines such as but not limited to hand spinning wheel, charka type reeling machine, sitting type reeling machine, multi-end reeling machine, semi-automatic reeling machine. The winding speed of reeling (herein referred to as the "reeling rate" may be adjusted depending on the required size of the raw silk fibers and the size of the cocoon. In some embodiments, the reeling rate may be adjusted to reduce breakage of the silk fibers. Reeling maybe performed at a temperature from about 20° C. to about 70° C., preferably from about 30° C. to about 45° C. In some embodiments, reeling may be performed in a water bath. In some embodiments, the reeling process may be repeated one or more times.

Raw silk may also be processed by "silk throwing". As used herein, "silk throwing" refers to raw silk that has been reeled into skeins, is cleaned, twisted and wound onto bobbins. During the winding process, single fibers may be given any desired amount of twist. Two or more fibers or yarns may be twisted more than one time, in the same direction or in opposing directions in a process referred to herein as "doubling". Depending on the method used, silk throwing may generate silk fibers such as but not limited to thrown singles, trams, organzine, and/or crepe. As used herein, "thrown singles" may refer to individual raw silk fibers, threads or yarns, that may be twisted in only one direction. The number of turns may depend on the quality desired. In some embodiments, three to eight strands of silk fibers, threads or yarns may be twisted together in one direction to form a thrown single. As used herein, "trams" may include two or more thrown singles, twisted, and doubled. As used herein, "organzine" may include thrown singles, twisted one way, then doubled and twisted in the opposite direction. As used herein, "crepe" may include thrown single with more than one twist.

Wet Spinning

In some embodiments, in addition to electrospinning and dry spinning, spinning may be carried out as wet spinning. Wet spinning may be used to prepare silk fibers from processed silk preparations. In wet spinning, fibers may be extruded directly into a liquid bath. Extrusion in a liquid bath, provides a greater drag force on the filaments when compared to dry spinning. A second liquid bath containing a non-solvent may be included to precipitate out the fibers.

In some embodiments, the liquid baths used for wet spinning may cause coagulation of silk proteins. A syringe pump may be used to inject processed silk preparations into a first liquid bath using a steel capillary tube resulting in the extrusion of processed silk into silk fibers. The silk fibers may be passed through a guide roller to stretch out and pull the silk fibers. The guide roller may be used to transfer the extruded silk fibers from the first liquid bath to a take up roller in the second liquid bath. The second liquid bath may be used to strengthen the silk fibers. In some embodiments, the first liquid bath may be prepared with sodium sulphate and/or ammonium sulphate. In one embodiment the first liquid bath may be or may include 10% w/v sodium sulfate and 10% w/v ammonium sulfate. In one embodiment, the first liquid bath may include Ajisawa's salt. In some embodiments, the second liquid bath may be or may include an alcohol. In one embodiment, the second liquid bath may include methanol. In one embodiment, the second liquid bath may be 80% methanol. In one embodiment, the second liquid bath may include ethanol. In some embodiments, the second liquid bath may increase beta sheet formation. In one embodiment, the second liquid bath may be removed colorants present in the silk fibers. The silk fibers may be subject to one or washing steps after extrusion from the second liquid bath. In one embodiment, the washing step may include a salt and/or a solvent.

In some embodiments, spinning may include the optional step of gassing. As used herein, "gassing" may involve the passing of the processed silk through a series of Bunsen gas flames in a gassing frame in order to burn off the projecting fibers to make it smoother.

Downstream Silk-Based Textile Processing

Processed Silk Preparation Characterization

Preparations of processed silk may include mixtures of silk fibroin polymers, silk fibroin monomers, silk fibroin heavy chains, silk fibroin light chains, sericin, and/or fragments of any of the foregoing. Where the exact contents and ratios of components in such processed silk preparations may be unknown, the preparations may be characterized by one or more properties of the preparation or by conditions or methods used to obtain the preparations. As a non-limiting example, the sericin content in the SBT and/or SBP compositions may be 0%, 0.5%, 1%, 1.5%, 2%, 2.5%, 3%, 3.5%, 4% or greater than 4%, or in the range of 0-1%, or 0-2%.

In some embodiments SBTs and/or SBPs produced from recycled and/or waste SBT/SBP silk sources may be subject to a colorant removal process prior to downstream processing.

Weaving and Knitting

In some embodiments, SBTs and/or SBPs may be prepared by weaving. In some embodiments, processing methods may include weaving. As used herein "weaving" refers to two or more set of fibers that may be interlaced. In some embodiments, the fibers may be interlaced at right angles. The fibers utilized in weaving may include silk fibers. In some aspects, the weaving may include two different types of fibers. In some embodiments, the longitudinal fibers may be referred to as the warp and the lateral fibers may be referred to as the weft. The format utilized to interweave the fibers may affect the characteristics of the SBTs and/or SBPs described herein. In some embodiments, weaving may be performed using a loom, and may include primary motions such as shedding (wherein the warp fibers may be separated), picking (wherein the weft fibers may be propelled across the loom) and/or battening (wherein the weft is pushed up). In some embodiments, SBTs may include a (i) plain weave (wherein the warp and weft fibers cross at right angles and may be aligned to form a criss-cross pattern (ii) twill weave (which includes a pattern of diagonal parallel ribs which may be achieved by passing the weft fiber over one or more warp fibers then under two or more warp fibers, with an offset, between rows to create the characteristic diagonal pattern (iii) satin weave (wherein four or more weft fibers float over a warp fibers, and/or four fibers floating over a single weft fiber (iv) pile (which includes knots in the warp and/or weft fiber). up). In some embodiments, SBTs may include a combination of one or more weaving methods described herein.

In some embodiments, the characteristics of SBT and/or SBP prepared using weaving processing methods may be altered by tuning several weaving parameters. In some embodiments, the number of warp fibers, weft fibers per unit length may be altered to tune the closeness of the weave. As used herein "textile balance" may refer to the proportion of the warp fibers to the weft fibers. A "good" balance may be achieved when the nearly the same number of warp and weft fibers may be utilized in the weave. In some embodiments, SBTs and/or SBPs prepared by weaving may be classified by their thread count. As used herein "thread count" may be defined as the number of warp and weft fibers per square inch. In some embodiments, weaving processing methods described herein may be used to produce a thread count from about 200 to about 1000.

In some embodiments, processing methods may include knitting. As used herein "knitting" may be defined as a production method that employs a continuous fiber or a set of fibers to form interlocking loops, and include a column of loops running lengthwise (also referred to as the wale) as well as a course of crosswise row of loops. In some embodiments, fibers utilized for knitting may be silk fibers. In some embodiments, silk fibers may be used in combination with non-silk fibers for knitting. Knitting needle size and stitch type may be altered to achieve SBTs with varying properties. Knitting may include one or more type of stitches such as a knit stitch wherein a loop is passed through the front of the preceding loop and/or a purl stitch where a loop is passed through the back of the preceding loop. Knitting may be performed by hand and/or by using a machine.

Web Formation and Bonding

In some embodiments, SBTs and/or SBPs may be prepared by web formation. Web formation may be utilized to generate textiles that may be or that include SBTs and/or SBPs. Fibers such as but not limited to silk fibers may be prepared as a mesh or a web using methods such as carding, air laying and/or wet laying. In some embodiments, web formation may be used to process silk sourced from SBT waste, SBP waste, RSBT, and/or RSBP. In some embodiments, the fibers may be or may include silk fibers. In some aspects, a blend of fibers may be utilized. As used herein, "carding" refers to the process of untangling, separating and organizing fibers. Carding may involve willowing a process wherein the fibers may be loosened and separated. Fibers may then be processed to remove dust to create a flat sheet or a lap of fibers. In the process of combing, the sheet of fibers is combed into a "sliver." Multiple steps of combing may be performed to separate fibers according to length. Carding may also include the process of drawing wherein slivers may be combined.

In some embodiments, SBT and/or SBP may be prepared by pneumatically gathering fibers to form a web in a process referred to herein as "air laying." Processing methods may also include wet laying wherein fibers may be passed through a liquid to generate inter and intra fiber connection resulting in the formation of a web. In some embodiments, a plurality of webs may be generated by the processing methods described herein.

In some embodiments, SBTs and/or SBPs may be prepared by processing methods described herein such as but not limited to bonding to enhance the strength of the fibers prepared by web formation. In chemical bonding, bonding agents may be used to hold the fibers together. In some embodiments, the bonding agents may be polymers and/or adhesives. In one embodiment, latex polymers may be used in the bonding process. Bonding agents may be applied by impregnating, coating, spraying, or printing. In some embodiments, bonding may be achieved by mechanical processing methods wherein fiber connectivity is achieved as a result of physical entanglement. Specially designed needles may be pushed and pulled through the web to connect the fibers using a technique referred to herein as "needle punching." Mechanical bonding may also be achieved by hydroentanglement wherein high pressure water jets may be utilized to interlace the fibers. Bonding may also be performed using thermal energy wherein the fibers may be melted using high temperature in a controlled environment followed by cooling which may solidify the bonding area. Thermal bonding processes may include calendering bonding, air bonding, infrared bonding, and ultrasonic bonding.

Finishing

In some embodiments, SBTs and/or SBPs may be prepared by finishing. As used herein "finishing" may be defined as mechanical and chemical processing methods applied to SBTs and/or SBPs to improve performance, appearance, function or otherwise achieve an end-use property of SBTs and/or SBPs. Finishing processing methods may be performed at any stage or step of the silk processing methods, prior to and/or after the completion of the processing methods described herein. Finishing methods may include but are not limited to singeing, calendering, sanforization, scouring, bleaching, chemical finishing, dyeing and printing. In some embodiments, finishing may add or impart features or properties to the SBTs and/or SBPs. In one embodiment finishing may be performed to improve the hand and the softness of the SBT. In some embodiments, finishing may be employed to increase the ease of wash, crease resistance, and/or ironing requirements of the SBTs and/or SBPs described herein. In some embodiments, finishing may be employed to impart resistance to dirt, water/moisture, odor, fire, UV, static charge, and/or damage caused by pests. In one embodiments, finishing may be employed to prepare SBTs and/or SBPs that are visually pleasing to a subject and include methods such as dyeing, and/or printing. In one embodiment, finishing may be employed to prepare SBTs and/or SPBs that are fragrant.

Singeing

In some embodiments, SBTs and/or SBPs may be prepared by singeing. As used herein "singeing" may refer to process of burning of surface or protruding fibers from processed silk, SBTs and/or SBPs. Singeing may improve smoothness and or luster of the processed silk. In some embodiments, brushing may precede singeing to elevate and expose the protruding fibers. Singeing may be performed using a hot plate, a roller or a gas singeing machine.

Calendering

In some embodiments, SBTs and/or SBPs may be prepared by calendering. In some embodiments, processed silk, SBTs and/or SBPs may be passed between heated rollers to generate smooth, polished and/or embossed effect on the SBTs and/or SBPs in a process referred to as "calendering." The generated effect may be dependent on the roller surface properties and/or roller speed.

Sanforization

In some embodiments, SBTs and/or SBPs may be prepared by sanforization. As used herein, "sanforization" refers to a method of stretching, shrinking and fixing processed silk, SBTs and/or SBPs to fix fibers and/or textiles in length and width prior to cutting. Such finishing methods may be used to reduce shrinkage that may occur due to washing. In sanforization, processed silk, SBTs and/or SBPs may be fed into a machine where they may be treated with water or steam to promote shrinkage, and then pressed against a heated rubber band to relax and re-contract the fibers.

Scouring and Bleaching

In some embodiments, SBTs and/or SBPs may be prepared by scouring and/or bleaching. In some embodiments, processed silk, SBTs and/or SBPs may contain natural color and/or impurities which may need to be removed in order to make the processed silk, SBTs and/or SBPs suitable for a specific application. The removal of natural color and/or impurities may involve scouring and/or bleaching. SBTs and/or SBPs described herein may be rinsed in an aqueous medium to remove dirt, contaminants and any undesired materials. Reagents may be optionally be added to the aqueous medium to remove select contaminants. For example, an alkaline solution may be used to remove free fatty acids. As used herein "bleaching" refers to the processing method that involves the removal of color from processed silk, SBTs and/or SBPs. Depending on the components and/or composition of the SBTs and/or SBPs oxidative bleaching agents (e.g. sodium hypochlorite, sodium chlorite) and/or reductive bleaching agents (e.g. sodium hydrosulphite) may be employed. Processed silk, SBTs and/or SBPs may optionally treated with chemical compounds that absorb light in the ultraviolet and violet region and re-emit light in the blue region by fluorescence (herein referred to as "optical brightening agents").

Chemical Finishing

In some embodiments, SBTs and/or SBPs may be prepared by chemical finishing. As used herein "chemical finishing" refers to the process of utilizing chemicals to improve performance, appearance, function or otherwise achieve an end-use property (herein referred to as "finishing agents") of the SBTs and/or SBPs. In some embodiments, chemical finishing may be durable, i.e. the finish is intended to last through the repeated use of the SBTs and/or SBPs, or transient, i.e. not intended to last through repeated use of the SBTs and/or SBPs. Chemical finish may be applied to processed silk, and/or during the processing methods described herein and/or after the preparation of SBTs and/or SBPs. In some embodiments, a finishing agent may be a solution or an emulsion. Finishing agents that have strong affinity for the processed silk, fibers, SBTs and/or SBPs may be applied by discontinuous/batch processes whereas finishing agents that have little to no affinity for the processed silk, fibers, SBTs and/or SBPs may be applied by a continuous process that may involve padding with finishing agent solution, squeezing, drying, and curing In some embodiments, chemical finishing may include coating and laminating. Coating agents may also be used as finishing agents. In some embodiments, processed silk, SBTs and/or SBPs may be coating agents. In some aspects, processed silk, fibers, SBTs and/or SBPs may include coating agents. "Laminating" as used herein refers to the joining of one or more layers of materials such as but not limited to processed silk, fibers, SBTs and/or SBPs. Adhesives, heat and/or pressure may be used during the lamination process.

Chemical finishing may be applied to desired properties of processed silk, SBTs and/or SBPs. Finishing agents may be utilized to increase the softness of the processed silk, SBTs and/or SBPs described herein. In one embodiment, finishing agents may be used to provide resistance against creasing or wrinkle formation. In some aspects, finishing agents may be used to facilitate soil release which may include treatment with finishing agents that facilitate removal of water-soluble and/or fat soluble stains from processed silk, SBTs and/or SBPs. In some embodiments, the finishing agent may be an antistatic agent that may reduce the accumulation of static electricity. Finishing agents may also have antibacterial and/or antifungal properties. In some embodiments, the finishing agent may be a moth-repellent which may repel the moths which can damage processed silk, SBTs and/or SBPs described herein. Finishing agents may also be water repellents. In some aspects, processed silk, SBTs and/or SBPs may be made fireproof by the application of finishing agents that that can cut off the oxygen supply around a flame or fire-resistant by the application of finishing agents that resist the spread of the flame. In some embodiments, chemical finishing may impart resistance to harmful ultraviolet rays. In some embodiments, cargos, therapeutics agents, and/or additives described herein may be used as finishing agents.

Dyeing

In some embodiments, SBTs and/or SBPs may be prepared by dyeing. As used herein "dyeing" refers to the process of applying colorants to achieve a desired color. Processed silk, SBTs and/or SBPs may be subject to the dyeing process during, before and/or after any other processing method described herein. In some embodiments, processed silk such as fibers, threads and yarns may be subject to the dyeing process. Dyeing may be carried out in a solution, such as but not limited to an aqueous solution. In some embodiments, heat may be applied during the dyeing process to transfer the colorant to the processed silk, SBTs and/or SBPs. Agitation may be employed to ensure even transfer of colorant. Colorants may be used alone or in combination to achieve a desired hue. In some embodiments, colorants may be dyes and/or pigments. In some embodiments, colorants utilized in dyeing may be natural colorants, biological colorants, synthetic colorants, metal-complex colorants and/or reactive colorants. SBTs and/or SBPs containing a blend of fibers may be treated with colorants compatible with the fiber type used.

In one embodiment, the SBTs and/or SBPs may be dyed using colorants that are dark in color. In one embodiment, the SBTs and/or SBPs may be dyed black.

Printing

In some embodiments, SBTs and/or SBPs may be prepared by printing. In some embodiments, the finishing process may include printing. As used herein, "printing" may involve the process of applying colorants to processed silks, SBPs and/or SBTs in patterns or designs. Printing may include (i) block printing. (ii) roller printing, (iii) stencil printing, (iv) screen printing, (v) spray printing, and/or (vi) screen printing. In block printing, a design may be drawn on, transferred to or prepared on a wooden block. A colorant may be applied on to the block and pressed on to processed silks, SBPs and/or SBTs. In roller printing, the design may be applied to an automated roller which may then be dipped in colorant causing the pattern and colorant to be transferred to processed silks, SBPs and/or SBTs. In stencil printing, the pattern may be cut out from a sheet of paper or thin metal which is then placed on the surface of the processed silks, SBPs and/or SBTs. The colorant is then applied to the stencil such that the colorant is transferred to the surface of the processed silks, SBPs and/or SBTs as the inverse of the pattern. In some embodiments, the colorant may be sprayed on the processed silk, SBT and/or SBPs using inkjet technology. In screen printing, the pattern and/or the colorant may be applied onto processed silk, SBTs, and/or SBPs using a screen. In some embodiments, the screen may be prepared using processed silk.

Compositions and Articles

Formats

SBTs and/or SBPs may include or be prepared to conform to a variety of formats. In some embodiments, such formats include compositions of processed silk with various cargos and/or additives, fibers, fiber blends, non-fiber materials and/or cargo. In some embodiments, SBP formats include, but are not limited to, threads, textiles, fibers, yarns, films, nets, mats, sheets, membranes, coatings, sprays, adhesives, capsules, foams, patches, particles, cocoons, combs, cones, cylinders, discs, emulsions, gels, grafts, hydrogels, implants, microspheres, nanofibers, nanoparticles, nanospheres, organogels, powders, rods, scaffolds, solids, solutions, sponges, spuns, suspensions, tablets, and/or vapors. In some embodiments, the formats may include a therapeutic agent.

In some embodiments, SBT formats may include but are not limited to yarns, fibers, sheets, nanofibers, threads, spuns, mats, films, membranes, nets, grids, webs, mesh, patch, and/or cords.

Fibers and Textile Blends

In some embodiments, SBTs and/or SBPs described herein may include one or more fibers. In some embodiments, SBTs and/or SBPs may one or more of the fibers described in Table 7. Fibers may be or may be derived from natural fibers or man-made fibers. In one embodiment, SBTs and/or SBPs may be or may include one or more natural fibers. As used herein, "natural fibers" may be defined as fibers that occur in nature in a filamentous form. In some embodiments, SBTs and/or SBPs may be or may include one or more man-made fibers. As used herein, "man-made fibers" refers to fibers that generated, or prepared, synthesized, formatted, manipulated, or altered through at least one human intervention. In some embodiments, SBPs and/or SBTs may be or may include polymeric fibers. As used herein, the term "polymeric fibers" may be any fiber that is formed through linkages between similar modules or units. Individual units may be referred to herein as "monomers.". Polymeric fibers may be natural fibers such as but not limited to silk or they may be man-made fibers such as but not limited to nylon.

In some embodiments, fibers utilized in SBTs and/or SBPs may be categorized based on their origin and/or source as (i) plant fibers (which include fibers that may be prepared or obtained from plants, or plant parts (e.g. leaf seed, stem, vegetables), (ii) wood fibers (which may include fibers that may be prepared and/or obtained from tree sources), (iii) animal fibers (which may include fibers derived from animal sources such as hair, fur, collagen), (iv) metal fibers (which may include fibers that may be prepared or obtained from metals and/or minerals), (v) inorganic fibers (which include fibers prepared from inorganic materials).

In some embodiments, SBTs and/or SBPs may include plant fibers. Non-limiting examples of SBT and/or SBP plant fibers include but are not limited to, Alpaca hair, Angora rabbit, Camel hair, Cashgora, Cashmere, Catgut, Chiengora, Guanaco, Horse hair, Llama fur and/or hair, Mohair, Pashmina, Qiviut, Rabbit fur and/or hair, Vicuña fur and/or hair, Wool, Yak fur and/or hair, *Byssus, abaca, Abroma augusta* fiber, *Abutilon avicennae* fiber, *Abutilon* hemp, Acetate, *Agave americana* fiber, *Agave cantala* fiber, *Agave foetida* fiber, *Agave fourcroydes* fiber, *Agave funkiana* fiber, *Agave lechugilla* fiber, *Agave sisalana* fiber, *Agave tequilana* fiber, Alfa, *Aloe* fiber, Ambari hemp, Aramina, Arghan, Bamboo, Banana plant fiber, Benares hemp, Berandine, Beraudine peat fiber, Bimli jute, Bimlipatam, *Boehmeria nivea* bast fiber, *Boehmeria-tenacissima* bast fiber, Bombay hemp, Bowstring hemp, Bromeliaceae family fiber, Cadillo, Caesarweed fiber, Calcutta hemp, *Cantala piteira* fiber, Carapicho, *Caroa ramie* fiber, Cattail plant fiber, China grass bast fiber, China jute, Ching-ma, *Clappertonia ficifolia* fiber, Coconut fiber, Coir, *Colombia pita* fiber, Congo jute, *Corchorus capsularis* fiber, *Corchorus olitorius* fiber, Cork fiber, Cotton, *Crotalaria juncea* fiber, Cuba jute, *Curana typha* fiber, Dah, Devil's cotton, Escobilla, Esparto fiber, Flax, *Furcraea gigantea* fiber, Gambo hemp, Green ramie bast, Guaxima, Haiti hemp, Hemp, Henequen, *Hibiscus cannabinus* fiber, *Hibiscus* hemp, *Hibiscus sabdariffa* fiber, Ifehemplstle, Indian flax, Ixtle, Jute, Kapok, Karates Maguey, Kenaf, King-ma, Lotus fiber flower, Lycocell, Madagascar jute, Madras hemp, *Malva blanca* fiber, *Malva roxa* fiber, Malvaisco, Manila hemp, Mauritius hemp, Meshta, Mexican hemp, Modal, *Musa textilis nee* fiber, Nettles, New Zealand flax, New Zealand hemp, Paka, Papoula de Sao Francisco, Peat fiber, *Phormium tenax* fiber, Piña, Pineapple fibers, *Pita, Pita floja* fiber, Punga, Queensland hemp, Raffia, Ramie, Rayon, Red jute, Rhea bast fiber, Rosella hemp, Roselle, *Sansevieria* fiber, Siam jute, *Sida*, Silkgrass fiber, Sisal, Soy plant fiber, Sunn, Tampico fiber, *Thespesia*, Tien-Tsin, *Tossa, Triumfetta*, True jute, *Urena lobate* fiber, *Urena sinuate* fiber, White jute, White ramie bast fiber, and/or *Yucca* fiber. In some embodiments, SBTs and/or SBPs may one or more of the plant fibers described in Table 7.

In some embodiments, SBTs and/or SBPs may include wood fibers. Non-limiting examples of SBT and/or SBP wood fibers include but are not limited to, Cultifibre, Fibralur®, Hortifibre, Pietal, Torabella, Toresa Nova®, Toresa Special®, and/or Toresa®. In some embodiments, SBTs and/or SBPs may one or more of the wood fibers described in Table 7.

In some embodiments, SBTs and/or SBPs may be or may include animal fibers. Non-limiting examples of SBT and/or SBP animal fibers include but are not limited to, Alpaca hair, Angora rabbit, *Byssus*, Camel hair, Cashgora, Cashmere, Catgut, Chiengora, Guanaco, Horsehair, Llama fur and/or hair, Mohair, Pashmina, Qiviut, Rabbit fur and/or hair, Vicuña fur and/or hair, Wool, and/or Yak fur. In some embodiments, SBTs and/or SBPs may one or more of the animal fibers described in Table 7.

In some embodiments, SBTs and/or SBPs may include metallic fibers. Non-limiting examples of SBT and/or SBP wood fibers include but are not limited to, Aluminum fiber, Copper fiber, Gold fiber, Silver fiber, Steel fiber, Titanium fiber, and/or Tungsten fiber. In some embodiments, SBTs and/or SBPs may one or more of the metallic fibers described in Table 7.

In some embodiments, SBTs and/or SBPs may include inorganic fibers. Non-limiting examples of SBT and/or SBP inorganic fibers include but are not limited to Activated Carbon Fiber, Alumina fiber, Asbestos, Basalt fiber, Carbon fiber, Ceramic fiber, Fiberglass, Glass fiber, Meerschaum (Hydrated Magnesium Silicate), Potassium Titanate Fiber, Rock Wool, and/or Wollastonite (Calcium Silicate Fiber). In some embodiments, SBTs and/or SBPs may one or more of the inorganic fibers described in Table 7.

In some embodiments, man-made fibers may be included in or in the preparation of SBTs and/or SBPs. Man-made fibers included in, used in or in the preparation of SBTs and/or SBPs may be classified based on the methods of preparation of the fibers and include (i) synthetic man-made fibers and (ii) semi-synthetic fibers. Synthetic man-made fibers may be produced by polymerization of monomers. In some embodiments, monomers may be organic and/or derived from petroleum distillates. In some embodiments, fibers may be semi-synthetic fibers. which may be prepared by transforming or manipulating natural occurring polymers to form fibers.

In some embodiments, SBTs and/or SBPs may include synthetic man-made fibers. Non-limiting examples of synthetic man-made fibers include but are not limited to Acrylic, Aramid, Derclon, Dyneema/Spectra, Elastane, Elastodiene, Kevlar, Lycra®, Modacrylic, Modal™, Nomex, Nylon, Olefin, Orlon, Polyacrylonitrile fiber, Polybenzimidazole fiber, Polyester, Polyethylene fiber, Polypropylene fiber, Polytetrafluoroethylene fiber, Polyvinyl chloride fiber, Polyurethane fiber, Saran, Spandex, Soronal fiber, Trivinyl, Vectran, Vinylal, Vinyon, and/or Zylong. In some embodiments, SBTs and/or SBPs may one or more of the synthetic man-made fibers described in Table 7.

In some embodiments, SBTs and/or SBPs may include semi-synthetic fibers. Non-limiting examples of semisynthetic man-made fibers include but are not limited to, Azlon, Ingeo, Lyocell, and/or Viscose. In some embodiments, SBTs and/or SBPs may one or more of the semi-synthetic fibers described in Table 7.

In some embodiments, SBTs and/or SBPs may include at least one, at least two, at least three, at least four, at least five types of fibers. In one embodiment, SBTs and/or SBPs may include textile blends that contain one or more fibers described in Table 7. In some embodiments, SBTs and/or SBPs may include a combination of natural fibers, synthetic fibers, polymeric fibers and/or non-polymeric fibers. SBTs and/or SBPs may also include textile blends. In some embodiments, textile blends in or used in preparing SBTs and/or SBPs described herein may be any of the textile blends described in Table 6. In some embodiments, textile blends may include processed silk. Textile blends may be prepared using natural fibers, synthetic fibers, polymeric fibers, non-polymeric fibers or any combination thereof. The percentage of a fiber in a textile blend may be from about 1% to about 10%, from about 5% to about 15%, from about 10% to about 20%, from about 15% to about 25%, from about 20% to about 30%, from about 25% to about 35%, from about 30% to about 40%, from about 35% to about 45%, from about 40% to about 50%, from about 45% to about 55%, from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 100% and/or from about 95% to about 100%. In some embodiments, SBTs and/or SBPs may include one or more textile blends described in Table 2.

Table 7 provides non-limiting examples of SBT and/or SBP fibers and textile blends. These categories may not be limiting and each fiber may fall under multiple categories (e.g., any of the categories of fibers described herein).

TABLE 7

Fibers and textile blends

| Name | Description & Category |
|---|---|
| Alpaca hair | fiber; animal fiber |
| Angora rabbit | fiber; animal fiber |
| Byssus | fiber; animal fiber |
| Camel hair | fiber; animal fiber |
| Cashgora | fiber; animal fiber |
| Cashmere | fiber; animal fiber |
| Catgut | fiber; animal fiber |
| Chiengora | fiber; animal fiber |

TABLE 7-continued

| Fibers and textile blends | |
|---|---|
| Name | Description & Category |
| Guanaco | fiber; animal fiber |
| Horsehair | fiber; animal fiber |
| Llama fur and/or hair | fiber; animal fiber |
| Mohair | fiber: animal fiber |
| Pashmina | fiber; animal fiber |
| Qiviut | fiber; animal fiber |
| Rabbit fur and/or hair | fiber: animal fiber |
| Vicuña fur and/or hair | fiber; animal fiber |
| Wool | fiber; animal fiber |
| Yak fur and/or hair | fiber; animal fiber |
| Abaca | fiber: plant fiber |
| Abroma augusta fiber | fiber; plant fiber |
| Abutilon avicennae fiber | fiber; plant fiber |
| Abutilon hemp | fiber: plant fiber |
| Acetate | fiber; plant fiber; artificial man-made fiber |
| Agave americana fiber | fiber; plant fiber |
| Agave cantala fiber | fiber; plant fiber |
| Agave foetida fiber | fiber; plant fiber |
| Agave fourcroydes fiber | fiber; plant fiber |
| Agave funkiana fiber | fiber; plant fiber |
| Agave lechugilla fiber | fiber: plant fiber |
| Agave sisalana fiber | fiber; plant fiber |
| Agave tequilana fiber | fiber; plant fiber |
| Alfa | fiber; plant fiber |
| Aloe fiber | fiber; plant fiber |
| Ambari hemp | fiber; plant fiber |
| Aramina | fiber; plant fiber |
| Arghan | fiber: plant fiber |
| Bamboo | fiber; plant fiber |
| Banana plant fiber | fiber; plant fiber |
| Benares hemp | fiber; plant fiber |
| Berandine | fiber; plant fiber |
| Beraudine peat fiber | fiber; plant fiber |
| Bimli jute | fiber; plant fiber |
| Bimlipatam | fiber; plant fiber |
| Boehmeria nivea bast fiber | fiber; plant fiber |
| Boehmeria-tenacissima bast fiber | fiber; plant fiber |
| Bombay hemp | fiber; plant fiber |
| Bowstring hemp | fiber; plant fiber |
| Bromeliaceae family fiber | fiber; plant fiber |
| Cadillo | fiber; plant fiber |
| Caesarweed fiber | fiber; plant fiber |
| Calcutta hemp | fiber; plant fiber |
| Cantala piteira fiber | fiber; plant fiber |
| Carapicho | fiber; plant fiber |
| Caroa ramie fiber | fiber; plant fiber |
| Cattail plant fiber | fiber; plant fiber |
| China grass bast fiber | fiber: plant fiber |
| China jute | fiber; plant fiber |
| Ching-ma | fiber; plant fiber |
| Clappertonia ficifolia fiber | fiber; plant fiber |
| Coconut fiber | fiber; plant fiber |
| Coir | fiber; plant fiber |
| Colombia pita fiber | fiber; plant fiber |
| Congo jute | fiber: plant fiber |
| Corchorus capsularis fiber | fiber; plant fiber |
| Corchorus olitorius fiber | fiber; plant fiber |
| Cork fiber | fiber: plant fiber |
| Cotton | fiber; plant fiber |
| Crotalaria juncea fiber | fiber; plant fiber |
| Cuba jute | fiber; plant fiber |
| Curana typha fiber | fiber; plant fiber |
| Dah | fiber; plant fiber |
| Devil's cotton | fiber; plant fiber |
| Escobilla | fiber; plant fiber |
| Esparto fiber | fiber; plant fiber |
| Flax | fiber; plant fiber |
| Furcraea gigantea fiber | fiber; plant fiber |
| Gambo hemp | fiber; plant fiber |
| Green ramie bast | fiber; plant fiber |
| Guaxima | fiber; plant fiber |
| Haiti hemp | fiber; plant fiber |
| Hemp | fiber; plant fiber |
| Henequen | fiber; plant fiber |
| Hibiscus cannabinus fiber | fiber; plant fiber |
| Hibiscus hemp | fiber; plant fiber |
| Hibiscus sabdariffa fiber | fiber; plant fiber |
| Ifehemplstle | fiber: plant fiber |
| Indian flax | fiber; plant fiber |
| Ixtle | fiber; plant fiber |
| Jute | fiber: plant fiber |
| Kapok | fiber; plant fiber |
| Karates Maguey | fiber; plant fiber |
| Kenaf | fiber; plant fiber |
| King-ma | fiber; plant fiber |
| Lotus fiber flower | fiber; plant fiber |
| Lycocell | fiber; plant fiber |
| Madagascar jute | fiber; plant fiber |
| Madras hemp | fiber; plant fiber |
| Malva blanca fiber | fiber; plant fiber |
| Malva roxa fiber | fiber; plant fiber |
| Malvaisco | fiber; plant fiber |
| Manila hemp | fiber; plant fiber |
| Mauritius hemp | fiber; plant fiber |
| Meshta | fiber: plant fiber |
| Mexican hemp | fiber; plant fiber |
| Modal | fiber; plant fiber |
| Musa textilis nee fiber | fiber: plant fiber |
| Nettles | fiber; plant fiber |
| New Zealand flax | fiber; plant fiber |
| New Zealand hemp | fiber; plant fiber |
| Paka | fiber; plant fiber |
| Papoula de Sao Francisco | fiber; plant fiber |
| Peat fiber | fiber; plant fiber |
| Phormium tenax fiber | fiber; plant fiber |
| Piña | fiber; plant fiber |
| Pineapple fibers | fiber; plant fiber |
| Pita | fiber: plant fiber |
| Pita floja fiber | fiber; plant fiber |
| Punga | fiber; plant fiber |
| Queensland hemp | fiber; plant fiber |
| Raffia | fiber: plant fiber |
| Ramie | fiber; plant fiber |
| Rayon | fiber; plant fiber; artificial man-made fiber |
| Red jute | fiber: plant fiber |
| Rhea bast fiber | fiber; plant fiber |
| Rosella hemp | fiber; plant fiber |
| Roselle | fiber; plant fiber |
| Sansevieria fiber | fiber; plant fiber |
| Siam jute | fiber; plant fiber |
| Sida | fiber; plant fiber |
| Silkgrass fiber | fiber; plant fiber |
| Sisal | fiber; plant fiber |
| Soy plant fiber | fiber; plant fiber |
| Sunn | fiber; plant fiber |
| Tampico fiber | fiber; plant fiber |
| Thespesia | fiber; plant fiber |
| Tien-Tsin | fiber; plant fiber |
| Tossa | fiber; plant fiber |
| Triumfetta | fiber; plant fiber |
| True jute | fiber; plant fiber |
| Urena lobate fiber | fiber; plant fiber |
| Urena sinuate fiber | fiber; plant fiber |
| White jute | fiber: plant fiber |
| White ramie bast fiber | fiber; plant fiber |
| Yucca fiber | fiber; plant fiber |
| Cultifibre | fiber; wood fiber |
| Fibralur ® | fiber; wood fiber |
| Hortifibre | fiber; wood fiber |
| Pietal | fiber; wood fiber |
| Torabella | fiber: wood fiber |
| Toresa Nova ® | fiber; wood fiber |
| Toresa Special ® | fiber; wood fiber |
| Toresa ® | fiber: wood fiber |
| Acrylic | fiber; synthetic man-made fiber |
| Aramid | fiber; synthetic man-made fiber |
| Derclon | fiber; synthetic man-made fiber |
| Dyneema/Spectra | fiber; synthetic man-made fiber |
| Elastane | fiber; synthetic man-made fiber |
| Elastodiene | fiber; synthetic man-made fiber |

TABLE 7-continued

Fibers and textile blends

| Name | Description & Category |
|---|---|
| Kevlar | fiber; synthetic man-made fiber |
| Lycra ® | fiber; synthetic man-made fiber |
| Modacrylic | fiber; synthetic man-made fiber |
| Modal ™ | fiber; synthetic man-made fiber |
| Nomex | fiber; synthetic man-made fiber |
| Nylon | fiber; synthetic man-made fiber |
| Olefin | fiber; synthetic man-made fiber |
| Orlon | fiber; synthetic man-made fiber |
| Polyacrylonitrile fiber | fiber; synthetic man-made fiber |
| Polybenzimidazole fiber | fiber; synthetic man-made fiber |
| Polyester | fiber; synthetic man-made fiber |
| Polyethylene fiber | fiber; synthetic man-made fiber |
| Polypropylene fiber | fiber; synthetic man-made fiber |
| Polytetrafluoroethylene fiber | fiber; synthetic man-made fiber |
| Polyvinyl chloride fiber | fiber; synthetic man-made fiber |
| Polyurethane fiber | fiber; synthetic man-made fiber |
| Saran | fiber; synthetic man-made fiber |
| Spandex | fiber; synthetic man-made fiber |
| Soronal fiber | fiber; synthetic man-made fiber |
| Trivinyl | fiber; synthetic man-made fiber |
| Vectran | fiber; synthetic man-made fiber |
| Vinylal | fiber; synthetic man-made fiber |
| Vinyon | fiber; synthetic man-made fiber |
| Zylong | fiber; synthetic man-made fiber |
| Azlon | fiber; semi-synthetic fiber |
| Ingeo | fiber; semi-synthetic fiber |
| Lyocell | fiber; semi-synthetic fiber |
| Viscose | fiber; semi-synthetic fiber |
| Activated Carbon Fiber | fiber; inorganic fiber |
| Alumina fiber | fiber; inorganic fiber |
| Asbestos | fiber; inorganic fiber |
| Basalt fiber | fiber; inorganic fiber |
| Carbon fiber | fiber; inorganic fiber |
| Ceramic Fiber | fiber; inorganic fiber |
| Fiberglass | fiber; inorganic fiber |
| Glass fiber | fiber; inorganic fiber |
| Meerschaum (Hydrated Magnesium Silicate) | fiber; inorganic fiber |
| Potassium Titanite Fiber | fiber; inorganic fiber |
| Rock Wool | fiber; inorganic fiber |
| Wollastonite (Calcium Silicate Fiber) | fiber; inorganic fiber |
| Aluminum fiber | fiber: metal fiber |
| Copper fiber | fiber; metal fiber |
| Gold fiber | fiber; metal fiber |
| Silver fiber | fiber; metal fiber |
| Steel fiber | fiber; metal fiber |
| Titanium fiber | fiber; metal fiber |
| Tungsten fiber | fiber; metal fiber |
| Canvas | Textile blend of cotton, polyester |
| Chenille | Textile blend of cotton, wool, polyester |
| Coating | Textile blend of wool, polyester, cashmere, mohair |
| Denim | Textile blend of Cotton |
| Flannel | Textile blend of cotton, wool |
| Gabardine | Textile blend of wool, cotton |
| Interlock | Textile blend of cotton, wool, polys |
| Linen blend | Textile blend of linen, cotton |
| Muslin blend | Textile blend of cotton |
| Pique | Textile blend of cotton |
| Slinky Knit | Textile blend of acetate, spandex |
| Stretch Velvet | Textile blend of polyester, spandex |
| Terry wool | Textile blend of polyester, wool |
| Terrycloth | Textile blend of cotton, rayon |
| — | Textile blend of polyester, viscose, rayon |
| — | Textile blend of polyester, cotton |
| — | Textile blend of nylon, wool |
| — | Textile blend of nylon, acetate |
| — | Textile blend of ramie, polyester |
| — | Textile blend of ramie, acrylic |
| — | Textile blend of wool, cotton |
| — | Textile blend of polyester, spandex |
| — | Textile blend of linen, cotton |
| — | Textile blend of linen, silk |
| — | Textile blend of linen, rayon |
| — | Textile blend of silk, wool |
| — | Textile blend of rayon, cotton |

In some embodiments, SBTs and/or SBPs may include fibers based on the fiber length. SBTs and/or SBPs may include long fibers to aid in the preparation of compositions with increased strength. In some embodiments, fiber length may be decreased to increase ease of processing and preparing SBTs.

In some embodiments, SBTs and/or SBPs may include fibers with one or more fiber cross sectional shapes. Natural fibers such as but not limited to silk fibers may have predefined cross sectional shaped whereas the cross-sectional shape of synthetic fibers may be determined by processing methods utilized. Cross sectional shape may be triangular, polygonal, lobular, oval, round, circular, lima bean (kidney) shaped, flat, collapsed, tubal, rectangular, square, and/or star. The cross-sectional shape may include rounded edges, pointed edges, lumen, convolutions, scales, striations, serrations, voids. In some embodiments, cross-sectional shape may be uniform or may include a combination of shapes described herein. Cross sectional shape of the fiber may influence hand of processed silk and/or SBTs. As used herein, the term "hand" may be defined as the feeling of smoothness, softness, thickness, roughness, weight, hardness, elasticity, stiffness, and/or combinations thereof of a textile as evaluated by a subject in contact with the textile. SBTs may be prepared with fibers that may have a hard hand which indicates a coarse and/or rough feeling. In some embodiments SBTs may be prepared with a soft hand which may have a fluid or smooth feeling.

In some embodiments, SBTs and SBPs may include fibers based on moisture content and moisture regain capacity of the fibers. As used herein, "moisture regain" may be defined as the percentage of water in a sample compared to its oven dry weight whereas "moisture content" may be defined as the percentage of the total weight of the sample that exists as water. In some embodiments, SBTs may include fibers with from about 0% to about 35% moisture content and/or moisture regain. In some embodiments, SBTs may include fibers with from about 35% to about 70% moisture content and/or moisture regain. In some embodiments, SBTs may include fibers with from about 70% to about 100% moisture content and/or moisture regain.

In some embodiments, SBTs and/or SBPs may include fibers based on their crimp. As used herein, "crimp" refers to the average number of waves per unit length of the fiber. Examples of the number of waves per unit length may be but not limited to 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, and/or 1000. In one embodiment, the unit length of the fiber may be 1 cm. In one embodiment, the unit length of the fiber may be 1 mm. In one embodiment, the unit length of the fiber may be 1 μM. In one embodiment, the unit length of the fiber may be 1 inch. Crimp may affect the affect the light scattering properties as well as the thickness of the fiber. In some embodiments, SBT properties may be modified by tuning fiber crimp. In some embodiments, increasing the fiber crimp may be used to increase the stretchability of the SBTs. In some embodiments, increasing fiber crimp may increase the particles of air trapped by the fiber, which may serve as insulation.

In some embodiments, SBTs and/or SBPs may include fibers that protect against UV light. Fibers shape and/or color may be tuned to increase protection against UV light. Fibers may be measured by their solar protection factor (SPF). As used herein "SPF" refers may be defined as the ratio of the potential erythemal effect to the actual erythemal effect transmitted in the presence of fiber. SPF may be calculated by spectroscopic measurements. In general, the larger the SPF value, the greater the protection against UV light. In some embodiments, SBTs and/or SBPs may include fibers that have SPF values such as but not limited to SPF 4, SPF 8, SPF 12, SPF 14, SPF 8-14, SPF 15, SPF 15-30, SPF 30, SPF 45, SPF 50, SPF 60, and/or SPF 50-100. In some embodiments, fibers include in SBTs and/or SBPs may be measured by their UV protection factor (UPF) which is measure of the amount of UV radiation absorbed by the fiber, and/or textile. In some embodiments, SBT and/or SBP fibers may have UPF values such as but not limited to from about UPF15 to about UPF24, from about UPF25 to about UPF39, from about UPF40 to about UPF 50, from about UPF50 to about UPF 100.

Materials

In some embodiments, SBTs and/or SBPs may include one or more materials. As used herein, the term "material" may be defined as a substance or chemical substance that may be used for the fabrication, production, and/or manufacture of an article. In some embodiments, materials may include SBTs and/or SBPs. The SBTs and/or SBPs may be part of the final product and/or may be used in the preparation of the materials. In some embodiments, SBT and/or SBPs may include one or more materials that are not fibers. Non-limiting categories of materials include metals, inorganic materials, biological materials, organic materials, polymers, ceramic materials, and/or composite materials. In some embodiments, materials may fall under one or more categories described herein.

In some embodiments SBTs and/or SBPs may include one or more materials that are metals. As used herein, "metals" may be defined as substances that may readily give up electrons to form metallic bonds and conduct electricity. In some embodiments, metals may be lustrous, malleable and ductile. In some embodiments, metals may include elements. In some embodiments, metals may be alloys. As used herein, an "alloy" may be defined as metal that may be formed when two or more metals are melted together and mixed. In some embodiments, SBTs and/or SBPs may include alloys. In some embodiments, SBTs and/or SBPs may include ferrous metals. As used herein ferrous metals includes metals that contain iron (Fe). In some embodiments, SBTs and/or SBPs may include non-ferrous metals. As used herein, "non-ferrous metals" refers to any metal that is not or does not include iron. Non-limiting examples of non-ferrous metals include copper, magnesium, aluminum, nickel, and/or titanium. In some embodiments, SBTs and/or SBPs may include metals that are resistant to corrosion, and/or display thermal and/or electrical conductivity. In some embodiments, metals may be magnetic, or non-magnetic in nature. As used herein, "magnetic" may be defined as property that relates to behavior of a metal as a magnet. As used herein, a "magnet" may be defined as any material that may have its component atoms so ordered that the material exhibits properties of magnetism, such as attracting other iron-containing objects or aligning itself in an external magnetic field. In some embodiments, metals may be in powder form.

In some embodiments, SBTs and/or SBPs materials may be polymers.

In some embodiments, materials may be inorganic materials. As used herein, "inorganic materials" may be defined as materials that may be derived from non-living sources. In some embodiments, inorganic materials may include minerals. As used herein, a "mineral" may be defined as an element or chemical compound that may be crystalline and may have been formed as a result of geological processes. Non-limiting examples of minerals include metals, clays, sand, rocks, gravels, and/or ceramics. In some embodiments, SBTs and/or SBPs may include inorganic materials.

In some embodiments, SBTs and/or SBPs may include biological materials. As used herein, "biological materials" may refer to materials that are or materials that are derived include organisms. Non-limiting examples of biological materials include cellulose, lignin, gelatin, gum, starch, resins, wax, bones, teeth, and/or leather is obtained from the skin of animals after cleaning and tanning operations.

In some embodiments, SBTs and/or SBPs may include organic materials. As used herein, "organic materials" may be defined as materials that are or that include carbon-based compounds and/or their derivatives. Non-limiting examples of organic materials include feathers, leather, and synthetic materials such as petroleum-based plastics. In some embodiments SBTs and/or SBPs may include organic materials that belong to one of more categories including but not limited to cellulosic materials, and/or proteinaceous materials. In one embodiment, SBPs and/or SBTs may include cellulosic materials. As used herein "cellulosic materials" include materials that may be or may be derived from materials that include cellulose and lignin. Examples include but are not limited to grass, wood, roots, bark, leaves, and/or flowers. In one embodiment, SBPs and/or SBTs may include proteinaceous materials. As used herein, "proteinaceous materials" may refer to materials that are or are enriched in protein and/or include materials that demonstrate physico-chemical properties of proteins. Non-limiting examples include leather, skin, parchment, gut, hides, fur and hair, wool, silk, feathers, quills, baleen, tortoiseshell, ivory, bone, antler, and/or shell.

In some embodiments, SBTs and/or SBPs may include ceramic materials. As used herein, a "ceramic material" may be defined as a solid material that may include one or more inorganic compound of metal, non-metal or metalloid atoms primarily held in ionic and covalent bonds. In some embodiments, the bonds in ceramic materials may be formed under high temperature. Non-limiting examples include earthenware, stoneware, porcelain, brick, cement, glass, aluminum oxide (or alumina, Al2O3), silicon dioxide (or silica, SiO2), silicon carbide (SIC), diamonds, and/or silicon nitride (Si3N4). SBT and/or SBP ceramics may be characterized by properties such as but not limited to high hardness, abrasion resistance, brittleness and chemical inertness, heat resistance, thermal resistance and/or heat resistance.

In some embodiments, SBTs and/or SBPs may include composites. As used herein, "a composite" may be defined as a composition that includes two or more materials. In some embodiments, the two or more materials in a composite may belong to the same category. In some embodiments, the two or more materials in a composite may belong to different categories. In some embodiments, SBT and/or SBP composites may be naturally occurring composites such as but not limited to bones, teeth, mollusk shells, pearls, and/or wood. In some embodiments, composites may be man-made such as but not limited to fiber glass, ceramics, and/or plywood. In some embodiments, SBTs and/or SBPs may include composites prepared by combining any of the fibers described herein with a material. In one embodiment, SBTs and/or SBPs may include composites that may be fiber reinforced polymers (FRP). In one embodiment, SBTs and/or SBPs may include composites that contain processed silk. In one embodiment, the SBTs and/or SBPs may include fiber reinforced composite such as artificial leather.

Textile Components

In some embodiments, SBTs and/or SBPs may include textile components. As used herein, a "textile component" may be defined as any article that may be added or included to aid in the preparation, function, appearance or otherwise improve the quality of the SBTs and/or SBPs.

Textile components may be used to enhance the aesthetic appearance (e.g., decorate) of SBTs and/or SBPs.

Textile components may be incorporated during preparation of SBT/and or SBP compositions and/or articles. In some embodiments, textile components may include SBTs and/or SBPs. The SBTs and/or SBPs may be part of the final product and/or may be used in the preparation of the textile components. Textile components may include but are not limited to interfacings which may be added to provide structure and shape to SBPs and/or SBTs and include backings and/or glues. In some embodiments, textile components may include fasteners. As used herein, a "fastener" may be defined as an article that may be used for closing, securing and/or enhancing SBTs and/or SBPs. Sewing threads may be used for fasteners. Ribbon, binding, cords, and braids prepared from fibers described herein may also be used as fasteners. Non-limiting examples of fasteners include but are not limited to, rivers, zippers, buttons, hooks, Velcro, press studs, eyelets, buckles, toggles, drawstrings, and/or laces. In some embodiments, fasteners may be added to enhance the appearance of the SBTs and/or SBPs.

In some embodiments, SBTs and/or SBPs may include sewing threads. Sewing threads may be derived from any of the fibers described herein. In one embodiment, the sewing threads may be derived from processed silk. Sewing threads may be used for decoration of the SBTs and/or SBPs. In some embodiments, SBTs and/or SBPs may include beads and sequins. Textile components may also include LED bulbs.

Cargos and Additives

In some embodiments, SBTs and/or SBPs may be or may include cargo, additives, or excipients as suggested in Table 5. As used herein, the term "cargo" may refer to any substance that is embedded in, enclosed within, attached to, or otherwise associated with a carrier. SBPs may be carriers for a large variety of cargo. Such cargo may include, but are not limited to, compounds, compositions, therapeutic agents, biological agents, materials, cosmetics, devices, agricultural compositions, particles, lipids, liposomes, sweeteners, colorants, preservatives, carbohydrates, small molecules, supplements, tranquilizers, ions, metals, minerals, nutrients, pesticides, herbicides, fungicides, and cosmetics. In one embodiment, the cargo may be a finishing agent or a payload as discussed above.

Repellents

In some embodiments, cargos and/or additives may include repellents. As used herein, the term "repellent" may be defined as an agent or a substance which may be able to ward off another agent, substance and/or organism.

In some embodiments, the repellent may be directed towards an organism.

In some embodiments, the SBTs and/or SBPs may include an agent or a substance that may be able to ward off one or more birds (herein referred to as "bird repellent"). Non-limiting examples of bird repellents included in SBTs and/or SBPs include but are not limited to Lindane, Captan, methyl anthranilate, Naphthalene, Polybutene, Aliphatic petroleum hydrocarbons, Polyisobutylene, Thiram, Thymol, denatonium saccharide, Fenthion, 4-Aminopyradine, 3-Chloro p-toluidine hydrochloride, Isotox Seed ireater, ReJeX-IT AG-145, ReJeX-IT AG-36, ReJeX-IT MA, ReJeX-IT TP-40, ReJeX-IT AP-50, Bird Shield Bird Repellent Concentrate, Dr. 7s Rabbit, Squirrel, Bat and Bird Repellent, Roost No More Repels Nuisance Birds, Tanglefoot Bird Repellent, 4 The Birds" Transparent Bird Repellent, Preferred Brand" Bird and Squirrel Repellent, Hot Foot Bird Repellent, Roost No More Bired Repellent, Roost No More Bird Repellent Liquid, Thiram 42% Dyed Flowable seed Protectant, RO-PEL Animal, rodent and Bird Repellent, Rid-a-Perch 1100 Solution, Avitrol FC Corn Chops, Avitrol Concentrate, Avitrol Double Strength Whole Corn, Avitrol whole Corn, Avitrol Corn Chops, Avirtol Double Strength Corn Chops, Avitrol Mixed Grains, Compound DRG1339 Concentrate-Staging Areas, Compound DRG1339 98% Concentrate-Livestock & Fodder Depredations, Compound DRG1339 98% Concentrate-Pigeons, and/or Compound DRC-1339 Starling poison 75% Concentrate.

In one embodiment, the SBTs and/or SBPs may include an agent or a substance that may be able to ward off one or more insects (herein referred to as "insect repellent"). Non-limiting examples of insect repellents included in SBTs and/or SBPs include but are not limited to Picaridin, N,N-Diethyl-meta-toluamide (DEET), 3-[N-Butyl-N-acetyl]-aminopropionic acid, ethyl ester, para-menthane-3,8-diol, Castor oil, Cedar oil, Citronella oil, Clove oil, Oil of Lemon Eucalyptus (PMD 65%), Geraniol oil, Lemongrass oil, Peppermint oil, Rosemary oil, Soybean oil, Cyfluthrin, Permethrin, Pyrethroid, Chlorinated triphenylmethane, Chlorophenylids, Sulcofenuron, Flucofenuron, Dieldrin and/or Hexahydropyrimidine.

In some embodiments, SBTs and/or SBPs may include one or more repellent that may be directed towards an agent or substance. In one embodiment, SBTs and/or SBPs may include repellents targeted against water (herein referred to as "water repellents"). In one embodiment, the SBTs and/or SBPs may include repellents targeted against oils and fats (herein referred to as "oil repellents"). Non limiting example of water repellents and/or oil repellents include formaldehyde, paraffin repellents that include aluminum or zirconium salts of fatty acids (e.g. stearic acid), stearic acid-melamine repellents, Polydimethylsiloxane products, Teflon, fluoropolymers, fatty acid metal salts, Polydimethylsiloxane products, polyacrylic esters, polymethacrylic esters, fluorocarbon-based repellents such as polyacrylic or polymethacrylic acid esters.

In some embodiments, repellent additives and/or cargos may include any of those presented in Table 3, above.

Dirt Release Agents

In some embodiments, cargos and/or additives may include dirt release agents. In the context of fiber and textiles, "dirt" may be defined as dust, oil, grease and/or unwanted stains that may accumulate in textiles. In some embodiments, processed silk, and/or SBTs described herein may include agents that allow the removal and/or escape of dirt from the fiber and/or textiles during washing (herein referred to as "dirt release agents"). The nature of the dirt present in processed silk, SBTs and/or SBPs may be particulate, hydrophobic, hydrophilic, liquid or solid. In some embodiments, SBPs and/or SBTs may include dirt release agents may include but are not limited PVA, CMC, caprolactam, oligomers, ethoxylated products, sulfonates, polyacrylic acid, adipic acid copolymers, hybrid fluorocarbons, polyacrylic acid esters, polyethylene terephthalate, block copolymers, anionic polymers, perfluoro-alkyl methacrylate, melamine formaldehyde condensate, paraffin wax, methyl hydrogen polysiloxane, acetyl dimethyl benzyl ammonium chloride, styrene-maleic anhydride copolymers, sodium carboxymethyl cellulose, methyl cellulose, ethyl cellulose, hydroxypropyl starch, hydroxyethyl cellulose, hydroxypropylmethyl cellulose, hydrolyzed cellulose acetates, olyethylene terephthalate, and/or polyxyethylene terephthalate.

Softeners

In some embodiments, cargos and/or additives may include softeners. As used herein a "softener" may be defined as any agent or substance that may improve the drape and/or hand of a textile. As used herein, the term "hand" may be defined as the feeling of smoothness, softness, thickness, roughness, weight, hardness, elasticity, stiffness, and/or combinations thereof of a textile as evaluated by a subject in contact with the textile. The term "drape" as used herein may be defined as the ability of a textile to deform when suspended under its own weight in specified conditions. In some embodiments, drape and/or hand may be subjectively evaluated by a subject. In some embodiments, SBTs and/or SBPs may include softeners such as but not limited to ceranine HCS/PNL liquid, Ratifix F liquid, Ceranine HCS/HCL liquid, Sandolube NV liquid, Sandoperm FEN liquid, Dicofix 801 liquid, Elfugin V liquid, Dilasoft TF, Finish MH liquid, Magnesium chloride, Amine salts, Imidazolines, Amino esters, Dicyanadiamide, stearylamine, Polyamine-based difatty amino imidazoline, Diethanolamine, Soaps, Sodium salt of fatty acids, Sulfosuccinates of fatty acid, sulfate and sulfonate of fatty acids, Wax emulsion, Polyethylene emulsion, Glycerol monostearate, Ethoxylates of fatty acids, Ethoxylates of fatty amines, Ethoxylated fatty alcohol, Ethoxylated fatty esters, Castor oil, Amine oxide, Betaine, Sulfobetaines, Amphoteric imidazoline, Polydimethyl siloxane (PDMS), Polymethyl hydrogen siloxane (PMHS), Amino functional silicone, Epoxysilicone, Amidosilicones and/or hydrophilic silicones.

In some embodiments, softener additives and/or cargos may include any of those presented in Table 3, above.

Resins

In some embodiments, cargos and/or additives may include resins. As used herein, "resins" may be defined as any non-crystalline or a viscous substance. In some embodiments, resins may be converted into polymers. In some embodiments, may be cross-linking agents. SBTs and/or SBPs may include resins that may be derived from plant sources and/or that may be synthetically prepared. Non-limiting examples of resins included in SBPs and/or SBTs include Alkyd resins, Di methylol Di hydroxy Ethylene Urea, Di methylol Ethylene Urea, Di methylol Urea, Ketone resins, Phenol-Formaldehyde resins, Urea formaldehyde resin and/or Vinyl resins.

In some embodiments, resin additives and/or cargos may include any of those presented in Table 3, above.

Fragrances

In some embodiments, cargos and/or additives may include fragrances. As used herein, the term "fragrance" may be defined as any agent or substance that imparts a distinctive smell. In one embodiment, the smell imparted by a fragrance may be pleasant. In some embodiments, SBPs and/or SBTs may include fragrances. In some embodiments, fragrances may be incorporated in SBTs and/or SBPs to replace the odors that may be released by a subject, and/or to produce a therapeutic effect in a subject. Non-limiting examples of SBP and/or SBT fragrances include but are not limited to 1-Hexanol, 2-Acetyl-1-pyrroline, 6-Acetyl-2,3,4,5-tetrahydropyridine, Acetaldehyde, Acetoin, Allyl thiol, alpha-Ionone, Anethole, Anisic aldehyde, Anisole, Benzaldehyde, Benzyl acetate, Camphor, Carvone, Cinnamaldehyde, cis-3-Hexen-1-ol, cis-3-Hexenal, Citral, lemonal, Citronellal, Citronellol, Compound name, Cuminaldehyde, Cyclopentadecanone, delta-Octalactone, Diacetyl, Dihydrojasmone, Estragole, Ethanethiol, Ethyl acetate, Ethyl butanoate, Ethyl butyrate, Ethyl maltol, Ethyl methylphenylglycidate, Eucalyptol, Eugenol, Fructone, Furan-2-yl-methanethiol, Furaneol, Furfural, gamma-Decalactone, gamma-Nonalactone, Geranial, neral, Geraniol, Geranyl acetate, Grapefruit mercaptan, Hexanal, Hexyl acetate, Hexyl cinnamaldehyde, Isoamyl acetate, Isovaleraldehyde, Jasmine lactone, Limonene, Linalool, Massoia lactone, Menthol, Methyl acetate, Methyl anthranilate, Methyl butanoate, Methyl butyrate, Methyl formate, Methyl propanoate, Methyl propionate, Myrcene, Nerol, Nerolidol, Nerolin, Oct-1-en-3-one, Octyl acetate, Pentyl butanoate, Pentyl butyrate, Pentyl pentanoate, Sotolon, Terpineol, Thioacetone, Thujone, Thymol, Vanillin, and/or Wine lactone.

In one embodiment, fragrances in SBPs and/or SBTs may be used for aromatherapy. As used herein, "aromatherapy" may be defined as the use of fragrances for therapeutic purposes. Non-limiting examples of aromatherapy fragrances included in SBPs and/or SBPs may be Angelica, Bay Laurel, Benzoin, Bergamot, Camphor, Cardamom, Cedarwood, Chamomile, Cinnamon, Clary Sage, Clove Basil, Cloves, Cypress, Eucalyptus, Fennel, Fir, Frankincense, Grapefruit, Hyssop, Jasmine, Lavender, Lemon, Lemon Rosemary, Lemon Balm, Lemon Verbena, Marjoram, Myrrh, Neroli, Nutmeg, Orange, Patchouli, Patchouli, Peach, Peppermint, Petitgrain, Pine, Rose, Rose Geranium, Rosemary, Sage, Salwood, Spiced Apple, Sweet Melissa, Tangerine, Valerian, Vanilla, Vanilla Ylang-ylang, Violet, Violet Leaf and/or Ylang-ylang.

In some embodiments, fragrance additives and/or cargos may include any of those presented in Table 3, above.

Flame Retardants

In some embodiments, cargos and/or additives may include flame retardants. In some embodiments, processed silk, SBPs and/or SBTs may be flame retardants. As used herein the term, "flame retardant" refers to any chemical or agent that may be resistant to combustion. Non-limiting examples of flame retardants included in SBPs and/or SBPs include but are not limited to aluminum diethyl phosphinate, aluminum hydroxide, ammonium bromide, ammonium polyphosphate, Ammonium salt of phosphonic acid, bisphenol A diphenyl phosphate, brominated carbonate oligomers, brominated epoxy oligomers, brominated flame retardants, brominated polystyrenes, cellulose reactive methyl olated phosphonamides, chlorendic acid derivatives, chlorinated paraffin waxes, chlorinated paraffins, cyclic oligomeric phosphonate, decabromodiphenyl ethane, decabromodiphenyl ether, diammonium phosphate, dimethyl methylphosphonate, hexabromocyclododecane, hexabromocyclododecane, huntite, hydromagnesite, magnesium hydroxide, organophosphate flame retardants, polybrominated diphenyl ethers, resorcinol bis(diphenylphosphate), tetrabromobisphenol A, tetrabromophthalic anhydride, tricresyl phosphate, triphenyl phosphate, tris(1,3-dichloro-2-propyl)phosphate, and/or tris(2,3-dibromopropyl)phosphate.

In some embodiments, flame retardant additives and/or cargos may include any of those presented in Table 3, above.

Anti-Static Agents

In some embodiments, cargos and/or additives may include anti-static agents. As used herein, the term "anti-static" agent may be defined as an agent that may reduce the buildup or accumulation of stationary electric charge (also referred to herein as the "static charge"). In some embodiments, the buildup of stationary electric charge in SBTs and/or SBPs may be caused by friction for e.g. friction between the fibers, or friction between the components of the SBTs and/or SBPs. In some embodiments, anti-static agents may be included to reduce static charge induced repulsion between fibers, yarns, threads, in processed silk, SBTs and/or SBPs. In some embodiments, anti-static agents may reduce the damage caused by static charges and/or enhance the safety of SBTs and/or SBPs. Non-limiting examples of anti-static agents included in SBTs and/or SBPs include, behentrimonium chloride, carbon black, cocamidopropyl betaine, dodecylbenzenesulfonic acid, glycerol monostearate, Indium tin oxide, long-chain aliphatic amines, phosphoric acid ester, poly(3,4-ethylenedioxythiophene) polystyrene sulfonate and/or polyethylene glycol ester.

In some embodiments, anti-static additives and/or cargos may include any of those presented in Table 3, above.

Elastomeric Agents

In some embodiments, cargos and/or additives may include elastomeric agents. As used herein, "elastomeric agents" may be defined as agents or substances that impart stretchability, extensibility or elasticity. In some embodiments, elastomeric agents may allow recovery of the SBTs and/or SBPs from stretching without deformation. In some embodiments, the elastomeric agents may be elastomeric fibers such as but not limited to polyurethanes. Non-limiting examples of elastomeric agents included in SBPs and/or include but are not limited Cellamine, T-C 9180 (Intex Chemical), Sandoperm, Dialkylammonium Methosulfate, Sarpifan, Vikomul W-50D, sodium polyacrylate, Rezthane and/or Polydiorganosiloxane.

In some embodiments, elastomeric agent additives and/or cargos may include any of those presented in Table 3, above.

Anti-UV Agents

In some embodiments, cargos and/or additives may be or may include anti-UV agents. As used herein, "anti-UV agents" may be defined as agents or substances that protect against damage caused by ultraviolet light. In some embodiments SBPs and/or SBTs may include anti-UV agents. In some embodiments, the anti-UV agents may protect from ultraviolet light of wavelength from about 280 nm to about 400 nm. In some embodiments, the anti-UV agents may protect from ultraviolet light of wavelength from about 305 nm to about 315 nm. In some embodiments, the anti-UV agents may protect from ultraviolet light of wavelength from about 290 nm to about 360 nm. In some embodiments, anti-UV agents may be measured by their solar protection factor (SPF). As used herein "SPF" refers may be defined as the ratio of the potential erythemal effect to the actual erythemal effect transmitted in the presence of anti-UV agents. SPF may be calculated by spectroscopic measurements. In general the larger the SPF value, the greater the protection against UV light. In some embodiments, anti-UV agents may have SPF values such as but not limited to SPF 4, SPF 8, SPF 12, SPF 14, SPF 8-14, SPF 15, SPF 15-30, SPF 30, SPF 45, SPF 50, SPF 60, and/or SPF 50-100. In some embodiments, anti-UV agents may be measured by their UV protection factor (UPF) which is measure of the amount of UV radiation absorbed by the fiber, and/or textile. In some embodiments, anti-UV agents may have UPF values such as but not limited to from about UPF15 to about UPF24, from about UPF25 to about UPF39, from about UPF40 to about UPF 50, from about UPF50 to about UPF 100.

In some embodiments, anti-UV agents may absorb ultraviolet light and may convert the UV radiation into thermal energy. Non-limiting examples of anti-UV agents include but are not limited to titanium oxide, zinc oxide, o-hydroxy benzophenone derivatives, o-hydroxy phenyl triazine derivatives, o-hydroxy phenyl hydrazine derivatives, 2-hydroxy benzophenone, 2-hydroxy phenyl benzotriazole, 2-hydroxy phenyl-striazines, benzoic acid ester, dibenzoylmethane derivatives, methylanthranilate, 1-N-acetylanthranilate, 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4-methoxydibenzoylmethane, 2-methyl-5-isopropyl-4'-methoxydibenzoylmethane, 2-methyl-5-tert-butyl-4'-methoxy dibenzoylmethane, 2,4-dimethyl-4-methoxydibenzoylmethane, 2,6-dimethyl-4-tert-butyl-4-methoxydibenzoylmethane, 4-(1,1-dimethylethyl)-4'-methoxydibenzoylmethane, 4-isopropyldibenzoylmethane, 4-(1,1-dimethylethyl)-4'-methoxydibenzoylmethane, 4-isoproplydibenzoyl methane, 2-ethylhexyl-2-cyano-3-2-ethylhexyl N,N-dimethyl-paminobenzoate, p-aminobenzoic acid, oxybenzone, homomethyl salicylate, octyl salicylate, 4,4'-methoxy-t-butyldibenzoylmethane, 4-isopropyldibenzoylmethane, 3-benzylidene camphor, 3-(4-methylbenzylidene) camphor, 3-diphenylacrylate, 2-phenyl-benzimidazole-5-sulphonic acid (PBSA), cinnamate esters, TEA triethanolamine salicylate, ethylhexylsaliycyilate, octyldimethyl para aminobenzoic acid (PABA), camphor derivatives, 2-ethylhexyl-2-cyano-3, 3-diphenylacrylate, 2-phenyl-benzimidazole-5-sulphonic acid (PBSA), and/or octyl-p-methoxycinnamate.

In some embodiments, anti-UV agent additives and/or cargos may be or may be formulated as a gel. Anti-UV agents may be prepared as gels by the incorporation of gelling agents. In one embodiment, the gelling agent may be processed silk. In some embodiments, anti-UV agents may include gelling agents such as but not limited to the gelling agents described in Table 3.

In some embodiments, anti-UV agent additives and/or cargos may include any of those presented in Table 3, above.

Anti-Wrinkle Agents

In some embodiments, cargos and/or additives may be or may include anti-wrinkle agents. As used herein, the term "wrinkle" may be defined as any fold or creases introduced unintentionally in a textile. As used herein, the term "anti-wrinkle agents" may be defined as any agent that prevents or minimizes wrinkles and/or creases in SBTs. In some embodiments, anti-wrinkle agents may be cross-link agents that may link molecules within the processed silk, SBPs and/or SBTs to reduce their movement in response to water or stress. The term "durable press" may be used to define processed silk, SBPs and/or SBTs that may have been prepared using processing methods that incorporate anti-wrinkle agents in SBPs and/or SBTs. Non-limiting examples of anti-wrinkle agents included in SBTs and/or SBPs may be Dimethoxymethyl urea, Hexamethylol melamine, Trimethoxymethyl melamine, Hexamethoxylmethyl melamine, Dihydroxyethylene urea heterocycle, N,N'-Dimethylol-4,5-dihydroxyethylene urea, N, V-Dimethyl-4,5-dihydroxyethylene urea, Dimethylurea glyoxalate, Dihydroxy dimethyl-2-imidazolidinone, 1,2,3,4-Butanetetracarboxylic acid, Dimethylol ethylene, Propylene urea, Diglyoxal urea, Triazon, Uron, Diepoxide, Diisocyanate and/or 3-chloro-hydroxypropyl trimethyl ammonium chloride.

In some embodiments, anti-wrinkle agent additives and/or cargos may include any of those presented in Table 3, above.

Polymers

In some embodiments, cargos and/or additives may include polymers. As used herein, the term "polymer" refers to any substance formed through linkages between similar modules or units. Individual units may be referred to herein as "monomers." Common polymers found in nature include, but are not limited to, carbon chains (e.g., lipids), polysaccharides, nucleic acids, and proteins. In some embodiments, polymers may be synthetic (e.g., thermoplastics, thermosets, elastomers, and synthetic fibers), natural (e.g., chitosan, cellulose, polysaccharides, glycogen, chitin, polypeptides, β-keratins, nucleic acids, natural rubber, etc.), or a combination thereof. In some embodiments, polymers may be irradiated. Non limiting examples of polymers include ethylcellulose and co-polymers of acrylic and methacrylic acid esters (EUDRAGIT® RS or RL), alginates, sodium carboxymethylcellulose, carboxypolymethylene, hydroxypropyl methylcellulose, hydroxypropyl cellulose, collagen, hydroxypropyl ethylcellulose, hydroxyethylcellulose, methylcellulose, xanthum gum, polyethylene oxide, polyethylene glycol, polysiloxane, polyphosphazene, low-density polyethylene (LDPE), high-density polyethylene (HDPE), polyvinyl chloride, polystyrene, nylon, nylon 6, nylon 6.6, polytetrafluoroethylene, thermoplastic polyurethanes, polycaprolactone, polyamide, polycarbonate, chitosan, cellulose, polysaccharides, glycogen, starch, chitin, polypeptides, keratins, β-keratins, nucleic acids, natural rubber, hyaluronan, polylactic acid, methacrylates, polyisoprene, shellac, amber, wool, synthetic rubber, silk, phenol formaldehyde resin, neoprene, nylon, polyacrylonitrile, silicone, polyvinyl butyral, polyhydroxybutyrate (also known as polyhydroxyalkanoate), polyhydroxyurethanes, bioplastics, genetically modified bioplastics, lipid-derived polymers, lignin, carbohydrate polymers, ultra-high-molecular-weight-polyethylene (UHMWPE), gelatin, dextrans, and polyamino acids.

Non-limiting examples of polymers include, but are not limited to poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho) esters, poly(butyric acid), poly(valeric acid), poly(lactide-co-caprolactone), and trimethylene carbonate, polyvinylpyrrolidone. In some embodiments, polymer additives and/or cargos may include any of those presented in Table 3, above.

Particles

In some embodiments, cargos and/or additives may include particles. Such particles may be of any size and shape, depending on the nature of associated SBPs. In some embodiments, additive and/or cargo particles may be nanoparticles. Non-limiting examples of nanoparticles include gold nanoparticles, silver nanoparticles, silver oxide nanoparticles, iron nanoparticles, iron oxide nanoparticles, platinum nanoparticles, silica nanoparticles, titanium dioxide nanoparticles, magnetic nanoparticles, cerium oxide nanoparticles, protein filled nanoparticles, carbon nanoparticles, nanodiamonds, curcumin nanoparticles, polymeric micelles, polymer coated iron oxide nanoparticles, ceramic silicon carbide nanoparticles, nickel nanoparticles, and silicon dioxide crystalline nanoparticles.

In some embodiments, nanoparticles may include carbohydrate nanoparticles. Carbohydrate nanoparticles may include carbohydrate carriers. As a non-limiting example, carbohydrate carriers may include, but are not limited to, anhydride-modified or glycogen-type materials, phytoglycogen octenyl succinate, phytoglycogen beta-dextrin, or anhydride-modified phytoglycogen beta-dextrin. (See e.g., International Publication Number WO2012109121, the contents of which are herein incorporated by reference in their entirety).

In some embodiments, cargos and/or additives nanoparticles may include lipid nanoparticles. Lipid nanoparticle cargos and/or additives may be carriers in some embodiments. In some embodiments, lipid nanoparticles may be formulated with cationic lipids. In some embodiments, cationic lipids may be biodegradable cationic lipids. Such cationic lipids may be used to form rapidly eliminated lipid nanoparticles. Cationic lipids may include, but are not limited, DLinDMA, DLin-KC2-DMA, and DLin-MC3-DMA. Biodegradable lipid nanoparticles may be used to avoid toxicity associated with accumulation of more stable lipid nanoparticles in plasma and tissues over time.

In some embodiments, nanoparticles include polymeric matrices. As used herein, the term "polymeric matrix" refers to a network of polymer fibers that may be bound together to form a material. The polymer fibers may be uniform or may include different lengths or monomer subunits. In some embodiments, polymer matrices may include one or more of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), or combinations thereof.

In some embodiments, polymers include diblock copolymers. As used herein, the term "diblock copolymer" refers to polymers with two different monomer chains grafted to form a single chain. Diblock polymers may be designed to aggregate in different ways, including aggregation as a particle. In some embodiments, diblock copolymers include polyethylene glycol (PEG) in combination with polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), or poly(4-hydroxy-L-proline ester).

In some embodiments, nanoparticles include acrylic polymers. As used herein, the term "acrylic polymer" refers to a polymer made up of acrylic acid monomers or derivatives or variants of acrylic acid. Monomers included in acrylic polymers may include, but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), and polycyanoacrylates.

Lipids

In some embodiments, cargos and/or additives include lipids. As used herein, the term "lipid" refers to members of a class of organic compounds that include fatty acids and various derivatives of fatty acids that may be soluble in organic solvents, but not in water. Examples of lipids include, but are not limited to, fats, triglycerides, oils, waxes, sterols (e.g. cholesterol, ergosterol, hopanoids, hydroxysteroids, phytosterol, and steroids), stearin, palmitin, triolein, fat-soluble vitamins (e.g., vitamins A, D, E, and K), monoglycerides (e.g. monolaurin, glycerol monostearate, and glyceryl hydroxystearate), diglycerides (e.g. diacylglycerol), phospholipids, glycerophospholipids (e.g., phosphatidic acid, phosphatidylethanolamine, phosphatidylcholine, phosphatidylserine, phosphoinositides), sphingolipids (e.g., sphingomyelin), and phosphosphingolipids. In some embodiments, lipids may include, but are not limited to, any of those listed (e.g., fats and fatty acids) in Table 3, above.

In some embodiments, lipid cargos and/or additives include amphiphilic lipids (e.g., phospholipids). As used herein, the term "amphiphilic lipid" refers to a class of lipids with both hydrophilic and hydrophobic domains. Amphiphilic lipids may be used to prepare vesicles as these molecules typically form layers along water: lipid interfaces. Non-limiting examples of amphiphilic lipids include, but are not limited to, phospholipids, phosphatidylcholines, phosphatidylethanolamines, palmitoyl-oleoyl-phosphatidylethanolamine (POPE), phosphatidylserines, phosphotidylglycerols, lysophospholipids such as lysophosphatidylethanolamines, mono-oleoyl-phosphatidylethanolamine (MOPE), mono-myristoyl-phosphatidylethanolamine (MMPE), lysolipids, mono-oleoyl-phosphatidic acid (MOPA), mono-oleoyl-phosphatidylserine (MOPS), mono-oleoyl-phosphatidylglycerol (MOPG), palmitoyloleoyl phosphatidylcholine, lysophosphatidylethanolamine, dipalmitoylphosphatidylcholine, dioleoylphosphatidylcholine; distearoylphosphatidylcholine, dilinoleoylphosphatidylcholine, 1,2-dioleoyl-sn-glycero-3-phosphocholine (DOPC), 1,2-dioleoyl-sn-glycero-3-phophoethanolamine (DOPE), 1,2-dilauroyl-sn-glycero-3-phosphocholine (DLPC), 1,2-dimyristoyl-sn-glycero-3-phosphocholine (DMPC) phosphatidylinositol, phosphatidic acid, palmitoyloleoyl phosphatidylcholine, lysophosphatidylethanolamines, monoglycerides, diglycerides, triglycerides.

Coating Agents

In some embodiments, SBTs and/or SBPs may be used as coating agents. As used herein, the term "coating agent" refers to a substance covering or used to cover an article, wherein the substance adheres to the article (also referred to herein as "coatings"). Coating agents may include, but are not limited to, processed silk, paints, lacquers, adhesives, surfactants, particles, liquids, metals, lipids, oils, proteins, plastics, polymers, insulations, films, and membranes. Coating agents may be used, for example, to coat cargo, payloads, devices, or device components. Coatings may be used to protect coated articles. Some coatings may be used to impart a desired property to the article coated (e.g., to provide a desired texture, flavor, hydrophobicity, etc.). In some embodiments, SBTs and/or SBP coating agents may be used as lubricants. Additional non-limiting examples of coating agents are listed in Table 3. In some embodiments, coating agents may include any of the additive and/or cargos listed in Table 3. In some embodiments, coating agents including processed silk may be applied to fibers, yarns, membranes, filaments, threads, materials and/or articles.

Uses

In some embodiments, SBTs and/or SBPs may be used in a variety of applications.

Apparel and Footwear

In some embodiments, apparel may include SBTs and/or SBPs. The SBTs and/or SBPs may be part of the final product and/or may be used in the preparation of the apparel. As used herein "apparel" may be defined as any article that is used to clothe, cover and/or is worn on the body of subject. As used herein, the term "subject" refers to any entity to which a particular process or activity relates to or is applied. In some embodiments, apparel may be prepared using textiles. Non-limiting examples of subjects may include humans, domesticated animals, and/or wild animals. In one embodiment, the textile may be silk-based textiles. In some embodiments, SBTs and/or SBPs may be combinations of processed silk with one or more textiles. In some embodiments, SBTs may be combinations of SBP with one or more textiles. In one embodiment, SBT and/or SBP apparel may include combinations of processed silk and materials. In some embodiments, SBTs and/or SBPs may be or may be used at any stage of apparel preparation. SBTs may also be prepared by the incorporation of SBPs in apparel. In some embodiments, SBTs and/or SBPs used may be or may include coating agents. Coating agents such as but not limited to processed silk may be applied to fibers, yarns, membranes, filaments, threads, materials and/or articles. Apparel may be prepared to include multiple layers of textiles. In one embodiment, apparel may include one or more layers of SBTs and/or SBPs. In some embodiments, SBTs and/or SBP may be a layer that is in contact with the skin.

In some embodiments, the apparel may include SBTs and/or SBPs to prepare apparel of different textile weight. As used herein, "textile weight" may be defined as the weight of the textile in ounces per square yard. Textile weight may also be defined using metric system units as the weight of a textile in grams per square meter (GSM). Textiles may be classified as but is not limited to very light weight (from about 2 to about 3 oz. per square yard (from about 57 to about 85 GSM); light weight (from about 4 to 5 about oz. per square yard (from about 113 to about 142 GSM); medium weight (from about 6 to about 8 oz. per square yard (from about 170 to about 227 GSM); medium heavy weight (from about 9 to about 12 oz. per square yard (from about 255 to about 340 GSM); heavy weight (greater than 12 oz. per square yard (greater than 340 GSM). In some embodiments, SBT and/or SBP apparel may be very light weight. In some embodiments, SBT and/or SBP apparel may be light weight. In some embodiments, SBT and/or SBP apparel may be medium weight. In some embodiments, SBT and/or SBP apparel may be medium heavy weight. In some embodiments, SBT and/or SBP apparel may be heavy weight. In some embodiments, SBT and/or SBP apparel do not restrict of motion by the subject. As a non-limiting example, SBT and/or SBP apparel may include elastomeric agents that impart stretchability, extensibility and/or elasticity to the apparel allowing the unrestricted movement of the subject. In some embodiments, SBTs and/or SBP apparel may be fashion apparel. As used herein "fashion apparel" refers to apparel prepared according to the prevailing and/or popular trends, styles, and/or designs. In some embodiments, SBT and/or SBP apparel may be form-fitting. As used herein "form fitting" may refer to an apparel that tightly follows the contours of the part of the body of the subject being covered.

SBTs and/or SBP apparel may facilitate moisture management. The release of moisture from the surface of the skin may be a mechanism of regulating body temperature in living organisms. As used herein, "moisture management" may be defined as the property of a fiber, textile and/or apparel to manage moisture by transporting or wicking moisture away from the skin to the fiber, textile and/or apparel's outer surface. In some embodiments, SBTs and/or SBPs apparel may be able to wick moisture away from the skin of the subject. The SBTs and/or SBP apparel may include fibers with a kidney bean and/or trilobal cross-sectional shape which may allow the moisture to be wicked away from the skin. In some embodiments, SBT and/or SBP apparel may include fibers such as but not limited to modal, micro-modal, and/or Tencel® have a high moisture regain (from about 35% to about 70%). In some embodiments, SBT and/or SBP apparel may include fibers that do not absorb moisture but allow the moisture to sit on the surface of the fiber and to move along the weave of the apparel. In one embodiment, SBT and/or SBPs apparel may be prepared with finishing agents that are water repellents. In other aspects, SBTs and/or SBPs may not be able to wick moisture away for the skin of the subject.

In some embodiments, SBT and/or SBP apparel may be wrinkled. As used herein, a "wrinkle" may be defined as any fold or creases introduced unintentionally in a textile. In one aspect, creases and folds may intentionally introduced in the SBT and/or SBP apparel. SBT and/or SBP apparel may be substantially free of wrinkles. Wrinkles may be prevented or removed from SBP and/or SBT apparel by the addition of anti-wrinkle agents in the SBTs and/or SBPs.

In some embodiments, SBT and/or SBP apparel may be repellent to an agent or an organism. SBT and/or SBP apparel may repel agents such as water, lipids, or a combination of both. SBT and/or SBP apparel may also be repel, kill or prevent the growth of organisms that such as but not limited to bacteria, fungi, dust mites, insects and/or pests. Organisms such as bacteria may be grown on apparel and metabolize dirt and sweat produced by subjects and release odors. By repelling, killing or preventing the growth of organisms, SBT and/or SBP apparel may be odor resistant. SBT and/or SBP apparel may also be or include fragrances which may mask the odors released by organisms.

Apparel may be exposed to dust, dirt and/or stains. In one embodiment, the dust, dirt and/or stains may be removed from the SBT and/or SBP apparel by washing with detergent, mechanical action, and/or solvents. In some embodiments, SBP and/or SBT apparel may be prepared with dirt release agents. Dirt release agents may include agents that allow the release dirt and unwanted stains upon washing.

In some embodiments, SBTs and/or SBPs apparel may provide protection to the subject against UV light. In some embodiments, anti-UV agents may be included in SBTs and/or SBPs apparel. The ability of SBTs and/or SBP apparel may be classified based on their UV protection factor (UPF). As used herein, UPF may be defined as the amount of UV radiation absorbed by a textile. In some embodiments, SBTs and/or SBPs apparel may have UPF values such as, but not limited to from about UPF15 to about UPF24, from about UPF25 to about UPF39, from about UPF40 to about UPF 50, from about UPF50 to about UPF 100.

In some embodiments, SBTs and/or SBPs may be or may be used in the preparation of outerwear apparel. The SBTs and/or SBPs may be part of the final product and/or may be used in the preparation of the outerwear apparel. As used herein, "outerwear" may be defined as apparel that may be designed to be worn by a subject when the subject ventures in the outdoor and/or apparel that may be worn over other apparel. In some embodiments SBP and/or SBT outerwear may include but are not limited to abaya, academic gown, anorak, apron, blazer, cagoule, cloak, coat, duffle coat, duster, frock coat, gilet, goggle jacket, greatcoat, hat, hoodie, jacket, leather jacket, jerkin, matchcoat, mess jacket, mino (straw cape), opera coat, overcoat, pea coat, poncho, raincoat, rain pants, redingote, robe, shawl, shrug, ski suit, sleeved blanket, sport coat, top coat, touque, trench coat, tuxedo, vest, and/or windbreaker.

In some embodiments, SBTs and/or SBPs may be or may be used in the preparation of undergarments. The SBTs and/or SBPs may be part of the final product and/or may be used in the preparation of the undergarments. As used herein, the term "undergarment" may be defined as apparel that may be worn by a subject beneath the outer wear and/or in direct contact with the skin. Non-limiting examples of SBPs and/or SBT apparel may be bra, panties, briefs, boxer briefs, boxer shorts, loincloths, T-shirts, sleeveless shirts, singlets, tank tops, bikini, thongs, G-strings, and/or long underwear.

In some embodiments, SBTs and/or SBPs may be or may be used in the preparation of apparel based on the region of the body that the apparel may be used to clothe or cover. The SBTs and/or SBPs may be part of the final product and/or may be used in the preparation of the apparel. In some embodiments, SBT and/or SBP apparel may be used to cover the torso e.g. short sleeve t-shirts, long sleeve t-shirts, polo shirts, button-down shirts, blouses, jerseys, sweaters, fleeces, sweatshirts, pullovers, jumpers, tank tops, halter tops, cardigans, paletots, tunics, yashmaks, tallits, serapes, shawls, and/or oversleeves. In some embodiments, SBT and/or SBP apparel may be used to cover the region of the body below the torso e.g. kameez, kaross, kilts, manteaus, palliums, skirts, overskirts, leotards, leggings, maillots, saron, pants, yoga pants, stretch pants, dungarees, jeans, khakis, slacks, cargo pants, cargo shorts, fatigues, lungi, dhotis, athletic shorts, athletic pants, casual pants, formal pants, shorts, posing trunks, gambesons, snow pants, joggers, jean shorts, pajamas, and/or kilts. In some embodiments, SBP and/or SBT apparel may be dresses, saris, and/or dressing gowns.

In some embodiments, SBTs and/or SBPs may be or may be used in the preparation of loungewear and/or sleepwear. The SBTs and/or SBPs may be part of the final product and/or may be used in the preparation of the loungewear and/or sleepwear. As used herein, "loungewear" may refer to apparel that may be suitable for wear during leisure, night and/or at home. As used herein, "sleepwear" may be defined as appear that may be worn by a subject that is suitable for bed and/or for sleeping. Loungewear and/or sleepwear may include apparel such as but not limited to bathrobes, peignoir, pajamas, dressing gowns, nightgowns and/or nightshirts.

In some embodiments, SBTs and/or SBPs may be or may be used in the preparation of uniforms. As used herein, "uniform" may be defined as a type of apparel worn by members of an organization or an entity, while participating in activities relating to the organization or entity. SBTs and/or SBPs may be part of the final product and/or may be used in the preparation of uniforms for organizations and/or entities such as but not limited to military, paramilitary organizations (e.g. police, emergency services, security guards); schools, workplace (e.g. academic, judicial, transportation crew), prisons, and/or sports teams. Non-limiting examples of SBP and/or SBT uniforms include but are not limited to coatee, czapka, epaulette, fez, fourragère, garrison cap, glengarry, gorget, gymnasterka, hackle, kepi, medal, peaked cap, pickelhaube, pith helmet, red coat, ribbon bar, rogatywka, sailor cap, sam browne belt, sash, shako, stable belt, tunic, ushanka, full dress military uniform, mess dress military uniform, service dress military uniform, combat military uniform, physical training military uniform, emergency medical service (ems) uniform, emergency medical technician (EMT) uniform, ems jumpsuit, ems squad suit, ems long sleeve shirt, over-the-clothes ems jumpsuit, flame resistant coverall style extrication suit, extrication pants (worn by emergency personnel), firefighter pants, tactical pants, ems high visibility uniforms, public safety uniform, prison guard uniform, prison inmate uniform, scrub tops, scrub pants, lab coats, scrub caps, baseball uniforms, basketball uniforms, ice hockey uniform, martial arts uniform, cricket uniform, American football uniform, graduation gown, and/or graduation cap.

In some embodiments, SBTs and/or SBPs may be or may be used in the preparation of costumes. The SBTs and/or SBPs may be part of the final product and/or may be used in the preparation of the costume. As used herein, "costume" may be defined as a type of apparel that may create the appearance characteristic of a particular period person, place or thing.

In some embodiments, SBTs and/or SBPs may be or may be used in the preparation of maternity apparel. The SBTs and/or SBPs may be part of the final product and/or may be used in the preparation of the maternity apparel. As used herein maternity apparel may be defined as apparel that worn by pregnant women that may be designed to adapt to changes in body size during gestation. In some embodiments, SBP and/or SBT maternity apparel may include elastomeric agents to allow for the apparel to adapt to the increase in growth and increasing size of the pregnant mother.

In some embodiments, SBTs and/or SBPs may be or may be used in the preparation of religious apparel. The SBTs and/or SBPs may be part of the final product and/or may be used in the preparation of the religious apparel. As used herein, religious apparel may be defined as apparel associated with religious practice, tradition and/or significance. Non-limiting examples of SBT and/or SBP religious apparel may include cassock, Ferraiolo, cape, Hat, clerical collar, neckband, clerical waistcoat, Rabat, Skufia, Kamilavka, Apostolnik, Epanokamelavkion, Klobuk, Hijab, Abaya, Tzitzit, Tefillin, Kippah, Mitpachat, Rekel coats, Bekishe coats, Kittel robe, Gartel, sacred thread (poonal), kimono, Buddhist robe, and/or chivara (robe).

In some embodiments, SBTs and/or SBPs may be or may be used in the preparation of sportswear. The SBTs and/or SBPs may be part of the final product and/or may be used in the preparation of the sportswear. As used herein, the term "sportswear" may be defined as an apparel worn by a sportsman or any other individual engaged in a sport. In some embodiments, sportswear may also be referred to as active wear. Non-limiting examples of sportswear include but are not limited to tracksuit, sports bra, swimwear, leggings, tights, leg warmers, breeches, bloomers, body suit, jersey, leotards, pants, suit, stirrup pants, sweatpants, and/or swimsuit. In some embodiments, SBP and/or SBT sportwear may be categorized by the sport with which they are associated and/or used for. Non-limiting categories of sportswear include cycling apparel, hiking apparel, fishing apparel, motorcycle racing apparel, baseball apparel, basketball apparel, American football apparel, martial arts apparel, skiing apparel, soccer apparel, tennis apparel, golf apparel, yoga apparel, hunting apparel, skydiving apparel, scuba diving apparel, mountaineering apparel, hockey apparel, and/or running apparel. In some embodiments, SBTs and/or SBPs may athleisure apparel. As used herein, the term "athleisure apparel" may be defined as apparel that may be sportswear or active wear that may be worn by a subject who may not be a sportsman and/or may not be engaged in a sport.

In some embodiments, SBTs and/or SBPs may be or may be used in the preparation of formal apparel i.e. apparel designated as suitable for occasions deemed formal by society, informal wear i.e. apparel suitable for individuals engaged in or conducting business, casual wear i.e. apparel suitable for occasions not deemed formal by society. The SBTs and/or SBPs may be part of the final product and/or may be used in the preparation of the formal apparel. Non limiting examples of SBP and/or SBT formal apparel include but may not be limited to morning coat, waiting coat, striped trousers, stiff front shirt, pique bow tie, waist coats, tailcoat, ball gowns, and/or evening gowns.

In some embodiment, SBTs and/or SBPs apparel may be or may be used in the preparation of traditional apparel. The SBTs and/or SBPs may be part of the final product and/or may be used in the preparation of the traditional apparel. As used herein, "traditional apparel" may be defined as the apparel worn by or identified with a group of individuals belonging to a geographical region, religion, caste or belief system. Non-limiting examples of SBP and/or SBT traditional apparel include but are not limited to Abaya, Aboyne dress, Achkan, Aelan dress, Afghan cap, Afrikaners, Agal, Agbada, Akubra slouch hat, Alasho, Aloha shirt, alpargatas, amauti, Áo bà ba, Áo dài, Áo giao lĩnh, Áo po'i, Áo tứ' thân, Apsara, Aran sweater, Arbereshe costumes, Arkhalig, Aso Oke Hat, Augemwalli, Australian work boots, Azerbaijani, Babban riga, Baju Kebarung (Kebaya/Kurung hybrid), Baju Kurung, Baju Lokchuan, Baju Melayu, Balgha, Balmoral bonnet, Barong, Baro't Saya, Barretina, Batakari, Batik shirt, Bedouin, Beret, Bermuda shorts, Beskap, Bikhmar (Ouargla), Binouar, Bisht, Blangkon, Bleu sårot, blouse, Blouza (Oran), Boubou, breech clouts, Breton shirt, brogues, Buba, buckskins, Bunad, Burnous, bush shirt, button blanket, Caftan, Caftan El-Bey, Caipiras, Canadian tuxedoes, Capote, Capulana, Ceinture fléchée, Chacabana, Chador, Chang kben, Changpao, Changshan, Chapan, Charro outfit, Chechia, Chemsa (Jijel), Cheongsam, Cheongsam Tangzhuang, Chilkat blanket, Chitenje, Chiton, Chokha, Choli, Chong kraben, Chosŏn-ot, Chuba, Chullo, Chupalla, Churidar, Chut thai, Coppola, cork hat, Corte skirt, Cowichan sweater, Cuera tamaulipeca, Cumbia pollera, Darra'a, Dashiki or Isiagu, Dashiki suit, Daura-Suruwal, Deel, Dhaka topi, Dhivehi libaas, Dhivehi mundu, Dhoti, Dirac, Dirndl, Dirndl, Dishdasha, Djellaba, doublet, Driza-Bone coat, Dupatta, Dutch cap, ean pollera, enaguas, espadrilles, Ethiopian suit, Faixa, Farmla, Fergani (Constantine), Fez hat, Firaq partug, flannel shirt, Folkedragt, Føroysk klæôi, Fouta, fundoshi, Fustanella, Gåkti, Galabeya, Garbasaar, Gaucho, Gaúcho, Gaung baung, Ghanaian smock, Ghlila, Gho, Ghonnella, Ghutrah, Gilaki, glass beads, Gomesi, Gorenjska noša, Grass skirt, guarachera, Guayabera, Guayabera, Guntiino, Gunyou Cholo, Habesha kemis, Haïek, Hanbok, Hanfu, Hashimi Dress, Holokū, Huaso costume: Chamanto, Huipil, Imvutano, Irish walking hat, I-sala, Jalabiyyah, Jamaican Tam, jambiya, Jebba, Jellaba, Jellabiya, Jilbab, Joropo, Junihitoe, Kaftan, Kanga, Kanzu, Karabela dress, Karakou Sarouel Mdawer (Algiers), Kebaya, Keffiyeh, Kelaghayi, Kente kaba, Khalat, Kidan Habesha, Kikoi, Kilt tam o'shanter, Kimono, Kira, Kitenge, Klompen, knee-high socks, knickerbockerspossum cloak, Kofia, Kokoshnik, Kontusz, Koofiyad, Kosovorotka, Koteka, Kotomisse, Krama, Kroj, Kroje, Kufi, Kurta, Kuspuks, Labbade, Labsa Kbaylia (Kabylie), Labsa M'zabia (M'zab), Labsa Naïlia (Ouled Naïl), Labsa Touratia (Hoggar), Lamba, Lap-lap, lap-lap, Lavalava, Lederhosen, Lefa we diala (Annaba), Lehenga, Lehengha, Leine, Lesso, Liechtenstein-Tracht, Lika cap, Llanero, Longyi, Luhkka, Macawiis, mackinaw jackets, Magua, Malo, Manou, Mãori Flax Skirts, Maria Clara gown, Melhfa Chaouïa (Aures), Melhfa Sahraouia, Melhfa Sahraouia (Tindouf), Meri blaus, Mizu happi, Mlaya, moccasins, Mokorotlo, Moleskin trousers, Montenegrin cap, montera, Montuno, mukluks, Mushanana, Muumuu, Newar, Niqab, Noisa, Opanci, Pagne, panama hat, Pangi cloth, Pano, Pano de terra, Pareo, Parka, parkas, Pathin, Patiala salwar, Pä'ū, Peplos, Peshawari pagri, pha biang, pha hang, Phiran, poffer, Pollera, Poncho, Puletasi, Pyjama, Qashabiya (Djelfa et Laghouat), Qashqai, Rahvariided, Rai, Rebozo, Robes mission, Rogatywka, Romanian dress, Rooineks, ruana, Sabai, Šajkača, Sami: Gákti, Sampot, Sarafan, Sarape, Sari, Sarong, Sarong, Sarouel, Sega dress, Senegalese kaftan, Shalvar, Shalwar Kameez, Sharovary, Sherwani, Shirt jacket, Sibenik cap, sinh, Sirwal, slouch hat, Slutsk stash, Sokutai, Sombrero, Sombrero cordobes, Sombrero Vueltiao, Songket, Songkok, Stola, Šubara, suea pat, Suea Phraratchathan, Sulu, Sunuwar, Sverigedräkten, Swanndri bush jacket, Tagelmust, Takchita, Tangzhuang, Tantour, Ta'ovala, Tapa cloth, Taqiyah, Taqiyyah, Tautastērps, Tautinis kostiumas, Tehuana, Terno, Thai Chakkri, Thawb, þjóðningurinn, Tocado, Todosantero suit, Toga, Toghu, Toob, Tracht, traditional pow-wow regalia, traje de flamenca, traje de luces, trousers, Tubeteika, Tudung, Tupenu, tuque, Turban, Ulos, Umbhaco, Ushanka, Valenki, veldskoen, Vyshyvanka, xout lao, Yaqui, Zupan, and/or Zuria.

SBTs and/or SBPs for use in apparel may be thermally insulated, which, as used herein may be defined as the reduction of heat transfer between objects in thermal contact or in range of radiative influence. In some embodiments, SBTs and/or SBPs may not be thermally insulated. Thermally insulated SBT and/or SBP apparel may be used to provide protection against environmental temperature and/or temperatures that are different than the body temperature of the subject. Body temperature of the subject may be at or around 37° C. In some embodiments, thermally insulated SBT and/or SBP apparel may be thermally insulated against temperatures colder than the body temperature of the subject. In some embodiments, thermally insulated SBT and/or SBP apparel may be thermally insulated against temperatures higher than the body temperature of the subject. Non-limiting examples of thermally insulated SBT and/or SBP apparel include but are not limited to jackets, fleece, rainwear, vests, shirts, pants, snowsuits, bunting, and/or underwear.

In some embodiments, SBTs and/or SBPs may be apparel accessories. In some embodiments, apparel accessories may include SBTs and/or SBPs. The SBTs and/or SBPs may be part of the final product and/or may be used in the preparation of the apparel accessories. As used herein, "apparel accessories" may be defined as articles that may be used in conjunction with apparel to enhance the appearance, and/or function of apparel. Non-limiting examples include, caps, hats, fedora, baseball cap, balaclava, skull cap, flap cap, sun hats, vizors, cloche hats, cowboy hats, berets, beanies, goggles, glasses, bandanas, scarfs, pashminas, infinity scarf, earmuffs, facemasks, gloves, mittens, bonnets, ribbons, durags, headbands, ties, bowties, belts, sashes, bibs, suspenders, garters, socks, panty hose, legwarmers, toe socks, gaiters, and/or jewelry.

In some embodiments, SBTs and/or SBPs may be or may be used in the preparation of footwear. In some embodiments, footwear may include SBTs and/or SBPs. The SBTs and/or SBPs may be part of the final product and/or may be used in the preparation of the footwear. As used herein, "footwear" may be defined as articles that may be worn on and/or used to cover feet of a subject. In some embodiments, SBT and/or SBP footwear may be utilized to aid in locomotion, to prevent injuries, to protect the subject from environmental factors such as but not limited to ground textures, temperature, moisture. In some embodiments, footwear may include an upper structure and a sole structure. In some embodiments, SBTs and/or SBPs may be or may be included in the upper structure, the sole structure, and/or both. In some embodiments, the upper structure may provide a partial or complete covering for the foot that securely receives and positions the foot with respect to the sole structure. In addition, the upper structure may be configured to protect the foot from damage caused by UV, dust, friction and/or water. In some embodiments, the upper structure of the SBP and/or SBT footwear may wick moisture away from the foot, thereby cooling the foot and removing perspiration. In some embodiments, the sole structure may be secured to a lower surface of the upper structure. The sole structure may be positioned between the foot and the ground. In some embodiments, the sole structure may attenuate ground reaction forces, absorb energy (i.e., cushioning), provide traction, and/or control potentially harmful foot motion. In some embodiments, the upper structure may form a void on the interior of the footwear for receiving the foot. The void may have the general shape of the foot, and access to the void may be provided by an ankle opening. In some embodiments, the upper and/or the sole structure may include fasteners to secure the foot to the footwear and/or permit the wearer to modify certain dimensions of the footwear. In some embodiments, SBT and/or SBP that may be used in footwear may promote resistance to wear and tear, flexibility, ventilation, comfort, moisture wicking, odor control, and/or thermal insulation. In some embodiments, SBT and/or SBP footwear may include other SBT and/or SBP components such as but not limited to leather, synthetic leather, rubber, and/or polymers.

In some embodiments, SBT and/or SBP footwear may be, but is not limited to, boots, shoes, sandals, slippers. In some embodiments, SBT and/or SBP footwear may be boots.

Non-limiting examples include chukka boots, combat boots, cowboy boots, derby boots, fashion boots, go-go boots, hiking boots, motorcycle boots, mukluk, platform boots, riding boots, Russian boots, railing boots, seaboots, tabi boot, tanker boots, thigh-length boots, Ugg boots, valenki, veldskoen, waders, wellington boots, and/or winklepicker. In some embodiments, SBT and/or SBP footwear may be shoes. Non-limiting examples include bowling shoes, football shoes, athletic shoes, ballet flats, brothel creepers, court shoes, diabetic shoes, espadrilles, galoshes, kitten heels, lace-up shoes, derby shoes, oxford shoes, brogues, blucher shoes, high-tops, loafers, Mary Janes, moccasins, monks, mules, platform shoes, plimsoll shoes, school shoes, skate shoes, sneakers, tap shoes, toe shoes, and/or vibram five fingers toe shoes. In some embodiments, SBT and/or SBP footwear may be sandals. Non-limiting examples include, Kolhapuri chappals, Peshawari chappal, flip-flops (thongs), slide, and/or Wörishofen. In some embodiments, SBT and/or SBP footwear may serve a specific function which may be indicated in the name of the footwear. Non-limiting examples include, climbing shoe, ballet shoes, boat shoes, high-heeled footwear, climbing shoes, clogs, football boots, sabaton, safety footwear, sailing boots, ski boots, snowshoes, surgical shoe, pointe shoes, and/or swim fins (flippers). In some embodiments, SBT and/or SBP footwear may be worn by or identified with a group of individuals belonging to a geographical region, religion, caste or belief system Non-limiting examples include but are not limited to Abarka, Areni, Bast shoe, Crakow, Galesh, Geta, Klompen, Opanci, and/or Pampooties. SBT and/or SBP footwear may be or may be used in the preparation of footwear that may companion to uniform, academic apparel, sports apparel, costume, religious apparel, and/or traditional apparel.

In some embodiments, SBT and/or SBP apparel may be prepared according to the methods described in International Patent Publication WO2016090055, the contents of which are herein incorporated by reference in their entirety.

In an embodiment, SBT and/or SBP apparel may include a coating prepared using a coating agent. In one aspect, the coating may include processed silk. In some embodiments, the processed silk, SBP and/or SBT coating may be positioned on the underlining of sportswear. In some embodiments, the processed silk, SBP and/or SBT coating of the present disclosure may be positioned on the shell, the lining, or the interlining of the sportswear. In some embodiments, the processed silk, SBP and/or SBT coating may be included in partially in the apparel. In some embodiments, SBP and/or SBT apparel may include coating agents such as but not limited to polyester, polyamide, polyaramid, polytetrafluorethylene, polyethylene, polypropylene, polyurethane, silicone, mixtures of polyurethane and polyethylene glycol, ultrahigh molecular weight polyethylene, high-performance polyethylene, nylon, LYCRA® (polyester-polyurethane copolymer, also known as SPANDEX and elastomer), and mixtures thereof. In some embodiments, SBP and/or SBT apparel may include elastomeric agents. In an embodiment, proportion of processed silk to the elastomeric agent may be varied in the SBPs and/or SBTs to achieve desired shrink or wrinkle resistant properties and desired moisture content against the skin surface. In an embodiment, a silk coating of the present disclosure is positioned on an internal layer of a shoe (textile or non-textile based). In some embodiments, the processed silk, SBP and/or SBT coating is positioned on an internal layer of a shoe and may help maintain optimal feet microenvironment, such as temperature and humidity while reducing any excessive perspiration.

In some embodiments, the processed silk, SBP and/or SBT coating of the present disclosure may be visible to the naked eye. In some embodiments, the processed silk, SBP and/or SBT coating of the present disclosure may be transparent. In some embodiments, the processed silk, SBP and/or SBT coating of the present disclosure may be included on the surface of the sportswear and/or apparel and may help control skin temperature of a subject wearing the apparel. In some embodiments, the processed silk, SBP and/or SBT coating of the present disclosure may be included to control fluid transfer away from the skin of a subject wearing the apparel. In one embodiment, SBTs and/or SBP described herein may be waterproof. As used herein, the term "waterproof" may be defined as a process and/or property of a material to remain unaffected by water and/or resist the ingress of water. In some embodiments, the SBTs and/or SBPs may improve the health of the skin of the subject. Health of the skin may be determined by the visible appearance of an even skin tone. In one embodiment, healthy skin may be determined by the visible appearance of smooth, glowing complexion. In one embodiment, SBTs and/or SBPs decreases irritation of the skin. In some embodiments, a decrease in irritation of the skin may result in a decrease in skin bumps or sores. In one embodiment, a decrease in irritation of the skin may result in a decrease in scaly or red skin. In one embodiment, a decrease in irritation of the skin may result in a decrease in itchiness or burning. In one embodiment, SBPs and/or SBTs may decrease inflammation of the skin.

The transfer of moisture between the subject and the SBTs and/or SBP apparel, or footwear may be measured using a device called a Moisture Management Tester (MMT). The device measures moisture in different directions of the fabric to obtain indices of moisture transfer, parameters measured may include wetting time (top/bottom), absorption rate (top/bottom), maximum wetted area (top/bottom), spreading speed (top/bottom), accumulative one-way transport index and overall moisture-management capacity (OMMC) may be measured to determine the appropriateness of the SBTs for different apparel uses. In some embodiments, SBTs may be classified into six grades, which are water-repellent fabric, slow absorbing fabric, fast absorbing and slow drying fabric, fast absorbing and quick drying fabric, water-penetration fabric and moisture-management fabric. These properties and related methods are described in Association of Textile, Apparel & Materials Professionals (AATCC) test method 195-5 2012 for the measurement, evaluation, and classification of liquid moisture management in textiles (the contents of which are incorporated by reference in their entirety). The absorption rate (ART) (top surface) and (ARB) (bottom surface) may be defined as the average speed of liquid moisture absorption for the top and bottom surfaces of the specimen during the initial change of water content during a test. The accumulative one-way transport capability (R) may be defined as the difference between the area of the liquid moisture content curves of the top and bottom surfaces of a specimen with respect to time. The bottom surface (B) may be defined for testing purposes as the side of the specimen placed down against the lower electrical sensor which is the side of the fabric that would be the outer exposed surface of a garment when it is worn or product when it is used. The top surface (T) for testing purposes may be defined as the side of a specimen that, when the specimen is placed on the lower electrical sensor, is facing the upper sensor. This is the side of the fabric that would come in contact with the skin when apparel is worn or when a product is used. Moisture management may be is defined, for liquid moisture management testing, as the engineered or inherent transport of aqueous liquids such as perspiration or water (relates to comfort) and includes both liquid and vapor forms of water. The overall (liquid) moisture management capability (OMMC), an index of the overall capability of a fabric to transport liquid moisture as calculated by combining three measured attributes of performance: the liquid moisture absorption rate on the bottom surface (ARB), the one-way liquid transport capability (R), and the maximum liquid moisture spreading speed on the bottom surface (SSB). The spreading speed (SSi) is defined as the accumulated rate of surface wetting from the center of the specimen where the test solution is dropped to the maximum wetted radius. The total water content (U) (%) is defined as the sum of the percent water content of the top and bottom surfaces. The wetting time (WTT) (top surface) and (WTB) (bottom surface) may be defined as the time in seconds when the top and bottom surfaces of the specimen begin to be wetted after the test is started.

In some embodiments, SBTs may have an accumulative one-way transport index of greater than 140. In some embodiments, SBTs may an accumulative one-way transport index of greater than 120. In some embodiments, SBTs may have an accumulative one-way transport index of greater than 100. In some embodiments, SBTs may have an accumulative one-way transport index of greater than 80.

In some embodiments, SBTs may have an overall moisture management capability of greater than 0.4. In some embodiments, SBTs may have an overall moisture management capability of greater than 0.35. In some embodiments, SBTs may have an overall moisture management capability of greater than 0.3. In some embodiments, SBTs may have a wetting time of at least 3 seconds. In some embodiments, SBTs may have a wetting time of at least 2.5 seconds. In some embodiments, SBTs may have a wetting time of at least 2 seconds. In some embodiments, SBTs may have a wetting time of at least 1.5 seconds.

In some embodiments, SBTs may have a top absorption time of at least 50 seconds. In some embodiments, SBTs may have a top absorption time of at least 40 seconds. In some embodiments, SBTs may have a top absorption time of at least 30 seconds.

In some embodiments, SBTs may have a bottom absorption time of at least 80 seconds. In some embodiments, SBTs may have a bottom absorption time of at least 70 seconds. In some embodiments, SBTs may have a bottom absorption time of at least 60 seconds. In some embodiments, SBTs may have a bottom absorption time of at least 50 seconds. In some embodiments, SBTs may have a bottom absorption time of at least 40 seconds.

In some embodiments, SBTs may have a spreading speed of at least 1.6 mm/second. In some embodiments, SBTs may have a spreading speed of at least 1.4 mm/second. In some embodiments, SBTs may have a spreading speed of at least 1.2 mm/second. In some embodiments, SBTs may have a spreading speed of at least 1.0 mm/second. In some embodiments, SBTs may have a spreading speed of at least 0.8 mm/second.

In some embodiments SBTs may be or may include anti-microbial preservatives and/or therapeutic agents such as antibacterial agents, anti-fungal agents. SBTs and/or SBPs may therefore slow, inhibit and/or reduce microbial growth, or specifically bacterial or fungal growth the over time. In some embodiments, SBTs may show less than 2000% microbial growth over 24 hours. In some embodiments, SBTs may show less 1000% microbial growth over 24 hours. In some embodiments, SBTs may show less than 500% microbial growth over 24 hours. In some embodiments, SBTs may show less than 400% microbial growth over 24 hours. In some embodiments, SBTs may show less 300% microbial growth over 24 hours. In some embodiments, SBTs may show less than 200% microbial growth over 24 hours. In some embodiments, SBTs may show less than 2000% bacterial growth over 24 hours. In some embodiments, SBTs may show less than 1000% bacterial growth over 24 hours. than 500% bacterial growth over 24 hours. In some embodiments, SBTs may show less than 400% bacterial growth over 24 hours. In some embodiments, SBTs may show less than 300% bacterial growth over 24 hours. than 200% bacterial growth over 24 hours.

In some embodiments, SBTs may show less than 2000% fungal growth over 24 hours. In some embodiments, SBTs may show less than 1000% fungal growth over 24 hours. In some embodiments, SBTs may show less than 500% fungal growth over 24 hours. In some embodiments, SBTs may show less than 400% fungal growth over 24 hours. In some embodiments, SBTs may show less than 300% fungal growth over 24 hours. In some embodiments, SBTs may show less than 200% fungal growth over 24 hours.

In some embodiments, SBTs may show less than 2000% growth of *Staphylococcus aureus* over 24 hours. In some embodiments, SBTs may show less than 1000% growth of *Staphylococcus aureus* over 24 hours. In some embodiments, SBTs may show less than 500% growth of *Staphylococcus aureus* over 24 hours. In some embodiments, SBTs may show less than 400%>growth of *Staphylococcus aureus* over 24 hours. In some embodiments, SBTs may show less than 300%>growth of *Staphylococcus aureus* over 24 hours. In some embodiments, SBTs may show less than 200% growth of *Staphylococcus aureus* over 24 hours.

In some embodiments, SBTs may show less than 2000% growth of *Klebsiella pneumoniae* over 24 hours. In some embodiments, SBTs may show less than 1000% growth of *Klebsiella pneumoniae* over 24 hours. In some embodiments, SBTs may show less than 500% growth of *Klebsiella pneumoniae* over 24 hours. In some embodiments, SBTs may show less than 400% growth of *Klebsiella pneumoniae* over 24 hours. In some embodiments, SBTs may show less than 300% growth of *Klebsiella pneumoniae* over 24 hours. In some embodiments, SBTs may show less than 200% growth of *Klebsiella pneumoniae* over 24 hours.

Containers and Bags

In some embodiments, containers may include SBTs and/or SBPs. The SBTs and/or SBPs may be part of the final product and/or may be used in the preparation of the containers. As used herein, a container may be defined as a receptacle or enclosure for holding, storing, packaging, and/or shipping an article, product, and/or materials. In some embodiments, SBT and/or SBP containers may be rigid. In some embodiments, SBT and/or SBP rigid containers may hold their shape and/or be able to stand upright. In some embodiments, SBT and/or SBP containers may be flexible. In one embodiment, SBP and/or SBT flexible containers may include containers whose shape may be modified and altered to suit an intended purpose. SBT and/or SBP container may protect article, product, and/or materials enclosed within from dust, moisture, shock. In some embodiments, SBTs and/or SBP containers may be formatted to be conducive to efficient stacking and storing, and easy recycling at the end of its useful life.

In some embodiments, SBTs and/or SBP containers may be formatted into a cylindrical shape e.g. barrels, cans, drums, and/or tubs. In some embodiments, SBTs and/or SBP containers may be formatted to rectilinear shape e.g. boxes, crates, wooden boxes, lift-vans, and/or corfs. In some embodiments, SBTs and/or SBP containers may be shipping containers. As used herein, "shipping containers", may be defined as containers that may be used in commercial movement of articles, products, and/or materials. Non-limiting examples include but are not limited to corrugated boxes, and/or intermodal containers.

In some embodiments, flexible SBT and/or SBP containers may be defined as "bags." In some embodiments, SBT and/or SBP bags may be designed and/or prepared for personal use. Not-limiting examples of bags include but not limited to hand bag, hobo bag, tote bag, duffle bag, messenger bag, backpack, satchel, doctor's bag, laptop bag, bucket bag, bowler bag, wristlet, pouch, clutch, beach Bag, shoulder bag, miniaudiere, shopping, grocery bag, draw-string bag, make up bags, fold-over bags, phone bag, camera case bags, baguette bags, barrel bag, basket bag, fanny pack, kelly bag, and/or lunch bag, briefcases, backpacks. In some embodiments, bags may include packets, gunny sacks and/or flour sacks.

In some embodiments, SBPs and/or SBTs may be used as coating or linings in containers and/or bags. In one embodiment, SBP and/or SBT coatings may be applied to prepare waterproof containers and/or bags. In some embodiments, the SBT and/or SBP coatings may be applied to the surface of the container and/or bag facing the exterior. In some embodiments, the SBT and/or SBP coatings may be applied to the surface of the container and/or bag facing the interior. In some embodiments, the SBT and/or SBP coatings may be entire container and/or bag.

Personal Protection Equipment Textiles

In some embodiments, personal protection equipment (PPE) may include SBTs and/or SBPs. The SBTs and/or SBPs may be part of the final product and/or may be used in the preparation of the PPE. As used herein, "PPE" may be defined as apparel, apparel accessories, footwear, helmets, goggles, or other apparel or equipment worn by a subject to protect the subject from hazards. As used herein, the term "hazard" may be defined as any agent or material that may be a source of potential damage, harm, and/or adverse health effect on a subject. In some embodiments, PPE may offer protection against hazards such as but not limited to physical hazards, electrical hazards, heat hazards, mechanical hazards, chemical hazards, biohazards, and/or airborne particulate matter hazard. In some embodiments, SBT PPE may serve as a barrier between the subject and the environment. In some embodiments, SBT PPE may eliminate the hazard. In other aspects, SBT PPE may reduce the hazard. In some embodiments, SBT PPE may be used for occupational safety, health purposes, sports and/or recreational activities.

In some embodiments, SBT PPE may be categorized by the area of the body protected. Non-limiting examples of categories include respirators, skin protection, eye protection, and/or hearing protection. In some embodiments, SBT PPE may include respirators. As used herein, a "respirator" may be defined as PPE that may protect the subject or wearer from inhaling hazardous materials such as but not limited to gases, chemical, and/or airborne particles. In some embodiments, SBT PPE respirators may act by filtering out the hazardous materials from the air being breathed by the subject or wearer. In some embodiments, SBT PPE respirators may provide an alternate source of clean breathable air to the subject or wearer. In some embodiments, SBT PPE may include skin protectors. Non-limiting examples of SBT PPE skin protectors include gloves, shoes, boots, helmets, caps, hats, hoods, long sleeved clothing, sleeve protectors, coveralls, leather jackets, leather trousers and/or spats. In one embodiment, SBT PPE may protect the skin from chemical agents that may come in contact with the skin directly, via aerosols, immersion or splashes. In one embodiment, SBT PPE may protect the skin from physical hazards such as but not limited to high temperature, ultraviolet light, solar radiation. In some embodiments, SBT PPE may protect the skin from mechanical hazards such as but not limited to friction, pressure, abrasions, lacerations, and/or contusions. In some embodiments, SBT PPE may protect the skin from biohazards and organisms such as but not limited to parasites, microorganisms, plants and/or animals. In some embodiments, SBT PPE may provide eye protection. SBT PPE may include spectacles, glasses, goggles and face shields. SBT PPE eye protection may guard against hazards such as chemical splashes, mechanical hazards, aerosols, particulate matter, biological agents, ultraviolet light, and/or organisms. In one embodiment, SBT PPE eye protection may provide protection against thermal agents, such as welding torches. In some embodiments, SBT PPE may provide hearing protection to prevent and/or minimize hearing loss. The National Institute for Occupational Safety and Health (NIOSH) recommends that a subject exposure to noise be limited to 85 dBA (A-weighted decibels) over a period of 8 hours. In some embodiments SBT PPE ear protection may include ear plugs and/or ear-muffs.

In some embodiments, SBT PPE may include apparel such as but not limited to gas-tight encapsulating suits, liquid splash-protective suits, permeable protective suits, boiler suits, hazmat suit, bomb suit, fire proximity suit, riding suit, space suits, splash suits, wet suits, dry suits, immersion suits, and/or chemical protection suits.

In some embodiments, SBT may be prepared by including materials such as but not limited to 4H™, Barricade™, Chemrel™, Kevlar™, Nomex™, Responder™, Saranex™, Teflon™, Trellchem™ Tychem™, Viton™, and/or Zytex™.

In some embodiments, SBT PPE may be or may include retroflectors. The SBTs and/or SBPs may be part of the final product and/or may be used in the preparation of the retroflectors. SBT retroflectors may be incorporated to increase the visibility of SBT PPE and/or to make the subject wearing the PPE more conspicuous in contrast to the background. In some embodiments, retroflectors may increase the safety of the SBT PPE in dark environments, low light and/or bright environments, in indoor or outdoor environments.

In some embodiments, the retroflectors may be applied as a coating on the surface of the SBT PPE. In some embodiments, the retroflectors may be formatted as tapes which may be applied to SBT PPE. In one embodiment, the retroflectors may be prepared as paints which may be applied to the SBT PPE.

In some embodiments, SBT PPE may be or may be prepared using colorants that are easily discernable from the background. In some embodiments, the colorants may be orange, yellow/lime, red, black, dark green, pink, and/or royal blue.

Furnishings

In some embodiments, SBTs and/or SBPs may be used in furnishings. The SBTs and/or SBPs may be part of the final product and/or may be used in the preparation of the furnishing. As used herein, "furnishings" may be defined as movable articles in a space that may be occupied by a subject that may make the space fit for living and/or working. In some embodiments SBT and/or SBP furnishings may include articles that improve the functionality and/or aesthetics of a space occupied by a subject.

In some embodiments, SBT and/or SBP furnishings may be or may include floor coverings. The SBTs and/or SBPs may be part of the final product and/or may be used in the preparation of the floor covering. As used herein, a "floor coverings" may be defined as any article applied to a floor structure to provide a walking surface for a subject or a user. In some embodiments SBT and/or SBP floor covering may include rugs and/or carpets. As used herein, "carpets" defined as floor covering that may be attached to the floor. As used herein, "rugs" may be defined as floor coverings that may be moveable. SBT and/or SBP floor coverings may be used to provide insulation, to protect the floor surface, to protect the subject from pests, dirt and/or to improve the aesthetics of a space occupied by a subject. In some embodiments, SBT and/or SBP floor coverings may include an upper layer of pile attached to a backing. In some embodiments, SBT and/or SBPs may be used in the upper layer, or the on the backing or a combination thereof. In some embodiments, SBT and/SBP floor coverings may be classified according to the height of their pile. In some embodiments, SBT and/SBP floor coverings may have a low-pile (around ¼ inch). In some embodiments, SBT and/SBP floor coverings may have a medium-pile carpet: (from about ¼ inch to about ½ inch). In some embodiments, SBT and/SBP floor coverings may have a high-pile carpet (from about ½ inch to about ¾ inch).

In some embodiments, SBT and/or SBP furnishings may be or may include bedding. The SBTs and/or SBPs may be part of the final product and/or may be used in the preparation of the bedding. As used herein, "bedding" may be defined as furnishings that are used in conjunction with or on the surface of a bed. Non-limiting examples may include sheets, quilt, bedspread, blanket, linen, comforter, pillows, pillowcase, coverlet, spread, cover, bedclothes, and/or duvets. In some embodiments, SBT and/or SBP bedding may be classified based on their thread count. Thread count may be 124, 128, 130, 140, 180, 200, 300, 400, 500, 600, 700, 800, 900 or 1000. SBT and/or SBP bedding may be wrinkle resistant, have a soft hand, resistant to wear and tear, may be thermally insulated and/or light weight.

In some embodiments, SBT and/or SBP furnishings may be or may include furnishings utilized in the bathroom. SBT and/or SBP bathroom furnishings may be prepared to have a soft hand, odor resistance, absorb moisture, and/or dry quickly after use. Non-limiting examples of SBT and/or SBP bathroom furnishings include bath towels, hand towels, washcloths, loofahs, shower curtains, and/or bathmats.

In some embodiments, SBT and/or SBP may be or may be included in kitchen furnishings. The SBTs and/or SBPs may be part of the final product and/or may be used in the preparation of the kitchen furnishings. SBT and/or SBP kitchen furnishings may be prepared to have a soft hand, odor resistance, resistant to dirt, absorb moisture, and/or dry quickly after use. Non-limiting examples of SBT and/or SBP kitchen furnishings include dish towels, pot-holder, aprons, oven mitts, tea towels, bibs, place mats, and/or napkins.

In some embodiments, SBT and/or SBP may be or may be included in upholstery. As used herein the term "upholstery", may be defined as any material that covers or is used on the surface of a furniture. The SBTs and/or SBPs may be part of the final product and/or may be used in the preparation of the upholstery. Non-limiting examples of furniture that may include SBP and/or SBT upholstery include single seat, chair, lift chair, bean bag, chaise longue, fauteuil, ottoman, recliner, stool, bar stool, footstool (ottoman), tuffet, fainting couch, rocking chair, bar chair, bench, couch (sofa), accubita, canapé, davenport, klinai, divan, love seat, chesterfield, bed, bunk bed, canopy bed, four-poster bed, murphy bed, platform bed, sleigh bed, waterbed, daybed, futon, hammock, headboard, infant bed (crib, cradle), mattress, sofa bed, billiard table, chess table, entertainment center, gramophone, hi-fi, jukebox, pinball machine, radiogram, home bar, television set, radio receiver, video game console, desktop pcs and laptops, chabudai, changing table, desk, davenport desk, drawing board, computer desk, writing desk, kotatsu, korsi, lowboy, monks bench, pedestal, table, game table, coffee table, dining table, refectory table, dropleaf table, end table, folding table, gateleg table, poker table, trestle table, tv tray table, wine table, washstand, workbench, baker's rack, bookcase, bathroom cabinet, chifforobe, closet, cupboard, curio cabinet, gun cabinet, hutch, hoosier cabinet, kitchen cabinet, liquor cabinet, pantry, pie safe, chest of drawers (dresser), chest, cellarette, hope chest, drawer (furniture), hall tree, hatstand, bar cabinet, filing cabinet, floating shelf, nightstand, ottoman, plan chest, plant stand, shelving, sideboard, safe, wardrobe (armoire), and/or wine rack.

In some embodiments, SBT and/or SBP may be or may be included in furnishings applied to windows. The SBTs and/or SBPs may be part of the final product and/or may be used in the preparation of the furnishings applied to windows. Non-limiting examples of furnishings applied to windows include to drapes, curtains and/or blinds.

In some embodiments, SBTs and/or SBPs may be decorative furnishings which may serve to enhance the appearance and aesthetic value of a space occupied by a subject. Non-limiting examples of decorative furnishings include wall hangings, paintings, and/or artificial plants.

In some embodiments, SBTs and/or SBPs may be outdoor furnishings. As used herein, the term, "outdoor furnishings" may be defined as furnishings utilized in outdoor spaces occupied by a subject. Outdoor spaces used by a subject may include but are not limited to deck, patio, pool, garden, yard, parking lot etc. Non-limiting examples of outdoor furnishings include, dining chairs, lounge chairs, chaise chairs, sectionals, sofa, loveseats, ottomans, adirondack chairs, benchers, gliders, hammocks, lawn chairs, beach chairs, folding chairs, pouffs, pillows, rugs, furniture covers, umbrellas, pool liners, solar pool covers, winter pool covers, and/or pool leaf covers.

Sports and/or Sporting Goods

In some embodiments, SBP and/or SBTs may be used in sports and/or in the preparation of sporting goods. The SBTs and/or SBPs may be part of the final product and/or may be used in the preparation of the sports and/or sporting goods. As used herein, the term "sports" may be defined as any physical activity that is played and/or performed according to rules, or for enjoyment. As used herein, any materials aiding in the preparation, the performance and/or the completion of the sport may be defined herein as "sporting goods." As used herein, a subject engaged in sports may be referred to as a sportsman.

In some embodiments, SBT and/or SBPs may be utilized in sportswear and/or footwear suitable for sports.

In some embodiments, SBT and/or SBP sporting goods may be sportsman goods. As used herein "sportsman goods" may be defined as materials worn by a sportsman in the preparation, the performance and/or the completion of the sport. In some embodiments, SBT and/or SBP sportsman goods may be footwear. Non-limiting examples of SBT and/or SBP footwear include but are not limited to cleats, surf boards, wakeboards, snowboards, roller skates, skis, golf shoes, boat shoes, prosthetics, hiking boots, flat pedal shoes, clipless shoes (e.g. for mountain biking). In some embodiments, SBT and/or SBP sportsman goods may include articles worn by the sportsman to protect against injury and/or environmental elements. SBP and/or SBT protective sportsman good include but are not limited to helmet, jock strap, mouthguards, shin pads, ski suits, elbow pads, shoulder pads, gloves, goggles, groin guards, braces, ace bandages, kinesio tapes, and/or gaiters. SBT and/or SBP sportsman goods may include articles utilized for training for a sport such as mats, resistance bands, punching bags, belts, and/or benches.

In some embodiments, SBT and/or SBP sporting goods may be game equipment. As used herein, the term "game equipment" may be defined as any sporting goods that is a not a sportsman goods.

In some embodiments, SBT and/or SBP game equipment may be used in nets. The SBTs and/or SBPs may be part of the final product and/or may be used in the preparation of the nets. In some embodiments, SBT and/or SBPs may be used in nets utilized for tennis, volleyball, basketball, hockey, soccer, lacrosse, football, and/or fishing.

In some embodiments, SBT and/or SBP game equipment may be used in balls. The SBTs and/or SBPs may be part of the final product and/or may be used in the preparation of the balls. In some embodiments, SBTs and/or SBPs may be used in balls for tennis ball, rugby ball, soccer, and/or cricket.

In some embodiments, SBT and/or SBP game equipment may be used in discs. The SBTs and/or SBPs may be part of the final product and/or may be used in the preparation of the game equipment. In some embodiments, SBPs and/or SBTs may be used in discs for freestyle disc, disc golf, and/or ultimate frisbee.

In some embodiments, SBT and/or SBP game equipment may be used in racquets. The SBTs and/or SBPs may be part of the final product and/or may be used in the preparation of the game equipment. In some embodiments, SBPs and/or SBTs may be used in racquets for tennis, squash, table tennis, and/or badminton.

In some embodiments, SBTs and/or SBPs may be part of the final product and/or may be used in the preparation of the rods, fishing rods, tent rods, hiking poles, floatation devices, tents, tarps, camping chairs, sleeping bags, parachutes, sails, boat covers, tires, cords, ropes, umbrellas, and/or turf.

Transportation

In some embodiments, SBT and/or SBPs may be used in transportation devices. The SBTs and/or SBPs may be part of the final product and/or may be used in the preparation of the transportation devices. As used herein, the term "transportation device" may be defined as a device that conveys organisms and/or things from one location to another location. Non-limiting examples of transportation devices that include SBPs and/or SBTs may be airplanes, ambulance, amphibious vehicles, articulated lorry, autocycle, autorickshaw, barrow, bicycle, bicycles, Black Maria, boat, boats, bulldozer, bus, buses, cab, cabriolet, camion, camper, camper van, car, caravan, carriage, cars, chaise, charabanc, chariot, coach, combine harvester, Conestoga wagon, coupé, cycle, delivery van, dray, dump truck, dustcart, electric scooter, electric skateboard, estate car, fire engine, fork-lift truck, go-cart, gritter, hansom or hansom cab, hatchback or hatch, helicopters, hoverboards, hovercraft, jaunting car or jaunty car, JCB™, Jeep IM, jet ski, jinricksha, jinrickshaw, kart, kibitka, komatik, koneke, landaulet or landaulette, light engine, limousine, litter, locomotive, lorry, low-loader, luge, milk float, minibus, moped, mopes, motor caravan, motor scooter, motor vehicle, motor vehicles, motorbicycle, motorbike, motorbus, motorcar, motorcycle, motorcycles, off-road vehicle, omnibus, panda car, pantechnicon, police car, post chaise, postbus, pram, racing car, railcar, railed vehicles, ratha, rickshaw, road train, roadroller, rocket, scooter, scout car, screw-propelled vehicle, segway, shandrydan, ship, ships, single-decker, skateboards, skates, skibob, sledge, sleigh, Sno-Cat, snow plough, snowmobile, space capsule, space probe, space shuttle, spacecraft, spaceship, sports car, stagecoach, steamroller, sulky, tandem, tank, tank engine, tanker, tarantass, taxi, telega, three-wheeler, tipper truck or lorry, toboggan, tonga, touring car, traction engine, tractor, trail bike, trailer, train, trains, tram, tramcar, trams, travois, treetcar or trolley car, tricycle, troika, trolley, trolleybus, troop carrier, truck, trucks, tumbrel or tumbril, unicycle, van, wagon, wagonette, wagons, watercraft, and/or wheelbarrow.

In some embodiments, SBT and/or SBP transportation device may be used in air bags. The SBTs and/or SBPs may be part of the final product and/or may be used in the preparation of the air bags.

In some embodiments, SBT and/or SBP transportation device may be used in cords and/or belts. In one embodiment, SBT and/or SBPs may be used in the preparation of hose, safety belts, and/or engine belts. The SBTs and/or SBPs may be part of the final product and/or may be used in the preparation of the cords and/or belts.

In some embodiments, SBT and/or SBP transportation device may be used in transportation upholstery. The SBTs and/or SBPs may be part of the final product and/or may be used in the preparation of transportation upholstery. Non-limiting examples of SBP and/or SBT transportation upholstery may include seats, seat covers, inner walls of transportation devices, floor mats, trunk covers, paneling, steering wheel, joystick, control coverings and/or wraps.

In some embodiments, SBT and/or SBP transportation device may be used in engines. The SBTs and/or SBPs may be part of the final product and/or may be used in the preparation of the engines. SBTs and/or SBPs may be used in radiator hoses, power steering, hydraulic lines, filters, and/or timing belt.

In some embodiments, SBT and/or SBP transportation device may be used in preparation of parts of the transportation devices. The SBTs and/or SBPs may be part of the final product and/or may be used in the preparation of the parts of transportation devices. SBPs and/or SBT may be used in the preparation of parts such as but not limited to bumpers, wheel covers, tires and/or door handles.

In some embodiments, SBT and/or SBP transportation device may be used in safety components. The SBTs and/or SBPs may be part of the final product and/or may be used in the preparation of the safety components. Non-limiting examples of safety components in transportation devices include but are not limited to seat belts, air bags, seat fire barriers, and/or air filtration devices.

In some embodiments, SBT and/or SBP transportation device may be used in parachutes, and/or inflatable boats. The SBTs and/or SBPs may be part of the final product and/or may be used in the preparation of parachutes and/or inflatable boats.

In some embodiments, SBPs and/or SBTs may be used as coating or linings in transportation devices. SBP and/or SBT coatings may be applied to but not limited to engines, air ducts, timing belts, air filters, and mufflers. The tensile strength of SBTs and/or SBPs also allow their use in the manufacture of tires, and/or hot air balloons. In some embodiments, SBTs and/or SBPs may be or may be used on the visible surface of the transportation device. In some embodiments, SBTs and/or SBPs may not be used on the visible surface of the transportation device.

Infrastructure Construction

In some embodiments, SBTs and/or SBPs may be used in for infrastructure construction. The SBTs and/or SBPs may be part of the final product and/or may be used in the preparation of the infrastructure construction. As used herein, the term "infrastructure construction" may be defined as the planning, design, building, operation and maintenance of infrastructure such as buildings, dams, bridges, tunnels and roads. SBTs and/or SBPs may be used in infrastructure construction due their mechanical properties such as light weight, strength and resilience as well as resistance to environmental factors such as light and temperature. In some embodiments, SBPs and/or SBTs may be used in hoardings and signages, scaffolding nets, awnings and canopies, tarpaulins, membranes, roofing materials, concrete reinforcement, façade foundation systems, interior construction, insulations, proofing materials, air conditioning, noise prevention, visual protection, protection against the sun, and/or building safety.

In some embodiments, SBTs and/or SBPs may be used in the manufacture of bridging cables and/or elements.

In one embodiment, SBTs and/or SBPs may be used in the reinforcement of dykes and/or water management systems.

In one embodiment, SBTs and/or SBPs may be used as water barrier between siding and the plywood around the house and/or between the shingles and/or the roof, Geotextiles In some embodiments, SBTs and/or SBPs may be or may be used as geotextiles. The SBTs and/or SBPs may be part of the final product and/or may be used in the preparation of the geotextiles. As used herein, the term "geotextile" may be defined as any as an article comprising a textile that may be used in conjunction with the soil, earth and/or land.

In some embodiments, SBTs and/or SBP geotextiles may be used in separation. As a non-limiting example, SBT and/or SBP geotextiles may be used to prevent two soil layers of different particle sizes from mixing with each other.

In some embodiments, SBT and/or SBP geotextiles may be used in drainage. As a non-limiting example, SBT and/or SBP geotextiles may be used to collect water from soil and discharge the water to a location away from the soil.

In some embodiments, SBT and/or SBP geotextiles may be used in filtration. As a non-limiting example, SBT and/or SBP geotextiles may be used to allow soil particles of a predetermined size to pass through whereas other particles may be halted and prevented from passing through.

In some embodiments, SBT and/or SBP geotextiles may be used to reinforce and/or augment the strength of structures.

In some embodiments, SBT and/or SBP geotextiles may be used for protection. As a non-limiting example, geotextiles may be used to protect from erosion of earth embankments by wave action, and/or currents. In some aspects, a layer of SBT and/or SBP geotextiles may be placed so as to prevent leaching of fine material. SBT and/or SBP geotextiles maybe used for rock beaching or as mattress structures. In some aspects, SBT and/or SBP geotextiles may be used under water.

In some embodiments, SBT and/or SBP geotextiles may be permeable textile material that may be used to increase soil stability, provide erosion control and/or aid in drainage.

SBT and/or SBP textiles may have properties such as but not limited to an (i) ability to separate, filter, drain, protect and reinforce, (ii) superior strength and durability, (iii) tear and puncture-resistance, (iv) elasticity, (v) permeability, (vi) low humidity, (vii) absorption, (viii) resistance to rotting, chemicals, bacteria and fungi, (ix) light weight, (x) temperature fluctuation tolerant, and/or (xi) stress-relieving.

In some embodiments SBT and/or SBP geotextiles may be used to provide planar water flow. In some embodiments, SBT and SBP geotextiles aggregate drains, asphalt pavement overlays and erosion control. In some embodiments SBT and/or SBP geotextiles, may reduce localized shear failure in weak subsoil conditions and aid construction over soft subsoils. Woven monofilament geotextiles are preferred for applications where both strength and filtration are a concern, such as shoreline rip rap applications. In some embodiments, SBTs and/or SBP geotextiles may be used road and rail building, dam, canal and pond lining, hydraulic works, sewer lines, soil stabilization, soil reinforcement, soil separation, drainage, landfill, filtration, sedimentation, erosion control, weed control, root barriers, sport surfaces, asphalt overlay, impregnation base, and/or drainage channel liners, landslide protection systems, piping, canalization, roadway underlayment, foundation stabilizers, geomembrane protection, frost protection, sand infiltration barrier for drainage tile, landscaping, pest control, and/or greenhouses.

Industrial Textiles

In some embodiments, SBT and/or SBP may be or may be used in industrial textiles. The SBTs and/or SBPs may be part of the final product and/or may be used in the preparation of the industrial textiles. As used herein, the term "industrial textiles" may be defined as textiles that may be used in the production of materials and/or articles such as chemicals, electronics, machines, devices and/or other textiles. Non-limiting examples of SBT and/or SBP industrial textiles include but are not limited to silk-screen printing, filtration, plasma screens, propulsion technology, lifting/conveying equipment, sound-proofing elements, melting processes, roller covers, grinding technology, insulations, seals, and/or fuel cells.

Electronic Textiles

In some embodiments, SBTs and/or SBPs may be or may be used in electronic textiles. The SBTs and/or SBPs may be part of the final product and/or may be used in the preparation of the electronic textiles. As used herein, "electronic textiles" may be defined as the textiles that are may be in the incorporated into or used conjunction with electronic devices.

In some embodiments, SBT and/or SBP electronic textiles may include sensors. As used herein, the term "sensor" may be defined as a device that measures input parameters in the environment surrounding a subject or an article such as but not limited to sound, light, movement and chemicals, gases and/or liquid vapors. Non-limiting examples of SBT and/or SBP sensors include as light sensors, acoustic sensors, heat sensors, motion sensors, activity recognition sensors, location detection sensors and chemical sensors. In some embodiments, SBT and/or SBP electronic textiles may include a conductive metal and/or fibers which may be needed to carry the signals created by the sensors.

In some embodiments, SBT and/or SBP electronic textiles improve the appearance or aesthetics of an article. As a non-limiting example, SBT and/or SBP electronic textile may be used to illuminate the article or the space surrounding the article, for example through the incorporation of light emitting diodes (LED).

In some embodiments, SBT and/or SBP electronic textiles may provide a specific function for any of the uses described herein. In one embodiment, SBT and/or SBP electronic textiles may be used to monitor and/or regulate vital parameters such as but not limited to body temperature, breathing rate, heart rate, blood pressure, and/or muscle vibration.

In some embodiments, SBT and/or SBP electronic textiles may be used in personal protective equipment to monitor environmental factors such as temperature, humidity, and/or radiation levels.

In some embodiments, SBT and/or SBP electronic textiles may be used in sports to track a sportsman's performance while the sportsman is engaged in the sport.

In some embodiments, SBT and/or SBP electronic textiles may be used in military applications. SBT and/or SBP electronic textiles may be used to track the position and/or status of military personnel. In one aspect, SBT and/or SBP electronic textiles may be used in military apparel which may include sensors to track whether the personnel may have been hit by a bullet.

In some embodiments, SBT and/or SBP electronic textiles may include radio frequency identification devices (RFID) wherein digital data encoded in tags or labels may be captured by a reader via radio waves.

In some embodiments, SBT and/or SBP electronic textiles may be or may be used in the preparation of conducting and semi-conducting materials.

Therapeutic Textiles

In some embodiments, SBTs and/or SBPs may be used in a variety of therapeutic applications. As used herein, the term "therapeutic application" refers to any method related to restoring or promoting the health, nutrition, and/or well-being of a subject; supporting or promoting reproduction in a subject; or treating, preventing, mitigating, alleviating, curing, or diagnosing a disease, disorder, or condition. As used herein, the term "condition" refers to a physical state of wellbeing. In some embodiments, therapeutic applications may include, but are not limited to, medical applications, surgical applications, and veterinary applications. As used herein, the term "medical application" refers to any method or use that involves treating, diagnosing, and/or preventing disease according to the science of medicine. "Surgical applications" refer to methods of treatment and/or diagnosis that involve operation on a subject, typically requiring incision and the use of instruments. "Veterinary applications" refer to therapeutic applications where the subject is a non-human animal. In some embodiments, therapeutic applications may include, but are not limited to, experimental, diagnostic, or prophylactic applications. In some embodiments, therapeutic applications include preparation and/or use of therapeutic devices. As used herein, the term "therapeutic device" refers to any article prepared or modified for therapeutic use.

In some embodiments, SBTs and/or SBPs may be or may be used in the preparation of therapeutic textiles. As used herein, "therapeutic textiles" may be defined as textiles that may be used for a therapeutic application.

SBT and/or SBP therapeutic textiles may be used for therapeutic applications and may include or may be combined with one or more pharmaceutical compositions, implants, therapeutic agents, coatings, foods, health supplements, additive and/or cargos or devices. In some embodiments, SBT and/or SBP therapeutic textiles facilitate the delivery and/or controlled release of therapeutic agent payloads. In some embodiments, SBPs described herein may be used in gene therapy and/or gene editing. In some embodiments, SBPs described herein may be used in immunotherapy. Some SBT and/or SBP therapeutic textiles may be used for diagnostic applications, in in vitro cell culture, tissue engineering, and/or surgery. In some embodiments, SBPs described herein may be used to stabilize therapeutic agents. Some SBPs may be used as tools, materials, or devices in therapeutic applications. Such SBPs may include, but are not limited to, delivery vehicles, scaffolds, structural supports, and sutures.

Therapeutic applications of the present disclosure may be applied to a variety of subjects. As used herein, the term "subject" refers to any entity to which a particular process or activity relates to or is applied. Subjects of therapeutic applications described herein may be human or non-human. Human subjects may include humans of different ages, genders, races, nationalities, or health status. Non-human subjects may include non-human animal subjects (also simply referred to herein as "animal subjects"). Animal subjects may be non-human vertebrates or invertebrates. Some animal subjects may be wild type or genetically modified organisms (e.g., transgenic). In some embodiments, subjects include patients. As used herein, the term "patient" refers to a subject seeking treatment, in need of treatment, requiring treatment, receiving treatment, expecting treatment, or who is under the care of a trained (e.g., licensed) professional for a particular disease, disorder, and/or condition.

In some embodiments, SBT and/or SBP therapeutic textiles may be used for in-vivo therapeutic agent delivery systems. In one embodiment, SBT and/or SBP therapeutic textiles may be used in the localized delivery to curved areas of an organ or for the encapsulation of drug-eluting cells.

In some embodiments, SBT and/or SBP therapeutic textiles may be used for in-ex-vivo therapeutic agent delivery systems. SBTs and/or SBPs may include therapeutic agent eluting particles that dissolve in sweat.

In some embodiments, SBT and/or SBP therapeutic textiles may be used as localized therapeutic agent delivery systems. In one embodiment, localized delivery systems for the treating the skin for dermatological conditions. In one aspect, the therapeutic agent may be incorporated into SBT dressings, patches, bandages, and applied directly to the skin. In one aspect, SBT and/or SBP therapeutic textiles may be used in the treatment of therapeutic indications such as the use of anti-inflammatory agents for the treatment of arthritic joints.

The semi-conductive nature of the SBT and/or SBP therapeutic textiles may also be used to facilitate electrical elevation of skin temperature. Joule heating bandages or patch like structure may locally raise temperature to a sufficient level to promote sweat production, and/or provide relief against pain.

In some embodiments, therapeutic applications utilizing SBT and/or SBP textiles may be used for tissue engineering. SBT and/or SBP textiles are attractive for tissue engineering due to their biocompatibility, bioavailability, low toxicity, non-inflammatory degradation products, and the ability to functionalize or formulate with other components needed for tissue culture. In some embodiments, SBT and/or SBP textiles may be engineered tissues or are combined with engineered tissues. In some embodiments, SBT and/or SBP textiles may be used for tissue engineering in vitro. In some embodiments, SBPs are used for tissue engineering in vivo. In some embodiments processed silks for tissue engineering are used to treat an indication in a subject. In some embodiments, processed silk is prepared and then applied to a tissue to treat the indication, as described in European Patent Number EP2276514, International Publication Number WO2017179069, Chantawong et al., and Du et al. (Chantawong et al. (2017) Mater Sci Mater Med 28 (12): 191; Du et al. (2017) Nanoscale Res Lett 12 (1): 573), the contents of each of which are herein incorporated by reference in their entirety. In some embodiments, processed silk is prepared, treated with tissue, and then utilized to treat the indication, as described in International Publication Number WO2017137611, Zhou et al., Perteghella et al., and Weili et al. (Zhou et al. (2017) S1742-7061 (17): 30569; Perteghella et al. (2017) Macromol Biosci 17 (9): 1700131; Weili et al. (2017) Advanced Materials 29 (29): e1701089), the contents of each of which are herein incorporated by reference in their entirety. Examples of tissues engineered with SBT and/or SBP textiles or processed silk scaffolds include, but are not limited to, bone tissue, cartilage and/or bone soft tissue, ear drum tissue, pancreatic tissue, skeletal muscle tissue, tympanic membrane tissue, bladder tissue, vascular tissue, nervous tissue, neural tissue, corneal tissue, spinal tissue, skin, and any other tissue relevant for the desired indication.

In some embodiments, SBT and/or SBP textiles for tissue engineering are prepared with one or more other materials. These materials include, but are not limited to, any bioresorbable polymer matrix, albumin, alginate, bacterial cellulose, cellulose, cellulose acetate, any ceramic, chitin, chitosan, collagen, duck's feet collagen, elastin, fibrin, gelatin, glycerol, ionic liquids, magnesium oxide, melanin, any metal scaffold (e.g. cobalt-chromium-molybdenum composite), nano-hydroxyapatite, polyaniline, polycaprolactone, any polyethylene glycol, polyethylene glycol diglycidyl ester, polyethylene oxide, polyurethane, quaternary ammonium chitosan, SBA15, silica, any poly(α-ester) (e.g. polyglycolides, poly(lactide-co-glycolide), polyhydroxyalkanoates, any polycaprolactone, poly(propylene fumarate), polyanhydrides, polyacetals, polyketals, polyorthoesters, polycarbonates, any polyurethane, polyphosphazenes, polyphosphoesters, any synthetic polyether, and any polysaccharide.

In some embodiments, tissue engineering with SBT and/or SBP textiles described herein may be used to repair existing tissue (e.g., as described in European Patent Numbers EP3215134 or EP3206725; or in Guo et al. (2017) Biomaterials 145:44-55; Chen et al. (2017) Stem Cell Research and Therapies 8:260; Xiao et al. (2017) Oncotarget 8 (49): 86471-86487; or Ruan et al. (2017) Biomed Pharmacother 97:600-606, the contents of each of which are herein incorporated by reference in their entirety). Examples of tissue repairs include, but are not limited to, bone repair, cartilage repair, bladder repair, organ repair, corneal repair, liver repair, muscle regeneration, vascular grafts, vascular patches, wound healing, and neuronal repair.

In some embodiments, SBT and/or SBP textiles used in tissue repair may be biodegradable or removable. Such SBPs may biodegrade or be removed after tissue repair and/or healing progresses or is completed. In some embodiments, SBT and/or SBP textiles may include or may be incorporated into devices used to stretch skin. Such devices may be used to prepare skin bubbles or flaps that can be used to cover or repair areas without skin or with skin damage. These devices may include balloons or other expandable materials that can be inflated or otherwise expanded over time. In some embodiments, SBT and/or SBP textiles are used to coat such devices to support biocompatibility.

In some embodiments, tissue engineering with SBT and/or SBP textiles described herein may be used to augment tissue (i.e., to add or expand tissue), as described in United States Publication Number US20170258573, European Patent Numbers EP2276514 or EP3206725 or in Yu et al. (2017) doi.10.1002/jbm.a.36297, the contents of each of which are herein incorporated by reference in their entirety. In some embodiments, SBPs may be used as implants or fillers to support tissue augmentation. In some embodiments, SBPs may be used in tissue augmentation related to or used for, implants, artificial organs, silk contact lenses, artificial blood vessels, stem cells, vascular patches, ear drum repair, tissue replacement, cartilage replacement, breast augmentation, surgical sutures, surgical meshes, wound dressing, bandages, and/or hemostatic sponges. In some embodiments, artificial organs may include artificial livers, as described in Janani et al. (2017) Acta Biomaterialia 157:161-176, the contents of which are herein incorporated by reference in their entirety.

In some embodiments, therapeutic applications utilizing SBT and/or SBP medical textiles may include surgical applications. In some embodiments, SBPs may be incorporated into surgical tools, devices, and fabrics as described in Wang et al. (2017) J Biomed Mater Res A 106 (1): 221-230, the contents of which are herein incorporated by reference in their entirety. In some embodiments, SBTs and/or SBPs may be used to prepare stents. As used herein, "a stent" may be defined as a mesh-like collar designed to serve as a temporary or permanent internal scaffold to maintain or increase the lumen of a vessel. SBTs and/or SBPs stent may be used due to their radial and torsional flexibility, biocompatibility, visibility by X-ray and reliable expandability. In some embodiments, SBT and/or SBP medical textiles may be porous or may include pores to allow for diffusion, elution, leaching, and/or transportation of therapeutic agents.

In one embodiment, SBT and/or SBP medical textiles may be used as or in the preparation of electrodes for neurosurgery. Electrical conductivity of SBP and/or SBT medical textiles may be increased by combining with electroconductive materials. In some embodiments, SBP and/or SBT medical textiles may be used in the preparation of distributed networks for electrical stimulation. In these applications, a SBT medical textiles may be wrapped around a target area and may be used to electrically stimulate an array of sites simultaneously.

In some embodiments, SBPs may be used in surgical applications due to their antibiotic properties, e.g., as described in European Patent Number EP3226835 and in Mane et al. (2017) Scientific Reports 7:15531, the contents of each of which are herein incorporated by reference in their entirety. These antibiotic properties may be a general property of SBT and/or SBP textiles. The antibiotic properties of SBT and/or SBP textiles of the present disclosure may also be due to its payload. In some embodiments, SBT and/or SBT of the present disclosure may be used for the delivery of therapeutics during and/or following surgery, e.g., as described in Sun et al. (Sun et al. (2017) Journal of Materials Chemistry B 5:8770-8779), the contents of which are herein incorporated by reference in their entirety. In some embodiments, SBPs may be used as bandages, patches, sponges, and/or sutures, e.g., as described in European Patent Number EP3215134, International Publication Number WO2001056626, and Seo et al. (Seo et al. (2017) J Biomater Appl 32 (4): 484-491), the contents of each of which are herein incorporated by reference in their entirety. In some embodiments, SBT and/or SBP textiles of the present disclosure may be used as a hemostatic agent to reduce bleeding and promote wound healing, e.g., as described in Seo et al. (Seo et al. (2017) J Biomater Appl 32 (4): 484-491), the contents of which are herein incorporated by reference in their entirety. In some embodiments, SBPs may be incorporated into surgical implants, e.g., as described in United States Publication Number US20170258573, the contents of which are herein incorporated by reference in their entirety. Examples of implants include, but are not limited to, breast implants, dental implants, bone implants, prostheses, buttock implants, cochlear implants, and implants for drug delivery.

In some embodiments, SBT and/or SBP textiles may be used in cosmetic surgery. Such SBPs may include prosthetics, implants, devices, sutures, or other components of cosmetic surgery known to those of skill in the art. In some embodiments, SBPs may be used in breast implants, e.g., as described in United States Publication Number US20170258573, the contents of which are herein incorporated by reference in their entirety.

In some embodiments, SBT and/or SBP textiles may be used postoperatively to improve outcome, stabilize surgical sites, reduce inflammation, protect against infection, or reduce pain. Such SBPs may include one or more therapeutic agents (e.g., any of those described herein) as payloads.

In some embodiments, SBT and/or SBP medical textiles may be used in dental implants for drug delivery. A dental implant with a built-in reservoir allows the slow release of therapeutic agents, which could alleviate invasive procedure associated with chronic diseases. In some embodiments, such therapeutic agent delivered by a dental implant may include, but are not limited to, any of those listed in Table 4, above. As a non-limiting example, SBT and/or SBP textiles may be incorporated into dental implants for continuous release of insulin, as described in Li (2016) Int J Diabetes Clin Res, 3:057, the contents of which are herein incorporated by reference in their entirety. As a further example, SBPs may be used in dental implants for drug delivery against bacterial infection. Sharma et al. demonstrated that silk fibroin nanoparticles support in vitro sustained antibiotic release on titanium surface (Sharma et al. (2016) Nanomedicine. 12 (5): 1193-204, the contents of which are herein incorporated by reference in their entirety).

SBTs and/or SBPs may be used in nasal strips. Nasal strips may be used to relieve nasal congestion and/or sinus pressure. In some embodiments, SBT and/or SBP nasal strips may be used to prevent snoring.

In some embodiments, SBTs and/or SBPs may be used to address one or more therapeutic indications. As used herein, the term "therapeutic indication" refers to a disease, disorder, condition, or symptom that may be cured, reversed, alleviated, stabilized, improved, or otherwise addressed through some form of therapeutic intervention (e.g., administration of a therapeutic agent or method of treatment).

SBP treatment of therapeutic indications may include contacting subjects with SBPs. SBPs may include therapeutic agents (e.g., any of those described herein) as cargo or payloads for treatment. In some embodiments, payload release may occur over a period of time (the "payload release period"). The payload release rate and/or length of the payload release period may be modulated by SBP components or methods of preparation.

In some embodiments, therapeutic indications may include, but are not limited to, any of those listed in Table 5 of International Patent Publication WO2019094700, the contents of which are herein incorporated by reference in its entirety. Non-limiting categories of therapeutic indications include autoimmune indications, cancer-related indications, cardiac indications, central nervous system indications, dryness, gastrointestinal indications, genetic indications, infectious disease, inflammatory indications, allergies, metabolic indications, ocular indications, otorhinolaryngological indications, pain, psychological indications, pulmonary indications, rare diseases, transplanti-related indications, and vascular indications.

Agrotextiles

In some embodiments, SBTs and/or SBPs may be prepared for use in agriculture. As used herein, the term "agriculture" refers to the cultivation of plants and animals to produce products useful for individual, communal, industrial, or commercial purposes. SBPs may be agricultural compositions. In one embodiment, SBTs and/or SBPs may be or may be used as "agrotextiles". As used herein, "agrotextiles" refers to textiles utilized in agriculture. In some embodiments, SBPs may include an agricultural composition. In some embodiments, SBPs and/or SBTs may be used to improve the growth, production, the shelf-life and stability of agricultural products. As used herein, the term "agriculture product" refers to any product of agriculture (e.g., food, medicines, materials, biofuels, etc.). In some embodiments, SBPs may be used in a variety of agricultural applications. As used herein, the term "agricultural application" refers to any method used to improve, promote or increase the production of products obtained through the cultivation of plants and animals, for the benefit of individuals, communities, or commercial entities.

In some embodiments, SBPs and/or SBTs may include cargos may include, but are not limited to, therapeutic agents, small molecules, chemicals, nutrients, micronutrients, macronutrients, pest control agents, pesticides, antibiotics, antifungal, fungicide, virus, virus fragment, virus particle, herbicide, insecticide, fertilizers, pH modulators, soil stabilizers, and flowability agents.

In one embodiment, SBPs and/or SBTs agrotextiles may be used as crop covers. As used herein, a "crop cover" may be defined as a textile that may be provide protection to plants, animals, and/or agricultural products against environmental elements. In some embodiments, SBPs and/or SBTs crop covers may be used to tune the rate of growth of plants. In some embodiments, SBPs and/or SBT crop covers may be used in weed control. In some embodiments, SBPs and/or SBT crop covers may be used to prevent or reduce damage caused by winds and/or by pests. In some embodiments, SBP and/or SBPT crop covers may be used to prevent damaged caused by direct sunlight and/or frost. In one aspect, SBT and/or SBP crop covers may be used to prevent newly planted seeds from being washed away. In one aspect, SBT and/or SBP crop covers may be used to prevent damage caused by hailstones In some embodiments, SBPs and/or SBTs may be used as or in the preparation of netting. SBPs and/or SBT may be used as side curtains in poultry farms, to provide ventilation, protection against insects, birds and other pests.

In one embodiment, SBPs and/or SBT may be used in the preparation of turf. In some embodiments, the SBPs and/or SBTs may be utilized to prepare a mesh which enables the grass to grow by entwining with the mesh. In some aspects, SBPs and/or SBTs may be used to accelerate turf production, reduce irrigation and maintenance costs. In one embodiment, SBPs and/or SBTs may be used in the preparation of artificial turf.

In some embodiments, SBTs and/or SBPs may be used in greenhouses. As used herein, a "greenhouse" refers to a building or an enclosure for growing plants that provides protection against the environmental elements such as but not limited to temperature, and humidity. SBTs and/or SBPs agrotextiles may be used in the preparation of capillary mats. SBP and/or SBT capillary mats may be designed to absorb water, and then deliver the moisture to the plants place on the mats. In some embodiments, SBPs and/or SBTs may be or may be used as window or door screens in green-houses to prevent or reduce damage caused by winds and/or by pests.

In some embodiments, SBTs and/or SBPs may be used to protect the root systems of plants from damage once they have been excavated from the soil such that they may be transported and/or replanted successfully.

SBT and/or SBP agrotextiles may be used in the preparation of nets that may be used to harvest agricultural products, to transport agricultural products without causing damage, or as packing materials for sale of agricultural products.

In some embodiments, the SBPs and/or SBTs may be used as or in the preparation soil or locus stabilizers. In some embodiments, SBPs may be soil stabilizers. Soil stabilization is the technique of changing the physical properties of a soil for a specific purpose. These properties may include, but are not limited to, the soil's weight bearing capabilities, tensile strength, and other aspects of soil performance known to those skilled in the art. In some embodiments, soil stabilizers may be selected chemicals, flowability agents, polymers, enzymes, surfactants, biopolymers, co-polymers, resins, ionic stabilizers, fiber reinforcements, salts, hydrophobic agents, and hydrophilic agents.

In some embodiments, SBTs and/or SBP cargos may include biological systems. These biological systems may include systems of symbiotes, microbiomes and/or probiotics. The compositions provided herein may include a SBPs and an active amount of beneficial microbes/probiotics. In some embodiments, SBPs may be used as stabilizers in the microbial compositions. In some embodiments, these microbiomes or symbiotes may incorporate species of fungi or bacteria. In some embodiments, the fungi are from the *Aspergillus* genus. In some embodiments, the bacteria are from the *Streptomyces* genus.

In some embodiments, the biological systems may be used to enable nitrogen fixation. These microbes, microorganisms, and/or microbiomes may incorporate *rhizobia* bacteria. *Rhizobia* bacteria enable nitrogen fixation in plants that do not independently fix nitrogen, such as legumes (Zahran et al. (1999) Microbiology and Molecular Biology Reviews 63 (4): 968-989, the contents of which are herein incorporated by reference in its entirety). In some embodiments, the biological systems described herein deliver *rhizobia* bacteria for the growth and production of other plants. In some embodiments, the SBP agricultural compositions described herein may be formulated with the nutrients needed to promote the growth of *rhizobia* bacteria. The beneficial microbe and/or probiotic can be any beneficial microbe and/or probiotic known in the art.

In some embodiments, SBP biological systems may include microbes, microorganisms, and/or microbiomes that promote plant growth. Such microbes, microorganisms, and/or microbiomes may include, but are not limited to, *Algoriphagus ratkowskyi, Altererythrobacter luteolus, Alternaria thalictrigena, Arthrobacter agilis, Arthrobacter arilaitensis, Arthrobacter aurescens, Arthrobacter citreus, Arthrobacter crystallopoeietes, Arthrobacter globiformis, Arthrobacter humicola, Arthrobacter oryzae, Arthrobacter oxydans, Arthrobacter pascens, Arthrobacter ramosus, Arthrobacter tumbae, Aspergillus fumigatiaffinis, Bacillus aquimaris, Bacillus benzoevorans, Bacillus cibi, Bacillus herbersteinensis, Bacillus idriensis, Bacillus licheniformis, Bacillus niacin, Bacillus psychordurans, Bacillus simplex, Bacillus simplex* 11, *Bacillus simplex* 237, *Bacillus simplex* 30N-5, *Bacillus subtilis* 30VD-1, *Bartonella elizabethae, Citricoccus alkalitolerans, Citricoccus nitrophenolicus, Cladosporium sphaerospermum, Curtobacterium flaccumfaciens, Exiguobacterium aurantiacum, Fusarium equiseti, Fusarium oxysporum, Georgenia ruanii, Halomonas aquamarina, Kocuria rosea, Massilia timonae, Mesorhizobium loti, Microbacterium aerolatum, Microbacterium oxydans, Microbacterium paludicola, Microbacterium paraoxydans, Microbacterium phyllosphaerae, Microbacterium testaceum, Micrococcus luteus, Mycobacterium sacrum, Nocardiopsis quinghaiensis, Oceanobacillus picturae, Ochroconis* sp., *Olivibacter soli, Paenibacillus tundrae, Penicillium chrysogenum, Penicillium commune, Phoma betae, Planococcus maritimus, Planococcus psychrotoleratus, Planomicrobium koreense, Planomicrobium okeanokoites, Promicromonospora kroppenstedtii, Pseudomonas brassicacearum, Pseudomonas fluorescens, Pseudomonas frederiksbergensis, Pseudomonas fulva, Pseudomonas geniculata, Pseudomonas gessardii, Pseudomonas libanensis, Pseudomonas mosselii, Pseudomonas plecogiossicida, Pseudomonas putida, Pseudomonas stutzeri, Pseudomonas syringae, Rhodococcus jostii, Sinorhizobium medicae, Sinorhizobium meliloti, Staphylococcus succinus, Stenotrophomonas maltophilia, Stenotrophomonas rhizophila, Streptomyces althioticus, Streptomyces azureus, Streptomyces bottropensis, Streptomyces candidus, Streptomyces chryseus, Streptomyces cirratus, Streptomyces coeruleofuscus, Streptomyces durmitorensis, Streptomyces flaveus, Streptomyces fradeiae, Streptomyces griseoruber, Streptomyces griseus, Streptomyces halstedii, Streptomyces marokkonensis, Streptomyces olivoviridis, Streptomyces peucetius, Streptomyces phaeochromogenes, Streptomyces pseudogriseolus, Terribacillus halophilus, Virgibacillus halodenitrificans*, and/or *Williamensia muralis*. In further embodiments, such plant growth-promoting microbes, microorganisms, and/or microbiomes may be selected from any of those microbial isolates described in US Publication Number US20140342905, and International Publication Number WO2014201044, the contents of which are hereby incorporated by reference in their entirety.

In some embodiments, SBT and/or SBP biological systems may be used as biopesticides. As used herein, the term "biopesticide" refers to a composition with a bacteria, microorganism, or biological cargo that displays pesticidal activity. Any of the biopesticides taught in U.S. Pat. No. 6,417,163 and in Kumar et al. ((2017) Probiotics and Plant Health doi. 10.1007/978-981-10-3473-2_4) may be used herein (the contents of which are herein incorporated by reference in their entirety).

Consumer Products and Textiles

In some embodiments, SBTs and/or SBPs may be used to produce or may be incorporated into consumer products. As used herein, the term "consumer products" refers to goods or merchandise purchasable by the public. Consumer products may include, but are not limited to, agricultural products, therapeutic products, veterinary products, and products for household use. Non-limiting examples of consumer products include cloths, protectors, sealant, adhesives, lubricants, protectants, apparel, footwear, apparel accessories, insulators, devices, bandages, screens, synthetic clothing, laundry pods or tablets, wet wipes, tires, tea bags, beer cozies, and/or mouse pads.

VI. Definitions

Absolute value: As used herein, the term "absolute value" describes the magnitude of a numerical number or measurement. The magnitude is listed as a non-negative number, but it can represent both positive and negative values.

Active pharmaceutical agent (API): As used herein, the term "active pharmaceutical agent," or "API," describes the component of a pharmaceutical composition that exhibits biological activity.

Cumulative release percentage: As used herein, the term "cumulative release percentage" describes the total percentage of a factor released from a source or depot over the course of a release period. This percentage may be determined from the total mass of released factor divided by initial mass of the factor in the source or depot. The "daily release percentage" describes the cumulative release percentage of factor per day. This value may be calculated from the best fit line slope of a plot of cumulative release percentage over time.

Effective concentration: As used herein, the term "effective concentration" refers to the concentration of a compound or factor required to elicit a particular response. The concentration needed to elicit half of a complete response is referred to as the "half maximal effective concentration" or "$EC_{50}$." The concentration of compound needed to elicit 80% of a complete response is referred to as the "$EC_{80}$". Where the compound or factor is inhibitory, the concentration needed to reduce or inhibit the response by half is referred to herein as the half maximal inhibitory concentration, or "$IC_{50}$."

Initial burst: As used herein, the term "initial burst" refers to a rate of factor release from a source or depot over an initial release period (e.g., after administration or other placement, for example in solution during experimental analysis) that is higher than rates during one or more subsequent release periods.

Linear viscoelastic region: As used herein, the term "linear viscoelastic region" or "LVR" refers to the range in amplitude of deformation in which the shear loss modulus and the shear storage modulus do not vary and the structure of the material does not change.

Phase angle: As used herein, the term "phase angle" refers to the difference in the stress and strain applied to a material during the application of oscillating shear stress. The lag between stress and strain represents a measure of a material's viscoelasticity.

Shear: As used herein, the term "shear" or "shear force" or refers to a force applied to a material that is parallel to the surface of said material.

Shear loss modulus: As used herein, the term "shear loss modulus" or "G" refers to the measure of a material's ability to dissipate energy, usually in the form of heat.

Shear rate: As used herein, the term "shear rate" refers to the rate of change in a material's strain over time.

Shear storage modulus: As used herein, the term "shear storage modulus" or "G" refers to the measure of a material's elasticity or reversible deformation as determined by the material's stored energy.

Shear stress: As used herein, the term "shear stress" refers to the force applied parallel to a material divided by the area along the force.

Strain: As used herein, the term "strain" refers to the ratio of displacement of material upon the application of a shear force to the height of the material.

Strain sweep: As used herein, the term "strain sweep" refers to a range of strain measurements over which an experimental parameter may be determined.

Tune: As used herein, the term "tune" refers to the control or modulation of a physical or chemical property. Physical or chemical properties of SBPs may be tuned through the control of silk fibroin molecular weight, silk concentration, the incorporation of excipients, and any other method of control described in the present disclosure.

Viscoelasticity: As used herein, the term "viscoelasticity" refers to the range of viscous and elastic properties of materials under stress.

Viscosity: As used herein, the term "viscosity" refers to a material's ability to resist deformation due to shear forces, and the ability of a fluid to resist flow. It is reflected by the shear stress over the shear rate.

The details of one or more embodiments of the disclosure are set forth in the accompanying description below. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

The present disclosure is further illustrated by the following non-limiting examples.

EXAMPLES

Example 1. Silk Fibroin Isolation

Silk yarn, purchased from Jiangsu SOHO International Group, was degummed to remove sericin. 30 grams of cut silk yarn were boiled or heated or degummed at 100° C. in 3 L of deionized (DI) water with 0.02M sodium carbonate with stirring. The yarn was then transferred to a new boiling 0.02M sodium carbonate aqueous solution and boiled at 100° C. with stirring. The total degumming time was discussed in terms of minute boil, or "mb." The total degumming time was 480 minutes, or 480 mb.

Alternatively, Silk yarn, purchased from Jiangsu SOHO International Group, was degummed to remove sericin. 30 grams of cut silk yarn were boiled or heated or degummed at 85° C. in 3 L of deionized (DI) water with 0.5M sodium carbonate with stirring. The total degumming time was 240 minutes or 240 mb. Alternatively, Silk yarn, purchased from Jiangsu SOHO International Group, was degummed to remove sericin. 30 grams of cut silk yarn were boiled or heated or degummed at 90° C. in 3 L of deionized (DI) water with 0.5M sodium carbonate with stirring. The total boiling or degumming time was 120 minutes or 120 mb.

The fibroin was washed in 3×3 L exchanges of 70° C. DI water for 20 minutes each followed by 3×3 L exchanges of room temperature (RT) DI water for 20 minutes each. The silk fibroin was dried overnight, weighed, and dissolved at 20% (w/v) in a 9.3M aqueous solution of lithium bromide (from Sigma-Aldrich, St. Louis, MO) for 5 hours at 60° C. The resulting fibroin solution was dialyzed against water (150 mL of fibroin solution against 5 L of water) at room temperature in 3.5 kDa or 50 kDa regenerated cellulose dialysis tubing for 48 hours, with 6 water changes to remove the excess salt. The conductivity was tested and recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and samples of the supernatant were diluted at 1:20 and 1:40 in water or 10 mM phosphate buffer. Samples for a standard curve were prepared for an A280 assay by diluting pre-measured fibroin solutions to 5, 2.5, 1.25, 0.625, 0.3125, and 0 mg/mL in water or 10 mM phosphate buffer. The silk concentration of the 1:20 and 1:40 diluted silk fibroin samples was measured against the standard curve by the absorbance at 280 nm.

The silk fibroin solutions were diluted to a final concentration of 3% (w/v) in 10 mM phosphate buffer (from Sigma Aldrich Fine Chemicals, St. Louis, MO), pH 7.4, and/or in 5% sucrose, and/or in water, and they were filtered through a 0.2 μm filter using a vacuum filter unit. 10 ml of each solution was aliquoted into 50 ml conical tubes, snap frozen, or frozen to −80° C., in liquid nitrogen for 10 minutes, transferred for 20 minutes in −80° C., and lyophilized for 72 hours.

Silk yarn, purchased from Jiangsu SOHO International Group, was degummed to remove sericin and modify silk fibroin molecular weight. 20 grams of cut silk yarn were split into four cotton drawstring bags with 5 grams of silk per bag. The four bags of yarn were then immersed in 2 L of degumming solution at either 0.05 μM, 0.1 μM, or 0.5 M sodium carbonate. The temperature of the solution was controlled with a ChefSteps Joule Sous Vide (ChefSteps, Seattle, WA, USA) at either 80, 85, 90° C. A control degumming was performed with four bags of yarn in 0.02 M carbonate at 100° C. Every two hours for each degumming, a bag would be taken from the solution and the pH of the solution would be measured. The silk fibroin in the bag was thoroughly rinsed under DI water and allowed to dry overnight in a fume hood. Table 8 lists the degumming conditions, pH values of the degumming solution at the time the silk fibroin was removed, and the dry weight of the silk fibroin after degumming.

TABLE 8

Silk fibroin degumming conditions, pH values, and dry weights

| Lot # | Silk Degumming Time (hr) | Silk Degumming Sodium Carbonate Concentration (M) | Silk Degumming Temperature (° C.) | Final Degumming Solution pH | Final Silk Fibroin Dry Weight (g) |
|---|---|---|---|---|---|
| 111.2 | 2 | 0.02 | 100 | 10.53 | 3.726 |
| 111.4 | 4 | 0.02 | 100 | 10.52 | 3.515 |
| 111.6 | 6 | 0.02 | 100 | 10.76 | 3.293 |
| 111.8 | 8 | 0.02 | 100 | 11.18 | 3.131 |
| 108A.2 | 2 | 0.05 | 80 | 11.11 | 3.776 |
| 108A.4 | 4 | 0.05 | 80 | 10.77 | 3.737 |
| 108A.6 | 6 | 0.05 | 80 | 10.84 | 3.717 |
| 108A.8 | 8 | 0.05 | 80 | 10.64 | 3.657 |
| 108B.2 | 2 | 0.05 | 85 | 10.77 | 3.870 |
| 108B.4 | 4 | 0.05 | 85 | 10.68 | 3.730 |
| 108B.6 | 6 | 0.05 | 85 | 10.93 | 3.670 |
| 108B.8 | 8 | 0.05 | 85 | 10.75 | 3.500 |
| 108C.2 | 2 | 0.05 | 90 | 10.74 | 3.730 |
| 108C.4 | 4 | 0.05 | 90 | 10.64 | 3.560 |
| 108C.6 | 6 | 0.05 | 90 | 10.91 | 3.390 |
| 108C.8 | 8 | 0.05 | 90 | 10.68 | 3.160 |
| 109A.2 | 2 | 0.1 | 80 | 10.67 | 3.804 |
| 109A.4 | 4 | 0.1 | 80 | 10.58 | 3.726 |
| 109A.6 | 6 | 0.1 | 80 | 11.13 | 3.528 |
| 109A.8 | 8 | 0.1 | 80 | 11.07 | 3.386 |
| 109B.2 | 2 | 0.1 | 85 | 10.76 | 3.684 |
| 109B.4 | 4 | 0.1 | 85 | 10.38 | 3.558 |
| 109B.6 | 6 | 0.1 | 85 | 11.10 | 3.257 |
| 109B.8 | 8 | 0.1 | 85 | 11.04 | 3.073 |
| 109C.2 | 2 | 0.1 | 90 | 10.95 | 3.690 |
| 109C.4 | 4 | 0.1 | 90 | 10.42 | 3.333 |
| 109C.6 | 6 | 0.1 | 90 | 11.02 | 2.755 |
| 109C.8 | 8 | 0.1 | 90 | 10.83 | 2.477 |
| 110A.2 | 2 | 0.5 | 80 | 10.65 | 3.717 |
| 110A.4 | 4 | 0.5 | 80 | 10.98 | 3.459 |
| 110A.6 | 6 | 0.5 | 80 | 11.09 | 2.958 |
| 110A.8 | 8 | 0.5 | 80 | 11.07 | 2.654 |
| 110B.2 | 2 | 0.5 | 85 | 11.05 | 3.443 |
| 110B.4 | 4 | 0.5 | 85 | 10.97 | 2.967 |
| 110B.6 | 6 | 0.5 | 85 | 11.37 | 2.153 |
| 110B.8 | 8 | 0.5 | 85 | 11.30 | 1.891 |
| 110C.2 | 2 | 0.5 | 90 | 10.99 | 3.054 |
| 110C.4 | 4 | 0.5 | 90 | 10.92 | 2.502 |
| 110C.6 | 6 | 0.5 | 90 | 11.34 | 1.785 |
| 110C.8 | 8 | 0.5 | 90 | 11.34 | 0.522 |

The silk fibroin samples were weighed and dissolved at 20% (w/v) in a 9.3M aqueous solution of lithium bromide (from Sigma-Aldrich, St. Louis, MO) for 5 hours at 60° C. The resulting fibroin solution was dialyzed against water at 4° C. in 50 kDa regenerated cellulose dialysis tubing for 48 hours, with 6 water changes to remove the excess salt. The conductivity was recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and samples of the supernatant were assessed for silk fibroin concentration via gravimetric analysis. Weigh boats were tared and 500 μL of solution was added onto it. The solution was dried overnight at 60° C. before a final weight was measured. The resulting weight of silk fibroin remaining was used to determine the silk fibroin percentage (w/v).

Silk fibroin solutions were diluted to a final concentration of 5% (w/v) and 50 mM sucrose (from Sigma Aldrich Fine Chemicals, St. Louis, MO). If the solution was below 5% (w/v) after dialysis, the solution was diluted as little as possible in order to reach a final concentration of 50 mM sucrose. Ten milliliters of each solution was aliquoted into 50 ml conical tubes, frozen overnight at −80° C., and then stored at −20° C. until use.

Example 2. Silk Fibroin Isolation and Preparation by Gravimetry

Silk yarn, purchased from Jiangsu SOHO International Group, was degummed to remove sericin. 30 grams of cut silk yarn were boiled at 100° C. in 3 L of deionized (DI) water with 0.02M sodium carbonate with stirring. The yarn was then transferred to a new boiling 0.02M sodium carbonate aqueous solution and boiled at 100° C. with stirring. The total degumming time was discussed in terms of minute boil, or "mb." The total degumming time was 480 minutes, or 480 mb.

Alternatively, Silk yarn, purchased from Jiangsu SOHO International Group, was degummed to remove sericin. 30 grams of cut silk yarn were boiled at 85° C. in 3 L of deionized (DI) water with 0.5M sodium carbonate with stirring. The total degumming time was 240 minutes or 240 mb. Alternatively, Silk yarn, purchased from Jiangsu SOHO International Group, was degummed to remove sericin. 30 grams of cut silk yarn were boiled at 90° C. in 3 L of deionized (DI) water with 0.5M sodium carbonate with stirring. The total boiling time was 120 minutes or 120 mb.

The fibroin was washed in 3×3 L exchanges of 70° C. DI water for 20 minutes each followed by 3×3 L exchanges of room temperature (RT) DI water for 20 minutes each. The silk fibroin was dried overnight, weighed, and dissolved at 20% (w/v) in a 9.3M aqueous solution of lithium bromide (from Sigma-Aldrich, St. Louis, MO) for 5 hours at 60° C. The resulting fibroin solution was dialyzed against water (150 ml of fibroin solution against 5 L of water) at room temperature in a 3.5 kDa or 50 kDa regenerated cellulose dialysis tubing for 48 hours, with 6 water changes to remove the excess salt. The conductivity was tested and recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and concentration of silk fibroin was determined via gravimetry. The weight of dried silk fibroin remaining was divided by the sample volume to determine the concentration of silk fibroin in solution. Samples of the supernatant were added to pre-tared weigh boats and dried at 60° C. overnight.

The silk fibroin solutions were diluted to a final concentration of 3% (w/v) in 10 mM phosphate buffer (from Sigma Aldrich Fine Chemicals, St. Louis, MO), pH 7.4, or to 5% (w/v) silk fibroin in 50 mM sucrose and they were filtered through a 0.2 μm PES filter using a vacuum filter unit. For those solutions diluted in phosphate buffer, 10 mL of each solution was aliquoted into 50 ml conical tubes, snap frozen in liquid nitrogen for 10 minutes, transferred for 20 minutes in −80° C., and lyophilized for 72 hours. For those solutions diluted in sucrose, 10 ml of each solution was aliquoted into 50 ml conical tubes, frozen overnight at −80° C., and then stored at −20° C. Some aliquots were lyophilized. Some aliquots were stored at 2-8° C. prior to freezing at −80° C.

Example 3. Silk Fibroin Isolation and Molecular Weight Determination

Silk yarn, purchased from Jiangsu SOHO International Group, was degummed to remove sericin. 30 grams of cut silk yarn were boiled at 100° C. in 3 L of deionized (DI) water with 0.02M sodium carbonate with stirring. The yarn was then transferred to a new boiling 0.02 M sodium carbonate aqueous solution and boiled at 100° C. with stirring. The total boiling time, or degumming time, was discussed in terms of minute boil, or "mb." The total boiling times ranged from 30-480 mb. The fibroin was dried overnight, weighed, and dissolved at 20% (w/v) in a 9.3 M aqueous solution of lithium bromide (from Sigma-Aldrich, St. Louis, MO) for 5 hours at 60° C. The resulting fibroin solution was dialyzed against water at room temperature in 50 kDa regenerated cellulose dialysis tubing for 48 hours, with 6 water changes to remove the excess salt. The conductivity was tested and recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and the concentration of silk fibroin was determined via gravimetry. Samples of the supernatant were added to pre-tared weigh boats and dried at 60° C. overnight. The dried weight of silk fibroin was used to determine the concentration in solution. The silk fibroin solutions were diluted to a final concentration of 5% (w/v) in 50 mM sucrose, separated into 10 ml was aliquots in 15 ml conical tubes, and frozen at ≤−20° C.

Silk fibroin molecular weight was determined using a UPLC SEC method. A Waters Aquity H-Class UPLC (Waters, Milford, MA) equipped with a Waters BEH 200 Å 1.7 am, 4.8×150 cm UPLC SEC column was used. Sample temperature was maintained at 4° C. An isocratic flow at 0.3 mL/min of 100 mM Tris-HCl with 400 mM sodium perchlorate, pH 8.0 was used to elute SF from the column. Elution was monitored at 280 nm. Molecular weights were calculated using Waters BEH200 Protein Standard Mix (Waters, Milford, MA). Some preparations of 480mb had an average molecular weight of 30 kDa. Other preparations resulted in molecular weights between 20 kDa and 40 kDa.

The molecular weight of each batch collected was determined by HPLC-SEC. A Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. Silk fibroin was diluted to 1% (w/v) in mobile phase after thawing before being run on SEC. Silk fibroin elution was monitored at 280 nm. Molecular weights were calculated using a standard curve prepared from Waters BEH 200 Å Protein SEC Standard Mix (Waters, Milford, MA). Table 9 lists these molecular weights for the select batches analyzed.

TABLE 9

SEC measurements of silk fibroin solution formulations

| Lot # | Average MW (kDa) | Average Viscosity at 1 1/s (cP) |
|---|---|---|
| 111.2 | 117.56 | 30.89 |
| 111.4 | 60.74 | 39.00 |
| 111.6 | 42.41 | 76.21 |
| 111.8 | 34.03 | 97.66 |
| 108A.2 | — | — |
| 108A.4 | — | — |
| 108A.6 | — | — |
| 108A.8 | 93.51 | 15.22 |
| 108B.2 | — | — |
| 108B.4 | — | — |
| 108B.6 | — | — |
| 108B.8 | 45.49 | 53.41 |
| 108C.2 | 122.52 | 12.54 |
| 108C.4 | 65.01 | 23.90 |
| 108C.6 | 49.87 | 54.18 |
| 108C.8 | 31.45 | 74.70 |
| 109A.2 | — | — |
| 109A.4 | — | — |
| 109A.6 | — | — |
| 109A.8 | 43.95 | 43.38 |
| 109B.2 | 118.93 | 27.46 |
| 109B.4 | 64.36 | 25.68 |
| 109B.6 | 38.21 | 82.10 |
| 1098.8 | 31.75 | 104.60 |
| 109C.2 | 82.76 | 17.12 |
| 109C.4 | 36.73 | 49.41 |
| 109C.6 | 25.04 | 106.95 |
| 109C.8 | 22.04 | 142.48 |
| 110A.2 | 68.74 | 18.16 |
| 110A.4 | 35.47 | 42.74 |
| 110A.6 | 22.59 | 78.72 |
| 110A.8 | 21.32 | 128.03 |
| 110B.2 | 37.88 | 41.37 |
| 110B.4 | 22.13 | 89.69 |
| 110B.6 | 17.60 | 178.79 |
| 110B.8 | — | — |
| 110C.2 | 24.25 | 99.74 |
| 110C.4 | 17.60 | 140.56 |
| 110C.6 | — | — |
| 110C.8 | — | — |

A decrease in silk fibroin molecular weight was observed over time under each degumming condition. This is a result of the hydrolysis occurring during the degumming process in the basic sodium carbonate buffer. Longer degumming times lead to decreased average silk fibroin MW. Silk fibroin degradation was also observed with increasing sodium carbonate concentration. For example, increasing the sodium carbonate concentration from 0.05 M to 0.5 M while at the same temperature (90° C.) and time (2 hrs.) decreased the average molecular weight of silk fibroin from 122.52 kDa to 24.25 kDa. Temperature also impacted the silk fibroin hydrolysis with increasing temperature leading to lower molecular weights. An example of this was shown with silk that was degummed with 0.5 M sodium carbonate for 2 hrs. The sample at 80° C. showed a molecular weight of 68.74 kDa, while increasing the temperature to 90° C. decreased the molecular weight average of the silk fibroin to 24.35 kDa. These results indicated that by controlling the time of degumming, the sodium carbonate concentration, and the temperature, it is possible to control the hydrolysis of silk fibroin.

Example 4. Formulation of Silk Fibroin Solutions

To prepare the solutions, dry silk fibroin of a designated mb, which had been lyophilized in phosphate buffer, was reconstituted in phosphate buffered saline to afford 30% and 10% (w/v) silk fibroin solutions. Formulations from silk of a 30mb were prepared from silk fibroin lyophilized with sucrose. Additional dilutions with phosphate buffered saline were performed on the 10% (w/v) silk fibroin solutions to obtain solutions with 5%, 2.5%, 1%, 0.5% and 0.1% (w/v) silk fibroin. The formulations were prepared as described in Table 10. The samples in Table 10 are named by the process used to prepare and formulate each solution. For example, in the sample named "30mb; sln; 10% SFf; 18% Suc" "30mb" refers to silk degummed with a 30 minute boil, "sln" refers to the formulation of the sample as a solution, "10% SFf" refers to a formulation with 10% (w/v) silk fibroin, and "18% Suc" refers to a formulation with 18% sucrose (w/v).

TABLE 10

Silk fibroin solution formulations

| Sample | Silk Fibroin Boil Time (mb) | Formulation Silk Concentration (w/v %) | Sample Name |
|---|---|---|---|
| 1A | 30 | 30 | 30 mb; sln; 30% SFf |
| 1B | 30 | 10 | 30 mb; sln; 10% SFf; 18% Suc |
| 1C | 30 | 5 | 30 mb; sln; 5% SFf; 9% Suc |
| 1D | 30 | 2.5 | 30 mb; sln; 2.5% SFf; 4.5% Suc |
| 1E | 30 | 1 | 30 mb; sln; 1% SFf; 1.8% Suc |
| 1F | 30 | 0.5 | 30 mb; sln; 0.5% SFf, 0.9% Suc |
| 1G | 30 | 0.1 | 30 mb; sln; 0.1% SFf 0.18% Suc |
| 2A | 90 | 30 | 90 mb; sln; 30% SFf |
| 2B | 90 | 10 | 90 mb; sln; 10% SFf |
| 2C | 90 | 5 | 90 mb; sln; 5% SFf |
| 2D | 90 | 2.5 | 90 mb; sln; 2.5% SFf |
| 2E | 90 | 1 | 90 mb; sln; 1% SFf |
| 2F | 90 | 0.5 | 90 mb; sln; 0.5% SFf |
| 2G | 90 | 0.1 | 90 mb; sln; 0.1% SFf |
| 3A | 120 | 30 | 120 mb; sln; 30% SFf |
| 3B | 120 | 10 | 120 mb; sln; 10% SFf |
| 3C | 120 | 5 | 120 mb; sln; 5% SFf |
| 3D | 120 | 2.5 | 120 mb; sln; 2.5% SFf |
| 3E | 120 | 1 | 120 mb; sln; 1% SFf |
| 3F | 120 | 0.5 | 120 mb; sln; 0.5% SFf |
| 3G | 120 | 0.1 | 120 mb; sln; 0.1% SFf |
| 4A | 480 | 30 | 480 mb; sln; 30% SFf |
| 4B | 480 | 10 | 480 mb; sln; 10% SFf |
| 4C | 480 | 5 | 480 mb; sln; 5% SFf |
| 4D | 480 | 2.5 | 480 mb; sln; 2.5% SFf |
| 4E | 480 | 1 | 480 mb; sln; 1% SFf |
| 4F | 480 | 0.5 | 480 mb; sln; 0.5% SFf |
| 4G | 480 | 0.1 | 480 mb; sln; 0.1% SFf |

To prepare the following solutions in Table 11, silk fibroin of a designated mb, which had either been frozen in 50 mM sucrose or stored at 4° C. in phosphate buffer, was used. A phosphate buffered saline stock solution containing sodium phosphate dibasic, potassium phosphate monobasic, and sodium chloride was prepared to reach final concentrations of 10 mM phosphate and 125 mM sodium chloride and buffered to pH 7.5. The formulations were prepared as described in Table 8. The samples in Table 11 are named by the process used to prepare and formulate each solution with each degumming process. For example, in the sample named "2% SFf; sln; 1.71% Suc; phosphate buffer", "1% SFf" refers to a formulation with 1% (w/v) silk fibroin, "sln" refers to the formulation of the sample as a solution, and "1.71% Suc" refers to a formulation with 1.71% (w/v), or 50 mM, sucrose. All formulations are in a "phosphate buffer" which refers to a vehicle containing final concentrations of 10 mM phosphate and 125 mM sodium chloride at pH 7.5. It is noted that the three variables that differ in the samples are carbonate concentration, temperature, and time duration. By altering these three variables, similar molecular weights can be achieved without having to boil the solution or keep the solution at a high or boiling temperature for a full eight hours.

TABLE 11

Silk Fibroin Formulations (prepared with each SF from Example 1)

| Sample | SF Conc. (%) | Description |
|---|---|---|
| 1 | 2 | 2% SFf; sln; phosphate buffer |
| 2 | 2.5 | 2.5% SFf; sln; phosphate buffer |
| 3 | 3 | 3% SFf; sln; phosphate buffer |
| 4 | 2 | 2% SFf; sln; 1.71% Suc; phosphate buffer |
| 5 | 2.5 | 2.5% SFf; sln; 1.71% Suc; phosphate buffer |
| 6 | 3 | 3% SFf; sln; 1.71% Suc; phosphate buffer |

Example 5. Formulation of Silk Fibroin Solutions with Lyophilized or Freeze-Thaw Silk Fibroin To prepare the solutions, silk fibroin was either reconstituted from a dry state or thawed from a frozen state. Dry silk fibroin of a designated mb, which had been lyophilized in phosphate buffer or sucrose, was reconstituted in phosphate buffered saline to afford 10% (w/v) silk fibroin solutions. Frozen silk fibroin solutions were left at room temperature until completely thawed and then gently mixed before use. Additional dilutions with phosphate buffered saline were performed on the 10% and 5% (w/v) silk fibroin solutions to obtain solutions with 5%, 1%, 0.5%, 0.1%, and 0.05% (w/v) silk fibroin. The formulations were prepared as described in Table 12. The samples in Table 12 are named by the process used to prepare and formulate each solution. For example, in the sample named "90mb; sln; 5% SFf; 1.7% Suc; frozen" "90mb" refers to silk degummed with a 90-minute boil, "sln" refers to the formulation of the sample as a solution, "5% SFf" refers to a formulation with 5% (w/v) silk fibroin, "1.7% Suc" refers to a formulation with 1.7% sucrose (w/v), "frozen" refers to the starting silk fibroin stock being frozen, and "lyo" refers to the starting silk fibroin stock being lyophilized.

TABLE 12

Silk fibroin solution formulations prepared with lyophilized or freeze-thaw silk fibroin

| Sample | Silk Fibroin Boil Time (mb) | Silk Concentration (w/v %) | Sample Name |
|---|---|---|---|
| 1 | 90 | 5 | 90 mb; sln; 5% SFf; 1.7% Suc; frozen |
| 2 | 90 | 1 | 90 mb; sln; 1% SFf; 0.34% Suc; frozen |
| 3 | 90 | 0.5 | 90 mb; sln; 0.5% SFf; 0.17% Suc; frozen |
| 4 | 90 | 0.1 | 90 mb; sln; 0.1% SFf; 0.034% Suc; frozen |
| 5 | 90 | 0.05 | 90 mb; sln; 0.05% SFf; 0.017% Suc; frozen |
| 6 | 120 | 5 | 120 mb; sln; 5% SFf; 1.7% Suc; frozen |
| 7 | 120 | 1 | 120 mb; sln; 1% SFf; 0.34% Suc; frozen |
| 8 | 120 | 0.5 | 120 mb; sln; 0.5% SFf; 0.17% Suc; frozen |
| 9 | 120 | 0.1 | 120 mb; sln; 0.1% SFf; 0.034% Suc; frozen |
| 10 | 120 | 0.05 | 120 mb; sln; 0.05% SFf; 0.017% Suc; frozen |
| 11 | 480 | 5 | 480 mb; sln; 5% SFf; 1.7% Suc; frozen |
| 12 | 480 | 1 | 480 mb; sln; 1% SFf; 0.34% Suc; frozen |
| 13 | 480 | 0.5 | 480 mb; sln; 0.5% SFf; 0.17% Suc; frozen |
| 14 | 480 | 0.1 | 480 mb; sln; 0.1% SFf; 0.034% Suc; frozen |
| 15 | 480 | 0.05 | 480 mb; sln; 0.05% SFf; 0.017% Suc; frozen |
| 16 | 480 | 5 | 480 mb; sln; 5% SFf; 1.7% Suc; lyo |
| 17 | 480 | 1 | 480 mb; sln; 1% SFf; 0.34% Suc; lyo |
| 18 | 480 | 0.5 | 480 mb; sln; 0.5% SFf; 0.17% Suc; lyo |
| 19 | 480 | 0.1 | 480 mb; sln; 0.1% SFf; 0.034% Suc; lyo |
| 20 | 480 | 0.05 | 480 mb; sln; 0.05% SFf; 0.017% Suc; lyo |

Example 6. Formulation of Silk Fibroin Solutions with Sucrose, Surfactant, and Borate Buffer To prepare the solutions, silk fibroin of a designated 480 mb (prepared as in Examples 1 or 2), which had been frozen in 50 mM sucrose, was thawed to room temperature. A borate buffer stock solution containing borate, potassium chloride, magnesium chloride, and calcium chloride was prepared and buffered to pH 7.3. A 10% (v/v) polysorbate 80 stock solution was prepared. The formulations and controls (no silk fibroin) were prepared as described in Table 13. The samples in Table 13 are named by the process used to prepare and formulate each solution. For example, in the sample named "480mb; sln; 1% SFf; 0.34% Suc; borate buffer" "480mb" refers to silk degummed with a 480-minute boil, "sln" refers to the formulation of the sample as a solution, "1% SF" refers to a formulation with 1% (w/v) silk fibroin, "0.34% Suc" refers to a formulation with 0.34% (w/v) sucrose, and "0.2% T80" refers to a formulation containing 0.2% (v/v) polysorbate 80. All formulations are in a "borate buffer" which refers to a vehicle containing final concentrations of 99.3 mM borate, 18.8 mM potassium chloride, 0.6 mM magnesium chloride, and 0.5 mM calcium chloride

TABLE 13

Silk Fibroin Formulations with sucrose and borate buffer

| Sample | SF Conc. (%) | Polysorbate 80 Conc. (%) | Description |
|---|---|---|---|
| 1 | 0 | 0 | 0% SFf; sln; borate buffer |
| 2 | 0 | 0.2 | 0% SFf; sln; borate buffer, 0.2% T80 |
| 3 | 1 | 0 | 480 mb; 1% SFf; sln; 0.34% Suc; borate buffer |
| 4 | 1 | 0.2 | 480 mb; 1% SFf; sln; 0.34% Suc; borate buffer; 0.2% T80 |

Example 7. Additional Formulation of Silk Fibroin Solutions with Sucrose, Surfactant, and Borate Buffer To prepare the solutions, silk fibroin of a designated 480 mb (prepared as in Examples 1 or 2), which had been frozen in 50 mM sucrose, was thawed to room temperature. A borate buffer stock solution containing borate, potassium chloride, magnesium chloride, and calcium chloride was prepared and buffered to pH 7.3. A 10% (v/v) polysorbate 80 stock solution was prepared. The formulations and controls (no silk fibroin) were prepared as described in Table 14. The samples in Table 14 are named by the process used to prepare and formulate each solution. For example, in the sample named “480mb; sln; 1% SFf; 0.34% Suc; borate buffer” “480mb” refers to silk degummed with a 480 minute boil, “sln” refers to the formulation of the sample as a solution, “1% SFf” refers to a formulation with 1% (w/v) silk fibroin, and “0.34% Suc” refers to a formulation with 0.34% (w/v) sucrose. All formulations are in a “borate buffer” which refers to a vehicle containing final concentrations of 99.3 mM borate, 18.8 mM potassium chloride, 0.6 mM magnesium chloride, and 0.5 mM calcium chloride.

TABLE 14

Silk Fibroin Formulations with 480 mb and sucrose and borate buffer

| Sample | SF Conc. (%) | Sucrose Conc. (%) | Description |
|---|---|---|---|
| 1 | 5 | 1.71 | 480 mb; 5% SFf; sln; 1.71% Suc; borate buffer |
| 2 | 1 | 0.34 | 480 mb; 1% SFf; sln; 0.34% Suc; borate buffer |
| 3 | 0.5 | 0.17 | 480 mb; 0.5% SFf; sln; 0.17% Suc; borate buffer |
| 4 | 0.1 | 0.03 | 480 mb; 0.1% SFf; sln; 0.03% Suc; borate buffer |
| 5 | 0.05 | 0.01 | 480 mb; 0.1% SFf; sln; 0.02% Suc; borate buffer |

Example 8. Rheological Measurements of Silk Solutions

Rheological measurements were performed on a Bohlin C-VOR 150 with a 4°/40 mm cone and plate geometry with a 0.5 mm gap. 1.4 mL of each sample were pipetted onto a Peltier plate system that maintained a steady temperature of 25° C. throughout the test. Four tests were then run. The first test comprised a strain sweep from 0.1% to 10% strain at 1 Hz over the course of 160 seconds(s), with 50 readings taken. This was to determine the linear viscoelastic region (LVR) of each sample. The second test comprised a strain hold at 5% (or 1% if the LVR was smaller) and 1 Hz for 145 s, with 15 readings taken. The third test comprised a shear rate sweep from 0.1 1/s to 10 1/s over the course of 100 s, followed by a hold at 10 1/s for 20 s, with 70 readings taken. Lastly, a shear rate hold was conducted at 1 1/s for 135 s, with 15 readings taken. The data was then analyzed to determine the average shear storage modulus (the elastic modulus (G'), shear loss modulus (the viscous modulus (G"), phase angle, and viscosity at shear rates of 1 1/s and 10 1/s. The results of the rheology measurements are listed in Table 15 and Table 20.

TABLE 15

Rheology measurements of silk fibroin solution formulations and controls

| Sample | Description | Avg. Viscosity at 1 1/s (cP) | Avg. Viscosity at 10 1/s (cP) | Avg. G' (Pa) | Avg. G" (Pa) | Avg. Phase Angle (°) |
|---|---|---|---|---|---|---|
| — | Refresh Liquigel | 79.90 | 46.29 | 1.69E−01 | 3.46E−01 | 64.05 |
| — | SYSTANE ® lubricant eye drop (Alcon) | 20.23 | 12.06 | 2.06E−02 | 7.83E−02 | 75.44 |
| — | SYSTANE ® lubricant eye gel (Alcon) | 1073.57 | 549.81 | 2.20E+00 | 3.03E+00 | 53.98 |
| 1B | 10% 30 mb | 71.58 | 47.41 | 7.60E−02 | 4.12E−01 | 79.56 |
| 1C | 5% 30 mb | 63.99 | 16.37 | 3.96E−01 | 5.67E−01 | 55.19 |
| 1D | 2.5% 30 mb | 69.77 | 13.22 | 3.24E−01 | 3.70E−01 | 48.99 |
| 1E | 1% 30 mb | 42.44 | 17.32 | 1.33E+01 | 3.57E+00 | 15.15 |
| 1F | 0.5% 30 mb | 31.17 | 10.18 | 3.12E−01 | 2.65E−01 | 40.42 |
| 1G | 0.1% 30 mb | 233.61 | 36.57 | 1.47E+01 | 3.40E+00 | 13.13 |
| 2B | 10% 90 mb | 12.89 | 6.50 | 1.11E−02 | 5.77E−02 | 79.50 |
| 2C | 5% 90 mb | 11.51 | 5.36 | 4.28E−02 | 4.36E−02 | 45.40 |
| 2D | 2.5% 90 mb | 13.00 | 4.22 | 4.09E−02 | 4.35E−02 | 46.23 |
| 2E | 1% 90 mb | 20.36 | 5.92 | 4.79E−02 | 7.50E−02 | 57.45 |
| 2F | 0.5% 90 mb | 51.25 | 10.44 | 1.37E+00 | 1.77E+00 | 52.64 |
| 2G | 0.1% 90 mb | 242.98 | 37.12 | 7.15E+00 | 2.47E+00 | 19.06 |
| 3A | 30% 120 mb | 148.68 | 125.72 | 2.90E−02 | 8.00E−01 | 87.93 |
| 3B | 10% 120 mb | 11.83 | 4.69 | 6.78E−03 | 4.15E−02 | 80.08 |
| 3C | 5% 120 mb | 8.74 | 4.15 | 2.77E−02 | 3.71E−02 | 53.00 |
| 3D | 2.5% 120 mb | 8.00 | 1.70 | 3.25E−02 | 2.79E−02 | 40.78 |
| 3E | 1% 120 mb | 13.23 | 4.58 | 1.10E−02 | 5.23E−02 | 78.14 |
| 3F | 0.5% 120 mb | 46.98 | 12.72 | 4.30E−01 | 3.45E−01 | 38.85 |
| 3G | 0.1% 120 mb | 469.61 | 74.17 | 6.69E+00 | 3.30E+00 | 26.22 |
| 4A | 30% 480 mb | 110.03 | 43.84 | 5.76E−01 | 5.30E−01 | 42.89 |
| 4B | 10% 480 mb | 55.18 | 12.76 | 3.40E−01 | 2.37E−01 | 35.14 |
| 4C | 5% 480 mb | 67.55 | 13.98 | 4.03E−01 | 2.91E−01 | 35.99 |
| 4D | 2.5% 480 mb | 77.45 | 15.06 | 4.86E−01 | 3.34E−01 | 34.61 |

TABLE 15-continued

| Rheology measurements of silk fibroin solution formulations and controls | | | | | | |
|---|---|---|---|---|---|---|
| Sample | Description | Avg. Viscosity at 1 1/s (cP) | Avg. Viscosity at 10 1/s (cP) | Avg. G' (Pa) | Avg. G'' (Pa) | Avg. Phase Angle (°) |
| 4E | 1% 480 mb | 113.09 | 20.44 | 6.51E−01 | 4.55E−01 | 35.16 |
| 4F | 0.5% 480 mb | 255.44 | 36.18 | 2.46E+00 | 1.52E+00 | 31.70 |
| 4G | 0.1% 480 mb | 432.52 | 47.05 | 1.37E+01 | 3.30E+00 | 13.52 |
| 5B | 180 mg/mL Sucrose | 10.54 | 2.41 | 6.08E−03 | 3.97E−02 | 81.30 |
| 5E | 18 mg/mL Sucrose | 10.86 | 1.92 | 1.01E−02 | 3.43E−02 | 73.85 |
| 5G | 1.8 mg/mL Sucrose | 14.96 | 2.72 | 9.53E−03 | 3.56E−02 | 74.70 |
| 6 | 1x PBS | 13.41 | 3.03 | 3.26E−02 | 3.55E−02 | 46.66 |

Table 16 provides the standard deviation of the rheology measurements in Table 15

TABLE 16

| Standard deviations of the rheology measurements of silk fibroin solution formulations and controls | | | | | | |
|---|---|---|---|---|---|---|
| Sample | Description | Std Dev. Avg. Viscosity at 1 1/s (cP) | Std. Dev. Avg. Viscosity at 10 1/s (cP) | Std. Dev. Avg. G' (Pa) | Std. Dev. Avg. G'' (Pa) | Std. Dev. Avg. Phase Angle (°) |
| — | Refresh Liquigel | 6.07 | 6.84 | 1.35E−02 | 9.89E−03 | 1.81 |
| — | SYSTANE ® lubricant eye drop (Alcon) | 7.60 | 6.33 | 8.25E−03 | 6.22E−03 | 5.24 |
| — | SYSTANE ® lubricant eye gel (Alcon) | 7.08 | 5.45 | 1.41E−02 | 1.54E−02 | 0.11 |
| 1B | 10% 30 mb | 7.17 | 5.61 | 1.26E−02 | 6.37E−03 | 1.68 |
| 1C | 5% 30 mb | 7.94 | 6.65 | 5.69E−02 | 5.06E−02 | 1.72 |
| 1D | 2.5% 30 mb | 4.40 | 6.59 | 5.67E−02 | 4.85E−02 | 2.17 |
| 1E | 1% 30 mb | 18.27 | 6.03 | 1.38E+00 | 1.97E−01 | 0.68 |
| 1F | 0.5% 30 mb | 7.75 | 5.78 | 1.41E−02 | 8.38E−03 | 1.24 |
| 1G | 0.1% 30 mb | 13.66 | 6.30 | 1.32E+00 | 1.34E−01 | 0.75 |
| 2B | 10% 90 mb | 5.17 | 1.82 | 9.02E−03 | 1.16E−02 | 6.91 |
| 2C | 5% 90 mb | 6.03 | 1.33 | 7.01E−03 | 7.83E−03 | 6.04 |
| 2D | 2.5% 90 mb | 7.96 | 2.10 | 7.76E−03 | 1.14E−02 | 7.90 |
| 2E | 1% 90 mb | 7.18 | 1.63 | 6.50E−03 | 5.90E−03 | 4.02 |
| 2F | 0.5% 90 mb | 10.85 | 1.59 | 2.39E−01 | 3.21E−02 | 4.55 |
| 2G | 0.1% 90 mb | 39.66 | 1.86 | 4.02E−01 | 5.14E−02 | 0.69 |
| 3A | 30% 120 mb | 4.99 | 1.35 | 1.02E−02 | 1.06E−02 | 0.71 |
| 3B | 10% 120 mb | 4.28 | 1.06 | 4.27E−03 | 8.25E−03 | 6.47 |
| 3C | 5% 120 mb | 3.51 | 1.54 | 8.24E−03 | 8.37E−03 | 12.40 |
| 3D | 2.5% 120 mb | 5.11 | 1.25 | 6.70E−03 | 6.08E−03 | 9.61 |
| 3E | 1% 120 mb | 3.06 | 1.56 | 7.58E−03 | 8.57E−03 | 7.62 |
| 3F | 0.5% 120 mb | 9.42 | 1.60 | 3.59E−02 | 1.11E−02 | 2.53 |
| 3G | 0.1% 120 mb | 32.15 | 4.17 | 9.19E−02 | 4.70E−02 | 0.59 |
| 4A | 30% 480 mb | 7.24 | 1.89 | 9.07E−02 | 3.09E−02 | 3.21 |
| 4B | 10% 480 mb | 4.88 | 1.29 | 4.11E−02 | 1.17E−02 | 2.33 |
| 4C | 5% 480 mb | 5.80 | 1.70 | 4.65E−02 | 1.99E−02 | 1.79 |
| 4D | 2.5% 480 mb | 5.61 | 1.48 | 4.89E−02 | 1.63E−02 | 1.68 |
| 4E | 1% 480 mb | 5.25 | 1.65 | 8.22E−02 | 2.58E−02 | 2.18 |
| 4F | 0.5% 480 mb | 8.00 | 1.31 | 2.16E−01 | 6.53E−02 | 1.29 |
| 4G | 0.1% 480 mb | 30.88 | 2.73 | 5.66E−01 | 5.21E−02 | 0.44 |
| 5B | 180 mg/mL Sucrose | 5.59 | 1.71 | 4.41E−03 | 1.03E−02 | 5.51 |
| 5E | 18 mg/mL Sucrose | 7.62 | 1.06 | 7.04E−03 | 8.92E−03 | 10.50 |
| 5G | 1.8 mg/mL Sucrose | 7.38 | 1.61 | 5.75E−03 | 7.31E−03 | 10.01 |
| 6 | 1x PBS | 4.56 | 1.14 | 5.57E−03 | 1.01E−02 | 8.93 |

All formulations were observed to demonstrate increased viscosity relative to the controls with sucrose or PBS (samples 5B-6). The viscosities of commercially available dry eye treatments (Refresh Liquigel, SYSTANE® lubricant eye drops (Alcon), and SYSTANE® lubricant eye gel (Alcon)) were also measured as a point of comparison. In general, the solutions prepared from silk fibroin with the longest boiling time (480 mb) and the shortest boil time (30 mb) were more viscous than the other solutions. At higher concentrations, the silk fibroin with a 480 mb and with a 30 mb demonstrated higher viscosities than the other formulations. When the concentration was below 1% (w/v) silk fibroin, the formulations prepared from silk fibroin with longer boiling times demonstrated higher viscosities. A relationship between the concentration of silk fibroin and the viscosity of the solutions was also observed regardless of the boiling time of the silk fibroin. When the silk fibroin concentration was varied between 1-30% (w/v), the viscosity remained consistent among samples prepared from silk fibroin with the same boiling times. When the silk fibroin concentration was between 0.1-0.5%, the solutions demonstrated an increase in viscosity as compared to their more concentrated counterparts. In addition, the storage modulus was higher for formulations with lower concentrations of silk fibroin, and the phase angle was measured to be lower for formulations with lower concentrations of silk fibroin. All of the formulations shear thinned, demonstrating lower viscosities at higher shear rates.

To prepare the solutions for rheological analysis, frozen silk fibroin solutions were thawed at room temperature and gently mixed before use. A borate buffer was prepared at 5× the final desired concentration by dissolving 1500 mg of boric acid, 213 mg of sodium borate decahydrate, 350 mg of potassium chloride, 850 mg of sodium chloride, 32 mg of magnesium chloride hexahydrate, and 20 mg of calcium chloride in DI water to reach 50 mL final. Each silk fibroin solution, after thawing, was diluted with DI water and this 5× borate buffer to reach 1% silk fibroin (w/v) final in 1× borate buffer (which indicates 6 mg/mL boric acid, 0.852 mg/mL sodium borate decahydrate, 1.4 mg/mL potassium chloride, 3.4 mg/mL sodium chloride, 0.128 mg/mL magnesium chloride hexahydrate, and 0.08 mg/mL calcium chloride dihydrate.) Rheological measurements were performed on a Bohlin C-VOR 150 with a 4° C./40 mm cone and plate geometry with a 0.15 mm gap. 1.2 mL of each sample were pipetted onto a Peltier plate system that maintained a steady temperature of 25° C. throughout the test. One test was then run. The test comprised of a pre-shear of 1 1/s for 20s followed by a shear rate hold at 1 1/s for 90 s, with 30 readings taken. The data was then analyzed to determine the average viscosity. The results of the rheology measurements are listed in Table 17.

TABLE 17

Rheology measurements of silk fibroin solution formulations

| Lot # | Average Viscosity at 1 1/s (cP) | Std. Dev. Of Viscosity at 1 1/s (cP) |
|---|---|---|
| 111.2 | 30.89 | 5.03 |
| 111.4 | 39.00 | 6.11 |
| 111.6 | 76.21 | 6.31 |
| 111.8 | 97.66 | 14.15 |
| 108A.2 | — | — |
| 108A.4 | — | — |
| 108A.6 | — | — |
| 108A.8 | 15.22 | 4.01 |
| 108B.2 | — | — |
| 108B.4 | — | — |
| 108B.6 | — | — |
| 108B.8 | 53.41 | 4.41 |
| 108C.2 | 12.54 | 3.12 |
| 108C.4 | 23.90 | 3.54 |
| 108C.6 | 54.18 | 5.58 |
| 108C.8 | 74.70 | 5.99 |
| 109A.2 | — | — |
| 109A.4 | — | — |
| 109A.6 | — | — |
| 109A.8 | 43.38 | 6.58 |
| 109B.2 | 27.46 | 8.29 |
| 109B.4 | 25.68 | 6.41 |
| 109B.6 | 82.10 | 4.84 |
| 109B.8 | 104.60 | 11.71 |
| 109C.2 | 17.12 | 3.91 |
| 109C.4 | 49.41 | 4.55 |
| 109C.6 | 106.95 | 10.12 |
| 109C.8 | 142.48 | 10.65 |
| 110A.2 | 18.16 | 3.97 |
| 110A.4 | 42.74 | 5.62 |
| 110A.6 | 78.72 | 5.98 |
| 110A.8 | 128.03 | 6.75 |
| 110B.2 | 41.37 | 5.20 |
| 110B.4 | 89.69 | 5.75 |
| 110B.6 | 178.79 | 4.62 |
| 110B.8 | — | — |
| 110C.2 | 99.74 | 4.36 |
| 110C.4 | 140.56 | 10.33 |
| 110C.6 | — | — |
| 110C.8 | — | — |

The viscosity of silk fibroin solutions increased with decreasing molecular weight. This was observed within the same conditions (sodium carbonate concentration and temperature) over the degumming timecourse. As time increased and molecular weight decreased, viscosity increased. Overall, silk fibroin solutions fell into three ranges. Solutions with average molecular weight ≤34.04 kDa displayed the highest viscosity that ranged from 78.72 to 178.79 centipoise (cPs). Silk fibroin solutions with average molecular weights that ranged from 35.47 to 60.74 kDa showed slightly lower viscosities which ranged from 39.00 to 82.10 cPs. The lowest viscosity was observed in the solutions with the highest average molecular weights of 64.36 to 122.52 kDa. These solutions displayed viscosities of 12.54 to 30.89 cPs. This effect of lower viscosity silk fibroin solutions which displayed higher viscosity is most likely due to the interfacial partitioning of silk fibroin to the air water interface. The lower molecular weight silk fibroin proteins most likely organize at the air-water interface more efficiently allowing for higher local concentrations and increased local viscosity.

Example 9. Rheological Measurements of Silk Solutions with Lyophilized or Freeze-Thaw Silk Fibroin Rheological measurements were performed on a Bohlin C-VOR 150 with a 4°/40 mm cone and plate geometry with a 0.15 mm gap. 1.2 ml of each sample were pipetted onto a Peltier plate system that maintained a steady temperature of 25° C. throughout the test. Three tests were then run. The first test comprised a strain sweep from 0.1% to 10% strain at 1 Hz over the course of 130 seconds(s), with 40 readings taken. This was to determine the linear viscoelastic region (LVR) of each sample. The second test comprised a strain hold at 5% (or 1% if the LVR was smaller) and 1 Hz for 160 s, with 12 readings taken. The third test comprised a shear rate hold at 1 1/s for 30 s, with 30 readings taken, followed by a hold at 10 1/s for 30 s, with 30 readings taken. The data was then analyzed to determine the average shear storage modulus (the elastic modulus (G')), shear loss modulus (the viscous modulus (G"), phase angle, and viscosity at shear rates of 1 1/s and 10 1/s. The results of the rheology measurements are listed in Table 18 and Table 19.

TABLE 18

Rheology measurements of silk fibroin solution formulations with lyophilized or freeze-thaw silk fibroin, and controls

| Sample | Description | Avg. Viscosity at 1 1/s (cP) | Avg. Viscosity at 10 1/s (cP) | Avg. G' (Pa) | Avg. G" (Pa) | Avg. Phase Angle (°) |
|---|---|---|---|---|---|---|
| 1 | 5% 90 mb | 24.21 | 12.23 | 7.89E−02 | 1.79E−01 | 66.03 |
| 2 | 1% 90 mb | 36.63 | 14.35 | 9.42E−02 | 1.52E−01 | 57.61 |
| 3 | 0.5% 90 mb | 65.94 | 19.57 | 1.86E−01 | 2.62E−01 | 54.71 |
| 4 | 0.1% 90 mb | 565.71 | 136.56 | 2.75E+00 | 1.02E+00 | 21.18 |
| 5 | 0.05% 90 mb | 492.38 | 79.65 | 9.81E+00 | 2.62E+00 | 15.21 |
| 6 | 5% 120 mb | 36.63 | 10.35 | 1.69E−01 | 3.04E−01 | 61.01 |
| 7 | 1% 120 mb | 23.09 | 10.90 | 4.52E−02 | 9.52E−02 | 64.35 |
| 8 | 0.5% 120 mb | 50.90 | 16.62 | 1.08E−01 | 1.72E−01 | 57.92 |
| 9 | 0.1% 120 mb | 302.36 | 43.97 | 1.98E+00 | 1.21E+00 | 31.59 |
| 10 | 0.05% 120 mb | 145.83 | 29.29 | 3.79E+00 | 1.25E+00 | 18.32 |
| 11 | 5% 480 mb | 54.85 | 16.64 | 1.95E−01 | 2.44E−01 | 51.50 |
| 12 | 1% 480 mb | 129.58 | 26.62 | 9.48E−01 | 9.51E−01 | 45.37 |
| 13 | 0.5% 480 mb | 117.32 | 21.45 | 8.24E−01 | 7.93E−01 | 44.19 |
| 14 | 0.1% 480 mb | 111.52 | 23.66 | 9.07E−01 | 6.55E−01 | 36.39 |
| 15 | 0.05% 480 mb | 120.76 | 35.64 | 1.17E+00 | 5.39E−01 | 26.95 |
| 16 | 5% 480 mb Lyo | 74.02 | 20.63 | 3.51E−01 | 3.66E−01 | 46.41 |
| 17 | 1% 480 mb Lyo | 155.43 | 29.82 | 9.23E−01 | 8.88E−01 | 44.04 |
| 18 | 0.5% 480 mb Lyo | 180.84 | 31.41 | 1.25E+00 | 1.09E+00 | 41.36 |
| 19 | 0.1% 480 mb Lyo | 127.93 | 36.58 | 1.08E+00 | 1.05E+00 | 47.47 |
| 20 | 0.05% 480 mb Lyo | 80.88 | 22.45 | 1.11E+00 | 1.08E+00 | 50.41 |

Table 19 provides the standard deviation of the rheology measurements in Table 18.

TABLE 19

Standard deviations of the rheology measurements of silk fibroin solution formulations and controls

| Sample | Description | Std. Dev. Avg. Viscosity at 1 1/s (cP) | Std. Dev. Avg. Viscosity at 10 1/s (cP) | Std. Dev. Avg. G' (Pa) | Std. Dev. Avg. G" (Pa) | Std. Dev. Avg. Phase Angle (°) |
|---|---|---|---|---|---|---|
| 1 | 5% 90 mb | 5.62 | 0.37 | 3.18E−02 | 8.32E−02 | 1.36 |
| 2 | 1% 90 mb | 12.48 | 2.48 | 5.13E−03 | 4.53E−02 | 6.48 |
| 3 | 0.5% 90 mb | 4.41 | 0.28 | 1.92E−03 | 2.36E−02 | 2.74 |
| 4 | 0.1% 90 mb | 102.17 | 5.17 | 1.15E+00 | 2.43E−01 | 3.80 |
| 5 | 0.05% 90 mb | 390.47 | 49.59 | 4.17E+00 | 9.28E−01 | 1.13 |
| 6 | 5% 120 mb | 8.51 | 0.53 | 2.84E−02 | 4.00E−02 | 0.85 |
| 7 | 1% 120 mb | 6.26 | 0.38 | 1.79E−02 | 6.64E−03 | 6.59 |
| 8 | 0.5% 120 mb | 4.88 | 0.47 | 2.51E−02 | 3.45E−02 | 0.94 |
| 9 | 0.1% 120 mb | 210.48 | 18.49 | 2.20E−01 | 2.42E−02 | 2.17 |
| 10 | 0.05% 120 mb | 113.49 | 18.36 | 1.07E+00 | 3.10E−01 | 0.47 |
| 11 | 5% 480 mb | 4.75 | 0.19 | 1.61E−02 | 1.96E−02 | 0.01 |
| 12 | 1% 480 mb | 21.17 | 3.70 | 1.84E−01 | 1.47E−01 | 1.21 |
| 13 | 0.5% 480 mb | 15.19 | 0.71 | 1.02E−01 | 8.08E−02 | 0.52 |
| 14 | 0.1% 480 mb | 15.68 | 1.88 | 2.03E−01 | 7.53E−02 | 9.20 |
| 15 | 0.05% 480 mb | 93.34 | 29.99 | 6.85E−01 | 1.76E−01 | 7.04 |
| 16 | 5% 480 mb Lyo | 0.44 | 0.12 | 1.97E−02 | 1.98E−03 | 1.73 |
| 17 | 1% 480 mb Lyo | 3.23 | 3.43 | 4.82E−02 | 3.72E−03 | 1.64 |
| 18 | 0.5% 480 mb Lyo | 13.39 | 0.77 | 2.37E−01 | 1.61E−01 | 1.23 |
| 19 | 0.1% 480 mb Lyo | 73.44 | 29.01 | 8.81E−01 | 5.87E−01 | 9.63 |
| 20 | 0.05% 480 mb Lyo | 49.81 | 8.37 | 1.19E+00 | 8.62E−01 | 13.37 |

The solutions prepared from silk fibroin with the longest boiling time (480 mb) were more viscous than solutions prepared with shorter boil times. At higher concentrations (5%, 1%, and 0.5% (w/v), the 480mb silk fibroin solutions demonstrated higher viscosities than the shorter boil time formulations. However, when the concentration of silk fibroin was below 0.5% (w/v), the formulations prepared from shorter boil times demonstrated higher viscosities. A relationship between the concentration of silk fibroin and the viscosity of the solutions was also observed. The general trend showed that the viscosity of the solutions with 5% (w/v) silk fibroin was lower than solutions with 1% (w/v) silk fibroin. At concentrations of 0.1% and 0.05% (w/v) silk fibroin, the viscosities of the 90mb and 120mb samples increased, whereas that of the 480mb samples remained constant. These trends hold for oscillatory properties as well, with the G' and G" values following the viscosity trends. The phase angle displayed lower values with increased viscosity, indicating a more viscous material. The 480mb samples prepared with lyophilized silk fibroin showed slightly lower viscosities at 5%, 1%, and 0.5% (w/v) silk fibroin than the solutions prepared with frozen silk fibroin stock. The lyophilized solution formulations matched the frozen silk fibroin samples at 0.1% and 0.05% (w/v). All of the formulations shear thinned, demonstrating lower viscosities at higher shear rates.

Example 10. Rheological Measurements Regarding the Interfacial Viscosity of Silk Fibroin Solutions The effect of adding a surfactant on the viscosity properties of silk fibroin solution formulations was assessed. Similar to a surfactant, hydrophobic proteins have been shown to migrate to the air-water boundary, resulting in an increase in the local concentration at this interface. This increase in the local concentration of a protein, such as silk fibroin, can lead to an increase in apparent viscosity. This effect is termed "interfacial viscosity." Incorporation of a surfactant, a molecule that can better and more efficiently associate to the air-water interface, will block the hydrophobic protein association and will negate any increase in viscosity due to the protein buildup at the boundary. We assessed the viscosity properties of silk fibroin formulations with and without the presence of a surfactant using a rotational rheometer.

Rheological measurements were performed on a Bohlin C-VOR 150 with a 4°/40 mm cone and plate geometry with a 0.15 mm gap. 1.2 mL of each sample were pipetted onto a Peltier plate system that maintained a steady temperature of 25° C. throughout the test. The test comprised a logarithmic shear rate sweep from 0.01 1/s to 1000 1/s over the course of 606 s with 100 viscosity readings. The test was performed on silk fibroin formulations after their preparation. The formulations tested were prepared using methods described in the previous examples. A standard oil (100 cP) was also evaluated to ensure accuracy of the measurements across this large shear range. The viscosity measurements are listed in Table 20 and Table 21.

TABLE 20

Shear Viscosity of Silk Fibroin Formulations

| Shear Rate (1/s) | 100 cP Oil Std. Viscosity (cP) | 0% SFf; sin; borate buffer Average Viscosity (cP) | 0% SFf; sin; borate buffer; 0.2% T80 Average Viscosity (cP) | 480 mb; 1% SFf; sin; 0.34% Suc; borate buffer Average Viscosity (cP) | 480 mb; 1% SFf; sin; 0.34% Suc; borate buffer; 0.2% T80 Average Viscosity (cP) |
|---|---|---|---|---|---|
| 0.10 | 137.67 | 26.15 | 12.85 | 470.03 | 27.73 |
| 0.11 | 136.36 | 50.98 | 15.89 | 432.36 | 43.58 |
| 0.13 | 125.49 | 29.37 | 6.47 | 404.69 | 44.84 |
| 0.15 | 70.37 | 26.54 | 7.76 | 356.65 | 36.53 |
| 0.16 | 106.89 | 27.47 | 31.77 | 337.79 | 28.39 |
| 0.18 | 106.75 | 18.73 | 9.84 | 316.25 | 23.51 |
| 0.21 | 112.05 | 22.77 | 24.58 | 285.04 | 28.04 |
| 0.23 | 92.07 | 22.73 | 28.37 | 263.86 | 26.75 |
| 0.26 | 105.37 | 21.92 | 18.64 | 239.22 | 25.60 |
| 0.29 | 100.39 | 24.97 | 12.64 | 230.36 | 30.24 |
| 0.33 | 84.72 | 9.69 | 22.31 | 186.51 | 24.47 |
| 0.37 | 83.06 | 20.69 | 23.15 | 180.08 | 14.57 |
| 0.41 | 89.68 | 17.10 | 17.00 | 158.27 | 15.79 |
| 0.46 | 100.45 | 15.32 | 20.27 | 151.15 | 13.29 |
| 0.52 | 87.69 | 38.20 | 24.42 | 128.86 | 16.82 |
| 0.59 | 98.09 | 11.24 | 14.67 | 127.66 | 11.09 |
| 0.66 | 96.52 | 8.89 | 18.03 | 114.52 | 5.56 |
| 0.74 | 97.34 | 11.06 | 12.89 | 106.66 | 11.27 |
| 0.83 | 98.63 | 4.54 | 6.75 | 92.54 | 5.40 |
| 0.93 | 95.38 | 6.67 | 7.43 | 83.53 | 8.81 |
| 1.05 | 101.01 | 6.33 | 4.18 | 78.63 | 7.58 |
| 1.18 | 92.76 | 7.82 | 4.52 | 67.05 | 7.37 |
| 1.32 | 94.63 | 6.73 | 5.97 | 62.58 | 6.30 |
| 1.48 | 99.90 | 6.72 | 5.21 | 59.37 | 8.20 |
| 1.67 | 100.40 | 4.79 | 3.91 | 51.99 | 4.71 |
| 1.87 | 102.84 | 3.86 | 5.53 | 47.74 | 3.83 |
| 2.10 | 91.83 | 4.23 | 6.45 | 39.50 | 3.43 |
| 2.36 | 96.82 | 4.01 | 5.81 | 41.94 | 4.20 |

TABLE 20-continued

Shear Viscosity of Silk Fibroin Formulations

| Shear Rate (1/s) | 100 cP Oil Std. Viscosity (cP) | 0% SFf; sin; borate buffer Average Viscosity (cP) | 0% SFf; sin; borate buffer; 0.2% T80 Average Viscosity (cP) | 480 mb; 1% SFf; sin; 0.34% Suc; borate buffer Average Viscosity (cP) | 480 mb; 1% SFf; sin; 0.34% Suc; borate buffer; 0.2% T80 Average Viscosity (cP) |
|---|---|---|---|---|---|
| 2.66 | 99.03 | 6.72 | 3.93 | 35.41 | 4.89 |
| 2.98 | 94.40 | 5.33 | 3.68 | 35.36 | 3.86 |
| 3.35 | 96.11 | 0.50 | 4.35 | 34.85 | 4.08 |
| 3.76 | 96.71 | 3.55 | 5.41 | 29.08 | 4.23 |
| 4.23 | 97.02 | 2.21 | 4.33 | 27.18 | 4.87 |
| 4.75 | 99.08 | 0.95 | 2.55 | 22.68 | 1.61 |
| 5.33 | 104.28 | 2.95 | 2.14 | 23.08 | 3.29 |
| 5.99 | 107.99 | 25.60 | 26.36 | 41.52 | 25.51 |
| 6.73 | 111.10 | 5.88 | 9.62 | 21.58 | 7.56 |
| 7.56 | 97.59 | 3.23 | 3.80 | 16.63 | 3.21 |
| 8.49 | 99.17 | 2.17 | 1.81 | 18.22 | 5.88 |
| 9.54 | 99.03 | 5.64 | 5.74 | 13.38 | 1.57 |
| 10.72 | 102.48 | 2.78 | 3.99 | 15.76 | 3.10 |
| 12.04 | 61.92 | 142.42 | 7.63 | 3.31 | 22.65 |
| 13.53 | 98.09 | 4.35 | 2.71 | 241.74 | 2.13 |
| 15.19 | 98.74 | 1.85 | 4.38 | 11.42 | 3.33 |
| 17.07 | 99.86 | 2.81 | 4.11 | 10.51 | 3.26 |
| 19.17 | 98.95 | 3.18 | 4.35 | 9.39 | 6.58 |
| 21.54 | 97.41 | 3.18 | 2.96 | 9.97 | 3.74 |
| 24.19 | 104.21 | 6.94 | 6.47 | 11.80 | 1.11 |
| 27.18 | 98.30 | 4.27 | 2.99 | 8.54 | 3.52 |
| 30.53 | 98.69 | 3.65 | 3.59 | 8.52 | 4.35 |
| 34.29 | 98.21 | 3.38 | 4.13 | 8.39 | 3.23 |
| 38.52 | 98.29 | 3.50 | 3.80 | 7.28 | 3.88 |
| 43.27 | 98.38 | 3.22 | 3.45 | 7.08 | 3.25 |
| 48.61 | 97.86 | 3.85 | 3.16 | 6.27 | 3.25 |
| 54.60 | 99.51 | 3.36 | 3.42 | 6.12 | 3.54 |
| 61.34 | 327.32 | 5.99 | 7.34 | 9.85 | 7.05 |
| 68.90 | 123.58 | 29.33 | 8.68 | 10.15 | 7.91 |
| 77.40 | 117.30 | 8.22 | 6.40 | 9.54 | 6.55 |
| 86.94 | 117.13 | 8.21 | 6.74 | 11.35 | 8.58 |
| 97.66 | 112.80 | 7.91 | 8.28 | 10.49 | 6.77 |
| 109.71 | 110.36 | 7.44 | 7.57 | 10.42 | 8.22 |
| 123.22 | 106.51 | 7.15 | 8.42 | 10.83 | 8.44 |
| 138.43 | 105.91 | 7.45 | 7.74 | 9.62 | 8.33 |
| 155.50 | 103.33 | 7.24 | 6.80 | 6.40 | 7.41 |
| 174.68 | 102.19 | 7.60 | 8.91 | 9.05 | 8.01 |
| 196.24 | 101.06 | 8.03 | 8.25 | 9.54 | 8.32 |
| 220.42 | 100.93 | 7.96 | 8.04 | 9.17 | 8.11 |
| 247.61 | 99.67 | 7.64 | 7.83 | 9.02 | 8.09 |
| 278.14 | 92.73 | 10.03 | 11.21 | 12.20 | 13.06 |
| 312.44 | 22.66 | 20.41 | 20.35 | 12.57 | 45.20 |
| 350.98 | 105.62 | 17.09 | 18.27 | 8.17 | 9.58 |
| 394.29 | 99.61 | 7.23 | 12.32 | 17.93 | 11.21 |
| 443.08 | 92.48 | 28.72 | 21.22 | 10.89 | 5.05 |
| 497.49 | 92.60 | 9.49 | 23.01 | 16.97 | 21.32 |
| 558.85 | 99.96 | 17.15 | 24.88 | 4.26 | 29.54 |
| 627.73 | 95.56 | 21.40 | 18.93 | 32.16 | 11.94 |
| 705.17 | 85.14 | 1.67 | 8.02 | 6.44 | 5.21 |
| 792.18 | 95.23 | 3.81 | 3.77 | 6.85 | 1.22 |
| 889.90 | 88.54 | 4.51 | 5.69 | 11.00 | 9.08 |
| 999.53 | 91.39 | 11.65 | 6.41 | 12.41 | 11.06 |

TABLE 21

| Standard Deviation of Shear Viscosity of Silk Fibroin Formulations | | | | |
|---|---|---|---|---|
| Shear Rate (1/s) | 0% SFf; sin; borate buffer Standard Deviation (cP) | 0% SFf; sin; borate buffer; 0.2% T80 Standard Deviation (cP) | 480 mb; 1% SFf; sin; 0.34% Suc; borate buffer Standard Deviation (cP) | 480 mb; 1% SFf; sin; 0.34% Suc; borate buffer; 0.2% T80 Standard Deviation (cP) |
| 0.10 | 183.21 | 259.48 | 370.04 | 121.43 |
| 0.11 | 113.76 | 28.46 | 397.78 | 379.43 |
| 0.13 | 48.59 | 117.59 | 345.17 | 153.38 |
| 0.15 | 172.35 | 239.23 | 250.15 | 130.21 |
| 0.16 | 274.44 | 79.64 | 356.87 | 269.20 |
| 0.18 | 108.99 | 79.30 | 211.10 | 131.32 |
| 0.21 | 62.00 | 102.73 | 137.40 | 150.49 |
| 0.23 | 174.88 | 59.71 | 246.07 | 212.97 |
| 0.26 | 41.72 | 88.83 | 155.11 | 82.60 |
| 0.29 | 33.42 | 66.11 | 137.49 | 264.30 |
| 0.33 | 44.47 | 14.79 | 164.96 | 30.89 |
| 0.37 | 28.32 | 39.87 | 208.57 | 39.79 |
| 0.41 | 84.89 | 61.00 | 162.86 | 87.22 |
| 0.46 | 61.60 | 33.17 | 119.86 | 12.43 |
| 0.52 | 74.92 | 20.12 | 117.38 | 23.07 |
| 0.59 | 46.31 | 6.54 | 92.01 | 95.79 |
| 0.66 | 12.20 | 18.90 | 101.13 | 49.55 |
| 0.74 | 23.71 | 15.03 | 77.60 | 11.40 |
| 0.83 | 22.47 | 40.76 | 70.79 | 40.35 |
| 0.93 | 14.94 | 23.77 | 40.81 | 24.14 |
| 1.05 | 15.01 | 7.93 | 75.35 | 20.04 |
| 1.18 | 6.46 | 7.53 | 37.63 | 40.49 |
| 1.32 | 24.69 | 3.23 | 59.65 | 36.10 |
| 1.48 | 5.95 | 5.47 | 39.75 | 22.63 |
| 1.67 | 10.29 | 17.84 | 39.72 | 14.55 |
| 1.87 | 17.73 | 9.92 | 32.55 | 14.91 |
| 2.10 | 10.80 | 18.38 | 26.43 | 7.00 |
| 2.36 | 10.97 | 5.47 | 27.16 | 19.05 |
| 2.66 | 8.06 | 7.19 | 15.91 | 8.66 |
| 2.98 | 4.69 | 11.54 | 8.37 | 6.22 |
| 3.35 | 10.58 | 12.60 | 17.45 | 0.82 |
| 3.76 | 10.44 | 5.84 | 7.57 | 8.83 |
| 4.23 | 12.37 | 8.87 | 5.75 | 7.85 |
| 4.75 | 5.90 | 9.31 | 7.37 | 4.44 |
| 5.33 | 1.61 | 11.87 | 17.69 | 5.67 |
| 5.99 | 2.31 | 7.17 | 6.03 | 4.25 |
| 6.73 | 5.34 | 8.04 | 3.08 | 1.72 |
| 7.56 | 7.60 | 1.76 | 9.48 | 2.28 |
| 8.49 | 1.49 | 5.16 | 6.15 | 6.15 |
| 9.54 | 4.67 | 2.76 | 5.88 | 1.95 |
| 10.72 | 5.77 | 3.23 | 1.84 | 2.55 |
| 12.04 | 4.66 | 2.09 | 2.04 | 2.11 |
| 13.53 | 1.37 | 1.29 | 2.55 | 1.63 |
| 15.19 | 2.98 | 3.42 | 5.36 | 2.47 |
| 17.07 | 1.72 | 2.94 | 4.59 | 2.52 |
| 19.17 | 2.58 | 1.77 | 5.3 | 4.18 |
| 21.54 | 1.80 | 1.58 | 6.85 | 3.32 |
| 24.19 | 0.80 | 1.48 | 4.69 | 1.72 |
| 27.18 | 2.55 | 1.89 | 5.21 | 1.48 |
| 30.53 | 1.90 | 0.58 | 4.83 | 2.71 |
| 34.29 | 0.43 | 2.07 | 2.32 | 1.85 |
| 38.52 | 0.70 | 0.67 | 0.98 | 0.82 |
| 43.27 | 1.10 | 2.68 | 5.94 | 1.81 |
| 48.61 | 1.07 | 0.63 | 2.43 | 1.25 |
| 54.60 | 2.98 | 2.07 | 1.49 | 3.06 |
| 61.34 | 4.46 | 8.70 | 6.58 | 5.84 |
| 68.90 | 5.94 | 3.88 | 3.98 | 2.44 |
| 77.40 | 2.75 | 2.41 | 4.45 | 0.96 |
| 86.94 | 1.25 | 0.49 | 2.28 | 0.79 |
| 97.66 | 2.37 | 4.26 | 2.66 | 0.57 |
| 109.71 | 3.43 | 3.01 | 3.25 | 1.72 |
| 123.22 | 232.03 | 2.38 | 3.76 | 17.99 |
| 138.43 | 3.46 | 1.59 | 391.52 | 1.72 |
| 155.50 | 2.03 | 0.43 | 0.47 | 0.45 |
| 174.68 | 0.15 | 0.55 | 0.38 | 0.98 |
| 196.24 | 1.13 | 1.23 | 0.63 | 5.03 |
| 220.42 | 1.17 | 0.38 | 1.10 | 0.31 |
| 247.61 | 3.81 | 3.80 | 4.33 | 1.79 |
| 278.14 | 1.05 | 0.43 | 1.08 | 0.59 |

TABLE 21-continued

| Standard Deviation of Shear Viscosity of Silk Fibroin Formulations | | | | |
|---|---|---|---|---|
| Shear Rate (1/s) | 0% SFf; sin; borate buffer Standard Deviation (cP) | 0% SFf; sin; borate buffer; 0.2% T80 Standard Deviation (cP) | 480 mb; 1% SFf; sin; 0.34% Suc; borate buffer Standard Deviation (cP) | 480 mb; 1% SFf; sin; 0.34% Suc; borate buffer; 0.2% T80 Standard Deviation (cP) |
| 312.44 | 0.32 | 0.08 | 0.55 | 0.75 |
| 350.98 | 0.39 | 0.35 | 0.68 | 0.60 |
| 394.29 | 0.14 | 0.83 | 1.29 | 0.21 |
| 443.08 | 0.23 | 0.41 | 0.92 | 0.71 |
| 497.49 | 1.07 | 0.18 | 1.42 | 0.87 |
| 558.85 | 0.31 | 0.26 | 0.74 | 0.28 |
| 627.73 | 2.30 | 0.40 | 0.93 | 1.17 |
| 705.17 | 40.59 | 0.89 | 1.09 | 1.04 |
| 792.18 | 1.24 | 1.04 | 0.91 | 1.30 |
| 889.90 | 1.61 | 0.20 | 1.74 | 0.69 |
| 999.53 | 1.22 | 1.43 | 0.53 | 0.49 |

The results displayed that silk fibroin formulations without surfactant display shear thinning, reaching viscosities of 470 cP at 0.1 1/s which is reduced to 79 cP at 1 1/s and 13 cP at 10 1/s. When shear rate was increased above 50 cP, the silk fibroin formulation with no surfactant showed viscosity similar to buffer controls (no silk fibroin). When surfactant was added to the silk fibroin formulation, it displayed the same shear viscosity profile as the buffer controls across the entire range of shear rates. Viscosity reached a maximum of 45 cP at a shear rate of 0.13 1/s, which fell below 10 cP at shear rates of 0.6 1/s and above. The controls (+/−polysorbate 80) showed the same trends in viscosity over the shear range tested. This increase in viscosity of silk fibroin formulations that was reduced with the addition of a surfactant (polysorbate 80) indicated that silk fibroin in solution possesses interfacial properties that lead to an increase in apparent viscosity.

Example 11. Rheological Measurements of Silk Fibroin Solutions Using Capillary Rheology Capillary rheology was utilized to further understand the interfacial viscosity rheology effects of silk fibroin in solution. Unlike the rotational rheometer, a capillary rheometer has a very low air-water interface. This will greatly reduce if not eliminate interfacial viscosity effects that are observed using other rheologic methods (cone and plate rotational rheology). Samples were evaluated using two tests. First, samples were evaluated using a VROC® microVISC™ capillary viscometer (Rheosense) at 25° C. at 500 1/s shear rate. Samples were then measured on the VROC® Initium automated viscometer (Rheosense) using the B05 chip. Aliquots of 40 μL for each sample were loaded into inserts and then, using a benchtop centrifuge, they were centrifuged at 8000 rpm for 20 seconds to remove any bubbles. The inserts with the sample volume were then placed in capped vials and loaded onto the Initium sample tray. The software was then programmed to run a shear rate sweep with 5 segments for each sample. The shear rates selected for each sample were determined by logic in the Initium software (3808, 4760, 6427, 16150, and 19040 1/s). All measurements were taken at 25° C. Each viscosity value reported is the average of 10 repeat measurements. The formulations were prepared as described in the previous examples, such as Example 6.

Results showed that silk fibroin solution formulations and buffer controls, in the presence or absence of a surfactant, displayed Newtonian viscosity at shear rates from 500 1/s to 19040 1/s. Borate buffer displayed viscosity that ranged from 0.910 cP to 1.00 cP over this range. The addition of polysorbate 80 to this buffer slightly increased the viscosity (0.931-1.07 cP). The silk fibroin formulations displayed higher viscosity than the buffer controls with the same trends. Silk fibroin without surfactant had a slightly lower viscosity over this shear range than the formulation containing polysorbate 80. Silk fibroin formulations displayed viscosities of 1.05 cP-1.19 cP while the addition of surfactant very slightly increased the viscosity to 1.06 cP-1.31 cP over the same shear range (Table 22 and Table 23).

TABLE 22

Capillary Viscosity of Silk Fibroin Formulations

| Temperature (° C.) | Shear Rate (1/s) | 0% SFf; sin; borate buffer Average Viscosity (cP) | 0% SFf; sin; borate buffer; 0.2% T80 Average Viscosity (cP) | 480 mb; 1% SFf; sin; 0.34% Suc; borate buffer Average Viscosity (cP) | 480 mb; 1% SFf; sin; 0.34% Suc; borate buffer; 0.2% T80 Average Viscosity (cP) |
|---|---|---|---|---|---|
| 25 | 500 | 1.00 | 1.07 | 1.18 | 1.31 |
| 25 | 3808 | 0.92 | 0.93 | 1.05 | 1.07 |
| 25 | 4759 | 0.92 | 0.94 | 1.06 | 1.07 |
| 25 | 6466 | 0.91 | 0.94 | 1.05 | 1.06 |
| 25 | 10310 | 0.91 | 0.94 | 1.05 | 1.07 |
| 25 | 19040 | 0.92 | 0.93 | 1.05 | 1.06 |

TABLE 23

Standard Deviation of Capillary Viscosity of Silk Fibroin Formulations

| Temperature (° C.) | Shear Rate (1/s) | 0% SFf; sin; borate buffer Standard Deviation | 0% SFf; sin; borate buffer; 0.2%T80 Standard Deviation | 480 mb; 1% SFf; sin; 0.34% Suc; borate buffer Standard Deviation | 480 mb; 1% SFf; sin; 0.34% Suc; borate buffer; 0.2% T80 Standard Deviation |
|---|---|---|---|---|---|
| 25 | 500 | 0.006 | 0.003 | 0.004 | 0.006 |
| 25 | 3808 | 0.005 | 0.004 | 0.004 | 0.003 |
| 25 | 4759 | 0.006 | 0.003 | 0.002 | 0.004 |
| 25 | 6466 | 0.007 | 0.006 | 0.004 | 0.007 |
| 25 | 10310 | 0.000 | 0.000 | 0.000 | 0.000 |
| 25 | 19040 | 0.001 | 0.001 | 0.004 | 0.003 |

The capillary rheology data is similar to the rotational data at these shear rates greater than or equal to 500 1/s for all of the formulations.

Example 12. Rheological Measurements of Stressed Silk Solutions

Formulations were prepared by dissolving lyophilized silk fibroin, which had been lyophilized in phosphate buffer, into phosphate buffered saline. Rheological measurements were performed on a Bohlin C-VOR 150 with a 4°/40 mm cone and plate geometry with a 0.5 mm gap. 1.4 mL of each sample were pipetted onto a Peltier plate system that maintained a steady temperature of 25° C. throughout the test. Five tests were then run. The first test comprised a strain sweep from 0.1% to 10% strain at 1 Hz over the course of 160 s, with 50 readings taken. This was to determine the linear viscoelastic region (LVR) of each sample. The second test comprised a strain hold at 5% (or 1% if the LVR was smaller) and 1 Hz for 145 s, with 15 readings taken. The third test comprised a shear rate sweep from 0.1 1/s to 10 1/s over the course of 100 s, followed by a hold at 10 1/s for 20 s. 70 readings were taken. Fourth, a shear rate hold was conducted at 1 1/s for 135 s, with 15 readings taken. Lastly, a shear ramp was conducted from 0.01 1/s to 1 1/s over 140s with 20 readings. The data was then analyzed to determine the average shear storage modulus (G'), shear loss modulus (G"), phase angle, and viscosity at shear rates of 0.1 1/s, 1 1/s, and 10 1/s. The experiments were performed on silk fibroin formulations after their preparation. The formulations were then stressed by incubation at 60° C. overnight, and the samples that did not gel were tested again. The formulations were then stressed by autoclave and the samples that did not gel were tested for a third time. The formulations were stressed to simulate a long shelf-life and terminal sterilization, and to see if the protein maintained rheological integrity. The formulations tested were described in Table 24, and the rheological measurements were listed in Table 25 and Table 26. The samples in the tables are named by the process used to prepare and formulate each solution. For example, in the sample named "480mb; sln; 1% SFf; 60° C.; Auto" the "480mb" refers to the silk degummed with a 480-minute boil, "sln" refers to the formulation of the sample as a solution, "1% SFf" refers to a formulation with 1% (w/v) silk fibroin, "60° C." refers to a preparation stressed by incubation at 60° C. overnight, and "Auto" refers to a preparation stressed by incubation at 60° C. overnight followed by autoclave. Table 24 provides characteristics of the formulations containing stressed silk fibroin.

TABLE 24

Silk solution formulations with stressed silk fibroin

| Sample | Description | Stress Condition | 480 mb Silk % (w/v) | Sample Name |
|---|---|---|---|---|
| — | REFRESH LIQUIGEL ® lubricant eye gel (Allergan) | None | 0 | REFRESH LIQUIGEL ® lubricant eye gel (Allergan) |
| — | SYSTANE ® lubricant eye drop (Alcon) | None | 0 | SYSTANE ® lubricant eye drop (Alcon) |
| | SYSTANE ® lubricant eye gel (Alcon) | None | 0 | SYSTANE ® lubricant eye gel (Alcon) |
| 1 | 10% Unstressed | None | 10 | 480 mb; sin; 10% SFf |
| 2 | 5% Unstressed | None | 5 | 480 mb; sin; 5% SFf |
| 3 | 1% Unstressed | None | 1 | 480 mb; sin; 1% SFf |
| 4 | 0.5% Unstressed | None | 0.5 | 480 mb; sin; 0.5% SFf |
| 5 | 0.1% Unstressed | None | 0.1 | 480 mb; sin; 0.1% SFf |
| 6 | 0.05% Unstressed | None | 0.05 | 480 mb; sin; 0.05% SFf |
| 7 | 0.01% Unstressed | None | 0.01 | 480 mb; sin; 0.01% SFf |
| 8 | 0.005% Unstressed | None | 0.005 | 480 mb; sin; 0.005% SFf |
| 9 | 1x PBS | None | 0 | PBS Control |
| — | REFRESH LIQUIGEL ® lubricant | 60° C. Overnight | 0 | REFRESH LIQUIGEL ® lubricant |

TABLE 24-continued

| Silk solution formulations with stressed silk fibroin | | | | |
|---|---|---|---|---|
| Sample | Description | Stress Condition | 480 mb Silk % (w/v) | Sample Name |
| | eye gel (Allergan) 60° C. | | | eye gel (Allergan) 60° C. |
| — | SYSTANE ® lubricant eye drop (Alcon) 60° C. | 60° C. Overnight | 0 | SYSTANE ® lubricant eye drop (Alcon) 60° C. |
| — | SYSTANE ® lubricant eye gel (Alcon) 60° C. | 60° C. Overnight | 0 | SYSTANE ® lubricant eye gel (Alcon) 60° C. |
| 10 | 10% 60° C. | 60° C. Overnight | 10 | 480 mb; sin; 10% SFf; 60° C. |
| 11 | 5% 60° C. | 60° C. Overnight | 5 | 480 mb; sin; 5% SFf; 60° C. |
| 12 | 1% 60° C. | 60° C. Overnight | 1 | 480 mb; sin; 1% SFf; 60° C. |
| 13 | 0.5% 60° C. | 60° C. Overnight | 0.5 | 480 mb; sin; 0.5% SFf; 60° C. |
| 14 | 0.1% ° C. | 60° C. Overnight | 0.1 | 480 mb; sin; 0.1% SFf; 60° C. |
| 15 | 0.05% 60° C. | 60° C. Overnight | 0.05 | 480 mb; sin; 0.05% SFf; 60° C. |
| 16 | 0.01% 60° C. | 60° C. Overnight | 0.01 | 480 mb; sin; 0.01% SFf; 60° C. |
| 17 | 0.005% 60° C. | 60° C. Overnight | 0.005 | 480 mb; sin; 0.005% SFf; 60° C. |
| 18 | 1x PBS 60° C. | 60° C. Overnight | 0 | PBS control; 60° C. |
| 19 | 1% Autoclave | 60° C. and Autoclave | 1 | 480 mb; sin; 1% SFf; 60° C.; Auto |
| 20 | 0.5% Autoclave | 60° C. and Autoclave | 0.5 | 480 mb; sin; 0.5% SFf; 60° C.; Auto |
| 21 | 0.1% Autoclave | 60° C. and Autoclave | 0.1 | 480 mb; sin; 0.1% SFf; 60° C.; Auto |
| 22 | 0.05% Autoclave | 60° C. and Autoclave | 0.05 | 480 mb; sin; 0.05% SFf; 60° C.; Auto |
| 23 | 0.01% Autoclave | 60° C. and Autoclave | 0.01 | 480 mb; sin; 0.01% SFf; 60° C.; Auto |
| 24 | 0.005% Autoclave | 60° C. and Autoclave | 0.005 | 480 mb; sin; 0.005% SFf; 60° C.; Auto |
| 25 | 1x PBS A utoclave | 60° C. and Autoclave | 0 | PBS control; 60° C.; Auto |

Table 25 provides rheological data for the formulations described in Table 24.

TABLE 25

| Rheological measurements of silk solutions with stressed silk fibroin | | | | | | | |
|---|---|---|---|---|---|---|---|
| Sample | Description | Avg. Viscosity at 0.01 1/s (cP) | Avg. Viscosity at 1 1/s (cP) | Avg. Viscosity at 10 1/s (cP) | Avg. G' (Pa) | Avg. G" (Pa) | Avg. Phase Angle (°) |
| — | REFRESH LIQUIGEL ® lubricant eye gel (Allergan) | — | 79.90 | 46.29 | 0.17 | 0.35 | 64.05 |
| — | SYSTANE ® lubricant eye drop (Alcon) | — | 20.2.3 | 12.06 | 0.02 | 0.08 | 75.44 |
| | SYSTANE ® lubricant eye gel (Alcon) | — | 1073.57 | 549.81 | 2.20 | 3.03 | 53.98 |
| 1 | 10% Unstressed | 483.28 | 61.29 | 13.90 | 0.18 | 0.19 | 46.54 |
| 2 | 5% Unstressed | 1241.98 | 77.42 | 15.54 | 0.33 | 0.25 | 37.93 |
| 3 | 1% Unstressed | 1211.40 | 152.93 | 24.45 | 0.82 | 0.59 | 36.14 |
| 4 | 0.5% Unstressed | 3168.00 | 164.13 | 23.96 | 0.87 | 0.58 | 34.04 |
| 5 | 0.1% Unstressed | 62996.50 | 848.57 | 71.80 | 6.80 | 2.17 | 17.65 |
| 6 | 0.05% Unstressed | 78834.00 | 1012.95 | 73.62 | 9.55 | 2.21 | 13.07 |
| 7 | 0.01% Unstressed | 42258.50 | 279.10 | 25.40 | 9.80 | 2.00 | 11.63 |
| 8 | 0.005% Unstressed | 13412.20 | 141.06 | 21.93 | 8.61 | 1.58 | 10.48 |
| 9 | 1x PBS | 448.98 | 10.33 | 2.90 | 0.01 | 0.04 | 68.70 |
| — | REFRESH LIQUIGEL ® lubricant eye gel (Allergan) 60° C. | 752.92 | 40.80 | 32.99 | 0.03 | 0.21 | 80.72 |
| — | SYSTANE ® lubricant eye drop (Alcon)60° C. | 1581.90 | 16.88 | 10.60 | 0.03 | 0.07 | 70.70 |
| — | SYSTANE ® lubricant eye gel (Alcon)60° C. | 3035.00 | 926.24 | 501.00 | 1.89 | 2.80 | 56.00 |
| 10 | 10% 60° C. | 1586.30 | 62.18 | 13.58 | 0.22 | 0.22 | 45.50 |
| 11 | 5% 60° C. | 1783.60 | 62.33 | 12.19 | 0.25 | 0.21 | 41.18 |
| 12 | 1% 60° C. | 2922.10 | 139.74 | 22.57 | 0.74 | 0.54 | 36.53 |
| 13 | 0.5% 60° C. | 3902.25 | 143.14 | 22.19 | 0.73 | 0.53 | 35.88 |
| 14 | 0.1% 60° C. | 16141.50 | 250.78 | 33.08 | 3.32 | 1.17 | 19.61 |
| 15 | 0.05% 60° C. | 30653.00 | 206.13 | 23.65 | 6.22 | 1.47 | 13.47 |
| 16 | 0.01% 60° C. | 27437.00 | 120.19 | 13.38 | 6.49 | 1.33 | 11.62 |
| 17 | 0.005% 60° C. | 27917.00 | 149.65 | 19.14 | 8.77 | 1.49 | 9.70 |

TABLE 25-continued

| Rheological measurements of silk solutions with stressed silk fibroin | | | | | | | |
|---|---|---|---|---|---|---|---|
| Sample | Description | Avg. Viscosity at 0.01 1/s (cP) | Avg. Viscosity at 1 1/s (cP) | Avg. Viscosity at 10 1/s (cP) | Avg. G' (Pa) | Avg. G'' (Pa) | Avg. Phase Angle (°) |
| 18 | 1x PBS 60° C. | 109.72 | 9.85 | 2.82 | 0.03 | 0.03 | 42.80 |
| 19 | 1% Autoclave | 4274.55 | 141.91 | 21.93 | 0.91 | 0.57 | 32.09 |
| 20 | 0.5% Autoclave | 5146.85 | 150.73 | 23.07 | 1.12 | 0.62 | 29.17 |
| 21 | 0.1% Autoclave | 6566.45 | 110.14 | 14.90 | 1.59 | 0.56 | 20.14 |
| 22 | 0.05% Autoclave | 9674.40 | 182.30 | 24.15 | 4.83 | 1.33 | 15.09 |
| 23 | 0.01% Autoclave | 19294.50 | 113.32 | 11.52 | 4.48 | 0.75 | 9.50 |
| 24 | 0.005% Autoclave | 707.12 | 7.10 | 3.51 | 0.05 | 0.03 | 37.33 |
| 25 | 1x PBS Autoclave | 2833.30 | 83.75 | 14.97 | 0.44 | 0.33 | 36.70 |

Table 26 provides the standard deviations for the rheological measurements described in Table 25.

TABLE 26

| Standard deviations of the rheological measurements of silk solutions with stressed silk fibroin | | | | | | | |
|---|---|---|---|---|---|---|---|
| Sample | Description | Std. Dev. Avg. Viscosity at 0.01 1/s (cP) | Std. Dev. Avg. Viscosity at 1 1/s (cP) | Std. Dev. Avg. Viscosity at 10 1/s (cP) | Std. Dev. Avg. G' (Pa) | Std. Dev. Avg. G'' (Pa) | Std. Dev. Avg. Phase Angle (°) |
| — | REFRESH LIQUIGEL ® lubricant eye gel (Allergan) | — | 6.07 | 6.84 | 0.01 | 0.01 | 1.81 |
| — | SYSTANE ® lubricant eye drop (Alcon) | — | 7.60 | 6.33 | 0.01 | 0.01 | 5.24 |
| | SYSTANE ® lubricant eye gel (Alcon) | — | 7.08 | 5.45 | 0.01 | 0.02 | 0.11 |
| 1 | 10% Unstressed | 0.00 | 5.11 | 0.64 | 0.02 | 0.02 | 5.94 |
| 2 | 5% Unstressed | 1494.72 | 8.11 | 2.23 | 0.09 | 0.04 | 3.45 |
| 3 | 1% Unstressed | 122.90 | 4.47 | 1.07 | 0.11 | 0.00 | 3.52 |
| 4 | 0.5% Unstressed | 561.44 | 9.15 | 0.43 | 0.07 | 0.05 | 0.08 |
| 5 | 0.1% Unstressed | 19771.41 | 7.32 | 14.43 | 0.22 | 0.29 | 1.71 |
| 6 | 0.05% Unstressed | 5313.20 | 174.63 | 19.72 | 0.67 | 0.20 | 0.26 |
| 7 | 0.01% Unstressed | 16087.39 | 130.05 | 17.16 | 0.35 | 0.03 | 0.30 |
| 8 | 0.005% Unstressed | 14438.84 | 20.29 | 7.83 | 1.15 | 0.18 | 0.24 |
| 9 | 1x PBS | 0.00 | 3.78 | 1.99 | 0.01 | 0.01 | 12.65 |
| — | REFRESH LIQUIGEL ® lubricant eye gel (Allergan) 60° C. | 0.00 | 5.41 | 1.50 | 0.01 | 0.01 | 2.03 |
| — | SYSTANE ® lubricant eye drop (Alcon)60° C. | 0.00 | 4.63 | 1.96 | 0.01 | 0.01 | 6.10 |
| — | SYSTANE ® lubricant eye gel (Alcon)60° C. | 0.00 | 6.00 | 1.30 | 0.01 | 0.01 | 0.14 |
| 10 | 10% 60° C. | 155.14 | 2.05 | 0.34 | 0.04 | 0.02 | 2.51 |
| 11 | 5% 60° C. | 192.33 | 17.86 | 3.46 | 0.09 | 0.07 | 0.77 |
| 12 | 1% 60° C. | 491.86 | 7.55 | 0.02 | 0.04 | 0.01 | 2.09 |
| 13 | 0.5% 60° C. | 535.77 | 1.70 | 0.52 | 0.03 | 0.03 | 0.41 |
| 14 | 0.1% 60° C. | 2926.71 | 16.47 | 2.71 | 0.50 | 0.16 | 0.31 |
| 15 | 0.05% 60° C. | 15813.74 | 47.39 | 8.45 | 1.12 | 0.11 | 1.34 |
| 16 | 0.01% 60° C. | 20776.21 | 18.64 | 2.47 | 2.82 | 0.59 | 0.03 |
| 17 | 0.005% 60° C. | 7448.66 | 63.16 | 6.20 | 0.75 | 0.06 | 0.42 |
| 18 | 1x PBS 60° C. | 0.00 | 5.20 | 0.19 | 0.01 | 0.01 | 10.68 |
| 19 | 1% Autoclave | 729.80 | 29.98 | 3.22 | 0.24 | 0.19 | 1.97 |
| 20 | 0.5% Autoclave | 525.73 | 6.93 | 1.23 | 0.02 | 0.10 | 3.36 |
| 21 | 0.1% Autoclave | 4329.26 | 115.43 | 14.66 | 0.98 | 0.28 | 2.37 |
| 22 | 0.05% Autoclave | 2750.08 | 75.77 | 9.32 | 2.15 | 0.74 | 1.79 |
| 23 | 0.01% Autoclave | 4848.63 | 23.18 | 0.65 | 0.92 | 0.17 | 0.17 |
| 24 | 0.005% Autoclave | 509.23 | 0.08 | 0.15 | 0.00 | 0.01 | 10.04 |
| 25 | 1x PBS Autoclave | 0.00 | 3.28 | 1.03 | 0.06 | 0.03 | 1.44 |

All of the formulations measured in Table 25 shear thinned, demonstrating lower viscosities at higher shear rates. The observed shear thinning was more pronounced in the silk fibroin formulations than in the corresponding experimental controls, which included commercially available treatments for dry eye (REFRESH LIQUIGEL® lubricant eye gel (Allergan), SYSTANE® lubricant eye drop (Alcon), SYSTANE® lubricant eye gel (Alcon). At lower shear rates (1 1/s), the silk fibroin formulations exhibited viscosities similar to that of a gel drop. At higher shear rates (10 1/s), the silk fibroin formulations exhibited viscosities similar to that of a liquid drop. The viscosities of the formulations were measured to be higher at lower concentrations of silk fibroin; however, the viscosity peaked when the formulations were between 0.1-0.5% silk fibroin. When the silk fibroin concentration was 0.1% (w/v) or below, the viscosity decreased with the use of stressed silk.

As seen in Table 25, the average shear storage modulus (G') was measured to be higher for formulations with a lower concentration of silk fibroin. When the silk fibroin concentration was 0.1% (w/v) or below, the shear storage modulus was lower for formulations prepared from stressed silk fibroin than from unstressed. The average phase angle was also measured to be lower for formulations with a lower concentration of silk fibroin. For the unstressed formulations and heat stressed formulations (60° C. Overnight), the average shear loss modulus (G") was measured to be higher for formulations with a lower concentration of silk fibroin. When the silk fibroin concentration was below 0.1% (w/v), the average shear loss modulus was lower for formulations prepared from stressed silk fibroin than for formulations prepared from unstressed silk fibroin.

Example 13. Preparation of Fluorescein Isothiocyanate (FITC)-Labeled Silk Fibroin (FITC-SF) Solution Silk fibroin (SF) was labeled with fluorescein isothiocyanate (FITC) for the residence time studies described in the Examples herein. 420 mg of sodium bicarbonate was dissolved in 9 mL of deionized (DI) water. The pH was adjusted to 9.0 using 1 N sodium hydroxide and 1 N hydrochloric acid. A quantity of DI water sufficient to raise the volume to 10 mL was added to prepare a 0.5 M sodium bicarbonate solution.

1.5 M hydroxylamine was prepared by dissolving 262 mg hydroxylamine in 2.0 ml of water. The pH was adjusted to 8.5 using 10 N sodium hydroxide, and a quantity of DI water sufficient to raise the volume to 2.5 mL was added.

Immediately before performing the labeling reaction, FITC (three 10 mg vials, ThermoFisher) was dissolved in 0.5 mL of dimethyl sulfoxide (DMSO; Sigma) resulting in a 20 mg/mL solution of FITC in DMSO.

All buffers and solutions were filtered through 0.2 μm filters under aseptic conditions with the exception of the silk fibroin solution and the FITC in DMSO solution.

A 5% (w/v) silk fibroin solution (480mb; Batch 88) containing 50 mM sucrose was thawed. 1 mL 0.5 M sodium bicarbonate buffer was added to a vial containing 4 mL of the thawed 5% (w/v) silk fibroin solution. If needed, the pH was adjusted to between 8.5-9.0 using 1N sodium hydroxide. A sample of the silk fibroin solution was retained as a control.

The labeling reaction was performed by adding 1.44 mL FITC in DMSO to 4.5 mL of the silk fibroin solution. The vial was kept protected from light at room temperature (RT) for 2 hours on a rocker resulting in FITC-labeled silk fibroin (FITC-SF).

The control sample of silk fibroin solution was prepared by adding 1.4 mL of DMSO to 4.5 mL of the thawed 5% (w/v) silk fibroin solution. The mixture was incubated at RT for 2 hours on a rocker protected from light.

After the two-hour incubation, 0.6 mL hydroxylamine solution was added to each reaction, and the mixture was placed on a rocker at RT for one hour. The pH was then adjusted to 7.0 using 1 N hydrochloric acid. Each solution was transferred to separate 20 kDa dialysis cassettes. Each solution was protected from light while dialyzed against 4.5 L of water with four complete exchanges at 4° C. over 72 hours. Dialyzed solutions were filtered under aseptic conditions through a 0.2 μm polyethersulfone (PES) filter unit. Final solutions were stored in sterile containers at 4° C. until use.

Example 14. Confirmation of the Conjugation of FITC to Silk Fibroin

High performance liquid chromatography (HPLC) was used to confirm conjugation is successful in the FITC-labeled silk fibroin (FITC-SF) solution. An Agilent 1260 BioInert HPLC system equipped with a Waters X-Bridge Protein BEH SEC, 200 Å, 3.5 μm column was used. An isocratic flow of mobile phase (100 mM Tris-HCl with 400 mM sodium perchlorate, pH 8.5) at 0.86 mL/min was used to elute analytes. Successful FITC labelling of SF was determined by monitoring protein absorbance at 280 nm and FITC emission at 525 nm following excitation at 490 nm. Samples were diluted to 1% (w/v) prior to injection. The data showed overlapping UV and fluorescence profiles for the silk fibroin and FITC-SF, which would represent successful conjugation since the molecular weight of unconjugated FITC is smaller than the silk fibroin (400 Da vs. >6 kDa, respectively) and would elute much later during this analysis.

Example 15. Preparation of Formulations of FITC-SF

Silk fibroin solutions containing varying percentages of FITC-SF were prepared. FITC-SF was prepared as described in Example 13. A frozen stock of 5% (w/v) silk fibroin solution (5% SF) in water was thawed for preparation of these formulations.

Stock solutions, including a 5× Borate Buffer, a 1× Borate Buffer, and a 0.86% (w/v) solution of FITC-SF in water, were prepared. The 5× Borate Buffer was prepared by combining the following: 1.5 g boric acid, 213.1 mg sodium borate decahydrate, 350 mg potassium chloride, 32 mg magnesium chloride hexahydrate, 20 mg calcium chloride dihydrate, and 40 ml DI water. The pH was adjusted to 7.3 using 1 N hydrochloric acid and 1 N sodium hydroxide. A quantity of deionized (DI) water sufficient to raise the volume to 50 mL was added. The 1× Borate Buffer (150 mOsm/L) was prepared by combining 4 mL of the 5× Borate Buffer with 12 mL DI water. The pH was adjusted to 7.3 using 1 N hydrochloric acid and 1 N sodium hydroxide. A quantity of DI water sufficient to raise the volume to 20 mL was added. The FITC-SF solution described in Example 13 was diluted with water to a concentration of 0.86% (w/v) after dialysis.

1% (w/v) silk fibroin solutions were prepared, in which varying percentages of the silk fibroin in solution was FITC-SF. These formulations were prepared by combining volumes of the solutions described below. Table 27 shows the volume of components in each formulation of the resulting 1% (w/v) silk fibroin solution (150 mOsm/L).

TABLE 27

| Formulation Volumes | | | | | |
|---|---|---|---|---|---|
| Sample | % FITC-SF of the 1% SF formulation | 5% Borate buffer [mL] | DI water [mL] | 5% SF [mL] | FITC-SF [mL] |
| 289-1 | SF Control | 0.8 | 2.0 | 0.8 | None |
| 289-2 | 40% | 0.8 | 0.5 | 0.48 | 1.850 |
| 289-3 | 30% | 0.8 | 1.0 | 0.56 | 1.387 |
| 289-4 | 20% | 0.8 | 1.5 | 0.64 | 0.924 |
| 289-5 | 10% | 0.8 | 1.75 | 0.72 | 0.462 |

For all the formulations, the pH was adjusted to 7.3 using sodium hydroxide and hydrochloric acid, and DI water sufficient to raise the volume to 4 mL was added. The final product was obtained through filtration with a 0.2 μm syringe filter.

Example 16. Effects of FITC Conjugation on the Viscosity of a Silk Fibroin Formulation A Bholin C-VOR 150 rheometer (Malvern) with a 4°/40 mm cone and plate was used to measure rheology characteristics at 25° C. and a gap of 0.15 mm.

To analyze the complex viscosity of each formulation, thirty samples were put in a strain hold at 5%, each with a delay time of 5 s, an integration time of 1s, and a wait time of 4 s. Table 28 provides the oscillation results. As used herein, the term "complex viscosity" refers to viscosity, measured under oscillatory conditions, that is dependent on the percent strain and frequency. "G" ("G prime") represents the storage modulus, and "G" ("G double prime") represents the loss modulus.

TABLE 28

| Oscillation Data | | | | | | | |
|---|---|---|---|---|---|---|---|
| Sample | % FITC-SF of the 1% SF formulation | Complex Viscosity [cP] | Standard Deviation | G' [Pa] | Standard Deviation | G" [Pa] | Standard Deviation |
| 289-1a | 0% | 130.6 | 7.6 | 0.686 | 0.053 | 0.415 | 0.023 |
| 289-1b | 0% | 58.9 | 8.9 | 0.311 | 0.059 | 0.198 | 0.026 |
| Average | 0% | 91 | 35.8 | 0.486 | 0.198 | 0.299 | 0.113 |
| 289-2a | 40% | 45.1 | 7.3 | 0.209 | 0.040 | 0.190 | 0.032 |
| 289-2b | 40% | 29.9 | 6.9 | 0.128 | 0.044 | 0.135 | 0.029 |
| Average | 40% | 37.5 | 10.4 | 0.168 | 0.058 | 0.162 | 0.041 |
| 289-3a | 30% | 83.4 | 9.3 | 0.430 | 0.060 | 0.299 | 0.027 |
| 289-3b | 30% | 97.8 | 12.2 | 0.505 | 0.076 | 0.348 | 0.033 |
| Average | 30% | 90.6 | 12.9 | 0.467 | 0.077 | 0.323 | 0.039 |
| 289-4a | 20% | 184.6 | 15.3 | 0.930 | 0.104 | 0.691 | 0.032 |
| 289-4b | 20% | 34.2 | 6.5 | 0.137 | 0.039 | 0.162 | 0.038 |
| Average | 20% | 143.6 | 69.8 | 0.714 | 0.372 | 0.547 | 0.243 |
| 289-5a | 10% | 122.9 | 81.9 | 0.602 | 0.432 | 0.479 | 0.291 |
| 289-5b | 10% | 247.2 | 38.6 | 1.235 | 0.188 | 0.941 | 0.158 |
| Average | 10% | 185.1 | 89.1 | 0.919 | 0.459 | 0.710 | 0.328 |

Effects of conjugation of FITC to silk fibroin on shear viscosity were also analyzed. Fifteen samples were held at a shear rate of 1 1/s. As used herein, the term "shear viscosity" or "viscosity" refers to the ratio between shear stress and shear rate. Shear viscosity is measured under shear conditions, which means that steady, simple shear in the same direction is applied to the sample. Results are shown in Table 29.

TABLE 29

Shear Viscosity Data

| Sample | % FITC-SF of the 1% SF formulation | Shear Viscosity (cP) | Stand. Dev. |
|---|---|---|---|
| 289-1a | 0% | 76.2 | 11.4 |
| 289-1b | 0% | 50.7 | 4.1 |
| Average | 0% | 63.4 | 15.5 |
| 289-2a | 40% | 39.3 | 5.0 |
| 289-2b | 40% | 33.5 | 4.7 |
| Average | 40% | 36.4 | 5.6 |
| 289-3a | 30% | 61.9 | 5.2 |
| 289-3b | 30% | 85.3 | 6.9 |
| Average | 30% | 73.6 | 13.3 |
| 289-4a | 20% | 91.7 | 11.9 |
| 289-4b | 20% | 23.3 | 6.6 |
| Average | 20% | 46.7 | 33.9 |
| 289-5a | 10% | 35.2 | 3.3 |
| 289-5b | 10% | 98.2 | 4.9 |
| Average | 10% | 66.7 | 12.9 |

Higher percentages of FITC-SF in the formulations was observed to decrease complex viscosity. The complex viscosity, G', G", and shear viscosity of the samples with 30% FITC-SF were determined to be the most similar to those of the control silk fibroin solution. As a result, silk fibroin solutions in future studies will comprise 30% FITC-SF. 30% FITC-SF was chosen in order to balance maintaining viscosity with effective labeling, because a 10% FITC-SF ration may result in weak labeling.

Example 17. Preparation of Silk Fibroin Formulations for Irritability Analysis in Rabbits The irritability in the eyes of rabbits was compared for silk fibroin formulations with different concentrations and molecular weights of silk fibroin. The materials used in the formulations are shown in Table 30.

TABLE 30

Materials for Silk Fibroin Formulations

| Product | Supplier | Catalog Identifier | Lot Number |
|---|---|---|---|
| Lyophilized LMW Silk-Fibroin (480 mb) | Cocoon Biotech | — | Batch #080-3C |
| Lyophilized LMW Silk-Fibroin (120 mb) | Cocoon Biotech | — | Batch #068-C |
| Boric Acid | Fisher | A73-500 | 163991 |
| Sodium Chloride | Sigma | S7653-1KG | SLBS2340V |
| Sodium Borate Decahydrate | Sigma | 31457-100G | BCBS7522V |
| Potassium Chloride | Sigma | 12636-250G | BCBV6226 |
| Magnesium Chloride Hexahydrate | Sigma | M7304-100G | SLBS4877 |
| Calcium Chloride Dihydrate | Fisher | C70-500 | 160760 |

Table 31 described the formulations analyzed in this Example. They were selected based on viscosity and surface tension.

TABLE 31

Silk Fibroin Formulations

| Sample | Description | Silk-Fibroin Boil Time (minutes) | Silk-Fibroin Conc. (%) |
|---|---|---|---|
| 1 | DED Buffer (Vehicle) | N/A | N/A |
| 2 | 1% 480 mb in DED Buffer (Silk Fibroin-LMW) | 480 | 1 |
| 3 | 1% 120 mb in DED Buffer (Silk Fibroin-HMW) | 120 | 1 |
| 4 | 1% 480 mb in DED Buffer with 1% Polyethylene Glycol (Silk Fibroin-LMW with Excipient) | 480 | 1 |

The DED buffer (Vehicle) was prepared by dissolving: 1.2 g boric acid, 170.5 mg sodium borate decahydrate, 680 mg sodium chloride, 280 mg potassium chloride, 25.6 mg magnesium chloride hexahydrate, and 15.9 mg calcium chloride dihydrate in a 250 ml beaker containing 190 ml DI water. The pH was adjusted to 7.3 final using 1 N sodium hydroxide and 1 N hydrochloric acid. A quantity of DI water sufficient to raise the volume to 200 ml was added.

The 1% 480 mb in DED buffer (Silk Fibroin-LMW) formulation was prepared by reconstituting 300 mg of 480 mb silk fibroin to 5% (w/v) by adding 5.7 mL DED buffer. The silk fibroin was allowed to dissolve for 30 minutes or until clear. The solution was diluted to 1% (w/v) silk fibroin by adding 24 mL of DED buffer.

The 1% 120mb in DED buffer (Silk Fibroin-HMW) formulation was prepared by reconstituting 300 mg of 120 mb silk fibroin to 5% (w/v) by adding 5.7 ml of DED buffer. The silk fibroin was allowed to dissolve for 30 minutes or until clear. The solution was diluted to 1% (w/v) silk fibroin by adding 24 ml of DED buffer.

The 1% 480mb in DED Buffer with 1% Propylene Glycol (Silk Fibroin-LMW with Excipient) formulation was prepared as follows. Propylene glycol may act as a demulcent. 1.25% propylene glycol in DED buffer was prepared by mixing 0.375 mL propylene glycol with 29.625 ml of DED buffer. One tube (300 mg) of 480mb silk fibroin was reconstituted to 5% (w/v) by adding 5.7 mL DED buffer. The silk fibroin was allowed to dissolve for 30 minutes or until clear. The solution was diluted to 1% (w/v) SF and 1% propylene glycol by adding 24 mL of 1.25% propylene glycol in DED buffer.

Final formulations were filtered through a 0.2 μm filtration unit with polyethersulfone membranes and stored at 4° C. For each formulation, ten 1.75 mL aliquots were placed in separate sterile 2 mL polypropylene Eppendorf® tubes (1 tube/day+3 extra). All samples were stored at 4° C.

Example 18. Rheological Studies of Silk Fibroin Formulations for Irritability Studies Silk fibroin formulations were prepared from the protocol as described in Example 17. Silk fibroin formulations were prepared from silk fibroin lyophilized either in water or in phosphate buffer (PB). The formulations tested were presented in Table 32. Some formulations were prepared with polypropylene glycol (PG). All formulations were prepared in Dry Eye Disease (DED) buffer, a borate buffer comprising 6 mg/mL boric acid, 0.45 mg/mL sodium borate, 3.4 mg/mL sodium chloride, 1.4 mg/mL potassium chloride, 0.06 mg/mL magnesium chloride, and 0.06 mg/mL calcium chloride, pH 7.3.

TABLE 32

| Formulations for irritability and rheology studies | | | | |
|---|---|---|---|---|
| Sample | Description | Silk Lyophilization Buffer | Silk Conc. (%) (w/v) | PG Conc. (%) |
| 254-1 | DED Buffer | — | 0 | 0 |
| 254-2 | 1% 480 mb in DED | Water | 1 | 0 |
| 254-3 | 1% 120 mb in DED | Water | 1 | 0 |
| 254-4 | 1% 480, 1% PG in DED | Water | 1 | 1 |
| 254-4V | DED Buffer, 1% PG | — | 0 | 1 |
| 254-2PB | 1% 480 mb (PB) in DED | PB | 1 | 0 |
| 254-3PB | 1% 120 mb (PB) in DED | PB | 1 | 0 |
| 254-4PB | 1% 480 (PB), 1% PG in DED | PB | 1 | 1 |

The rheological properties of the silk fibroin formulations were then analyzed. The experiments were conducted on a Bohlin C-VOR 150 rotational rheometer with a 4°/40 mm cone and plate geometry, a 0.15 mm gap size, and a temperature of 25° C. The first test comprised a strain sweep from 0.1% to 10% strain at 1 Hz over the course of 160 s, with 50 readings taken. This was to determine the linear viscoelastic region (LVR) of each sample. The second test comprised a strain hold at 5% (or 1% if the LVR was smaller) and 1 Hz for 145 s, with 15 readings taken. The third test comprised a shear ramp from 0.1 1/s to 10 1/s over 100 s, followed by a shear hold for 20 s, for a total time of 120 s, with 70 samples. A fourth test was also conducted with a shear rate of 1 1/s, a time of 135 s, and 15 samples. The data from the rheological experiments are presented in Table 33.

TABLE 33

| Rheological studies of silk fibroin formulations for irritability studies | | | | | | | |
|---|---|---|---|---|---|---|---|
| Sample | 254-1 | 254-2 | 254-3 | 254-4 | 254-2PB | 254-3PB | 254-4PB |
| Viscosity at 1 1/s (cP) | 7.07 | 62.85 | 38.95 | 81.96 | 57.78 | 43.14 | 56.30 |
| Viscosity Standard deviation (1 1/s) | 4.25 | 3.23 | 2.64 | 4.59 | 3.45 | 4.29 | 6.03 |
| Viscosity at 10 1/s (cP) | 4.76 | 12.86 | 11.64 | 16.95 | 11.69 | 10.42 | 10.92 |
| Viscosity Standard Deviation (10 1/s) | 5.67 | 5.68 | 6.79 | 6.22 | 1.69 | 1.04 | 1.52 |
| G' (Pa) | 2.24E−02 | 2.41E−01 | 8.76E−02 | 4.39E−01 | 3.07E−01 | 1.48E−01 | 4.24E−01 |
| G' Standard Deviation | 9.10E−03 | 5.26E−02 | 1.87E−02 | 4.72E−02 | 3.72E−02 | 1.66E−02 | 5.22E−02 |
| G'' (Pa) | 4.15E−02 | 2.43E−01 | 1.35E−01 | 3.74E−01 | 2.45E−01 | 2.09E−01 | 3.55E−01 |
| G'' Standard Deviation | 1.03E−02 | 2.76E−02 | 1.23E−02 | 2.31E−02 | 1.87E−02 | 1.09E−02 | 2.91E−02 |
| Phase Angle (°) | 61.11 | 45.73 | 57.27 | 40.56 | 38.71 | 54.76 | 40.05 |
| Phase Angle Standard Deviation | 13.39 | 3.48 | 5.16 | 1.61 | 1.94 | 2.66 | 1.63 |

All of the formulations showed evidence of shear thinning; the viscosities were measured to be lower at higher shear rates. The formulations with lower molecular weight silk fibroin (480 mb) were more viscous than the formulations with higher molecular weight silk fibroin (120 mb). Preparation from silk fibroin lyophilized in PB did not affect the viscosity of the formulations. Formulations with PG were more viscous than formulations without this excipient. The G' and G" were measured to be lower for formulations with higher molecular weight silk fibroin. G' and G" were also increased by the preparation from silk fibroin lyophilized in PB or formulations with PG. The phase angle was higher for formulations with higher molecular weight silk fibroin.

Example 19. Analysis of Irritability of Silk Fibroin Formulations in Rabbits

Non-GLP ocular irritability/tolerability was evaluated by measuring the effects of topical administration of the silk fibroin formulations described herein in New Zealand White (NZW) Rabbits. Animals received seven days of four times daily (QID) topical administrations of test article or vehicle (bilateral) and underwent full ophthalmic exams at baseline, post the first dose on Day 1, post the last dose on Day 1, post the last dose on Day 4, and post the last dose on Day 8.

Rabbits were individually housed in suspended wire bottom caging in a procedure room. Rabbit Diet 5P25 (lab diet specially formulated per lab animal diet) was provided according to U.S. Department of Agriculture (USDA) guidelines. Filtered tap water or spring water was provided to the animals ad libitum. Environmental controls were set to maintain temperatures 16-22° C. (61-72° F.) with relative humidity between 50±20%. A 12-hour light/12-hour dark cycle was maintained. A staff veterinarian was available as needed throughout the study. Prior to study initiation, the veterinarian released the animals from quarantine.

Animals were assigned to dose groups after a baseline ocular examination. Table 34 provides the group assignments for the 16 animals selected for the study.

TABLE 34

Group Assignments for Animals

| Group | Number of Animals | Silk Fibroin minute boil (mb) | Route | No. of Doses per Day | SF Dose Concentration % (w/v) | Propylene Glycol Dose Concentration (mg/mL) | Dose Volume (μL/eye) |
|---|---|---|---|---|---|---|---|
| 1/Vehicle | 4 | N/A | Topical | QID | 0 | 0 | 40 |
| 2/Silk Fibroin-LMW Concentration 1 | 4 | 480 | Topical | QID | 10 | 0 | 40 |
| 3/Silk Fibroin-HMW Concentration 2 | 4 | 120 | Topical | QID | 10 | 0 | 40 |
| 4/Silk Fibroin-LMW + 1% PG Formulation | 4 | 480 | Topical | QID | 10 | 10 | 40 |

40 μL of test article or vehicle (bilateral) was administered to the ocular surface of the rabbit using a calibrated micropipette. Care was taken to ensure no dose fell out of the rabbit's eye. QID dosing occurred at approximately 8 am, 11 am, 2 μm, and 4 μm. All times are ±60 minutes.

The weight of each animal was measured on Day 1 and Day 8. Values were rounded to the nearest 0.1 kg. A full ophthalmic exam was performed at baseline, twice on Day 1 (after the first dose and after the fourth dose), Day 4, and Day 8. After all animals were dosed, cage side observations were made for each animal specifically focusing on the eyes. If any indication of ocular pain was observed (squinting, pawing at the eye, or other signs of distress), the technician took the animal out and performed a gross examination of the eye. Gross exams observed the general appearance of the eye (whether or not there is hyperemia, discharge, swelling, squinting, etc.). All exams were 15 minutes post dose.

A hand-held slit-lamp was used to assess anterior abnormalities. If tolerability issues arose, the fundus of the eye was observed using an indirect ophthalmoscope. Prior to posterior examination, animals were dilated with a mydriatic (tropicamide).

Animals underwent full front of the eye exams and a quick vitreous scan via slitlamp. Endpoints included hyperemia, chemosis, discharge, aqueous flare, aqueous cells, presentation of keratic precipitates, and vitritis (as noted via slitlamp). Throughout the study, animals showed no signs of ocular discomfort or pain and the majority of endpoints were scored at zero.

Results indicate the silk fibroin formulations and vehicle are well tolerated in the eyes of New Zealand White rabbits. Results indicate that topical administration of the solution of silk fibroin was tolerated well throughout the duration of the study. Observations and clinical scoring of endpoints maintained baseline levels throughout the entire study. The concentrations of this test article show that it is safe to be administered topically. There were no significant endpoint changes in the hyperemia and discharge evaluations, and the remaining endpoints maintained scores of zero throughout all evaluations. Animals showed no signs of ocular pain or discomfort throughout all dosing time points as well.

Example 20. Ocular Silk Fibroin Residence

Formulation Preparation

To track the residence of the silk fibroin (SF) formulations in the eye, SF formulations were labelled with fluorescent dye, FITC. 5% (w/v) SF, (480mb) degummed as described above, was prepared in water and 50 mM sucrose. This solution was separated into 5 mL aliquots and frozen to −80° C. to be thawed as needed. FITC labelled silk fibroin (FITC-SF) was prepared as described in Example 13. A 5× stock of the borate (DED) buffer was prepared by combining the following components: 1.5 g boric acid, 213.1 mg sodium borate decahydrate, 350 mg potassium chloride, 32 mg magnesium chloride hexahydrate, 20 mg calcium chloride dihydrate, and 40 ml deionized (DI) water. The pH was adjusted 7.3 using 1 N hydrochloric acid and 1 N sodium hydroxide and brought up to 50 mL with DI water. The 5× stock was prepared so that the final solution of FITC-SF and unlabeled silk fibroin would be in a 1×DED buffer, the contents of which were described in earlier examples. 0.86% (w/v) FITC-SF in water was used to prepare the 30% FITC-SF formulation. A sample of 1% SF in DED with an osmolarity of 150 mOsm/L was prepared by combining 3 mL 5% SF in water, 3 mL 5× borate buffer, and 9 mL DI water in a 20 ml conical tube. The pH was adjusted to 7.3 using 1 N hydrochloric acid and 1 N sodium hydroxide and brought up to 15 mL with DI water. A second sample, a 30% FITC-SF formulation (containing 1% SF in DED with 150mOsm/L), was also prepared. 5.201 mL 0.86% (w/v) FITC-SF was combined with 2.1 mL 5% (w/v) SF in water, 3.0 mL 5× borate buffer and 4.699 ml DI water. The pH of the solution was adjusted to 7.3 using 1 N hydrochloric acid and 1 N sodium hydroxide and brought up to 15 mL with DI water. The resulting solution has FITC labelled SF and unlabeled SD in the ratio of 3:7. Both formulations were filtered with a 0.2 μm syringe filter.

Rheology of Formulations

The complex viscosity, elastic modulus (G'), viscous modulus (G"), phase angle, and shear viscosity of the formulations to be tested for residence time were measured. The rheological properties were measured on a Bohlin C-VOR 150 rotational rheometer with a 4°/40 mm cone and plate geometry, a gap size of 0.15 mm, a temperature of 25° C., a frequency of 1 Hz, and pre-shear conditions of 1 1/s for 10s with a 10 second equilibration. The experiment consisted of two tests. The first test involved a strain hold at 5% with 30 samples, each with a delay time of 5 s, an integration time of 1s, and a wait time of 4 s. The second test used a hold at a shear rate of 1 1/s for 15 samples. The results of the experiments are presented in Table 35.

TABLE 35

Rheology data of silk fibroin formulations for residence studies

| | Sample | | | | | | | |
|---|---|---|---|---|---|---|---|---|
| | 1% SF in borate buffer | | | | 30% FITC-SF Formulation | | | |
| Sample | 291-1a | 291-1b | 291-1c | Average | 291-2a | 291-2b | 291-2c | Average |
| Complex viscosity (cP) | 89.64 | 217.01 | 315.31 | 207.32 | 252.18 | 238.09 | 325.11 | 271.79 |
| Complex viscosity standard deviation | 18.48 | 46.29 | 50.70 | 101.52 | 35.54 | 40.71 | 48.58 | 56.39 |
| G' (Pa) | 0.42 | 1.10 | 1.58 | — | 1.13 | 1.08 | 1.50 | — |
| G' standard deviation | 0.11 | 0.28 | 0.31 | — | 0.21 | 0.25 | 0.29 | — |
| G" (Pa) | 0.38 | 0.81 | 1.19 | — | 1.11 | 1.03 | 1.38 | — |
| G" standard deviation | 0.06 | 0.12 | 0.12 | — | 0.11 | 0.12 | 0.14 | — |
| Phase Angle (°) | 42.95 | 37.14 | 37.44 | 39.18 | 44.94 | 44.44 | 43.05 | 44.14 |
| Phase angle standard deviation | 4.90 | 3.78 | 2.94 | 4.73 | 2.97 | 4.03 | 3.20 | 3.47 |
| Shear Viscosity (cP) | 71.32 | 82.03 | 154.21 | 102.52 | 100.58 | 90.42 | 140.34 | 110.45 |
| Shear viscosity standard deviation | 8.86 | 19.86 | 28.30 | 42.32 | 21.79 | 37.13 | 41.39 | 40.12 |

These results suggested that the incorporation of FITC-SF into the silk fibroin solution formulation produced formulations with similar properties.

Ocular Residence Time

The fluorescence intensity of the formulations was established in vitro. The FITC-SF formulation was diluted 10×, 50×, and 100× in saline solution. 15 μL of the formulations were pipetted onto the end of a wicking strip. The formulations utilized include undiluted FITC-SF and 10×, 50×, and 100× dilutions of the FITC-SF solution in saline. Images of each of the wicking strips were taken through an orange filter with illumination using a cobalt blue light and the fluorescence brightness was analyzed and quantified using Fiji Image software. A segment of the image just adjacent to the end of the wicking strip was used to normalize the background brightness of the images. After brightness correction, a circle was drawn to encompass the end of the wicking strip. The brightness intensity of the wicking strip was then recorded. Two images of each sample were analyzed and averaged to generate the value for each timepoint from each animal. There were 6 animals per timepoint. The results are shown in Table 36.

TABLE 36

| Fluorescence intensity | | | |
|---|---|---|---|
| % FITC-SF Formulation | Dilution | Corrected Intensity Avg. | Standard Deviation |
| 100 | 0 | 86.1 | 0.8 |
| 10 | 10X | 40.2 | 7.5 |
| 2 | 50X | 17.5 | 3.4 |
| 1 | 100X | 4.2 | 0.1 |
| 0 | 100 (Saline) | 0.0 | 0.1 |

As the concentration of FITC-SF in the formulation decreased, the fluorescence intensity also decreased. The R squared value obtained was 0.935 suggesting a strong correlation between concentration of FITC and fluorescence brightness measured.

To measure the ocular residence time of the FITC-SF formulation, 40 μL of FITC-SF formulation was administered into the lower left lid of each rabbit. Eyes were manually blinked 2-3 times prior to the first sampling (TO). Sampling was performed by placing a wicking strip into the bottom eyelid of the rabbit for 5 sec. to collect ≤5 μl of tears. Images of the wicking strips were taken and the fluorescence was quantified as described above. Sampling was performed at TO, 15 minutes, 30 minutes, 1 hour, 2 hours, and 24 hours. The eyes were also scored clinically for the presence of fluorescence using the Fluorescence Intensity (FI) scale just prior to sampling. Images of the eyes were taken through an orange filter with illumination using a cobalt blue light.

Table 37 shows the Fluorescence Intensity (FI) scale for the tears collected from the fornix of the tear lake.

TABLE 37

| Fluorescence Intensity (FI) scale | |
|---|---|
| Score | Description |
| 0 | No fluorescence |
| 1 | ≤25% fluorescence |
| 2 | ≤50% fluorescence |
| 3 | ≤75% fluorescence |
| 4 | ≥75% fluorescence |

Based on the FI scale in Table 37, the clinical fluorescence score for each time point was calculated as shown in Table 38.

TABLE 38

| Clinical Fluorescence Score | | | |
|---|---|---|---|
| Time (min) | Average | St Dev | SEM |
| 0 | 4.0 | 0.0 | 0.0 |
| 0.25 | 2.0 | 0.6 | 0.2 |
| 0.5 | 1.3 | 0.8 | 0.2 |
| 1 | 1.0 | 0.6 | 0.2 |
| 2 | 0.2 | 0.4 | 0.1 |
| 24 | 0.0 | 0.0 | 0.0 |

Clinical Fluorescence Score decreased over time indicating that the FITC-SF is cleared from the tear lake over time. The Clinical Fluorescence Score decreased to less than one by 2 hours, indicating that the residence time of the FITC-SF formulations in the eye is ≤2 hours. The reduction in Clinical Fluorescence Score over time was strongly correlated with an R squared value of 0.97.

Images of the wicking strips used to collect the tears from the rabbits were quantified as shown in Table 39. As described above, images were analyzed using Fiji Image software. A segment of the image just adjacent to the end of the wicking strip was used to normalize the brightness of the images. After brightness correction, a circle was drawn to encompass the end of the wicking strip. The brightness intensity of the wicking strip was then recorded. Two images of each sample were analyzed and averaged to generate the value for the timepoint from each animal. There were a total of 6 animals per timepoint.

TABLE 39

| Quantified Fluorescence | | | |
|---|---|---|---|
| Time (hrs) | Intensity Average | Standard Deviation | SEM |
| 0 | 139.8 | 20.7 | 1.7 |
| 0.25 | 110.1 | 25.1 | 2.1 |
| 0.5 | 97.5 | 14.7 | 1.2 |
| 1 | 93.8 | 20.5 | 1.7 |
| 2 | 86.3 | 6.3 | 0.5 |
| 24 | 89.3 | 4.5 | 0.4 |

Similar to the Clinical Fluorescence Score, the quantified fluorescence decreased over time. A sharp reduction in the quantified fluorescence was observed by 0.5 hours which slowly plateaued over the next hour to reach the values close to the lower limit of detection (86.3) by 2 hours. The lower limit of detection was determined from the dilution study of the fluorescence intensity and was approximately 2% of the initial formulation (a 50× dilution).

Example 21. Tribological Analysis of Silk Fibroin

In this test silk fibroin solutions were analyzed for their lubricating properties by applying a layer of the test sample to a substrate and forcing an upper geometry to slide against it at a number of speeds while under a defined load. Testing was performed using a research rheometer (DHR2, TA Instruments) fitted with a custom 3-balls-on-plate setup with a pliant lower substrate. A tribology assembly was employed that comprised a geometry of 3 glass spheres that slide against a pliant lower substrate, under a defined load of 1 N, onto which the sample has been spread. The rotational angular velocity is ramped from 0.05 rad/s to 20 rad/s, 8 points per decade, with each point maintained for 20 s with the coefficient of friction averaged over the final 15 s. The lower surface was made to hold 25° C. throughout the analysis. This test was performed in triplicate for each sample. The test was performed on silk fibroin formulation 480mb; 1% SFf; sln; 0.34% Suc; borate buffer. The formulation tested was prepared as described in previous examples. The silk fibroin solution exhibited a clear "stick-slip" behavior across all sliding speeds. Stick-slip behavior is the spontaneous jerking motion that may occur while two objects are sliding over each other.

Example 22. Surface Tension Measurements of Silk Fibroin Solutions Using Dynamic Analysis Surface tension was employed to determine the spreading properties of silk fibroin solutions. The test analyzed the relationship between the volume, density, and shape of the liquid drop suspended from the end of a needle to calculate the surface tension of that liquid. It was performed on a drop shape analyzer (DSA30R, Kruss Scientific) fitted with the pendant drop module. An aliquot of each sample was equilibrated to 25° C. immediately prior to testing. A pendant drop was formed in a cuvette with a saturated atmosphere to minimize evaporation. This drop was imaged, and the surface tension measured every second over a period of 600s. This test was performed in triplicate for each sample. The tests were performed on silk fibroin formulations after their preparation. Deionized water served as a control. The formulations tested were prepared as described in previous examples. The results of the experiments are displayed in Table 40.

TABLE 40

Surface Tension of Silk Fibroin Solutions

| | Sample 1 Surface Tension (mN/m) | Sample 2 Surface Tension (mN/m) | Sample 3 Surface Tension (mN/m) | Average Surface Tension (mN/m) | RSD (%) | Standard Dev. |
|---|---|---|---|---|---|---|
| DI Water | 71.32 | 71.46 | 71.46 | 71.41 | 0.092 | 0.066 |
| 480 mb; 5% SFf; sln; 1.71% Suc; borate buffer | 42.48 | 42.15 | 42.08 | 42.24 | 0.412 | 0.174 |
| 480 mb; 1% SFf; sln; 0.34% Suc; borate buffer | 44.27 | 44.57 | 44.82 | 44.55 | 0.505 | 0.225 |
| 480 mb; 0.5% SFf; sln; 0.17% Suc; borate buffer | 45.80 | 45.99 | 46.03 | 45.94 | 0.218 | 0.100 |
| 480 mb; 0.1% SFf; sln; 0.03% Suc; borate buffer | 46.37 | 46.77 | 46.89 | 46.66 | 0.464 | 0.217 |
| 480 mb; 0.05% SFf; sln; 0.01% Suc: borate buffer | 49.06 | 49.12 | 49.10 | 49.09 | 0.051 | 0.025 |

Increasing silk fibroin concentration lead to a decrease in calculated surface tension. The presence of 0.05% (w/v) silk fibroin decreased the surface tension to 49.99 mN/m. This is a large decrease from water which displayed a surface tension of 71.41 mN/m. As silk concentration in the samples increased, the surface tension was further decreased reaching a low of 42.24 mN/m with the 5% (w/v) silk fibroin sample (Table 40).

Example 23. Treatment of Dry Eye Disease in Humans

To demonstrate safety and tolerability, optimize a formulation or dose, and show efficacy compared to a placebo, the following study will be performed in humans and animals. Both a single site, open label, placebo controlled safety study and a multi-site, randomized, double-masked, parallel group, placebo or vehicle-controlled, efficacy study will be performed with about 30 subjects and up to 150 patients, respectively. Standardized inclusion and exclusion criteria will be used for enrollment. The subjects will be randomized to a treatment arm after a wash-out or two-week vehicle run-in period.

Treatment arms will be the silk formulation administered four times a day (QID), twice a day (BID), or once a day (QD) compared to a placebo group (patients will serve as their own placebo) and will include between 8-10 subjects per arm. Treatment duration will be one month. The primary endpoint will be safety as measured by visual acuity, slit lamp biomicroscopy of intraocular pressure (IOP), fundoscopy, and adverse event query. The secondary endpoint will be efficacy as measured by corneal fluorescein staining, staining of individual regions of cornea (e.g. inferior, central, superior, nasal, and temporal), conjunctival staining, tear film break-up time, Schirmer's Test, and conjunctival redness. All the results are expected to change from the baseline. Ocular discomfort, such as dryness, grittiness, burning, stinging, etc., and the ocular surface disease index (OSDI) may also be used to characterize the results.

Example 24. Stability of Silk Fibroin Formulations

The stability of multiple silk fibroin formulations may be compared after storage at 4° C. for three weeks, room temperature for three weeks, or 40° C. for one week. A silk fibroin solution was formulated with a concentration of 0.5%, 1%, or 3% (w/v) silk fibroin with either 10 mM phosphate buffer (pH 7.5) or 10 mM borate buffer (pH 7.5) to result in an osmolarity of 150 mOsm/L or 290 mOsm/L. Aggregation was observed to be below 0.1% for all formulations and under all conditions. Silk fibroin formulations maintain their silk fibroin concentration, physical properties, and rheological properties after storage.

Example 25. Preparation of SBP Hydrogel Formulations

Silk was degummed using either a 90 or a 480-minute boil (90mb and 480mb), processed as described in Example 1 and lyophilized in 10 mM phosphate buffer (PB). Lyophilized silk fibroin was dissolved in ultrapure water containing Tween-80 to obtain 10, 20, and 30% (w/v) silk fibroin with 0.4% Tween-80. The hydrogels were formed by mixing with a gelling agent (e.g. PEG 4 kDa). 2.5 mL of the silk solution was mixed with 2.5 mL one of the following excipients: (i) 20% P188, (ii) 80% PEG 4 kDa, or (iii) 80% glycerol. 1 N hydrochloric acid was added to the formulations containing 80% PEG 4 kDa, to afford a final concentration of 15 mM hydrochloric acid. The final pH of all formulations was estimated to be approximately 7.4+/−0.1. The SBP hydrogel formulations are summarized in Table 41 below. The samples in Table 41 are named by the process used to prepare and formulate each hydrogel. For example, the sample named "90mb; hyd; 10% st; 5% SFf; 10% P188f" refers to a formulation where the silk was degummed with a 90-minute boil (90mb), "hyd" refers to the formulation of the sample as a hydrogel, "10% st" refers to the % (w/v) concentration of the stock solution of silk fibroin, "5% SFf" refers to a formulation with 5% (w/v) final silk fibroin concentration, and "10% P188f" refers to a formulation with 10% P188.

TABLE 41

SBP hydrogel formulations

| No. | Sample name | Boil Time (min) | [Silk] (%) | Excipient name | [Excipient] (%) | [Phosphate Buffer] (mM) |
|---|---|---|---|---|---|---|
| 1 | 90 mb; hyd; 10% st; 5% SFf; 10% P188f | 90 | 5 | P188 | 10 | 16.7 |
| 2 | 90 mb; hyd; 10% st; 5% SFf; 40% PEG4kf | 90 | 5 | PEG 4k | 40 | 16.7 |
| 3 | 90 mb; hyd; 10% st; 5% SFf; 40% Glycf | 90 | 5 | Glycerol | 40 | 16.7 |
| 4 | 90 mb; hyd; 20% st; 10% SFf; 10% P188f | 90 | 10 | P188 | 10 | 33.3 |
| 5 | 90 mb; hyd; 20% st; 10% SFf; 40% PEG4kf | 90 | 10 | PEG 4k | 40 | 33.3 |
| 6 | 90 mb; hyd; 20% st; 10% SFf; 40% Glycf | 90 | 10 | Glycerol | 40 | 33.3 |
| 7 | 480 mb; hyd; 10% st; 5% SFf; 10% P188f | 480 | 5 | P188 | 10 | 16.7 |
| 8 | 480 mb; hyd; 10% st; 5% SFf; 40% PEG4kf | 480 | 5 | PEG 4k | 40 | 16.7 |
| 9 | 480 mb; hyd; 10% st; 5% SFf; 40% Glycf | 480 | 5 | Glycerol | 40 | 16.7 |
| 10 | 480 mb; hyd; 20% st; 10% SFf; 10% P188f | 480 | 10 | P188 | 10 | 33.3 |
| 11 | 480 mb; hyd; 20% st; 10% SFf; 40% PEG4kf | 480 | 10 | PEG 4k | 40 | 33.3 |
| 12 | 480 mb; hyd; 20% st; 10% SFf; 40% Glycf | 480 | 10 | Glycerol | 40 | 33.3 |
| 13 | 480 mb; hyd; 30% st; 15% SFf; 10% P188f | 480 | 15 | P188 | 10 | 50 |
| 14 | 480 mb; hyd; 30% st; 15% SFf; 40% PEG4kf | 480 | 15 | PEG 4k | 40 | 50 |
| 15 | 480 mb; hyd, 30% st; 15% SFf; 40% Glycf | 480 | 15 | Glycerol | 40 | 50 |

Example 26. Freeze Thaw Studies with Varying Silk Fibroin Concentrations and Buffers To date, lyophilization has been utilized for long term storage of silk fibroin. However, this can be costly and time-consuming in product manufacturing. In this study, various silk fibroin concentrations and buffer conditions were examined to test the feasibility of freezing silk fibroin without altering the protein quality. The samples were evaluated using rheology for viscosity and modulus, and size exclusion chromatography (SEC) for molecular weight and aggregation.

This study evaluated the properties of formulations with silk fibroin concentration varied at 1% and 3% (w/v) in phosphate buffer, borate buffer, or phosphate buffered saline, with or without propylene glycol. The formulation in each sample is described in Table 42. In the Table, "PB" is potassium phosphate buffer (from Sigma Aldrich Fine Chemicals, St. Louis, MO), pH 7.4; "PBS" is 1× phosphate buffered saline; "DED" is 1× borate buffer as described in Example 15; and "PG" is propylene glycol. The "baseline" measurements were made prior to freezing at −80° C.

The borate buffer stock solution (5×) was prepared by dissolving 3000 mg boric acid, 426.25 mg sodium borate decahydrate, 1700 mg of sodium chloride, 700 mg potassium chloride, 64 mg magnesium chloride hexahydrate, and 40 mg calcium chloride dihydrate in DI water, adjusting pH to 7.3 final using 1 N sodium hydroxide and 1 N hydrochloric acid, and filling up to 100 mL with DI water. The borate buffer was filtered through 0.2 μm polyethersulfone membrane filtration units prior to use. The final formulations contained 1× of this buffer (6 mg/mL boric acid, 0.45 mg/mL sodium borate, 3.4 mg/mL sodium chloride, 1.4 mg/mL potassium chloride, 0.06 mg/mL magnesium chloride, and 0.06 mg/mL calcium chloride, pH 7.3).

TABLE 42

Formulations with varying silk fibroin concentrations and buffers

| Sample No. | Description | Silk % | Buffer | Frozen |
|---|---|---|---|---|
| 82-1 | 3% Water, Baseline | 3 | Water | — |
| 82-1A | 3% Water, Not Frozen | 3 | Water | N |
| 82-1B | 3% Water, Frozen | 3 | Water | Y |
| 82-2 | 3% PB, Baseline | 3 | 10 mM PB | — |
| 82-2A | 3% PB, Not Frozen | 3 | 10 mM PB | N |
| 82-2B | 3% PB, Frozen | 3 | 10 mM PB | Y |
| 82-3 | 3% DED, Baseline | 3 | DED | — |
| 82-3A | 3% DED, Not Frozen | 3 | DED | N |
| 82-3B | 3% DED, Frozen | 3 | DED | Y |
| 82-4 | 1% PBS, Baseline | 1 | PBS | — |
| 82-4A | 1% PBS, Not Frozen | 1 | PBS | N |
| 82-4B | 1% PBS, Frozen | 1 | PBS | Y |
| 82-5 | 1% DED, Baseline | 1 | DED | — |
| 82-5A | 1% DED, Not Frozen | 1 | DED | N |
| 82-5B | 1% DED, Frozen | 1 | DED | Y |
| 82-6 | 1% PBS + PG, Baseline | 1 | PBS + 1% PG | — |
| 82-6A | 1% PBS + PG, Not Frozen | 1 | PBS + 1% PG | N |
| 82-6B | 1% PBS + PG, Frozen | 1 | PBS + 1% PG | Y |
| 82-7 | 1% DED + PG, Baseline | 1 | DED + 1% PG | — |
| 82-7A | 1% DED + PG, Not Frozen | 1 | DED + 1% PG | N |
| 82-7B | 1% DED + PG, Frozen | 1 | DED + 1% PG | Y |

The rheology results and the size exclusion chromatography (SEC) results for the solutions are presented in Table 43 and Table 44, respectively, where viscosity, elastic modulus (G'), viscous modulus (G"), and phase angle were determined. G', G" and phase angle were measured using a Bohlin C-VOR 150 rotational rheometer. The temperature was held constant at 25° C. via a Peltier Plate system, and the gap was held at 0.15 mm. First a strain ramp was applied from 0.0014 to 5% strain with a constant frequency of 1 Hz, with 30 samples taken, each with a delay time of 9 s and an integration time of 1 s. Next a logarithmic shear ramp was applied from 0.00014 to 1 1/s, with holds at 0.00014, 0.001, 0.01, 0.1, and 1 1/s. Overall, the rheological properties did not change significantly following freezing with the exception of the 1% (w/v) silk fibroin in borate buffer with propylene glycol. The molecular weight as measured by SEC did not change following freeze/thaw, nor did the total peak area. Increases in aggregation were observed for all solutions containing borate buffer with the greatest increase in aggregation occurring with the addition of propylene glycol. Given these results, phosphate buffer performed better upon freeze/thaw than borate buffer.

TABLE 43

Rheological properties after freeze thaw

| | | Viscosity (Pa*s) | | G' (Pa) | | G" (Pa) | | Phase Angle (°) | |
|---|---|---|---|---|---|---|---|---|---|
| Sample No. | Frozen | Avg. | Standard Dev. | Avg. | Standard Dev. | Avg. | Standard Dev. | Avg. | Standard Dev. |
| 82-1 | — | 65.19 | 2.25 | 4.03E−01 | 0 | 4.47E−01 | 0 | 48.01 | 0 |
| 82-1A | N | 50.91 | 5.69 | 1.45E−01 | 2.66E−02 | 2.53E−01 | 4.07E−02 | 59.73 | 7.91 |
| 82-1B | Y | 49.77 | 5.1 | 1.45E−01 | 9.34E−03 | 2.24E−01 | 1.52E−02 | 57.02 | 2.78 |
| 82-2 | — | 38.18 | 3.17 | 3.28E−01 | 0 | 3.06E−01 | 0 | 43.05 | 0 |
| 82-2A | N | 60.42 | 7.66 | 3.33E−01 | 5.78E−02 | 3.43E−01 | 5.08E−03 | 46.08 | 5.55 |
| 82-2B | Y | 51.63 | 4.71 | 3.19E−01 | 6.16E−02 | 3.07E−01 | 1.44E−02 | 44.22 | 6.2.5 |
| 82-3 | — | 81.34 | 3.01 | 2.80E−01 | 0 | 3.67E−01 | 0 | 52.73 | 0 |
| 82-3A | N | 79.23 | 1.75 | 3.16E−01 | 4.08E−02 | 3.97E−01 | 1.91E−02 | 51.65 | 2.23 |
| 82-3B | Y | 76.64 | 23.4 | 4.28E−01 | 3.36E−02 | 4.20E−01 | 4.56E−02 | 44.45 | 2.47 |
| 82-4 | — | 93.78 | 4.89 | 5.84E−01 | 0 | 5.13E−01 | 0 | 41.28 | 0 |
| 82-4A | N | 75.67 | 4.05 | 2.93E−01 | 4.79E−02 | 3.25E−01 | 3.87E−02 | 48.08 | 5.01 |
| 82-4B | Y | 62.5 | 9.67 | 3.12E−01 | 5.82E−02 | 3.16E−01 | 1.02E−01 | 44.66 | 4.43 |
| 82-5 | — | 115.1 | 7.78 | 5.66E−01 | 0 | 7.49E−01 | 0 | 52.89 | 0 |
| 82-5A | N | 82.94 | 19.47 | 4.47E−01 | 1.25E−01 | 4.76E−01 | 1.15E−01 | 47.04 | 1.69 |
| 82-5B | Y | 72.05 | 15.33 | 3.17E−01 | 4.23E−02 | 3.53E−01 | 6.76E−02 | 47.83 | 3.86 |
| 82-6 | — | 91.32 | 3.57 | 3.17E−01 | 0 | 4.34E−01 | 0 | 53.85 | 0 |
| 82-6A | N | 64.97 | 5.43 | 2.62E−01 | 1.31E−02 | 3.25E−01 | 3.00E−02 | 51.08 | 3.82 |
| 82-6B | Y | 52.32 | 10.46 | 2.03E−01 | 5.77E−02 | 2.70E−01 | 8.27E−02 | 52.86 | 0.99 |
| 82-7 | — | 113.82 | 5.15 | 5.33E−01 | 0 | 6.14E−01 | 0 | 49.04 | 0 |
| 82-7A | N | 87.53 | 24.46 | 4.40E−01 | 1.17E−01 | 4.67E−01 | 9.24E−02 | 46.96 | 2.26 |
| 82-7B | Y | 48.81 | 12.4 | 2.59E−01 | 3.78E−02 | 2.86E−01 | 2.78E−02 | 47.92 | 6.46 |

TABLE 44

Molecular weight, peak area and aggregation after freeze thaw

| Sample No. | Frozen | MW (Da) Avg. | MW (Da) Standard Dev. | Peak Area Avg. | Peak Area Standard Dev. | Aggregation (%) Avg. | Aggregation (%) Standard Dev. |
|---|---|---|---|---|---|---|---|
| 82-1 | — | 18218 | 0 | 25183515 | 0 | 0 | 0 |
| 82-1A | N | 18043 | 1190 | 24592650 | 210277 | 0 | 0 |
| 82-1B | Y | 18223 | 1008 | 24541530 | 207449 | 0 | 0 |
| 82-2 | — | 18075 | 0 | 26649930 | 0 | 0 | 0 |
| 82-2A | N | 17943 | 1006 | 26433232 | 96728 | 0 | 0 |
| 82-2B | Y | 18023 | 987 | 26385803 | 9567 | 0 | 0 |
| 82-3 | — | 18123 | 0 | 26161084 | 0 | 0 | 0 |
| 82-3A | N | 18008 | 1069 | 25858311 | 65572 | 0 | 0 |
| 82-3B | Y | 17953 | 1110 | 25937330 | 1196173 | 0.32 | 0.09 |
| 82-4 | — | 18434 | 0 | 8206505 | 0 | 0 | 0 |
| 82-4A | N | 18381 | 1237 | 8102340 | 43772 | 0 | 0 |
| 82-4B | Y | 18375 | 980 | 8008933 | 38407 | 0.04 | 0.01 |
| 82-5 | — | 18627 | 0 | 8590083 | 0 | 0 | 0 |
| 82-5A | N | 18301 | 884 | 8529287 | 16053 | 0 | 0 |
| 82-5B | Y | 18182 | 964 | 8130534 | 115760 | 1.31 | 0.36 |
| 82-6 | — | 18603 | 0 | 8191389 | 0 | 0 | 0 |
| 82-6A | N | 18283 | 1139 | 8137815 | 13188 | 0 | 0 |
| 82-6B | Y | 18345 | 1085 | 8130532 | 18074 | 0 | 0 |
| 82-7 | — | 18675 | 0 | 8613387 | 0 | 0 | 0 |
| 82-7A | N | 18262 | 925 | 8527920 | 57162 | 0 | 0 |
| 82-7B | Y | 17305 | 991 | 7919038 | 87323 | 7.27 | 1.7 |

Example 27. Freeze Thaw Studies with Varying Cryoprotectants

Silk fibroin processing will be more efficient and cheaper if there is no need for lyophilization. Removing a drying condition will require that silk fibroin solutions are stable through a freeze-thaw process. This will allow for aseptic preparation and shipment of silk fibroin from the manufacturing site to the fill/finish facility. This study investigated the effect of silk fibroin concentration as well as cryoprotectants (sucrose and trehalose) on the freeze-thaw stability silk fibroin.

The silk fibroin concentration was varied from 0.5% to 5% (w/v) in 10 mM phosphate buffer and the concentration of each cryoprotect was varied from 10 to 150 mM. The formulation in each sample is described in Table 45. All formulations contained 10 mM phosphate buffer at pH 7.4 and the baseline measurements were made prior to freezing at −80° C. The five 5 ml replicates were prepared for each group in separate 15 cc. conical tubes. In the Table, "SF" refers to silk fibroin.

TABLE 45

Formulations with varying silk fibroin concentrations and cryoprotectants

| Sample No. | Description | Silk Fibroin Conc. (mg/mL) | Cryo-protectant | [Cryo-protectant] mM |
|---|---|---|---|---|
| 83-1 | 0.5% SF in 10 mM phosphate, pH 7.4 | 5 | — | — |
| 83-2 | 1% SF in 10 mM phosphate, pH 7.4 | 10 | — | — |
| 83-3 | 2.5% SF in 10 mM phosphate, pH 7.4 | 25 | — | — |
| 83-4 | 5% SF in 10 mM phosphate, pH 7.4 | 50 | — | — |
| 83-5 | 5% SF, 10 mM sucrose in 10 mM phosphate, pH 7.4 | 50 | Sucrose | 10 |
| 83-6 | 5% SF, 50 mM sucrose in 10 mM phosphate, pH 7.4 | 50 | Sucrose | 50 |
| 83-7 | 5% SF, 100 mM sucrose in 10 mM phosphate, pH 7.4 | 50 | Sucrose | 100 |
| 83-8 | 5% SF, 150 mM sucrose in 10 mM phosphate, pH 7.4 | 50 | Sucrose | 150 |
| 83-9 | 5% SF, 10 mM trehalose in 10 mM phosphate, pH 7.4 | 50 | Trehalose | 10 |
| 83-10 | 5% SF, 50 mM trehalose in 10 mM phosphate, pH 7.4 | 50 | Trehalose | 50 |
| 83-11 | 5% SF, 100 mM trehalose in 10 mM phosphate, pH 7.4 | 50 | Trehalose | 100 |
| 83-12 | 5% SF, 150 mM trehalose in 10 mM phosphate, pH 7.4 | 50 | Trehalose | 150 |

The silk batch number 83 had a concentration of dialyzed silk fibroin of 5.9% as determined using UV-Vis assessment. The phosphate stock buffer (100 mM) was prepared by combining 20 ml of 100 mM monobasic potassium phosphate and 80 mL of 100 mM dibasic potassium phosphate and adjusting the pH to 7.4 using the 100 mM mono or dibasic phosphate solutions. The 1 M sucrose, 67 mM phosphate stock was prepared by dissolving 3.42 g sucrose in 6.7 mL of 100 mM phosphate buffer and filling up to 10 mL with DI water. The 0.67 M sucrose, 67 mM phosphate stock was prepared by dissolving 2.29 g of sucrose in 6.7 mL of 100 mM phosphate buffer and filling up to 10 mL with DI water. The 1 M sucrose stock was prepared by dissolving 3.42 g of sucrose in 6.7 mL of DI water and filling up to 10 mL with DI water. The 1 M trehalose, 67 mM phosphate stock was prepared by dissolving 3.42 g of trehalose in 6.7 mL of 100 mM phosphate buffer and filing up to 10 mL with DI water. The 0.67 M trehalose, 67 mM phosphate stock was prepared by dissolving 3.42 g of trehalose in 6.7 mL of 100 mM phosphate buffer and filing up to 10 mL with DI water. The 1 M trehalose stock was prepared by dissolving 3.42 g of trehalose in 6 mL DI water and filling up to 10 mL with DI water.

Each of the formulations was prepared as follows. Sample 83-1 (0.5% SF in 10 mM phosphate, pH 7.4) was prepared by adding 2.54 mL 5.9% silk fibroin stock, 3 mL 100 mM phosphate, pH 7.4, and 24.46 mL DI water in a 50 cc conical tube. Sample 83-2 (1% SF in 10 mM phosphate, pH 7.4) was prepared by adding 5.08 mL 5.9% silk fibroin stock, 3 mL 100 mM phosphate, pH 7.4, and 21.92 mL DI water in a 50 cc conical tube. Sample 83-3 (2.5% SF in 10 mM phosphate, pH 7.4) was prepared by adding 12.7 mL 5.9% silk fibroin stock, 3 mL 100 mM phosphate, pH 7.4, and 14.3 mL DI water in a 50 cc conical tube. Sample 83-4 (5% SF in 10 mM phosphate, pH 7.4) was prepared by adding 25.4 mL 5.9% silk fibroin stock, 3 mL 100 mM phosphate, pH 7.4, and 1.6 mL DI water in a 50 cc conical tube. Sample 83-5 (5% SF, 10 mM sucrose in 10 mM phosphate, pH 7.4) was prepared by adding 25.4 mL 5.9% silk fibroin stock, 3 mL 100 mM phosphate, pH 7.4, 300 μL 1M sucrose, and 1.3 ml DI water in a 50 cc conical tube. Sample 83-6 (5% SF, 50 mM sucrose in 10 mM phosphate, pH 7.4) was prepared by adding 25.4 mL 5.9% silk fibroin stock, 3 mL 100 mM phosphate, pH 7.4, 1.5 mL 1M sucrose, and 100 μL DI water in a 50 cc conical tube. Sample 83-7 (5% SF, 100 mM sucrose in 10 mM phosphate, pH 7.4) was prepared by adding 25.4 mL 5.9% silk fibroin stock, 4.5 ml 0.67M sucrose, 67 mM phosphate buffer, and 100 μL DI water in a 50 cc conical tube. Sample 83-8 (5% SF, 150 mM sucrose in 10 mM phosphate, pH 7.4) was prepared by adding 25.4 mL 5.9% silk fibroin stock, 4.5 mL 1M sucrose, 67 mM phosphate buffer, and 100 μL DI water in a 50 cc conical tube. Sample 83-9 (5% SF, 10 mM trehalose in 10 mM phosphate, pH 7.4) was prepared by adding 25.4 ml 5.9% silk fibroin stock, 3 mL 100 mM phosphate, pH 7.4, 300 μL 1M trehalose, and 1.3 ml DI water in a 50 cc conical tube. Sample 83-10 (5% SF, 50 mM trehalose in 10 mM phosphate, pH 7.4) was prepared by adding 25.4 ml. 5.9% silk fibroin stock, 3 mL 100 mM phosphate, pH 7.4, 1.5 ml. 1M trehalose, and 100 μL DI water in a 50 cc conical tube. Sample 83-11 (5% SF, 100 mM trehalose in 10 mM phosphate, pH 7.4) was prepared by adding 25.4 ml 5.9% silk fibroin stock, 4.5 mL 0.67M trehalose, 67 mM phosphate buffer, and 100 μL DI water in a 50 cc conical tube. Sample 83-12 (5% SF, 150 mM trehalose in 10 mM phosphate, pH 7.4) was prepared by adding 25.4 ml 5.9% silk fibroin stock, 4.5 ml 1M trehalose, 67 mM phosphate buffer, and 100 μL DI water in a 50 cc conical tube.

The rheology results and the size exclusion chromatography (SEC) results are presented in Table 46 and Table 47, respectively. In all conditions, the rheological properties of the silk fibroin solutions remained the same or showed a slight increase following freeze/thaw. The molecular weight by SEC did not change following freeze/thaw, however, a very slight increase in aggregation was observed for all samples. When sucrose or trehalose was used as an excipient, aggregation was shown to remain the same or decrease compared the control (no cryoprotectant at 5% (w/v).

TABLE 46

Rheological properties after freeze thaw

| Sample No. | Frozen | Viscosity (Pa*s) Avg. | Viscosity (Pa*s) Standard Dev. | G' (Pa) Avg. | G' (Pa) Standard Dev. | G" (Pa) Avg. | G" (Pa) Standard Dev. | Phase Angle (°) Avg. | Phase Angle (°) Standard Dev. |
|---|---|---|---|---|---|---|---|---|---|
| 83-1 | — | — | — | — | — | — | — | — | — |
| 83-1 | Y | — | — | — | — | — | — | — | — |
| 83-2 | — | 208.24 | 10.52 | 1.07E+00 | 7.56E−02 | 7.49E−01 | 2.55E−02 | 34.99 | 1.99 |
| 83-2 | Y | 265.7 | 39.98 | 1.32E+00 | 1.21E−01 | 1.01E+00 | 2.54E−01 | 37.1 | 4.24 |
| 83-3 | — | — | — | — | — | — | — | — | — |
| 83-3 | Y | — | — | — | — | — | — | — | — |
| 83-4 | — | 86.71 | 7.93 | 4.11E−01 | 4.73E−02 | 3.57E−01 | 2.74E−02 | 41.11 | 2.41 |
| 83-4 | Y | 120.28 | 15.33 | 5.48E−01 | 6.75E−02 | 5.19E−01 | 7.26E−02 | 43.69 | 1.75 |
| 83-5 | — | 118.53 | 11.54 | 5.74E−01 | 6.46E−02 | 4.73E−01 | 4.48E−02 | 39.57 | 2.35 |
| 83-5 | Y | 122.43 | 34.8 | 5.60E−01 | 1.47E−01 | 5.26E−01 | 1.64E−01 | 43.11 | 2.12 |
| 83-6 | — | — | — | — | — | — | — | — | — |
| 83-6 | Y | 134.4 | 1.76 | 6.40E−01 | 5.47E−02 | 5.47E−01 | 5.07E−02 | 40.67 | 5.03 |
| 83-7 | — | 82.57 | 10.4 | 3.92E−01 | 6.08E−02 | 3.39E−01 | 3.53E−02 | 41.01 | 2.92 |
| 83-7 | Y | 108.28 | 7.24 | 5.04E−01 | 4.65E−02 | 4.55E−01 | 4.39E−02 | 42.28 | 3.87 |
| 83-8 | — | 94.85 | 11.97 | 4.52E−01 | 7.23E−02 | 3.87E−01 | 4.19E−02 | 40.82 | 3.53 |
| 83-8 | Y | 112.06 | 32.05 | 5.22E−01 | 1.57E−01 | 4.71E−01 | 1.28E−01 | 42.43 | 1.1 |
| 83-9 | — | 84.11 | 10.1 | 3.95E−01 | 5.80E−02 | 3.50E−01 | 3.68E−02 | 41.66 | 2.93 |
| 83-9 | Y | 130.05 | 15.31 | 6.09E−01 | 7.05E−02 | 5.43E−01 | 6.83E−02 | 41.88 | 1.4 |
| 83-10 | — | 79.88 | 9.05 | 3.49E−01 | 6.10E−02 | 3.57E−01 | 4.44E−02 | 45.84 | 5.67 |
| 83-10 | Y | 105.12 | 30.49 | 4.74E−01 | 1.36E−01 | 4.58E−01 | 1.40E−01 | 44.22 | 3.07 |
| 83-11 | — | 70.31 | 8.22 | 3.26E−01 | 4.58E−02 | 2.97E−01 | 3.46E−02 | 42.5 | 3.28 |
| 83-11 | Y | 92.24 | 44.09 | 4.36E−01 | 1.95E−01 | 3.79E−01 | 2.00E−01 | 40.63 | 3.51 |
| 83-12 | — | 80.52 | 9.49 | 3.75E−01 | 6.29E−02 | 3.37E−01 | 3.00E−02 | 42.25 | 4.2 |
| 83-12 | Y | 113.08 | 17.18 | 5.32E−01 | 7.89E−02 | 4.70E−01 | 7.47E−02 | 41.64 | 0.93 |

TABLE 47

| Molecular weight and aggregation after freeze thaw | | | | | |
|---|---|---|---|---|---|
| Sample | | MW (Da) | | Aggregation (%) | |
| No. | Frozen | Avg. | Standard Dev. | Avg. | Standard Dev. |
| 83-1 | — | — | — | — | — |
| 83-1 | Y | 22730 | 166 | 0.17 | 0.01 |
| 83-2 | — | — | — | — | — |
| 83-2 | Y | 22768 | 162 | 0.25 | 0.09 |
| 83-3 | — | — | — | — | — |
| 83-3 | Y | 22659 | 229 | 0.11 | 0.04 |
| 83-4 | — | 23175 | — | 0.00 | — |
| 83-4 | Y | 22688 | 77 | 0.08 | 0.03 |
| 83-5 | — | 23151 | — | 0.00 | — |
| 83-5 | Y | 22491 | 595 | 0.09 | 0.03 |
| 83-6 | — | — | — | — | — |
| 83-6 | Y | 22377 | 408 | 0.08 | 0.05 |
| 83-7 | — | 23004 | — | 0.00 | — |
| 83-7 | Y | 22815 | 503 | 0.07 | 0.01 |
| 83-8 | — | 22955 | — | 0.00 | — |
| 83-8 | Y | 22818 | 224 | 0.07 | 0.05 |
| 83-9 | — | 23175 | — | 0.02 | — |
| 83-9 | Y | 22296 | 648 | 0.06 | 0.04 |
| 83-10 | — | 23102 | — | 0.00 | — |
| 83-10 | Y | 22506 | 555 | 0.18 | 0.09 |
| 83-11 | — | 23028 | — | 0.00 | — |
| 83-11 | Y | 22583 | 402 | 0.10 | 0.02 |
| 83-12 | — | 23004 | — | 0.00 | — |
| 83-12 | Y | 22486 | 325 | 0.06 | 0.02 |

Example 28. Residence Time of Silk Fibroin in Rabbit Tears

Silk Fibroin Isolation

Silk yarn, purchased from Jiangsu SOHO International Group, was degummed to remove sericin. 210 grams of cut silk yarn were degummed at 85° C. in 7 L of deionized (DI) water with 0.5 M sodium carbonate with agitation for 4 hrs. Following degumming, the silk was squeezed to remove the degumming solution and rinsed in 3×10 minute DI water rinses at 70° C. Water was squeezed from the silk masses between each rinse. This was followed by rinsing under running DI water at RT for 2 minutes. All 70° C. rinses were performed at the same initial silk/degumming solution ratio of 30 g/L. Following the final rinse, silk was squeezed to remove water. The fibroin was dried overnight, weighed, and dissolved at 20% (w/v) in a 9.3 M aqueous solution of lithium bromide (from Sigma-Aldrich, St. Louis, MO) for 4 hours at 60° C. The resulting fibroin solution was dialyzed against water at 4° C. in 50 kDa regenerated cellulose dialysis tubing for 48 hours, with 8 water changes to remove the excess salt. The conductivity was recorded after each water change with a digital quality tester. When the conductivity was under 5 ppm, the fibroin solution was determined to be ready.

The resulting solution was filtered under aseptic conditions through a 0.2 μm filter using a vacuum filtration unit and stored at 4° C. Concentration of the silk fibroin was determined using gravimetric analysis

Formulation Preparation

2% and 3% (w/v) SF formulations were prepared from an aseptically prepared 4.81% (w/v) SF stock solution, degummed, purified, and filtered as described above. Stock solutions of 100 mM Phosphate Buffer, pH 7.4 and 1 M sodium chloride were used in formulation preparation. The 100 mM phosphate stock solution was prepared by dissolving 568 mg of disodium phosphate and 136 mg of monopotassium phosphate in 90 ml DI water. The pH was adjusted to 7.4 with 1 N hydrochloric acid and sodium hydroxide. The solution was brought to a final volume of 100 mL with DI water. Under aseptic conditions, the solution was filtered through a 0.22 μm polyether sulfone (PES) filter into a sterile container. The 1 M sodium chloride in water stock solution was prepared by dissolving 2.922 g sodium chloride in 40 mL DI water. The volume was adjusted to 50 mL with DI water and the solution was filtered through a 0.22 μm polyether sulfone (PES) filter into a sterile container under aseptic conditions.

The SF formulations were prepared as described in Table 48. The 2% (w/v) SF in phosphate buffer formulation was prepared by combining 20.79 mL of a 4.81% (w/v) SF stock solution, 5 mL of the 100 mM phosphate buffer (pH 7.4) stock, 6.75 mL 1M sodium chloride stock, and 17.46 mL DI water under aseptic conditions. The pH was adjusted to 7.3 using 1N NaOH and 1N HCl and DI water was added to bring to a final volume of 50 mL. The formulation was filtered through a sterile 0.22 μm PES filter into a sterile container under aseptic conditions and stored at 4° C. prior to use. The 3% (w/v) SF in phosphate buffer formulation was prepared by combining 31.19 mL of a 4.81% (w/v) SF stock solution, 5 mL of a 100 mM phosphate buffer (pH 7.4) stock solution, 6.75 mL 1M sodium chloride stock solution, and 7.07 mL DI water under aseptic conditions. The pH was adjusted to 7.3 using 1N NaOH and 1N HCl and DI water was added to bring to a final volume of 50 mL. The formulation was filtered through a sterile 0.22 μm PES filter into a sterile container under aseptic conditions and stored at 4° C. prior to use.

TABLE 48

| SF Formulations for Rabbit Tear Film Residence | | | | | | | | |
|---|---|---|---|---|---|---|---|---|
| Formulation ID# | Description | Silk Fibroin Conc. (%) | Phosphate Buffer Conc. (mM) | NaCl Conc. (mM) | 4.81% SF Stock (mL) | 100 mM PB Stock (mL) | 1M NaCl Stock (mL) | DI water (mL) |
| RT-01-A | 2% (w/V) SF in Phosphate Buffer | 2 | 10 | 135 | 20.79 | 5 | 6.75 | 17.46 |
| RT-01-B | 3% (w/v) SF in Phosphate Buffer | 3 | 10 | 135 | 31.19 | 5 | 6.75 | 7.07 |

Ocular Residence Time

A total of 12 rabbits were used to collect tears at the following timepoints: naïve, 0, 0.5, 1, 2, 4, 8, 16, and 24 hrs. post SF formulation dosing. Tear samples from naïve animals were collected using the following procedure. 20 μL saline was administered into the lower lid (right) of each rabbit (n=4/timepoint). Rabbits had not previously received any SF formulations. Eyes were manually blinked 3-4 times prior to sampling to ensure tear homogeneity with the saline drop. A 10 μL glass capillary was placed in the lower eye lid and maneuvered until a ~7-10 μL tear fluid sample was collected. Tears were dispensed into individual pre-tared 500 μL Eppendorf tubes and stored at 4° C. prior to analysis. Animals were re-enrolled following naïve collection.

To determine the residence time of silk in the tear film, 40 μL of a SF formulation was administered into the lower eye lid (n=4/timepoint). The rabbits' right eyes received the 2% (w/v) SF formulation and left eyes received the 3% (w/v) SF formulation. Rabbits were dosed separately for each timepoint. After timepoint collection, eyes were flushed with saline and animals were re-enrolled for another dose and timepoint collection (as described below).

A To sample was collected as follows. Eyes were manually blinked 3-4 times after the formulation was administered. A 10 μL glass capillary was placed in the lower eye lid and maneuvered until a ~7-10 μL tear fluid sample was collected. Tears were dispensed into individual pre-tared 500 μL Eppendorf tubes and stored at 4° C. prior to analysis For timepoint collection of tears, 20 μL saline was administered into the lower lid (left or right) of the eye at the time of collection. Eyes were manually blinked 3-4 times prior to sampling to ensure tear homogeneity with the saline. A 10 μL glass capillary was placed in the lower eye lid and maneuvered until a ~7-10 μL tear fluid sample was collected. Tears were dispensed into individual pre-tared 500 μL Eppendorf tubes and stored at 4° C. prior to analysis. Following collection of tears, the eyes were flushed with 1cc. saline. Animals were left to rest for at least 30 min. prior to being re-enrolled for an additional timepoint. The dosing and collection schedule can be seen in Table 49 and the tear collection and sample weights in Table 50.

TABLE 49

Rabbit dosing and Collection Schedule

| Timepoint (hrs.) | Actual Timepoint (hrs.) | Formulation | Animal # | Tube # |
|---|---|---|---|---|
| 0 | N/A | N/A | B1-R | 1 |
| 0 | N/A | N/A | B2-R | 2 |
| 0 | N/A | N/A | B3-R | 3 |
| 0 | N/A | N/A | B4-R | 4 |
| 0 | 0.0 | 2% SF | B1-R | 5 |
| 0 | 0.0 | 2% SF | B2-R | 6 |
| 0 | 0.0 | 2% SF | B3-R | 7 |
| 0 | 0.0 | 2% SF | B4-R | 8 |
| 0.5 | 0.5 | 2% SF | C1-R | 9 |
| 0.5 | 0.5 | 2% SF | C2-R | 10 |
| 0.5 | 0.5 | 2% SF | C3-R | 11 |
| 0.5 | 0.6 | 2% SF | C4-R | 12 |
| 1 | 1.0 | 2% SF | B1-R | 13 |
| 1 | 1.0 | 2% SF | B2-R | 14 |
| 1 | 1.1 | 2% SF | B3-R | 15 |
| 1 | 1.1 | 2% SF | B4-R | 16 |
| 2 | 2.0 | 2% SF | A1-R | 17 |
| 2 | 2.0 | 2% SF | A2-R | 18 |
| 2 | 2.1 | 2% SF | A3-R | 19 |
| 2 | 2.2 | 2% SF | A4-R | 20 |

TABLE 49-continued

Rabbit dosing and Collection Schedule

| Timepoint (hrs.) | Actual Timepoint (hrs.) | Formulation | Animal # | Tube # |
|---|---|---|---|---|
| 4 | 4.0 | 2% SF | B1-R | 21 |
| 4 | 4.0 | 2% SF | B2-R | 22 |
| 4 | 4.0 | 2% SP | B3-R | 23 |
| 4 | 4.1 | 2% SF | B4-R | 24 |
| 8 | 8.0 | 2% SF | A1-R | 25 |
| 8 | 7.9 | 2% SF | A2-R | 26 |
| 8 | 7.9 | 2% SF | A3-R | 27 |
| 8 | 7.8 | 2% SF | A4-R | 28 |
| 16 | 16.0 | 2% SF | B1-R | 29 |
| 16 | 16.0 | 2% SF | B2-R | 30 |
| 16 | 16.1 | 2% SF | B3-R | 31 |
| 16 | 16.1 | 2% SF | B4-R | 32 |
| 24 | 23.8 | 2% SF | C1-R | 33 |
| 24 | 23.9 | 2% SF | C2-R | 34 |
| 24 | 24.0 | 2% SF | C3-R | 35 |
| 24 | 24.0 | 2% SF | C4-R | 36 |
| 0 | 0.0 | 3% SF | B1-L | 37 |
| 0 | 0.0 | 3% SF | B2-L | 38 |
| 0 | 0.0 | 3% SF | B3-L | 39 |
| 0 | 0.0 | 3% SF | B4-L | 40 |
| 0.5 | 0.5 | 3% SF | C1-L | 41 |
| 0.5 | 0.6 | 3% SF | C2-L | 42 |
| 0.5 | 0.6 | 3% SF | C3-L | 43 |
| 0.5 | 0.6 | 3% SF | C4-L | 44 |
| 1 | 1.0 | 3% SF | B1-L | 45 |
| 1 | 1.1 | 3% SF | B2-L | 46 |
| 1 | 1.1 | 3% SF | B3-L | 47 |
| 1 | 1.1 | 3% SF | B4-L | 48 |
| 2 | 2.0 | 3% SF | A1-L | 49 |
| 2 | 2.1 | 3% SF | A2-L | 50 |
| 2 | 2.1 | 3% SF | A3-L | 51 |
| 2 | 2.2 | 3% SF | A4-L | 52 |
| 4 | 4.0 | 3% SF | B1-L | 53 |
| 4 | 4.0 | 3% SF | B2-L | 54 |
| 4 | 4.1 | 3% SF | B3-L | 55 |
| 4 | 4.1 | 3% SF | B4-L | 56 |
| 8 | 8.0 | 3% SF | A1-L | 57 |
| 8 | 8.0 | 3% SF | A2-L | 58 |
| 8 | 7.9 | 3% SF | A3-L | 59 |
| 8 | 7.8 | 3% SF | A4-L | 60 |
| 16 | 16.0 | 3% SF | B1-L | 61 |
| 16 | 16.1 | 3% SF | B2-L | 62 |
| 16 | 16.1 | 3% SF | B3-L | 63 |
| 16 | 16.2 | 3% SF | B4-L | 64 |
| 24 | 23.8 | 3% SF | C1-L | 65 |
| 24 | 24.0 | 3% SF | C2-L | 66 |
| 24 | 24.0 | 3% SF | C3-L | 67 |
| 24 | 24.1 | 3% SF | C4-4 | 68 |

Weights of all of the tear samples were recorded (Table 50) and 7 μL of a protease inhibitor cocktail was added to each tube. The protease inhibitor cocktail was prepared as an aqueous solution containing 5 mM EDTA, 0.5 mM AEBSF, 5 mM benzamidine, 1 μM pepstatin, and 1 mM leupeptin under aseptic conditions Tubes containing tear samples in protease cocktail were stored at 4° C. prior to analysis via meso scale discovery.

TABLE 50

Tear Collection Sample Weights

| Samples | Formulation | Timepoint | Tare Weight (mg) | Final Weight (mg) | Sample Weight (mg) |
|---|---|---|---|---|---|
| PARF-RES-2-1 | N/A | Naive | 503.7 | 510.8 | 7.1 |
| PARF-RES-2-2 | N/A | Naive | 504.6 | 512.6 | 8.0 |
| PARF-RES-2-3 | N/A | Naive | 508.5 | 516.0 | 7.5 |
| PARF-RES-2-4 | N/A | Naive | 502.6 | 510.5 | 7.9 |
| PARF-RES-2-5 | 2% SF | 0 | 505.9 | 512.0 | 6.1 |
| PARF-RES-2-6 | 2% SF | 0 | 504.5 | 512.7 | 8.2 |
| PARF-RES-2-7 | 2% SF | 0 | 503.1 | 511.1 | 8.0 |
| PARF-RES-2-8 | 2% SF | 0 | 504.4 | 513.5 | 9.1 |

TABLE 50-continued

| Tear Collection Sample Weights | | | | | |
|---|---|---|---|---|---|
| Samples | Formulation | Timepoint | Tare Weight (mg) | Final Weight (mg) | Sample Weight (mg) |
| PARF-RES-2-9 | 2% SF | 0.5 | 502.7 | 508.9 | 6.2 |
| PARF-RES-2-10 | 2% SF | 0.5 | 498.8 | 507.0 | 8.2 |
| PARF-RES-2-11 | 2% SF | 0.5 | 503.6 | 510.7 | 7.1 |
| PARF-RES-2-12 | 2% SF | 0.5 | 500.0 | 505.4 | 5.4 |
| PARF-RES-2-13 | 2% SF | 1 | 504.5 | 512.0 | 7.5 |
| PARF-RES-2-14 | 2% SF | 1 | 503.0 | 510.8 | 7.8 |
| PARF-RES-2-15 | 2% SF | 1 | 506.1 | 512.6 | 6.5 |
| PARF-RES-2-16 | 2% SF | 1 | 505.9 | 509.8 | 3.9 |
| PARF-RES-2-17 | 2% SF | 2 | 503.7 | 509.1 | 5.4 |
| PARF-RES-2-18 | 2% SF | 2 | 499.9 | 506.6 | 6.7 |
| PARF-RES-2-19 | 2% SF | 2 | 503.6 | 511.4 | 7.8 |
| PARF-RES-2-20 | 2% SF | 2 | 499.8 | 509.2 | 9.4 |
| PARF-RES-2-21 | 2% SF | 4 | 499.9 | 507.6 | 7.7 |
| PARF-RES-2-22 | 2% SF | 4 | 498.8 | 505.8 | 7.0 |
| PARF-RES-2-23 | 2% SF | 4 | 498.9 | 506.7 | 7.8 |
| PARF-RES-2-24 | 2% SF | 4 | 504.5 | 509.0 | 4.5 |
| PARF-RES-2-25 | 2% SF | 8 | 502.6 | 510.0 | 7.4 |
| PARF-RES-2-26 | 2% SF | 8 | 502.5 | 508.2 | 5.7 |
| PARF-RES-2-27 | 2% SF | 8 | 503.7 | 513.3 | 9.6 |
| PARF-RES-2-28 | 2% SF | 8 | 502.8 | 510.0 | 7.2 |
| PARF-RES-2-29 | 2% SF | 16 | 504.5 | 516.6 | 12.1 |
| PARF-RES-2-30 | 2% SF | 16 | 502.9 | 511.6 | 8.7 |
| PARF-RES-2-31 | 2% SF | 16 | 506.8 | 513.3 | 6.5 |
| PARF-RES-2-32 | 2% SF | 16 | 500.0 | 506.7 | 6.7 |
| PARF-RES-2-33 | 2% SF | 24 | 498.9 | 505.1 | 6.2 |
| PARF-RES-2-34 | 2% SF | 24 | 499.7 | 502.5 | 2.8 |
| PARF-RES-2-35 | 2% SF | 24 | 502.5 | 511.4 | 8.9 |
| PARF-RES-2-36 | 2% SF | 24 | 492.4 | 498.2 | 5.8 |
| PARF-RES-2-37 | 3% SF | 0 | 502.3 | 506.4 | 4.1 |
| PARF-RES-2-38 | 3% SF | 0 | 506.9 | 516.4 | 9.5 |
| PARF-RES-2-39 | 3% SF | 0 | 500.0 | 506.9 | 6.9 |
| PARF-RES-2-40 | 3% SF | 0 | 501.3 | 510.2 | 8.9 |
| PARF-RES-2-41 | 3% SF | 0.5 | 502.7 | 510.0 | 7.3 |
| PARF-RES-2-42 | 3% SF | 0.5 | 502.5 | 511.7 | 9.2 |
| PARF-RES-2-43 | 3% SF | 0.5 | 501.3 | 507.6 | 6.3 |
| PARF-RES-2-44 | 3% SF | 0.5 | 504.5 | 513.4 | 8.9 |
| PARF-RES-2-45 | 3% SF | 1 | 498.8 | 500.1 | 1.3 |
| PARF-RES-2-46 | 3% SF | 1 | 504.5 | 511.2 | 6.7 |
| PARF-RES-2-47 | 3% SF | 1 | 502.7 | 509.0 | 6.3 |
| PARF-RES-2-48 | 3% SF | 1 | 506.7 | 512.0 | 5.3 |
| PARF-RES-2-49 | 3% SF | 2 | 506.9 | 515.7 | 8.8 |
| PARF-RES-2-50 | 3% SF | 2 | 502.6 | 508.9 | 6.3 |
| PARF-RES-2-51 | 3% SF | 2 | 501.2 | 509.1 | 7.9 |
| PARF-RES-2-52 | 3% SF | 2 | 502.4 | 510.0 | 7.6 |
| PARF-RES-2-53 | 3% SF | 4 | 508.7 | 514.8 | 6.1 |
| PARF-RES-2-54 | 3% SF | 4 | 502.7 | 511.6 | 8.9 |
| PARF-RES-2-55 | 3% SF | 4 | 502.7 | 506.8 | 4.1 |
| PARF-RES-2-56 | 3% SF | 4 | 502.5 | 507.2 | 4.7 |
| PARF-RES-2-57 | 3% SF | 8 | 499.9 | 503.3 | 3.4 |
| PARF-RES-2-58 | 3% SF | 8 | 501.4 | 508.0 | 6.6 |
| PARF-RES-2-59 | 3% SF | 8 | 501.2 | 505.7 | 4.5 |
| PARF-RES-2-60 | 3% SF | 8 | 502.7 | 511.4 | 8.7 |
| PARF-RES-2-61 | 3% SF | 16 | 503.0 | 509.5 | 6.5 |
| PARF-RES-2-62 | 3% SF | 16 | 499.7 | 508.1 | 8.4 |
| PARF-RES-2-63 | 3% SF | 16 | 501.2 | 511.6 | 10.4 |
| PARF-RES-2-64 | 3% SF | 16 | 502.6 | 509.9 | 7.3 |
| PARF-RES-2-65 | 3% SF | 24 | 503.6 | 511.4 | 7.8 |
| PARF-RES-2-66 | 3% SF | 24 | 500.0 | 504.3 | 4.3 |
| PARF-RES-2-67 | 3% SF | 24 | 502.7 | 509.5 | 6.8 |
| PARF-RES-2-68 | 3% SF | 24 | 500.0 | 508.5 | 8.5 |

The concentration of SF in the tear samples was determined using a meso scale discovery (MSD) assay as follows. A SF standard curve was prepared from 97 ng/mL-25 μg/mL SF using the 3% (w/v) SF formulation used in the residence time study.

Quality control samples were prepared by making dilutions of SF standards in the protease cocktail solution (PC) using the 1 g/mL SF standard. The 1 μg/mL SF standard was diluted 25-fold by diluting 20 μL with 480 μL of PC. The resulting 40 ng/mL solution was then diluted 8-fold by diluting 60 μL with 420 μL of PC. The resulting 5 ng/mL SF solution was then diluted 33.33-fold by diluting 15 μL with 485 μL of PC to generate a 150 μg/mL SF solution. The 40 ng/mL, 5 ng/mL and 150 μg/mL solutions were then diluted 10-fold in universal assay buffer (UAB) to prepare a 15 μg/mL SF solution.

A solution of 2 μg/mL E8186 anti-silk fibroin capture antibody was prepared in PBS. The MSD plate was coated overnight with 50 μL of capture antibody at 4° C. The following morning, the plate was washed three times with 300 μL/well with phosphate buffered saline with Tween (PBST). To prevent non-specific binding, the wells were blocked with 150 μL of PBST containing 3% BSA for 1 hour with gentle shaking at room temperature. The wells were then washed 3 times with 150 μL of PBST. 25 μL of the SF standards, QC samples, and in vivo tear samples were then added to the appropriate wells. The plate was incubated for 1 hour at room temperature with gentle shaking. The wells were then washed 3 times with 150 μL of PBST. 25 μL of E8185 anti-silk fibroin ruthenylated detection antibody was added to each well. The plate was incubated for 1 hour at room temperature with gentle shaking. The wells were then washed with 150 μL of PBST. 150 μL of 2×MSD Read Buffer was added to each well and the plates were read on an s600 MSD instrument.

SF was detected in all of the tear fluid samples throughout the study. Tear sample dilutions were based on previous residence time data using a fluorescein tagged SF for timepoints 0-4 hrs., while timepoints from 8 hrs.-24 hrs. (assumed to be low concentration) were analyzed with no dilution. Both 2% and 3% SF formulations displayed similar residence and clearance profiles. Concentrations dropped to 0.1-0.2 mg/mL over the first hour, but were maintained in this range (0.1-0.7 mg/mL) over 4 hrs. By 8 hrs., concentrations had dropped 1000-fold to 0.2 μg/mL. This concentration (0.1-0.2 μg/mL) was maintained and silk fibroin was detected in tear fluid at 16 and 24 hrs. Analysis of samples from 4 hrs.-24 hrs. produced values that were above the detection limit for the MSD assay. This indicated that the calculated values were higher than the extrapolated values calculated.

TABLE 50a

Concentration of silk fibroin in rabbit tear fluid over 24 hours

| Formulation | Timepoint | Dilution Factor | MSD Signal | Average (mg/mL) | Standard Deviation (mg/mL) |
|---|---|---|---|---|---|
| N/A | Naïve | 1 | 1865 | $9.65 \times 10^{-6}$ | $1.37 \times 10^{-5}$ |
| 2% SF | 0 | 1000000 | 9912 | 85.3 | 36.2 |
| | 0.5 | 250000 | 2738 | 6.63 | 10.2 |
| | 1 | 50000 | 571 | 0.121 | 0.178 |
| | 2 | 50000 | 5199 | 0.701 | 0.622 |
| | 4 | 5000 | 30437 | 0.24 | 0.172 |
| | 8 | 1 | 20463 | $2.33 \times 10^{-4}$ (n = 1) | N/A |
| | 16 | 1 | 18968 | AQL | N/A |
| | 24 | 1 | 16579 | $1.27 \times 10^{-4}$ (n = 2) | $1.37 \times 10^{-4}$ |
| 3% SF | 0 | 1000000 | 18193 | 119.3 | 19 |
| | 0.5 | 250000 | 7589 | 25.4 | 32.6 |
| | 1 | 50000 | 1059 | 0.189 | 0.253 |
| | 2 | 50000 | 3590 | 0.458 | 0.441 |
| | 4 | 5000 | 8890 | 0.454 | 0.346 |
| | 8 | 1 | 11727 | $2.22 \times 10^{-4}$ (n = 2) | $2.55 \times 10^{-4}$ |
| | 16 | 1 | 14353 | $9.25 \times 10^{-5}$ (n = 1) | N/A |
| | 24 | 1 | 13126 | $8.9 \times 10^{-5}$ (n = 2) | $5.95 \times 10^{-5}$ |

Example 29. Meso Scale Discovery Assay Development

Optimization of Signal to Noise Ratio

In order to determine the residence time of silk fibroin solutions dosed on the front of the eye, a Meso Scale Discovery Assay (MSD) was developed in conjunction with KCAS Bioanalytical Services. MSD assays are utilized due to the higher limit of quantitation due to the use of a ruthenylated detection antibody.

1 L of 0.5 M sodium carbonate was prepared by dissolving 53 g of sodium carbonate in sufficient water to reach 1 L. The sodium carbonate solution was heated to 85° C. in a circulating water bath. When the temperature reached 85° C., 30 g of silk yarn (SOHO) was added to the bottle. The silk yarn was degummed for 4 hours at 85° C. After 4 hours, the silk fibroin fibers were removed from the carbonate solution and washed 3 times in 3 L of 70° C. DI water followed by an additional 3 washes in 3 L of room temperature DI water. The fibers were squeezed to remove excess water, stretched, and dried overnight in a fume hood.

The fibroin fibers were dissolved at 20% in a 9.3 M lithium bromide solution overnight at 60° C. Following dissolution, the silk fibroin was dialyzed for 48 hours at room temperature against 5 L of DI water. The dialysis solution was exchanged 4 times over the 48 hours.

The concentration of silk fibroin was determined by loss on drying. The mass of five hexagonal weigh boats was recorded. To each weigh boat, 1 mL of silk fibroin solution was added. The samples were placed at 60° C. overnight. The following morning the mass of the weigh boat and silk fibroin were recorded and the concentration of silk fibroin determined. The silk fibroin was then diluted to 5% SF and sucrose was added to final concentration of 50 mg/mL. The SF solutions were frozen at −80° C.

The molecular weight of the SF was determined by size exclusion chromatography (SEC). For SEC analysis, a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 ml of DI water. The pH was adjusted to 8.0 with 6N HCl. DI water was added to a final volume of 1 L. The solution was sterile filtered through a 0.2 μm polyethersulfone membrane filter. SF elution was monitored at 280 nm. Molecular weights were calculated using a standard curve prepared from Waters BEH 200 Å Protein SEC Standard Mix (Waters, Milford, MA). The molecular weight of SF solution (Batch 114) was 30.5 kDa.

A polyclonal antibody against silk fibroin (E8185) was ruthenylated by KCAS Bioanalytical Services according to the MSD Gold Sulfo-Tag NHS-Ester conjugation pack protocol provided by Meso Scale Discovery (cat #R31AA).

To determine the best concentration of capture and detection antibody, a screen was run at varying concentration of capture and detection antibodies over a silk fibroin concentration range of 0.1 ng/mL to 80 ng/mL. An MSD small spot plate was incubated with 25 μL per well of 0.1 μg/mL, 0.5 μg/mL, 1.0 μg/mL, and 2.0 μg/mL capture antibody E8186 overnight at 4° C. Wells were prepared in duplicate. The following morning, the plate was then washed 3 times with 150 μL/well of PBS-T. The wells were then incubated with 150 μL of blocking buffer consisting of PBS-T with 3% BSA at room temperature for 1 hr.

Quality control samples of silk fibroin were prepared in UAB consisting of PBS with 0.1% Tween 20 and 0.5 mg/mL ovalabumin, pH 7.4. Silk fibroin samples were prepared at 100 μg/mL, 5,000 μg/mL, and 80,000 μg/mL. The wells were incubated with 25 μL of silk fibroin samples and incubated at room temperature for 1 hr with shaking at 450 rpm on an orbital shaker. The wells were then washed 3 times with 150 μL per well of PBS-T.

To each well, 25 μL of ru-E8185 was added and incubated at room temperature for 1 hr. with shaking at 450 rpm. The plate was then washed 3 times with 150 μL PBS-T. 150 μL of 2×MSD Read Buffer was added to each well. The plate was read on an s600 MSD instrument.

The signal to noise ratio (S:N) was calculated based up the ratio of mean absorbance at 450 nm for the silk fibroin samples vs the mean absorbance at 450 nm for blank wells containing no silk fibroin. As shown in Table 51, the best S:N ratio was achieved at 2.0 μg/mL capture antibody ru-E8185 with either 1.0 μg/mL or 0.5 μg/mL detection antibody E8186. Given the limited availability of the polyclonal antibodies; 0.5 μg/mL ru-E8185 was selected as the concentration in future studies.

TABLE 51

Results for Determining the Optimal Ratios of Capture: Detection Antibody for Use in SF MSD Assay.

ru-E8185 Detection Ab at 1.0 ug/mL E8186 0.1 ug/mL

| pg/mL SF | 80000 | | 5000 | | 100 | | Blank |
|---|---|---|---|---|---|---|---|
| Raw Data | 1365 | 1611 | 830 | 825 | 204 | 199 | 101 |
| Mean | 1488 | | 827.5 | | 201.5 | | — |
| Blank Mean | 101 | | 101 | | 101 | | — |
| S:N Ratio | 14.7 | | 8.2 | | 2.0 | | — |

ru-E8185 Detection Ab at 1.0 ug/mL E8186 0.5 ug/ml

| pg/mL SF | 80000 | | 5000 | | 100 | | Blank |
|---|---|---|---|---|---|---|---|
| Raw Data | 8274 | 8510 | 4322 | 3925 | 606 | 604 | 101.5 |
| Mean | 8392 | | 4123.5 | | 605 | | — |
| Blank Mean | 101.5 | | 101.5 | | 101.5 | | — |
| S:N Ratio | 82.7 | | 40.6 | | 6.0 | | — |

ru-E8185 Detection Ab at 1.0 ug/mL E8186 1.0 ug/mL

| pg/mL SF | 80000 | | 5000 | | 100 | | Blank |
|---|---|---|---|---|---|---|---|
| Raw Data | 20287 | 18400 | 9040 | 8938 | 905 | 935 | 103.5 |
| Mean | 19343.5 | | 8989 | | 920 | | — |
| Blank Mean | 103.5 | | 103.5 | | 103.5 | | — |
| S:N Ratio | 186.9 | | 86.9 | | 8.9 | | — |

ru-E8185 Detection Ab at 1.0 ug/mL E8186 2.0 ug/ml

| pg/mL SF | 80000 | | 5000 | | 100 | | Blank |
|---|---|---|---|---|---|---|---|
| Raw Data | 36841 | 30710 | 15911 | 13247 | 961 | 979 | 101.5 |
| Mean | 33775.5 | | 14579 | | 970 | | — |
| Blank Mean | 101.5 | | 101.5 | | 101.5 | | — |
| S:N Ratio | 332.8 | | 143.6 | | 9.6 | | — |

ru-E8185 Detection Ab at 0.5 ug/mL E8186 0.1 ug/ml

| pg/mL SF | 80000 | | 5000 | | 100 | | Blank |
|---|---|---|---|---|---|---|---|
| Raw Data | 1552 | 1575 | 798 | 808 | 196 | 204 | 89.5 |
| Mean | 1563.5 | | 803 | | 200 | | — |
| Blank Mean | 89.5 | | 89.5 | | 89.5 | | — |
| S:N Ratio | 17.5 | | 9.0 | | 2.2 | | — |

ru-E8185 Detection Ab at 0.5 ug/mL E8186 0.1 ug/ml

| pg/mL SF | 80000 | | 5000 | | 100 | | Blank |
|---|---|---|---|---|---|---|---|
| Raw Data | 8293 | 8353 | 3721 | 4366 | 565 | 595 | 84.5 |
| Mean | 8323 | | 4043.5 | | 580 | | — |
| Blank Mean | 84.5 | | 84.5 | | 84.5 | | — |
| S:N Ratio | 98.5 | | 47.9 | | 6.9 | | — |

TABLE 51-continued

Results for Determining the Optimal Ratios of Capture: Detection Antibody for Use in SF MSD Assay.

ru-E8185 Detection Ab at 0.5 ug/mL E8186 0.1 ug/ml

| pg/mL SF | 80000 | | 5000 | | 100 | | Blank |
|---|---|---|---|---|---|---|---|
| Raw Data | 19061 | 18497 | 9424 | 8839 | 847 | 774 | 96 |
| Mean | 18779 | | 9131.5 | | 810.5 | | — |
| Blank Mean | 96 | | 96 | | 96 | | — |
| S:N Ratio | 195.6 | | 95.1 | | 8.4 | | — |

ru-E8185 Detection Ab at 0.5 ug/mL E8186 2.0 ug/mL

| pg/mL SF | 80000 | | 5000 | | 100 | | Blank |
|---|---|---|---|---|---|---|---|
| Raw Data | 35175 | 31913 | 17478 | 14505 | 977 | 899 | 107 |
| Mean | 33544 | | 15991.5 | | 938 | | — |
| Blank Mean | 107 | | 107 | | 107 | | — |
| S:N Ratio | 313.5 | | 149.5 | | 8.8 | | — |

Dynamic Range of MSD Assay for Silk Fibroin

To determine the dynamic range of the MSD assay, silk fibroin concentrations were varied from 48.8 μg/mL to 100,000 μg/mL and assayed using 2.0 μg/mL capture antibody and 0.5 μg/mL detection antibody.

MSD small spot plate was incubated overnight at room temperature with 2.0 μg/mL E8186 capture antibody. The following morning the plate was washed 3 times with 150 μL per well of PBS-T. The plate was then blocked for 1 hr. at room temperature with PBS-T containing 3% BSA. The plate was then washed 3 times with 150 μl of PBS-T. 25 μL of silk fibroin solutions ranging from 48.8 μg/mL to 100,000 μg/mL in UAB were incubated at room temperature for 1 hr. with shaking at 450 rpm. The wells were then washed 3 times with 150 μL PBS-T. The wells were then incubated with 25 μl of ru-E8185 at room temperature for 1 hr. with shaking at 450 rpm. The wells were then washed three times with 150 μL of PBS-T. To each well, 150 μL of 2×MSD Read Buffer was added and the absorbance at 450 nm measured with a s600 MSD plate reader.

As shown in Table 52, the dynamic range of the MSD assay appears to be 48.8-3125 μg/mL. At concentrations above 3125 μg/mL the assay under measures the concentration of silk fibroin. At or below 3125 μg/mL, the assay measures to ≥90% of the known concentration.

TABLE 52

MSD Results Using Known Concentrations of Silk Fibroin relative to a Standard Curve of Silk Fibroin Standards (Treated as Unknowns)

| Standard | Nominal Concentration (pg/mL) | Calculated Concentration (pg/mL) | % Recovery | % CV |
|---|---|---|---|---|
| 1 | 100000 | 31117 | 31.1 | 21.2 |
| 2 | 50000 | 24931 | 49.9 | 16.5 |
| 3 | 25000 | 9829 | 39.3 | 5.05 |
| 4 | 12500 | 5255 | 42.0 | 10.4 |
| 5 | 6250 | 4161 | 66.6 | 12.8 |
| 6 | 3125 | 2832 | 90.6 | 18.1 |
| 7 | 1563 | 1707 | 109 | 8.77 |
| 8 | 781 | 917 | 117 | 0.098 |
| 9 | 391 | 392 | 100 | 22.8 |
| 10 | 195 | 187 | 95.9 | 1.97 |
| 11 | 97.7 | 88.8 | 90.9 | 5.46 |
| 12 | 48.8 | 51.0 | 105 | 4.35 |

When performing in vivo residence time studies, the volume recovered from the front of the rabbit eye is ≤10 μL.

Due to the limited sample volume, a 10-fold dilution is required to supply sufficient volume for the assay. A repeat assaying using 10-fold dilutions of the silk fibroin standards described above was then used to determine the dynamic range of the assay with 10-fold dilution of SF samples in UAB. As shown in Table 53, the dilution requirement extends the dynamic range of the assay to 195-25,000 μg/mL.

TABLE 53

MSD Results Using Known Concentrations of Silk Fibroin Relative to a Standard Curve of Silk Fibroin 1:10 Standards (MRD 1:10)

| Standard | Nominal Concentration (pg/mL) | Calculated Concentration (pg/mL) | % Recovery | % CV |
|---|---|---|---|---|
| 1 | 100000 | 109696 | 110 | 28.2 |
| 2 | 50000 | 54288 | 109 | 50.3 |
| 3 | 25000 | 24566 | 98.3 | 7.27 |
| 4 | 12500 | 12457 | 100 | 2.54 |
| 5 | 6250 | 6418 | 103 | 3.26 |
| 6 | 3125 | 2999 | 96.0 | 11.6 |
| 7 | 1563 | 1607 | 103 | 4.70 |
| 8 | 781 | 828 | 106 | 0.000 |
| 9 | 391 | 373 | 95.6 | 0.000 |
| 10 | 195 | 169 | 86.3 | 6.52 |
| 11 | 97.7 | 144 | 147 | 65.5 |
| 12 | 48.8 | 37.2 | 76.3 | 59.6 |

Evaluation of Matrix Effects on Sample Analysis

To evaluate matrix effects on MSD assay sensitivity, the assay was conducted using silk fibroin samples in the presence of rabbit tears and human plasma. New Zealand White rabbits were given a pre-anesthetic of 1.1 mg/kg xylazine and 2-6 mcg/kg buprenorphine HCL. 20 μL of saline was administered into the lower eye lid of each rabbit (n=4). The eyes were then blinked manually 3-4 times. Tears were collected by placing a 10 μL glass capillary in the lower eyelid until 7-10 μL of sample was collected. The tears were dispensed into 500 μl Eppendorf tubes.

Matrix effects were evaluated using a standard curve of silk fibroin samples over a concentration range of 97.9 μg/mL to 25,000 μg/mL in UAB and a 10% solution of rabbit tear matrix. The concentrations of silk fibroin solutions were back calculated based upon the non-linear regression fit for the standard curve.

MSD assay was performed as described above. Table 54 shows the results for silk fibroin solutions prepared by a 1:10 dilution in UAB. The percent recovery ranged from 91.4-119%. As shown in Table 55, total recovery of silk fibroin solution prepared in a 10% rabbit tear solution show similar recovery values ranging from 94.8-107%. These results show good correlation between silk fibroin solutions prepared in either diluent and suggest that rabbit tears matrix does not drastically alter assay sensitivity.

TABLE 54

Silk fibroin standard solutions prepared by a 1:10 dilution in UAB. Standards (1:10) UAB Diluent

| Standard | Nominal Concentration (pg/mL) | Calculated Concentration (pg/mL) | % Recovery | % CV |
|---|---|---|---|---|
| 1 | 25000 | 22839 | 91.4 | 9.98 |
| 2 | 12500 | 14891 | 119 | 10.7 |
| 3 | 6250 | 6132 | 98.1 | 21.1 |
| 4 | 3125 | 2852 | 91.3 | 0.934 |
| 5 | 1563 | 1730 | 111 | 16.0 |
| 6 | 781 | 779 | 99.8 | 13.6 |
| 7 | 391 | 390 | 99.9 | 11.1 |
| 8 | 195 | 188 | 96.4 | 9.05 |
| 9 | 97.7 | 100 | 103 | 4.44 |

TABLE 55

Silk fibroin standard solutions prepared by a 1:10 dilution in rabbit tears. Standards (1:10) 10% Rabbit Tears

| Standard | Nominal Concentration (pg/mL) | Calculated Concentration (pg/mL) | % Recovery | % CV |
|---|---|---|---|---|
| 1 | 25000 | 25947 | 104 | 4.55 |
| 2 | 12500 | 12367 | 98.9 | 1.60 |
| 3 | 6250 | 6076 | 97.2 | 2.38 |
| 4 | 3125 | 3117 | 99.7 | 1.26 |
| 5 | 1563 | 1596 | 102 | 2.96 |
| 6 | 781 | 809 | 104 | 0.976 |
| 7 | 391 | 379 | 96.9 | 0.797 |
| 8 | 195 | 185 | 94.8 | 3.43 |
| 9 | 97.7 | 105 | 107 | 1.06 |

To further evaluate any interference by matrix components, spike and recovery samples were prepared at 500, 2000, and 16000 μg/mL SF in 10% rabbit tear matrix and 10% human serum. As shown in Table 56, the calculated silk fibroin concentrations from 82.4-103% of the known value in 10% rabbit tears. These results are comparable to the standard curve of silk fibroin prepared in 10% rabbit tears. Similarly, as shown in Table 57, silk fibroin spike and recovery samples prepared by a 1:10 dilution in human serum showed good correlation between the known and measured silk fibroin concentrations. Given the strong correlation between the known and calculated SF concentrations in the spike and recovery samples, the matrix background has little effect on assay sensitivity.

TABLE 56

Spike and recovery MSD assay results for SF solutions prepared by a 1:10 dilution in rabbit tear matrix Spike and Recovery-10% Rabbit Tears

| QC | Nominal Concentration (pg/mL) | Calculated Concentration (pg/mL) | % Recovery | % CV |
|---|---|---|---|---|
| HQC | 16000 | 16460 | 103 | 16.7 |
| MQC | 2000 | 1647 | 82.4 | 14.8 |
| LQC | 500 | 437 | 87.3 | 2.59 |

TABLE 57

Spike and recovery MSD assay results for SF solutions prepared by a 1:10 dilution in human serum
Spike and Recovery-10% Human Plasma

| QC | Nominal Concentration (pg/mL) | Calculated Concentration (pg/mL) | % Recovery | % CV |
|---|---|---|---|---|
| HQC1 | 16000 | 17808 | 111 | 9.98 |
| MQC1 | 2000 | 1790 | 89.5 | 3.82 |
| LQC1 | 500 | 437 | 87.4 | 0.00 |

Example 30. Effects of Silk Fibroin on Cell Proliferation in Human Corneal Epithelial Cells Silk fibroin has been shown in increase cell proliferation. However, many of those studies utilized silk fibroin with a higher molecular weight than Cocoon's silk fibroin product. The goal of these studies was to determine if silk fibroin produced utilizing Cocoon's proprietary processing improves cell proliferation.

Silk fibroin was prepared by degumming silk yarn in a sodium carbonate solution, dissolution in lithium bromide and purification via tangential flow filtration. A 0.5 M sodium carbonate degumming solution was prepared by dissolving 53.0 g of sodium carbonate in 900 ml of DI water. The solution was brought to 1.0 L with DI water. A circulating water bath was used to heat the solution to 85° C. Once the solutions reached 85° C., 30 g of silk yarn were added to each 1 L bottle of sodium carbonate. The silk was degummed in this solution for 4 hr. at 85° C. After 4 hours, the silk yarn was removed from the degumming solution and transferred to 1 L of 70° C. DI water for 20 mins. to remove residual sericin and sodium carbonate. The warm water wash was repeated 2 additional times for a total of 3 washes. The fibers were then washed 3 times in 1 L of room temperature DI water. Excess water was squeezed from the fibers and the fibers were stretched on a clean surface to dry overnight.

Following sericin removal from silk yarn, the material remains as a solid fiber. Dissolution of the silk fibroin fibers was achieved by using 9.3 M lithium bromide solution. 96.6 g of lithium bromide was dissolved in water to a final volume 120 mL. 25 g of silk fibroin was pressed tightly into the bottom of a 250 ml beaker and the lithium bromide poured on top. The solution was incubated at 60° C. overnight to allow for complete dissolution of the fibers.

Prior to tangential flow filtration, the silk fibroin solution was diluted from 20% (w/v) SF to 5% (w/v) SF with DI water. The diluted solution was then centrifuged at 5000×g for 10 mins to pellet any precipitated particulates.

A tangential flow filtration (TFF) system with a two Pellicon® 3 cassettes with Ultracel® 5 kDa membranes was used for removal of lithium bromide. Prior to introduction of silk fibroin to the system, the system was washed with DI water and sanitized with 0.1 N sodium hydroxide. The system was then flushed with water to remove sodium hydroxide.

Using the TFF system, the solution was concentrated from 5% (w/v) to 10% (w/v) SF. Diafiltration was performed at 10% (w/v) SF to remove lithium bromide. The silk fibroin was diafiltered for 10 diavolumes against DI water. Following TFF, the solution was collected and filtered through a 0.2 µm PES membrane bottle top filter.

The molecular weight of TF_10 was determined by size exclusion chromatography. For SEC analysis, a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 µm polyethersulfone membrane filter. Silk fibroin elution was monitored at 280 nm. Molecular weights were calculated using a standard curve prepared from Waters BEH 200 Å Protein SEC Standard Mix (Waters, Milford, MA). The molecular weight of TF_15 was 36.3 kDa.

Immortalized human corneal epithelial cells (HCEC) were purchased from ATCC® (CRL-11135). The frozen cell stock was thawed to 37° C. in a dry bath. The cell stock was diluted into 6 ml of prewarmed complete keratinocyte media (CKM, Gibco) which consisted of serum free keratinocyte growth media containing 0.05 mg/mL bovine pituitary extract, 5 ng/mL epidermal growth factor, 500 ng/mL hydrocortisone, and 0.005 mg/mL insulin. The cells were centrifuged at 150×g for 5 min. to pellet the cells. Following centrifugation, the media was aspirated from the cell pellets and the pellets were resuspended in 1 mL CKM and transferred to a 25 $cm^2$ tissue culture flasks containing 5 mL CKM. The cells were then incubated at 37° C. with 5% CO2.

When the cells reached ~80% confluence they were sub-cultured. For sub-culture, the growth media was aspirated and the cells were washed with 5 ml of prewarmed PBS. 1 ml of 0.025% trypsin was then added to detach the cells. Cell suspensions were then diluted into 6 mL CKM supplemented with 1% FBS to quench the trypsin. The cells suspensions were centrifuged for 5 min. at 150×g, the media aspirated, and the cells resuspended in 1 mL CKM. The cells were then transferred to a 75 $cm^2$ flask. Sub-culturing was performed as needed to plate cells and maintain the cell culture. All tissue culture flasks were precoated overnight at 37° C. with 1 mL-5 ml of 10 µg/mL fibronectin, 10 µg/mL collagen and 30 µg/mL bovine serum albumin (BSA) in PBS.

HCEC cells were detached from a 75 $cm^2$ tissue culture flask as described above with the following exception. Following resuspension in 1 mL of CKM, the cells were diluted into 9 mL CKM. Cell concentration was determined by diluting a 10 µL aliquot of cell suspension with 10 µL of trypan blue which was counted using a Countess II (Invitrogen). Cells were diluted to 100,000 cells/mL with CKM. 100 µL of cell suspension was plated in four 96-well collagen-coated tissue culture plate. The cells were allowed to adhere and divide for 72 hrs.

For cell proliferation assays, silk fibroin concentrations between 1 mg/mL and 10 ng/mL were prepared. A 10 mg/mL working solution of SF was prepared by diluting 250 µL of an 80 mg/mL. SF stock (TF_10) with 1.75 ml of PBS. Working solutions of SF were prepared in growth factor free keratinocyte media (GFF) by serial dilutions of the 10 mg/mL SF solution. The solutions were prepared as described in Table 58.

TABLE 58

| Serial dilution protocol for preparation of SF samples in GFF media | | | | |
|---|---|---|---|---|
| | SF Concentration | Prepared From | μL SF Solution | μL GFF |
| CS-07_01 | 1 mg/mL | 10 mg/mL working solution | 200 | 1800 |
| CS-07_02 | 500 μg/mL | CS-07_01 | 500 | 500 |
| CS-07_03 | 100 μg/ml | CS-07_01 | 100 | 900 |
| CS-07_04 | 50 μg/mL | CS-07_02 | 100 | 900 |
| CS-07_05 | 10 μg/mL | CS-07_03 | 100 | 900 |
| CS-07_06 | 5 μg/mL | CS-07_04 | 100 | 900 |
| CS-07_07 | 1 μg/mL | CS-07 05 | 100 | 900 |
| CS-07_08 | 500 ng/mL | CS-07_06 | 100 | 900 |
| CS-07_09 | 100 ng/mL | CS-07_07 | 100 | 900 |
| CS-07_10 | 50 ng/mL | CS-07_08 | 100 | 900 |
| CS-07_11 | 10 ng/mL | CS-07_09 | 100 | 900 |

When HCEC reached ~70% confluence, the media was aspirated from each well of two 96-well tissue culture plates. 100 μL of the SF working solutions were added to the appropriate wells. All samples were run with 5 replicates. GFF media was added to an additional 5 wells to serve as a negative control. CKM was added to 5 wells to serve as a positive control. After the addition of the SF solutions, the plates were returned to a 37° C. incubator with 5% CO2 for 24 and 48 hours.

At 24 or 48 hours, 10 μL of CCK-8 reagent (Sigma Aldrich) was added to each well. The plates were then returned to the incubator for 1-2 hours. The absorbance was measured at 450 nm 2 hours post addition of CCK-8.

As shown in Table 58a, increase proliferation was observed at only 48 hours over a SF concentration range of 0.05 μg/mL to 100 μg/mL. However, not all concentrations were statistically different from the no treatment control. Therefore, the study was repeated in the exact manner as described above.

TABLE 58a

| HCEC study displaying enhanced effects of SF proliferation | | | | |
|---|---|---|---|---|
| | 24 Hours | | 48 Hours | |
| | Average | Std. Dev. | Average | Std. Dev. |
| Complete Media | 1.26 | 0.08 | 1.08 | 0.04 |
| 0 ug/mL SF | 1 | 0.21 | 1 | 0.05 |
| 0.01 ug/mL SF | 1.01 | 0.15 | 1.16 | 0.09 |
| 0.05 ug/mL SF | 1.11 | 0.06 | 1.11 | 0.07 |
| 0.1 ug/mL SF | 1.12 | 0.04 | 1.11 | 0.05 |
| 0.5 ug/mL SF | 1.07 | 0.03 | 1.09 | 0.06 |
| 1 ug/mL SF | 1.11 | 0.03 | 1.12 | 0.04 |
| 5 ug/mL SF | 1.09 | 0.05 | 1.12 | 0.04 |
| 10 ug/mL SF | 1.09 | 0.04 | 1.14 | 0.04 |
| 50 ug/mL SF | 1.09 | 0.07 | 1.15 | 0.04 |
| 100 ug/mL SF | 1.22 | 0.05 | 1.15 | 0.11 |
| 1000 ug/mL SF | 1.11 | 0.10 | 0.93 | 0.11 |

No statistically significant increase in proliferation was observed at 24 hours with the exception of the 100 μg/mL SF condition. By 48 hours, there was a statistically significant increase in cell proliferation relative to the no treatment control in nearly all conditions tested. These results indicate that SF improved cell proliferation after 48 hours in corneal epithelial cells.

Example 31. Effects of Silk Fibroin on Cell Proliferation in Fibroblasts

Silk Fibroin was Prepared as Described in 300 g Scale Up Manufacturing Example.

The molecular weight of the SF solution (TF_10) was determined by size exclusion chromatography (SEC). For SEC analysis, a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 ml/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. SF elution was monitored at 280 nm. Molecular weights were calculated using a standard curve prepared from Waters BEH 200 Å Protein SEC Standard Mix (Waters, Milford, MA). The molecular weight of SF solution (TF_15) was 36.5 kDa.

NIH3T3 fibroblasts were purchased from American Type Culture Collection (ATCC®). The frozen cell stock was thawed in a 37° C. dry bath. The cell stock was diluted into 6 mL of prewarmed complete media (CM) consisting of Dulbecco's modified eagle media (DMEM) with 10% fetal bovine serum (FBS), 100 I.U./mL penicillin, and 100 μg/mL streptomycin. The cells were pelleted with centrifugation at 200×g or 5 mins and the media was removed by aspiration. The cells were then resuspended in 1 ml of fresh CM. The cells were transferred to a 25 $cm^2$ tissue culture flask containing 4 mL of CM and incubated at 37° C. with 5% CO2.

When the cells reached ~80% confluence they were sub-cultured by aspirating the growth media and rinsing the cells with 5 mL of prewarmed phosphate buffered saline (PBS). 1 ml of 0.25% trypsin was then added to detach the cells. The cell suspension was diluted into 15 ml of pre-warmed CM to quench the trypsin. The cells transferred to a 75 $cm^2$ tissue culture flask. Sub-culturing was performed as needed for plating cells and maintaining culture.

For proliferation assays, NIH3T3 cells were detached from a 75 $cm^2$ tissue culture flask as described above with the following exception. Following detachment, the cells were diluted into 9 mL instead of 15 mL of CM. Cell concentration was determined by diluting a 10 μL aliquot of cell suspension with 10 μL of trypan blue which was counted using a Countess II (Invitrogen). Cells suspensions were diluted to 10,000 cells/ml with CM. 100 μL of cell suspension was plated in each well of 4×96-well tissue culture plate. The cells were allowed to adhere and divide in culture for 48 hrs.

A 10 mg/mL stock solution of SF was prepared by diluting 250 μL of an 80 mg/mL SF stock (TF_10) with 1.75 mL of PBS. Working solutions of silk fibroin were prepared in low serum growth media (LS) containing 0.1% FBS via serial dilution as described in Table 59.

TABLE 59

Serial dilution protocol for preparation of SF solutions in growth media supplemented with 0.1% FBS

| Sample # | SF Concentration | Prepared From | Volume of SF Solution (μl) | Volume of 0.1% FBS Media (μl) |
|---|---|---|---|---|
| CS-09_01 | 1 mg/mL | 10 mg/mL working solution | 200 | 1800 |
| CS-09_02 | 500 μg/mL | CS-09_01 | 500 | 500 |
| CS-09_03 | 100 μg/mL | CS-09_01 | 100 | 900 |
| CS-09 04 | 50 μg/mL | CS-09_02 | 100 | 900 |
| CS-09_05 | 10 μg/mL | CS-09_03 | 100 | 900 |
| CS-09_06 | 5 μg/mL | CS-09_04 | 100 | 900 |
| CS-09_07 | 1 μg/mL | CS-09_05 | 100 | 900 |
| CS-09_08 | 500 ng/mL | CS-09_06 | 100 | 900 |
| CS-09_09 | 100 ng/mL | CS-09_07 | 100 | 900 |
| CS-09_10 | 50 ng/mL | CS-09_08 | 100 | 900 |
| CS-09_11 | 10 ng/mL | CS-09_09 | 100 | 900 |
| CS-09_12 | 5 ng/mL | CS-09_10 | 100 | 900 |
| CS-09_13 | 1 ng/mL | CS-09_11 | 100 | 900 |
| CS-09_14 | 500 pg/mL | CS-09_12 | 100 | 900 |
| CS-09_19 | 100 pg/mL | CS-09_13 | 100 | 900 |
| CS-09_16 | 50 pg/mL | CS-09_14 | 100 | 900 |

When the NIH3T3 cells reached ~70% confluence, the media was aspirated from each well of two 96-well tissue culture plates. 100 μL of the SF working solutions were added to the appropriate wells. All samples were run with n=5. Growth media containing 0.1% FBS was added to an additional 5 wells to serve as a negative control. CM was added to 5 wells to serve as a positive control. After the addition of the SF solutions, the plates were returned to a 37° C. incubator with 5% CO2 for 24 and 48 hours.

At 24 and 48 hours, 10 μL of CCK-8 reagent (Sigma Aldrich) was added to each well. The plates were then returned to the incubator for 1-2 hours. The absorbance was measured at 450 nm 2 hours post addition of CCK-8.

No increased cell proliferation was observed at either 25 or 48 hours indicating SF does not increase cell proliferation in NIH3T3 cells, as shown in Tables 59a-d.

TABLE 59a

Proliferation results for NIH3T3 cells treated with SF in growth media supplemented with 0.1% FBS; low 24 h

| | Low 24 h |
|---|---|
| 10% FBS | 1.44 |
| 0 pg/mL SF | 1 |
| 50 pg/mL SF | 1.00 |
| 100 pg/mL SF | 0.98 |
| 500 pg/mL SF | 1.08 |
| 1 ng/mL SF | 1.04 |
| 5 ng/mL SF | 1.06 |
| 10 ng/mL SF | 1.07 |
| 50 ng/mL SF | 1.04 |
| 100 ng/mL SF | 1.11 |
| 500 ng/mL SF | 1.11 |
| 1 ug/mL SF | 1.15 |

TABLE 59b

Proliferation results for NIH3T3 cells treated with SF in growth media supplemented with 0.1% FBS; high 24 h

| | High 24h |
|---|---|
| 0 ng/mL SF | 1 |
| 50 ng/mL SF | 0.94 |
| 100 ng/mL SF | 0.88 |
| 500 ng/mL SF | 0.96 |
| 1 ug/mL SF | 0.90 |
| 5 ug/mL SF | 0.90 |
| 10 ug/mL SF | 0.90 |
| 50 ug/mL SF | 0.90 |
| 100 ug/mL SF | 0.95 |
| 500 ug/mL SF | 0.94 |
| 1 mg/mL SF | 1.01 |
| 10% FBS | 1.80 |

TABLE 59c

Proliferation results for NIH3T3 cells treated with SF in growth media supplemented with 0.1% FBS; low 48 h

| | Low 48 h |
|---|---|
| 0 pg/mL SF | 1 |
| 50 pg/mL SF | 0.78 |
| 100 pg/mL SF | 0.75 |
| 500 pg/mL SF | 0.82 |
| 1 ng/mL SF | 0.80 |
| 5 ng/mL SF | 0.79 |
| 10 ng/mL SF | 0.89 |
| 50 ng/mL SF | 0.91 |
| 100 ng/mL SF | 0.89 |
| 500 ng/mL SF | 0.91 |
| 1 ug/mL SF | 0.98 |
| 10% FBS | 1.92 |

TABLE 59d

Proliferation results for NIH3T3 cells treated with SF in growth media supplemented with 0.1% FBS; high 48 h

| | High 48 |
|---|---|
| 1 mg/mL SF | 0.89 |
| 500 ug/mL SF | 1.31 |
| 100 ug/mL SF | 1.24 |
| 50 ug/mL SF | 1.30 |
| 10 ug/mL SF | 1.19 |
| 5 ug/mL SF | 1.16 |
| 1 ug/mL SF | 1.14 |
| 500 ng/mL SF | 0.99 |
| 100 ng/mL SF | 1.09 |
| 50 ng/mL SF | N/A |
| 0 ng/mL SF | 1.26 |
| 10% FBS | 2.45 |

Example 32. Filtration Studies

Pre-Filtration Studies

A study was conducted with Pall filter membranes to determine the most appropriate membrane for clarification of the diluted SF solution prior to tangential flow filtration.

Degumming of Silk Yarn

The 0.5 M sodium carbonate degumming solution was prepared by dissolving 87.65 g of sodium carbonate in 1.65 L of DI water. Eleven of these 0.5 M solutions were prepared in separate 2 L glass containers. A circulating water bath was used to heat the carbonate solutions to 85° C. Once the solutions reached temperature, 132 g of silk yarn was added to each 2 L glass vessel containing sodium carbonate solution (1,452 g total silk yarn; 80 g/L). The silk was degummed with intermittent stirring for 4 hr. at 85° C. After 4 hours, the silk yarn was removed from the degumming solution and placed in room temperature water for 5 minutes. The silk fibers manually pressed to expel the water and rinsed under running water for an additional five minutes to remove residual sericin and sodium carbonate solution. The fibers were stretched on a clean surface in a fume hood to dry overnight.

Dissolution of Silk Fibers

SF fibers were dissolved in 9.3 M LiBr at 20% (w/v). In each of 4×2 L glass jars, 200 g of degummed SF was packed tightly into the bottom. One additional glass jar was packed with the remaining 179 g of SF. 9.3M LiBr solution was prepared by dissolving 3, 198 g of LiBr to a final volume of 4 L with water. 800 mL of 9.3 M LiBr solution was added to each of the 4×2 L glass jars containing 200 g SF, while 716 mL was added to the 179 g SF sample. The solutions were incubated at 60° C. overnight to allow for complete dissolution of the fibers.

Dilution and Filtration of SF Solution

The dissolved SF solution in LiBr was removed from the 60° C. oven and combined into a 5 gallon plastic container. The final volume of dissolved SF was 4.225 L. Quickly, 10.372 L of deionized (DI) water was added to the warm SF solution. This diluted the concentration of SF from 20% (w/v) to 6.7% (w/v) and causes a precipitate layer to form and partition into the foam on top of the diluted solution.

For the filtration studies, material was pumped from the bottom of the vessel as to not to disturb the top layer of precipitate. Constant pressure was maintained at a low pressure of 6-8 psi until the feed solution no longer passed the filter. These values were used to determine the maximum filter capacity (Vmax). The turbidity of the filtered solutions was also measured to determine the effectiveness of the filter to remove particulates. Multiple polypropylene prefilters were screened, including Profile II, Profile Ultipleat, and HDC II in various filter sizes. The Profile II filter has a spun-bonded fiber with a filament matrix density increasing at the core. The Profile Ultipleat is similar to Profile II, but it has a thinner depth filter media that is pleated. The HDC II is a tapered pore polypropylene prefilter media and is more similar to a membrane than a depth filter. It was found that the Profile II 5 μm filter provided the highest capacity of 4741 L/m$^2$ membrane as well as reduced turbidity most effectively (Table 60).

TABLE 60

Clarification filter capacity with SF solutions

| Filter Media | Absolute Retention Rating (um) | Filter Capacity Vmax (L/m$^2$) | Test Pressure (psig) | Filtrate Turbidity (NTU) |
|---|---|---|---|---|
| Feed Material | — | — | — | 40.4 |
| HDC II | 2.5 | 32 | 6 | 4.8 |
| | 4.5 | 33 | 6 | 8.5 |
| | 6.0 | 574 | 6 | 17.8 |
| | 10 | 1028 | 6 | 27.2 |
| Profile Ultipleat | 4.5 | 402 | 6 | 10.4 |
| | 6 | <200 | 6 | 10.2 |
| Profile II | 3 | 162 | 8 | N/A |
| | 5 | 4741 | 8 | 1.9-2.3 |

Final SF Solution Filtration

Ten separate 0.5 M sodium carbonate solutions were prepared in separate 2 L glass containers as described; 79.5 g of sodium carbonate was dissolved in 1.5 L of deionized (DI) water. A recirculating water bath was used to heat the carbonate solutions to 85° C. Once the solutions reached temperature, 103.7 g of silk yarn (Jiangsu SOHO) was added to each 2 L glass vessel containing sodium carbonate solution (1,037 g total silk yarn; 80 g silk/L carbonate solution). The silk was degummed with intermittent stirring for 4 hours at 85° C. After 4 hours, the silk yarn was removed from the degumming solution and placed in excess room temperature water for 5 minutes. The silk fibers manually pressed to expel the water and rinsed under running water for an additional five minutes to remove residual sericin and sodium carbonate solution. The fibers were stretched on a clean surface to dry.

Silk Fibroin Dissolution

In each of 6×1 L glass bottles, 100 g of dried, degummed silk fibroin (SF) was packed tightly into the bottom. One additional glass bottle was packed with the remaining 78 g of SF. 9.3 M lithium bromide solution was prepared by dissolving 2,524 g of lithium bromide to a final volume of 3 L with water. 400 mL of 9.3 M lithium bromide solution was added to each of the 6×1 L glass bottles containing 100 g of SF, while 380 mL was added to the 78 g SF sample. The solutions were incubated at 60° C. overnight to allow for complete dissolution.

Silk Fibroin Dilution and Clarification

The 20% (w/v) SF solutions in lithium bromide were removed from the 60° C. oven and combined into a 5 gallon plastic container. The final volume of dissolved SF was 3.38 L. 6.15 L of room temperature deionized (DI) water was quickly added to the warm SF solution. This diluted the concentration of SF from 20% (w/v) to 7.1% (w/v) and caused a precipitate layer to form and partition into the foam on top of the diluted solution.

The solution was filtered using a Millipore Opticap® XL 5 Capsule filter with a Polygard®-CN 5.0 μm nominal filter. The final 500 mL, which contained most of the precipitate, was not passed through the filter. It was added to 500 mL centrifuge bottles and was centrifuged at 4000×g at 4° C. for 10 minutes. A small amount of precipitate remained in this small volume and was filtered through a 0.2 μm vacuum filter unit. Containers were rinsed with 870 ml DI water, which was pumped through the filter to flush out the remaining solution and the filter was pumped until it was dry. This diluted the SF solution to a concentration of 6.5% (w/v) SF. The filtered material, including the flush, as well as the flush and centrifuged solution, were combined and weighed in a 2.5 gallon container. The mass of the solution after clarification was 11.4 kg. The solution was clear and had an amber color.

Tangential Flow Filtration Purification of Silk Fibroin

A tangential flow filtration (TFF) system with a 1.14 m$^2$ Ultracel® 5 kDa Pellicon® 3 cassette was used for final purification of SF. Prior to the introduction of SF solution, the system was flushed with 20-30 L of DI water to remove any 0.1N NaOH storage solution. The feed pressure was maintained below 30 psi and system was inspected for leaks by increasing the transmembrane pressure (TMP) to 20-40 psi. When the pH of the permeate and retentate lines were neutral, the normal water permeability of the system was determined and the system was drained. The degummed, dissolved, and filtered 6.5% (w/v) SF solution was concentrated to half of its initial volume under stirring. During concentration, a TMP of ~20-25 psi and a feed rate of 5 L/m$^2$/min. were maintained. The lithium bromide was removed from the silk fibroin solution by diafiltration against 40-45 L of DI water (7 total diavolumes) while maintaining a silk fibroin solution volume of ~5.7 L. The TMP was maintained between 25-30 psi with a feed rate of 4-6 L/m$^2$/min throughout the diafiltration. After 7 total diavolumes, the SF was concentrated until an additional 1 kg of permeate had been removed. The TFF process to purify silk fibroin was successfully performed using 1.14 m$^2$ of a 5 kDa Ultracel® membrane to process a total of 678 g of silk fibroin in 5-6 hours.

The SF solution was transferred to a 10 L carboy. Following purification of the silk fibroin, the TFF system was cleaned, sanitized with 10 L of 0.1 N sodium hydroxide, the NWP was determined, and the membrane was stored in 0.1N sodium hydroxide.

Approximately 500 ml of the purified SF solution from this preparation was used for final filtration studies. The objective of the final filtration study was to determine the most cost effective and efficient final filter. A Golander pump (Model: BT100SV2-CE) was used to pump the silk through the filters, which were connected to the end of the tubing via luer lock with an in-line pressure gauge. With each filter, SF solution was pumped through the filters controlling the flow rate so that the pressure was maintained at or below 10 psi. The SF solutions were pumped through the filters until the flow had to be reduced to the point at which no more solution could be filtered. The volume of solution that was passed through the filter as well as the time of processing was used to calculate the max volume (Vmax) for each membrane. Six different Millipore filters were assessed (Table 61). These included polyethersulfone (includes PES, SHC, and SHF membrane filters) and polyvinylidene fluoride (Durapore) membranes with different pore sizes. The Express SHF filter (sterilizing grade PES membrane) displayed the lowest Vmax of 62 L/m$^2$ while the Milligard PES 1.2/0.8 μm membrane showed the highest Vmax of 368 L/m$^2$. In general, we saw that a multi-layer filter improved the Vmax of the membrane with the Express SHC 0.5/0.2 μm filter providing the highest Vmax in a sterilization grade membrane. Along with the Vmax, cost of the filters needs to be taken into account when selecting the appropriate filter for the process.

TABLE 61

| Maximum membrane capacity during SF solution filtration | | |
|---|---|---|
| Filter | Filter Size (μm) | Vmax L/m2) |
| Express SHF | 0.2 | 62 |
| Express SHC | 0.5/0.2 | 311 |
| Durapore | 0.45 | 89 |
| Milligard PES | 1.2/0.2 | 233 |
| Milligard PES | 1.2/0.45 | 255 |
| Milligard PES | 1.2/0.8 | 368 |

MANUFACTURING EXAMPLES

Example 33. 80 g/L Degumming for Silk Fibroin Manufacturing

Silk Degumming 0.5 M sodium carbonate solution was prepared separately in 6×2 L glass containers as described; 79.5 g of sodium carbonate was dissolved in 1.5 L of DI water. A recirculating water bath was used to heat the sodium carbonate solutions to 85° C. Once the solutions reached temperature, different masses of silk yarn (Jiangsu SOHO) were added to each 2 L glass vessel containing the sodium carbonate solution:

TABLE 62

| Silk Mass Yield | | | |
|---|---|---|---|
| Sample | Total Silk Mass (g) | Silk mass per volume of Carbonate Solution (g/L) | Yield (%) |
| 1 | 45 | 30 | 69.55% |
| 2 | 60 | 40 | 69.83% |
| 3 | 75 | 50 | 64.00% |
| 4 | 90 | 60 | 66.33% |
| 5 | 105 | 70 | 69.14% |
| 6 | 120 | 80 | 71.00% |

After 4 hours, the silk yarn was removed from the degumming solutions and placed in excess room temperature deionized (DI) water for 5 minutes. The silk fibers were manually pressed to expel the water and rinsed under DI water for an additional five minutes to remove residual sericin and sodium carbonate solution. The fibers were stretched on a clean surface to dry. The yield of dried SF was determined by mass. All of the conditions generated yields of 64%-71% which is within range of our standard 30 g/L degumming process (65%-70%) as shown in the Table 62 above.

Silk Fibroin Dissolution

Dissolution of 30 g Silk/L Sample 25.35 g of dried SF, degummed at 30 g silk/L, was dissolved at 20% (w/v) in 9.3M lithium bromide. The SF was packed into the bottom of a 500 mL glass vessel and 101.4 mL of 9.3 M lithium bromide was added. The SF and the sample in lithium bromide solution was incubated at 60° C. overnight (~16 hrs.) to allow for complete dissolution.

Dissolution of 60 g Silk/L Sample 25 g of dried SF, degummed at 30 g silk/L, was dissolved at 20% (w/v) in 9.3M lithium bromide. The SF was packed into the bottom of a 500 mL glass vessel and 100.0 ml of 9.3 M lithium bromide was added. The SF and the sample in lithium bromide solution was incubated at 60° C. overnight (~16 hrs.) to allow for complete dissolution.

Dissolution of 80 g Silk/L Sample 25 g of dried SF, degummed at 30 g silk/L, was dissolved at 20% (w/v) in 9.3M lithium bromide. The SF was packed into the bottom of a 500 mL glass vessel and 100.0 ml of 9.3 M lithium bromide was added. The SF and the sample in lithium bromide solution was incubated at 60° C. overnight (~16 hrs.) to allow for complete dissolution.

Silk Fibroin Dilution and Clarification

Dilution and Clarification of 30 g Silk/L Sample

The 20% (w/v) SF solution in lithium bromide was removed from the 60° C. oven and quickly diluted to 5% (w/v) SF with the addition of 382 mL of room temperature DI water. This caused a thin, precipitate layer to form which migrated to a foam layer on top of the diluted SF solution. The SF solution was centrifuged at 4000×g at 4° C. for 20 min. to produce a clear, amber solution of SF in lithium bromide.

Dilution and Clarification of 60 g Silk/L Sample

The 20% (w/v) SF solution in lithium bromide was removed from the 60° C. oven and quickly diluted to 5% (w/v) SF with the addition of 375 ml of room temperature DI water. This caused a thin, precipitate layer to form which migrated to a foam layer on top of the diluted SF solution. The SF solution was centrifuged at 4000×g at 4° C. for 20 min. to produce a clear, amber solution of SF in lithium bromide.

Dilution and Clarification of 80 g Silk/L Sample

The 20% (w/v) SF solution in lithium bromide was removed from the 60° C. oven and quickly diluted to 6.5% (w/v) SF with the addition of 375 ml of room temperature DI water. This caused a thin, precipitate layer to form which migrated to a foam layer on top of the diluted SF solution. The SF solution was centrifuged at 4000×g at 4° C. for 20 min. to produce a clear, amber solution of SF in lithium bromide.

Tangential Flow Filtration Purification of Silk Fibroin

A tangential flow filtration (TFF) system with two x 0.11 $m^2$ Ultracel® 5 kDa Pellicon® 3 cassettes was used for final purification for each of the following SF solutions.

TFF Purification of SF Degummed at 30 g Silk/L

Prior to the introduction of SF solution, the system was flushed with 10 L of DI water to remove any 0.05 sodium hydroxide (NaOH) storage solution. When the permeate and retentate lines were neutral, DI water was flushed through the system to stabilize pressures and check for leaks in the system. The transmembrane pressure (TMP) was maintained between 30-31 psi. The degummed, dissolved, and centrifuged 5% (w/v) SF solution was then introduced to the system and concentrated 2×, to ~10% (w/v) SF with stirring. During concentration, a TMP of ~30-33 psi and a feed rate of 5 L/m/min. were maintained. The lithium bromide was removed from the ~250 mL SF solution by diafiltration against 2-2.5 L of DI water (8 total diavolumes) with stirring. The TMP was maintained between 28-31 psi with a feed rate of 4-6 L/m/min throughout the diafiltration.

TFF Purification of SF Degummed at 60 g Silk/L

Prior to the introduction of SF solution, the system was flushed with 10 L of DI water to remove any 0.05 sodium hydroxide (NaOH) storage solution. When the permeate and retentate lines were neutral, DI water was flushed through the system to stabilize pressures and check for leaks in the system. The transmembrane pressure (TMP) was maintained between 30-31 psi. The degummed, dissolved, and centrifuged 5% (w/v) SF solution was then introduced to the system and concentrated 2×, to ~10% (w/v) SF with stirring. During concentration, a TMP of ~25-28 psi and a feed rate of 5 L/m/min. were maintained. The lithium bromide was removed from the ~250 mL of SF solution by diafiltration against 2-2.5 L of DI water (8 total diavolumes). The TMP was maintained between 28-31 psi with a feed rate of 4-6 L/m/min throughout the diafiltration.

TFF Purification of SF of 80 g Silk/L Sample

Prior to the introduction of SF solution, the system was flushed with 10 L of DI water to remove any 0.05 sodium hydroxide (NaOH) storage solution. When the permeate and retentate lines were neutral, DI water was flushed through the system to stabilize pressures and check for leaks in the system. The transmembrane pressure (TMP) was maintained between 30-31 psi. The degummed, dissolved, and centrifuged 5% (w/v) SF solution was then introduced to the system and concentrated 2×, to ~10% (w/v) SF with stirring. During concentration, a TMP of ~25-28 psi and a feed rate of 5 L/m/min. were maintained. The lithium bromide was removed from the ~250 ml of SF solution by diafiltration against 2-2.5 L of DI water (8 total diavolumes). The TMP was maintained between 30-32 psi with a feed rate of 4-6 $L/m^2$/min throughout the diafiltration.

After 8 total diavolumes, each SF sample was collected. The SF processing took ~2 hours to complete each 25 g sample. The purified SF solutions were filtered through separate 0.2 μm vacuum filtration units.

The TFF system was flushed with 5 L of DI water and then sanitized by flushing 500 mL of 0.05 N sodium hydroxide and recirculating this solution at a TMP of 20-40 psi for 15 minutes between each run.

pH and Conductivity of Silk Fibroin Solution Through TFF pH and Conductivity of SF of 30 g Silk/L Sample The conductivity and pH of the retentate was measured after each diavolume. Over the course of the TFF process, the pH was between 8.5-9.5. The initial pH was 8.37 which slowly increased to 8.95 by the fifth diavolume. By the end of the run, the pH decreased to 8.78. The initial conductivity of the SF solution was 101.6 mS/cm and gradually decreased to a final conductivity of 0.717 mS/cm over the TFF cleanup.

pH and Conductivity of SF of 60 g Silk/L Sample

The conductivity and pH of the retentate was measured after each diavolume. Over the course of the TFF process, the pH was between 8.5-9.5. The initial pH was 8.50 which slowly increased to 9.1 by the fifth diavolume. By the end of the run, the pH decreased to 8.89. The initial conductivity of the SF solution was 9.27 mS/cm and gradually decreased to a final conductivity of 0.763 mS/cm over the TFF cleanup.

pH and Conductivity of SF of 80 g Silk/L Sample

The conductivity and pH of the retentate was measured after each diavolume. Over the course of the TFF process, the pH was between 8.5-9.5. The initial pH was 8.48 which slowly increased to 9.02 by the fifth diavolume. The initial conductivity of the SF solution was 9.5 mS/cm and gradually decreased to a final conductivity of 0.820 mS/cm over the TFF cleanup.

These data are similar to the pH and conductivity results that were observed during other small and large TFF runs, starting with conductivities in the range of 100-150 mS/cm and ending with conductivities in the 0.6-0.8 mS/cm range, Silk Fibroin Molecular Weight Determination The average molecular weight of the SF was measured by ultra-performance liquid chromatography size exclusion chromatography (UPLC-SEC). A Waters Acquity H-Class UPLC equipped with a Waters BEH 200 Å 1.7 μm, 4.8×300 cm UPLC SEC column was used. Sample temperature was maintained at 4° C. throughout the analysis. An isocratic flow rate of 0.3 mL/min using mobile phase (100 mM Tris-HCl with 400 mM sodium perchlorate, pH 8.0) was used to elute SF from the column. Mobile phase was prepared by dissolving 12.1 g of Tris base and 48.1 g of sodium perchlorate in 800 mL of DI water. The pH was adjusted to 8.0 with 6N HCl. DI water was added to a final volume of 1 L. The mobile phase was filtered through a 0.2 μm polyethersulfone membrane filter. SF elution was monitored at 280 nm. Molecular weights were calculated using a standard curve prepared from Waters BEH 200 Å Protein SEC Standard Mix.

SF Molecular Weight

The average molecular weight of SF sample degummed at 30 g/L was determined to be 30.4 kDa. The average molecular weight of SF degummed at 60 g/L was determined to be 31.2 kDa, while the average MW of the SF degummed at 80 g/L was determined to be 32.4 kDa. All of the samples were in the range of our standard degumming process (10 g/L-30 g/L) which produces an average MW range of SF of 28-40 kDa. This shows that the mass of silk in the degumming solution can be increased to 80 g silk per liter of 0.5M carbonate solution without effecting the final, purified, SF.

Example 34. 1 kg Silk Fibroin

Silk Degumming

Eleven separate 0.5M sodium carbonate solutions were prepared in separate 2 L glass containers as described; 87.65 g of sodium carbonate was dissolved in 1.65 L of DI water. A recirculating water bath was used to heat the carbonate solutions to 85° C. Once the solutions reached temperature, 132 g of silk yarn (Jiangsu SOHO) was added to each 2 L glass vessel containing sodium carbonate solution (1,452 g total silk yarn; 80 g silk/L carbonate solution). The silk was degummed with intermittent stirring for 4 hr. at 85° C. After 4 hours, the silk yarn was removed from the degumming solution and placed in excess room temperature water for 5 minutes. The silk fibers manually pressed to expel the water and rinsed under running water for an additional five minutes to remove residual sericin and sodium carbonate solution. The fibers were stretched on a clean surface to dry.

Silk Fibroin Dissolution

In each of 4×2 L glass jars, 200 g of dried, degummed silk fibroin was packed tightly into the bottom. One additional glass jar was packed with the remaining 179 g of silk fibroin. 9.3M lithium bromide solution was prepared by dissolving 3,198 g of lithium bromide to a final volume of 4 L with water. 800 mL of 9.3 M lithium bromide solution was added to each of the 4×2 L glass jars containing 200 g SF, while 716 mL was added to the 179 g SF sample. The solutions were incubated at 60° C. overnight to allow for complete dissolution.

Silk Fibroin Dilution and Clarification

The 20% (w/v) SF solutions in lithium bromide were removed from the 60° C. oven and combined into a 5 gallon plastic container. The final volume of dissolved SF was 4.225 L. 10.372 L of room temperature deionized (DI) water was quickly added to the warm SF solution. This diluted the concentration of SF from 20% (w/v) to 6.7% (w/v) and caused a precipitate layer to form and partition into the foam on top of the diluted solution.

The solution was filtered by pumping the solution from the bottom of the vessel, as to not to disturb the layer of precipitate, at constant low pressure of 6-8 psi. The solution was filtered through a 1" Pall Profile® II 5 μm polypropylene filter cartridge ensuring not to introduce the foam layer. This produced a clear, amber solution of silk fibroin in lithium bromide at 6.7% (w/v).

Tangential Flow Filtration Purification of Silk Fibroin

A tangential flow filtration (TFF) system with a 1.14 $m^2$ Ultracel® 5 kDa Pellicon® 3 cassette was used for final purification of the 979 g of SF. Prior to the introduction of SF solution, the system was flushed with 20-30 L of DI water to remove any 0.1N NaOH storage solution. The feed pressure was maintained below 30 psi and system was inspected for leaks by increasing the transmembrane pressure (TMP) to 20-40 psi. The system was then drained and the pH of the final wash measured. The TFF system was then sanitized by flushing with 5 L of 0.1 N sodium hydroxide and recirculating this solution at a transmembrane pressure of 20-40 psi for 30 min. Following the sodium hydroxide sanitization, the system was flushed with 20-30 L of DI water until the pH of the permeate and retentate were below 7.5. The normal water permeability of the system was determined and the system was then drained. The degummed, dissolved, and filtered 6.7% (w/v) SF solution was transferred to a 15 L reservoir with stirring. The SF solution was then concentrated to half its initial volume under stirring. During concentration, a TMP of ~25 psi and a feed rate of 5 L/$m^2$/min. were maintained. The lithium bromide was removed from the SF solution via diafiltration against 50-55 L of DI water (7 total diavolumes) while maintaining a SF solution volume of 7.3 L in the reservoir. The TMP was maintained between 30-35 psi with a feed rate of 4-6 L/$m^2$/min throughout the diafiltration. After 7 total diavolumes, the SF was concentrated until an additional 1.5 kg of permeate had been removed. The TFF process to purify SF was successfully performed using 1.14 $m^2$ of a 5 kDa Ultracel® membrane to process a total of 979 g of silk fibroin in 6-7 hrs.

The SF solution was transferred to a 10 L carboy. Following purification of the silk fibroin, the TFF system was cleaned, sanitized, the NWP was determined, and the membrane was stored in 0.1N sodium hydroxide.

Silk Fibroin Solution Collection and Final Filtration

Following final concentration of silk fibroin solution, the TFF system was stopped. The permeate valve was then closed completely and the retentate line was removed from the sample reservoir and placed into a clean, 10 L plastic carboy for collection. The SF solution was pumped from the reservoir at 1-2 L/min until the sample reservoir was empty, ensuring not to introduce air. 500 ml of DI water was then added to the reservoir, pumped through the system, and collected. This was performed a total of three times to ensure all of the silk fibroin solution was collected. The final mass of the SF solution was determined.

The purified SF solution was filtered through an Opticap XL 600 Capsule Millipore SHC 0.5/0.2 μm filter. The filtration was performed under low pressure as to not exceed 20 psi. The filtered material was collected under clean conditions in multiple sterile 500 mL polyethylene terephthalate copolyester, glycol modified (PETG) bottles.

pH and Conductivity of Silk Fibroin Solution Through TFF

The conductivity and pH of the retentate was measured after each diavolume. Over the course of the TFF process, the pH was between 8.5-9. The initial pH was 8.46 which slowly increased to 8.96 by the fifth diavolume. By the end of the run, the pH decreased to 8.84. With past small-scale TFF runs, we have seen that the pH typically stays in the 8-9 range throughout the process. The initial conductivity of the SF solution was 8.01 mS/cm and gradually decreased to a final conductivity of 0.927 mS/cm (927 μS/cm) over the TFF cleanup.

Silk Fibroin Concentration

The final concentration of the SF solution was measured via gravimetric analysis. 5 small plastic weigh boats were tared and weights recorded. 1 ml of the SF solution was added to each weigh boat using a positive displacement pipette. Samples were left to dry overnight at 60° C. The following day, the samples were weighed and the dry silk fibroin in each weigh boat was calculated. The concentration of SF per unit volume was then calculated using the average of the five samples. The final concentration of SF was determined to be 11.16% (w/v).

Silk Fibroin Molecular Weight Determination

The average molecular weight of the SF was measured by ultra-performance liquid chromatography size exclusion chromatography (UPLC-SEC). A Waters Acquity H-Class UPLC equipped with a Waters BEH 200 Å 1.7 μm, 4.8×300 cm UPLC SEC column was used. Sample temperature was maintained at 4° C. throughout the analysis. An isocratic flow rate of 0.3 mL/min using mobile phase (100 mM Tris-HCl with 400 mM sodium perchlorate, pH 8.0) was used to elute SF from the column. Mobile phase was prepared by dissolving 12.1 g of Tris base and 48.1 g of sodium perchlorate in 800 ml of DI water. The pH was adjusted to 8.0 with 6N HCl. DI water was added to a final volume of 1 L. The mobile phase was filtered through a 0.2 μm polyethersulfone membrane filter. SF elution was monitored at 280 nm. Molecular weights were calculated using a standard curve prepared from Waters BEH 200 Å Protein SEC Standard Mix. The average molecular of SF was determined to be 40.2 kDa.

Example 35. 300 g Scale Silk Fibroin 500 g of silk yarn was divided into 10 porous PEEK bags which were then placed inside a larger PTFE porous bag and placed into a 20 L jacketed reactor. A solution of 0.5 M sodium carbonate was prepared by dissolving 3444.5 g of sodium carbonate in 44.5 L of DI water. The solution was stirred for 30 minutes to dissolve the salt. The sodium carbonate degumming solution was heated to 86° C. A second reactor containing 50 L DI water was heated to 90° C. The jacketed reactor containing the silk fibroin was charged with 20-25 L of the heated DI water (until the PTFE bag was submerged) to bring the vessel and its contents to temperature. The vessel was quickly discharged of the water, and 20-25 L of the 86° C. sodium carbonate solution was added again submerging the PTFE bag. The silk yarn was degummed at 86° C. in 0.5 M sodium carbonate for 4 hours with gentle agitation at 30 rpm to remove sericin and digest the fibroin into lower molecular weight fragments. After the silk yarn had been degummed for 4 hours, the degumming solution was drained from the reactor.

25 L of 70-80° C. warm water (heated in a separate 50 L vessel) was added to the silk fibers to remove residual sericin and sodium carbonate. The fibers were washed in the warm water for 10 mins. with gentle agitation at 30 rpm. The water was then drained and the wash steps repeated 2 additional times for a total of 3 washes. After the fibers were washed with warm DI water, the same wash steps were repeated using room temperature DI water. The residual water was removed from the fibers by squeezing the bags by hand. The fibers were removed from the bags and dried under nitrogen flow at 60-75° C. until the mass of the samples decreased by less than 1% between measurements.

Dissolution of Silk Fibroin

A solution of 9.3 M LiBr was prepared by dissolving 1615.4 g of LiBr in 1280 g of deionized water (DI) water and the solution volume brought to 2 L with DI water. 300 g of dried silk fibers were placed in a 20 L jacketed reactor to which 1.2 L 9.3 M lithium bromide solution was added (20% silk fiber by weight/volume). The vessel was heated and maintained at 60-65° C. and the fibers were dissolved overnight with gentle stirring. The following morning, the dissolved silk fibroin was diluted to 5% (w/v) using DI water. The 5% (w/v) SF solution was then filtered through a Millipore Opticap® XL 5 Capsule filter with a Polygard®-CN 5.0 μm nominal filter. The pressure was monitored through the filtering process so as not exceed 30 psi.

Tangential Flow Filtration Purification of Silk Fibroin

A tangential flow filtration (TFF) system with a 1.14 $m^2$ Ultracel® 5 kDa Pellicon® 3 cassette was used. Prior to the introduction of the 5% (w/v) silk fibroin solution, the dead volume of the system was measured while flushing with 20-30 L of DI water. The feed pressure was maintained below 30 psi and system was inspected for leaks by increasing the transmembrane pressure to 20-40 psi. The system was then drained and the pH of the final wash determined. The TFF system was then sanitized with 5 L of 0.05 N sodium hydroxide in the same manner. Following the sodium hydroxide washes, the system was again flushed with 20-30 L of DI water until the pH of the permeate and retentate were below 7.5.

After the system and membrane had been flushed and sanitized, the normal water permeability was measured. The NWP was measured by recording the length of time to collect 250 ml of DI water while maintaining a feed pressure of 30-40 psi. The system was then drained.

The degummed, dissolved, diluted and filtered 5% (w/v) silk fibroin solution was transferred to a 6 L reservoir. The SF was then concentrated to half its initial volume. During concentration, a TMP of ~24 psi and a feed rate of 4-6 $L/m^2/min$ were maintained. The lithium bromide was removed from the silk fibroin by diafiltration against 30-40 L of DI water (10 total diavolumes) while keeping the silk fibroin reservoir at a constant volume of ~3 L. The TMP was maintained at 24 psi with a feed rate of 4-6 $L/m^2/min$. Water was added to the reservoir to maintained the silk fibroin solution volume at 3 L. The conductivity of the retentate and permeate were measured at each diavolume. After 10 diavolumes, the silk fibroin was concentrated to ~2 L and collected into a 4 L plastic bottle.

Following purification of the silk fibroin, the TFF system was cleaned similarly to the initial preparation procedure with first with 20 L of DI water followed by 0.05 N sodium hydroxide for 60 mins and again flushed with 20 L of DI water. Membranes were stored in 0.05 N sodium hydroxide for future use.

Silk Fibroin Sterile Filtration

The purified silk fibroin solution was filtered through an Opticap XL 150 Capsule Millipore SHC 0.5/0.2 μm filter. The filtration was performed under low pressure as to not exceed 20 psi. The filtered material was collected under aseptic conditions into multiple sterile 500 mL polyethylene terephthalate copolyester, glycol modified (PETG) bottles.

Measurement of Silk Fibroin Concentration

5×50 ml conical tubes were tared. 10 mL of the silk fibroin solution was added to each tube and then frozen at −80° C. overnight. The following morning, the tubes were placed in a lyophilizer to remove water. The mass of the silk fibroin was determined by weighing the tubes and subtracting the added mass of silk fibroin from the original weight of the tubes. The final concentration was calculated in mg/mL by dividing the weight of the silk fibroin by 10 ml of starting material. The final concentration of silk fibroin was 80 mg/mL.

Molecular Weight of Silk Fibroin

The average molecular weight of the silk fibroin was measured by UPLC-SEC. A Waters Acquity H-Class UPLC equipped with a Waters BEH 200 Å 1.7 μm, 4.8×300 cm UPLC SEC column was used. Sample temperature was maintained at 4° C. An isocratic flow at 0.3 mL/min of mobile phase (100 mM Tris-HCl with 400 mM sodium perchlorate, pH 8.0 was used to elute SF from the column. Mobile phase was prepared by dissolving 12.1 g of Tris base and 48.1 g of sodium perchlorate in 800 mL of DI water. The pH was adjusted to 8.0 with 6N HCl, DI water was added to a final volume of 1 L. The mobile phase was sterile filtered through a 0.2 μm polyethersulfone membrane filter. Silk fibroin elution was monitored at 280 nm. Molecular weights were calculated using a standard curve prepared from Waters BEH 200 Å Protein SEC Standard Mix. The average molecular weight was 34.5 kDa.

Measurement of Elemental Impurities by ICP-AES

Inductively coupled plasma atomic emission spectroscopy (ICP-AES) was performed to analyze elemental impurities remaining in the silk fibroin following purification.

Elements tested for include Ag, Al, As, B, Ba, Be, Ca, Cd, Cr, Cu, Fe, K, Li, Mg, Mn, Mo, Na, Ni, P, Pb, S, Sb, Se, Si, Sn, Sr, Ti, TI, V, and Zn levels, shown in Table 63. Inductively coupled plasma mass spectrometry (ICP-MS) was used to measure lithium concentrations. For both ICP-AES and ICP-MS 1 ml milliliter aliquots of a 1% silk fibroin solution were transfer to Teflon digestion tubes. To the digestion tube, 2 mL of 2% nitric acid was added and the solution allowed to react. An additional 2 mL of 0.5% perchloric acid were then added and the tube heated to 180° C. to drive off nitric acid and complete the digestion. The solution was then diluted to 20 ml with the addition of ultrapure water. The sample was then diluted an additional 10-fold with ultrapure water and analyzed by ICP-AES or ICP-MS. Metal ion levels were quantified via standard curves for each element. Residual lithium levels were measured by ICP-mS to be 0.23 ppm per gram of silk fibroin. Of the 28 elements assayed via ICP-AES, only 9 were above the limit of detection for the assay.

TABLE 63

ICP-AES and ICP_MS Elemental Impurity Analysis Results

| Element | ppm/g Silk Fibroin |
|---|---|
| Aluminum | 0.1 |
| Antimony | <LOQ |
| Arsenic | 0.6 |
| Barium | <LOQ |
| Beryllium | <LOQ |
| Boron | <LOQ |
| Cadmium | <LOQ |
| Calcium | 0.228 |
| Chromium | <LOQ |
| Iron | <LOQ |
| Lead | <LOQ |
| Lithium | 0.23 |
| Magnesium | <LOQ |
| Manganese | <LOQ |
| Molybdenum | <LOQ |
| Nickel | 0.02 |
| Phosphorus | <LOQ |
| Potassium | <LOQ |
| Selenium | <LOQ |
| Silicon | <LOQ |
| Silver | <LOQ |
| Sodium | 0.8 |
| Sulfur | 4.4 |
| Thallium | 0.1 |
| Tin | <LOQ |
| Titanium | <LOQ |
| Vanadium | <LOQ |
| Zinc | 0.05 |

Measurement of Bromide and Chloride Concentration by Ion Chromatography

Bromide concentrations were measured via ion chromatography. For ion chromatography measurements, 1 mL of silk fibroin solution was diluted to 10 ml with ultrapure water to leach soluble bromide and chloride from the samples. The samples were then analyzed directly by ion chromatography using a Dionex AS14a separator column with an eluent consisting of a 1:1 mixture of 8.0 mM $Na_2CO_3$ and 1.0 mM $NaHCO_3$ at a flow rate of 1.0 ml/min. The elution of bromide was detected with a conductivity detector as it eluted from the column. Anion levels were measured against a standard curve. Bromide concentration for the SF solution (TF_10) was measured to be 0.05 ppm per gram of silk fibroin.

Residual Sericin Determination

Residual levels of sericin in the final silk fibroin solution was measured by amino acid analysis. The relative abundance of glycine and serine were measured and a standard curve of known sericin and fibroin concentrations was used to calculate remaining sericin in fibroin preparations.

A pure fibroin standard, which was free of sericin, was degummed as described above with an additional wash step. Following the room temperature water washes, the silk fibroin was then incubated in 2 L of 8 M urea for 20 mins. Following the urea soak, the fibers where then rinsed for 5 mins under flowing DI water to remove excess urea. The molecular weight of the urea washed silk fibroin standard (TF_14) was 35.4 kDa indicating that the urea wash did not breakdown the silk fibroin any further than the standard degumming process.

Sericin powder (Sigma) and the fibroin standard were used to prepare a standard curve in which the concentration of SF was held constant at 100 mg/mL while the sericin concentration was varied from 0 to 50 mg/mL. A 200 mg/mL SF standard (Solution 1) was prepared by dissolving 500 mg of fibroin fibers in 2.0 mL of trifluoroacetic acid (TFA). A 250 mg/mL sericin stock solution (Solution 2) was prepared by dissolving 500 mg of sericin powder in 1.5 mL of DI water. A 25 mg/mL sericin stock solution (Solution 3) was prepared by diluting 100 μL of Solution 2 with 900 μL of DI water. The standard curve was prepared as follows:

AA_02_1 (100 mg/mL SF w/10% sericin) was prepared by mixing 250 μL of SF Solution 1 with 200 μL of sericin Solution 2. The final volume was brought to 500 μL with 50 μL of DI water.

AA_02_2 (100 mg/mL SF w/5% sericin) was prepared by mixing 250 μL of SF Solution 1 with 100 μL of sericin Solution 2. The final volume was brought to 500 μL with 150 μL of DI water.

AA_02_3 (100 mg/mL SF w/2% sericin) was prepared by mixing 250 μL of SF Solution 1 with 40 μL of sericin Solution 2. The final volume was brought to 500 μL with 210 μL of DI water.

AA_02_4 (100 mg/mL SF w/1% sericin) was prepared by mixing 250 μL of SF solution 1 with 20 μL of sericin solution 2. The final volume was brought to 500 μL with 230 μL of DI water.

AA_02_5 (100 mg/mL SF w/0.5% sericin) was prepared by mixing 250 μL of SF solution 1 with 10 μL of sericin solution 2. The final volume was brought to 500 μL with 240 μL of DI water.

AA_02_6 (100 mg/mL SF w/0.1% sericin) was prepared by mixing 250 μL of SF solution 1 with 20 μL of sericin solution 2. The final volume was brought to 500 μL with 230 μL of DI water.

AA_02_7 (100 mg/mL SF w/0% sericin) was prepared by mixing 250 μL of SF solution 1 with 250 μL of DI water.

The percent abundance of each amino acid was determined by HPLC analysis following protein digestion and derivatization. 20 μL of each sample was dried via speed vacuum to remove the TFA. The samples were then transferred to a vacuum hydrolysis tube where it was subjected to vapor-phase acid hydrolysis overnight to digest the peptide into free amino acids. The hydrolyzed samples were then reconstituted in a minimal volume of 0.02 N HCl. The dissolved samples were then prepared for derivatization using the Waters AccQ-Tag derivatization kit. For derivatization, 10 μL of each sample was diluted in 70 μL of Waters-supplied borate buffer. 20 μL of derivatization reagent was added and the samples incubated at 55° C. for 10 mins. Amino acid standards of 500, 400, 300, 200, 100, 50, 10, 5, and 1 μM were prepared in the same manner.

An Agilent 1100 Series HPLC equipped with a Waters Eclipse Amino Acid Analysis column was used to quantify amino acid content. A gradient of elution buffers composed of 40 mM sodium potassium phosphate pH 7.8 (Buffer A) and 45% acetonitrile, 45% methanol and 10% water (Buffer B) was used to elute the amino acids from the column at a flow rate of 2 mL/min. Elution was monitored 338 nm.

Amino acid analysis for the SF solution (TF_10) was performed as described above. The measured G: S ratio for was 4.74, putting it below the 0.1% sericin limit of detection of the assay. This indicates that the purity of the SF was >99.9%.

Example 36. 700 g Silk Fibroin Manufacturing with Final Filtration Study

Silk Degumming

Ten separate 0.5 M sodium carbonate solutions were prepared in separate 2 L glass containers as described; 79.5 g of sodium carbonate was dissolved in 1.5 L of deionized (DI) water. A recirculating water bath was used to heat the carbonate solutions to 85° C. Once the solutions reached temperature, 103.7 g of silk yarn (Jiangsu SOHO) was added to each 2 L glass vessel containing sodium carbonate solution (1,037 g total silk yarn; 80 g silk/L carbonate solution). The silk was degummed with intermittent stirring for 4 hours at 85° C. After 4 hours, the silk yarn was removed from the degumming solution and placed in excess room temperature water for 5 minutes. The silk fibers manually pressed to expel the water and rinsed under running water for an additional five minutes to remove residual sericin and sodium carbonate solution. The fibers were stretched on a clean surface to dry.

Silk Fibroin Dissolution

In each of 6×1 L glass bottles, 100 g of dried, degummed silk fibroin (SF) was packed tightly into the bottom. One additional glass bottle was packed with the remaining 78 g of SF. 9.3 M lithium bromide solution was prepared by dissolving 2,524 g of lithium bromide to a final volume of 3 L with water. 400 mL of 9.3 M lithium bromide solution was added to each of the 6×1 L glass bottles containing 100 g of SF, while 380 mL was added to the 78 g SF sample. The solutions were incubated at 60° C. overnight to allow for complete dissolution.

Silk Fibroin Dilution and Clarification

The 20% (w/v) SF solutions in lithium bromide were removed from the 60° C. oven and combined into a 5 gallon plastic container. The final volume of dissolved SF was 3.38 L. 6.15 L of room temperature deionized (DI) water was quickly added to the warm SF solution. This diluted the concentration of SF from 20% (w/v) to 7.1% (w/v) and caused a precipitate layer to form and partition into the foam on top of the diluted solution.

The solution was filtered using a Millipore Opticap® XL 5 Capsule filter with a Polygard®-CN 5.0 μm nominal filter. The final 500 mL, which contained most of the precipitate, was not passed through the filter. It was added to 500 mL centrifuge bottles and was centrifuged at 4000×g at 4° C. for 10 minutes. A small amount of precipitate remained in this small volume and was filtered through a 0.2 μm vacuum filter unit. Containers were rinsed with 870 ml DI water, which was pumped through the filter to flush out the remaining solution and the filter was pumped until it was dry. This diluted the SF solution to a concentration of 6.5% (w/v) SF. The filtered material, including the flush, as well as the flush and centrifuged solution, were combined and weighed in a 2.5 gallon container. The mass of the solution after clarification was 11.4 kg. The solution was clear and had an amber color.

Tangential Flow Filtration Purification of Silk Fibroin

A tangential flow filtration (TFF) system with a 1.14 $m^2$ Ultracel® 5 kDa Pellicon® 3 cassette was used for final purification of SF. Prior to the introduction of SF solution, the system was flushed with 20-30 L of DI water to remove any 0.1N NaOH storage solution. The feed pressure was maintained below 30 psi and system was inspected for leaks by increasing the transmembrane pressure (TMP) to 20-40 psi. When the pH of the permeate and retentate lines were neutral, the normal water permeability of the system was determined and the system was drained. The degummed, dissolved, and filtered 6.5% (w/v) SF solution was concentrated to half of its initial volume under stirring. During concentration, a TMP of ~20-25 psi and a feed rate of 5 L/$m^2$/min. were maintained. The lithium bromide was removed from the silk fibroin solution by diafiltration against 40-45 L of DI water (7 total diavolumes) while maintaining a silk fibroin solution volume of ~5.7 L. The TMP was maintained between 25-30 psi with a feed rate of 4-6 L/$m^2$/min throughout the diafiltration. After 7 total diavolumes, the SF was concentrated until an additional 1 kg of permeate had been removed. The TFF process to purify silk fibroin was successfully performed using 1.14 $m^2$ of a 5 kDa Ultracel® membrane to process a total of 678 g of silk fibroin in 5-6 hours.

The SF solution was transferred to a 10 L carboy. Following purification of the silk fibroin, the TFF system was cleaned, sanitized with 10 L of 0.1 N sodium hydroxide, the NWP was determined, and the membrane was stored in 0.1N sodium hydroxide.

Silk Fibroin Solution Collection and Final Filtration

Following final concentration of silk fibroin solution, the TFF system was stopped. The permeate valve was then closed completely and the retentate line was removed from the sample reservoir and placed into a clean, 10 L plastic carboy for collection. The SF solution was pumped from the reservoir at 1-2 liters/min until the sample reservoir was empty, ensuring not to introduce air. 700 ml of DI water was then added to the reservoir, pumped through the system, and collected. This was performed a total of three times to ensure all of the SF solution was collected. The final mass of the SF solution was determined to be 11.2 kg.

The purified SF solution was filtered through an Opticap XL 600 Capsule Millipore SHC 0.5/0.2 μm filter. The filtration was performed under low pressure as to not exceed 20 psi. The filtered material was collected under clean conditions in multiple sterile 500 mL polyethylene terephthalate copolyester, glycol modified (PETG) bottles.

pH and Conductivity of Silk Fibroin Solution Through TFF

The conductivity and pH of the retentate was measured after each diavolume. Over the course of the TFF process, the pH was between 8.5-9.5. The initial pH was 8.44 which slowly increased to 9.35 by the fifth diavolume. By the end of the run, the pH decreased to 8.59. With past small-scale TFF runs, we have seen that the pH typically stays in the 8-9 range throughout the process. The initial conductivity of the SF solution was 8.53 mS/cm and gradually decreased to a final conductivity of 0.256 mS/cm (256 μS/cm) over the TFF cleanup. These data are similar to the conductivity results that were observed during other large TFF runs have very high starting conductivities (100-150 mS/cm) and end with similar final conductivities (0.6-0.8 mS/cm), representative of efficient removal of the lithium bromide salt.

Silk Fibroin Concentration

The final concentration of the silk fibroin solution was measured via gravimetric analysis. 5 small plastic weigh boats were tared and weights recorded. 1 mL of the silk fibroin solution was added to each weigh boat using a positive displacement pipette. Samples were left to dry overnight at 60° C. The following day, the samples were weighed and the dry silk fibroin in each weigh boat was calculated. The concentration of silk fibroin per unit volume was then calculated using the average of the five samples. The final concentration of silk fibroin was determined to be 11.81% (w/v).

Silk Fibroin Molecular Weight Determination

The average molecular weight of the silk fibroin was measured by ultra-performance liquid chromatography size exclusion chromatography (UPLC-SEC). A Waters Acquity H-Class UPLC equipped with a Waters BEH 200 Å 1.7 μm, 4.8×300 cm UPLC SEC column was used. Sample temperature was maintained at 4° C. throughout the analysis. An isocratic flow rate of 0.3 mL/min using mobile phase (100 mM Tris-HCl with 400 mM sodium perchlorate, pH 8.0) was used to elute SF from the column. Mobile phase was prepared by dissolving 12.1 g of Tris base and 48.1 g of sodium perchlorate in 800 ml of DI water. The pH was adjusted to 8.0 with 6N HCl. DI water was added to a final volume of 1 L. The mobile phase was filtered through a 0.2 μm polyethersulfone membrane filter. Silk fibroin elution was monitored at 280 nm. Molecular weights were calculated using a standard curve prepared from Waters BEH 200A Protein SEC Standard Mix. The molecular weight for TF_54 was 39.4 kDa.

Example 37. 20 kg Silk Fibroin Manufacturing Process

Silk Fibroin Degumming 312.5 L of 0.5M sodium carbonate was charged into a 100 gallon jacketed reactor containing a false bottom grate. The pores in the grate were small enough as to not allow the silk yarn to pass through. The reactor was fitted with either a recirculating pump that pumped the sodium carbonate solution from below the false bottom and back into the top of the reactor or a stirring mechanism below the false bottom. The sodium carbonate degumming solution was heated to 85° C. 25 kg of silk yarn was added to the reactor while maintaining a temperature of 85° C. The silk yarn was degummed at 85° C. in 0.5 M sodium carbonate for 4 hours with constant recirculation of the degumming solution or constant stirring below the false bottom. After the silk yarn was degummed for 4 hours, the degumming solution was drained from the reactor.

The degummed SF was rinsed on the false bottom of the reactor with 70-80° C. warm water to remove residual sericin and sodium carbonate. The SF fibers were removed from the reactor and excess water was removed via standard solid/liquid manufacturing separation techniques including centrifugation, manual press, disc stack separators, etc., and dried using air drying or elevated temperature dry heat drying at up to 60° C. Alternatively, the wet silk fibers can be directly dissolved without water removal or drying.

Dissolution of Silk Fibroin 20 kg SF fibers were charged into a 50 gallon jacketed reactor (or similar container) fitted with an overhead paddle stirrer. A simple, alternative reactor may involve the use of a 55 gallon stainless steel drum fitted with a temperature controlled heating jacket and overhead stirrer. The reactor was then charged with 80 L of 9.3M lithium bromide to produce 20% (w/v) SF in 9.3M lithium bromide. Alternatively, this concentration may be adjusted if the SF fibers were not completely dried to account for water in the fibers. If necessary, dry lithium bromide and water may be added to the wet SF fibers to generate the final conditions of 20% (w/v) SF in 9.3M lithium bromide. The reactor was heated to 60° C. for at least 4 hrs.-16 hrs. to allow for dissolution with slow stirring.

Silk Fibroin Dilution and Clarification

The 100 L of 20% (w/v) SF solution in lithium bromide was pumped from the 50-55 gallon reactor to a 125 gallon reactor or larger. The 50 gallon reactor was rinsed with 3×100 liters of room temperature water which was quickly pumped onto the 125 gallon reactor and mixed with the SF solution (final SF solution volume of 400 L). Diluting the SF solution from 20% (w/v) to 6.5% (w/v) SF while warm caused the SF precipitate that was formed to separate to the foam layer on top of the SF solution. This is important to allow for filtration from the bottom of the reactor minimizing the filter surface area needed for clarification of the SF solution.

The solution was filtered by pumping the solution from the bottom of the vessel, as to not to disturb the layer of precipitate, at constant low pressure of 6-8 psi. The solution was filtered through at least 0.1 $m^2$ of a Pall Profile® II 5 μm polypropylene filter cartridge or equivalent ensuring not to introduce the foam layer. The SF solution was pumped into a second 125 gallon vessel. This produced a clear, amber solution of SF in lithium bromide at 6.5% (w/v).

Tangential Flow Filtration Purification of Silk Fibroin

The final SF purification was performed using a tangential flow filtration (TFF) system with 22.8 $m^2$ Ultracel® 5 kDa Pellicon® 3 membrane (one option is 20×1.14 $m^2$ cassettes) fitted with in-line pressure, pH, and conductivity monitoring.

The degummed, dissolved, diluted and filtered 5% (w/v) silk fibroin solution was transferred to a 125 gallon reservoir. The SF was then concentrated to half its initial mass or volume (400 L to 200 L) at a feed rate of 4-6 L/$m^2$/min. The lithium bromide was removed from the SF solution via diafiltration against 1400-1600 L of DI water (7-8 total diavolumes) while keeping the silk fibroin reservoir at a constant volume of 200 L. The feed rate of 4-6 L/$m^2$/min was maintained. The pressure, conductivity, and pH of the system were measured continuously. After 7-8 diavolumes, the SF solution was concentrated by 10-20% of its volume to allow for rinsing of the system.

Silk Fibroin Sterile Filtration

The purified SF solution was filtered through 3× Opticap XL5 Capsule Millipore Express SHC 0.5/0.2 μm filters or 2×XL10 Milligard PES 1.2/0.2 μm Millipore filters or an equivalent. The filtration was performed under low pressure as to not exceed 20 psi. The filtered material was collected under aseptic conditions into multiple sterile containers.

Lithium Bromide Recycling

Lithium bromide solution collected from the permeate of the TFF can be recycled for use in other industries. The permeate can be concentrated using wastewater evaporators (such as Poly Products, Inc. Evaporative Tank-III-W or an equivalent) fitted with a condenser unit. The concentrated lithium bromide solution can be reused either in another industry (refrigeration, etc.) or concentrated to be reused in the SF dissolution process. Water collected from the condenser can be used for future degumming processes increasing the efficiency of the SF manufacturing process.

Example 38. 200 kg Silk Fibroin Manufacturing Process

Silk Fibroin Degumming 3125.0 L of 0.5M sodium carbonate was charged into a 1000 gallon jacketed reactor containing a false bottom grate. The pores in the grate were small enough as to not allow the silk yarn to pass through. The reactor was fitted with either a recirculating pump that pumped the sodium carbonate solution from below the false bottom and back into the top of the reactor or a stirring mechanism below the false bottom. The sodium carbonate degumming solution was heated to 85° C. 250 kg of silk yarn was added to the reactor while maintaining a temperature of 85° C. The silk yarn was degummed at 85° C. in 0.5 M sodium carbonate for 4 hours with constant recirculation of the degumming solution or constant stirring below the false bottom. After the silk yarn was degummed for 4 hours, the degumming solution was drained from the reactor.

The degummed SF was rinsed on the false bottom of the reactor with 70-80° C. warm water to remove residual sericin and sodium carbonate. The SF fibers were removed from the reactor and excess water was removed via standard solid/liquid manufacturing separation techniques including centrifugation, manual press, disc stack separators, etc., and dried using air drying or elevated temperature dry heat drying at up to 60° C. Alternatively, the wet silk fibers can be directly dissolved without water removal or drying.

Dissolution of Silk Fibroin 200 kg SF fibers were charged into a 500 gallon jacketed reactor (or similar container) fitted with an overhead paddle stirrer. The reactor was then charged with 800 L of 9.3M lithium bromide to produce 20% (w/v) SF in 9.3M lithium bromide. Alternatively, this concentration may be adjusted if the SF fibers were not completely dried to account for water in the fibers. If necessary, dry lithium bromide and water may be added to the wet SF fibers to generate the final conditions of 20% (w/v) SF in 9.3M lithium bromide. The reactor was heated to 60° C. for at least 4 hrs.-16 hrs. to allow for dissolution with slow stirring.

Silk Fibroin Dilution and Clarification

The 1000 L of 20% (w/v) SF solution in lithium bromide was pumped from the 500 gallon reactor to a 1250 gallon reactor or larger. The 500 gallon reactor was rinsed with 3×1000 liters of room temperature water which was quickly pumped onto the 1250 gallon reactor and mixed with the SF solution (final SF solution volume of 4000 L). Diluting the SF solution from 20% (w/v) to 6.5% (w/v) SF while warm caused the SF precipitate that was formed to separate to the foam layer on top of the SF solution. This is important to allow for filtration from the bottom of the reactor minimizing the filter surface area needed for clarification of the SF solution.

The SF solution was filtered by pumping the solution from the bottom of the 1250 gallon vessel, as to not to disturb the layer of precipitate, at constant low pressure of 6-8 psi. The solution was filtered through at least 1 $m^2$ of a Pall Profile® II 5 μm polypropylene filter cartridge or equivalent ensuring not to introduce the foam layer. The SF solution was pumped into a second 1250 gallon vessel. This produced a clear, amber solution of SF in lithium bromide at 6.5% (w/v). The foam layer containing the precipitate can be collected liquid separated using centrifugation or an equivalent technique.

Tangential Flow Filtration Purification of Silk Fibroin

The final SF purification was performed using a tangential flow filtration (TFF) system with at least 228 $m^2$ Ultracel® 5 kDa Pellicon® 3 membrane fitted with in-line pressure, pH, and conductivity monitoring.

The degummed, dissolved, diluted and filtered 5% (w/v) silk fibroin solution was transferred to a 1250 gallon reservoir. The SF was then concentrated to half its initial mass or volume (4000 L to 2000 L) at a feed rate of 4-6 L/$m^2$/min. The lithium bromide was removed from the SF solution via diafiltration against 14,000-16,000 L of DI water (7-8 total diavolumes) while keeping the silk fibroin reservoir at a constant volume of 2000 L. The feed rate of 4-6 L/$m^2$/min was maintained. The pressure, conductivity, and pH of the system were measured continuously. After 7-8 diavolumes, the SF solution was concentrated by 10-20% of its volume to allow for rinsing of the system.

Silk Fibroin Sterile Filtration

The purified SF solution was filtered through 30× Opticap XL5 Capsule Millipore Express SHC 0.5/0.2 μm filters or 20×XL10 Milligard PES 1.2/0.2 μm Millipore filters or an equivalent. The filtration was performed under low pressure as to not exceed 20 psi. The filtered material was collected under aseptic conditions into multiple sterile containers.

Lithium Bromide Recycling

Lithium bromide solution collected from the permeate of the TFF can be recycled for use in other industries. The permeate can be concentrated using wastewater evaporators (such as Poly Products, Inc. Evaporative Tank-III-W or an equivalent) fitted with a condenser unit. The concentrated lithium bromide solution can be reused either in another industry (refrigeration, etc.) or concentrated to be reused in the SF dissolution process. Water collected from the condenser can be used for future degumming processes increasing the efficiency of the SF manufacturing process.

Example 39. Hot Dilution

Silk Degumming

Silk yarn was degummed in 0.5M sodium carbonate with intermittent stirring for 4 hr. at 85° C. After 4 hours, the silk yarn was removed from the degumming solution and placed in excess room temperature water for 5 minutes. The silk fibers manually pressed to expel the water and rinsed under running water for an additional five minutes to remove residual sericin and sodium carbonate solution. The fibers were stretched on a clean surface to dry.

Silk Fibroin Dissolution 50 g of degummed silk fibroin was packed tightly into the bottom of a 500 ml glass jar. 200 ml of 9.3 M lithium bromide solution was added to the 500 ml glass jar. The solution was incubated at 60° C. overnight (~16 hrs.) to allow for complete dissolution.

Silk Fibroin Dilution and Clarification

TF-24A: 125 ml of 20% (w/v) SF solution was cooled to room temperature. The solution was then diluted to 5% (w/v) SF with 450 ml deionized (DI) water. Upon dilution, the solution was initially clear. However, a haziness developed in the SF solution over time.

The 5% (w/v) SF solution was filtered using a peristaltic pump through an Optiscale 47 Capsule Polygard-CN 2.5 μm Nominal (Millipore Cat #SN25A47HH3) filter. After 200 ml of solution had passed through the filter, the pressure gauge in line before the filter exceeded 30 psi. An additional 75 ml of solution was filtered slowly before filter was clogged.

TF-24B: 125 ml of 20% (w/v) SF solution was diluted to 450 ml total volume immediately after being removed from the 60° C. oven. The SF solution, instead of starting out clear and slowly becoming hazy, immediately created aggregate clumps that rose to the top of the solution and remained in the foam layer.

The pellet was carefully decanted from the 5% (w/v) SF solution and the remaining, clear SF solution was successfully filtered entirely through an Optiscale 47 Capsule Polygard-CN 2.5 μm Nominal (Millipore Cat #SN25A47HH3) filter with no pressure issues.

The decanted pellet (TF-24C) containing some SF solution was filtered reusing that the end of TF-24 B filtration and passed without issue. The three solutions can be seen in FIG. 3. Even after filtration, the cold dilution (TF-24A) contained a hazy precipitate as did the filtered pellet solution (TF-24C). The SF solution produced after immediate dilution (while warm at 60° C.), however, produced a clear, amber solution after filtration.

The dilution of warm SF solution allowed for silk precipitate to form at the top of the solution and resulting in a clear, easily filtered SF solution. This will be very advantageous during manufacturing to allow for maximum efficiency of clarification filtration and a simple means of removing the precipitate. Filtering directly from the bottom of the tank could allow for significant reduction of filter fouling reducing both manufacturing time and costs.

Example 40. Silk Fibroin Stability

Following purification, the silk fibroin (SF) solution must be stable and free of microbial contamination. The stability of the purified SF solution in the presence of two common preservatives (propanediol and potassium sorbate) as well as elevated pH was tested at various temperatures.

Silk fibroin was prepared by degumming silk yarn in a 0.5 M sodium carbonate solution. To each of 9×2 L glass bottles, 106 g of sodium carbonate was added. DI water was added to each to a final volume of 2 L. The glass bottles were placed into a recirculating water bath and the system warmed to 85° C. To each of the bottles, 60 g of silk yarn was added. The silk yarn was degummed for 4 hours at 85° C. After 4 hours, the silk yarn was removed from the bottles and rinsed under DI water to remove excess sericin and carbonate solution. The fibroin fibers were then squeezed to remove water and spread in a fume hood to dry overnight. The entire process was repeated an addition time to degum a total of 1080 g of silk yarn.

To dissolve the SF fibers, 120 g of SF (batch SBL_194) was placed in each of 3×1 L glass bottles along with 600 ml of 9.3 M lithium bromide. The bottles were incubated at 60° C. overnight to dissolve the SF fibers. To an additional 3×1 L glass bottles, 140 g of wet SF fibers (SBL_195) was incubated with 488 mL of 9.3 M lithium bromide. The bottles were incubated at 60° C. overnight to allow for complete dissolution of the fibers.

Prior to tangential flow filtration, the SF solution was diluted 5% by adding sufficient DI water to bring the final volume to 11.14 L then filtered through a 0.5 μm Optiscale® 25 Capsule filter to remove any particulates.

A tangential flow filtration (TFF) system with two 0.11 $m^2$ Pellicon® 3 cassettes with Ultracel® 5 kDa membranes was used for purification of the SF. Prior to introduction of SF to the system, the system was washed with DI water and sanitized with 0.1 N sodium hydroxide. The system was then flushed with DI water to remove sodium hydroxide.

Using the TFF system, the SF solution was initially concentrated from 5% (w/v) to 10% (w/v) SF. Diafiltration was performed at 10% (w/v) SF to remove lithium bromide. The silk fibroin was diafiltered for 10 diavolumes against DI water. Following TFF, the solution was collected and filtered through a 0.5/0.2 μm Opticap® 47 capsule filter.

The concentration of silk fibroin in TF_44 was determined by loss on drying. The dry mass of 5 hexagonal weigh boats was measured and recorded. To each, 1 mL of silk fibron was added. The weigh boats were then placed at 60° C. overnight. The final mass was recorded and the weight of the dry silk fibroin was measured. The final concentration of TF-44 was 9.1%

The molecular weight of the SF solution (TF_44) was determined by size exclusion chromatography (SEC). For SEC analysis, a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. SF elution was monitored at 280 nm. Molecular weights were calculated using a standard curve prepared from Waters BEH 200A Protein SEC Standard Mix (Waters, Milford, MA). The molecular weight of the SF solution (TF_44) was 35.2 kDa.

SF Stability Sample Preparation

- SS_01_02 consisting of 8.18% SF with 10% Propanediol at pH 9.0 was prepared by mixing 180 g SF solution (TF_44) and 20 g of ZEMEA propanediol using a sterile serological pipet. The solution was aliquoted into 9×50 ml conical tubes.
- SS_01_03 consisting of 8.62% SF with 5% Propanediol at pH 9.0 was prepared by mixing 190 g SF solution (TF_44) with 10 g of propanediol using a sterile serological pipet. The solution was aliquoted into 9×50 ml conical tubes.
- SS_01_04 consisting of 8.98% SF with 1% Potassium Sorbate at pH 6.5 was prepared by mixing 198 g SF solution (TF_44) with 2 g of potassium sorbate with a stir bar. The pH of the solution was adjusted to 6.5 using 1 N HCl. The solution was sterile filtered using a 0.2 μm PES membrane filter. The solution was aliquoted into 9×50 ml conical tubes.
- SS_01_05 consisting of 9.08% SF at pH 6.5 was prepared by adjusting the pH of 200 g SF solution (TF-44) to pH 6.5 using 1 N HCl. The solution was sterile filtered through a 0.2 μm PES membrane filter. The solution was aliquoted into nine 50 ml conical tubes.
- SS_01_06 consisting of 9.09% SF at pH 9.1 was prepared from 200 g SF solution (TF_44) without any adjustments. The solution was aliquoted into nine 50 ml conical tubes.

For each sample, 3 conical tubes were placed at 4° C., room temperature (RT), or 37° C. to assess the shelf-life of concentrated SF solutions.

The stability of the SF solutions was accessed via ultra-performance liquid chromatography (UPLC) using size-exclusion chromatography (SEC). A Waters Acquity H-Class UPLC equipped with a Waters BEH 200 Å 1.7 mm, 4.8×300 cm UPLC SEC column was used. Sample temperature was maintained at 4° C. An isocratic flow at 0.3 mL/min of mobile phase 100 mM Tris-HCl with 400 mM anhydrous sodium perchlorate, pH 8.0 was used to elute SF from the column. Mobile phase was prepared by dissolving 12.1 g of Tris base and 48.1 g of sodium perchlorate in 800 mL of DI water. The pH was adjusted to 8.0 with 6N HCl. DI water was added to a final volume of 1 L. The solution was sterile filtered through a 0.2 μm polyethersulfone membrane filter. SF solutions were diluted to 1% SF in mobile phase and 2 μL injections were used. SF elution was monitored at 280 nm and 220 nm. The average molecular weight was calculated using a standard curve prepared from Waters BEH 200 Å Protein SEC Standard Mix.

SF samples were taken for analysis 1 week, 1 month and 2 months post incubation. The stability was accessed by examining changes in molecular weight (MW) which may indicate aggregation or fragmentation of the protein, the presence of distinct aggregate peaks, and peak area which reflects the total amount of protein in solution, as well as visually inspecting the samples for precipitation or gelation.

No visual changes in the solutions were observed at 1 month. At the 2-month time point, the samples containing 5% propanediol at room temperature and 37° C. had gelled as well as the 10% propanediol solution at 37° C. This indicates that propanediol induces SF gel formation over time.

At two months, a small, front-ended shoulder appeared in the SEC trace for all samples. However, the total peak area of this shoulder was <1% indicating only a small amount of SF aggregate was present in the samples. The samples containing 1% potassium sorbate at pH 6.0 and SF at pH 6.0 showed the highest levels of aggregation at 0.7% and 0.6%, respectively.

For samples at 4° C. and room temperature, there was very little change in molecular weight of the silk fibroin as shown in Table 64. Of the 37° C. samples which had not formed a gel, a decrease in molecular weight was observed with the SF solution at pH 6.0 showing the greatest reduction of ~5000 Da.

TABLE 64

Molecular weight analysis for silk fibroin stability samples

| Sample # | Condition | Average MW Baseline | 1 week | 1 month | 2 months |
|---|---|---|---|---|---|
| 2 | 5% Propanediol, 4° C. | 35119 | 35128 | 34829 | 35219 |
| 3 | 10% Propanediol, 4° C. | 35119 | 35426 | 35450 | 36393 |
| 4 | 1% Potassium Sorbate, 4° C. | 35119 | 35128 | 34531 | 34931 |
| 5 | pH 9.0, 4° C. | 35119 | 35128 | 34240 | 34931 |
| 6 | pH 6.0, 4° C. | 35119 | 34538 | 35128 | 36098 |
| 8 | 5% Propanediol, RT | 35119 | 34531 | 35426 | — |
| 9 | 10% Propanediol, RT | 35119 | 34531 | 34531 | 35507 |
| 10 | 1% Potassium Sorbate, RT | 35119 | 33957 | 33390 | 34643 |
| 11 | pH 9.0, RT | 35119 | 34240 | 33949 | 34081 |
| 12 | pH 6.0, RT | 35119 | 33092 | 35128 | 35507 |
| 14 | 5% Propanediol, 37° C. | 35119 | 33375 | 32546 | — |
| 15 | 10% Propanediol, 37° C. | 35119 | 33092 | 31979 | — |
| 16 | 1% Potassium Sorbate, 37° C. | 35119 | 33659 | 32815 | 32710 |
| 17 | pH 9.0, 37° C. | 35119 | 34538 | 33092 | 32576 |
| 18 | pH 6.0, 37° C. | 35119 | 33375 | 31178 | 30628 |

The peak areas for SF appear to show a trend of decreasing with time and temperature as shown in Table 65. However, the peak areas fall within the error of the assay, indicating no significant changes in total SF protein over time.

TABLE 65

Peak area analysis for silk fibroin stability samples

| | Condition | Baseline | 1 week | 1 month | 2 months |
|---|---|---|---|---|---|
| 2 | 5% Propanediol, 4° C. | 0.07875 | 0.0706695 | 0.1202797 | 0.0666081 |
| 3 | 10% Propanediol, 4° C. | 0.07875 | 0.0789317 | 0.1286169 | 0.0679998 |
| 4 | 1% Potassium Sorbate, 4° C. | 0.07875 | 0.0854806 | 0.1665602 | 0.0650843 |
| 5 | pH 9.0, 4° C. | 0.07875 | 0.0666213 | 0.1709022 | 0.0674268 |
| 6 | pH 6.0, 4° C. | 0.07875 | 0.0736672 | 0.1245516 | 0.0682720 |
| 8 | 5% Propanediol, RT | 0.07875 | 0.0707141 | 0.1019679 | — |
| 9 | 10% Propanediol, RT | 0.07875 | 0.0802288 | 0.0987339 | 0.0672689 |
| 10 | 1% Potassium Sorbate, RT | 0.07875 | 0.0778734 | 0.1135878 | 0.0684691 |
| 11 | pH 9.0, RT | 0.07875 | 0.0644361 | 0.1204349 | 0.0675777 |
| 12 | pH 6.0, RT | 0.07875 | 0.0663687 | 0.1016545 | 0.0786802 |
| 14 | 5% Propanediol, 37° C. | 0.07875 | 0.0693329 | 0.1173466 | — |
| 15 | 10% Propanediol, 37° C. | 0.07875 | 0.0745127 | 0.1152459 | — |
| 16 | 1% Potassium Sorbate, 37° C. | 0.07875 | 0.0777348 | 0.1061961 | 0.0655001 |
| 17 | pH 9.0, 37° C. | 0.07875 | 0.0759090 | 0.1114905 | 0.0662196 |
| 18 | pH 6.0, 37° C. | 0.07875 | 0.0768169 | 0.1029814 | 0.0638830 |

Based upon the results of these studies, silk fibroin forms a gel in the presence of propanediol within 2 months at RT and 37° C. This gelation seems to be inhibited slightly by higher concentrations of propanediol as the 5% propanediol solution gelled at room temperatures at 2 months whereas the 10% solution at room temperature did not. After 2 months at either 4° C. or room temperature, the silk fibroin solutions containing 10% propanediol, 1% potassium sorbate or silk fibroin at either pH 6.0 or 9.0 remained stable with only minor aggregation and insignificant changes in molecular weight with no precipitation.

CONSUMER PRODUCTS EXAMPLES

Example 41. Optically Clear Silk Fibroin Hydrogels

Silk Fibroin Isolation

Silk yarn, purchased from Jiangsu SOHO International Group, was degummed to remove sericin. 103.7 grams of cut silk yarn were heated at 85° C. in 10 separate glass vessels (for 1.037 kilograms total) filled with 1.5 L of deionized (DI) water with 0.5M sodium carbonate each with occasional stirring. After 6 hours, the fibroin was removed and rinsed under DI water for 1 minute. The fibroin was dried overnight, weighed, and dissolved in a 9.3M aqueous solution of lithium bromide (from Sigma-Aldrich, St. Louis, MO) at a ratio of 20% silk fiber by weight per volume for ~16 hours, or overnight, at 60° C. The following morning, the dissolved silk fibroin was diluted to 5% (w/v) silk fiber using DI water. The solution was then transferred to a tangential flow filtration (TFF) system. The SF was then concentrated to half its initial volume and the lithium bromide was removed from the solution by TFF against ~75 L of DI water in 8 diavolumes using a 5 kDa cellulose membrane. The final SF solution was filtered through a 0.5/0.2 μm PES filter unit into clean containers. These containers were stored at −20° C. until use.

To determine the SF molecular weight a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. Silk fibroin was diluted to 1% (w/v) in mobile phase after thawing before being run on SEC. Silk fibroin elution was monitored at 280 nm. Molecular weights were calculated using a standard curve prepared from Waters BEH 200A Protein SEC Standard Mix (Waters, Milford, MA).

To determine silk fibroin concentration, gravimetric analysis was used. For the gravimetric analysis, five small plastic weigh boats were tared on an analytic balance to +0.1 mg, 1 ml of the stock solution was pipetted onto each weigh boat using a positive displacement pipette. The weigh boats with the solution were then placed in an oven set at 60° C. overnight (or approximately 16 hours). Once fully dried, the weigh boats were massed again on the balance to determine the weight of silk fibroin remaining. Each mass represents the amount of silk fibroin in 1 ml of material. The average value across the five replicates was then determined. This is the concentration of the solution in mg/mL.

Formation of Optically Clear Silk Fibroin Hydrogels

A silk fibroin solution, prepared as above with an average molecular weight ranging from 22 KDa-28.5 kDa, was diluted to a concentration of 3% (w/v) SF with DI water. The final volume of solution was 100 mL in an 800 mL plastic beaker. The solution was then agitated with an immersion blender (Mueller Multi-Purpose Ultra-Stick Hand Blender) for 10 seconds on half speed, producing a foamy solution. The solution was allowed to settle for 60 seconds, and the resulting solution and foam was centrifuged at 4,000×g and 4° C. for 10 minutes to remove entrapped air. The supernatant was collected.

This agitated SF solution was diluted with DI water to 1% (w/v) SF in a 50 ml conical tube by mixing 16.667 mL of 3% (w/v) stock with 33.333 mL of DI water. This 1% (w/v) SF solution was incubated at 60° C. overnight (~16 hours) which produced an optically clear SF hydrogel in DI water.

In other experiments, hydrogels were successfully formed by diluting the silk fibroin solution to 3.5, 5.5, and 7.5% (w/v) in DI water prior to agitation with the hand blender. Optically clear SF hydrogels were also formed at 0.25% and 0.5% (w/v) SF from these agitated stocks of SF.

Example 42. Optically Clear Silk Fibroin Hydrogels with Humectant and Preservatives Silk Fibroin Isolation Silk yarn, purchased from Jiangsu SOHO International Group, was degummed to remove sericin. 103.7 grams of cut silk yarn were heated at 85° C. in 10 separate glass vessels (for 1.037 kilograms total) filled with 1.5 L of deionized (DI) water with 0.5M sodium carbonate each with occasional stirring. After 6 hours, the fibroin was removed and rinsed under DI water for 1 minute. The fibroin was dried overnight, weighed, and dissolved in a 9.3M aqueous solution of lithium bromide (from Sigma-Aldrich, St. Louis, MO) at a ratio of 20% silk fiber by weight per volume for ~16 hours, or overnight, at 60° C. The following morning, the dissolved silk fibroin was diluted to 5% (w/v) silk fiber using DI water. The solution was then transferred to a tangential flow filtration (TFF) system. The SF was then concentrated to half its initial volume and the lithium bromide was removed from the solution by TFF against ~75 L of DI water in 8 diavolumes using a 5 kDa cellulose membrane. The final SF solution was filtered through a 0.5/0.2 μm PES filter unit into clean containers. These containers were stored at −20° C. until use.

To determine the SF molecular weight a Waters Acquity H-Class UPLC (Waters, Milford, MA) equipped with a Waters BEH 200 Å1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. Silk fibroin was diluted to 1% (w/v) in mobile phase after thawing before being run on SEC. Silk fibroin elution was monitored at 280 nm. Molecular weights were calculated using a standard curve prepared from Waters BEH 200 Å Protein SEC Standard Mix (Waters, Milford, MA).

To determine silk fibroin concentration, gravimetric analysis was used. For the gravimetric analysis, five small plastic weigh boats were tared on an analytic balance to +0.1 mg, 1 mL of the stock solution was pipetted onto each weigh boat using a positive displacement pipette. The weigh boats with the solution were then placed in an oven set at 60° C. overnight (or approximately 16 hours). Once fully dried, the weigh boats were massed again on the balance to determine the weight of silk fibroin remaining. Each mass represents the amount of silk fibroin in 1 mL of material. The average value across the five replicates was then determined. This is the concentration of the solution in mg/mL.

Optically Clear Silk Fibroin Hydrogels with Additives

Clear SF hydrogels were formed with either 5 or 10% (v/v) glycerol or 5 or 10% (v/v) propylene glycol. The relevant humectant was added to a SF solution either prior to or after agitation with a hand blender. For samples with pre-addition, 100 ml of the following solutions was agitated with a hand mixer; a SF solution, as prepared above, glycerol or propylene glycol, and DI water in 800 ml beakers in these amounts: 3% (w/v) SF with 5 or 10% (v/v) glycerol or propylene glycol. The solutions were then agitated with an immersion blender (Mueller Multi-Purpose Ultra-Stick Hand Blender) for 10 seconds on half speed, producing a foamy solution. The solutions were allowed to settle for 60 seconds, and the resulting solutions and foams were centrifuged at 3,000×g and 4° C. for 10 minutes to remove entrapped air. The supernatants were then poured into 50 ml conical tubes and incubated at 60° C. overnight to induce gelation.

For samples with humectant addition after agitation, SF stock solution, prepared as above, was diluted to a final silk fibroin concentration of 4% (w/v) with DI water. The final volume of solution was 200 mL in an 800 mL plastic beaker. The solution was then agitated with an immersion blender (Mueller Multi-Purpose Ultra-Stick Hand Blender) for 10 seconds on half speed, producing a foamy mixture. After this, the solution was allowed to settle for 60 second, and the resulting solution and foam was centrifuged at 4,000×g and 4° C. for 10 minutes to remove entrapped air. Clear SF hydrogel samples were then prepared by mixing this agitated stock SF, glycerol or propylene glycol, and DI water in 50 ml conical tubes to reach final concentrations of 3% (w/v) SF and either 5 or 10% (v/v) glycerol or propylene glycol. The samples were incubated at 60° C. overnight to induce gelation.

All of these samples gelled within 21 hours at 60° C. with the exception of 10% (v/v) propylene glycol added prior to agitation. It's possible that such a high concentration of additive could be preventing the sol-gel transition of SF.

Other experiments have been able to produce clear silk fibroin hydrogels at various SF concentrations from 0.25 to 7% (w/v) with the addition of 1% (v/v) benzyl alcohol as a preservative. Additionally, hydrogels were formed at 3 and 5% (w/v) silk fibroin with 1% (w/v) sodium gluconate as a potential preservative. All of these hydrogels were prepared as described earlier in this example, with all additives being added prior to agitation via hand blender and incubation at 60° C.

Example 43. Optically Clear Silk Fibroin Hydrogels with Buffer and Salt

Silk Fibroin Isolation

Silk yarn, purchased from Jiangsu SOHO International Group, was degummed to remove sericin. 103.7 grams of cut silk yarn were heated at 85° C. in 10 separate glass vessels (for 1.037 kilograms total) filled with 1.5 L of deionized (DI) water with 0.5M sodium carbonate each with occasional stirring. After 6 hours, the fibroin was removed and rinsed under DI water for 1 minute. The fibroin was dried overnight, weighed, and dissolved in a 9.3M aqueous solution of lithium bromide (from Sigma-Aldrich, St. Louis, MO) at a ratio of 20% silk fiber by weight per volume for ~16 hours, or overnight, at 60° C. The following morning, the dissolved silk fibroin was diluted to 5% (w/v) silk fiber using DI water. The solution was then transferred to a tangential flow filtration (TFF) system. The SF was then concentrated to half its initial volume and the lithium bromide was removed from the solution by TFF against ~75 L of DI water in 8 diavolumes using a 5 kDa cellulose membrane. The final SF solution was filtered through a 0.5/0.2 μm PES filter unit into clean containers. These containers were stored at −20° C. until use.

To determine the SF molecular weight a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. Silk fibroin was diluted to 1% (w/v) in mobile phase after thawing before being run on SEC. Silk fibroin elution was monitored at 280 nm. Molecular weights were calculated using a standard curve prepared from Waters BEH 200 Å Protein SEC Standard Mix (Waters, Milford, MA).

To determine silk fibroin concentration, gravimetric analysis was used. For the gravimetric analysis, five small plastic weigh boats were tared on an analytic balance to +0.1 mg, 1 mL of the stock solution was pipetted onto each weigh boat using a positive displacement pipette. The weigh boats with the solution were then placed in an oven set at 60° C. overnight (or approximately 16 hours). Once fully dried, the weigh boats were massed again on the balance to determine the weight of silk fibroin remaining. Each mass represents the amount of silk fibroin in 1 ml of material. The average value across the five replicates was then determined. This is the concentration of the solution in mg/mL.

Optically Clear Silk Fibroin Hydrogels with Buffer and Salt

Clear hydrogels were formed with a range of 1-10 mM phosphate buffer. First, a 100 mM stock phosphate buffer was prepared by dissolving 284 mg of disodium phosphate and 60 mg of monopotassium phosphate in 18 mL of DI water. The pH was adjusted to 7.4 using 1 N hydrochloric acid and sodium hydroxide and the final volume was brought to 20 mL using DI water. Next, an agitated solution of SF at 3.5% (w/v) was prepared. In a plastic 800 ml beaker, SF was diluted to 3.5% (w/v) with DI water to a final volume of 100 mL. The solution was agitated with an immersion blender (Mueller Multi-Purpose Ultra-Stick Hand Blender) for 10 seconds on half speed, producing a foamy mixture. The solution was allowed to settle for 60 seconds, and centrifuged at 3,000×g and 4° C. for 10 minutes to remove entrapped air. SF clear gel formulation were then prepared in 15 ml conical tubes to final concentrations of 1% (w/v) silk fibroin, 1% (v/v) benzyl alcohol, and either 0, 1, 2, 3, 4, 5, 6, 7, 8, 9, 10 mM phosphate buffer. These formulations were then incubated at 60° C. overnight to induce gelation. All of the samples showed evidence of gelation, with the 0 mM phosphate buffer group outputting a pH of 9.05 and the 10 mM phosphate group outputting a pH of 7.92. See Table 66 for pH values.

TABLE 66

CCN-DSC-CG-19 pH Results

| Sample Lot # | Phosphate Buffer Concentration (mM) | PH |
|---|---|---|
| CCN-DSC-CG-19-1 | 0 | 9.05 |
| CCN-DSC-CG-19-2 | 1 | 8.52 |
| CCN-DSC-CG-19-3 | 2 | 8.39 |
| CCN-DSC-CG-19-4 | 3 | 8.28 |
| CCN-DSC-CG-19-5 | 4 | 8.17 |
| CCN-DSC-CG-19-6 | 5 | 8.10 |
| CCN-DSC-CG-19-7 | 6 | 8.06 |
| CCN-DSC-CG-19-8 | 7 | 8.02 |
| CCN-DSC-CG-19-9 | 8 | 7.99 |
| CCN-DSC-CG-19-10 | 9 | 7.95 |
| CON-DSC-CG-19-11 | 10 | 7.92 |

In another experiment, hydrogels were prepared with 1% (w/v) SF, either 0 or 1% (v/v) benzyl alcohol, 10 mM phosphate buffer, and either 0, 10, 25, 50, 75, 100, or 130 mM sodium chloride. First, a 100 mM phosphate buffer stock solution was prepared by dissolving 284 mg of disodium phosphate and 60 mg of monopotassium phosphate in 18 mL of DI water. The pH was adjusted to 7.4 using 1 N hydrochloric acid and sodium hydroxide and the final volume was brought to 20 mL using DI water. Next, a 1 M sodium chloride stock solution was prepared by dissolving 0.584 g of sodium chloride in 9 mL of DI water, after which the final volume was brought to 10 mL with DI water. Next, a 3% (w/v) agitated SF solution was prepared. In a plastic 800 ml beaker, 100 ml of a silk fibroin solution in water at 3% (w/v) SF was prepared. The solution was agitated with an immersion blender (Mueller Multi-Purpose Ultra-Stick Hand Blender) for 10 seconds on half speed, producing a foamy mixture. The solution was allowed to settle for 60 seconds and centrifuged at 3,000×g and 4° C. for 10 minutes to remove entrapped air. SF clear gel formulations were prepared in 15 mL conical tubes at final concentrations of 1% (w/v) silk fibroin, either 0 or 1% (v/v) benzyl alcohol, 10 mM phosphate buffer, and either 0, 10, 25, 50, 75, 100, or 130 mM sodium chloride. These samples were incubated at 60° C. overnight to induce gelation. All samples showed evidence of gelation. All gels were optically clear with the following exceptions. With no benzyl alcohol present, samples with 75 mM sodium chloride or higher showed slight haziness. With benzyl alcohol present, samples with 25 mM sodium chloride or higher showed slight haziness.

In another experiment, silk fibroin hydrogels were prepared with 0.25, 0.5, 0.75, or 1% (w/v) silk fibroin, either 0 or 1% (v/v) benzyl alcohol, 10 mM phosphate buffer, and either 0, 50, 100, or 150 mM sodium chloride. 100 mM phosphate buffer and 1M sodium chloride stock solutions were prepared as described above. An agitated, 3% (w/v) SF solution was prepared. In a plastic 800 mL beaker, a SF solution was diluted to a volume of 100 ml and 3% (w/v) SF with DI water. The solution was agitated with an immersion blender (Mueller Multi-Purpose Ultra-Stick Hand Blender) for 10 seconds on half speed, producing a foamy mixture. The solution was allowed to settle for 60 seconds and centrifuged at 3,000×g and 4° C. for 10 minutes to remove entrapped air. SF clear hydrogel formulations were then prepared in 15 ml conical tubes to final concentrations of 0.25, 0.5, 0.75, or 1% (w/v) SF, either 0 or 1% (v/v) benzyl alcohol, 10 mM phosphate buffer, and either 0, 50, 100, or 150 mM sodium chloride. These samples were incubated at 60° C. overnight to induce gelation. All samples showed evidence of gelation, with greater salt content resulting in stiffer hydrogels. 0.25% (w/v) SF hydrogels were very weak and runny. 0.5% (w/v) SF formulations containing 1% (v/v) benzyl alcohol and either 100 or 150 mM sodium chloride were slightly hazy. At 0.75 and 1% (w/v) silk fibroin, samples with 100 or 150 mM sodium chloride and samples with benzyl alcohol and 50, 100, or 150 mM sodium chloride were slightly hazy. See Table 67 for specific results.

TABLE 67

CCN-DSC-CG-21 Qualitative Gelation Results

| Sample Lot # | Silk fibroin conc. (% (w/v) | Phosphate buffer conc. (mM) | Benzyl alcohol conc. (% (v/v) | Sodium chloride conc. (mM) | Gelation status after 16 hours at 60° C. |
|---|---|---|---|---|---|
| CCN-DSC-CG-21-1 | 0.25 | 10 | 0 | 0 | Weak, runny gel |
| CCN-DSC-CG-21-2 | 0.25 | 10 | 0 | 50 | Weak, runny gel |
| CCN-DSC-CG-21-3 | 0.25 | 10 | 0 | 100 | Weak, runny gel |
| CCN-DSC-CG-21-4 | 0.25 | 10 | 0 | 150 | Weak, runny gel |
| CCN-DSC-CG-21-5 | 0.25 | 10 | 1 | 0 | Weak, runny gel |
| CCN-DSC-CG-21-6 | 0.25 | 10 | 1 | 50 | Weak, runny gel |
| CCN-DSC-CG-21-7 | 0.25 | 10 | 1 | 100 | Weak, runny gel |
| CON-DSC-CG-21-8 | 0.25 | 10 | 1 | 150 | Very weak, runny gel |
| CCN-DSC-CG-21-9 | 0.5 | 10 | 0 | 0 | Clear gel |
| CCN-DSC-CG-21-10 | 0.5 | 10 | 0 | 50 | Clear gel |
| CCN-DSC-CG-21-11 | 0.5 | 10 | 0 | 100 | Clear gel |
| CCN-DSC-CG-21-12 | 0.5 | 10 | 0 | 150 | Clear gel |
| CCN-DSC-CG-21-13 | 0.5 | 10 | 1 | 0 | Clear gel |
| CCN-DSC-CG-21-14 | 0.5 | 10 | 1 | 50 | Clear gel |
| CCN-DSC-CG-21-15 | 0.5 | 10 | 1 | 100 | Slightly hazy gel |
| CCN-DSC-CG-21-16 | 0.5 | 10 | 1 | 150 | Slightly hazy gel |
| CCN-DSC-CG-21-17 | 0.75 | 10 | 0 | 0 | Clear gel |
| CCN-DSC-CG-21-18 | 0.75 | 10 | 0 | 50 | Clear gel |
| CCN-DSC-CG-21-19 | 0.75 | 10 | 0 | 100 | Slightly hazy gel |
| CCN-DSC-CG-21-20 | 0.75 | 10 | 0 | 150 | Slightly hazy gel |
| CCN-DSC-CG-21-21 | 0.75 | 10 | 1 | 0 | Clear gel |
| CON-DSC-CG-21-22 | 0.75 | 10 | 1 | 50 | Slightly hazy gel |
| CCN-DSC-CG-21-23 | 0.75 | 10 | 1 | 100 | Slightly hazy gel |
| CCN-DSC-CG-21-24 | 0.75 | 10 | 1 | 150 | Slightly hazy gel |
| CCN-DSC-CG-21-25 | 1 | 10 | 0 | 0 | Clear gel |
| CCN-DSC-CG-21-26 | 1 | 10 | 0 | 50 | Clear gel |
| CCN-DSC-CG-21-27 | 1 | 10 | 0 | 100 | Slightly hazy gel |
| CCN-DSC-CG-21-28 | 1 | 10 | 0 | 150 | Slightly hazy gel |
| CCN-DSC-CG-21-29 | 1 | 10 | 1 | 0 | Clear gel |
| CCN-DSC-CG-21-30 | 1 | 10 | 1 | 50 | Slightly hazy gel |
| CCN-DSC-CG-21-31 | 1 | 10 | 1 | 100 | Slightly hazy gel |
| CON-DSC-CG-21-32 | 1 | 10 | 1 | 150 | Slightly hazy gel |

In another experiment, silk fibroin hydrogels were made with 0.2, 0.25, 0.3, 0.4, 0.5, 0.6, 0.7, 0.75, 0.8, 0.9, or 1% (w/v) silk fibroin, 10 mM phosphate buffer, and 135 mM sodium chloride. SF clear hydrogel formulations were prepared in 15 ml conical tubes from a 3% (w/v) agitated SF solution, 100 mM phosphate stock solution, and 1M sodium chloride stock solution. The formulations had final concentrations of 0.1, 0.2, 0.25, 0.3, 0.4, 0.5, 0.6, 0.7, 0.75, 0.8, 0.9, or 1% (w/v) silk fibroin, 10 mM phosphate buffer, and 135 mM sodium chloride. These samples were incubated at 60° C. overnight to induce gelation. All samples showed evidence of gelation with the exception of the 0.1% (w/v) silk fibroin sample, which remained a clear, SF solution. Samples containing silk fibroin at or above 0.5% (w/v) were slightly hazy. Formulations containing between 0.4 and 0.6% (w/v) silk fibroin showed evidence of being thixotropic (hydrogels were slightly runny when the tube was shaken, but would immediately set back up as a stiff hydrogel and when the shaking stopped). This thixotropic effect would be very beneficial for a material that needs to be able to shear thin but recover quickly and efficiently, to aid in injection through small gauge needles or to improve comfort as a corneal gel would under stress from blinking.

These optically clear hydrogels were formulated to for optimal physiologic compatibility, with neutral pH values of ~7.4 and neutral osmolarity of ~290-320 mOsm/L. These hydrogels have the potential for parenteral or topical administration, for example, as ocular formulations for the front of the eye, or drug delivery vehicles, dermal fillers, subdermal filler carriers, or as the base for a lotion, medicated cream or gel, or topical ointment.

Example 44. Temperature Stability of Optically Clear Silk Fibroin Hydrogels

Silk Fibroin Isolation

Silk yarn, purchased from Jiangsu SOHO International Group, was degummed to remove sericin. 103.7 grams of cut silk yarn were heated at 85° C. in 10 separate glass vessels (for 1.037 kilograms total) filled with 1.5 L of deionized (DI) water with 0.5M sodium carbonate each with occasional stirring. After 6 hours, the fibroin was removed and rinsed under DI water for 1 minute. The fibroin was dried overnight, weighed, and dissolved in a 9.3M aqueous solution of lithium bromide (from Sigma-Aldrich, St. Louis, MO) at a ratio of 20% silk fiber by weight per volume for ~16 hours, or overnight, at 60° C. The following morning, the dissolved silk fibroin was diluted to 5% (w/v) silk fiber using DI water. The solution was then transferred to a tangential flow filtration (TFF) system. The SF was then concentrated to half its initial volume and the lithium bromide was removed from the solution by TFF against ~75 L of DI water in 8 diavolumes using a 5 kDa cellulose membrane. The final SF solution was filtered through a 0.5/0.2 μm PES filter unit into clean containers. These containers were stored at −20° C. until use.

To determine the SF molecular weight a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. Silk fibroin was diluted to 1% (w/v) in mobile phase after thawing before being run on SEC. Silk fibroin elution was monitored at 280 nm. Molecular weights were calculated using a standard curve prepared from Waters BEH 200A Protein SEC Standard Mix (Waters, Milford, MA).

To determine silk fibroin concentration, gravimetric analysis was used. For the gravimetric analysis, five small plastic weigh boats were tared on an analytic balance to +0.1 mg, 1 mL of the stock solution was pipetted onto each weigh boat using a positive displacement pipette. The weigh boats with the solution were then placed in an oven set at 60° C. overnight (or approximately 16 hours). Once fully dried, the weigh boats were massed again on the balance to determine the weight of silk fibroin remaining. Each mass represents the amount of silk fibroin in 1 ml of material. The average value across the five replicates was then determined. This is the concentration of the solution in mg/mL.

Temperature Stability of Optically Clear Silk Fibroin Hydrogels

In this experiment, hydrogels were prepared with 0.25, 0.5, or 1% (w/v) SF, with either no buffer and salt or 10 mM phosphate buffer and 135 mM sodium chloride. All of the samples were then assessed under storage conditions at 4° C. (3 months), 20 (0.5, 1, 2, and 3 months), and 37° C. (0.5, 1, 2, and 3 months). See Table 68 for sample list. Samples were assessed via pH, transmittance, and rheological measurement. First, a 100 mM phosphate buffer stock solution was prepared by dissolving 710 mg of disodium phosphate and 150 mg of monopotassium phosphate in 40 mL of DI water. The pH was adjusted to 7.4 using 1 N hydrochloric acid and sodium hydroxide and the final volume was brought to 50 mL using DI water. Next, a 1 M sodium chloride stock solution was prepared by dissolving 2.922 g of sodium chloride in 45 mL of DI water, after which the final volume was brought to 50 mL with DI water. Next, a 3% (w/v) agitated SF solution was prepared. In a plastic 800 ml beaker, 200 ml of a silk fibroin solution in water at 3% (w/v) SF was prepared. The solution was agitated with an immersion blender (Mueller Multi-Purpose Ultra-Stick Hand Blender) for 10 seconds on half speed, producing a foamy mixture. The solution was allowed to settle for 60 seconds and centrifuged at 3,000×g and 4° C. for 10 minutes to remove entrapped air. The agitated solution was then recombined and aseptically filtered through a 0.22 μm polyethersulfone (PES) vacuum filter unit. All other stock solutions were aseptically filtered with 0.22 μm PES syringe filter units. SF clear gel formulations were prepared aseptically in 50 ml conical tubes at final concentrations of 0.25, 0.5, or 1% (w/v) silk fibroin, with either no additive or 10 mM phosphate buffer with 135 mM sodium chloride added. 2 mL samples were aliquoted for the study samples. These samples were incubated at 60° C. overnight to induce gelation. Samples were then assessed for baseline measurements and then placed at the relevant temperatures for the entire time course.

For pH measurements, the average pH of the three replicates was recorded using a glass pH probe. See Table 69 for these results.

For transmittance measurements, 200 μL of each sample was pipetted into a UV-readable 96-well plate. The plate was centrifuged at 4,000×g and 20° C. for 10 minutes to remove any bubbles. The absorbance of each sample was measured on a Molecular Devices SpectraMax iD3 from 230 to 1000 nm in 10 nm increments. The percent transmittance at each wavelength for each sample was determined by the equation: % Transmittance=10^(2−(Absorbance Value). The percent transmittance for each sample was then averaged over the visual wavelength range (380 to 740 nm) for each replicate, averaged between the three replicates, and reported. See Table 70 for these results.

For rheological measurements, a Bohlin C-VOR 150 rheometer was used. A 4°/40 mm cone and plate geometry was used with a Peltier Plate system kept at 25° C. 1.2 ml of each sample was loaded onto the stage and the geometry was lowered to a 0.15 mm gap size. The following test was run: a pre-shear was applied at 1 $s^{-1}$ for 20 seconds; a shear hold at 1 $s^{-1}$ was applied for 60 seconds while taking 20 samples; a shear hold at 10 $s^{-1}$ was applied for 30 seconds while taking 10 samples; a shear hold at 100 $s^{-1}$ was applied for 30 seconds while taking 10 samples; a shear hold at 1 $s^{-1}$ was applied for 30 seconds while taking 10 samples. The average viscosity in cP was then calculated for each shear rate (disregarding the first three data points to account for equilibration), averaged between the three replicates, and reported. The average percent recovery was determined by dividing the average viscosity from the second shear hold at 1 $s^{-1}$ by the average viscosity from the first shear hold at 1 s1. See Tables 69, 70, 71, and 72 for these results.

TABLE 68

CCN-DSC-CG-23 Sample List

| Sample Lot # | Silk fibroin conc. (% (w/v)) | Phosphate buffer conc. (mM) | Sodium chloride conc. (mM) | Storage temperature (° C.) | Timepoint (days) |
|---|---|---|---|---|---|
| CCN-DSC-CG-23-1 | 0.25 | 0 | 0 | — | Baseline |
| CON-DSC-CG-23-2 | 0.25 | 10 | 135 | — | Baseline |
| CON-DSC-CG-23-3 | 0.5 | 0 | 0 | — | Baseline |
| CCN-DSC-CG-23-4 | 0.5 | 10 | 135 | — | Baseline |
| CCN-DSC-CG-23-5 | 1 | 0 | 0 | — | Baseline |
| CCN-DSC-CG-23-6 | 1 | 10 | 135 | — | Baseline |
| CON-DSC-CG-23-7 | 0.25 | 0 | 0 | 4 | 84 |
| CCN-DSC-CG-23-8 | 0.25 | 10 | 135 | 4 | 84 |
| CON-DSC-CG-23-9 | 0.5 | 0 | 0 | 4 | 84 |
| CCN-DSC-CG-23-10 | 0.5 | 10 | 135 | 4 | 84 |
| CCN-DSC-CG-23-11 | 1 | 0 | 0 | 4 | 84 |
| CCN-DSC-CG-23-12 | 1 | 10 | 135 | 4 | 84 |
| CON-DSC-CG-23-13 | 0.25 | 0 | 0 | 20 | 14 |
| CCN-DSC-CG-23-14 | 0.25 | 10 | 135 | 20 | 14 |
| CCN-DSC-CG-23-15 | 0.5 | 0 | 0 | 20 | 14 |
| CCN-DSC-CG-23-16 | 0.5 | 10 | 135 | 20 | 14 |
| CCN-DSC-CG-23-17 | 1 | 0 | 0 | 20 | 14 |
| CCN-DSC-CG-23-18 | 1 | 10 | 135 | 20 | 14 |
| CCN-DSC-CG-23-19 | 0.25 | 0 | 0 | 20 | 28 |
| CCN-DSC-CG-23-20 | 0.25 | 10 | 135 | 20 | 28 |
| CCN-DSC-CG-23-21 | 0.5 | 0 | 0 | 20 | 28 |
| CCN-DSC-CG-23-22 | 0.5 | 10 | 135 | 20 | 28 |
| CON-DSC-CG-23-23 | 1 | 0 | 0 | 20 | 28 |
| CCN-DSC-CG-23-24 | 1 | 10 | 135 | 20 | 28 |
| CCN-DSC-CG-23-25 | 0.25 | 0 | 0 | 20 | 56 |
| CCN-DSC-CG-23-26 | 0.25 | 10 | 135 | 20 | 56 |
| CCN-DSC-CG-23-27 | 0.5 | 0 | 0 | 20 | 56 |
| CCN-DSC-CG-23-28 | 0.5 | 10 | 135 | 20 | 56 |
| CCN-DSC-CG-23-29 | 1 | 0 | 0 | 20 | 56 |
| CCN-DSC-CG-23-30 | 1 | 10 | 135 | 20 | 56 |
| CCN-DSC-CG-21-31 | 0.25 | 0 | 0 | 20 | 84 |
| CCN-DSC-CG-23-32 | 0.25 | 10 | 135 | 20 | 84 |
| CCN-DSC-CG-23-33 | 0.5 | 0 | 0 | 20 | 84 |
| CON-DSC-CG-23-34 | 0.5 | 10 | 135 | 20 | 84 |
| CCN-DSC-CG-23-35 | 1 | 0 | 0 | 20 | 84 |
| CON-DSC-CG-23-36 | 1 | 10 | 135 | 20 | 84 |
| CCN-DSC-CG-23-37 | 0.25 | 0 | 0 | 37 | 14 |
| CCN-DSC-CG-23-38 | 0.25 | 10 | 135 | 37 | 14 |
| CCN-DSC-CG-23-39 | 0.5 | 0 | 0 | 37 | 14 |
| CCN-DSC-CG-23-40 | 0.5 | 10 | 135 | 37 | 14 |
| CCN-DSC-CG-23-41 | 1 | 0 | 0 | 37 | 14 |
| CCN-DSC-CG-23-42 | 1 | 10 | 135 | 37 | 14 |
| CCN-DSC-CG-23-43 | 0.25 | 0 | 0 | 37 | 28 |
| CON-DSC-CG-23-44 | 0.25 | 10 | 135 | 37 | 28 |
| CCN-DSC-CG-23-45 | 0.5 | 0 | 0 | 37 | 28 |
| CCN-DSC-CG-23-46 | 0.5 | 10 | 135 | 37 | 28 |
| CCN-DSC-CG-23-47 | 1 | 0 | 0 | 37 | 28 |
| CCN-DSC-CG-23-48 | 1 | 10 | 135 | 37 | 28 |
| CCN-DSC-CG-23-49 | 0.25 | 0 | 0 | 37 | 56 |
| CCN-DSC-CG-23-50 | 0.25 | 10 | 135 | 37 | 56 |
| CCN-DSC-CG-23-51 | 0.5 | 0 | 0 | 37 | 56 |
| CCN-DSC-CG-23-52 | 0.5 | 10 | 135 | 37 | 56 |
| CCN-DSC-CG-23-53 | 1 | 0 | 0 | 37 | 56 |
| CCN-DSC-CG-23-54 | 1 | 10 | 135 | 37 | 56 |
| CCN-DSC-CG-23-55 | 0.25 | 0 | 0 | 37 | 84 |
| CCN-DSC-CG-23-56 | 0.25 | 10 | 135 | 37 | 84 |
| CCN-DSC-CG-23-57 | 0.5 | 0 | 0 | 37 | 84 |
| CCN-DSC-CG-23-58 | 0.5 | 10 | 135 | 37 | 84 |

TABLE 68-continued

| CCN-DSC-CG-23 Sample List | | | | | |
|---|---|---|---|---|---|
| Sample Lot # | Silk fibroin conc. (% (w/v)) | Phosphate buffer conc. (mM) | Sodium chloride conc. (mM) | Storage temperature (° C.) | Timepoint (days) |
| CCN-DSC-CG-23-59 | 1 | 0 | 0 | 37 | 84 |
| CCN-DSC-CG-23-60 | 1 | 10 | 135 | 37 | 84 |

TABLE 69

| CCN-DSC-CG-23 pH Data | | |
|---|---|---|
| Sample Lot # | Average pH | Standard Deviation pH |
| CCN-DSC-CG-23-1 | 8.80 | 0.12 |
| CCN-DSC-CG-23-2 | 7.48 | 0.04 |
| CCN-DSC-CG-23-3 | 9.05 | 0.03 |
| CCN-DSC-CG-23-4 | 7.49 | 0.01 |
| CCN-DSC-CG-23-5 | 9.20 | 0.02 |
| CCN-DSC-CG-23-6 | 7.61 | 0.02 |
| CCN-DSC-CG-23-7 | 8.83 | 0.14 |
| CCN-DSC-CG-23-8 | 7.63 | 0.05 |
| CCN-DSC-CG-23-9 | 9.10 | 0.02 |
| CCN-DSC-CG-23-10 | 7.76 | 0.04 |
| CCN-DSC-CG-23-11 | 9.42 | 0.06 |
| CON-DSC-CG-23-12 | 7.77 | 0.03 |
| CCN-DSC-CG-23-13 | 8.78 | 0.10 |
| CON-DSC-CG-23-14 | 7.39 | 0.02 |
| CCN-DSC-CG-23-15 | 9.12 | 0.09 |
| CCN-DSC-CG-23-16 | 7.48 | 0.01 |
| CCN-DSC-CG-23-17 | 8.96 | 0.28 |
| CCN-DSC-CG-23-18 | 7.58 | 0.01 |
| CCN-DSC-CG-23-19 | 9.22 | 0.07 |
| CCN-DSC-CG-23-20 | 7.45 | 0.11 |
| CCN-DSC-CG-23-21 | 8.87 | 0.12 |
| CCN-DSC-CG-23-22 | 7.49 | 0.07 |
| CCN-DSC-CG-23-23 | 9.25 | 0.10 |
| CCN-DSC-CG-23-24 | 7.69 | 0.01 |
| CCN-DSC-CG-23-25 | 9.04 | 0.50 |
| CCN-DSC-CG-23-26 | 7.44 | 0.04 |
| CCN-DSC-CG-23-27 | 8.89 | 0.18 |
| CCN-DSC-CG-23-28 | 7.47 | 0.03 |
| CCN-DSC-CG-23-29 | 8.94 | 0.11 |
| CON-DSC-CG-23-30 | 7.51 | 0.03 |
| CCN-DSC-CG-21-31 | 8.39 | 0.34 |
| CCN-DSC-CG-23-32 | 7.56 | 0.05 |
| CCN-DSC-CG-23-33 | 8.65 | 0.03 |
| CCN-DSC-CG-23-34 | 7.62 | 0.08 |
| CCN-DSC-CG-23-35 | 8.90 | 0.07 |
| CCN-DSC-CG-23-36 | 7.60 | 0.03 |
| CCN-DSC-CG-23-37 | 6.27 | 0.06 |
| CON-DSC-CG-23-38 | 6.54 | 0.03 |
| CCN-DSC-CG-23-39 | 6.23 | 0.05 |
| CCN-DSC-CG-23-40 | 6.67 | 0.09 |
| CCN-DSC-CG-23-41 | 6.52 | 0.08 |
| CCN-DSC-CG-23-42 | 6.69 | 0.03 |
| CON-DSC-CG-23-43 | 6.20 | 0.06 |
| CCN-DSC-CG-23-44 | 6.71 | 0.06 |
| CCN-DSC-CG-23-45 | 6.30 | 0.03 |
| CCN-DSC-CG-23-46 | 6.72 | 0.03 |
| CCN-DSC-CG-23-47 | 6.60 | 0.19 |
| CON-DSC-CG-23-48 | 6.74 | 0.10 |
| CON-DSC-CG-23-49 | 6.15 | 0.14 |
| CCN-DSC-CG-23-50 | 6.48 | 0.09 |
| CCN-DSC-CG-23-51 | 6.28 | 0.09 |
| CON-DSC-CG-23-52 | 6.54 | 0.02 |
| CON-DSC-CG-23-53 | 6.38 | 0.03 |
| CCN-DSC-CG-23-54 | 6.58 | 0.03 |
| CCN-DSC-CG-23-55 | 6.17 | 0.13 |
| CCN-DSC-CG-23-56 | 6.74 | 0.03 |
| CCN-DSC-CG-23-57 | 6.27 | 0.06 |
| CON-DSC-CG-23-58 | 6.79 | 0.02 |
| CCN-DSC-CG-23-59 | 6.53 | 0.09 |
| CCN-DSC-CG-23-60 | 6.78 | 0.04 |

TABLE 70

| CCN-DSC-CG-23 Transmittance Data | | |
|---|---|---|
| Sample Lot # | Average Transmittance (%) | Standard Deviation Transmittance (%) |
| CCN-DSC-CG-23-1 | 92.07 | 0.96 |
| CCN-DSC-CG-23-2 | 87.47 | 2.89 |
| CCN-DSC-CG-23-3 | 92.35 | 1.59 |
| CCN-DSC-CG-23-4 | 62.87 | 7.27 |
| CCN-DSC-CG-23-5 | 89.09 | 3.02 |
| CCN-DSC-CG-23-6 | 49.66 | 11.95 |
| CCN-DSC-CG-23-7 | 98.08 | 0.95 |
| CCN-DSC-CG-23-8 | 87.09 | 4.92 |
| CCN-DSC-CG-23-9 | 97.63 | 1.69 |
| CON-DSC-CG-23-10 | 58.83 | 8.25 |
| CCN-DSC-CG-23-11 | 93.92 | 3.44 |
| CCN-DSC-CG-23-12 | 53.40 | 12.55 |
| CCN-DSC-CG-23-13 | 98.23 | 0.94 |
| CCN-DSC-CG-23-14 | 88.10 | 4.65 |
| CCN-DSC-CG-23-15 | 97.96 | 1.61 |
| CCN-DSC-CG-23-16 | 51.20 | 6.26 |
| CON-DSC-CG-23-17 | 94.66 | 3.33 |
| CCN-DSC-CG-23-18 | 46.25 | 10.82 |
| CCN-DSC-CG-23-19 | 98.17 | 1.02 |
| CON-DSC-CG-23-20 | 87.54 | 4.89 |
| CCN-DSC-CG-23-21 | 96.80 | 1.75 |
| CCN-DSC-CG-23-22 | 57.17 | 7.97 |
| CCN-DSC-CG-23-23 | 94.93 | 3.44 |
| CON-DSC-CG-23-24 | 52.86 | 12.51 |
| CCN-DSC-CG-23-25 | 98.39 | 1.00 |
| CCN-DSC-CG-23-26 | 86.15 | 5.21 |
| CON-DSC-CG-23-27 | 97.90 | 1.75 |
| CCN-DSC-CG-23-28 | 42.83 | 4.82 |
| CCN-DSC-CG-23-29 | 94.11 | 3.59 |
| CCN-DSC-CG-23-30 | 52.75 | 12.68 |
| CCN-DSC-CG-21-31 | 98.20 | 1.04 |
| CCN-DSC-CG-23-32 | 84.01 | 5.64 |
| CCN-DSC-CG-23-33 | 97.80 | 1.73 |
| CCN-DSC-CG-23-34 | 48.06 | 6.18 |
| CON-DSC-CG-23-35 | 93.66 | 3.66 |
| CCN-DSC-CG-23-36 | 47.54 | 12.27 |
| CCN-DSC-CG-23-37 | 98.12 | 1.43 |
| CON-DSC-CG-23-38 | 87.93 | 4.85 |
| CCN-DSC-CG-23-39 | 94.46 | 2.77 |
| CCN-DSC-CG-23-40 | 67.34 | 9.83 |
| CCN-DSC-CG-23-41 | 93.15 | 4.88 |
| CCN-DSC-CG-23-42 | 32.34 | 5.58 |
| CCN-DSC-CG-23-43 | 96.90 | 1.61 |
| CCN-DSC-CG-23-44 | 85.83 | 5.42 |
| CON-DSC-CG-23-45 | 96.38 | 2.70 |
| CCN-DSC-CG-23-46 | 47.95 | 5.76 |
| CCN-DSC-CG-23-47 | 90.57 | 4.94 |
| CON-DSC-CG-23-48 | 48.35 | 12.38 |
| CCN-DSC-CG-23-49 | 98.04 | 1.80 |
| CCN-DSC-CG-23-50 | 83.72 | 6.29 |
| CCN-DSC-CG-23-51 | 94.67 | 2.94 |
| CON-DSC-CG-23-52 | 67.60 | 9.75 |
| CCN-DSC-CG-23-53 | 93.71 | 4.87 |
| CCN-DSC-CG-23-54 | 39.67 | 8.61 |
| CON-DSC-CG-23-55 | 95.02 | 2.34 |
| CCN-DSC-CG-23-56 | 84.86 | 5.62 |
| CCN-DSC-CG-23-57 | 96.10 | 3.31 |

TABLE 70-continued

| CCN-DSC-CG-23 Transmittance Data | | |
|---|---|---|
| Sample Lot # | Average Transmittance (%) | Standard Deviation Transmittance (%) |
| CCN-DSC-CG-23-58 | 48.23 | 6.88 |
| CCN-DSC-CG-23-59 | 84.02 | 5.49 |
| CCN-DSC-CG-23-60 | 44.65 | 11.19 |

TABLE 71

| CCN-DSC-CG-23 Viscosity at 1 $s^{-1}$ Data | | |
|---|---|---|
| Sample Lot # | Average Viscosity at 1 $s^{-1}$ (cP) | Standard Deviation of Viscosity at 1 $s^{-1}$ (cP) |
| CCN-DSC-CG-23-1 | 97.56 | 27.24 |
| CCN-DSC-CG-23-2 | 345.65 | 24.66 |
| CCN-DSC-CG-23-3 | 588.94 | 47.14 |
| CCN-DSC-CG-23-4 | 3805.38 | 621.88 |
| CCN-DSC-CG-23-5 | 4230.24 | 95.75 |
| CCN-DSC-CG-23-6 | 24180.45 | 3903.74 |
| CON-DSC-CG-23-7 | 149.69 | 22.10 |
| CCN-DSC-CG-23-8 | 417.87 | 69.65 |
| CCN-DSC-CG-23-9 | 931.43 | 35.07 |
| CON-DSC-CG-23-10 | 1632.42 | 152.87 |
| CCN-DSC-CG-23-11 | 5488.31 | 130.50 |
| CCN-DSC-CG-23-12 | 13286.84 | 1535.13 |
| CCN-DSC-CG-23-13 | 141.42 | 27.18 |
| CON-DSC-CG-23-14 | 649.77 | 222.46 |
| CCN-DSC-CG-23-15 | 933.93 | 41.06 |
| CCN-DSC-CG-23-16 | 4650.98 | 770.86 |
| CON-DSC-CG-23-17 | 5286.79 | 186.20 |
| CCN-DSC-CG-23-18 | 16131.33 | 3120.61 |
| CCN-DSC-CG-23-19 | 201.86 | 33.35 |
| CON-DSC-CG-23-20 | 671.06 | 111.13 |
| CCN-DSC-CG-23-21 | 880.05 | 47.35 |
| CCN-DSC-CG-23-22 | 3859.26 | 699.61 |
| CCN-DSC-CG-23-23 | 5286.11 | 548.89 |
| CON-DSC-CG-23-24 | 12823.89 | 2827.81 |
| CON-DSC-CG-23-25 | 206.54 | 24.14 |
| CCN-DSC-CG-23-26 | 697.01 | 116.75 |
| CCN-DSC-CG-23-27 | 1061.38 | 57.80 |
| CCN-DSC-CG-23-28 | 3388.19 | 341.35 |
| CCN-DSC-CG-23-29 | 6305.22 | 171.75 |
| CCN-DSC-CG-23-30 | 14578.76 | 773.55 |
| CCN-DSC-CG-21-31 | 296.73 | 25.18 |
| CCN-DSC-CG-23-32 | 450.42 | 130.37 |
| CCN-DSC-CG-23-33 | 1236.55 | 29.92 |
| CCN-DSC-CG-23-34 | 1775.04 | 386.25 |
| CON-DSC-CG-23-35 | 6278.20 | 75.34 |
| CCN-DSC-CG-23-36 | 12589.11 | 2928.83 |
| CCN-DSC-CG-23-37 | 1836.67 | 123.92 |
| CCN-DSC-CG-23-38 | 685.15 | 101.08 |
| CCN-DSC-CG-23-39 | 4464.58 | 82.15 |
| CCN-DSC-CG-23-40 | 3074.94 | 345.73 |
| CCN-DSC-CG-23-41 | 11777.06 | 357.50 |
| CCN-DSC-CG-23-42 | 6918.76 | 2368.86 |
| CCN-DSC-CG-23-43 | 2031.66 | 382.68 |
| CCN-DSC-CG-23-44 | 756.05 | 133.47 |
| CCN-DSC-CG-23-45 | 4583.54 | 163.78 |
| CCN-DSC-CG-23-46 | 3223.23 | 582.25 |
| CCN-DSC-CG-23-47 | 12289.31 | 635.35 |
| CCN-DSC-CG-23-48 | 17574.10 | 4908.24 |
| CCN-DSC-CG-23-49 | 2329.94 | 36.49 |
| CCN-DSC-CG-23-50 | 444.06 | 82.00 |
| CCN-DSC-CG-23-51 | 4993.90 | 121.70 |
| CON-DSC-CG-23-52 | 2603.17 | 268.03 |
| CCN-DSC-CG-23-53 | 12819.43 | 680.91 |
| CCN-DSC-CG-23-54 | 16672.89 | 6736.74 |
| CON-DSC-CG-23-55 | 2788.93 | 305.25 |
| CCN-DSC-CG-23-56 | 302.30 | 41.15 |
| CCN-DSC-CG-23-57 | 5812.52 | 52.40 |
| CCN-DSC-CG-23-58 | 1289.25 | 153.66 |

TABLE 71-continued

| CCN-DSC-CG-23 Viscosity at 1 $s^{-1}$ Data | | |
|---|---|---|
| Sample Lot # | Average Viscosity at 1 $s^{-1}$ (cP) | Standard Deviation of Viscosity at 1 $s^{-1}$ (cP) |
| CON-DSC-CG-23-59 | 13270.24 | 286.72 |
| CCN-DSC-CG-23-60 | 8865.95 | 2235.29 |

TABLE 72

| CCN-DSC-CG-23 Viscosity at 10 $s^{-1}$ Data | | |
|---|---|---|
| Sample Lot # | Average Viscosity at 10 $s^{-1}$ (cP) | Standard Deviation of Viscosity at 10 $s^{-1}$ (cP) |
| CCN-DSC-CG-23-1 | 25.31 | 4.96 |
| CCN-DSC-CG-23-2 | 78.03 | 3.82 |
| CCN-DSC-CG-23-3 | 100.97 | 4.57 |
| CCN-DSC-CG-23-4 | 467.56 | 77.38 |
| CCN-DSC-CG-23-5 | 555.04 | 9.06 |
| CCN-DSC-CG-23-6 | 2276.79 | 296.79 |
| CCN-DSC-CG-23-7 | 32.45 | 6.24 |
| CCN-DSC-CG-23-8 | 134.30 | 9.29 |
| CCN-DSC-CG-23-9 | 136.72 | 4.37 |
| CON-DSC-CG-23-10 | 456.61 | 81.76 |
| CCN-DSC-CG-23-11 | 707.02 | 14.92 |
| CCN-DSC-CG-23-12 | 2065.46 | 152.29 |
| CCN-DSC-CG-23-13 | 32.23 | 4.58 |
| CCN-DSC-CG-23-14 | 175.80 | 24.16 |
| CCN-DSC-CG-23-15 | 134.27 | 7.07 |
| CCN-DSC-CG-23-16 | 618.73 | 60.74 |
| CCN-DSC-CG-23-17 | 693.79 | 37.16 |
| CCN-DSC-CG-23-18 | 2348.15 | 403.66 |
| CCN-DSC-CG-23-19 | 40.08 | 4.38 |
| CCN-DSC-CG-23-20 | 168.02 | 13.38 |
| CCN-DSC-CG-23-21 | 133.35 | 6.50 |
| CCN-DSC-CG-23-22 | 584.74 | 139.14 |
| CCN-DSC-CG-23-23 | 721.03 | 88.01 |
| CCN-DSC-CG-23-24 | 1580.67 | 242.51 |
| CON-DSC-CG-23-25 | 42.71 | 5.95 |
| CCN-DSC-CG-23-26 | 190.61 | 27.57 |
| CCN-DSC-CG-23-27 | 142.81 | 8.25 |
| CON-DSC-CG-23-28 | 627.65 | 71.16 |
| CCN-DSC-CG-23-29 | 828.81 | 28.30 |
| CCN-DSC-CG-23-30 | 2190.57 | 237.28 |
| CCN-DSC-CG-21-31 | 53.96 | 4.01 |
| CCN-DSC-CG-23-32 | 169.42 | 18.20 |
| CCN-DSC-CG-23-33 | 170.03 | 5.94 |
| CCN-DSC-CG-23-34 | 506.98 | 42.68 |
| CCN-DSC-CG-23-35 | 807.60 | 16.28 |
| CCN-DSC-CG-23-36 | 2411.72 | 290.87 |
| CCN-DSC-CG-23-37 | 320.21 | 13.22 |
| CCN-DSC-CG-23-38 | 211.93 | 12.48 |
| CCN-DSC-CG-23-39 | 692.40 | 23.19 |
| CCN-DSC-CG-23-40 | 486.73 | 31.27 |
| CCN-DSC-CG-23-41 | 1944.48 | 43.54 |
| CCN-DSC-CG-23-42 | 1333.60 | 525.78 |
| CCN-DSC-CG-23-43 | 334.16 | 36.05 |
| CCN-DSC-CG-23-44 | 164.47 | 24.69 |
| CON-DSC-CG-23-45 | 764.47 | 17.73 |
| CCN-DSC-CG-23-46 | 432.69 | 45.47 |
| CCN-DSC-CG-23-47 | 2063.64 | 80.07 |
| CCN-DSC-CG-23-48 | 1846.82 | 271.88 |
| CCN-DSC-CG-23-49 | 415.53 | 16.32 |
| CCN-DSC-CG-23-50 | 182.65 | 9.90 |
| CCN-DSC-CG-23-51 | 832.72 | 9.11 |
| CON-DSC-CG-23-52 | 516.60 | 89.13 |
| CCN-DSC-CG-23-53 | 2187.65 | 78.72 |
| CCN-DSC-CG-23-54 | 1959.80 | 697.18 |
| CCN-DSC-CG-23-55 | 545.57 | 41.94 |
| CCN-DSC-CG-23-56 | 152.43 | 13.15 |
| CCN-DSC-CG-23-57 | 1086.30 | 23.51 |
| CCN-DSC-CG-23-58 | 432.72 | 43.65 |
| CCN-DSC-CG-23-59 | 2938.96 | 242.47 |
| CCN-DSC-CG-23-60 | 1314.52 | 183.14 |

TABLE 73

| CCN-DSC-CG-23 Viscosity at 100 $s^{-1}$ Data | | |
|---|---|---|
| Sample Lot # | Average Viscosity at 100 $s^{-1}$ (cP) | Standard Deviation of Viscosity at 100 $s^{-1}$ (cP) |
| CCN-DSC-CG-23-1 | 19.42 | 3.63 |
| CON-DSC-CG-23-2 | 32.22 | 2.69 |
| CCN-DSC-CG-23-3 | 34.10 | 3.17 |
| CCN-DSC-CG-23-4 | 95.68 | 12.80 |
| CCN-DSC-CG-23-5 | 87.98 | 2.25 |
| CCN-DSC-CG-23-6 | 218.60 | 25.14 |
| CCN-DSC-CG-23-7 | 18.35 | 2.21 |
| CCN-DSC-CG-23-8 | 40.95 | 2.29 |
| CCN-DSC-CG-23-9 | 40.31 | 2.33 |
| CCN-DSC-CG-23-10 | 95.37 | 5.08 |
| CCN-DSC-CG-23-11 | 98.91 | 3.07 |
| CCN-DSC-CG-23-12 | 246.38 | 29.37 |
| CCN-DSC-CG-23-13 | 18.16 | 2.18 |
| CCN-DSC-CG-23-14 | 43.60 | 6.00 |
| CCN-DSC-CG-23-15 | 39.08 | 2.04 |
| CCN-DSC-CG-23-16 | 94.18 | 8.82 |
| CCN-DSC-CG-23-17 | 95.17 | 2.29 |
| CCN-DSC-CG-23-18 | 178.72 | 23.17 |
| CCN-DSC-CG-23-19 | 19.98 | 2.19 |
| CCN-DSC-CG-23-20 | 44.29 | 4.16 |
| CCN-DSC-CG-23-21 | 39.38 | 2.54 |
| CCN-DSC-CG-23-22 | 104.99 | 22.90 |
| CCN-DSC-CG-23-23 | 94.04 | 7.81 |
| CCN-DSC-CG-23-24 | 156.69 | 26.69 |
| CCN-DSC-CG-23-25 | 19.88 | 2.35 |
| CCN-DSC-CG-23-26 | 41.67 | 3.11 |
| CCN-DSC-CG-23-27 | 39.32 | 2.89 |
| CCN-DSC-CG-23-28 | 101.73 | 8.65 |
| CCN-DSC-CG-23-29 | 102.44 | 3.30 |
| CCN-DSC-CG-23-30 | 225.81 | 31.39 |
| CCN-DSC-CG-21-31 | 22.04 | 2.27 |
| CCN-DSC-CG-23-32 | 43.07 | 4.07 |
| CCN-DSC-CG-23-33 | 46.02 | 1.99 |
| CCN-DSC-CG-23-34 | 96.95 | 17.37 |
| CCN-DSC-CG-23-35 | 102.57 | 2.73 |
| CCN-DSC-CG-23-36 | 250.52 | 31.48 |
| CCN-DSC-CG-23-37 | 93.74 | 3.02 |
| CCN-DSC-CG-23-38 | 44.97 | 4.62 |
| CCN-DSC-CG-23-39 | 160.08 | 4.23 |
| CCN-DSC-CG-23-40 | 104.43 | 11.95 |
| CCN-DSC-CG-23-41 | 349.73 | 9.95 |
| CCN-DSC-CG-23-42 | 178.64 | 30.45 |
| CCN-DSC-CG-23-43 | 94.30 | 8.55 |
| CCN-DSC-CG-23-44 | 42.29 | 5.59 |
| CON-DSC-CG-23-45 | 170.04 | 5.05 |
| CON-DSC-CG-23-46 | 93.70 | 7.52 |
| CCN-DSC-CG-23-47 | 373.21 | 13.72 |
| CCN-DSC-CG-23-48 | 190.15 | 32.60 |
| CCN-DSC-CG-23-49 | 107.02 | 2.96 |
| CCN-DSC-CG-23-50 | 41.57 | 3.99 |
| CCN-DSC-CG-23-51 | 184.29 | 4.75 |
| CCN-DSC-CG-23-52 | 91.33 | 18.70 |
| CCN-DSC-CG-23-53 | 402.27 | 17.81 |
| CCN-DSC-CG-23-54 | 196.35 | 32.24 |
| CCN-DSC-CG-23-55 | 115.70 | 3.08 |
| CCN-DSC-CG-23-56 | 44.71 | 3.59 |
| CCN-DSC-CG-23-57 | 211.42 | 6.47 |
| CCN-DSC-CG-23-58 | 96.42 | 6.83 |
| CCN-DSC-CG-23-59 | 461.81 | 16.15 |
| CCN-DSC-CG-23-60 | 206.83 | 27.84 |

TABLE 74

| CCN-DSC-CG-23 Percent Recovery Data | | |
|---|---|---|
| Sample Lot # | Average Viscosity at 1 $s^{-1}$ Recovery (%) | Standard Deviation of Viscosity at 1 $s^{-1}$ Recovery (%) |
| CCN-DSC-CG-23-1 | 410% | 128% |
| CCN-DSC-CG-23-2 | 101% | 12% |
| CCN-DSC-CG-23-3 | 117% | 17% |
| CCN-DSC-CG-23-4 | 31% | 5% |
| CCN-DSC-CG-23-5 | 82% | 2% |
| CCN-DSC-CG-23-6 | 20% | 3% |
| CCN-DSC-CG-23-7 | 126% | 24% |
| CCN-DSC-CG-23-8 | 70% | 14% |
| CON-DSC-CG-23-9 | 97% | 5% |
| CCN-DSC-CG-23-10 | 55% | 7% |
| CCN-DSC-CG-23-11 | 82% | 4% |
| CCN-DSC-CG-23-12 | 46% | 9% |
| CCN-DSC-CG-23-13 | 154% | 33% |
| CCN-DSC-CG-23-14 | 52% | 19% |
| CCN-DSC-CG-23-15 | 97% | 6% |
| CON-DSC-CG-23-16 | 20% | 4% |
| CCN-DSC-CG-23-17 | 78% | 3% |
| CCN-DSC-CG-23-18 | 21% | 7% |
| CCN-DSC-CG-23-19 | 132% | 35% |
| CCN-DSC-CG-23-20 | 47% | 9% |
| CCN-DSC-CG-23-21 | 98% | 7% |
| CCN-DSC-CG-23-22 | 24% | 5% |
| CCN-DSC-CG-23-23 | 74% | 11% |
| CCN-DSC-CG-23-24 | 37% | 11% |
| CON-DSC-CG-23-25 | 135% | 49% |
| CON-DSC-CG-23-26 | 40% | 8% |
| CCN-DSC-CG-23-27 | 93% | 8% |
| CON-DSC-CG-23-28 | 31% | 5% |
| CON-DSC-CG-23-29 | 75% | 4% |
| CCN-DSC-CG-23-30 | 42% | 8% |
| CCN-DSC-CG-21-31 | 101% | 11% |
| CCN-DSC-CG-23-32 | 60% | 20% |
| CCN-DSC-CG-23-33 | 95% | 3% |
| CCN-DSC-CG-23-34 | 50% | 12% |
| CON-DSC-CG-23-35 | 78% | 1% |
| CON-DSC-CG-23-36 | 46% | 11% |
| CCN-DSC-CG-23-37 | 78% | 9% |
| CCN-DSC-CG-23-38 | 40% | 8% |
| CON-DSC-CG-23-39 | 76% | 3% |
| CCN-DSC-CG-23-40 | 26% | 4% |
| CCN-DSC-CG-23-41 | 79% | 5% |
| CON-DSC-CG-23-42 | 30% | 13% |
| CON-DSC-CG-23-43 | 80% | 21% |
| CCN-DSC-CG-23-44 | 28% | 6% |
| CCN-DSC-CG-23-45 | 82% | 4% |
| CON-DSC-CG-23-46 | 24% | 5% |
| CCN-DSC-CG-23-47 | 86% | 5% |
| CCN-DSC-CG-23-48 | 14% | 4% |
| CCN-DSC-CG-23-49 | 90% | 3% |
| CCN-DSC-CG-23-50 | 57% | 13% |
| CCN-DSC-CG-23-51 | 88% | 3% |
| CCN-DSC-CG-23-52 | 32% | 6% |
| CON-DSC-CG-23-53 | 90% | 6% |
| CCN-DSC-CG-23-54 | 18% | 8% |
| CCN-DSC-CG-23-55 | 93% | 17% |
| CON-DSC-CG-23-56 | 72% | 14% |
| CCN-DSC-CG-23-57 | 89% | 2% |
| CCN-DSC-CG-23-58 | 51% | 8% |
| CCN-DSC-CG-23-59 | 92% | 2% |
| CON-DSC-CG-23-60 | 27% | 7% |

The initial pH of the formulations ranged from 8.8 to 9.2 for formulations containing no phosphate buffer and 7.5 to 7.6 for formulations containing 10 mM phosphate buffer. The pH of formulations was unchanged over 84 days at both 4° C. and 20° C. All groups saw a decrease in pH after incubation at 37° C. to a range of 6.2 to 6.7 after 14 days that was maintained for 84 days.

The transmittance of the baseline samples with no salt ranged from 89% to 92%. Increasing the SF concentration slightly decreased transmittance. The transmittance of formulations containing SF in water were maintained at 80-100% throughout the length of the study at all temperatures. The addition of 135 mM NaCl decreased the transmittance of the formulations compared to the SF formulations in water. The transmittance of these formulations ranged from 85-90% at 0.25% (w/v) SF, to 40-70% at 0.5% SF, and 30%-50% at 1% SF over the course of the study. These samples are visually cloudier than those with SF alone. There is a trend toward decreasing transmittance in the 0.5% (w/v) SF formulation in buffer at 20° C. which is not observed in with storage at 37° C. No significant trends in changing transmittance were observed in the 1% (w/v) SF formulations at 37° C.

The initial viscosity of the hydrogels was 98 cP, 589 cP, and 4230 cP at 1 $s^{-1}$ for 0.25%, 0.5%, and 1% SF formulations in water respectively. At 20° C. SF formulations in water exhibited a thickening with increased storage time over 56 days. 0.25% (w/v) SF formulations reached 207 cP, 0.5% (w/v) SF formulations reached 1061 cP, and 1% (w/v) SF formulations reached 6305 cP at 56 days. With buffer present, the baseline viscosities of 0.25%, 0.5%, and 1% SF formulations was much greater than the same formulations in water, displaying viscosities of 386 cP, 3805 cP, and 24, 180 cP.

The viscosity data also shows that samples shear thin, ranging from 100-25,000 cP at 1 $s^{-1}$ to 20-470 cP at 100 $s^{-1}$. The ability for the sample to recover its thickness after this shear ramp was then determined by returning the sample to a low shear rate at the end of the test. Samples with no salt or buffer almost completely recover (generally >75% recovery of viscosity). This remained stable through the testing. These experiments have shown that the clear gels are largely stable through incubation at different temperatures for relevant amounts of time for commercial purposes.

Example 45. Silk Fibroin Film Dissolution Study

Silk Fibroin Isolation

Silk yarn, purchased from Jiangsu SOHO International Group, was degummed to remove sericin. 30 grams of cut silk yarn were heated at 85° C. in 1 L of deionized (DI) water with 0.5M sodium carbonate with occasional stirring. After 4 hours, the fibroin was removed and washed in 70° C. three separate times for ten minutes. The fibroin was then removed and rinsed under DI water. The fibroin was dried overnight, weighed, and dissolved at 20% (w/v) in a 9.3M aqueous solution of lithium bromide (from Sigma-Aldrich, St. Louis, MO) for 5 hours at 60° C. The resulting fibroin solution was dialyzed against water in a 50 kDa regenerated cellulose dialysis tubing for 48 hours, with 6 water changes to remove the excess salt. The conductivity was recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and samples of the supernatant were diluted at 1:20 and 1:40 in water. Samples for a standard curve were prepared for an A280 assay by diluting pre-measured fibroin solutions to 5, 2.5, 1.25, 0.625, 0.3125, and 0 mg/mL in water. The silk concentration of the 1:20 and 1:40 diluted silk fibroin samples was measured against the standard curve by the absorbance at 280 nm.

The silk fibroin solution was diluted to a final concentration of 3% (w/v) in water and filtered through a 0.2 μm filter using a vacuum filter unit. 10 mL of each solution was aliquoted into 50 ml conical tubes, frozen overnight at −80° C., and then lyophilized for 72 hours. Samples were then stored at −20° C. until use.

Silk Fibroin Film Formation

Lyophilized silk fibroin was removed from the freezer and allowed to reach room temperature. Water was then added to the lyophilized cakes to prepare a 15% (w/v) SF solution. 10% (w/v) and 5% (w/v) SF solutions were prepared by diluting the 15% (w/v) SF solution in water. These SF solutions were used to cast SF films.

1 ml of each solution was pipetted into small weight boats (38×25×9 mm). Ten samples were prepared at each concentration, for a total of 30. The weight boats were then incubated at 60° C. overnight (~16 hrs.) to dry. The films were removed from the weight boats and broken into pieces (~1 cm×0.5 cm). The films were then treated in a variety of ways to modulate their beta-sheet content.

Control samples were left without any further treatment. Films (n=3 per concentration) were treated in methanol by dipping the film fragment into a petri dish containing methanol, leaving it for 1 minute, transferring it to a petri dish of DI water for 10 seconds to rinse, and placing into a 4 mL glass vial to dry. Films (n=3 per concentration) were treated in ethanol by dipping the film fragment into a petri dish with ethanol, leaving it for 1 minute, transferring it to a petri dish of DI water for 10 seconds to rinse, and placing in a 4 mL glass vial to dry. Films (n=3 per concentration) were treated with water annealing at room temperature. A small amount of DI water was placed in the bottom of a desiccator. The film segments were put onto weigh boats and placed on the platform in the desiccator above the water. The desiccator was placed under continuous vacuum for ~10 minutes and the port was sealed. The films were left under vacuum for 2 hours at room temperature. Air was then flushed into the system by opening the port, and the samples were removed and left to dry in their weigh boats overnight at room temperature. Films (n=3 per concentration) were treated with water annealing at 37° C. A small amount of DI water was placed in the bottom of a desiccator. The film segments were put onto weigh boats and placed on the platform in the desiccator above the water. The desiccator was placed under continuous vacuum for ~10 minutes and the port was sealed. The films were left under vacuum for 2 hours at 37° C. and 100% humidity. However, after approximately 30 minutes, it was noticed that the seal on the desiccator had allowed air to enter the system and the vacuum was lost. The samples were left instead for the remainder of the 2 hours in the completely humidified 37° C. incubator. The samples were removed and left to dry in their weigh boats overnight. Films (n=3 per concentration) were treated via autoclaving. The segments of film were placed into individual 4 mL glass vials and the opening of each was covered with aluminum foil. The vials were placed into the autoclave and a solids cycle was run for 30 minutes at 121° C. When the cycle was complete, the fragments were immediately removed, capped, and left to cool to room temperature overnight.

Silk Fibroin Film Dissolution

~10 mg film samples (n=3 per concentration per post-processing condition) were weighed and placed into separate 4 mL glass vials. Mock seawater was prepared by dissolving 26.29 g of sodium chloride, 0.74 g of potassium chloride, 0.99 g of calcium chloride dihydrate, 6.09 g of magnesium chloride hexahydrate, and 2.27 g of sodium sulfate in 900 ml of DI water. The final volume was brought up to 1 L with DI water and cooled to 4° C. 4 mL of the mock seawater was pipetted into each 4 mL glass vial containing a film fragment. All of the vials were put onto an orbital shaker moving at a slow speed in a 4° C. refrigerator.

After 30 minutes, the samples were removed, inverted briefly to ensure complete and homogeneous mixing, and then allowed to settle. 200 μL of mock seawater from each sample was then removed and pipetted directly into a UV-readable 96-well plate. A standard curve of silk in the seawater was prepared at 0.3125, 0.625, 1.25, 2.5, and 5 mg/mL SF and pipetted into the plate. The absorbance of each sample was then measured at 280 nm to determine the concentration of silk in solution. The samples were then capped and placed back under rotation at 4° C. overnight. This process was then repeated after 17 hours to determine the film dissolution rate.

Table 75 lists the average percentage of each film remaining after the relevant time in the mock seawater.

TABLE 75

SF-01 Dissolution Results (reported as mean ± SD)

| Silk Concentration (% w/v) | Post Treatment | Average % Remaining After 0.5 Hours | Average % Remaining After 17 Hours |
|---|---|---|---|
| 5 | Untreated | 2.12 ± 0.38 | 5.46 ± 0.25 |
| 5 | Methanol | 91.59 ± 12.47 | 91.96 ± 15.55 |
| 5 | Ethanol | 41.77 ± 16.23 | 38.47 ± 15.70 |
| 5 | Room Temp. Annealing | 12.61 ± 9.29 | 15.79 ± 6.78 |
| 5 | 37° C. Annealing | 20.99 ± 0 | 23.91 ± 0 |
| 5 | Autoclave | 100.36 ± 0.85 | 101.16 ± 0.74 |
| 10 | Untreated | 9.85 ± 1.57 | 11.08 ± 1.56 |
| 10 | Methanol | 80.03 ± 1.55 | 79.25 ± 2.97 |
| 10 | Ethanol | 26.88 ± 6.06 | 25.60 ± 3.57 |
| 10 | Room Temp. Annealing | 16.78 ± 16.98 | 18.82 ± 17.10 |
| 10 | 37° C. Annealing | 20.73 ± 13.27 | 21.11 ± 15.54 |
| 10 | Autoclave | 100.56 ± 0.41 | 100.91 ± 0.30 |
| 15 | Untreated | 3.15 ± 1.40 | 2.86 ± 0.60 |
| 15 | Methanol | 44.53 ± 8.49 | 47.04 ± 7.59 |
| 15 | Ethanol | 32.13 ± 13.64 | 33.77 ± 13.43 |
| 15 | Room Temp. Annealing | 37.60 ± 3.13 | 37.06 ± 4.18 |
| 15 | 37° C. Annealing | 27.04 ± 19.68 | 27.44 ± 19.22 |
| 15 | Autoclave | 100.80 ± 1.42 | 101.78 ± 1.17 |

SF films prepared with from the different SF stock solutions behaved similarly. The untreated control films almost entirely dissolved (90-98%) within the first half hour. For all concentrations, the films treated via autoclaving were almost entirely intact after an overnight in the solution, with no dissolution observed. At 5 and 10% silk fibroin, methanol treatment slightly less effective than autoclaving, reducing the amount dissolved to 9-20%. SF films prepared from a 15% (w/v) stock solution may have produced a network that was too dense to allow for the methanol to penetrate and increase the beta-sheet content. This resulted in 53-55% dissolution. In all SF films, ethanol or water annealing at any temperature displayed similar results of 60%-80% dissolution of the film's mass after 17 hours.

Overall, the beta-sheet content of SF films can be effectively altered and tuned with a variety of different techniques to control their dissolution rate, as demonstrated herein. Among these, autoclaving appears to be a method that results in near total insolubility while treatments with methanol, ethanol, and water annealing reduce the solubility in mock seawater at 4° C.

Example 46. Silk Fibroin Glass Coating for Anti-Fog Protection

Silk Fibroin Isolation

Silk yarn, purchased from Jiangsu SOHO International Group, was degummed to remove sericin. 103.7 grams of cut silk yarn were heated at 85° C. in 10 separate glass vessels (for 1.037 kilograms total) filled with 1.5 L of deionized (DI) water with 0.5M sodium carbonate each with occasional stirring. After 4 hours, the fibroin was removed and rinsed under DI water for 1 minute. The fibroin was dried overnight, weighed, and dissolved in a 9.3M aqueous solution of lithium bromide (from Sigma-Aldrich, St. Louis, MO) at a ratio of 20% SF fiber by weight per volume for ~16 hours, or overnight, at 60° C. The following morning, the dissolved SF solution was diluted to 5% (w/v) SF using DI water. The solution was filtered through a 5 μm polypropylene filter for clarification and then transferred to a tangential flow filtration (TFF) system. The SF was concentrated to half its initial volume and the lithium bromide was removed from the solution by TFF against ~75-80 L of DI water in 8 diavolumes using a 5 kDa cellulose membrane. The final SF solution was filtered through a 0.5/0.2 μm PES sterile filter unit into clean containers. These containers were stored at −20° C. until use.

To determine the SF molecular weight a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. SF was diluted to 1% (w/v) in mobile phase after thawing before being run on SEC. SF elution was monitored at 280 nm. Molecular weights were calculated using a standard curve prepared from Waters BEH 200 Å Protein SEC Standard Mix (Waters, Milford, MA).

To determine SF concentration, gravimetric analysis was used. For the gravimetric analysis, five small plastic weigh boats were tared on an analytic balance to +0.1 mg, 1 mL of the stock solution was pipetted onto each weigh boat using a positive displacement pipette. The weigh boats with the solution were then placed in an oven set at 60° C. overnight (or approximately 16 hours). Once fully dried, the weigh boats were massed again on the balance to determine the weight of silk fibroin remaining. Each mass represents the amount of silk fibroin in 1 ml of material. The average value across the five replicates was then determined. This is the concentration of the solution in mg/mL.

Solution Formulation

A purified SF solution in DI water was prepared as described above. The stock was measured to contain 11.16% (w/v) silk fibroin in water via gravimetric analysis with an average molecular weight of 40.2 kDa via size exclusion chromatography.

SF solutions were prepared for anti-fog efficacy testing as shown in Table 76. 10 ml of each sample was mixed until homogeneous in a 15 cc. conical tube using a SF stock solution in water, glycerol, propylene glycol, isopropyl alcohol, and DI water. Samples contained 0.5, 3, and 6% (w/v) silk fibroin in water, 0, 1%, or 5% (v/v) glycerol or propylene glycol, 0 or 10% (v/v) isopropyl alcohol, and 5% (v/v) glycerol or propylene glycol and 10% (v/v) isopropyl alcohol (Table 74). Samples were used the same day of preparation.

TABLE 76

| Solutions made for anti-fog testing | | | | |
|---|---|---|---|---|
| Sample Lot # | Silk Fibroin Concentration (% (w/v)) | Glycerol Concentration (% (v/v)) | Propylene Glycol Concentration (% (v/V)) | Isopropyl Alcohol Concentration (% (v/V) |
| CCN-DSC-GC-04-1 | 0.5 | 0 | 0 | 0 |
| CCN-DSC-GC-04-2 | 3 | 0 | 0 | 0 |
| CCN-DSC-GC-04-3 | 6 | 0 | 0 | 0 |
| CCN-DSC-GC-04-4 | 0.5 | 1 | 0 | 0 |
| CCN-DSC-GC-04-5 | 3 | 1 | 0 | 0 |
| CCN-DSC-GC-04-6 | 6 | 1 | 0 | 0 |
| CCN-DSC-GC-04-7 | 0.5 | 5 | 0 | 0 |
| CON-DSC-GC-04-8 | 3 | 5 | 0 | 0 |
| CCN-DSC-GC-04-9 | 6 | 5 | 0 | 0 |
| CON-DSC-GC-04-10 | 0.5 | 0 | 1 | 0 |
| CCN-DSC-GC-04-11 | 3 | 0 | 1 | 0 |
| CCN-DSC-GC-04-12 | 6 | 0 | 1 | 0 |
| CCN-DSC-GC-04-13 | 0.5 | 0 | 5 | 0 |
| CON-DSC-GC-04-14 | 3 | 0 | 5 | 0 |
| CCN-DSC-GC-04-15 | 6 | 0 | 5 | 0 |
| CCN-DSC-GC-04-16 | 0.5 | 0 | 0 | 10 |
| CON-DSC-GC-04-17 | 3 | 0 | 0 | 10 |
| CCN-DSC-GC-04-18 | 0.5 | 5 | 0 | 10 |
| CCN-DSC-GC-04-19 | 3 | 5 | 0 | 10 |
| CON-DSC-GC-04-20 | 0.5 | 0 | 5 | 10 |
| CON-DSC-GC-04-21 | 3 | 0 | 5 | 10 |

Application and Testing of the Silk Fibroin Anti-Fog Coatings

Clear panes of glass with a thickness of ~2 mm was cut into 2 inch by 2 inch square pieces. The glass was cleaned with DI water and 70% ethanol solution and then dried completely.

The SF solutions were applied to the glass on both sides in one of two ways. The first was by direct application. The second was by wiping. Samples 1-15 were all applied using the direct application. For this method, 1 mL of the relevant solution was pipetted onto one side of the glass. As it was being deposited, the glass was tilted, and the pipette tip was used to evenly spread the solution across the surface. Once both sides were coated, any excess solution was blotted off the bottom and the glass was taped to dry vertically to ensure an even film layer. Samples 1, 2, 7, 8, 13, 14, and 16-21 were applied using a wiping method. For the wiping method, 1-2 ml of the solution was poured onto a KimWipe. The saturated wipe was then used to apply the solution to the glass surface until the surface was fully coated with solution. The piece of glass was then hung up to dry in the same manner as the direct application samples. The glass was dried at room temperature overnight (~16 hours).

To test the anti-fog efficacy of the coatings, 1 L of DI water was boiled in a 2 L glass beaker. A ring stand was set up with a clamp ~8 inches above the surface of the boiling water. A baseline image was taken of the Cocoon logo through the SF coated glass. Then the piece of glass was placed in the grip ~8 inches above the boiling water for 30 seconds to induce fogging. After this time, the glass was removed and quickly placed back over the logo for a second image. This was also done with an uncoated piece of glass as a control. FIGS. 1-29 show these images. The qualitative fogging results are listed in Table 77.

TABLE 77

| GC-04 Anti-Fog Results (Clear =full transparency, Slightly foggy = legible company logo but with haze and water droplets, Foggy = Illegible company logo) | | | |
|---|---|---|---|
| Sample Lot # | Application Method | Baseline Status | Fogging Status After 30 Seconds |
| CCN-DSC-GC-04-1 | Direct | Clear | Clear |
| CCN-DSC-GC-04-1 | Wiping | Clear | Slightly foggy |
| CCN-DSC-GC-04-2 | Direct | Clear | Clear |
| CON-DSC-GC-04-2 | Wiping | Clear | Clear |
| CCN-DSC-GC-04-3 | Direct | Clear | Clear |
| CCN-DSC-GC-04-4 | Direct | Clear | Foggy |
| CON-DSC-GC-04-5 | Direct | Clear | Clear |
| CCN-DSC-GC-04-6 | Direct | Clear | Clear |
| CCN-DSC-GC-04-7 | Direct | Clear | Slightly foggy |
| CCN-DSC-GC-04-7 | Wiping | Clear | Slightly foggy |
| CON-DSC-GC-04-8 | Direct | Clear | Foggy |
| CCN-DSC-GC-04-8 | Wiping | Clear | Foggy |
| CCN-DSC-GC-04-9 | Direct | Clear | Slightly foggy |
| CCN-DSC-GC-04-10 | Direct | Clear | Foggy |
| CCN-DSC-GC-04-11 | Direct | Clear | Clear |
| CCN-DSC-GC-04-12 | Direct | Clear | Clear |
| CCN-DSC-GC-04-13 | Direct | Clear | Foggy |
| CCN-DSC-GC-04-13 | Wiping | Clear | Foggy |
| CCN-DSC-GC-04-14 | Direct | Clear | Foggy |
| CCN-DSC-GC-04-14 | Wiping | Clear | Foggy |
| CON-DSC-GC-04-15 | Direct | Clear | Foggy |
| CCN-DSC-GC-04-16 | Wiping | Clear | Slightly foggy |
| CON-DSC-GC-04-17 | Wiping | Clear | Clear |
| CON-DSC-GC-04-18 | Wiping | Clear | Slightly foggy |
| CCN-DSC-GC-04-19 | Wiping | Clear | Foggy |
| CCN-DSC-GC-04-20 | Wiping | Clear | Foggy |
| CCN-DSC-GC-04-21 | Wiping | Clear | Foggy |

Direct application of the silk fibroin solutions performed well in prevention of fogging. The addition of glycerol or propylene glycol at 1% (v/v) was effective with 3 and 6% (w/v) silk fibroin, but not with 0.5% (w/v) silk fibroin. At 5% (v/v) glycerol and propylene glycol, none of the coating reduced fogging compared to controls. Application of the SF coating with a wiping method did not change the anti-fog efficacy. The addition of 10% (v/v) isopropyl alcohol allowed the formulations to dry much more quickly than those without. The formulation with 0.5% (w/v) silk fibroin and isopropyl alcohol showed a slight decrease in effectiveness, while the other coatings performed the same.

This study confirmed that silk fibroin is an effective anti-fog coating. It was shown that humectant additives did not assist in preventing fog formation further. Silk fibroin is thought to act as a humectant in these coatings in such a way as to react with the water to prevent droplet formation. Isopropyl alcohol allowed for faster drying without impacting the final efficacy of the coating at concentrations above 0.5% (w/v) SF. Wiping on solutions was shown to be a successful alternative application method to direct application. The anti-fog coating may be used on surgical instruments as well as personal consumables, eye glasses, mirrors, food packaging, and other surfaces.

Example 47. Silk Fibroin Ocular Drop Product in a Comparative Surface Spreading and Rheological Study

Silk Fibroin Isolation

Silk yarn, purchased from Jiangsu SOHO International Group, was degummed to remove sericin. 103.7 grams of cut silk yarn were heated at 85° C. in 10 separate glass vessels (for 1.037 kilograms total) filled with 1.5 L of deionized (DI) water with 0.5M sodium carbonate each with occasional stirring. After 4 hours, the fibroin was removed and rinsed under DI water for 1 minute. The fibroin was dried overnight, weighed, and dissolved in a 9.3M aqueous solution of lithium bromide (from Sigma-Aldrich, St. Louis, MO) at a ratio of 20% SF fiber by weight per volume for ~16 hours, or overnight, at 60° C. The following morning, the dissolved SF solution was diluted to 5% (w/v) SF using DI water. The solution was filtered through a 5 μm polypropylene filter for clarification and then transferred to a tangential flow filtration (TFF) system. The SF was concentrated to half its initial volume and the lithium bromide was removed from the solution by TFF against ~75-80 L of DI water in 8 diavolumes using a 5 kDa cellulose membrane. The final SF solution was filtered through a 0.5/0.2 μm PES sterile filter unit into clean containers. These containers were stored at −20° C. until use.

To determine the SF molecular weight a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. SF was diluted to 1% (w/v) in mobile phase after thawing before being run on SEC. SF elution was monitored at 280 nm. Molecular weights were calculated using a standard curve prepared from Waters BEH 200 Å Protein SEC Standard Mix (Waters, Milford, MA). The MW of TF_57 was 40.2 kDa.

To determine SF concentration, gravimetric analysis was used. For the gravimetric analysis, five small plastic weigh boats were tared on an analytic balance to +0.1 mg, 1 mL of the stock solution was pipetted onto each weigh boat using a positive displacement pipette. The weigh boats with the solution were then placed in an oven set at 60° C. overnight (or approximately 16 hours). Once fully dried, the weigh boats were massed again on the balance to determine the weight of silk fibroin remaining. Each mass represents the amount of silk fibroin in 1 mL of material. The average value across the five replicates was then determined. This is the concentration of the solution in mg/mL. The concentration of TF_57 was 11.16% (w/v)

Solution Formulation

A SF solution was prepared as described above. The stock was measured to contain 11.16% (w/v) silk fibroin in water via gravimetric analysis with an average molecular weight of 40.2 kDa via size exclusion chromatography.

A 0.1 M phosphate buffer was made by dissolving 114 mg of sodium phosphate dibasic and 27 mg of potassium phosphate monobasic in 9 mL of DI water. The pH was adjusted to 7.4 using 1 N hydrochloric acid and sodium hydroxide and the final volume was brought to 10 mL with DI water. A 1 M sodium chloride solution was made by dissolving 2.922 g of sodium chloride in 45 mL of DI water. After mixing, the final volume was brought to 50 mL with DI water.

To prepare a 2% SF formulation in phosphate buffer, 1.792 mL of 11.16% (w/v) silk fibroin solution was added to a 15 ml conical tube. Next, 1 mL of the 0.1 M phosphate buffer and 1.35 ml of the 1 M sodium chloride were added and the mixture was gently inverted to mix. Finally, 5.858 mL of DI water was added and the solution was mixed until homogeneous.

To prepare a 1% (w/v) SF clear gel, 26.88 mL of the 11.16% (w/v) silk fibroin stock was mixed with 73.12 mL of DI water in an 800 mL plastic beaker until homogeneous to form a 3% (w/v) SF solution. This was then agitated with a hand blender at half speed for 10 seconds, and centrifuged at 4,000×g and 4° C. for 10 minutes to remove bubbles and particulates. In a 50 ml conical tube, 16.667 mL of this agitated 3% (w/v) SF stock was mixed with 33.333 mL of DI water until homogeneous. The conical tube was capped and incubated at 60° C. for 1 week to induce gelation.

As comparators, Refresh Plus (Allergan, Inc.; lot #E87598) and Remend Corneal Repair Gel (Bayer; lot #AHSC665T) were acquired and used for the silk fibroin solution and clear gel formulations in the following tests. 1×PBS was prepared by diluting 50 ml of 10×PBS (Boston BioProducts; lot #G08K 102) in 450 ml of DI water.

Rheological Characterization

This test examined the differing rheological characteristics of the starting solutions (2% (w/v) SF solution, 1% (w/v) silk fibroin clear gel, Refresh, and Remend) and serial dilutions of these solutions in 1×PBS (2×, 4×, 8×, and 16×). Each solution was first tested on the rheometer, and then 2.5 ml of each was combined with 2.5 mL of 1×PBS to dilute. This was then repeated down to a final 16× dilution.

A Bohlin C-VOR 150 was used to measure the viscosity of the solutions. A 4°/40 mm cone and plate geometry was attached. The gap was set at 0.15 mm. A Peltier Plate system with electronic control was used to maintain sample temperature at 25° C.

The following test was performed on each sample. A pre-shear was performed of a 1 $s^{-1}$ shear rate for 20 seconds with no equilibrium time. A shear ramp from 0.01 to 1 $s^{-1}$ over 30 seconds with 15 data points taken. A shear hold at 1 $s^{-1}$ over 60 seconds with 30 data points taken. A shear ramp from 1 to 100 $s^{-1}$ over 30 seconds with 15 data points taken. A shear ramp from 100 to 1 $s^{-1}$ over 30 seconds with 15 data points taken. A shear hold at 1 $s^{-1}$ over 60 seconds with 30 data points taken. A shear ramp from 1 to 0.01 $s^{-1}$ over 30 seconds with 15 data points taken.

The viscosity at 1 $s^{-1}$ was reported in cP by averaging the viscosity at each data point across the first shear hold step, disregarding the first three points to allow for sample equilibration. A recovery percentage for each solution was determined by dividing the viscosity at 1 $s^{-1}$ from the second shear hold step by the viscosity at 1 $s^{-1}$ from the first shear hold step. This was then presented as a percent recovery of viscosity. The results can be seen in Table 78.

TABLE 78

LY-01 Samples and Rheology Results (mean ± standard deviation)

| Sample Lot # | Description | Viscosity at 1 $s^{-1}$ (cP) | Recovery (%) |
|---|---|---|---|
| CCN-OPH-LY-01-1 | Refresh | 7.59 ± 3.57 | 108 ± 71 |
| CCN-OPH-LY-01-2 | Refresh, 2x Dilution | 8.64 ± 4.72 | 86 ± 57 |
| CCN-OPH-LY-01-3 | Refresh, 4x Dilution | 5.76 ± 2.61 | 133 ± 91 |
| CON-OPH-LY-01-4 | Refresh, 8x Dilution | 8.68 ± 3.76 | 65 ± 48 |
| CCN-OPH-LY-01-5 | Refresh, 16x Dilution | 9.22 ± 5.67 | 104 ± 72 |
| CCN-OPH-LY-01-6 | Remend | 1995.97 ± 20.28 | 114 ± 5 |
| CCN-OPH-LY-01-7 | Remend, 2x Dilution | 265.23 ± 3.33 | 99 ± 3 |
| CCN-OPH-LY-01-8 | Remend, 4x Dilution | 24.81 ± 5.40 | 103 ± 25 |
| CCN-OPH-LY-01-9 | Remend, 8x Dilution | 12.73 ± 4.82 | 89 ± 42 |
| CCN-OPH-LY-01-10 | Remend, 16x Dilution | 8.82 ± 5.35 | 64 ± 57 |
| CON-OPH-LY-01-11 | Silk solution | 30.63 ± 3.11 | 112 ± 17 |
| CCN-OPH-LY-01-12 | Silk Solution, 2x Dilution | 49.88 ± 6.33 | 137 ± 19 |
| CCN-OPH-LY-01-13 | Silk Solution, 4x Dilution | 56.61 ± 5.37 | 158 ± 17 |
| CON-OPH-LY-01-14 | Silk Solution, 8x Dilution | 83.30 ± 7.91 | 128 ± 13 |
| CCN-OPH-LY-01-15 | Silk Solution, 16x Dilution | 50.10 ± 3.01 | 183 ± 16 |
| CCN-OPH-LY-01-16 | Silk solution, 32x Dilution | — | — |
| CCN-OPH-LY-01-17 | Silk solution, 64x Dilution | — | — |
| CCN-OPH-LY-01-18 | Silk solution, 128x Dilution | — | — |
| CCN-OPH-LY-01-19 | Silk solution, 256x Dilution | — | — |
| CCN-OPH-LY-01-20 | Silk solution, 512x Dilution | — | — |
| CON-OPH-LY-01-21 | Silk solution, 1024x Dilution | — | — |
| CCN-OPH-LY-01-22 | Silk Clear Gel | 6283.44 ± 21.69 | 84 ± 1 |
| CCN-OPH-LY-01-23 | Silk Clear Gel, 2x Dilution | 2096.77 ± 49.23 | 128 ± 4 |
| CCN-OPH-LY-01-24 | Silk Clear Gel, 4x Dilution | 1892.97 ± 309.78 | 62 ± 16 |
| CCN-OPH-LY-01-25 | Silk Clear Gel, 8x Dilution | 252.62 ± 46.74 | 33 ± 7 |
| CCN-OPH-LY-01-26 | Silk Clear Gel, 16x Dilution | 74.66 ± 5.42 | 51 ± 11 |

The 2% (w/v) SF solution had a higher viscosity than Refresh Plus throughout the entire dilution series. Samples 16 through 21 were only assessed in the surface spreading study. The 1% (w/v) SF clear gel maintained a higher viscosity than any other formulation throughout the entire dilution series. The Remend product had a higher viscosity than Refresh until the 16× dilution, and had a higher viscosity than the 2% (w/v) SF solution until the 4× dilution, at which point the SF solution maintained a higher viscosity for the remainder of the study (4×-16× dilution). The recovery data showed that the SF solution was able to recover at least 100% or greater, over the course of the study, while the recovery percentage of the SF clear gel decreased with each successive dilution. Remend and Refresh also displayed good shear recovery of 65-greater than 100% across the dilution range.

This study confirmed that silk fibroin formulations maintain high viscosities through a wide series of dilutions in PBS. These viscosity trends will ensure that the SF formulations, if applied to the surface of the eye, will maintain viscoelastic efficacy even through natural dilution from mixing with the tear film, enabling long term retention.

Lycopodium Powder Surface Spreading Test

To measure the interfacial properties of the formulations, a lycopodium powder study was performed. For each sample that was tested, a glass petri dish (Corning, 100×15 mm) was filled with 20 mL of 1×PBS. A thin layer of lycopodium powder was distributed on the PBS, such that the entire surface was coated evenly.

For each sample tested, 50 μL of the formulation was pipetted into the center of the lycopodium powder. The Remend, Refresh, SF clear gel, SF solution, and SF diluted solutions (samples LY-01-1, 6, and 11-21; Table 78) were assessed. The SF solution samples were continuously diluted until they did not show any surface spreading, which was observed at a 1024× dilution. If the sample exhibited active surface spreading effects, the droplet would push the lycopodium powder to the edges of the petri dish forming a clear circle of PBS. Images were then taken of the areas formed by these droplets. See FIGS. 1-15 for these images (black arrow denotes where droplet was placed).

The Remend and Refresh products did not show any surface active properties and did not change the lycopodium coating. The solutions passed directly through the lycopodium and did not disturb it. The SF clear gel formulations formed a very small, clear circle where the formulation was applied. This may be due to soluble SF present in the clear gel formulation. This formulation did not display strong active spreading of the powder. All of the SF solution samples caused spreading of the lycopodium powder, showing surface activity and amphiphilic properties. The magnitude of the active spreading and size of the circle created decreased with decreasing SF concentration. This study proved that SF solutions exhibit surface active spreading at an air-liquid interface after application to an aqueous solution. This effect was observed at concentrations as low as 0.0039% (w/v) silk fibroin in the formulation or 97.4 ng/mL SF in the solution. This effect could be beneficial to aid an ocular formulation in surface spreading and coating as well as reformation of the tear film after blinking.

Silk Fibroin Incorporated in Silk Eye Wash with Hydroxycobalamin

Hydroxycobalamin and/or hydroxo(aquo)cobalamin may be used in an eye wash to prevent ocular surface damage after exposure to pollutant gases, see U.S. Pat. No. 9,585,908, which is incorporated herein by reference in its entirety. Silk fibroin reduces the surface tension allowing for improved spreading and faster contact on application. Silk fibroin will allow for longer term residence of the active ingredient once applied based on viscosity and residence time data. Silk fibroin enhances corneal epithelial cell viability reducing pollutant damage, see HCEC data above. The concentration of the active ingredient may be 0.001 wt % to about 2.0 wt %.

Example 48: Silk Fibroin Lotions with Various Emollients

To determine the compatibility of SF to emulsify and thicken lotions was tested by preparing simple silk fibroin, water and oil emulsions with several common emollients used in moisturizing lotions and creams.

Silk fibroin was prepared by degumming silk yarn in a sodium carbonate solution, dissolution in lithium bromide and purification via tangential flow filtration. To 9×2 L glass bottles, 106 g of sodium carbonate was added. DI water was added to a final volume of 2 L. The glass bottles were placed into a circulating water bath and the system warmed to 85° C. To each of the bottles, 60 g of silk yarn was added. The silk yarn was degummed for 4 hours at 85° C. After 4 hours, the silk yarn was removed from the bottles and rinsed under DI water to remove excess carbonate solution. The fibroin fibers were then squeezed to remove water and spread in a fume hood to dry overnight. The entire process was repeated an addition time to degum 1080 g of silk yarn.

To dissolve the SF fibers, 120 g of SF (batch SBL_194) was placed in each of 3×1 L glass bottles along with 600 ml of 9.3 M lithium bromide. The bottles were incubated at 60° C. overnight to dissolve the SF fibers. To an additional 3×1 L glass bottles, 140 g of wet SF fibers (SBL_195) was incubated with 488 mL of 9.3 M lithium bromide. The bottles were incubated at 60° C. overnight to allow for complete dissolution of the fibers.

Prior to tangential flow filtration, the silk fibroin solution was diluted from 20% (w/v) SF to 6.5% (w/v) SF with DI water. The diluted solution was then centrifuged at 5000×g for 10 mins to pellet any remaining particulates.

A tangential flow filtration (TFF) system with a two Pellicon® 3 cassettes with Ultracel® 1.14 $m^2$, 5 kDa membranes was used for removal of lithium bromide. Prior to introduction of silk fibroin to the system, the system was washed with DI water and sanitized with 0.1 N sodium hydroxide. The system was then flushed with water to remove sodium hydroxide Using the TFF system, the solution was concentrated from 5% (w/v) to 10% (w/v) SF. Diafiltration was performed at 10% (w/v) SF to remove lithium bromide. The silk fibroin was diafiltered for 10 diavolumes against DI water. Following TFF, the solution was collected and filtered through a 0.5/0.2 μm Optical 47 capsule filter.

The molecular weight of TF_42 was determined by size exclusion chromatography. For SEC analysis, a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. Silk fibroin elution was monitored at 280 nm. Molecular weights were calculated using a standard curve prepared from Waters BEH 200 Å Protein SEC Standard Mix (Waters, Milford, MA). The molecular weight of SF solution (TF_42) was 32.5 kDa.

Lotions were prepared using a working solution of 3% (w/v) SF solution, pH 5.5. To prepare the 3% working solution, 189.9 g of 7.9% (w/v) SF solution (TF_42) was diluted to 500 g with DI water. The 3% SF solution as well as the MCT, 76° F. coconut, and avocado oils were heated to 60° C. A total of 100 g of each emulsion was prepared according to the Table 79 below.

TABLE 79

Lotion formulations prepared with SF and MCT, avocado and 76° coconut oil

| Sample # | Mass of 3% (w/v) SF Solution (g) | Final SF concentration (%) | Oil Phase | Mass of Oil (g) |
|---|---|---|---|---|
| SL_26_1 | 90 | 2.7% | MCT | 10 |
| SL_26_2 | 80 | 2.4% | MCT | 20 |
| SL_26_3 | 50 | 1.5% | MCT | 50 |
| SL_26_4 | 25 | 0.75% | MCT | 75 |
| SL_26_5 | 90 | 2.7% | Avocado | 10 |
| SL_26_6 | 75 | 2.25% | Avocado | 25 |
| SL_26_7 | 50 | 1.5% | Avocado | 50 |
| SL_26_8 | 25 | 0.75% | Avocado | 75 |
| SL_26_9 | 10 | 0.3% | Avocado | 90 |
| SL_26_10 | 95 | 2.85% | 76° F. Coconut Oil | 5 |
| SL_26_11 | 90 | 2.7% | 76° F. Coconut Oil | 10 |
| SL_26_12 | 75 | 2.25% | 76° F. Coconut Oil | 25 |
| SL_26_13 | 50 | 1.5% | 76° F. Coconut Oil | 50 |
| SL_26_14 | 25 | 0.75% | 76° F. Coconut Oil | 75 |

The lotions were prepared using an immersion blender for 1 min to emulsify the lotions. Following emulsification, the lotions were rotated overnight at room temperature.

The lotions were inspected to determine if the emulsification had thickened or separated following overnight rotation. Emulsions were thickened and set for formulations with a SF concentration ≥ 0.75% SF regardless of the emollient. Formulations with higher SF concentrations were thicker than those prepared with lower SF concentrations. The results are summarized in Table 80.

TABLE 80

Results of silk fibroin emulsions prepared with MCT, avocado and 76° coconut oils

| | % Aqueous | SF Concentration (%) | Oil | Oil Conc. (%) | Result |
|---|---|---|---|---|---|
| SL_26_1 | 90 | 2.7 | MCT | 10 | Set, thick |
| SL_26_2 | 80 | 2.4 | MCT | 20 | Set, thick |
| SL_26_3 | 50 | 1.5 | MCT | 50 | Set, thick |
| SL_26_4 | 25 | 0.75 | MCT | 75 | Set, thin |
| SL_26_5 | 90 | 2.7 | Avocado | 10 | Separated |
| SL_26_6 | 75 | 2.25 | Avocado | 25 | Set, thick |
| SL_26_7 | 50 | 1.5 | Avocado | 50 | Set thick |
| SL_26_8 | 25 | 0.75 | Avocado | 75 | Separated |
| SL_26_9 | 10 | 0.3 | Avocado | 90 | Separated |
| SL_26_10 | 95 | 2.85 | Coconut Oil 76° F. | 5 | Set, thick |
| SL_26_11 | 90 | 2.7 | Coconut Oil 76° F. | 10 | Set, thick |
| SL_26_12 | 75 | 2.25 | Coconut Oil 76° F. | 25 | Set, thick |
| SL_26_13 | 50 | 1.5 | Coconut Oil 76° F. | 50 | Set, thin |
| SL_26_14 | 25 | 0.75 | Coconut Oil 76° F. | 75 | Set, thin |

Example 49: pH Dependence of Silk Fibroin Lotion on Gelation

To determine the pH range at which silk fibroin will function as an emulsifier and thickener, lotions were prepared using an oil phase consisting MCT oil, shea butter, and cocoa butter and an aqueous phase consisting of 3% (w/v) SF in water.

Two 3% SF solutions were prepared at pH 9.1 and pH 5.5. The pH 9.1 SF solution was prepared by diluting 113.9 g of 7.9% (w/v) SF solution (TF_42) to 300 g using DI water. Following dilution of the SF, the pH remained at 9.1. The pH 5.5 SF solution was prepared by diluting 113.9 g of 7.9% (w/v) SF solution (TF_42) with sufficient water to bring the total mass to 250 g. The pH was adjusted to 5.5 using 2 M citric acid. Water was added to bring the total mass to 300 g.

200 g of each lotion was prepared according to Table 81. Prior to emulsification, the SF solutions and oils were heated to 60° C. The emulsions were blended for 1 min using an immersion blender. After emulsification, the lotions were allowed to set and thicken overnight.

The lotions were inspected for gelation and the pH was measured. As shown in Table 81, all lotions thickened, with the lotion at pH 9.1 taking 2 days to set. The pH for the lotions prepared with the acidic preservatives gluconolactone and benzoic acid were pH 3.0 the following morning. This is likely due to the slow dissolution of the oil-soluble preservatives. The lotions at pH 3.0 were very similar to those at pH 5.5 and 9.1.

TABLE 81

Results of lotion formulations prepared at pH 9.1 and 5.5 with and without acidifying preservatives

| Sample # | Formulation | pH Initial | pH Final | Result |
|---|---|---|---|---|
| SL-25_1 | 47% Aqueous, 1.5% SF, 32% MCT oil, 8% cocoa butter, 8% shea butter | 9.1 | 9.1 | Set (2 days) |
| SL-25_2 | 47% Aqueous, 1.5% SF, 32% MCT oil, 8% cocoa butter, 8% shea butter | 5.5 | 5.5 | Set |
| SL-25_3 | 45% Aqueous, 1.5% SF, 32% MCT oil, 8% cocoa butter, 8% shea butter, 1.5% gluconolactone, 0.5% benzoic acid | 5.1 | 3 | Set |
| SL-25_4 | 45% Aqueous, 1.5% SF, 32% MCT oil, 8% cocoa butter, 8% shea butter, 1.5% gluconolactone, 0.5% benzoic acid | 5.1 | 3 | Set |

Example 50: Jojoba Oil Lotions

Lotions using silk fibroin as an emulsifier and thickener were prepared using jojoba oil as the primary emollient. To prepare the lotions, a stock solution of SF at 9.1% (w/v) SF solution (TF_44), jojoba oil and shea butter were warmed to 60° C. The formulations were prepared according to Table 82. Similar formulations were prepared at both 2 or 3% (w/v) SF. The emulsion was formed by adding the oil phase to the aqueous phase containing SF while blending with an immersion blender. Lotions were emulsified for 1 min. The lotions were then transferred to two 50 ml conical tubes. One tube was rotated overnight and the other was allowed to set without rotation at room temperature.

TABLE 82

Weights used for SL_34 Lotion Formulations

| Sample # | Mass of Jojoba Oil (g) | Mass of Shea Butter (g) | Mass of SF stock (9.1%) (g) | Mass of Water (g) |
|---|---|---|---|---|
| SL_26_1 | 15 | 1 | 22.0 | 62.0 |
| SL_26_2 | 25 | 1 | 22.0 | 52.0 |
| SL_26_3 | 15 | 2.5 | 22.0 | 60.5 |
| SL_26_4 | 25 | 2.5 | 22.0 | 50.5 |
| SL_26_5 | 15 | 5 | 22.0 | 58.0 |
| SL_26_6 | 25 | 5 | 22.0 | 48.0 |
| SL_26_7 | 15 | 1 | 33.0 | 51.0 |
| SL_26_8 | 25 | 1 | 33.0 | 41.0 |
| SL_26_9 | 15 | 2.5 | 33.0 | 49.5 |
| SL_26_10 | 25 | 2.5 | 33.0 | 39.5 |
| SL_26_11 | 15 | 5 | 33.0 | 47.0 |
| SL_26_12 | 25 | 5 | 33.0 | 37.0 |

In all cases, lotions prepared with 2% (w/v) SF did not set while lotions prepared with 3% (w/v) SF set with or without rotation. Lotions prepared with higher shea butter concentrations were thicker than those with lower concentrations. These results suggest that with jojoba oil, higher concentrations of SF and a solid oil are required to prepare stable, thick formulas.

Example 51: Additional Lotion Formulations

Lotion formulations were prepared using a 7.93% stock solution of silk fibroin TF_42. All reagents were heated to 70° C. prior to use. 77.6 g of water was mixed with 40 g of SF TF_42. In a 1 L beaker, 30 g of Zemea propanediol (DuPont, Tate & Lyle), was blended with 2 g Velsan SC sorbitan carprylate (Clariant), 2 g Zeastat (Inolex), 10 g TEXTURLUX Stabil modified corn starch (Dupont Tate &Lyle), and 0.4 g Keltrol xanthan gum (CP Kelco). The water/silk fibroin solution was mixed with an immersion blender into the oil phase. While blending, 30 g jojoba oil, 4 g cetearyl alcohol, and 4 g Velsan SC were added. 33.8 g of water was mixed with 20 g of In a 1 L beaker, 30 g of Zemea propanediol (DuPont, Tate & Lyle), was blended with 2 g Zeastat (Inolex), 10 g TEXTURLUX Stabil modified corn starch (Dupont Tate &Lyle), and 0.4 g Keltrol xanthan gum (CP Kelco). The water/silk fibroin solution was mixed with an immersion blender into the oil phase. While blending, 30 g jojoba oil, 4 g cetearyl alcohol were added. 33.8 g of water was mixed with 20 g of SF TF_42.

In a 1 L beaker, 25 g of jojoba oil was mixed with 1 g 1 Lipex SheaSoft (AAK Personal Care). In a separate beaker, 25.2 g of TF_42 was mixed with 100 g of DI water. The aqueous phase was slowly poured into the oil phase while blending with an immersion blender.

In a 1 L beaker, 25 g of jojoba oil was mixed with 1 g yellow beeswax (Bulk Apothecary). In a separate beaker, 25.2 g of TF_42 was mixed with 100 g of DI water. The aqueous phase was slowly poured into the oil phase while blending with an immersion blender.

In a 1 L beaker, 25 g of jojoba oil was mixed with 1 g Kester Wax K69 (Koster Keunen). In a separate beaker, 25.2 g of TF_42 was mixed with 100 g of DI water. The aqueous phase was slowly poured into the oil phase while blending with an immersion blender.

In a 1 L beaker, 25 g of jojoba oil was mixed with 1 g Kester Wax K24 (Koster Keunen). In a separate beaker, 25.2 g of TF_42 was mixed with 100 g of DI water. The aqueous phase was slowly poured into the oil phase while blending with an immersion blender.

In a 1 L beaker, 25 g of jojoba oil was mixed with 1 g carnauba wax (Koster Keunen). In a separate beaker, 25.2 g of TF_42 was mixed with 100 g of DI water. The aqueous phase was slowly poured into the oil phase while blending with an immersion blender.

In a 1 L beaker, 25 g of jojoba oil was mixed with 1 g rice bran wax (Koster Keunen). In a separate beaker, 25.2 g of TF_42 was mixed with 100 g of DI water. The aqueous phase was slowly poured into the oil phase while blending with an immersion blender.

In a 1 L beaker, 25 g of jojoba oil was mixed with 1 g jojoba wax (Koster Keunen). In a separate beaker, 25.2 g of TF_42 was mixed with 100 g of DI water. The aqueous phase was slowly poured into the oil phase while blending with an immersion blender.

In a 1 L beaker, 25 g of jojoba oil was mixed with 1 g *candelilla* wax (Koster Keunen). In a separate beaker, 25.2 g of TF_42 was mixed with 100 g of DI water. The aqueous phase was slowly poured into the oil phase while blending with an immersion blender.

Example 52: Silk Fibroin Sunscreens and Emulsion Stability

Initial work aimed to determine the feasibility of using SF as an emulsifier and/or thickening agent. To this end, formulations of SF-based sunscreen were prepared and subjected to accelerated stability studies. This allowed for rapid determination of the ability of SF to be used as an emulsifier. Three formulations that were determined to have desirable application aesthetics were subject to exposure to elevated temperatures and several round of freeze/thaw cycles to determine emulsion stability.

Silk fibroin was prepared by degumming silk and purifying SF as described in Example 35. manufacturing example. A 3% (w/v) SF solution was prepared from an 8% stock of silk fibroin (TF_10) and pH adjusted to 6.5 with 1 N HCl. The 3% (w/v) SF solution, 76° F. coconut oil, and cocoa butter were heated to 60° C. in an oven. The sunscreen formulations were prepared by weight.

SL_19_01 consisting of 1.5% SF, 48.5% water, 15% zinc oxide, 23% 76° coconut oil, 10% cocoa butter, 1.5% gluconolactone, 0.5% benzoic acid was prepared by mixing the oil phase and aqueous phase separately. In a 1 L beaker, 30 g of zinc oxide was combined with 46 g 76° F. coconut oil and 20 g of cocoa butter. The dispersion was mixed until homogenous. After mixing, 100 g of 3% (w/v) SF, 1 g of benzoic acid, and 3 g of gluconolactone were added under high shear mixing. The pH was adjusted to 6.5 with 1 N sodium hydroxide and the formula was blended for 1 min. SL_19-02 (2% SF, 64% water, 15% zinc oxide, 5% cocoa butter, 12% coconut oil 76° C., 1.5% gluconolactone, 0.5% benzoic acid) was prepared by mixing 30 g of zinc oxide with 24 g 76° F. coconut oil and 10 g of cocoa butter in a 1 L beaker. The dispersion was mixed with until homogeneous. After mixing, 132 g of 3% (w/v) SF, 1 g of benzoic, acid and 3 g of gluconolactone were added under high shear mixing. The pH was adjusted to 6.5 with 1 N sodium hydroxide and blended for 1 min. SL_19_3 (2.3% SF, 72.7% water, 10% zinc oxide, 13% coconut oil 76° C., 0.5% benzoic acid, 1.5% gluconolactone) was prepared by mixing 20 g of zinc oxide with 26 g 76° F. coconut oil in a 1 L beaker. The dispersion was mixed with until homogeneous. After mixing. 132 g of 3% (w/v) SF, 1 g of benzoic, acid and 3 g of gluconolactone were added under high shear mixing. The pH was adjusted to 6.5 with 1 N sodium hydroxide and blended for 1 min.

Each formulation was transferred to 5 mL Eppendorf tubes for stability testing.

Triplicate samples were placed into a −20° C. for freeze/thaw stability. Samples were frozen overnight, removed from the freezer, and thawed at room temperature for 24 hours. The cycle was repeated for a total of 3 freeze/thaw cycles.

The formulations were also evaluated for elevated temperature stability. Samples were incubated at 37° C. for 2 months. Formulations were inspected visually for separation, desiccation and fluidity. Following freeze/thaw cycling, none of the sunscreens showed any separation or changes in viscosity. After 2 months at 37° C., SL-19_01 and SL-19_02 showed no signs of separation while SL-19_03 showed minor separation. All three sunscreens were similar in viscosity

Example 53: Optimization of Silk Fibroin Sunscreen Formulation and In Vitro SPF Testing Silk fibroin was prepared by degumming silk yarn in a sodium carbonate solution, dissolution in lithium bromide and purification via tangential flow filtration. To nine 2 L glass bottles, 106 g of sodium carbonate was added. DI water was added to a final volume of 2 L. The glass bottles were placed into a circulating water bath and the system warmed to 85° C. To each of the bottles, 60 g of silk yarn was added. The silk yarn was degummed for 4 hours at 85° C. After 4 hours, the silk yarn was removed from the bottles and rinsed under DI water to remove excess carbonate solution. The fibroin fibers were then squeezed to remove water and spread in a fume hood to dry overnight. The entire process was repeated an addition time to degum 1080 g of silk yarn.

To dissolve the SF fibers, 120 g of SF (batch SBL_194) was placed in each of 3×1 L glass bottles along with 600 mL of 9.3 M lithium bromide. The bottles were incubated at 60° C. overnight to dissolve the SF fibers. To an additional 3×1 L glass bottles, 140 g of wet SF fibers (SBL_195) was incubated with 488 mL of 9.3 M lithium bromide. The bottles were incubated at 60° C. overnight to allow for complete dissolution of the fibers.

Prior to tangential flow filtration, the silk fibroin solution was diluted from 20% (w/v) SF to 5% (w/v) SF with DI water. The diluted solution was then centrifuged at 5000×g for 10 mins to pellet any remaining particulates.

A tangential flow filtration (TFF) system with a two Pellicon® 3 cassettes with Ultracel® 5 kDa membranes was used for removal of lithium bromide Prior to introduction of silk fibroin to the system, the system was washed with DI water and sanitized with 0.1 N sodium hydroxide. The system was then flushed with water to remove sodium hydroxide Using the TFF system, the solution was concentrated from 5% (w/v) to 10% (w/v) SF. Diafiltration was performed at 10% (w/v) SF to remove lithium bromide. The silk fibroin was diafiltered for 10 diavolumes against DI water. Following TFF, the solution was collected and filtered through a 0.5/0.2 μm Optical 47 capsule filter.

The molecular weight of TF 42 was determined by size exclusion chromatography. For SEC analysis, a Waters Acquity H-Class UPLC (Waters, Milford, MA) equipped with a Waters BEH 200 Å 1.7 mm, 4.8×300 cm UPLC SEC column (from Waters, Milford, MA) was used. Sample temperature was maintained at 4° C. An isocratic flow at 0.3 mL/min of mobile phase (100 mM Tris-HCl with 400 mM sodium perchlorate (Alfa Aesar, Ward Hill, MA), pH 8.0 was used to elute SF from the column. Mobile phase was prepared by dissolving 12.1 g of Tris base (VWR, Pittsburgh, PA) and 48.1 g of sodium perchlorate (Alfa Aesar, Ward Hill, MA) in 800 mL of DI water. The pH was adjusted to 8.0 with 6N HCl. DI water was added to a final volume of 1 L. The solution was sterile filtered through a 0.2 μm polyethersulfone membrane filter. Silk fibroin elution was monitored at 280 nm. Molecular weights were calculated using a standard curve prepared from Waters BEH 200 Å Protein SEC Standard Mix (Waters, Milford, MA). The molecular weight of TF_42 was 32.5 kDa.

SF-based sunscreens were prepared to evaluate aesthetics, in vitro SPF, and broad-spectrum UVA/UVB coverage. The sunscreens were prepared using a variety of sources of zinc oxide and titanium dioxide as these play a critical role in SPF and broad-spectrum coverage. To prepare the formulations, the aqueous and oil phases were prepared separately and heated to 70° C. Sunscreens were prepared by blending the aqueous phase slowly into the oil phase. After emulsification, the ZinClear XP powder was blended into the final emulsion.

TABLE 83

Materials used in sunscreen formulations

| Ingredient | Manufacturer | Catalog # | Lot # |
|---|---|---|---|
| Silk Fibroin | Cocoon Biotech | n/a | TF_42 |
| MCT Oil | Bulk Apothecary | BNA-120 | N/A |
| Lipex Shea Butter | AAK | AAK-09-78 | KLB0222S |
| Zemea Propanediol | Dupont Tate & Lyle | 504-63-2 | LP19K00058 |
| ZinClear XP | Antaria | 19-0000050031 | XP-148 |
| Solaveil CT-300 | Croda | TT01264/SAMP | 1438532 |
| Kobo Zinc Oxide Dispersion | Kobo | GCP45XZJ | WD2000 |
| Kobo Zinc Oxide Dispersion | Kobo | GCP55TJ | WD1048 |
| Kobo Titanium Dioxide Dispersion | Kobo | JOSP50TJE | MB3500 |
| Kobo Zinc Oxide Dispersion | Kobo | SO60MZJ | MD636 |
| Kobo Zinc Oxide Dispersion | Kobo | CO55MZJ | MD829 |
| Kobo Zinc Oxide Dispersion | Kobo | JOSP55XZJ | WE951 |
| Non-nano Zinc Oxide | Kobo | 112UPS_API | 9A1M450 |

TABLE 84

Formulations prepared for in vitro SPF and broad-spectrum coverage analysis

| Sample # | Composition |
|---|---|
| 21270 | 44.6% Water, 3.8% SF, 10% Propanediol, 10% MCT Oil, 1% Shea Butter, 6% Titanium Dioxide, 10% Zinc Oxide |
| 21271 | 40.6% Water, 3.8% SF, 10% Propanediol, 10% MCT Oil, 1% Shea Butter, 6% Titanium Dioxide, 10% Zinc Oxide |
| 21275 | 36.8% Water, 3.17% SF, 10% Propanediol, 10% MCT Oil, 1% Shea Butter, 1% Dracorin GOC, 1% Kester Wax K606 % Titanium Dioxide, 10% Zinc Oxide |
| 21277 | 36.8% Water, 3.17% SF, 10% Propanediol, 10% MCT Oil, 1% Shea Butter, 6% Titanium Dioxide, 10% Zinc Oxide |
| SL_31_1 | 51.25% Water, 1% SF, 6% titanium dioxide, 10% zinc oxide, 10% propanediol, 10% MCT, 1% Shea Butter |
| SL_31_2 | 53.1% Water, 1% SF, 10% MCT, 1% Shea Butter, 10% Zinc Oxide, 6% Titanium Dioxide |
| SL_31_3 | 43%, 1% SF, 10% MCT Oil, 1% Shea Butter, 25% Zinc Oxide |
| SL_31_4 | 40% Water, 1% SF, 10% MCT Oil, 1% Shea Butter, 25% Zinc Oixde |
| SL_31_5 | 63% Water, 1% SF, 10% MCT Oil, 2% Shea Butter, 25% Zinc Oxide |
| SL_31_6 | 50.8% Water, 1.5% SF, 10% MCT Oil, 2% Shea Butter, 6% Titanium Dioxide, 10% Zinc Oxide |
| SL_31_7 | 49.9% Water, 1.5% SF, 10% MCT, 1% Shea Butter, 6% Titanium Dioxide, 10% Zinc Oxide |
| SL_31_8 | 62.3% Water, 1.5% SF, 10% MCT, 2% Shea Butter, 25% Zinc Oxide |
| SL_31_9 | 62.3% Water, 1.5% SF, 10% MCT, 2% Shea Butter, 25% Zinc Oxide |
| SL_31_10 | 61.5% Water, 1.5% SF, 10% MCT Oil, 2% Shea Butter, 25% Zinc Oxide |
| SL_31_11 | 48% Water, 1% SF, 10% MCT, 1% Shea Butter, 6% Titanium Dioxide, 10% Zinc Oxide |
| SL_31_12 | 49.3% Water, 1% SF, 26.5% MCT, 1% Shea Butter, 10% Zinc Oxide, 6% Titanium Dioxide |
| SL_31_13 | 43.9% Water, 1% SF, 23.2% MCT Oil, 1% Shea Butter, 6% Titanium Dioxide |
| 21378 | 21.2% Water, 0.87% SF, 20% Propanediol, 20% MCT Oil, 6% titanium dioxide, 15% Zinc Oxide, 1% Shea Butter, 1% Dracorin GOC, 1% Kester Wax K60 |
| 21379 | 26% Water, 1.1% SF, 15% Propanediol, 20% MCT Oil, 6% Titanium Dioxide, 15% Zinc Oxide, 1% Shea Butter, 1% Dracorin GOC, 1% Kester Wax K60 |
| 21398 | 20.3% Water, 1.74% SF, 20% Propanediol, 20% MCT Oil, 6% Titanium Dioxide, 15% Zinc Oxide, 1% Shea Butter, 1% Dracorin GOC, 1% Polyhydroxystearic acid |

21270: 48.5 g of a 7.93% silk fibroin solution was mixed with 10.1 g of Zemea Propanediol (DuPont Tate and Lyle). In a 1 L beaker, 10 g of MCT oil, 1 g of Lipex shea butter (AAK AB), 20 g of Solaveil CT-300 were blended. To the oils, the silk fibroin/propanediol solution was added while blending. After emulsification, 30 g of ZinClear zinc oxide (Antaria) was added. The mixture was blended for an additional 1 min.

21271: 48.5 g of a 7.93% silk fibroin solution was mixed with 40 g of Zemea Propanediol (DuPont Tate and Lyle). In a 1 L beaker, 20 g of MCT oil, 1 g of Lipex shea butter (AAK AB), 20 g of Solaveil CT-300 were blended. To the oils, the silk fibroin/propanediol solution was added while blending. After emulsification, 10 g of ZinClear zinc oxide (Antaria) was added. The mixture was blended for an additional 1 min.

21271: 22 g of a 7.93% silk fibroin solution was mixed with 20 g of Zemea Propanediol (DuPont Tate and Lyle). In a 1 L beaker, 20 g of MCT oil, 1 g of Lipex shea butter (AAK AB), 20 g of Solaveil CT-12 W (Croda), 1 g Dracorin GOC (Symrise), and 1 g Pelmol PHS-8 (Phoenix Chemical). were blended. To the oils, the silk fibroin/propanediol solution was added while blending. After emulsification, 10 g of ZinClear zinc oxide (Antaria) was added. The mixture was blended for an additional 1 min.

21275: 40 g of a 7.93% silk fibroin solution was mixed with 10.1 g of Zemea Propanediol (DuPont Tate and Lyle). In a 1 L beaker, 17 g of MCT oil, 1 g of shea butter (AAK AB), 1 g of Dracorin GOC (Symrise), 1 g Kester Wax K60 (Koster Keunen), and 20 g of Solaveil CT-300 were blended. To the oils, the silk fibroin/propanediol solution was added while blending. After emulsification, 10 g of ZinClear zinc oxide (Antaria) was added. The mixture was blended for an additional 1 min.

21277: 40 g of a 7.93% silk fibroin solution was mixed with 10.1 g of Zemea Propanediol (DuPont Tate and Lyle). In a 1 L beaker, 17 g of MCT oil, 1 g of shea butter (AAK AB), 9.6 g ZinClear XP65COC (Antaria) and 20 g of Solaveil CT-300 (Croda) were blended. To the oils, the silk fibroin/propanediol solution was added while blending. After emulsification, 10 g of ZinClear zinc oxide (Antaria) was added. The mixture was blended for an additional 1 min SL_35_1: To a 1 L beaker, 48.3 g of zinc oxide dispersion (Kobo GCP45XZJ) was mixed with 25 g of titanium dioxide dispersion (Kobo GCP55TJ), 20 g of MCT oil, and 2 g of Lipex Shea Butter. The dispersions and oils were heated to 60° C. 25.2 g of SF solution (TF_44) and sufficient water to bring the total mass to 200 g were added. The sunscreen was blended with an immersion blender for 1 min.

SL_35_2: To a 1 L beaker, 38.2 g zinc oxide dispersion (Kobo JOSP55XZJ) was mixed with 31.7 g of Kobo JOSP50TJE titanium dioxide dispersion, 20 g of MCT oil and 2 g of Lipex Shea Butter (Antaria). The dispersions and oils were heated to 60° C. To the oil phase, 25.2 g of SF solution (TF_44) and sufficient water to bring the total mass to 200 g were added. The sunscreen was blended with an immersion blender for 1 min.

SL_35_3: To a 1 L beaker, 89.84 g of zinc oxide dispersion (Kobo SO60MZJ) was mixed with 20 g of MCT oil and 2 g of Lipex Shea Butter. The dispersions and oils were heated to 60° C. To the oil phase, 25.2 g of SF solution (TF_44) and sufficient water to bring the total mass to 200 g were added. The sunscreen was blended with an immersion blender for 1 min.

SL 35_4: To a 1 L beaker, 96 g of zinc oxide dispersion (Kobo CO55MZJ) was mixed with 20 g of MCT oil and 2 g of Lipex Shea Butter. The dispersions and oils were heated to 60° C. To the oil phase, 25.2 g of SF solution (TF_44) and sufficient water to bring the total mass to 200 g were added. The sunscreen was blended with an immersion blender for 1 min.

SL_35_5: To a 1 L beaker, 50 g of ZinClear XP zinc oxide powder was mixed with 20 g of MCT oil and 2 g of Lipex Shea Butter. The dispersions and oils were heated to 60° C. To the oil phase, 25.2 g of SF solution (TF_44) and sufficient water to bring the total mass to 200 g were added. The sunscreen was blended with an immersion blender for 1 min.

SL_35_6: To a 1 L beaker, 48.3 g of zinc oxide dispersion (Kobo GCP45XZJ) was mixed with 25 g of dioxide dispersion (Kobo GCP55TJ titanium), 20 g of MCT oil and 2 g of Lipex Shea Butter. The dispersions and oils were heated to 60° C. To the oil phase, 37.8 g of SF solution (TF_44) and sufficient water to bring the total mass to 200 g were added. The sunscreen was blended with an immersion blender for 1 min.

SL_35_7: To a 1 L beaker, 48.3 g of zinc oxide dispersion (Kobo JOSP55XZJ) was mixed with 25 g of titanium dioxide dispersion (Kobo JOSP50TJE), 20 g of MCT oil and 2 g of Lipex Shea Butter. The dispersions and oils were heated to 60° C. To the oil phase, 37.8 g of SF solution (TF_44) and sufficient water to bring the total mass to 200 g were added. The sunscreen was blended with an immersion blender for 1 min.

SL_35_8: To a 1 L beaker, 48.3 g of zinc oxide dispersion (Kobo SO60MZJ) was mixed with 20 g of MCT oil and 4 g of Lipex Shea Butter. The dispersions and oils were heated to 60° C. To the oil phase, 37.8 g of SF solution (TF_44) and sufficient water to bring the total mass to 200 g were added. The sunscreen was blended with an immersion blender for 1 min.

SL 35_9: To a 1 L beaker, 48.3 g of zinc oxide dispersion (Kobo CO55MZJ) was mixed with 20 g of MCT oil and 4 g of Lipex Shea Butter. The dispersions and oils were heated to 60° C. To the oil phase, 37.8 g of SF solution (TF_44) and sufficient water to bring the total mass to 200 g were added. The sunscreen was blended with an immersion blender for 1 min.

SL_35_10: To a 1 L beaker, 50 g of ZinClear XP zinc oxide powder was mixed with 20 g of MCT oil and 4 g of Lipex Shea Butter. The dispersions and oils were heated to 60° C. To the oil phase, 37.8 g of SF solution (TF_44) and sufficient water to bring the total mass to 200 g were added. The sunscreen was blended with an immersion blender for 1 min.

SL_35_11: To a 1 L beaker, 20 g of ZinClear XP zinc oxide powder was mixed with 40 of titanium dioxide dispersion (Croda), 20 g of MCT oil and 2 g of Lipex Shea Butter. The dispersions and oils were heated to 60° C. To the oil phase, 25.2 g of SF solution (TF_44) and sufficient water to bring the total mass to 200 g were added. The sunscreen was blended with an immersion blender for 1 min. SL_35_12: To a 1 L beaker, 20 g of ZinClear XP zinc oxide powder was mixed with 25 g of titanium dioxide dispersion (Kobo GCP55TJ), 52.5 g of MCT oil and 2 g of Lipex Shea Butter. The dispersions and oils were heated to 60° C. To the oil phase, 25.2 g of SF solution (TF_44) and sufficient water to bring the total mass to 200 g were added. The sunscreen was blended with an immersion blender for 1 min. SL_35_13: To a 1 L beaker, 20 g of ZinClear XP zinc oxide powder was mixed with 41.7 g of titanium dioxide dispersion (Kobo JOSP50TJE), 46.4 g of MCT oil and 2 g of Lipex Shea Butter. The dispersions and oils were heated to 60° C. To the oil phase, 25.2 g of SF solution (TF_44) and sufficient water to bring the total mass to 200 g were added. The sunscreen was blended with an immersion blender for 1 min.

21378: 44 g of a 7.93% silk fibroin solution was mixed with 40 g of Zemea Propanediol (DuPont Tate and Lyle). In a 1 L beaker, 40 g of MCT oil, 2 g of Lipex shea butter (AAK AB), 2 g Dracorin GOC (Chemispire), 2 g Kester Wax K60, and 40 g of Solaveil CT-300 were blended. To the oils, the silk fibroin/propanediol solution was added while blending. After emulsification, 30 g of ZinClear XP zinc oxide (Antaria) was added. The mixture was blended for an additional 1 min.

21379: 54 g of a 7.93% silk fibroin solution was mixed with 10.1 g of Zemea Propanediol (DuPont Tate and Lyle). In a 1 L beaker, 10 g of MCT oil, 1 g of Lipex shea butter (AAK AB), 20 g of Solaveil CT-300 were blended. To the oils, the silk fibroin/propanediol solution was added while blending. After emulsification, 10 g of ZinClear XP zinc oxide (Antaria) was added. The mixture was blended for an additional 1 min.

21398: 44 g of a 7.93% silk fibroin solution was mixed with 10.1 g of Zemea Propanediol (DuPont Tate and Lyle). In a 1 L beaker, 10 g of MCT oil, 1 g of Lipex shea butter (AAK AB), 20 g of Solaveil CT-12 W were blended. To the oils, the silk fibroin/propanediol solution was added while blending. After emulsification, 10 g of ZinClear XP zinc oxide (Antaria) was added. The mixture was blended for an additional 1 min.

The formulations that thickened were then subjected to in vitro SPF testing and broad-spectrum measurements. The results are shown in Table 85. Sunscreen formulations prepared with silk fibroin and mineral sunscreen actives achieve SPF ≥30 with broad spectrum coverage.

TABLE 85

In vitro SPF and broad-spectrum UVA/UVB coverage results

| Formulation | In vitro SPF | Broad Spectrum (Yes/No) |
|---|---|---|
| 21270 | 28 | No |
| 21271 | 30 | Yes |
| 21275 | 34 | No |
| 21276 | 9.5 | Yes |
| 21277 | 43 | No |
| SL_35_4 | 88 | Yes |
| SL_35_5 | 1.3 | Yes |
| SL_35_7 | 265 | Yes |
| SL_35_11 | 36 | Yes |
| SL_35_12 | 71 | Yes |
| SL_35_13 | 129 | Yes |
| SL_35_14 | 1.4 | Yes |

Example 54: Silk Fibroin Lotion as Insect Repellent

Silk fibroin-based lotions may be combined with different actives for use as an insect repellent. Examples of the active ingredients include Catnip oil (*Nepeta cataria* or catmint) at 7% to 15% catnip oil. Citronella oil may be added to a silk fibroin based lotions with 4.2% to 5% concentration. An example of the active ingredients include DEET at 5% to 98.1% concentration in silk fibroin-based lotion. An example of the active ingredients include IR 3535 (3-[N-Butyl-N-acetyl]-aminopropionic acid, ethyl ester at 7% to 20% concentration in silk fibroin-based lotion. An example of the active ingredients include p-Menthane-3,8-diol (pmd) at 8% to 10% concentration in silk fibroin-based lotion. An example of the active ingredients include oil of lemon eucalyptus (contains pmd) at 30% to 40% concentration in silk fibroin-based lotion. An example of the active ingredients include picaridin at 5% to 20% concentration in silk fibroin-based lotion. An example of the active ingredients include 2-undecanone (or methyl nonyl ketone) at 7.75% concentration in silk fibroin-based lotion.

Example 55: Silk Fibroin Lotion as a Hand Sanitizer

Silk fibroin-based lotions may be combined with different actives for use as a hand sanitizer. Examples of active ingredients include benzalkonium chloride, ethanol, or isopropanol. Benzalkonium chloride is deemed eligible by the FDA for use in the formulation of healthcare personnel hand rubs. Silk fibroin lotion with benzalkonium chloride may be effective in killing coronaviruses when benzalkonium chloride is at a concentration of at least 0.12% to 0.5%.

SOLIDS EXAMPLES

Example 56. Silk Fibroin Film Dissolution Study

Silk Fibroin Isolation

Silk yarn, purchased from Jiangsu SOHO International Group, was degummed to remove sericin. 30 grams of cut silk yarn were heated at 85° C. in 1 L of deionized (DI) water with 0.5M sodium carbonate with occasional stirring. After 4 hours, the fibroin was removed and washed in 70° C. three separate times for ten minutes. The fibroin was then removed and rinsed under DI water. The fibroin was dried overnight, weighed, and dissolved at 20% (w/v) in a 9.3M aqueous solution of lithium bromide (from Sigma-Aldrich, St. Louis, MO) for 5 hours at 60° C. The resulting fibroin solution was dialyzed against water in a 50 kDa regenerated cellulose dialysis tubing for 48 hours, with 6 water changes to remove the excess salt. The conductivity was recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and samples of the supernatant were diluted at 1:20 and 1:40 in water. Samples for a standard curve were prepared for an A280 assay by diluting pre-measured fibroin solutions to 5, 2.5, 1.25, 0.625, 0.3125, and 0 mg/mL in water. The silk concentration of the 1:20 and 1:40 diluted silk fibroin samples was measured against the standard curve by the absorbance at 280 nm.

The silk fibroin solution was diluted to a final concentration of 3% (w/v) in water and filtered through a 0.2 μm filter using a vacuum filter unit. 10 ml of each solution was aliquoted into 50 ml conical tubes, frozen overnight at −80° C., and then lyophilized for 72 hours. Samples were then stored at −20° C. until use.

Silk Fibroin Film Formation

Lyophilized silk fibroin was removed from the freezer and allowed to reach room temperature. Water was then added to the lyophilized cakes to prepare 20 mL of 15% silk fibroin solution. 10 ml of 10% silk fibroin and 10 ml of 5% silk fibroin was prepared by diluting the 20% silk fibroin stock in water. These were the three solutions from which silk films were cast.

1 mL of each solution was pipetted onto 10 individual small weight boats (38×25×9 mm), for 30 total samples. The weight boats were then placed in an oven at 60° C. overnight and allowed to totally dry. Samples were removed after approximately 16 hours and the films were removed from the weight boats. The films were then broken into smaller pieces (approximately 1 cm long by 0.5 cm wide). Samples were then treated in a variety of different ways to increase their beta-sheet content.

Control samples were left without any further treatment. Three segments of film from each concentration were treated in methanol by dipping the film fragment into a petri dish with 100% methanol, leaving it for 1 minute, then transferring it to a petri dish of DI water for a 10 second rinse, after which the sample was put into a 4 mL glass vial. Three segments of film from each concentration were treated in ethanol by dipping the film fragment into a petri dish with 100% ethanol, leaving it for 1 minute, then transferring it to a petri dish of DI water for a 10 second rinse, after which the sample was put into a 4 mL glass vial. Three segments of film from each concentration were treated with water annealing at room temperature by first placing a small amount of DI water in the bottom of a desiccator. The film segments were put onto weigh boats and placed on the platform in the desiccator, at which point the entire container was placed under continuous vacuum. After vacuum was reached (about 10 minutes), the port was sealed and the samples were left for 2 hours at room temperature. Air was then flushed into the system by opening the port, and the samples were removed and left to dry in their weigh boats overnight. Three segments of film from each concentration were treated with water annealing at 37° C. by first placing a small amount of DI water in the bottom of a desiccator. The film segments were put onto weigh boats and placed on the platform in the desiccator, at which point the entire container was placed under continuous vacuum. After vacuum was reached (about 10 minutes), the port was sealed and the samples were left for 2 hours in a 37° C. incubator. However, after approximately 30 minutes, it was noticed that the seal on the desiccator had allowed air to enter the system and the vacuum was lost. The samples were left instead for the remainder of the 2 hours in the completely humidified 37° C. incubator. The samples were then removed and left to dry in their weigh boats overnight. Three segments of film from each concentration were treated via autoclaving. The segments of film were placed into individual 4 mL glass vials and the opening of each was covered with aluminum foil. The vials were placed into the autoclave and a solid cycle was run for 30 minutes at 121° C. When the cycle was complete, the fragments were immediately removed, capped, and left to cool to room temperature overnight.

Silk Fibroin Film Dissolution

Three segments of film from each silk concentration and post-processing condition were weighed after drying (each was broken until it was around 10 mg) and placed into individual 4 mL glass vials. Mock seawater was prepared by dissolving 26.29 g of sodium chloride, 0.74 g of potassium chloride, 0.99 g of calcium chloride dihydrate, 6.09 g of magnesium chloride hexahydrate, and 2.27 g of sodium sulfate in 900 mL of DI water. The final volume was brought up to 1 L with DI water. The solution was then chilled to 4° C. prior to aliquoting. 4 mL of the mock seawater was then pipetted into each 4 mL glass vial containing a film fragment. All of the vials were put onto an orbital shaker moving at a slow speed in a 4° C. refrigerator to incubate.

After 30 minutes, the samples were removed, inverted briefly to ensure complete and homogeneous mixing, and then allowed to settle. 200 μL of mock seawater from each sample was then removed and pipetted directly into a UV-readable 96-well plate. A standard curve of silk in the seawater was prepared at 5, 2.5, 1.25, 0.625, 0.3125, and 0 mg/mL and pipetted into the plate. The absorbance of each sample was then measured at 280 nm to determine the concentration of silk in solution. The samples were then capped and placed back under rotation at 4° C. overnight. This process was then repeated after 17 hours to determine if more sample had dissolved overnight.

The amount of dissolved silk was determined via the concentration and then the triplicates were averaged. Table 86 lists the average percentage of each film remaining after the relevant time in the mock seawater.

TABLE 86

SF-01 Dissolution Results (reported as mean ± SD)

| Silk Concentration (% w/v) | Post Treatment | Average % Remaining After 0.5 Hours | Average % Remaining After 17 Hours |
|---|---|---|---|
| 5 | Untreated | 2.12 ± 0.38 | 5.46 ± 0.25 |
| 5 | Methanol | 91.59 ± 12.47 | 91.96 ± 15.55 |
| 5 | Ethanol | 41.77 ± 16.23 | 38.47 ± 15.70 |
| 5 | Room Temp. Annealing | 12.61 ± 9.29 | 15.79 ± 6.78 |
| 5 | 37° C. Annealing | 20.99 ± 0 | 23.91 ± 0 |
| 5 | Autoclave | 100.36 ± 0.85 | 101.16 ± 0.74 |
| 10 | Untreated | 9.85 ± 1.57 | 11.08 ± 1.56 |
| 10 | Methanol | 80.03 ± 1.55 | 79.25 ± 2.97 |
| 10 | Ethanol | 26.88 ± 6.06 | 25.60 ± 3.57 |
| 10 | Room Temp. Annealing | 16.78 ± 16.98 | 18.82 ± 17.10 |
| 10 | 37° C. Annealing | 20.73 ± 13.27 | 21.11 ± 15.54 |
| 10 | Autoclave | 100.56 ± 0.41 | 100.91 ± 0.30 |
| 15 | Untreated | 3.15 ± 1.40 | 2.86 ± 0.60 |
| 15 | Methanol | 44.53 ± 8.49 | 47.04 ± 7.59 |
| 15 | Ethanol | 32.13 ± 13.64 | 33.77 ± 13.43 |
| 15 | Room Temp. Annealing | 37.60 ± 3.13 | 37.06 ± 4.18 |
| 15 | 37° C. Annealing | 27.04 ± 19.68 | 27.44 ± 19.22 |
| 15 | Autoclave | 100.80 ± 1.42 | 101.78 ± 1.17 |

All three silk concentrations behaved similarly. The untreated control films almost entirely dissolved within the first half hour for all silk fibroin concentrations. For all concentrations, the films treated via autoclaving were almost entirely intact after an overnight in the solution, with little to no dissolution observed. At 5 and 10% silk fibroin, methanol treatment was almost as effective as autoclaving. At 15% silk fibroin, the network of fibroin in the film may have been too dense to allow for the methanol to effectively raise the beta-sheet content. In all films, ethanol or water annealing treatments at any temperature resulted in a loss of over 50% of the film's mass within 17 hours.

Overall, the beta-sheet content of silk films can be effectively altered and tuned with a variety of different techniques, as demonstrated herein. Among these, autoclaving appears to be a method that results in near total insolubility in mock seawater at 4° C.

Example 57. Silk Fibroin Buttons

Silk Fibroin Isolation

Silk yarn, purchased from Jiangsu SOHO International Group, was degummed to remove sericin. 30 grams of cut silk yarn were heated at 85° C. in 1 L of deionized (DI) water with 0.5M sodium carbonate with occasional stirring. After 4 hours, the fibroin was removed and washed in 70° C. three separate times for ten minutes. The fibroin was then removed and rinsed under DI water. The fibroin was dried overnight, weighed, and dissolved at 20% (w/v) in a 9.3M aqueous solution of lithium bromide (from Sigma-Aldrich, St. Louis, MO) for 5 hours at 60° C. The resulting fibroin solution was dialyzed against water in a 50 kDa regenerated cellulose dialysis tubing for 48 hours, with 6 water changes to remove the excess salt. The conductivity was recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and samples of the supernatant were diluted at 1:20 and 1:40 in water. Samples for a standard curve were prepared for an A280 assay by diluting pre-measured fibroin solutions to 5, 2.5, 1.25, 0.625, 0.3125, and 0 mg/mL in water. The silk concentration of the 1:20 and 1:40 diluted silk fibroin samples was measured against the standard curve by the absorbance at 280 nm.

The silk fibroin solution was diluted to a final concentration of 3% (w/v) in water and filtered through a 0.2 μm filter using a vacuum filter unit. 10 mL of each solution was aliquoted into 50 ml conical tubes, frozen overnight at −80° C., and then lyophilized for 72 hours. Samples were then stored at −20° C. until use.

Silk Fibroin Button Formation

Lyophilized silk fibroin was removed from the freezer and allowed to reach room temperature. Water was then added to the lyophilized cakes to prepare 5 ml of 40% silk fibroin solution. This was the solution from which silk buttons were cast.

Silicone button molds were used to cast the silk fibroin. Silk fibroin solution was pipetted into the mold, being careful to avoid any bubbles, until just reaching the top of the mold. The mold was then placed in a 37° C. incubator at 5% carbon dioxide and 100% humidity. After approximately 16 hours, or overnight, the buttons were removed. By this point, they had solidified optically clear, and were able to be pulled from the silicone. This casting method would likely work with any simple mold with concentrated silk fibroin solution.

Silk Fibroin Button Formation with Structural Additives

Lyophilized silk fibroin was removed from the freezer and allowed to reach room temperature. Water was then added to the lyophilized cakes to prepare 40% silk fibroin solution. Additives were manually mixed into the silk fibroin solution until homogeneous to provide additional structural support to the solids. This formed either a viscous, flowable solution or pastes, dependent on the property and concentration of the additives. These additives included 5-20% wood flour (System Three Resins, Inc.), 5-10% zinc oxide (Bulk Apothecary), 5-10% titanium dioxide (Bulk Apothecary), 5-10% glycerol (Spectrum Chemicals), or 5-10% sericin (Sigma Aldrich). Silicone button molds were used to cast the silk fibroin solids. Silk fibroin solutions containing additives were pipetted or manually spatulated to completely fill the molds, being careful to avoid any bubbles. The mold was placed in a 37° C. incubator at 5% carbon dioxide and 100% humidity. After approximately 16 hours, or overnight, the buttons were removed. By this point, they had solidified optically clear, and were able to be pulled from the silicone. This casting method would likely work with any simple mold with concentrated silk fibroin solution.

TEXTILE EXAMPLES

Example 58. Silk Fibroin Isolation from Silk-Based Textile Waste

Silk-based textile waste containing yarns, and/or threads that cannot be reeled continuously are used as a silk source. SBT waste is degummed twice using sodium carbonate aqueous solution (0.5% (w/v). Silk fibroin solutions are washed thoroughly washed using distilled water and dried at room temperature for 48 hours. Degummed and washed SBT waste are cut into small pieces and dissolved in Lithium Bromide aqueous solution (9.3M) at 60° C. for 2 hours and silk fibroin solutions at different concentrations namely 5, 10, 13, 15, 18, 20 and 23% (w/v) are prepared. The prepared solutions are sequentially filtered by 50 μm polyester filer and 4.5 μm cellulose filter. The SF solutions are degassed through storing at room temperature for 24 hours.

Example 59. SF Fiber Preparation from Silk-Based Textile Waste

SF fibers are prepared from SBT waste using methods described in Mollahosseini, et al. (2019). Recycling of waste silk fibers towards silk fibroin fibers with different structures through wet spinning technique. Journal of Cleaner Production. 236. 117653. 10.1016/j.jclepro.2019.117653. (the contents of which are herein incorporated by reference in their entirety). SF solutions are extruded into first liquid bath containing $Na_2SO_4$ and $(NH_4)_2SO_4$ with solid concentration of 20 or 30% (w/v) using a syringe pump. The extrusion is conducted using a steel capillary tube as a spinneret having an inner diameter of 0.2 mm. At the end of first liquid bath, the spinning jet is partially coagulated due to the presence of Li+ and Br− ions within the spinning jet. The filaments produced are guided into the second liquid bath containing methanol/water (80/20 (v/v) mixture (with or without polyethylene glycol) at 23° C. and wound up on a roller. After spinning, the fibers are collected on a roller and are rotated in the second liquid bath for additional 15 min. The SF fibers are thoroughly rinsed and kept in distilled water for 120 min and are dried at room temperature.

SF fibers are also prepared by degumming 10.5 grams of 18% silk and 10.5 grams of a black cloth containing silk by boiling in degumming solution containing 4.24 g of $Na_2CO3$ for 2 L for 10 grams of silk. The preparations are boiled for 15 minutes. Some samples are not degummed prior to further processing. Degummed samples are solubilized using lithium bromide or Ajisawa's salt. Table 87 describes the samples and the processing methods to be used.

TABLE 87

SF fiber preparation samples

| Sample Name | Preparation |
|---|---|
| C-L-D | Black cloth, lithium bromide, degummed |
| C-A-D | Black cloth, Ajisawa's salt, degummed |
| C-L-G | Black cloth, lithium bromide, not degummed |
| C-A-G | Black cloth, Ajisawa's salt, not degummed |
| S-L-D | 18% Silk, lithium bromide, degummed |
| S-A-D | Silk fiber, Ajisawa's salt, degummed |

The samples described in Table 87 are extruded through a 27 gauge syringe. Samples are degassed by placing a 50 ml conical tube and centrifuging for 2 minutes at 1500 g. The samples are extruded onto the surface of first liquid bath containing 10% sodium sulfate, 10% ammonium sulfate (pH 4; adjusted with acetic acid). The fibers formed in the first liquid bath are pulled out using tweezers and are transferred to a second liquid bath containing 80% methanol and 20% water. The fibers are left in the second liquid bath for 2 hours.

Example 60. Preparation of SBTs with SBP Coating

A 0.5% silk fibroin solution is applied to a textile using a spray gun from a distance of about 10 inches. The textile used for the experiment are cotton, LYCRA®, polyester, nylon and combinations thereof. The formats of the textiles are cloth, apparel, and footwear. The process is repeated three times spraying from left to right and three times from right to left. Samples are placed in a 50° C. oven on aluminum foil over a water bath for about 1.5 hours. Methods are repeated with a second polyester fabric sample with an about 5.8% silk fibroin solution spray application. Smoothness and hand of the textile are measured by touch.

Example 61. Evaluating SBTs Properties

The properties of SBTs prepared using methods described herein are characterized using one of more tests described by the American Association of Textile Chemists and Colorists (AATCC). SBTs are expected to show superior properties in one or more of the tests. The test methods are listed below with the AATCC test method number provided in parenthesis: Colorfastness to Acids and Alkalis (AATCC TM6), Colorfastness to Crocking. Crockmeter Method (AATCC TM8), Colorfastness to Perspiration (AATCC TM15), Colorfastness to Light: Outdoor (AATCC TM16.1), Colorfastness to Light: Carbon-Arc (AATCC TM16.2), Colorfastness to Light: Xenon-Arc (AATCC TM16.3), Wetting Agents: Evaluation of (AATCC TM17), Fiber Analysis: Qualitative (AATCC TM20), Fiber Analysis: Quantitative (AATCC TM20A), Water Repellency-Spray Test (AATCC TM22), Colorfastness to Burnt Gas Fumes (AATCC TM23), Ageing of Sulfur-Dyed Textiles: Accelerated (AATCC TM26), Wetting Agents: Evaluation of Rewetting Agents (AATCC TM27), Antifungal Activity, Assessment on Textile Materials: Mildew and Rot Resistance of Textiles (AATCC TM30), Water Resistance: Rain Test (AATCC TM35), Water Resistance: Impact Penetration Test (AATCC TM42), Wetting Agents for Mercerization (AATCC TM43), Colorfastness to Laundering: Accelerated (AATCC TM61), Wrinkle Recovery of Fabrics: Recovery Angle Method (AATCC TM66), Water Repellency-Tumble Jar Dynamic Absorption Test (AATCC TM70), Electrical Surface Resistivity of Fabrics (AATCC TM76), Absorbency of Textiles (AATCC TM79), pH of the Water-Extract from Bleached Textiles (AATCC TM81), Fluidity of Dispersions of Cellulose from Bleached Cotton Cloth (AATCC TM82), Electrical Resistance of Yarns (AATCC TM84), Drycleaning: Durability of Applied Designs and Finishes (AATCC TM86), Seam Smoothness in Fabrics after Home Laundering (AATCC TM88B), Crease Retention in Fabrics after Home Laundering (AATCC TM88C), Mercerization in Cotton (AATCC TM89), Antimicrobial Activity Assessment of Textile Materials: Agar Plate Method (AATCC TM90), Chlorine, Retained; Tensile Loss: Single Sample Method (AATCC TM92), Abrasion Resistance of Fabrics: Accelerotor Method (AATCC TM93), Finishes in Textiles: Identification (AATCC TM94), Dimensional Changes in Commercial Laundering of Woven and Knitted Fabrics Except Wool (AATCC TM96), Extractable Content of Textiles (AATCC TM97), Alkali in Bleach Baths Containing Hydrogen Peroxide (AATCC TM98), Antibacterial Finishes on Textile Materials: Assessment of (AATCC TM100), Colorfastness to Bleaching with Hydrogen Peroxide (AATCC TM101), Hydrogen Peroxide by Potassium Permanganate Titration: Determination of (AATCC TM102), Bacterial Alpha-Amylase Enzymes Used in Desizing, Assay of (AATCC TM103), Colorfastness to Water Spotting (AATCC TM104), Colorfastness to Water: Sea (AATCC TM106), Colorfastness to Water (AATCC TM107), Colorfastness to Ozone in the Atmosphere Under Low Humidities (AATCC TM109), Whiteness of Textiles (AATCC TM110), Weather Resistance of Textiles: Exposure to Daylight and Weather (AATCC TM111), Formaldehyde Release from Fabric, Determination of—Sealed Jar Method (AATCC TM112), Chlorine, Retained; Tensile Loss: Multiple Sample Method (AATCC TM114), Electrostatic Clinging of Fabrics: Fabric-to-Metal Test (AATCC TM115), Colorfastness to Crocking: Rotary Vertical Crockmeter Method (AATCC TM116), Colorfastness to Heat: Dry (excluding Pressing) (AATCC TM117), Oil Repellency: Hydrocarbon Resistance Test (AATCC TM118), Color Change Due to Flat Abrasion (Frosting): Screen Wire Method (AATCC TM119), Color Change Due to Flat Abrasion (Frosting): Emery Method (AATCC TM120), Carpet Soiling: Visual Rating Method (AATCC TM121), Carpet Soiling: Service Soiling Method (AATCC TM122), Smoothness Appearance of Fabrics after Home Laundering (AATCC TM124), Colorfastness to Perspiration and Light (AATCC TM125), Water Resistance: Hydrostatic Pressure Test (AATCC TM127), Wrinkle Recovery of Fabrics: Appearance Method (AATCC TM128), Colorfastness to Ozone in the Atmosphere Under High Humidities (AATCC TM129), Soil Release: Oily Stain Release Method (AATCC TM130), Colorfastness to Pleating; Steam Pleating (AATCC TM131), Colorfastness to Drycleaning (AATCC TM132), Colorfastness to Heat: Hot Pressing (AATCC TM133), Electrostatic Propensity of Carpets (AATCC TM134), Dimensional Changes of Fabrics after Home Laundering (AATCC TM135), Rug Back Staining on Vinyl Tile (AATCC TM137), Cleaning: Washing of Textile Floor Coverings (AATCC TM138), Dye and Pigment Migration in a Pad-Dry Process: Evaluation of (AATCC TM140), Compatibility of Basic Dyes for Acrylic Fibers (AATCC TM141), Appearance of Flocked Fabric after Repeated Home Laundering and/or Coin-Op Drycleaning (AATCC TM142), Appearance of Apparel and Other Textile End Products After Home Laundering (AATCC TM143), Alkali in Wet Processed Textiles: Total (AATCC TM144), Dispersibility of Disperse Dyes: Filter Test (AATCC TM146), Antibacterial Activity of Fabrics, Assessment of Textile Materials: Parallel Streak Method (AATCC TM147), Light Blocking Effect of Textiles and Related Materials: Photodetector Method (AATCC TM148), Chelating Agents: Chelation Value of Aminopolycarboxylic Acids and Their Salts; Calcium Oxalate Method (AATCC TM149), Dimensional Changes of Garments after Home Laundering (AATCC TM150), Thermal Fixation Properties of Disperse Dyes (AATCC TM154), Colorfastness to Solvent Spotting: Perchloroethylene (AATCC TM157), Dimensional Changes on Drycleaning in Perchloroethylene: Machine Method (AATCC TM158), Transfer of Acid and Premetallized Acid Dyes on Nylon (AATCC TM159), Chelating Agents: Disperse Dye Shade Change Caused by Metals; Control of (AATCC TM161), Colorfastness to Water: Chlorinated Pool (AATCC TM162), Colorfastness: Dye Transfer in Storage; Fabric-to Fabric (AATCC TM163), Colorfastness to Oxides of Nitrogen in the Atmosphere Under High Humidities (AATCC TM164), Colorfastness to Crocking: Textile Floor Coverings-Crockmeter Method (AATCC TM165), Foaming Propensity of Disperse Dyes (AATCC TM167), Chelating Agents: Active Ingredient Content of Polyaminopolycarboxylic Acids and Their Salts; Copper PAN Method (AATCC TM168), Weather Resistance of Textiles: Xenon Lamp Exposure (AATCC TM169), Dusting Propensity of Powder Dyes: Evaluation of—(AATCC TM170), Carpets: Cleaning of, Hot Water Extraction Method (AATCC TM171), Colorfastness to Powdered Non-Chlorine Bleach in Home Laundering (AATCC TM172), CMC: Calculation of Small Color Differences for Acceptability (AATCC TM173), Antimicrobial Activity Assessment of Carpets (AATCC TM174), Stain Resistance: Pile Floor Coverings (AATCC TM175), Speckiness of Colorant Dispersions: Evaluation of (TAATCC TM176), Skew Change in Fabrics After Home Laundering (AATCC TM179), Relative Color Strength of Dyes in Solutions (AATCC TM182), Transmittance or Blocking of Erythemally Weighted UltraViolet Radiation through Fabrics (AATCC TM183), Dusting Behavior of Dyes: Determination of (AATCC TM184), Chelating Agents: Percent Content in Hydrogen Peroxide Bleach Baths; Copper PAN Indicator Method (AATCC TM185), Weather Resistance: UV Light and Moisture Exposure (AATCC TM186), Dimensional Changes of Fabrics: Accelerated (AATCC TM187), Colorfastness to Sodium Hypchlorite Bleach in Home Laundering (AATCC TM188), Flourine Content of Carpet Fibers (AATCC TM189), Colorfastness to Home Laundering with Activated Oxygen Bleach Detergent: Accelerated (AATCC TM190), Acid Cellulase Enzymes, Effect of: Top Loading Washer (AATCC TM191), Weather Resistance of Textiles: Sunshine-Arc Lamp Exposure with and without Wetting (AATCC TM192), Aqueous Liquid Repellency: Water/Alcohol Solution Resistance Test (AATCC TM193), Assessment of the Anti-House Dust Mite Properties of Textiles under Long-Term Test Conditions (AATCC TM194), Liquid Moisture Management Properties of Textile Fabrics (AATCC TM195), Colorfastness to Sodium Hypochlorite of a Textile Floor Covering (AATCC TM196), Vertical Wicking of Textiles (AATCC TM197), Horizontal Wicking of Textiles (AATCC TM198), Drying Time of Textiles: Moisture Analyzer Method (AATCC TM199), Drying Rate of Textiles at their Absorbent Capacity: Air Flow Method (AATCC TM200), Drying Rate of Fabrics: Heated Plate Method (AATCC TM201), Relative Hand Value of Textiles: Instrumental Method (AATCC TM202), Light Blocking Effect of Textiles: Spectrophotometric Method (AATCC TM203), Water Vapor Transmission of Textiles (AATCC TM204), Carpet: Liquid Penetration by Spillage (AATCC TM205), Free and Hydrolyzed Formaldehyde, Determination of: Water Extraction Method (AATCC TM206), Seam Twist in Garments Before and After Home Laundering (AATCC TM207), and Water Resistance: Hydrostatic Pressure Test Using a Restraint (AATCC TM208).

EQUIVALENTS AND SCOPE

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure. The present disclosure is further illustrated by the following nonlimiting examples.

The invention claimed is:

1. A method of preparing processed silk fibroin, comprising providing silk yarn harvested from a silk producer, the silk yarn comprising silk fibers containing silk fibroin and sericin, degumming the silk yarn in greater than 0.3 to 0.5 M sodium carbonate at a temperature of about 80 to about 90° C., and for a time of 60 to 480 minutes, to provide degummed silk fibers having a sericin concentration of 0-0.5 wt %, dissolving the degummed silk fibers using 5M to 13M lithium bromide for 4 hours to overnight at 60° C. to 85° C. to provide dissolved silk fibers, or dissolving the degummed silk fibers using a mixture of calcium chloride, ethanol, and water in a molar ratio of 1:2:8, diluting the dissolved silk fibers in water to form a solution with a concentration of 5 to 20% w/v silk fibers and optionally filtering the solution through a polypropylene prefilter to remove particulates and provide a clarified silk fiber solution, performing tangential flow filtration (TFF) on the diluted or clarified silk fiber solution using a regenerated cellulose filter, and concentrating and recovering processed silk fibroin from the TFF, wherein the processed silk fibroin has an average molecular weight of 5-50 kDa as determined by high pressure liquid chromatography using a standard comprising Thyroglobulin, IgG, bovine serum albumin (BSA), Myoglobin, and Uracil.

2. The method of claim 1, wherein the TFF is performed with a 5 kDa cut-off regenerated cellulose filter.

3. The method of claim 1, wherein the silk producer is a species selected from the group consisting of *Bombyx mandarina, Bombyx mori, Bombyx sinesis, Anaphe moloneyi, Anaphe panda, Anaphe reticulate, Anaphe ambrizia, Anaphe carteri, Anaphe venata, Anapha infracta, Antheraea assamensis, Antheraea assama, Antheraea mylitta, Antheraea pernyi, Antheraea yamamai, Antheraea polyphemus, Antheraea oculea, Anisota senatoria, Apis mellifera, Araneus diadematus, Araneus cavaticus, Automeris io, Atticus atlas, Copaxa multifenestrata, Coscinocera hercules, Callosamia promethea, Eupackardia calleta, Eurprosthenops australis, Gonometa postica, Gonometa rufobrunnea, Hyalophora cecropia, Hyalophora euryalus, Hyalophora gloveri, Miranda auretia, Nephila madagascarensis, Nephila clavipes, Pachypasa otus, Pachypasa atus, Philosamia ricini, Pinna squamosa, Rothschildia hesperis, Rothschildia lebeau, Samia cynthia*, and *Samia ricini*.

4. The method of claim 3, wherein the species is *Bombyx mori*.

* * * * *